(12) United States Patent
Wu

(10) Patent No.: US 11,421,028 B2
(45) Date of Patent: Aug. 23, 2022

(54) FABS-IN-TANDEM IMMUNOGLOBULIN AND USES THEREOF

(71) Applicant: EpimAb Biotherapeutics, Inc., Shanghai (CN)

(72) Inventor: Chengbin Wu, Shanghai (CN)

(73) Assignee: EPIMAB BIOTHERAPEUTICS, INC., Shanghai (CN)

( * ) Notice: Subject to any disclaimer, the term of this patent is extended or adjusted under 35 U.S.C. 154(b) by 912 days.

(21) Appl. No.: 16/075,922

(22) PCT Filed: Feb. 6, 2017

(86) PCT No.: PCT/US2017/016691
§ 371 (c)(1),
(2) Date: Aug. 6, 2018

(87) PCT Pub. No.: WO2017/136820
PCT Pub. Date: Aug. 10, 2017

(65) Prior Publication Data
US 2019/0233517 A1 Aug. 1, 2019

(30) Foreign Application Priority Data
Feb. 6, 2016 (WO) ................ PCT/CN2016/073722

(51) Int. Cl.
| | | |
|---|---|---|
| C07K 16/00 | (2006.01) |
| C07K 16/28 | (2006.01) |
| C07K 16/22 | (2006.01) |
| C07K 16/24 | (2006.01) |
| C07K 16/32 | (2006.01) |
| C07K 16/36 | (2006.01) |
| A61K 39/395 | (2006.01) |
| C07K 16/18 | (2006.01) |
| A61P 25/28 | (2006.01) |
| A61P 37/06 | (2006.01) |
| A61P 29/00 | (2006.01) |
| A61P 35/00 | (2006.01) |
| A61K 39/00 | (2006.01) |

(52) U.S. Cl.
CPC ........ *C07K 16/2818* (2013.01); *A61K 39/395* (2013.01); *A61P 25/28* (2018.01); *A61P 29/00* (2018.01); *A61P 35/00* (2018.01); *A61P 37/06* (2018.01); *C07K 16/18* (2013.01); *C07K 16/22* (2013.01); *C07K 16/241* (2013.01); *C07K 16/244* (2013.01); *C07K 16/2803* (2013.01); *C07K 16/2809* (2013.01); *C07K 16/2827* (2013.01); *C07K 16/2863* (2013.01); *C07K 16/2887* (2013.01); *C07K 16/32* (2013.01); *C07K 16/36* (2013.01); *A61K 2039/505* (2013.01); *C07K 2317/14* (2013.01); *C07K 2317/31* (2013.01); *C07K 2317/35* (2013.01); *C07K 2317/55* (2013.01); *C07K 2317/64* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 5,006,309 A | 4/1991 | Khalil et al. |
| 5,063,081 A | 11/1991 | Cozzette et al. |
| 5,089,424 A | 2/1992 | Khalil et al. |
| 5,294,404 A | 3/1994 | Grandone et al. |
| 5,714,350 A | 2/1998 | Co et al. |
| 5,955,264 A | 9/1999 | Seed et al. |
| 6,350,861 B1 | 2/2002 | Co et al. |
| 6,579,676 B1 | 6/2003 | Seed et al. |
| 6,984,488 B1 | 1/2006 | Gershoni et al. |
| 7,419,821 B2 | 9/2008 | Davis et al. |
| 7,498,420 B2 | 3/2009 | Michaud et al. |
| 7,682,833 B2 | 3/2010 | Miller et al. |
| 7,838,638 B2 | 11/2010 | Allan et al. |
| 7,854,930 B2 | 12/2010 | Goetsch et al. |
| 8,628,773 B2 | 1/2014 | Guo |
| 8,722,859 B2 | 5/2014 | Miller et al. |
| 8,802,375 B2 | 8/2014 | Sampson et al. |
| 2002/0004587 A1 | 1/2002 | Miller et al. |
| 2002/0137134 A1 | 9/2002 | Gerncross |
| 2004/0018577 A1 | 1/2004 | Emerson Campbell et al. |
| 2004/0018590 A1 | 1/2004 | Gerncross et al. |

(Continued)

FOREIGN PATENT DOCUMENTS

| | | |
|---|---|---|
| CN | 107840887 A | 3/2018 |
| CN | 107614013 A | 1/2019 |

(Continued)

OTHER PUBLICATIONS

Almagro & Fransson, Frontiers in Bioscience 2008; 13:1619-33 (Year: 2008).*

(Continued)

*Primary Examiner* — Meera Natarajan
(74) *Attorney, Agent, or Firm* — Finnegan, Henderson, Farabow, Garrett & Dunner, LLP

(57) ABSTRACT

The present invention provides multivalent and multispecific binding proteins that are capable of binding two or more antigens, or two or more epitopes. The present invention also provides methods of making and using such multivalent and multispecific binding proteins, including methods of using such binding proteins for prevention or treatment of various diseases, or for detecting specific antigens in vitro or in vivo.

6 Claims, 51 Drawing Sheets
Specification includes a Sequence Listing.

(56) References Cited

U.S. PATENT DOCUMENTS

| | | |
|---|---|---|
| 2005/0042664 A1 | 2/2005 | Wu et al. |
| 2005/0054019 A1 | 3/2005 | Michaud et al. |
| 2005/0074821 A1 | 4/2005 | Wild et al. |
| 2005/0100546 A1 | 5/2005 | Jakobovits et al. |
| 2005/0180972 A1 | 8/2005 | Wahl et al. |
| 2005/0250185 A1 | 11/2005 | Murphy et al. |
| 2006/0160164 A1 | 7/2006 | Miller et al. |
| 2006/0206947 A1 | 9/2006 | Scallon et al. |
| 2006/0235208 A1 | 10/2006 | Lazar et al. |
| 2007/0065912 A1 | 3/2007 | Carson et al. |
| 2007/0071675 A1 | 3/2007 | Wu et al. |
| 2008/0269467 A1 | 10/2008 | Allen et al. |
| 2009/0055944 A1 | 2/2009 | Korman et al. |
| 2009/0155275 A1 | 6/2009 | Wu et al. |
| 2009/0162360 A1 | 6/2009 | Klein et al. |
| 2009/0226443 A1 | 9/2009 | Filvaroff et al. |
| 2009/0252683 A1 | 10/2009 | Kischel et al. |
| 2009/0311253 A1 | 12/2009 | Ghayur et al. |
| 2010/0076178 A1 | 3/2010 | Ghayur et al. |
| 2010/0260668 A1 | 10/2010 | Ghayur et al. |
| 2012/0301400 A1 | 11/2012 | Williams et al. |
| 2012/0321626 A1 | 12/2012 | Zhou |
| 2013/0058937 A1 | 3/2013 | Auer et al. |
| 2013/0066054 A1 | 3/2013 | Humphreys et al. |
| 2013/0078249 A1 | 3/2013 | Ast et al. |
| 2014/0056897 A1 | 2/2014 | Buelow et al. |
| 2014/0194599 A1 | 7/2014 | Pass et al. |
| 2015/0093387 A1 | 4/2015 | Wu et al. |
| 2016/0017045 A1 | 1/2016 | Liu et al. |
| 2016/0120999 A1 | 5/2016 | Shen et al. |
| 2016/0289341 A1 | 10/2016 | Wu |
| 2017/0247456 A1 | 8/2017 | Freeman et al. |
| 2018/0194845 A1 | 7/2018 | De Goeij et al. |
| 2019/0085075 A1 | 3/2019 | La Motte-Mohs et al. |
| 2019/0256602 A1 | 8/2019 | Campbell et al. |
| 2019/0345252 A1 | 11/2019 | Kinsella et al. |

FOREIGN PATENT DOCUMENTS

| | | |
|---|---|---|
| EP | 1 176 195 A1 | 1/2002 |
| EP | 2 443 154 B1 | 12/2013 |
| JP | 2003-531588 A | 10/2003 |
| JP | 2007-501013 A | 1/2007 |
| JP | 2010-535032 A | 11/2010 |
| JP | 2012-522527 | 9/2012 |
| JP | 2012-530088 A | 11/2012 |
| JP | 2013-538204 | 10/2013 |
| JP | 2014-504860 A | 2/2014 |
| JP | 2014-526895 A | 10/2014 |
| JP | 2015-505319 A | 2/2015 |
| KR | 10-2015-0014551 | 2/2015 |
| RU | 2339696 C2 | 11/2008 |
| RU | 2433831 C2 | 11/2011 |
| RU | 2011121419 A | 12/2012 |
| RU | 2012121189 A | 11/2013 |
| TW | 201613962 A | 4/2016 |
| TW | 201702265 A | 1/2017 |
| TW | 201803906 A | 2/2018 |
| WO | WO 1999/054342 A1 | 10/1999 |
| WO | WO 2001/077342 A1 | 10/2001 |
| WO | WO 2002/072636 A2 | 9/2002 |
| WO | WO 2003/016466 A2 | 2/2003 |
| WO | WO 2003/035835 A2 | 5/2003 |
| WO | WO 2005/016382 A1 | 2/2005 |
| WO | WO 2005/095457 A2 | 10/2005 |
| WO | WO2005/117973 | 12/2005 |
| WO | WO 2009/018386 A1 | 2/2009 |
| WO | WO 2009/080253 A1 | 7/2009 |
| WO | WO 2010/000721 A1 | 1/2010 |
| WO | WO 2010/112193 A1 | 10/2010 |
| WO | WO 2010/115589 A1 | 10/2010 |
| WO | WO 2010/145792 A1 | 12/2010 |
| WO | WO 2011/117330 A1 | 9/2011 |
| WO | WO 2012/025525 A1 | 3/2012 |
| WO | WO 2012/121775 A1 | 9/2012 |
| WO | WO 2013/026831 A1 | 2/2013 |
| WO | WO 2013/104804 A2 | 7/2013 |
| WO | WO 2013/150043 A1 | 10/2013 |
| WO | WO 2014/083178 A1 | 6/2014 |
| WO | WO 2014/144357 | 9/2014 |
| WO | WO 2014/161845 A1 | 10/2014 |
| WO | WO 2014/167022 A1 | 10/2014 |
| WO | WO 2015/016559 A1 | 2/2015 |
| WO | WO 2015/087279 A1 | 6/2015 |
| WO | WO 2015/103072 A1 | 7/2015 |
| WO | WO 2015/134411 A1 | 9/2015 |
| WO | WO 2015/175375 A1 | 11/2015 |
| WO | WO 2015/176033 A1 | 11/2015 |
| WO | WO 2015/193352 A1 | 12/2015 |
| WO | WO 2016/020309 A1 | 2/2016 |
| WO | WO 2016/044224 A1 | 3/2016 |
| WO | WO 2016/079081 A1 | 5/2016 |
| WO | WO 2017/024515 A1 | 2/2017 |
| WO | WO 2017/133540 A1 | 8/2017 |
| WO | WO 2017/220569 A1 | 12/2017 |

OTHER PUBLICATIONS

De Genst et al., Dev Comp Immunol 2006; 30:187-98 (Year: 2006).*

Yoshinaga et al., J. Biochem 2008; 143:593-601 (Year: 2008).*

Apantaku et al. (Breast cancer diagnosis and screening, American Family Physician 2000) (Year: 2000).*

Martin et al (Journal of the National Cancer Institute, vol. 92, No. 14: pp. 1126-1135, Jul. 19, 2000) (Year: 2000).*

European Application No. 17748342.7, by Epimab Biotherapeutics, Inc., Examination Report, dated Feb. 8, 2021 (7 pages).

Sela-Culang et al., (2013) "The structural basis of antibody-antigen recognition", Frontiers in Immunology, 4(302):1-13.

Castoldi et al., "A novel bispecific EGFR/Met antibody blocks tumor-promoting phenotypic effects induced by resistance to EGFR inhibition and has potent antitumor activity", Oncogene, 32(50): 5593-5601 (2013) XP055129019, ISSN:0950-9232, DOI: 10.1038/onc.2013.245.

Jarantow et al., "Impact of Cell-surface Antigen Expression on Target Engagement and Function of an Epidermal Growth Factor Receptor c-MET Bispecific Antibody," J. Biol. Chem., 290(41): 24689-24704 (2015).

Kontermann and Brinkmann, "Bispecific Antibodies," Drug Discovery Today, 20(7): 838-847 (2015).

Moores et al., "A Novel Bispecific Antibody Targeting EGFR and cMet Is Effective against EGFR Inhibitor-Resistant Lung Tumors", Cancer Res., 76(13): 3942-3953 (2016) XP055431654, us ISSN: 0008-5472, DOI: 10.1158/0008-5472.CAN-15-2833.

Wu, Xiufeng, et al., "Fab-based bispecific antibody formats with robust biophysical properties and biological activity", mAbs, Landes Bioscience US, 7(3): 470-482 (2015) XP009185560, ISSN: 1942-0870, DOI: 10.1080/19420862.2015.1022694.

Partial Supplementary European Search Report and provisional search opinion dated Oct. 15, 2019, in counterpart European Application No. EP 17748342.7.

Aoki et al., "Endothelial Progenitor Cell Capture by Stents Coated With Antibody Against CD34," J. Am. Coll. Cardiol., 45(10): 1574-1579 (2005).

Arancio et al., "RAGE potentiates Aβ-induced perturbation of neuronal function in transgenic mice," EMBO J., 23: 4096-4105 (2004).

Arndt et al., "Bispecific Diabodies for Cancer Therapy," Methods Mol. Biol., 207: 305-321 (2003).

Bargou et al., "Tumor Regression in Cancer Patients by Very Low Doses of a T-Cell-Engaging Antibody," Science, 321: 974-977 (2008).

Bornemann et al., "Aβ-Induced Inflammatory Processes in Microglia Cells of APP23 Transgenic Mice," Am. J. Pathol., 158(1): 63-73 (2001).

Bostrom et al., "Variants of the Antibody Herceptin That Interact with HER2 and VEGF at the Antigen Binding Site," Science, 323: 1610-1614 (2009)

(56) References Cited

OTHER PUBLICATIONS

Boyce et al., "No audible wheezing: nuggets and conundrums from mouse asthma models," *J. Exp. Med.*, 201(12): 1869-1873 (2005).
Brand, D.D., "Rodent Models of Rheumatoid Arthritis," *Comparative Medicine*, 55(2): 114-122 (2005).
Brennan et al., "Preparation of Bispecific Antibodies by Chemical Recombination of Monoclonal Immunoglobulin $G_1$ Fragments," *Science*, 229: 81-83 (1985).
Buras et al., "Animal Models of Sepsis: Setting the Stage," *Nat. Rev. Drug Discovery*, 4: 854-865 (2005).
Burke et al., "Zotarolimus (ABT-578) eluting stents," *Adv. Drug Del. Rev.*, 58: 437-446 (2006).
Calandra et al., "Protection from septic shock by neutralization of macrophage migration inhibitory factor," *Nature Med.*, 6(2): 164-170 (2000).
Coffman et al., "Nonhuman primate models of asthma," *J. Exp. Med.*, 201(12): 1875-1879 (2005).
Coloma and Morrison, "Design and production of novel tetravalent bispecific antibodies," *Nature Biotechnol.*, 15: 159-163 (1997).
Deane et al., "RAGE mediates amyloid-β peptide transport across the blood-brain barrier and accumulation in brain," *Nature Med.*, 9(7): 907-913 (2003).
Descotes J., "Immunotoxicology of Immunomodulators," *Develop. Biol. Standard*, 77: 99-102 (1992).
Dickson, B.J., "Molecular Mechanisms of Axon Guidance," *Science*, 298: 1959-1964 (2002).
Domeniconi et al., "Overcoming inhibitors in myelin to promote axonal regeneration," *J. Neurolog. Sciences*, 233: 43-47 (2005).
Dong et al., "A stable IgG-like bispecific antibody targeting the epidermal growth factor receptor and the type I insulin-like growth factor receptor demonstrates superior anti-tumor activity," *mAbs* 3: 273-288 (2011).
Doppalapudi et al., "Chemical generation of bispecific antibodies," *Proc. Natl. Acad. Sci. USA*, 107: 22611-22616 (2010).
Durocher et al., "High-level and high-throughput recombinant protein production by transient transfection of suspension-growing human 293-EBNA1 cells," *Nucl. Acids Res.*, 30(2e9): 1-9 (2002).
Economides et al., "Cytokine traps: multi-component, high-affinity blockers of cytokine action," *Nature Med.*, 9(1): 47-52 (2003).
Hinotto et al., "Asthmatic changes in mice lacking T-bet are mediated by IL-13," *Int. Immunol.*, 17(8): 993-1007 (2005).
Genain et al., "Creation of a model for multiple sclerosis in *Callithrix jacchus* marmosets," *J. Mol. Med.*, 75(3): 187-197 (1997)
Genovese et al., "Abatacept for Rheumatoid Arthritis Refractory to Tumor Necrosis Factor α Inhibition," *N. Engl. J. Med.*, 353: 1114-1123 (2005).
Glennie et al., "Preparation and Performance of Bispecific F(ab' γ)$_2$ Antibody Containing Thioether-Linked Fab'γ Fragments," *J. Immunol.*, 139(7): 2367-2375 (1987).
Goldspiel et al., "Human Gene Therapy," *Clin. Pharm.*, 12: 488-505 (1993).
Gracie et al., "A proinflammatory role for IL-18 in rheumatoid arthritis," *J. Clin. Invest.*, 104(10): 1393-1401 (1999).
Griffin et al., "Blockade of T Cell Activation Using a Surface-Linked Single Chain Antibody to CTLA-4 (CD152)," *J. Immunol.*, 164: 4433-4442 (2000).
Harriman et al., "Summary of clinical trials in rheumatoid arthritis using infliximab, an anti-TNFα treatment," *Ann. Rheum. Dis.*, 58: (Suppl. I) I61-I64 (1999).
Hart et al., "Preclinical efficacy and safety of mepolizumab (SB-240563), a humanized monoclonal antibody to IL-5, in cynomolgus monkeys," *J. Allergy Clin. Immunol.*, 108(2): 250-257 (2001).
Hildebrand et al., "Surface coatings for biological activation and functionalization of medical devices," *Surface & Coatings Technology*, 200: 6318-6324 (2006).
Holliger et al., "'Diabodies': Small bivalent and bispecific antibody fragments," *Proc. Natl. Acad. Sci. USA*, 90: 6444-6448 (1993).
Holliger et al., "Diabodies: small bispecific antibody fragments," *Cancer Immunol. Immunother.*, 45: 128-130 (1997).

Hwang et al., "Cutting Edge: Targeted Ligation of CTLA-4 In Vivo by Membrane-Bound Anti-CTLA-4 Antibody Prevents Rejection of Allogeneic Cells," *J. Immunol.*, 163: 633-637 (2002).
Ito et al., "Transfer of Severe Experimental Autoimmune Encephalomyelitis by IL-12- and IL-18-Potentiated T Cells is Estrogen Sensitive," *J. Immunol.*, 170(9): 4802-4809 (2003).
Janelsins et al., "Early correlation of microglial activation with enhanced tumor necrosis factoralpha and monocyte chemoattractant protein-I expression specifically within the entorhinal cortex of triple transgenic Alzheimer's disease mice," *J. Neuroinflammation*, 2(23): 1-12 (2005).
Johansson et al., "Efficient expression of recombinant human monoclonal antibodies in *Drosophilia* S2 cells," *J. Immunol. Meth.*, 318: 37-46 (2006); Genbank supplement pp. 1-2, DOI: 10.1016/j.jim.2006.08.017.
Jones, R., "Rovelizumab—ICOS Corp," *IDrugs*, 3(4): 442-446 (2000).
Karnezis et al., "The neurite outgrowth inhibitor Nogo A is involved in autoimmune-mediated demyelination," *Nature Neurosci.*, 7: 736 (2004).
Karni et al., "IL-18 is linked to raised IFN-y in multiple sclerosis and is induced by activated CD4$^+$T cells via CD40-CD40 ligand interactions," *J. Neuroimmunol.*, 125: 134-140 (2002)
Klein, W. L., "Aβ toxicity in Alzheimer's disease: globular oligomers (ADDLs) as new vaccine and drug targets," *Neurochem. Int.*, 41: 345-352 (2002).
Klyubin et al., "Amyloid β protein immunotherapy neutralizes Aβ oligomers that disrupt synaptic plasticity in vivo," *Nature Med.*, 11: 556-561 (2005).
Kriangkum et al., "Bispecific and bifunctional single chain recombinant antibodies," *Biomol. Eng.*, 18: 31-40 (2001).
Leung et al., "Combined Effects of IL-12 and IL-18 on the Induction of Collagen-Induced Arthritis," *J. Immunol.*, 164(12): 6495-6502 (2000).
Lindhofer et al., "Preferential species-restricted heavy/light chain pairing in rat/mouse quadromas. Implications for a single-step purification of bispecific antibodies," *J. Immunol.*, 155: 219-225 (1995).
Lloyd et al., "Mouse Models of Allergic Airway Disease," *Adv. Immunol.*, 77: 263-295 (2001).
Lu, et al., "Fab-scFv fusion protein: an efficient approach to production of bispecific antibody fragments," *J. Immunol. Methods*, 267: 213-226 (2002).
Lu et al., "Simultaneous blockade of both the epidermal growth factor receptor and the insulin-like growth factor receptor signaling pathways in cancer cells with a fully human recombinant bispecific antibody," *J. Biol. Chem.*, 279(4): 2856-2865 (2004).
Lublin, F.D., "Relapsing experimental allergic encephalomyelitis an autoimmune model of multiple sclerosis," *Springer Semin. Immunopathol.*, 8: 197-208 (1985).
Luster et al., "Use of animal studies in risk assessment for immunotoxicology," *Toxicology*, 92(1-3): 229-243 (1994).
Mack et al., "A small bispecific antibody construct expressed as a functional single-chain molecule with high tumor cell cytotoxicity," *Proc. Natl. Acad. Sci. USA*, 92: 7021-7025 (1995).
Makwana et al., "Molecular mechanisms in successful peripheral regeneration," *FEBS J.*, 272: 2628-2638 (2005).
Marques et al., "Mediation of the cytokine network in the implantation of orthopedic devices," Chapter 21, In *Biodegradable Systems in Tissue Engineering and Regenerative Medicine*, (Reis et al., eds.) (CRC Press LLC, Boca Raton, 2005) pp. 377-397.
Masliah et al., "Effects of α-Synuclein Immunization in a Mouse Model of Parkinson's Disease," *Neuron*, 46: 857-868 (2005).
McDonnell et al., "TNF Antagonism," In *New Drugs for Asthma, Allergy and COPD* (*Prog Respir Res.*, vol. 31), (Hansel et al., eds.) (Karger, Basel, 2001) pp. 247-250.
McGee et al., "The Nogo-66 receptor: focusing myelin inhibition of axon regeneration," *Trends Neurosciences*, 26(4): 193-198 (2003).
Miller et al., "Design, Construction, and In Vitro Analyses of Multivalent Antibodies," *J. Immunol.*, 170: 4854-4861 (2003)
Milstein et al., "Hybrid hybridomas and their use in immunohistochemistry," *Nature*, 305: 537-540 (1983).

(56) References Cited

OTHER PUBLICATIONS

Mizushima et al., "pEF-BOS, a powerful mammalian expression vector," *Nucl. Acids Res.*, 18(17): 5322 (1990).
Morgan and Anderson, "Human Gene Therapy," *Annu. Rev. Biochem.*, 62:191-217 (1993).
Mulligan, R.C., "The Basic Science of Gene Therapy," *Science*, 260: 926-932 (1993).
Nakanishi et al., "Interleukin-18 Regulates Both TH1 and TH2 Responses," *Annu. Rev Immunol.*, 19: 423-474 (2001).
Nelson, R.B., "The Dualistic Nature of Immune Modulation in Alzheimer's Disease: Lessons from the Transgenic Models," *Curr. Pharm. Des.*, 11: 3335-3352 (2005).
Okamoto et al., "Rituximab for Rheumatoid Arthritis," *N. Engl. J. Med.*, 351: 1909 (2004).
Owens et al., "The Immunology of Multiple Sclerosis and Its Animal Model, Experimental Allergic Encephalomyelitis," *Neurol. Clin.*, 13(1): 51-73 (1995).
Padilla et al., "IL-13 Regulates the Immune Response to Inhaled Antigens," *J. Immunol.*, 174(12): 8097-8105 (2005).
Pauli et al., "*Staphylococcus aureus* infection induces protein A-mediated immune evasion in humans," *J. Exp. Med.*, 211: 2331-2339 (2014); Genbank supplement pp. 1-2, DOI: 10.1084/jem.20141404.
Peipp et al., "Bispecific antibodies targeting cancer cells," *Biochem. Soc. Trans.*, 30(4): 507-511 (2002).
Peng, S.L., "Experimental Use of Murine Lupus Models," *Methods Mol. Med.*, 102: 227-272 (2004).
Plückthun and Pack, "New protein engineering approaches to multivalent and bispecific antibody fragments," *Immunotechnology*, 3: 83-105 (1997).
Ridgway et al., "'Knobs-into-holes' engineering of antibody $C_H 3$ domains for heavy chain heterodimerization," *Protein Eng.*, 9(7): 617-621 (1996).
Robinson, C., "Gene therapy—proceeding from laboratory to clinic," *Trends Biotechnol.*, 11(5): 155 (1993).
Schaefer et al., "Immunoglobulin domain crossover as a generic approach for the production of bispecific IgG antibodies," *Proc. Natl. Acad. Sci. USA*, 108: 11187-11192 (2011).
Sfikakis et al., "Rituximab anti-B-cell therapy in systemic lupus erythematosus: pointing to the future," *Curr. Opin. Rheumatol.*, 17: 550-557 (2005).
Shepherd et al., "Novel 'inflammatory plaque' pathology in presenilin-1 Alzheimer's disease," *Neuropathol. Appl. Neurobiol.*, 31: 503-511 (2005)
Snibson et al., "Airway remodelling and inflammation in sheep lungs after chronic airway challenge with house dust mite," *Clin. Exp. Allergy* 35: 146-152 (2005).
Soloman, B., "Alzheimer's Disease and Immunotherapy," *Curr. Alzheimer. Res.*, 1: 149-163 (2004).
Spiess et al., "Alternative Molecular Formats and Therapeutic Applications for Bispecific Antibodies," Mol. Immunol., 67: 95-106 (2015).
Staerz et al., "Hybrid antibodies can target sites for attack by T cells," *Nature*, 314: 628-631 (1985).
Stamper et al., "Crystal structure of the B7-1/CTLA-4 complex that inhibits human immune responses," *Nature*, 410: 608-611 (2001).
Steinman et al., "Virtues and pitfalls of EAE for the development of therapies for multiple sclerosis," *Trends Immunol.*, 26(11):565-571 (2005).
Stubenrauch et al., "Impact of Molecular Processing in the Hinge Region of Therapeutic IgG4 Antibodies on Disposition Profiles in Cynomolgus Monkeys," *Drug Metab. Dispos.*, 38: 84-91 (2010).
'T Hart et al., "Suppression of Ongoing Disease in a Nonhuman Primate Model of Multiple Sclerosis by a Human-Anti-Human IL-12p40 Antibody," *J. Immunol.*, 175(7): 4761-4768 (2005).
Teng et al., "Nogo Signaling and Non-Physical Injury-Induced Nervous System Pathology," *J. Neurosci. Res.*, 79: 273-278 (2005).
Tolstoshev, P., "Gene Therapy, Concepts, Current Trials and Future Directions," *Annu. Rev. Pharmacol. Toxicol.*, 32: 573-596 (1993).

Tuohy et al., "Spontaneous Regression of Primary Autoreactivity during Chronic Progression of Experimental Autoimmune Encephalomyelitis and Multiple Sclerosis," *J. Exp Med.*, 189(7): 1033-1042 (1999).
Van der Neut Kolfschoten, et al., "Anti-Inflammatory Activity of Human IgG4 Antibodies by Dynamic Fab Arm Exchange," *Science*, 317: 1554-1557 (2007).
Von Mehren et al., "Monoclonal Antibody Therapy for Cancer," *Annu. Rev. Med.*, 54: 343-369 (2003).
Wu and Wu., "Delivery systems for gene therapy," *Biotherapy*, 3: 87-95 (1991).
Wu, A.M., et al., "Tumor localization of anti-CEA single-chain Fvs: improved targeting by non-covalent dimers," *Immunotechnology*, 2(1): 21-36 (1996).
Wu, Peng, et al., "Drug/device combinations for local drug therapies and infection prophylaxis," *Biomaterials*, 27: 2450-2467 (2006).
Xing, Yi, et al., "A site of varicella-zoster virus vulnerability identified by structural studies of neutralizing antibodies bound to the glycoprotein complex gHgL," Proc. Natl. Acad. Sci. USA, 112: 6056-6061 (2015); Genbank supplement pp. 1 3, DOI: 10.1073/pnas.l501176112.
Xu, Gang, et al., "Recombinant DNA vaccine encoding multiple domains related to inhibition of neurite outgrowth: a potential strategy for axonal regeneration," *J. Neurochem.*, 91: 1018-1023 (2004)
Zola et al., "CD molecules 2005: human cell differentiation molecules," *Blood*, 106: 3123-3126 (2005).
International Search Report and Written Opinion ("ISR-WO") dated Jul. 19, 2019, issued in PCT/US17/16691.
Chen et al., "Upregulation of PD-L1 by EGFR Activation Mediates the Immune Escape in EGFR-Driven NSCLC: Implication for Optional Immune Targeted Therapy for NSCLC Patients with EGFR Mutation", *Journal of Thoracic Oncology*, 10(6): 910-923 (Jun. 1, 2015).
Tang et al., "The association between PD-L1 and EGER status and the prognostic value of PD-L1 in advanced non-small cell lung cancer patients treated with EGFR-TKIs", *Oncotarget*, 6(16): 14209-14219 (Mar. 29, 2015).
Extended European Search Report and Search Opinion dated Feb. 18, 2020, in counterpart European Application No. EP 17748342.7.
Alsaab et al., (2017) "PD-I and PD-LI Checkpoint Signaling Inhibition for Cancer Immunotherapy: Mechanism, Combinations, and Clinical Outcome," *Frontiers in Pharmacology*, 8: Article 561 (doi: 10.3389/fphar.2017.00561).
Arndt et al., (1999) "A Bispecific Diabody That Mediates Natural Killer Cell Cytotoxicity Against Xenotransplantated Human Hodgkin's Tumors," *Blood*, 94: 2562-2568.
Atwell et al., (1997) "Stable Heterodimers from Remodeling the Domain Interface of a Homodimer using a Phage Display Library," *J. Mal. Biol.*, 270: 26-35.
Baker et al., (2011) "NF-KB, inflammation and metabolic disease," *Cell Metab.*, 13(1): 11-22 (doi:10.1016/j.cmet.2010.12.008).
Belikov (2007) "Connection between chemical structure, properties of substances and their action on organism," *Pharmaceutical Chemistry*, Chapter 2.6 Moscow, MEDpress-inform, 27-29.
Belyaeva et al., (2007) "Autoantibodies to cirtullinated antigens for diagnosis and prediction of clinical course in early rheumatoid arthritis," [in Russian], *Meditsinskaya immunologiya*, 9(1):77-84.
Blake et al., (2014) "Role of IL-17 and IL-22 in autoimmunity and cancer," *Actas Dermo-Sifiliogr.*, 105(Supl. 1): 41-50.
Brinkmann et al., (2017) "The making of bispecific antibodies," *mAbs*, 9(2): 182-212 http://dx.doi.org/10.1080/19420862.2016.1268307.
Burmester et al., (2013) "Emerging cell and cytokine targets in rheumatoid arthritis," *Nat. Rev. Rheumatol*, (doi: 10.1038/nrrheum.2013.168).
Canfield et al., (1991) "The Binding Affinity of Human IgG for its High Affinity Fe Receptor Is Determined by Multiple Amino Acids in the CH2 Domain and Is Modulated by the Hinge Region," *J. Exp. Med,.* 173(6): 1483-1491.
Co et al., (1993) "Genetically engineered deglycosylation of the variable domain increases the affinity of an anti-CD33 monoclonal antibody," *Mal. Immunol.*, 30(15): 1361-1367.

(56) References Cited

OTHER PUBLICATIONS

Curran et al., (2010) "PD-I and CTLA-4 combination blockade expands infiltrating T cells and reduces regulatory T and myeloid cells within B16 melanoma tumors," *Proc. Natl. Acad. Sci. USA*, 107: 4275-4280.
Dhimolea et al., (2012) "Poster Sessions," mAbs, 4(1), p. 14-16. doi:10.4161/mabs.19908, p. 16.
Diamond et al., (1984) "Somatic mutation of the T15 heavy chain gives rise to an antibody with autoantibody specificity," *Proc. Natl. Acad. Sci. USA* 81:5841-5844.
DiGiammarino et al., (2011) "Ligand association rates to the inner-variable-domain of a dual-variable domain immunoglobulin are significantly impacted by linker design," mAbs, 3(5): 487-494.
EPO Communication dated Aug. 9, 2017, enclosing Extended European Search Report, which includes (pursuant to Rule 62 EPC) the supplementary European search report, and the European search opinion dated Jul. 28, 2017, issued in corresponding EP Application No. 14 87 7308.8 (13 pgs.).
European Application No. 17841965, Supplemental European Search Report, dated Mar. 23, 2020. (10 pgs).
Fan et al., (2015) "Bispecific antibodies and their applications," *J. Hematol. Oneal.*, 8, 130 (doi: 10.1186/S13045-015-0227-0).
Gall et al., (2005) "T cells armed with anti-CD3 × anti-CD20 bispecific antibody enhance killing of CD20+ malignant B cells and bypass complement-mediated rituximab resistance in vitro," *Experimental Hematology*, v.33, No. 4, p. 452-459. doi:10.1016/j.exphem.2005.01.007.
Giege et al., (1999) "Chapter 1, in Crystallization of Nucleic Acids and Proteins, a Practical Approach, 2nd ed., Ducruix and Giege, eds.," *Oxford University Press* pp. 1-16.
Gong et al., (2017) "Fabs-in-tandem immunoglobulin is a novel and versatile bispecific design for engaging multiple therapeutic targets," *MAbs*, 9(7):1118-1128.
Gong et al., (2019) "Generation of Fabs-in-tandem immunoglobulin molecules for dual-specific targeting," *Methods.*, 154:87-92.
Griffin et al., (2012) "IL-17 and TNF-α Sustain Neutrophil Recruitment during Inflammation through Synergistic Effects on Endothelial Activation," *J. Immunol.*, 188(12): 6287-6299.
Huston et al., (1988) "Protein engineering of antibody binding sites: recovery of specific activity in an antidigoxin single-chain Fv analogue produced in *Escherichia coli*," *Proc. Natl. Acad. Sci. USA*, 85: 5879-5883.
International Search Report and Written Opinion issued in PCT/CN2019/085164, dated Aug. 8, 2019 (14 pgs.).
International Search Report and Written Opinion issued in PCT/US2014/072336, dated Apr. 28, 2015 (13 pgs.).
International Search Report and Written Opinion issued in PCT/US2017/046875, dated Dec. 28, 2017 (19 pgs.).
International Search Report and Written Opinion issued in PCT/US2019/040762, dated Dec. 3, 2019 (15 pgs.).
Jacobsen et al., (2017) "Engineering an IgG Scaffold Lacking Effector Function with Optimized Developability," *J Biol Chem.*, 292(5): 1865-1875.
Jakob et al., (2013) "Structure reveals function of the dual variable domain immunoglobulin (DVD-Ig™) molecule," mAbs, 5(3): 358-363.
Jefferis, (2005) "Glycosylation of recombinant antibody therapeutics," *Biotechnol. Prag.*, 21: 11-16.
Jin et al., (2008) "MetMAb, the one-armed 5D5 anti-c-Met antibody, inhibits orthotopic pancreatic tumor growth and improves survival," *Cancer Res.*, 68(11):4360-4368.
Johnson, et al., (2010) "Effector cell recruitment with novel Fv-based dual-affinity re-targeting protein leads to potent tumor cytolysis and in vivo B-cell depletion," *J. Mal. Biol.*, 399: 436-449.
Kadomatsu et al., (2010) "Angiopoietin-like proteins: emerging targets for treatment of obesity and related metabolic diseases," *FEES J.*, 278: 559-564.

Kanda et al., (2007) "Establishment of a GDP-mannose 4,6-dehydratase (GMD) knockout host cell line: a new strategy for generating completely non-fucosylated recombinant therapeutics," *J. Biotechnol.*, 130(3):300-310.
Kipriyanov et al., (1999) "Bispecific Tandem Diabody for Tumor Therapy with Improved Antigen Binding and Pharmacokinetics," *J. Mal. Biol.*, 293: 41-56.
Klein et al., (2012) "Progress in overcoming the chain association issue in bispecific heterodimeric IgG antibodies," mAbs, 4(6): 653-663.
Klein et al., (2016) "The use of CrossMAb technology for the generation of bi- and multispecific antibodies," mAbs, 8(6): 1010-1020.
Kontermann, (2005) "Recombinant bispecific antibodies for cancer therapy," *Acta Pharmacologica Sinica*, 26(1): 1-9.
Koopmans et al., (2018) "A novel bispecific antibody for EGFR-directed blockade of the PD-1/PD-L1 immune checkpoint," *Oncoimmunology*, 7(8):e1466016 (11 pages).
Li et al., (2013) "Bispecific Antibody to ErbB2 Overcomes Trastuzumab Resistance through Comprehensive Blockade of ErbB2 Heterodimerization," *Cancer Res.*, 73(21): 6471-6483.
Lu et al., (2005) "A Fully Human Recombinant IgG-like Bispecific Antibody to Both the Epidermal Growth Factor Receptor and the Insulin-like Growth Factor Receptor for Enhanced Anti tumor Activity," *The Journal of Biological Chemistry*, vol. 280, No. 20, Issue of May 20, pp. 19665-19672.
Mariuzza et al., (1987) "The structural basis of antigen-antibody recognition" *Ann. Rev. Biophys. Chem.* 16:139-159.
Marvin et al., (2005) "Recombinant approaches to IgG-like bispecific antibodies," *Acta Pharmacologica Sinica*, 26(6): 649-658.
Merchant et al., (1998) "An efficient route to human bispecific IgG," *Nature Biotechnol.*, 16: 677-681.
Miossec et al., (2012) "Targeting IL-17 and TH17 cells in chronic inflammation," *Nature Reviews Drug Discovery*, v.11, p. 763-776;.
Neuberger, et al., (1985) "A hapten-specific chimaeric IgE antibody with human physiological effector function," *Nature 314*, 268-270 https://doi.org/10.1038/314268a0.
Office Action in Japanese Patent Application No. 2019-508956 dated Jul. 7, 2021.
Office Action and Search Report dated Jul. 2, 2021 issued in Russian Application No. 2020142965.
Office Action and Search Report, dated Nov. 30, 2020 in Russian Application No. 2019103230 for Epimab Biotherapeutics, Inc., filed Aug. 15, 2017 (16 pgs.).
Office Action dated Jul. 30, 2021, in Russian Application No. 2019103230/10 for EPIMAB Biotherapeutics, Inc., filed Aug. 15, 2017, citing Belyaeva et al. (12 pgs.).
Office Action Decision to Refuse Grant dated Sep. 25, 2020, in Russian Application No. 2016129959 for EPIMAB Biotherapeutics, Inc., filed Dec. 24, 2014, citing Belikov.
Ohno et al., (1985) "Antigen-binding specificities of antibodies are primarilydetermined by seven residues of VH," *Proc. Natl. Acad. Sci. USA*, 82:2945-2949.
Oike et al., (2009) "Angiopoietin-Like Proteins—Potential Therapeutic Targets for Metabolic Syndrome and Cardiovascular Disease," *Cir. J.*, 73: 2192-2197.
Pardoll, (2012) "The blockade of immune checkpoints in cancer immunotherapy," *Nat. Rev. Cancer*, 12: 252-264.
Peterson et al., (2018) "Macrophage-Targeted Therapeutics for Metabolic Disease," *Trends Pharmacol. Sci.* 39(6):536-546 (doi.org/10.1016/j.tips.2018.03.001).
Presta, (2008) "Molecular engineering and design of therapeutic antibodies," *Curr. Opin. Immunol.*, 20: 460-470.
ProSpec-Tany TechnoGene Ltd.: "TNF a Human" [Content Pages, 3 pp.] Retrieved Sep. 10, 2013 from <http://www.prospecbio.com/english/PrintContentPage.aspx>.
Qi et al., (2019) "Conventional and Chemically Programmed Asymmetric Bispecific Antibodies Targeting Folate Receptor," *Front Immunol.*, 10:1994 (13 pages).
Riechmann et al., (1988) "Reshaping human antibodies for therapy," *Nature*, 332: 323-327.
Riethmuller, (2012) "Symmetry breaking: bispecific antibodies, the beginnings, and 50 years on," *Cancer Immun.*, 12: 12-18.

(56) References Cited

OTHER PUBLICATIONS

Rudikoff et al., (1982) "Single amino acid substitution altering antigen-binding specificity," *Proc. Natl. Aca. Sci. USA*, 79:1979-1983.
Satta et al., (2013) "Redirection of T-cell effector functions for cancer therapy: bispecific antibodies and chimeric antigen receptors," *Future Oneal.*, 9(4): 527-539 DOI: http://dx.doi.org/10.2217/fon.12.203.
Shan et al., (2009) "The Angiopoietin-like Proteins ANGPTL3 and ANGPTL4 Inhibit Lipoprotein Lipase Activity through Distinct Mechanisms," *J. Biol. Chem.*, 284(3): 1419-1424.
Shields et al., (2002) "Lack of Fucose on Human IgG 1 N-Linked Oligosaccharide Improves Binding to Human FcyRIII and Antibody-dependent Cellular Toxicity," *J. Biol. Chem.*, 277(30): 26733-26740.
Stanglmaier et al., (2008) "Bi20 (FBTA05), a novel trifunctional bispecific antibody (anti-CD20 × anti-CD3), mediates efficient killing of B-cell lymphoma cells even with very low CD20 expression levels," *Int. J. Cancer*, 123(5): 1181-1189.
Sung et al., (2015) "Dual-Affinity Re-Targeting Proteins Direct T Cell-Mediated Cytolysis of Latently HIVInfected Cells," *J. Clin. Invest.*, 125(11): 4077-4090.
TNF tumor necrosis factor [*Homo Sapiens* (human)]—Gene ID: 7124, updated on Jul. 28, 2013 (16 pgs.), National Center for Biotechnology Information. U.S. National Library of Medicine. Jul. 30, 2013 <http://www.ncbi.nlm.nih.gov/gene/7124>.
Umana et al., (1999) "Engineered glycoforms of an antineuroblastoma IgG 1 with optimized antibodydependent cellular cytotoxic activity," *Nature Biotechnol.*, 17: 176-180.
Vajdos et al., (2002) "Comprehensive Functional Maps of the Antigen-binding Site of an Anti-ErbB2 Antibody Obtained with Shotgun Scanning Mutagenesis," *J. Mal. Biol.*, 320: 415-428.
Wallick et al., (1988) "Glycosylation of a VH Residue of a Monoclonal Antibody Against a(1-->6) Dextran Increases Its Affinity for Antigen," *J. Exp. Med.*, 168: 1099-1109.
Wang et al., (2017) "A Human Bi-specific Antibody against Zika Virus with High Therapeutic Potential," *Cell*, 171:229-241.
Weiner et al., (1995) "Phase I trial of 2BI, a bispecific monoclonal antibody targeting c-cerbB-2 and Fc gamma Rlii," *Cancer Res.*, 55: 4586-4593.
Wörn et al., (2001) "Stability engineering of antibody single-chain Fv fragments," *J Mol Biol.*, 305(5):989-1010.
Wright et al.,(1991) "Antibody variable region glycosylation: position effects on antigen binding and carbohydrate structure," *EMBO J.*, 10(10): 2717-2723.
Wu et al., (2007) "Simultaneous targeting of multiple disease mediators by a dual-variable-domain immunoglobulin," *Nature Biotechnol.*, 25(11): 1290-1297.
Xu et al., (2015) "Production of bispecific antibodies in "knobs-into-holes" using a cell-free expression system," *mAbs*, 7(1): 231-242.
Yarilin, (1999) "Foundations of Immunology," *Moscow, Meditsina* 172-174.
Yarilin, (1999) "Foundations of Immunology," *Moscow, Meditsina* 354-358.
Zocher et al., (2004) "A Bispecific Single-Chain Antibody Fusion Protein for Targeted Depletion of Autoreactive B Cells via Unstimulated Human T Lymphocytes," *Mal. Immunol.*, 41(5): 511-518.
Alam et al., (2016) "Inflammatory Process in Alzheimer's and Parkinson's Diseases: Central Role of Cytokines," *Curr. Pharm. Design*, 22(5): 541-548.
Breder et al. "Panitumumab (vectibix) in chemoresistant metastatic colorectal cancer treatment. Retrospective clinical trial of chemotherapy department", Oncological Coloproctology, 2013, No. 1, pp. 41-51.
Decision of Grant in RU Application No. 2018129878, dated Dec. 17, 2021.
Zapata et al., (1995) "Engineering linear F(ab')2 fragments for efficient production in *Escherichia coli* and enhanced antiproliferative activity," *Protein Eng.*, 8(10): 1057-1062.

\* cited by examiner

| PK parameters | CTLA-4 plate<br>IV, 5 mg/kg | PD-1 plate<br>IV, 5 mg/kg |
|---|---|---|
| CL, mL/day/kg | 11.8 | 11.0 |
| Alpha $t_{1/2}$, Day | 0.106 | 0.113 |
| Beta $t_{1/2}$, Day | 8.58 | 9.13 |
| V1, mL/kg | 48.6 | 59.7 |
| $C_{max}$, μg/mL | NA | NA |
| $T_{max}$, day | NA | NA |
| F% | NA | NA |

FABS-IN-TANDEM IMMUNOGLOBULIN AND USES THEREOF

CROSS-REFERENCE TO RELATED APPLICATIONS

This application is a United States national stage filing under 35 U.S.C. § 371 of International Application No. PCT/US2017/016691, filed Feb. 6, 2017, designating the U.S., which claims priority to International Application No. PCT/CN2016/073722, filed Feb. 6, 2016, the contents of which are incorporated herein by reference in their entireties.

FIELD OF INVENTION

The present invention relates to multivalent and multispecific binding proteins, and to methods of making and using multivalent and multispecific binding proteins.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: EPBI_002_01WO_SeqList_ST25.txt, date recorded: Feb. 3, 2017, file size 510 KB).

BACKGROUND OF THE INVENTION

Bispecific or multispecific antibodies have been generated in attempts to prepare molecules useful for the treatment of various inflammatory diseases, cancers, and other disorders.

Bispecific antibodies have been produced using the quadroma technology (see Milstein, C. and A. C. Cuello, Nature, 1983. 305(5934): p. 537-40) based on the somatic fusion of two different hybridoma cell lines expressing murine monoclonal antibodies with the desired specificities of the bispecific antibody. Bispecific antibodies can also be produced by chemical conjugation of two different mAbs (see Staerz, U. D., et al., Nature, 1985. 314(6012): p. 628-31). Other approaches have used chemical conjugation of two different monoclonal antibodies or smaller antibody fragments (see Brennan, M., et al., Science, 1985. 229 (4708): p. 81-3).

Another method is the coupling of two parental antibodies with a hetero-bifunctional crosslinker. In particular, two different Fab fragments have been chemically crosslinked at their hinge cysteine residues in a site-directed manner (see Glennie, M. J., et al., J Immunol, 1987. 139(7): p. 2367-75).

Other recombinant bispecific antibody formats have been developed in the recent past (see Kriangkum, J., et al., Biomol Eng, 2001. 18(2): p. 31-40). Amongst them tandem single-chain Fv molecules and diabodies, and various derivatives thereof, have been used for the construction of recombinant bispecific antibodies. Normally, construction of these molecules starts from two single-chain Fv (scFv) fragments that recognize different antigens (see Economides, A. N., et al., Nat Med, 2003. 9(1): p. 47-52). Tandem scFv molecules (taFv) represent a straightforward format simply connecting the two scFv molecules with an additional peptide linker. The two scFv fragments present in these tandem scFv molecules form separate folding entities. Various linkers can be used to connect the two scFv fragments and linkers with a length of up to 63 residues (see Nakanishi, K., et al., Annu Rev Immunol, 2001. 19: p. 423-74).

In a recent study, in vivo expression by transgenic rabbits and cattle of a tandem scFv directed against CD28 and a melanoma-associated proteoglycan was reported (see Gracie, J. A., et al., J Clin Invest, 1999. 104(10): p. 1393-401). In this construct the two scFv molecules were connected by a CH1 linker and serum concentrations of up to 100 mg/L of the bispecific antibody were found. A few studies have now reported expression of soluble tandem scFv molecules in bacteria (see Leung, B. P., et al., J Immunol, 2000. 164(12): p. 6495-502; Ito, A., et al., J Immunol, 2003. 170(9): p. 4802-9; Karni, A., et al., J Neuroimmunol, 2002. 125(1-2): p. 134-40) using either a very short Ala3 linker or long glycine/serine-rich linkers.

In a recent study, phage display of a tandem scFv repertoire containing randomized middle linkers with a length of 3 or 6 residues enriched those molecules which are produced in soluble and active form in bacteria. This approach resulted in the isolation of a preferred tandem scFv molecule with a 6 amino acid residue linker (see Arndt, M. and J. Krauss, Methods Mol Biol, 2003. 207: p. 305-21).

Bispecific diabodies (Db) utilize the diabody format for expression. Diabodies are produced from scFv fragments by reducing the length of the linker connecting the VH and VL domain to approximately 5 residues (see Peipp, M. and T. Valerius, Biochem Soc Trans, 2002. 30(4): p. 507-11). This reduction of linker size facilitates dimerization of two polypeptide chains by crossover pairing of the VH and VL domains. Bispecific diabodies are produced by expressing two polypeptide chains with either the structure VHA-VLB and VHB-VLA (VH-VL configuration) or VLA-VHB and VLB-VHA (VL-VH configuration) within the same cell. A recent comparative study demonstrates that the orientation of the variable domains can influence expression and formation of active binding sites (see Mack, M., G. Riethmuller, and P. Kufer, Proc Natl Acad Sci USA, 1995. 92(15): p. 7021-5).

One approach to force the generation of bispecific diabodies is the production of knob-into-hole diabodies (see Holliger, P., T. Prospero, and G. Winter, Proc Natl Acad Sci USA, 1993. 90(14): p. 6444-8.18). This was demonstrated for a bispecific diabody directed against HER2 and CD3. A large knob was introduced in the VH domain by exchanging Val37 with Phe and Leu45 with Trp and a complementary hole was produced in the VL domain by mutating Phe98 to Met and Tyr87 to Ala, either in the anti-HER2 or the anti-CD3 variable domains. By using this approach the production of bispecific diabodies could be increased from 72% by the parental diabody to over 90% by the knob-into-hole diabody.

Single-chain diabodies (scDb) represent an alternative strategy to improve the formation of bispecific diabody-like molecules (see Holliger, P. and G. Winter, Cancer Immunol Immunother, 1997. 45(3-4): p. 128-30; Wu, A. M., et al., Immunotechnology, 1996. 2(1): p. 21-36). Bispecific single-chain diabodies are produced by connecting the two diabody-forming polypeptide chains with an additional middle linker with a length of approximately 15 amino acid residues. Consequently, all molecules with a molecular weight corresponding to monomeric single-chain diabodies (50-60 kDa) are bispecific. Several studies have demonstrated that bispecific single chain diabodies are expressed in bacteria in soluble and active form with the majority of purified molecules present as monomers (see Holliger, P. and G. Winter, Cancer Immunol Immunother, 1997. 45(3-4): p. 128-30;

Wu, A. M., et al., Immunotechnology, 1996. 2(1): p. 21-36; Pluckthun, A. and P. Pack, Immunotechnology, 1997. 3(2): p. 83-105; Ridgway, J. B., et al., Protein Eng, 1996. 9(7): p. 617-21).

Diabody have been fused to Fc to generate more Ig-like molecules, named di-diabody (see Lu, D., et al., J Biol Chem, 2004. 279(4): p. 2856-65). In addition, multivalent antibody construct comprising two Fab repeats in the heavy chain of an IgG and capable of binding four antigen molecules has been described (see U.S. Pat. No. 8,722,859 B2, and Miller, K., et al., J Immunol, 2003. 170(9): p. 4854-61).

The most recent examples are tetravalent IgG-single-chain variable fragment (scFv) fusions (Dong J, et al. 2011 MAbs 3:273-288; Coloma M J, Morrison S L 1997 Nat Biotechnol 15:159-163; Lu D, et al. 2002 J Immunol Methods 267:213-226), catumaxomab, a trifunctional rat/mouse hybrid bispecific epithelial cell adhesion molecule-CD3 antibody (Lindhofer H, et al 1995 J Immunol 155:219-225), the bispecific CD19-CD3 scFv antibody blinatumomab (Bargou R, et al. 2008 Science 321:974-977), "dual-acting Fab" (DAF) antibodies (Bostrom J, et al. 2009 Science 323:1610-1614), covalently linked pharmacophore peptides to catalytic anti-bodies (Doppalapudi V R, et al. 2010 Proc Natl Acad Sci USA 107:22611-22616), use of the dynamic exchange between half IgG4 molecules to generate bispecific antibodies (van der Neut Kolfschoten M, et al. 2007 Science 317:1554-1557; Stubenrauch K, et al. 2010 Drug Metab Dispos 38:84-91), or by exchange of heavy-chain and light-chain domains within the antigen binding fragment (Fab) of one half of the bispecific antibody (CrossMab format) (Schaefer W et al 2011 Proc Natl Acad Sci 108: 11187-92).

There is a need in the art for single molecular entities with dual antigen binding function, and for methods of generating such multivalent and multispecific binding proteins. The present invention addresses these and other needs.

SUMMARY OF THE INVENTION

The present invention provides multivalent and multispecific binding proteins, and methods of making and using such binding proteins. In one embodiment, the multivalent and multispecific binding proteins provided herein are Fabs-in-tandem immunoglobulins (FIT-Ig), and are capable of binding two or more antigens, or two or more epitopes of the same antigen, or two or more copies of the same epitope. The multivalent and multispecific binding proteins provided herein are useful for treatment and/or prevention of acute and chronic inflammatory diseases and disorders, autoimmune diseases, cancers, spinal cord injuries, sepsis, and other diseases, disorders, and conditions. Pharmaceutical compositions comprising the multivalent and multispecific binding proteins are provided herein. In addition, nucleic acids, recombinant expression vectors, and host cells for making such FIT-Igs are provided herein. Methods of using the FIT-Igs of the invention to detect specific antigens, in vivo or in vitro, are also encompassed by the invention.

The present invention provides a family of binding proteins that are capable of binding two or more antigens, e.g., with high affinity. In one aspect, the present invention provides an approach to construct a bispecific binding protein using two parental monoclonal antibodies: mAb A, which binds to antigen A, and mAb B, which binds to antigen B. The binding proteins disclosed herein, in one embodiment, are capable of binding antigens, cytokines, chemokines, cytokine receptors, chemokine receptors, cytokine- or chemokine-related molecules, or cell surface proteins.

Thus, in one aspect, binding proteins capable of binding two or more antigens are provided. In one embodiment, the present invention provides a binding protein comprising at least two polypeptide chains, wherein the polypeptide chains pair to form IgG-like molecules capable of binding two or more antigens. In one embodiment, the binding protein comprises two, three, four, five, or more polypeptide chains. In one embodiment, the binding protein comprises at least one $VL_A$, at least one $VL_B$, at least one $VH_A$, at least one $VH_B$, at least one CL, and at least one CH1, wherein VL is a light chain variable domain, VH is a heavy chain variable domain, CL is a light chain constant domain, CH1 is the first constant domain of the heavy chain, A is a first antigen, and B is a second antigen. In a further embodiment, the first polypeptide chain comprises a $VL_A$, a CL, a $VH_B$, and a CH1. In a further embodiment, the binding protein further comprises an Fc. In another embodiment, the Fc region is a variant Fc region. In a further embodiment, the variant Fc region exhibits modified effector function, such as ADCC or CDC. In another embodiment, the variant Fc region exhibits modified affinity or avidity for one or more FcγR.

In one embodiment, the binding protein comprises three polypeptide chains, wherein the first polypeptide chain comprises a $VL_A$, a CL, a $VH_B$, and a CH1, the second polypeptide chain comprises $VH_A$ and CH1, and the third polypeptide chain comprises $VL_B$ and CL. In a further embodiment, the first polypeptide chain of the binding protein further comprises an Fc. In another embodiment, the binding protein comprises two polypeptide chains, wherein the first polypeptide chain comprises a $VL_A$, a CL, a $VH_B$, and a CH1, the second polypeptide chain comprises $VH_A$, CH1, $VL_B$, and CL. In a further embodiment, the first polypeptide chain further comprises an Fc.

In one embodiment, the binding protein comprises three polypeptide chains, and their corresponding cDNA during co-transfection are present at a molar ratio of first:second: third of 1:1:1, 1:1.5:1, 1:3:1, 1:1:1.5, 1:1:3, 1:1.5:1.5, 1:3: 1.5, 1:1.5:3, or 1:3:3. In another embodiment, the binding protein comprises two polypeptide chains, and their corresponding cDNA during co-transfection are present at a molar ratio of first:second of 1:1, 1:1.5, or 1:3, or any other ratios, through optimization, in an effort to maximize the monomeric FIT-Ig fraction in any given transfection.

In one embodiment, the binding protein of the present invention does not comprise a peptide linker. In one embodiment, the binding protein of the present invention comprises at least one amino acid or polypeptide linker. In a further embodiment, the linker is selected from the group consisting of G, GS, SG, GGS, GSG, SGG, GGG, GGGS (SEQ ID NO: 489), SGGG (SEQ ID NO: 490), GGGGS (SEQ ID NO: 491), GGGGSGS (SEQ ID NO: 492), GGGGSGGS (SEQ ID NO: 493), GGGGSGGGGS (SEQ ID NO: 494), GGGGSGGGGSGGGGS (SEQ ID NO: 495), AKTTPKLEEGEFSEAR (SEQ ID NO: 496), AKTTPKLEEGEFSEARV (SEQ ID NO: 497), AKTTPKLGG (SEQ ID NO: 498), SAKTTPKLGG (SEQ ID NO: 499), SAKTTP (SEQ ID NO: 500), RADAAP (SEQ ID NO: 501), RADAAPTVS (SEQ ID NO: 502), RADAAAGGPGS (SEQ ID NO: 503), RADAAAA $(G_4S)_4$ (SEQ ID NO: 504), SAKTTPKLEEGEFSEARV (SEQ ID NO: 505), ADAAP (SEQ ID NO: 506), ADAAPTVSIFPP (SEQ ID NO: 507), TVAAP (SEQ ID NO: 508), TVAAPSVFIFPP (SEQ ID NO: 509), QPKAAP (SEQ ID NO: 510), QPKAAPSVTLFPP (SEQ ID NO: 511), AKTTPP (SEQ ID NO: 512), AKTTPPSVTPLAP (SEQ ID NO: 513), AKTTAPSVYPLAP (SEQ ID NO: 514), ASTKGP (SEQ ID NO: 515), ASTKGPSVFPLAP (SEQ ID NO: 516), GENKVEYAPALMALS (SEQ ID NO: 517), GPAKELTPLKEAKVS (SEQ ID NO: 518), GHEAAAVMQVQYPAS (SEQ ID NO: 519), and AKTTAP (SEQ ID NO: 80). The linkers can also be in vivo cleavable peptide linkers, protease (such as MMPs) sensitive linkers, disulfide bond-based linkers that can be cleaved by reduction, etc., as previously described (Fusion Protein Technologies for Biopharmaceuticals: Applications and Challenges, edited by Stefan R. Schmidt), or any cleavable linkers known in the art. Such cleavable linkers can be used to release the top Fab in vivo for various purposes, in order to improve tissue/cell penetration and distribution, to enhance binding to targets, to reduce potential side effect, as well as to modulate in vivo functional and physical half-life of the 2 different Fab regions.

In one embodiment, the binding protein comprises a first polypeptide comprising, from amino to carboxyl terminus, $VL_A$-CL-$VH_B$-CH1-Fc, a second polypeptide chain comprising, from amino to carboxyl terminus, $VH_A$-CH1, and a third polypeptide chain comprising, from amino to carboxyl terminus, $VL_B$-CL; wherein VL is a light chain variable domain, CL is a light chain constant domain, VH is a heavy chain variable domain, CH1 is the first constant domain of the heavy chain, A is a first epitope or antigen, and B is a second epitope or antigen. In one embodiment, the Fc region is human IgG1. In another embodiment, the Fc region is a variant Fc region. In a further embodiment, the amino acid sequence of the Fc region is at least 65%, at least 70%, at least 75%, at least 80%, at least 85%, at least 90%, at least 95%, at least 99%, or 100% identical to SEQ ID NO: 20. In a further embodiment, the CL of the first polypeptide chain is fused directly to $VH_B$. In another embodiment, the CL of the first polypeptide chain is linked to $VH_B$ via an amino acid or an oligopeptide linker. In a further embodiment, the linker is GSG (SEQ ID NO: 26) or GGGGSGS (SEQ ID NO: 28).

In another embodiment, the binding protein comprises a first polypeptide comprising, from amino to carboxyl terminus, $VH_B$-CH1-$VL_A$-CL-Fc, a second polypeptide chain comprising, from amino to carboxyl terminus, $VH_A$-CH1, and a third polypeptide chain comprising, from amino to carboxyl terminus, $VL_B$-CL; wherein VL is a light chain variable domain, CL is a light chain constant domain, VH is a heavy chain variable domain, CH1 is the first constant domain of the heavy chain, A is a first epitope or antigen, and B is a second epitope or antigen. In one embodiment, the Fc region is human IgG1. In another embodiment, the Fc region is a variant Fc region. In a further embodiment, the amino acid sequence of the Fc region is at least 65%, at least 70%, at least 75%, at least 80%, at least 85%, at least 90%, at least 95%, at least 99%, or 100% identical to SEQ ID NO: 20. In one embodiment, the CH1 of the first polypeptide chain is fused directly to $VL_A$. In another embodiment, the CH1 of the first polypeptide chain is linked to $VL_A$ via an amino acid or an oligopeptide linker. In a further embodiment, the linker is GSG (SEQ ID NO: 26) or GGGGSGS (SEQ ID NO: 28).

In another embodiment, the binding protein comprises a first polypeptide comprising, from amino to carboxyl terminus, $VL_A$-CL-$VH_B$-CH1-Fc, and a second polypeptide chain comprising, from amino to carboxyl terminus, $VH_A$-CH1-$VL_B$-CL; wherein VL is a light chain variable domain, CL is a light chain constant domain, VH is a heavy chain variable domain, CH1 is the first constant domain of the heavy chain, A is a first epitope or antigen, and B is a second epitope or antigen. In one embodiment, the Fc region is human IgG1. In another embodiment, the Fc region is a variant Fc region. In a further embodiment, the amino acid sequence of the Fc region is at least 65%, at least 70%, at least 75%, at least 80%, at least 85%, at least 90%, at least 95%, at least 99%, or 100% identical to SEQ ID NO: 20. In a further embodiment, the CL of the first polypeptide chain is fused directly to $VH_B$. In another embodiment, the CL of the first polypeptide chain is linked to $VH_B$ via an amino acid or an oligopeptide linker. In a further embodiment, the linker is GSG (SEQ ID NO: 26) or GGGGSGS (SEQ ID NO: 28).

In another embodiment, binding protein comprises a first polypeptide comprising, from amino to carboxyl terminus, $VH_B$-CH1-$VL_A$-CL-Fc, and a second polypeptide chain comprising, from amino to carboxyl terminus, $VL_B$-CL-$VH_A$-CH1; wherein VL is a light chain variable domain, CL is a light chain constant domain, VH is a heavy chain variable domain, CH1 is the first constant domain of the heavy chain, A is a first epitope or antigen, and B is a second epitope or antigen. In one embodiment, the Fc region is human IgG1. In another embodiment, the Fc region is a variant Fc region. In a further embodiment, the amino acid sequence of the Fc region is at least 65%, at least 70%, at least 75%, at least 80%, at least 85%, at least 90%, at least 95%, at least 99%, or 100% identical to SEQ ID NO: 20. In one embodiment, the CH1 of the first polypeptide chain is fused directly to $VL_A$. In another embodiment, the CH1 of the first polypeptide chain is linked to $VL_A$ via an amino acid or an oligopeptide linker. In a further embodiment, the linker is GSG (SEQ ID NO: 26) or GGGGSGS (SEQ ID NO: 28).

The binding proteins of the present invention are capable of binding pairs of cytokines. For example, the binding proteins of the present invention are capable of binding pairs of cytokines selected from the group consisting of IL-1α and IL-1β; IL-12 and IL-18, TNFα and IL-23, TNFα and IL-13; TNF and IL-18; TNF and IL-12; TNF and IL-1beta; TNF and MIF; TNF and IL-6, TNF and IL-6 Receptor, TNF and IL-17; IL-17 and IL-20; IL-17 and IL-23; TNF and IL-15; TNF and VEGF; VEGFR and EGFR; PDGFR and VEGF, IL-13 and IL-9; IL-13 and IL-4; IL-13 and IL-5; IL-13 and IL-25; IL-13 and TARC; IL-13 and MDC; IL-13 and MIF; IL-13 and TGF-β; IL-13 and LHR agonist; IL-13 and CL25; IL-13 and SPRR2a; IL-13 and SPRR2b; IL-13 and ADAM8; and TNFα and PGE4, IL-13 and PED2, TNF and PEG2. In one embodiment, the binding proteins of the present invention are capable of binding IL-17 and IL-20. The binding proteins of the present invention, in one embodiment, are capable of binding IL-17 and IL-20 and comprise variable heavy and light chains derived from the anti-IL-17 antibody LY and the anti-IL-20 antibody 15D2. In one embodiment, the binding proteins of the present invention are capable of binding IL-17 and TNF. The binding proteins of the present invention, in one embodiment, are capable of binding IL-17 and TNF and comprise variable heavy and light chains derived from the anti-IL-17 antibody LY and the TNF antibody golimumab.

In one embodiment, the binding proteins of the present invention bind IL-17 and IL-20 and comprise a first polypeptide comprising, consisting essentially of, or consisting of an amino acid sequence selected from the group consisting of SEQ ID NOs: 15, 25, and 27; a second polypeptide chain comprising, consisting essentially of, or consisting of an amino acid sequence according to SEQ ID NO: 21; and a third polypeptide chain comprising, consisting essentially of, or consisting of a sequence according to SEQ ID NO: 23. In another embodiment, the binding proteins of the present invention bind IL-27 and IL-20 and comprise a first polypeptide chain comprising, consisting essentially of, or consisting of an amino acid sequence selected from the group consisting of SEQ ID NOs: 15, 25, and 27, and a second polypeptide chain comprising, consisting essentially of, or consisting of an amino acid sequence selected from the group consisting of SEQ ID NOs: 29, 30, and 31.

In one embodiment, the binding proteins of the present invention bind TNF and IL-17 and comprise a first polypeptide comprising, consisting essentially of, or consisting of an amino acid sequence according to SEQ ID NOs: 87; a second polypeptide chain comprising, consisting essentially of, or consisting of an amino acid sequence according to SEQ ID NO: 89; and a third polypeptide chain comprising, consisting essentially of, or consisting of a sequence according to SEQ ID NO: 91. In another embodiment, the binding protein is capable of binding pairs of targets selected from the group consisting of CD137 and CD20, CD137 and EGFR, CD137 and Her-2, CD137 and PD-1, CD137 and PDL-1, VEGF and PD-L1, Lag-3 and TIM-3, OX40 and PD-1, TIM-3 and PD-1, TIM-3 and PDL-1, EGFR and DLL-4, CD138 and CD20; CD138 and CD40; CD19 and CD20; CD20 and CD3; CD3 and CD33; CD3 and CD133; CD47 and CD20, CD38 and CD138; CD38 and CD20; CD20 and CD22; CD38 and CD40; CD40 and CD20; CD-8 and IL-6; CSPGs and RGM A; CTLA-4 and BTNO2; IGF1 and IGF2; IGF1/2 and Erb2B; IGF-1R and EGFR; EGFR and CD13; IGF-1R and ErbB3; EGFR-2 and IGFR; VEGFR-2 and Met; VEGF-A and Angiopoietin-2 (Ang-2); IL-12 and TWEAK; IL-13 and IL-1beta; PDGFR and VEGF, EpCAM and CD3, Her2 and CD3, CD19 and CD3, EGFR and Her3, CD16a and CD30, CD30 and PSMA, EGFR and CD3, CEA and CD3, TROP-2 and HSG, TROP-2 and CD3, MAG and RGM A; NgR and RGM A; NogoA and RGM A; OMGp and RGM A; PDL-1 and CTLA-4; CTLA-4 and PD-1; PD-1 and TIM-3; RGM A and RGM B; Te38 and TNFα; TNFα and Blys; TNFα and CD-22; TNFα and CTLA-4 domain; TNFα and GP130; TNFα and IL-12p40; and TNFα and RANK ligand, Factor IXa and Factor X; EGFR and PD-L1; EGFR and cMet; Her3 and IGF-IR; DLL-4 and VEGF; PD-1 and PD-L1; and Her3 and PD-1.

In one embodiment, the binding proteins of the present invention are capable of binding CD3 and CD20. The binding proteins of the present invention, in one embodiment, are capable of binding CD3 and CD20 and comprise variable heavy and light chains derived from the anti-CD3 antibody OKT3 or the anti-CD3 antibody disclosed in U.S. 2009/0252683, which is incorporated herein by reference in it entirety; and the anti-CD20 antibody ofatumumab. In some embodiments, the polypeptide derived from CD3 antibody is in the upper domain and the polypeptide derived from CD20 antibody is in the lower domain. As used herein, the upper domain is the N-terminal or "amino proximal" domain, and the lower domain is the C-terminal domain or the domain closer to the Fc, if present. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is CD3, and antigen B is CD20. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is CD3, and antigen A is CD20. In some embodiments, polypeptide derived from CD3 antibody is in the lower domain and polypeptide derived from CD20 antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is CD20, and antigen B is CD-3. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is CD20, and antigen A is CD3.

In one embodiment, the binding proteins of the present invention bind CD3 and CD20 and comprise a first polypeptide chain comprising, consisting essentially of, or consisting of an amino acid sequence selected from the group consisting of SEQ ID NOs: 41 and 48; a second polypeptide chain comprising, consisting essentially of, or consisting of an amino acid sequence according to SEQ ID NO: 44; and a third polypeptide chain comprising, consisting essentially of, or consisting of an amino acid sequence according to SEQ ID NO: 46. In another embodiment, the binding proteins of the present invention bind CD20 and CD3 and comprise a first polypeptide chain comprising, consisting essentially of, or consisting of an amino acid sequence according to SEQ ID NO: 114; a second polypeptide chain comprising, consisting essentially of, or consisting of an amino acid sequence according to SEQ ID NO: 115; and a third polypeptide chain comprising, consisting essentially of, or consisting of an amino acid sequence according to SEQ ID NO: 116.

In one embodiment, the binding protein of the present invention is capable of binding the same epitope of CD20 and the same epitope of CD3 as that of bispecific binding protein FIT018a, wherein the bispecific binding protein FIT018a comprises a first polypeptide chain comprising an amino acid sequence of SEQ ID NO: 316; a second polypeptide chain comprising an amino acid sequence of SEQ ID NO: 325; and a third polypeptide chain comprising an amino acid sequence of SEQ ID NO: 330.

In one embodiment, the binding proteins of the present invention bind CD3 and CD20 and comprise a $VL_A$ on the first polypeptide, wherein the $VL_A$ of the first polypeptide comprises a $VL_A$ CDR1 of SEQ ID NO: 318, a $VL_A$ CDR2 of SEQ ID NO: 319, and a $VL_A$ CDR3 of SEQ ID NO: 320.

In one embodiment, the binding proteins of the present invention bind CD3 and CD20 and comprise a $VH_B$ on the first polypeptide, wherein the $VH_B$ of the first polypeptide comprises a $VH_B$ CDR1 of SEQ ID NO: 322, a $VH_B$ CDR2 of SEQ ID NO: 323, and a $VH_B$ CDR3 of SEQ ID NO: 324.

In one embodiment, the binding proteins of the present invention bind CD3 and CD20 and comprise a $VH_A$ on the second polypeptide, wherein the $VH_A$ of the second polypeptide comprises a $VH_A$ CDR1 of SEQ ID NO: 327, a $VH_A$ CDR2 of SEQ ID NO: 328, and a $VH_A$ CDR3 of SEQ ID NO: 329.

In one embodiment, the binding proteins of the present invention bind CD3 and CD20 and comprise a $VL_B$ on the third polypeptide, wherein the $VL_B$ of the third polypeptide comprises a $VL_B$ CDR1 of SEQ ID NO: 332, a $VL_B$ CDR2 of SEQ ID NO: 333, and a $VL_B$ CDR3 of SEQ ID NO: 334.

In one embodiment, the binding proteins of the present invention bind CD3 and CD20 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 318, a $VL_A$ CDR2 of SEQ ID NO: 319, and a $VL_A$ CDR3 of SEQ ID NO: 320; wherein the $VH_B$ of the first polypeptide comprises a $VH_B$ CDR1 of SEQ ID NO: 322, a $VH_B$ CDR2 of SEQ ID NO: 323, and a $VH_B$ CDR3 of SEQ ID NO: 324, wherein the $VH_A$ of the second polypeptide comprises a $VH_A$ CDR1 of SEQ ID NO: 327, a $VH_A$ CDR2 of SEQ ID NO: 328, and a $VH_A$ CDR3 of SEQ ID NO: 329; and wherein the $VL_B$ of the third polypeptide comprises a $VL_B$ CDR1 of SEQ ID NO: 332, a $VL_B$ CDR2 of SEQ ID NO: 333, and a $VL_B$ CDR3 of SEQ ID NO: 334.

In one embodiment, the binding proteins of the present invention bind CD3 and CD20 and comprise a first polypeptide chain comprising a $VL_A$ having the sequence of SEQ ID NO: 317, and a $VH_B$ having the sequence of SEQ ID NO: 321, wherein the binding protein comprises a second polypeptide chain comprising a $VH_A$ having the sequence of SEQ ID NO: 326, and wherein the binding protein comprises a third polypeptide chain comprising a $VL_B$ having the sequence of SEQ ID NO: 331.

In one embodiment, the binding proteins of the present invention bind CD3 and CD20 and comprising, consisting essentially of, or consisting of a first polypeptide chain comprising an amino acid sequence of SEQ ID NO: 316; a second polypeptide chain comprising an amino acid sequence of SEQ ID NO: 325; and a third polypeptide chain comprising an amino acid sequence of SEQ ID NO: 330.

In one embodiment, the binding proteins of the present invention bind CD3 and CD20, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding CTLA-4 and PD-1. The binding proteins of the present invention, in one embodiment, are capable of binding CTLA-4 and PD-1 and comprise variable heavy and light chains derived from the CTLA-4 antibody ipilimumab and the PD-1 antibody nivolumab.

In one embodiment, the binding proteins of the present invention bind CTLA-4 and PD-1 and comprise a first polypeptide chain comprising, consisting essentially of, or consisting of an amino acid sequence according to SEQ ID NO: 92; a second polypeptide chain comprising, consisting essentially of, or consisting of an amino acid sequence according to SEQ ID NO: 95; and a third polypeptide chain comprising, consisting essentially of, or consisting of an amino acid sequence according to SEQ ID NO: 97. In one embodiment, the binding protein provided herein is capable of binding one or more epitopes on CTLA-4. In one embodiment, the binding protein provided herein is capable of binding one or more epitopes on PD-1. In some embodiments, polypeptide derived from CTLA-4 antibody is in the upper domain and polypeptide derived from PD-1 antibody is in the lower domain. For example, in some embodiments, the binding proteins comprise a first polypeptide of $VL_A$-$CL$-$VH_B$-CH1-Fc, a second polypeptide of $VH_A$-CH1, and a third polypeptide of $VL_B$-CL, wherein antigen A is CTLA-4, and antigen B is PD-1. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is CTLA-4, and antigen A is PD-1. In some embodiments, polypeptide derived from CTLA-4 antibody is in the lower domain and polypeptide derived from PD-1 antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is PD-1, and antigen B is CTLA-4. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is PD-1, and antigen A is CTLA-4.

In one embodiment, the binding protein of the present invention is capable of binding the same epitope of CTLA-4 and the same epitope of PD-1 as that of bispecific binding proteins NBS3, NBS3R, NBS3-C, or NBS3R-C, as described herein.

The bispecific binding protein NBS3 comprises a first polypeptide chain comprising an amino acid sequence of SEQ ID NO: 126; a second polypeptide chain comprising an amino acid sequence of SEQ ID NO: 135; and a third polypeptide chain comprising an amino acid sequence of SEQ ID NO: 140.

The bispecific binding protein NBS3R comprises a first polypeptide chain comprising an amino acid sequence of SEQ ID NO: 145; a second polypeptide chain comprising an amino acid sequence of SEQ ID NO: 154; and a third polypeptide chain comprising an amino acid sequence of SEQ ID NO: 159.

The bispecific binding protein NBS3-C comprises a first polypeptide chain comprising an amino acid sequence of SEQ ID NO: 164; a second polypeptide chain comprising an amino acid sequence of SEQ ID NO: 173; and a third polypeptide chain comprising an amino acid sequence of SEQ ID NO: 178.

The bispecific binding protein NBS3R-C comprises a first polypeptide chain comprising an amino acid sequence of SEQ ID NO: 183; a second polypeptide chain comprising an amino acid sequence of SEQ ID NO: 192; and a third polypeptide chain comprising an amino acid sequence of SEQ ID NO: 197.

In one embodiment, the binding proteins of the present invention bind CTLA4 and PD-1 and comprise a $VL_A$ on the first polypeptide, wherein the $VL_A$ of the first polypeptide comprises a $VL_A$ CDR1 of SEQ ID NO: 128, a $VL_A$ CDR2 of SEQ ID NO: 129, and a $VL_A$ CDR3 of SEQ ID NO: 130 (e.g., those on NBS3). In one embodiment, the binding proteins of the present invention bind CTLA4 and PD-1 and comprises a $VL_A$ on the first polypeptide, wherein the $VL_A$ of the first polypeptide comprises a $VL_A$ CDR1 of SEQ ID NO: 147, a $VL_A$ CDR2 of SEQ ID NO: 148, and a $VL_A$ CDR3 of SEQ ID NO: 149 (e.g., those on NBS3R). In one embodiment, the binding proteins of the present invention bind CTLA4 and PD-1 and comprises a $VL_A$ on the first polypeptide, wherein the $VL_A$ of the first polypeptide comprises a $VL_A$ CDR1 of SEQ ID NO: 166, a $VL_A$ CDR2 of SEQ ID NO: 167, and a $VL_A$ CDR3 of SEQ ID NO: 168 (e.g., those on NBS3-C). In one embodiment, the binding proteins of the present invention bind CTLA4 and PD-1 and comprises a $VL_A$ on the first polypeptide, wherein the $VL_A$ of the first polypeptide comprises a $VL_A$ CDR1 of SEQ ID NO: 185, a $VL_A$ CDR2 of SEQ ID NO: 186, and a $VL_A$ CDR3 of SEQ ID NO: 187 (e.g., those on NBS3R-C).

In one embodiment, the binding proteins of the present invention bind CTLA4 and PD-1 and comprise a $VH_B$ on the first polypeptide, wherein the $VH_B$ of the first polypeptide comprises a $VH_B$ CDR1 of SEQ ID NO: 132, a $VH_B$ CDR2 of SEQ ID NO: 133, and a $VH_B$ CDR3 of SEQ ID NO: 134 (e.g., those on NBS3). In one embodiment, the binding proteins of the present invention bind CTLA4 and PD-1 and comprise a $VH_B$ on the first polypeptide, wherein the $VH_B$ of the first polypeptide comprises a $VH_B$ CDR1 of SEQ ID NO: 151, a $VH_B$ CDR2 of SEQ ID NO: 152, and a $VH_B$ CDR3 of SEQ ID NO: 153 (e.g., those on NBS3R). In one embodiment, the binding proteins of the present invention bind CTLA4 and PD-1 and comprise a $VH_B$ on the first polypeptide, wherein the $VH_B$ of the first polypeptide comprises a VH$_B$ CDR1 of SEQ ID NO: 166, a VH$_B$ CDR2 of SEQ ID NO: 167, and a VH$_B$ CDR3 of SEQ ID NO: 168 (e.g., those on NBS3-C). In one embodiment, the binding proteins of the present invention bind CTLA4 and PD-1 and comprise a VH$_B$ on the first polypeptide, wherein the VH$_B$ of the first polypeptide comprise a VH$_B$ CDR1 of SEQ ID NO: 185, a VH$_B$ CDR2 of SEQ ID NO: 186, and a VH$_B$ CDR3 of SEQ ID NO: 187 (e.g., those on NBS3R-C).

In one embodiment, the binding proteins of the present invention bind CTLA4 and PD-1 and comprise a VH$_A$ on the second polypeptide, wherein the VH$_A$ of the second polypeptide comprises a VH$_A$ CDR1 of SEQ ID NO: 137, a VH$_A$ CDR2 of SEQ ID NO: 138, and a VH$_A$ CDR3 of SEQ ID NO: 139 (e.g., those on NBS3). In one embodiment, the binding proteins of the present invention bind CTLA4 and PD-1 and comprises a VH$_A$ on the second polypeptide, wherein the VH$_A$ of the second polypeptide comprises a VH$_A$ CDR1 of SEQ ID NO: 156, a VH$_A$ CDR2 of SEQ ID NO: 157, and a VH$_A$ CDR3 of SEQ ID NO: 158 (e.g., those on NBS3R). In one embodiment, the binding proteins of the present invention bind CTLA4 and PD-1 and comprises a VH$_A$ on the second polypeptide, wherein the VH$_A$ of the second polypeptide comprises a VH$_A$ CDR1 of SEQ ID NO: 175, a VH$_A$ CDR2 of SEQ ID NO: 176, and a VH$_A$ CDR3 of SEQ ID NO: 177 (e.g., those on NBS-C). In one embodiment, the binding proteins of the present invention bind CTLA4 and PD-1 and comprises a VH$_A$ on the second polypeptide, wherein the VH$_A$ of the second polypeptide comprises a VH$_A$ CDR1 of SEQ ID NO: 194, a VH$_A$ CDR2 of SEQ ID NO: 195, and a VH$_A$ CDR3 of SEQ ID NO: 196 (e.g., those on NBS3R-C).

In one embodiment, the binding proteins of the present invention bind CTLA4 and PD-1 and comprise a VL$_B$ on the third polypeptide, wherein the VL$_B$ of the third polypeptide comprises a VL$_B$ CDR1 of SEQ ID NO: 142, a VL$_B$ CDR2 of SEQ ID NO: 143, and a VL$_B$ CDR3 of SEQ ID NO: 144 (e.g., those on NBS3). In one embodiment, the binding proteins of the present invention bind CTLA4 and PD-1 and comprises a VL$_B$ on the third polypeptide, wherein the VL$_B$ of the third polypeptide comprises a VL$_B$ CDR1 of SEQ ID NO: 161, a VL$_B$ CDR2 of SEQ ID NO: 162, and a VL$_B$ CDR3 of SEQ ID NO: 163 (e.g., those on NBS3R). In one embodiment, the binding proteins of the present invention bind CTLA4 and PD-1 and comprises a VL$_B$ on the third polypeptide, wherein the VL$_B$ of the third polypeptide comprises a VL$_B$ CDR1 of SEQ ID NO: 180, a VL$_B$ CDR2 of SEQ ID NO: 181, and a VL$_B$ CDR3 of SEQ ID NO: 182 (e.g., those on NBS3-C). In one embodiment, the binding proteins of the present invention bind CTLA4 and PD-1 and comprises a VL$_B$ on the third polypeptide, wherein the VL$_B$ of the third polypeptide comprises a VL$_B$ CDR1 of SEQ ID NO: 199, a VL$_B$ CDR2 of SEQ ID NO: 200, and a VL$_B$ CDR3 of SEQ ID NO: 201 (e.g., those on NBS3R-C).

In one embodiment, the binding proteins of the present invention bind CTLA4 and PD-1 and comprise a VL$_A$ and VH$_B$ on the first polypeptide, a VH$_A$ on the second polypeptide, and a VL$_B$ on the third polypeptide, wherein the VL$_A$ of the first polypeptide comprises a VL$_A$ CDR1 of SEQ ID NO: 128, a VL$_A$ CDR2 of SEQ ID NO: 129, and a VL$_A$ CDR3 of SEQ ID NO: 130; wherein the VH$_B$ of the first polypeptide comprises a VH$_B$ CDR1 of SEQ ID NO: 132, a VH$_B$ CDR2 of SEQ ID NO: 133, and a VH$_B$ CDR3 of SEQ ID NO: 134; wherein the VH$_A$ of the second polypeptide comprises a VH$_A$ CDR1 of SEQ ID NO: 137, a VH$_A$ CDR2 of SEQ ID NO: 138, and a VH$_A$ CDR3 of SEQ ID NO: 139; and wherein the VL$_B$ of the third polypeptide comprises a VL$_B$ CDR1 of SEQ ID NO: 142, a VL$_B$ CDR2 of SEQ ID NO: 143, and a VL$_B$ CDR3 of SEQ ID NO: 144 (e.g., those on NBS3).

In one embodiment, the binding proteins of the present invention bind CTLA4 and PD-1 and comprise a VL$_A$ and VH$_B$ on the first polypeptide, a VH$_A$ on the second polypeptide, and a VL$_B$ on the third polypeptide, wherein the VL$_A$ of the first polypeptide comprises a VL$_A$ CDR1 of SEQ ID NO: 147, a VL$_A$ CDR2 of SEQ ID NO: 148, and a VL$_A$ CDR3 of SEQ ID NO: 149; wherein the VH$_B$ of the first polypeptide comprises a VH$_B$ CDR1 of SEQ ID NO: 151, a VH$_B$ CDR2 of SEQ ID NO: 152, and a VH$_B$ CDR3 of SEQ ID NO: 153; wherein the VH$_A$ of the second polypeptide comprises a VH$_A$ CDR1 of SEQ ID NO: 156, a VH$_A$ CDR2 of SEQ ID NO: 157, and a VH$_A$ CDR3 of SEQ ID NO: 158; and wherein the VL$_B$ of the third polypeptide comprises a VL$_B$ CDR1 of SEQ ID NO: 161, a VL$_B$ CDR2 of SEQ ID NO: 162, and a VL$_B$ CDR3 of SEQ ID NO: 163 (e.g., those on NBS3R).

In one embodiment, the binding proteins of the present invention bind CTLA4 and PD-1 and comprise a VL$_A$ and VH$_B$ on the first polypeptide, a VH$_A$ on the second polypeptide, and a VL$_B$ on the third polypeptide, wherein the VL$_A$ of the first polypeptide comprises a VL$_A$ CDR1 of SEQ ID NO: 166, a VL$_A$ CDR2 of SEQ ID NO: 167, and a VL$_A$ CDR3 of SEQ ID NO: 168; wherein the VH$_B$ of the first polypeptide comprises a VH$_B$ CDR1 of SEQ ID NO: 170, a VH$_B$ CDR2 of SEQ ID NO: 171, and a VH$_B$ CDR3 of SEQ ID NO: 172; wherein the VH$_A$ of the second polypeptide comprises a VH$_A$ CDR1 of SEQ ID NO: 175, a VH$_A$ CDR2 of SEQ ID NO: 176, and a VH$_A$ CDR3 of SEQ ID NO: 177; and wherein the VL$_B$ of the third polypeptide comprises a VL$_B$ CDR1 of SEQ ID NO: 180, a VL$_B$ CDR2 of SEQ ID NO: 181, and a VL$_B$ CDR3 of SEQ ID NO: 182 (e.g., those on NBS3-C).

In one embodiment, the binding proteins of the present invention bind CTLA4 and PD-1 and comprise a VL$_A$ and VH$_B$ on the first polypeptide, a VH$_A$ on the second polypeptide, and a VL$_B$ on the third polypeptide, wherein the VL$_A$ of the first polypeptide comprises a VL$_A$ CDR1 of SEQ ID NO: 166, a VL$_A$ CDR2 of SEQ ID NO: 167, and a VL$_A$ CDR3 of SEQ ID NO: 168; wherein the VH$_B$ of the first polypeptide comprises a VH$_B$ CDR1 of SEQ ID NO: 170, a VH$_B$ CDR2 of SEQ ID NO: 171, and a VH$_B$ CDR3 of SEQ ID NO: 172; wherein the VH$_A$ of the second polypeptide comprises a VH$_A$ CDR1 of SEQ ID NO: 175, a VH$_A$ CDR2 of SEQ ID NO: 176, and a VH$_A$ CDR3 of SEQ ID NO: 177; and wherein the VL$_B$ of the third polypeptide comprises a VL$_B$ CDR1 of SEQ ID NO: 180, a VL$_B$ CDR2 of SEQ ID NO: 181, and a VL$_B$ CDR3 of SEQ ID NO: 182 (e.g., those on NBS3R-C).

In one embodiment, the binding proteins of the present invention bind CTLA4 and PD-1 and comprise a first polypeptide chain comprising a VL$_A$ having the sequence of SEQ ID NO: 127, and a VH$_B$ having the sequence of SEQ ID NO: 131, wherein the binding protein comprises a second polypeptide chain comprising a VH$_A$ having the sequence of SEQ ID NO: 136, and wherein the binding protein comprises a third polypeptide chain comprising a VL$_B$ having the sequence of SEQ ID NO: 141 (e.g., those on NBS3).

In one embodiment, the binding proteins of the present invention bind CTLA4 and PD-1 and comprise a first polypeptide chain comprising a VL$_A$ having the sequence of SEQ ID NO: 146, and a VH$_B$ having the sequence of SEQ ID NO: 150, wherein the binding protein comprises a second polypeptide chain comprising a VH$_A$ having the sequence of SEQ ID NO: 155, and wherein the binding protein comprises a third polypeptide chain comprising a $VL_B$ having the sequence of SEQ ID NO: 160 (e.g., those on NBS3R).

In one embodiment, the binding proteins of the present invention bind CTLA4 and PD-1 and comprise a first polypeptide chain comprising a $VL_A$ having the sequence of SEQ ID NO: 165, and a $VH_B$ having the sequence of SEQ ID NO: 169, wherein the binding protein comprises a second polypeptide chain comprising a $VH_A$ having the sequence of SEQ ID NO: 174, and wherein the binding protein comprises a third polypeptide chain comprising a $VL_B$ having the sequence of SEQ ID NO: 179 (e.g., those on NBS3-C).

In one embodiment, the binding proteins of the present invention bind CTLA4 and PD-1 and comprise a first polypeptide chain comprising a $VL_A$ having the sequence of SEQ ID NO: 184, and a $VH_B$ having the sequence of SEQ ID NO: 188, wherein the binding protein comprises a second polypeptide chain comprising a $VH_A$ having the sequence of SEQ ID NO: 193, and wherein the binding protein comprises a third polypeptide chain comprising a $VL_B$ having the sequence of SEQ ID NO: 198 (e.g., those on NBS3R-C).

In one embodiment, the binding proteins of the present invention bind CTLA4 and PD-1 and comprising, consisting essentially of, or consisting of a first polypeptide chain comprising an amino acid sequence of SEQ ID NO: 126; a second polypeptide chain comprising an amino acid sequence of SEQ ID NO: 135; and a third polypeptide chain comprising an amino acid sequence of SEQ ID NO: 140 (e.g., those on NBS3).

In one embodiment, the binding proteins of the present invention bind CTLA4 and PD-1 and comprising, consisting essentially of, or consisting of a first polypeptide chain comprising an amino acid sequence of SEQ ID NO: 145; a second polypeptide chain comprising an amino acid sequence of SEQ ID NO: 154; and a third polypeptide chain comprising an amino acid sequence of SEQ ID NO: 159 (e.g., those on NBS3R).

In one embodiment, the binding proteins of the present invention bind CTLA4 and PD-1 and comprising, consisting essentially of, or consisting of a first polypeptide chain comprising an amino acid sequence of SEQ ID NO: 164; a second polypeptide chain comprising an amino acid sequence of SEQ ID NO: 173; and a third polypeptide chain comprising an amino acid sequence of SEQ ID NO: 178 (e.g., those on NBS3-C).

In one embodiment, the binding proteins of the present invention bind CTLA4 and PD-1 and comprising, consisting essentially of, or consisting of a first polypeptide chain comprising an amino acid sequence of SEQ ID NO: 183; a second polypeptide chain comprising an amino acid sequence of SEQ ID NO: 192; and a third polypeptide chain comprising an amino acid sequence of SEQ ID NO: 197 (e.g., those on NBS3R-C).

In one embodiment, the binding proteins of the present invention bind CTLA4 and PD-1, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution.

In one embodiment, the binding proteins of the present invention are capable of binding EGFR and PD-L1. The binding proteins of the present invention, in one embodiment, are capable of binding EGFR and PD-L1 and comprise variable heavy and light chains derived from the EGFR antibody panitumumab and the PD-L1 antibody 1B12. In some embodiments, polypeptide derived from EGFR antibody is in the upper domain and polypeptide derived from PD-L1 antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is EGFR, and antigen B is PD-L1. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is EGFR, and antigen A is PD-L1. In some embodiments, polypeptide derived from EGFR antibody is in the lower domain and polypeptide derived from PD-L1 antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is PD-L1, and antigen B is EGFR. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is PD-L1, and antigen A is EGFR.

In one embodiment, the binding proteins of the present invention bind EGFR and PD-L1 and comprise a first polypeptide chain comprising, consisting essentially of, or consisting of an amino acid sequence according to SEQ ID NO: 99; a second polypeptide chain comprising, consisting essentially of, or consisting of an amino acid sequence according to SEQ ID NO: 100; and a third polypeptide chain comprising, consisting essentially of, or consisting of an amino acid sequence according to SEQ ID NO: 101. In one embodiment, the binding proteins of the present invention are capable of binding the same epitope of EGFR and the same epitope of PD-L1 as that of bispecific binding protein FIT012a, wherein the bispecific binding protein FIT012a comprises a first polypeptide chain comprising an amino acid sequence of SEQ ID NO: 99; a second polypeptide chain comprising an amino acid sequence of SEQ ID NO: 100; and a third polypeptide chain comprising an amino acid sequence of SEQ ID NO: 101 (e.g., those on FIT012a).

In one embodiment, the binding proteins of the present invention are capable of binding the same epitope of EGFR and the same epitope of PD-L1 as that of bispecific binding protein FIT012b, wherein the bispecific binding protein FIT012b comprises a first polypeptide chain comprising an amino acid sequence of SEQ ID NO: 202; a second polypeptide chain comprising an amino acid sequence of SEQ ID NO: 211; and a third polypeptide chain comprising an amino acid sequence of SEQ ID NO: 216 (e.g., those on FIT012b).

In one embodiment, the binding proteins of the present invention are capable of binding the same epitope of EGFR and the same epitope of PD-L1 as that of bispecific binding protein FIT012d, wherein the bispecific binding protein FIT012d comprises a first polypeptide chain comprising an amino acid sequence of SEQ ID NO: 221; a second polypeptide chain comprising an amino acid sequence of SEQ ID NO: 230; and a third polypeptide chain comprising an amino acid sequence of SEQ ID NO: 235 (e.g., those on FIT012d).

In one embodiment, the binding proteins of the present invention bind EGFR and PD-L1 and comprise a $VL_A$ on the first polypeptide, wherein the $VL_A$ of the first polypeptide comprises a $VL_A$ CDR1 of SEQ ID NO: 204, a $VL_A$ CDR2 of SEQ ID NO: 205, and a $VL_A$ CDR3 of SEQ ID NO: 206 (e.g., those on FIT012b). In one embodiment, the binding proteins of the present invention bind EGFR and PD-L1 and comprise a $VL_A$ on the first polypeptide, wherein the $VL_A$ of the first polypeptide comprises a $VL_A$ CDR1 of SEQ ID NO:

223, a VL$_A$ CDR2 of SEQ ID NO: 224, and a VL$_A$ CDR3 of SEQ ID NO: 225 (e.g., those on FIT012d).

In one embodiment, the binding proteins of the present invention bind EGFR and PD-L1 and comprise a VH$_B$ on the first polypeptide, wherein the VH$_B$ of the first polypeptide comprises a VH$_B$ CDR1 of SEQ ID NO: 208, a VH$_B$ CDR2 of SEQ ID NO: 209, and a VH$_B$ CDR3 of SEQ ID NO: 210 (e.g., those on FIT012b). In one embodiment, the binding proteins of the present invention bind EGFR and PD-L1 and comprise a VH$_B$ on the first polypeptide, wherein the VH$_B$ of the first polypeptide comprises a VH$_B$ CDR1 of SEQ ID NO: 227, a VH$_B$ CDR2 of SEQ ID NO: 228, and a VH$_B$ CDR3 of SEQ ID NO: 229 (e.g., those on FIT012d).

In one embodiment, the binding proteins of the present invention bind EGFR and PD-L1 and comprise a VH$_A$ on the second polypeptide, wherein the VH$_A$ of the second polypeptide comprises a VH$_A$ CDR1 of SEQ ID NO: 213, a VH$_A$ CDR2 of SEQ ID NO: 214, and a VH$_A$ CDR3 of SEQ ID NO: 215 (e.g., those on FIT012b). In one embodiment, the binding proteins of the present invention bind EGFR and PD-L1 and comprise a VH$_A$ on the second polypeptide, wherein the VH$_A$ of the second polypeptide comprises a VH$_A$ CDR1 of SEQ ID NO: 232, a VH$_A$ CDR2 of SEQ ID NO: 233, and a VH$_A$ CDR3 of SEQ ID NO: 234 (e.g., those on FIT012d).

In one embodiment, the binding proteins of the present invention bind EGFR and PD-L1 and comprise a VL$_B$ on the third polypeptide, wherein the VL$_B$ of the third polypeptide comprises a VL$_B$ CDR1 of SEQ ID NO: 218, a VL$_B$ CDR2 of SEQ ID NO: 219, and a VL$_B$ CDR3 of SEQ ID NO: 220 (e.g., those on FIT012b). In one embodiment, the binding proteins of the present invention bind EGFR and PD-L1 and comprise a VL$_B$ on the third polypeptide, wherein the VL$_B$ of the third polypeptide comprises a VL$_B$ CDR1 of SEQ ID NO: 237, a VL$_B$ CDR2 of SEQ ID NO: 238, and a VL$_B$ CDR3 of SEQ ID NO: 239 (e.g., those on FIT012d).

In one embodiment, the binding proteins of the present invention bind EGFR and PD-L1 and comprise a VL$_A$ and VH$_B$ on the first polypeptide, a VH$_A$ on the second polypeptide, and a VL$_B$ on the third polypeptide, wherein the VL$_A$ comprises a VL$_A$ CDR1 of SEQ ID NO: 204, a VL$_A$ CDR2 of SEQ ID NO: 205, and a VL$_A$ CDR3 of SEQ ID NO: 206, the VH$_B$ comprises a VH$_B$ CDR1 of SEQ ID NO: 208, a VH$_B$ CDR2 of SEQ ID NO: 209, and a VH$_B$ CDR3 of SEQ ID NO: 210, the VH$_A$ comprises a VH$_A$ CDR1 of SEQ ID NO: 213, a VH$_A$ CDR2 of SEQ ID NO: 214, and a VH$_A$ CDR3 of SEQ ID NO: 215, and the VL$_B$ comprises a VL$_B$ CDR1 of SEQ ID NO: 218, a VL$_B$ CDR2 of SEQ ID NO: 219, and a VL$_B$ CDR3 of SEQ ID NO: 220 (e.g., those on FIT012b).

In one embodiment, the binding proteins of the present invention bind EGFR and PD-L1 and comprise a VL$_A$ and VH$_B$ on the first polypeptide, a VH$_A$ on the second polypeptide, and a VL$_B$ on the third polypeptide, wherein the VL$_A$ of the first polypeptide comprises a VL$_A$ CDR1 of SEQ ID NO: 223, a VL$_A$ CDR2 of SEQ ID NO: 224, and a VL$_A$ CDR3 of SEQ ID NO: 225; wherein the VH$_B$ of the first polypeptide comprises a VH$_B$ CDR1 of SEQ ID NO: 227, a VH$_B$ CDR2 of SEQ ID NO: 228, and a VH$_B$ CDR3 of SEQ ID NO: 229; wherein the VH$_A$ of the second polypeptide comprises a VH$_A$ CDR1 of SEQ ID NO: 232, a VH$_A$ CDR2 of SEQ ID NO: 233, and a VH$_A$ CDR3 of SEQ ID NO: 234; and wherein the VL$_B$ of the third polypeptide comprises a VL$_B$ CDR1 of SEQ ID NO: 237, a VL$_B$ CDR2 of SEQ ID NO: 238, and a VL$_B$ CDR3 of SEQ ID NO: 239 (e.g., those on FIT012d).

In one embodiment, the binding proteins of the present invention bind EGFR and PD-L1 and comprise a first polypeptide chain comprising a VL$_A$ having the sequence of SEQ ID NO: 203, and a VH$_B$ having the sequence of SEQ ID NO: 207, wherein the binding protein comprises a second polypeptide chain comprising a VH$_A$ having the sequence of SEQ ID NO: 212, and wherein the binding protein comprises a third polypeptide chain comprising a VL$_B$ having the sequence of SEQ ID NO: 217 (e.g., those on FIT012b).

In one embodiment, the binding proteins of the present invention bind EGFR and PD-L1 and comprise a first polypeptide chain comprising a VL$_A$ having the sequence of SEQ ID NO: 222, and a VH$_B$ having the sequence of SEQ ID NO: 226, wherein the binding protein comprises a second polypeptide chain comprising a VH$_A$ having the sequence of SEQ ID NO: 231, and wherein the binding protein comprises a third polypeptide chain comprising a VL$_B$ having the sequence of SEQ ID NO: 236 (e.g., those on FIT012d).

In one embodiment, the binding proteins of the present invention bind EGFR and PD-L1 and comprising, consisting essentially of, or consisting of a first polypeptide chain comprising an amino acid sequence of SEQ ID NO: 202; a second polypeptide chain comprising an amino acid sequence of SEQ ID NO: 211; and a third polypeptide chain comprising an amino acid sequence of SEQ ID NO: 216 (e.g., those on FIT012b).

In one embodiment, the binding proteins of the present invention bind EGFR and PD-L1 and comprising, consisting essentially of, or consisting of a first polypeptide chain comprising an amino acid sequence of SEQ ID NO: 221; a second polypeptide chain comprising an amino acid sequence of SEQ ID NO: 230; and a third polypeptide chain comprising an amino acid sequence of SEQ ID NO: 235 (e.g., those on FIT012d).

In one embodiment, the binding proteins of the present invention bind EGFR and PD-L1, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding cMet and EGFR. The binding proteins of the present invention, in one embodiment, are capable of binding cMet and EGFR and comprise variable heavy and light chains derived from the cMet antibody (h1332 (13.3.2L-A91T,H-42K,S97T)) and the EGFR antibody panitumumab. In some embodiments, polypeptide derived from cMet antibody is in the upper domain and polypeptide derived from EGFR antibody is in the lower domain. For example, in some embodiments, the binding proteins comprise a first polypeptide of VL$_A$-CL-VH$_B$-CH1-Fc, a second polypeptide of VH$_A$-CH1, and a third polypeptide of VL$_B$-CL, wherein antigen A is cMet, and antigen B is EGFR. For another example, in some embodiments, the binding proteins comprise a first polypeptide of VH$_B$-CH1-VL$_A$-CL-Fc, a second polypeptide of VL$_B$-CL, and a third polypeptide of VH$_A$-CH1, wherein antigen B is cMet, and antigen A is EGFR. In some embodiments, polypeptide derived from cMet antibody is in the lower domain and polypeptide derived from EGFR antibody is in the upper domain. For example, in some embodiments, the binding proteins comprise a first polypeptide of VL$_A$-CL-VH$_B$-CH1-Fc, a second polypeptide of VH$_A$-CH1, and a third polypeptide of VL$_B$-CL, wherein antigen A is EGFR, and antigen B is cMet. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is EGFR, and antigen A is cMet.

In one embodiment, the binding proteins of the present invention bind cMet and EGFR and comprise a first polypeptide chain comprising, consisting essentially of, or consisting of an amino acid sequence according to SEQ ID NO: 102; a second polypeptide chain comprising, consisting essentially of, or consisting of an amino acid sequence according to SEQ ID NO: 103; and a third polypeptide chain comprising, consisting essentially of, or consisting of an amino acid sequence according to SEQ ID NO: 104.

In one embodiment, the binding protein of the present invention is capable of binding the same epitope of cMet and the same epitope of EGFR as that of bispecific binding protein FIT013a, wherein the bispecific binding protein FIT013a comprises a first polypeptide chain comprising an amino acid sequence of SEQ ID NO: 240; a second polypeptide chain comprising an amino acid sequence of SEQ ID NO: 249; and a third polypeptide chain comprising an amino acid sequence of SEQ ID NO: 254.

In one embodiment, the binding proteins of the present invention bind cMet and EGFR and comprise a $VL_A$ on the first polypeptide, wherein the $VL_A$ of the first polypeptide comprises a $VL_A$ CDR1 of SEQ ID NO: 242, a $VL_A$ CDR2 of SEQ ID NO: 243, and a $VL_A$ CDR3 of SEQ ID NO: 244.

In one embodiment, the binding proteins of the present invention bind cMet and EGFR and comprise a $VH_B$ on the first polypeptide, wherein the $VH_B$ of the first polypeptide comprises a $VH_B$ CDR1 of SEQ ID NO: 246, a $VH_B$ CDR2 of SEQ ID NO: 247, and a $VH_B$ CDR3 of SEQ ID NO: 248.

In one embodiment, the binding proteins of the present invention bind cMet and EGFR and comprise a $VH_A$ on the second polypeptide, wherein the $VH_A$ of the second polypeptide comprises a $VH_A$ CDR1 of SEQ ID NO: 251, a $VH_A$ CDR2 of SEQ ID NO: 252, and a $VH_A$ CDR3 of SEQ ID NO: 253.

In one embodiment, the binding proteins of the present invention bind cMet and EGFR and comprise a $VL_B$ on the third polypeptide, wherein the $VL_B$ of the third polypeptide comprises a $VL_B$ CDR1 of SEQ ID NO: 256, a $VL_B$ CDR2 of SEQ ID NO: 257, and a $VL_B$ CDR3 of SEQ ID NO: 258.

In one embodiment, the binding proteins of the present invention bind cMet and EGFR and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 242, a $VL_A$ CDR2 of SEQ ID NO: 243, and a $VL_A$ CDR3 of SEQ ID NO: 244; wherein the $VH_B$ of the first polypeptide comprises a $VH_B$ CDR1 of SEQ ID NO: 246, a $VH_B$ CDR2 of SEQ ID NO: 247, and a $VH_B$ CDR3 of SEQ ID NO: 248; wherein the $VH_A$ of the second polypeptide comprises a $VH_A$ CDR1 of SEQ ID NO: 251, a $VH_A$ CDR2 of SEQ ID NO: 252, and a $VH_A$ CDR3 of SEQ ID NO: 253; wherein the $VL_B$ of the third polypeptide comprises a $VL_B$ CDR1 of SEQ ID NO: 256, a $VL_B$ CDR2 of SEQ ID NO: 257, and a $VL_B$ CDR3 of SEQ ID NO: 258.

In one embodiment, the binding proteins of the present invention bind cMet and EGFR and comprise a first polypeptide chain comprising a $VL_A$ having the sequence of SEQ ID NO: 241, and a $VH_B$ having the sequence of SEQ ID NO: 245, wherein the binding protein comprises a second polypeptide chain comprising a $VH_A$ having the sequence of SEQ ID NO: 250, and wherein the binding protein comprises a third polypeptide chain comprising a $VL_B$ having the sequence of SEQ ID NO: 255.

In one embodiment, the binding proteins of the present invention bind cMet and EGFR and comprising, consisting essentially of, or consisting of a first polypeptide chain comprising an amino acid sequence of SEQ ID NO: 240; a second polypeptide chain comprising an amino acid sequence of SEQ ID NO: 249; and a third polypeptide chain comprising an amino acid sequence of SEQ ID NO: 254.

In one embodiment, the binding proteins of the present invention bind cMet and EGFR, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding Factor IXa and Factor X. The binding proteins of the present invention, in one embodiment, are capable of binding Factor IXa and Factor X and comprise variable heavy and light chains derived from an anti-Factor IXa antibody and variable light and heavy chains derived from an anti-Factor X antibody. In some embodiments, polypeptide derived from Factor IXa antibody is in the upper domain and polypeptide derived from Factor X antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is Factor IXa, and antigen B is Factor X. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is Factor IXa, and antigen A is Factor X. In some embodiments, polypeptide derived from Factor IXa antibody is in the lower domain and polypeptide derived from Factor X antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is Factor X, and antigen B is Factor IXa. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is Factor X, and antigen A is Factor IXa.

In one embodiment, the binding proteins of the present invention bind Factor IXa and Factor X and comprise a first polypeptide chain comprising, consisting essentially of, or consisting of an amino acid sequence according to SEQ ID NO: 105; a second polypeptide chain comprising, consisting essentially of, or consisting of an amino acid sequence according to SEQ ID NO: 106; and a third polypeptide chain comprising, consisting essentially of, or consisting of an amino acid sequence according to SEQ ID NO: 107.

In one embodiment, the binding protein of the present invention is capable of binding the same epitope of Factor IXa and the same epitope of Factor X as that of bispecific binding protein FIT014a, wherein the bispecific binding protein FIT014a comprises a first polypeptide chain comprising an amino acid sequence of SEQ ID NO: 259; a second polypeptide chain comprising an amino acid sequence of SEQ ID NO: 268; and a third polypeptide chain comprising an amino acid sequence of SEQ ID NO: 273.

In one embodiment, the binding proteins of the present invention bind Factor IXa and Factor X and comprise a $VL_A$ on the first polypeptide, wherein the $VL_A$ of the first polypeptide comprises a $VL_A$ CDR1 of SEQ ID NO: 261, a $VL_A$ CDR2 of SEQ ID NO: 262, and a $VL_A$ CDR3 of SEQ ID NO: 263.

In one embodiment, the binding proteins of the present invention bind Factor IXa and Factor X and comprise a $VH_B$ on the first polypeptide, wherein the $VH_B$ of the first polypeptide comprises a $VH_B$ CDR1 of SEQ ID NO: 265, a $VH_B$ CDR2 of SEQ ID NO: 266, and a $VH_B$ CDR3 of SEQ ID NO: 267.

In one embodiment, the binding proteins of the present invention bind Factor IXa and Factor X and comprise a $VH_A$ on the second polypeptide, wherein the $VH_A$ of the second polypeptide comprises a $VH_A$ CDR1 of SEQ ID NO: 270, a $VH_A$ CDR2 of SEQ ID NO: 271, and a $VH_A$ CDR3 of SEQ ID NO: 272.

In one embodiment, the binding proteins of the present invention bind Factor IXa and Factor X and comprise a $VL_B$ on the third polypeptide, wherein the $VL_B$ of the third polypeptide comprises a $VL_B$ CDR1 of SEQ ID NO: 275, a $VL_B$ CDR2 of SEQ ID NO: 276, and a $VL_B$ CDR3 of SEQ ID NO: 277.

In one embodiment, the binding proteins of the present invention bind Factor IXa and Factor X and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 261, a $VL_A$ CDR2 of SEQ ID NO: 262, and a $VL_A$ CDR3 of SEQ ID NO: 263; wherein the $VH_B$ of the first polypeptide comprises a $VH_B$ CDR1 of SEQ ID NO: 265, a $VH_B$ CDR2 of SEQ ID NO: 266, and a $VH_B$ CDR3 of SEQ ID NO: 267; wherein the $VH_A$ of the second polypeptide comprises a $VH_A$ CDR1 of SEQ ID NO: 270, a $VH_A$ CDR2 of SEQ ID NO: 271, and a $VH_A$ CDR3 of SEQ ID NO: 272; and wherein the $VL_B$ of the third polypeptide comprises a $VL_B$ CDR1 of SEQ ID NO: 275, a $VL_B$ CDR2 of SEQ ID NO: 276, and a $VL_B$ CDR3 of SEQ ID NO: 277.

In one embodiment, the binding proteins of the present invention bind Factor IXa and Factor X and comprise a first polypeptide chain comprising a $VL_A$ having the sequence of SEQ ID NO: 260, and a $VH_B$ having the sequence of SEQ ID NO: 264, wherein the binding protein comprises a second polypeptide chain comprising a $VH_A$ having the sequence of SEQ ID NO: 269, and wherein the binding protein comprises a third polypeptide chain comprising a $VL_B$ having the sequence of SEQ ID NO: 274.

In one embodiment, the binding proteins of the present invention bind Factor IXa and Factor X and comprising, consisting essentially of, or consisting of a first polypeptide chain comprising an amino acid sequence of SEQ ID NO: 259; a second polypeptide chain comprising an amino acid sequence of SEQ ID NO: 268; and a third polypeptide chain comprising an amino acid sequence of SEQ ID NO: 273.

In one embodiment, the binding proteins of the present invention bind Factor IXa and Factor X, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding Her3 and IGF-1R. The binding proteins of the present invention, in one embodiment, are capable of binding Her3 and IGF-1R and comprise variable heavy and light chains derived from the Her3 antibody patritumab and the IGF-1R antibody figitumumab. In some embodiments, polypeptide derived from Her3 antibody is in the upper domain and polypeptide derived from IGF-1R antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is Her3, and antigen B is IGF-1R. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is Her3, and antigen A is IGF-1R. In some embodiments, polypeptide derived from Her3 antibody is in the lower domain and polypeptide derived from IGF-1R antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is IGF-1R, and antigen B is Her3. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is IGF-1R, and antigen A is Her3.

In one embodiment, the binding proteins of the present invention bind Her3 and IGF-1R and comprise a first polypeptide chain comprising, consisting essentially of, or consisting of an amino acid sequence according to SEQ ID NO: 108; a second polypeptide chain comprising, consisting essentially of, or consisting of an amino acid sequence according to SEQ ID NO: 109; and a third polypeptide chain comprising, consisting essentially of, or consisting of an amino acid sequence according to SEQ ID NO: 110.

In one embodiment, the binding protein of the present invention is capable of binding the same epitope of Her3 and the same epitope of IGF-1R as that of bispecific binding protein FIT016a, wherein the bispecific binding protein FIT016a comprises a first polypeptide chain comprising an amino acid sequence of SEQ ID NO: 278; a second polypeptide chain comprising an amino acid sequence of SEQ ID NO: 287; and a third polypeptide chain comprising an amino acid sequence of SEQ ID NO: 292.

In one embodiment, the binding proteins of the present invention bind Her3 and IGF-1R and comprise a $VL_A$ on the first polypeptide, wherein the $VL_A$ of the first polypeptide comprises a $VL_A$ CDR1 of SEQ ID NO: 280, a $VL_A$ CDR2 of SEQ ID NO: 281, and a $VL_A$ CDR3 of SEQ ID NO: 282.

In one embodiment, the binding proteins of the present invention bind Her3 and IGF-1R and comprise a $VH_B$ on the first polypeptide, wherein the $VH_B$ of the first polypeptide comprises a $VH_B$ CDR1 of SEQ ID NO: 284, a $VH_B$ CDR2 of SEQ ID NO: 285, and a $VH_B$ CDR3 of SEQ ID NO: 286.

In one embodiment, the binding proteins of the present invention bind Her3 and IGF-1R and comprise a $VH_A$ on the second polypeptide, wherein the $VH_A$ of the second polypeptide comprises a $VH_A$ CDR1 of SEQ ID NO: 289, a $VH_A$ CDR2 of SEQ ID NO: 290, and a $VH_A$ CDR3 of SEQ ID NO: 291.

In one embodiment, the binding proteins of the present invention bind Her3 and IGF-1R and comprise a $VL_B$ on the third polypeptide, wherein the $VL_B$ of the third polypeptide comprises a $VL_B$ CDR1 of SEQ ID NO: 294, a $VL_B$ CDR2 of SEQ ID NO: 295, and a $VL_B$ CDR3 of SEQ ID NO: 296.

In one embodiment, the binding proteins of the present invention bind Her3 and IGF-1R and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 280, a $VL_A$ CDR2 of SEQ ID NO: 281, and a $VL_A$ CDR3 of SEQ ID NO: 282; wherein the $VH_B$ of the first polypeptide comprises a $VH_B$ CDR1 of SEQ ID NO: 284, a $VH_B$ CDR2 of SEQ ID NO: 285, and a $VH_B$ CDR3 of SEQ ID NO: 286; wherein the $VH_A$ of the second polypeptide comprises a $VH_A$ CDR1 of SEQ ID NO: 289, a $VH_A$ CDR2 of SEQ ID NO: 290, and a $VH_A$ CDR3 of SEQ ID NO: 291; wherein the $VL_B$ of the third polypeptide comprises a $VL_B$ CDR1 of SEQ ID NO: 294, a $VL_B$ CDR2 of SEQ ID NO: 295, and a $VL_B$ CDR3 of SEQ ID NO: 296.

In one embodiment, the binding proteins of the present invention bind Her3 and IGF-1R and comprise a first polypeptide chain comprising a $VL_A$ having the sequence of SEQ ID NO: 279, and a $VH_B$ having the sequence of SEQ ID NO: 283, wherein the binding protein comprises a second polypeptide chain comprising a $VH_A$ having the sequence of SEQ ID NO: 288, and wherein the binding protein comprises a third polypeptide chain comprising a $VL_B$ having the sequence of SEQ ID NO: 293.

In one embodiment, the binding proteins of the present invention bind Her3 and IGF-1R and comprising, consisting essentially of, or consisting of a first polypeptide chain comprising an amino acid sequence of SEQ ID NO: 278; a second polypeptide chain comprising an amino acid sequence of SEQ ID NO: 287; and a third polypeptide chain comprising an amino acid sequence of SEQ ID NO: 292.

In one embodiment, the binding proteins of the present invention bind Her3 and IGF-1R, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding DLL-4 and VEGF. The binding proteins of the present invention, in one embodiment, are capable of binding DLL-4 and VEGF and comprise variable heavy and light chains derived from the DLL-4 antibody demcizumab and the VEGF antibody bevicizumab.

In some embodiments, polypeptide derived from DLL-4 antibody is in the upper domain and polypeptide derived from VEGF antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is DLL-4, and antigen B is VEGF. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is DLL-4, and antigen A is VEGF. In some embodiments, polypeptide derived from DLL-4 antibody is in the lower domain and polypeptide derived from VEGF antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is VEGF, and antigen B is DLL-4. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is VEGF, and antigen A is DLL-4.

In one embodiment, the binding proteins of the present invention bind DLL-4 and VEGF and comprise a first polypeptide chain comprising, consisting essentially of, or consisting of an amino acid sequence according to SEQ ID NO: 111; a second polypeptide chain comprising, consisting essentially of, or consisting of an amino acid sequence according to SEQ ID NO: 112; and a third polypeptide chain comprising, consisting essentially of, or consisting of an amino acid sequence according to SEQ ID NO: 113.

In one embodiment, the binding protein of the present invention is capable of binding the same epitope of DLL-4 and the same epitope of VEGF as that of bispecific binding protein FIT017a, wherein the bispecific binding protein FIT017a comprises a first polypeptide chain comprising an amino acid sequence of SEQ ID NO: 297; a second polypeptide chain comprising an amino acid sequence of SEQ ID NO: 306; and a third polypeptide chain comprising an amino acid sequence of SEQ ID NO: 311.

In one embodiment, the binding proteins of the present invention bind DLL-4 and VEGF and comprise a $VL_A$ on the first polypeptide, wherein the $VL_A$ of the first polypeptide comprises a $VL_A$ CDR1 of SEQ ID NO: 299, a $VL_A$ CDR2 of SEQ ID NO: 300, and a $VL_A$ CDR3 of SEQ ID NO: 301.

In one embodiment, the binding proteins of the present invention bind DLL-4 and VEGF and comprise a $VH_B$ on the first polypeptide, wherein the $VH_B$ of the first polypeptide comprises a $VH_B$ CDR1 of SEQ ID NO: 303, a $VH_B$ CDR2 of SEQ ID NO: 304, and a $VH_B$ CDR3 of SEQ ID NO: 305.

In one embodiment, the binding proteins of the present invention bind DLL-4 and VEGF and comprise a $VH_A$ on the second polypeptide, wherein the $VH_A$ of the second polypeptide comprises a $VH_A$ CDR1 of SEQ ID NO: 308, a $VH_A$ CDR2 of SEQ ID NO: 309, and a $VH_A$ CDR3 of SEQ ID NO: 310.

In one embodiment, the binding proteins of the present invention bind DLL-4 and VEGF and comprise a $VL_B$ on the third polypeptide, wherein the $VL_B$ of the third polypeptide comprises a $VL_B$ CDR1 of SEQ ID NO: 313, a $VL_B$ CDR2 of SEQ ID NO: 314, and a $VL_B$ CDR3 of SEQ ID NO: 315.

In one embodiment, the binding proteins of the present invention bind DLL-4 and VEGF and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 299, a $VL_A$ CDR2 of SEQ ID NO: 300, and a $VL_A$ CDR3 of SEQ ID NO: 301; wherein the $VH_B$ of the first polypeptide comprises a $VH_B$ CDR1 of SEQ ID NO: 303, a $VH_B$ CDR2 of SEQ ID NO: 304, and a $VH_B$ CDR3 of SEQ ID NO: 305; wherein the $VH_A$ of the second polypeptide comprises a $VH_A$ CDR1 of SEQ ID NO: 308, a $VH_A$ CDR2 of SEQ ID NO: 309, and a $VH_A$ CDR3 of SEQ ID NO: 310; and wherein the $VL_B$ of the third polypeptide comprises a $VL_B$ CDR1 of SEQ ID NO: 313, a $VL_B$ CDR2 of SEQ ID NO: 314, and a $VL_B$ CDR3 of SEQ ID NO: 315.

In one embodiment, the binding proteins of the present invention bind DLL-4 and VEGF and comprise a first polypeptide chain comprising a $VL_A$ having the sequence of SEQ ID NO: 298, and a $VH_B$ having the sequence of SEQ ID NO: 302, wherein the binding protein comprises a second polypeptide chain comprising a $VH_A$ having the sequence of SEQ ID NO: 307, and wherein the binding protein comprises a third polypeptide chain comprising a $VL_B$ having the sequence of SEQ ID NO: 312.

In one embodiment, the binding proteins of the present invention bind DLL-4 and VEGF and comprising, consisting essentially of, or consisting of a first polypeptide chain comprising an amino acid sequence of SEQ ID NO: 297; a second polypeptide chain comprising an amino acid sequence of SEQ ID NO: 306; and a third polypeptide chain comprising an amino acid sequence of SEQ ID NO: 311.

In one embodiment, the binding proteins of the present invention bind DLL-4 and VEGF, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding Her3 and EGFR. The binding proteins of the present invention, in one embodiment, are capable of binding Her3 and EGFR and comprise variable heavy and light chains derived from the Her3 antibody patritumab and the EGFR antibody panitumumab. In some embodiments, polypeptide derived from Her3 antibody is in the upper domain and polypeptide derived from EGFR antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is Her3, and antigen B is EGFR. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is Her3, and antigen A is EGFR.

In some embodiments, polypeptide derived from Her3 antibody is in the lower domain and polypeptide derived from EGFR antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is EGFR, and antigen B is Her3. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is EGFR, and antigen A is Her3.

In one embodiment, the binding proteins of the present invention bind Her3 and EGFR and comprise a first polypeptide chain comprising, consisting essentially of, or consisting of an amino acid sequence according to SEQ ID NO: 117; a second polypeptide chain comprising, consisting essentially of, or consisting of an amino acid sequence according to SEQ ID NO: 118; and a third polypeptide chain comprising, consisting essentially of, or consisting of an amino acid sequence according to SEQ ID NO: 119.

In one embodiment, the binding protein of the present invention is capable of binding the same epitope of Her3 and the same epitope of EGFR as that of bispecific binding protein FIT019a, wherein the bispecific binding protein FIT019a comprises a first polypeptide chain comprising an amino acid sequence of SEQ ID NO: 335; a second polypeptide chain comprising an amino acid sequence of SEQ ID NO: 344; and a third polypeptide chain comprising an amino acid sequence of SEQ ID NO: 349. In one embodiment, the binding protein of the present invention is capable of binding the same epitope of Her3 and the same epitope of EGFR as that of bispecific binding protein FIT019b, wherein the bispecific binding protein FIT019b comprises a first polypeptide chain comprising an amino acid sequence of SEQ ID NO: 354; a second polypeptide chain comprising an amino acid sequence of SEQ ID NO: 363; and a third polypeptide chain comprising an amino acid sequence of SEQ ID NO: 368.

In one embodiment, the binding proteins of the present invention bind Her3 and EGFR and comprise a $VL_A$ on the first polypeptide, wherein the $VL_A$ of the first polypeptide comprises a $VL_A$ CDR1 of SEQ ID NO: 337, a $VL_A$ CDR2 of SEQ ID NO: 338, and a $VL_A$ CDR3 of SEQ ID NO: 339 (e.g., those on FIT019a). In one embodiment, the binding proteins of the present invention bind Her3 and EGFR and comprise a $VL_A$ on the first polypeptide, wherein the $VL_A$ of the first polypeptide comprises a $VL_A$ CDR1 of SEQ ID NO: 356, a $VL_A$ CDR2 of SEQ ID NO: 357, and a $VL_A$ CDR3 of SEQ ID NO: 358 (e.g., those on FIT019b).

In one embodiment, the binding proteins of the present invention bind Her3 and EGFR and comprise a $VH_B$ on the first polypeptide, wherein the $VH_B$ of the first polypeptide comprises a $VH_B$ CDR1 of SEQ ID NO: 341, a $VH_B$ CDR2 of SEQ ID NO: 342, and a $VH_B$ CDR3 of SEQ ID NO: 343 (e.g., those on FIT019a). In one embodiment, the binding proteins of the present invention bind Her3 and EGFR and comprise a $VH_B$ on the first polypeptide, wherein the $VH_B$ of the first polypeptide comprises a $VH_B$ CDR1 of SEQ ID NO: 360, a $VH_B$ CDR2 of SEQ ID NO: 361, and a $VH_B$ CDR3 of SEQ ID NO: 362 (e.g., those on FIT019b).

In one embodiment, the binding proteins of the present invention bind Her3 and EGFR and comprise a $VH_A$ on the second polypeptide, wherein the $VH_A$ of the second polypeptide comprises a $VH_A$ CDR1 of SEQ ID NO: 346, a $VH_A$ CDR2 of SEQ ID NO: 347, and a $VH_A$ CDR3 of SEQ ID NO: 348 (e.g., those on FIT019a). In one embodiment, the binding proteins of the present invention bind Her3 and EGFR and comprise a $VH_A$ on the second polypeptide, wherein the $VH_A$ of the second polypeptide comprises a $VH_A$ CDR1 of SEQ ID NO: 365, a $VH_A$ CDR2 of SEQ ID NO: 366, and a $VH_A$ CDR3 of SEQ ID NO: 367 (e.g., those on FIT019b).

In one embodiment, the binding proteins of the present invention bind Her3 and EGFR and comprise a $VL_B$ on the third polypeptide, wherein the $VL_B$ of the third polypeptide comprises a $VL_B$ CDR1 of SEQ ID NO: 351, a $VL_B$ CDR2 of SEQ ID NO: 352, and a $VL_B$ CDR3 of SEQ ID NO: 353 (e.g., those on FIT019a). In one embodiment, the binding proteins of the present invention bind Her3 and EGFR and comprise a $VL_B$ on the third polypeptide, wherein the $VL_B$ of the third polypeptide comprises a $VL_B$ CDR1 of SEQ ID NO: 370, a $VL_B$ CDR2 of SEQ ID NO: 371, and a $VL_B$ CDR3 of SEQ ID NO: 372 (e.g., those on FIT019b).

In one embodiment, the binding proteins of the present invention bind Her3 and EGFR and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 337, a $VL_A$ CDR2 of SEQ ID NO: 338, and a $VL_A$ CDR3 of SEQ ID NO: 339; wherein the $VH_B$ of the first polypeptide comprises a $VH_B$ CDR1 of SEQ ID NO: 341, a $VH_B$ CDR2 of SEQ ID NO: 342, and a $VH_B$ CDR3 of SEQ ID NO: 343; wherein the $VH_A$ of the second polypeptide comprises a $VH_A$ CDR1 of SEQ ID NO: 346, a $VH_A$ CDR2 of SEQ ID NO: 347, and a $VH_A$ CDR3 of SEQ ID NO: 348; and wherein the $VL_B$ of the third polypeptide comprises a $VL_B$ CDR1 of SEQ ID NO: 351, a $VL_B$ CDR2 of SEQ ID NO: 352, and a $VL_B$ CDR3 of SEQ ID NO: 353 (e.g., those on FIT019a).

In one embodiment, the binding proteins of the present invention bind Her3 and EGFR and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 356, a $VL_A$ CDR2 of SEQ ID NO: 357, and a $VL_A$ CDR3 of SEQ ID NO: 358; wherein the $VH_B$ of the first polypeptide comprises a $VH_B$ CDR1 of SEQ ID NO: 360, a $VH_B$ CDR2 of SEQ ID NO: 361, and a $VH_B$ CDR3 of SEQ ID NO: 362; wherein the $VH_A$ of the second polypeptide comprises a $VH_A$ CDR1 of SEQ ID NO: 365, a $VH_A$ CDR2 of SEQ ID NO: 366, and a $VH_A$ CDR3 of SEQ ID NO: 367; and wherein the $VL_B$ of the third polypeptide comprises a $VL_B$ CDR1 of SEQ ID NO: 370, a $VL_B$ CDR2 of SEQ ID NO: 371, and a $VL_B$ CDR3 of SEQ ID NO: 372 (e.g., those on FIT019b).

In one embodiment, the binding proteins of the present invention bind Her3 and EGFR and comprises a first polypeptide chain comprising a $VL_A$ having the sequence of SEQ ID NO: 336, and a $VH_B$ having the sequence of SEQ ID NO: 340, wherein the binding protein comprises a second polypeptide chain comprising a $VH_A$ having the sequence of SEQ ID NO: 345, and wherein the binding protein comprises a third polypeptide chain comprising a $VL_B$ having the sequence of SEQ ID NO: 350 (e.g., those on FIT019a). In one embodiment, the binding proteins of the present invention bind Her3 and EGFR and comprises a first polypeptide chain comprising a $VL_A$ having the sequence of SEQ ID NO: 355, and a $VH_B$ having the sequence of SEQ ID NO: 359, wherein the binding protein comprises a second polypeptide chain comprising a $VH_A$ having the sequence of SEQ ID NO: 364, and wherein the binding protein comprises a third polypeptide chain comprising a $VL_B$ having the sequence of SEQ ID NO: 369 (e.g., those on FIT019b).

In one embodiment, the binding proteins of the present invention bind Her3 and EGFR and comprising, consisting essentially of, or consisting of a first polypeptide chain comprising an amino acid sequence of SEQ ID NO: 335; a second polypeptide chain comprising an amino acid sequence of SEQ ID NO: 344; and a third polypeptide chain comprising an amino acid sequence of SEQ ID NO: 349 (e.g., those on FIT019a). In one embodiment, the binding proteins of the present invention bind Her3 and EGFR and comprising, consisting essentially of, or consisting of a first polypeptide chain comprising an amino acid sequence of SEQ ID NO: 354; a second polypeptide chain comprising an amino acid sequence of SEQ ID NO: 363; and a third polypeptide chain comprising an amino acid sequence of SEQ ID NO: 368 (e.g., those on FIT019b).

In one embodiment, the binding proteins of the present invention bind Her3 and EGFR, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding PD-1 and PD-L1. The binding proteins of the present invention, in one embodiment, are capable of binding PD-1 and PD-L1 and comprise variable heavy and light chains derived from the PD-1 antibody nivolumab and the PD-L1 antibody 1B12. In some embodiments, polypeptide derived from PD-1 antibody is in the upper domain and polypeptide derived from PD-L1 antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is PD-1, and antigen B is PD-L1. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is PD-1, and antigen A is PD-L1. In some embodiments, polypeptide derived from PD-1 antibody is in the lower domain and polypeptide derived from PD-L1 antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is PD-L1, and antigen B is PD-1. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is PD-L1, and antigen A is PD-1.

In one embodiment, the binding proteins of the present invention bind PD-1 and PD-L1 and comprise a first polypeptide chain comprising, consisting essentially of, or consisting of an amino acid sequence according to SEQ ID NO: 120; a second polypeptide chain comprising, consisting essentially of, or consisting of an amino acid sequence according to SEQ ID NO: 121; and a third polypeptide chain comprising, consisting essentially of, or consisting of an amino acid sequence according to SEQ ID NO: 122.

In one embodiment, the binding protein of the present invention is capable of binding the same epitope of PD-1 and the same epitope of PD-L1 as that of bispecific binding protein FIT020a, wherein the bispecific binding protein FIT020a comprises a first polypeptide chain comprising an amino acid sequence of SEQ ID NO: 120; a second polypeptide chain comprising an amino acid sequence of SEQ ID NO: 121; and a third polypeptide chain comprising an amino acid sequence of SEQ ID NO: 122.

In one embodiment, the binding protein of the present invention is capable of binding the same epitope of PD-1 and the same epitope of PD-L1 as that of bispecific binding protein FIT020b, wherein the bispecific binding protein FIT020b comprises a first polypeptide chain comprising an amino acid sequence of SEQ ID NO: 297; a second polypeptide chain comprising an amino acid sequence of SEQ ID NO: 306; and a third polypeptide chain comprising an amino acid sequence of SEQ ID NO: 311.

In one embodiment, the binding proteins of the present invention bind PD-1 and PD-L1 and comprise a $VL_A$ on the first polypeptide, wherein the $VL_A$ of the first polypeptide comprises a $VL_A$ CDR1 of SEQ ID NO: 389, a $VL_A$ CDR2 of SEQ ID NO: 390, and a $VL_A$ CDR3 of SEQ ID NO: 391 (e.g., those on FIT020a).

In one embodiment, the binding proteins of the present invention bind PD-1 and PD-L1 and comprise a $VL_A$ CDR1 of SEQ ID NO: 375, a $VL_A$ CDR2 of SEQ ID NO: 376, and a $VL_A$ CDR3 of SEQ ID NO: 377 (e.g., those on FIT020b).

In one embodiment, the binding proteins of the present invention bind PD-1 and PD-L1 and comprise a $VH_B$ on the first polypeptide, wherein the $VH_B$ of the first polypeptide comprises a $VH_B$ CDR1 of SEQ ID NO: 384, a $VH_B$ CDR2 of SEQ ID NO: 385, and a $VH_B$ CDR3 of SEQ ID NO: 386 (e.g., those on FIT020a).

In one embodiment, the binding proteins of the present invention bind PD-1 and PD-L1 and comprise a $VH_B$ CDR1 of SEQ ID NO: 379, a $VH_B$ CDR2 of SEQ ID NO: 380, and a $VH_B$ CDR3 of SEQ ID NO: 381 (e.g., those on FIT020b).

In one embodiment, the binding proteins of the present invention bind PD-1 and PD-L1 and comprise a $VH_A$ on the second polypeptide, wherein the $VH_A$ of the second polypeptide comprises a $VH_A$ CDR1 of SEQ ID NO: 379, a $VH_A$ CDR2 of SEQ ID NO: 380, and a $VH_A$ CDR3 of SEQ ID NO: 381 (e.g., those on FIT020a).

In one embodiment, the binding proteins of the present invention bind PD-1 and PD-L1 and comprise a $VH_A$ on the second polypeptide, wherein the $VH_A$ of the second polypeptide comprises a $VH_A$ CDR1 of SEQ ID NO: 384, a $VH_A$ CDR2 of SEQ ID NO: 385, and a $VH_A$ CDR3 of SEQ ID NO: 386 (e.g., those on FIT020b).

In one embodiment, the binding proteins of the present invention bind PD-1 and PD-L1 and comprise a $VL_B$ on the third polypeptide, wherein the $VL_B$ of the third polypeptide comprises a $VL_B$ CDR1 of SEQ ID NO: 375, a $VL_B$ CDR2 of SEQ ID NO: 376, and a $VL_B$ CDR3 of SEQ ID NO: 377 (e.g., those on FIT020a).

In one embodiment, the binding proteins of the present invention bind PD-1 and PD-L1 and comprise a $VL_B$ on the third polypeptide, wherein the $VL_B$ of the third polypeptide comprises a $VL_B$ CDR1 of SEQ ID NO: 389, a $VL_B$ CDR2 of SEQ ID NO: 390, and a $VL_B$ CDR3 of SEQ ID NO: 391 (e.g., those on FIT020b).

In one embodiment, the binding proteins of the present invention bind PD-1 and PD-L1 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 389, a $VL_A$ CDR2 of SEQ ID NO: 390, and a $VL_A$ CDR3 of SEQ ID NO: 391; wherein the $VH_B$ of the first polypeptide comprises a $VH_B$ CDR1 of SEQ ID NO: 384, a $VH_B$ CDR2 of SEQ ID NO: 385, and a $VH_B$ CDR3 of SEQ ID NO: 386; wherein the $VH_A$ of the second polypeptide comprises a $VH_A$ CDR1 of SEQ ID NO: 379, a $VH_A$ CDR2 of SEQ ID NO: 380, and a $VH_A$ CDR3 of SEQ ID NO: 381; and wherein the $VL_B$ of the third polypeptide comprises a $VL_B$ CDR1 of SEQ ID NO: 375, a $VL_B$ CDR2 of SEQ ID NO: 376, and a $VL_B$ CDR3 of SEQ ID NO: 377 (e.g., those on FIT020a).

In one embodiment, the binding proteins of the present invention bind PD-1 and PD-L1 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 375, a $VL_A$ CDR2 of SEQ ID NO: 376, and a $VL_A$ CDR3 of SEQ ID NO: 377; wherein the $VH_B$ of the first polypeptide comprises a $VH_B$ CDR1 of SEQ ID NO: 379, a $VH_B$ CDR2 of SEQ ID NO: 380, and a $VH_B$ CDR3 of SEQ ID NO: 381; wherein the $VH_A$ of the second polypeptide comprises a $VH_A$ CDR1 of SEQ ID NO: 384, a $VH_A$ CDR2 of SEQ ID NO: 385, and a $VH_A$ CDR3 of SEQ ID NO: 386; and wherein the $VL_B$ of the third polypeptide comprises a $VL_B$ CDR1 of SEQ ID NO: 389, a $VL_B$ CDR2 of SEQ ID NO: 390, and a $VL_B$ CDR3 of SEQ ID NO: 391 (e.g., those on FIT020b).

In one embodiment, the binding proteins of the present invention bind PD-1 and PD-L1 and comprise a first polypeptide chain comprising a $VL_A$ having the sequence of SEQ ID NO: 388, and a $VH_B$ having the sequence of SEQ ID NO: 383, wherein the binding protein comprises a second polypeptide chain comprising a $VH_A$ having the sequence of SEQ ID NO: 378, and wherein the binding protein comprises a third polypeptide chain comprising a $VL_B$ having the sequence of SEQ ID NO: 374 (e.g., those on FIT020a).

In one embodiment, the binding proteins of the present invention bind PD-1 and PD-L1 and comprise a first polypeptide chain comprising a $VL_A$ having the sequence of SEQ ID NO: 374, and a $VH_B$ having the sequence of SEQ ID NO: 378, wherein the binding protein comprises a second polypeptide chain comprising a $VH_A$ having the sequence of SEQ ID NO: 383, and wherein the binding protein comprises a third polypeptide chain comprising a $VL_B$ having the sequence of SEQ ID NO: 388 (e.g., those on FIT020b).

In one embodiment, the binding proteins of the present invention bind PD-1 and PD-L1 and comprising, consisting essentially of, or consisting of a first polypeptide chain comprising an amino acid sequence of SEQ ID NO: 120; a second polypeptide chain comprising an amino acid sequence of SEQ ID NO: 121; and a third polypeptide chain comprising an amino acid sequence of SEQ ID NO: 122 (e.g., those on FIT020a).

In one embodiment, the binding proteins of the present invention bind PD-1 and PD-L1 and comprising, consisting essentially of, or consisting of a first polypeptide chain comprising an amino acid sequence of SEQ ID NO: 373; a second polypeptide chain comprising an amino acid sequence of SEQ ID NO: 382; and a third polypeptide chain comprising an amino acid sequence of SEQ ID NO: 387 (e.g., those on FIT020b).

In one embodiment, the binding proteins of the present invention bind PD-1 and PD-L1, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding Her3 and PD-1. The binding proteins of the present invention, in one embodiment, are capable of binding Her3 and PD-1 and comprise variable heavy and light chains derived from the Her3 antibody patritumab and the EGFR antibody nivolumab. In some embodiments, polypeptide derived from Her3 antibody is in the upper domain and polypeptide derived from PD-1 antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is Her3, and antigen B is PD-1. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is Her3, and antigen A is PD-1. In some embodiments, polypeptide derived from Her3 antibody is in the lower domain and polypeptide derived from PD-1 antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is PD-1, and antigen B is Her3. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is PD-1, and antigen A is Her3.

In one embodiment, the binding proteins of the present invention bind Her3 and PD-1 and comprise a first polypeptide chain comprising, consisting essentially of, or consisting of an amino acid sequence according to SEQ ID NO: 123; a second polypeptide chain comprising, consisting essentially of, or consisting of an amino acid sequence according to SEQ ID NO: 124; and a third polypeptide chain comprising, consisting essentially of, or consisting of an amino acid sequence according to SEQ ID NO: 125.

In one embodiment, the binding protein of the present invention is capable of binding the same epitope of Her3 and the same epitope of PD-1 as that of bispecific binding protein FIT022a, wherein the bispecific binding protein FIT022a comprises a first polypeptide chain comprising an amino acid sequence of SEQ ID NO: 411; a second polypeptide chain comprising an amino acid sequence of SEQ ID NO: 420; and a third polypeptide chain comprising an amino acid sequence of SEQ ID NO: 425.

In one embodiment, the binding proteins of the present invention bind Her3 and PD-1 and comprise a $VL_A$ on the first polypeptide, wherein the $VL_A$ of the first polypeptide comprises a $VL_A$ CDR1 of SEQ ID NO: 413, a $VL_A$ CDR2 of SEQ ID NO: 414, and a $VL_A$ CDR3 of SEQ ID NO: 415.

In one embodiment, the binding proteins of the present invention bind Her3 and PD-1 and comprise a $VH_B$ on the first polypeptide, wherein the $VH_B$ of the first polypeptide comprises a $VH_B$ CDR1 of SEQ ID NO: 417, a $VH_B$ CDR2 of SEQ ID NO: 418, and a $VH_B$ CDR3 of SEQ ID NO: 419.

In one embodiment, the binding proteins of the present invention bind Her3 and PD-1 and comprise a $VH_A$ on the second polypeptide, wherein the $VH_A$ of the second polypeptide comprises a $VH_A$ CDR1 of SEQ ID NO: 422, a $VH_A$ CDR2 of SEQ ID NO: 423, and a $VH_A$ CDR3 of SEQ ID NO: 424.

In one embodiment, the binding proteins of the present invention bind Her3 and PD-1 and comprise a $VL_B$ on the third polypeptide, wherein the $VL_B$ of the third polypeptide comprises a $VL_B$ CDR1 of SEQ ID NO: 427, a $VL_B$ CDR2 of SEQ ID NO: 428, and a $VL_B$ CDR3 of SEQ ID NO: 429.

In one embodiment, the binding proteins of the present invention bind Her3 and PD-1 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 413, a $VL_A$ CDR2 of SEQ ID NO: 414, and a $VL_A$ CDR3 of SEQ ID NO: 415; wherein the $VH_B$ of the first polypeptide comprises a $VH_B$ CDR1 of SEQ ID NO: 417, a $VH_B$ CDR2 of SEQ ID NO: 418, and a $VH_B$ CDR3 of SEQ ID NO: 419; wherein the $VH_A$ of the second polypeptide comprises a $VH_A$ CDR1 of SEQ ID NO: 422, a $VH_A$ CDR2 of SEQ ID NO: 423, and a $VH_A$ CDR3 of SEQ ID NO: 424; and wherein the $VL_B$ of the third polypeptide comprises a $VL_B$ CDR1 of SEQ ID NO: 427, a $VL_B$ CDR2 of SEQ ID NO: 428, and a $VL_B$ CDR3 of SEQ ID NO: 429.

In one embodiment, the binding proteins of the present invention bind Her3 and PD-1 and comprise a first polypeptide chain comprising a $VL_A$ having the sequence of SEQ ID NO: 412, and a $VH_B$ having the sequence of SEQ ID NO: 416, wherein the binding protein comprises a second polypeptide chain comprising a $VH_A$ having the sequence of SEQ ID NO: 421, and wherein the binding protein comprises a third polypeptide chain comprising a $VL_B$ having the sequence of SEQ ID NO: 426.

In one embodiment, the binding proteins of the present invention bind Her3 and PD-1 and comprising, consisting essentially of, or consisting of a first polypeptide chain comprising an amino acid sequence of SEQ ID NO: 411; a second polypeptide chain comprising an amino acid sequence of SEQ ID NO: 420; and a third polypeptide chain comprising an amino acid sequence of SEQ ID NO: 425.

In one embodiment, the binding proteins of the present invention bind Her3 and PD-1, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding cMet and PD-L1. The binding proteins of the present invention, in one embodiment, are capable of binding cMet and PD-L1 and comprise variable heavy and light chains derived from the cMet antibody h1332 and the PD-L1 antibody 1B12. In some embodiments, polypeptide derived from cMet antibody is in the upper domain and polypeptide derived from PD-L1 antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is cMet, and antigen B is PD-L1. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is cMet, and antigen A is PD-L1. In some embodiments, polypeptide derived from cMet antibody is in the lower domain and polypeptide derived from PD-L1 antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is PD-L1, and antigen B is cMet. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is PD-L1, and antigen A is cMet.

In one embodiment, the binding protein of the present invention is capable of binding the same epitope of cMet and the same epitope of PD-L1 as that of bispecific binding protein FIT023a, wherein the bispecific binding protein FIT023a comprises a first polypeptide chain comprising an amino acid sequence of SEQ ID NO: 430; a second polypeptide chain comprising an amino acid sequence of SEQ ID NO: 439; and a third polypeptide chain comprising an amino acid sequence of SEQ ID NO: 444.

In one embodiment, the binding proteins of the present invention bind cMet and PD-L1 and comprise a $VL_A$ on the first polypeptide, wherein the $VL_A$ of the first polypeptide comprises a $VL_A$ CDR1 of SEQ ID NO: 432, a $VL_A$ CDR2 of SEQ ID NO: 433, and a $VL_A$ CDR3 of SEQ ID NO: 434.

In one embodiment, the binding proteins of the present invention bind cMet and PD-L1 and comprise a $VH_B$ on the first polypeptide, wherein the $VH_B$ of the first polypeptide comprises a $VH_B$ CDR1 of SEQ ID NO: 436, a $VH_B$ CDR2 of SEQ ID NO: 437, and a $VH_B$ CDR3 of SEQ ID NO: 438.

In one embodiment, the binding proteins of the present invention bind cMet and PD-L1 and comprise a $VH_A$ on the second polypeptide, wherein the $VH_A$ of the second polypeptide comprises a $VH_A$ CDR1 of SEQ ID NO: 441, a $VH_A$ CDR2 of SEQ ID NO: 442, and a $VH_A$ CDR3 of SEQ ID NO: 443.

In one embodiment, the binding proteins of the present invention bind cMet and PD-L1 and comprise a $VL_B$ on the third polypeptide, wherein the $VL_B$ of the third polypeptide comprises a $VL_B$ CDR1 of SEQ ID NO: 446, a $VL_B$ CDR2 of SEQ ID NO: 447, and a $VL_B$ CDR3 of SEQ ID NO: 448.

In one embodiment, the binding proteins of the present invention bind cMet and PD-L1 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 432, a $VL_A$ CDR2 of SEQ ID NO: 433, and a $VL_A$ CDR3 of SEQ ID NO: 434; wherein the $VH_B$ of the first polypeptide comprises a $VH_B$ CDR1 of SEQ ID NO: 436, a $VH_B$ CDR2 of SEQ ID NO: 437, and a $VH_B$ CDR3 of SEQ ID NO: 438; wherein the $VH_A$ of the second polypeptide comprises a $VH_A$ CDR1 of SEQ ID NO: 441, a $VH_A$ CDR2 of SEQ ID NO: 442, and a $VH_A$ CDR3 of SEQ ID NO: 443; and wherein the $VL_B$ of the third polypeptide comprises a $VL_B$ CDR1 of SEQ ID NO: 446, a $VL_B$ CDR2 of SEQ ID NO: 447, and a $VL_B$ CDR3 of SEQ ID NO: 448.

In one embodiment, the binding proteins of the present invention bind cMet and PD-L1 and comprise a first polypeptide chain comprising a $VL_A$ having the sequence of SEQ ID NO: 431, and a $VH_B$ having the sequence of SEQ ID NO: 435, wherein the binding protein comprises a second polypeptide chain comprising a $VH_A$ having the sequence of SEQ ID NO: 440, and wherein the binding protein comprises a third polypeptide chain comprising a $VL_B$ having the sequence of SEQ ID NO: 445.

In one embodiment, the binding proteins of the present invention bind cMet and PD-L1 and comprising, consisting essentially of, or consisting of a first polypeptide chain comprising an amino acid sequence of SEQ ID NO: 430; a second polypeptide chain comprising an amino acid sequence of SEQ ID NO: 439; and a third polypeptide chain comprising an amino acid sequence of SEQ ID NO: 444.

In one embodiment, the binding proteins of the present invention bind cMet and PD-L1, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding BTLA and PD-1. The binding proteins of the present invention, in one embodiment, are capable of binding BTLA and PD-1 and comprise variable heavy and light chains derived from the BTLA antibody 6A5 and the PD-1 antibody Nivolumab. In some embodiments, polypeptide derived from BTLA antibody is in the upper domain and polypeptide derived from PD-1 antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is BTLA, and antigen B is PD-1. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is BTLA, and antigen A is PD-1. In some embodiments, polypeptide derived from BTLA antibody is in the lower domain and polypeptide derived from PD-1 antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is PD-1, and antigen B is BTLA. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is PD-1, and antigen A is BTLA.

In one embodiment, the binding protein of the present invention is capable of binding the same epitope of BTLA and the same epitope of PD-1 as that of bispecific binding protein FIT024a, wherein the bispecific binding protein FIT024a comprises a first polypeptide chain comprising an amino acid sequence of SEQ ID NO: 449; a second polypeptide chain comprising an amino acid sequence of SEQ ID NO: 458; and a third polypeptide chain comprising an amino acid sequence of SEQ ID NO: 463.

In one embodiment, the binding protein of the present invention is capable of binding the same epitope of BTLA and the same epitope of PD-1 as that of bispecific binding protein FIT024b, wherein the bispecific binding protein FIT024b comprises a first polypeptide chain comprising an amino acid sequence of SEQ ID NO: 468; a second polypeptide chain comprising an amino acid sequence of SEQ ID NO: 477; and a third polypeptide chain comprising an amino acid sequence of SEQ ID NO: 482.

In one embodiment, the binding proteins of the present invention bind BTLA and PD-1 and comprise a $VL_A$ on the first polypeptide, wherein the $VL_A$ of the first polypeptide comprises a $VL_A$ CDR1 of SEQ ID NO: 451, a $VL_A$ CDR2 of SEQ ID NO: 452, and a $VL_A$ CDR3 of SEQ ID NO: 453 (e.g., those of FIT024a).

In one embodiment, the binding proteins of the present invention bind BTLA and PD-1 and comprise a $VL_A$ on the first polypeptide, wherein the $VL_A$ of the first polypeptide comprises a $VL_A$ CDR1 of SEQ ID NO: 470, a $VL_A$ CDR2 of SEQ ID NO: 471, and a $VL_A$ CDR3 of SEQ ID NO: 472 (e.g., those of FIT024b).

In one embodiment, the binding proteins of the present invention bind BTLA and PD-1 and comprise a $VH_B$ on the first polypeptide, wherein the $VH_B$ of the first polypeptide comprises a $VH_B$ CDR1 of SEQ ID NO: 455, a $VH_B$ CDR2 of SEQ ID NO: 456, and a $VH_B$ CDR3 of SEQ ID NO: 457 (e.g., those of FIT024a).

In one embodiment, the binding proteins of the present invention bind BTLA and PD-1 and comprise a $VH_B$ on the first polypeptide, wherein the $VH_B$ of the first polypeptide comprises a $VH_B$ CDR1 of SEQ ID NO: 474, a $VH_B$ CDR2 of SEQ ID NO: 475, and a $VH_B$ CDR3 of SEQ ID NO: 476 (e.g., those of FIT024b).

In one embodiment, the binding proteins of the present invention bind BTLA and PD-1 and comprise a $VH_A$ on the second polypeptide, wherein the $VH_A$ of the second polypeptide comprises a $VH_A$ CDR1 of SEQ ID NO: 460, a $VH_A$ CDR2 of SEQ ID NO: 461, and a $VH_A$ CDR3 of SEQ ID NO: 462 (e.g., those of FIT024a).

In one embodiment, the binding proteins of the present invention bind BTLA and PD-1 and comprise a $VH_A$ on the second polypeptide, wherein the $VH_A$ of the second polypeptide comprises a $VH_A$ CDR1 of SEQ ID NO: 479, a $VH_A$ CDR2 of SEQ ID NO: 480, and a $VH_A$ CDR3 of SEQ ID NO: 481 (e.g., those of FIT024b).

In one embodiment, the binding proteins of the present invention bind BTLA and PD-1 and comprise a $VL_B$ on the third polypeptide, wherein the $VL_B$ of the third polypeptide comprises a $VL_B$ CDR1 of SEQ ID NO: 465, a $VL_B$ CDR2 of SEQ ID NO: 466, and a $VL_B$ CDR3 of SEQ ID NO: 467 (e.g., those of FIT024a).

In one embodiment, the binding proteins of the present invention bind BTLA and PD-1 and comprise a $VL_B$ on the third polypeptide, wherein the $VL_B$ of the third polypeptide comprises a $VL_B$ CDR1 of SEQ ID NO: 484, a $VL_B$ CDR2 of SEQ ID NO: 485, and a $VL_B$ CDR3 of SEQ ID NO: 486 (e.g., those of FIT024b).

In one embodiment, the binding proteins of the present invention bind BTLA and PD-1 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 451, a $VL_A$ CDR2 of SEQ ID NO: 452, and a $VL_A$ CDR3 of SEQ ID NO: 453; wherein the $VH_B$ of the first polypeptide comprises a $VH_B$ CDR1 of SEQ ID NO: 455, a VH$_B$ CDR2 of SEQ ID NO: 456, and a VH$_B$ CDR3 of SEQ ID NO: 457; wherein the VH$_A$ of the second polypeptide comprises a VH$_A$ CDR1 of SEQ ID NO: 460, a VH$_A$ CDR2 of SEQ ID NO: 461, and a VH$_A$ CDR3 of SEQ ID NO: 462; and wherein the VL$_B$ of the third polypeptide comprises a VL$_B$ CDR1 of SEQ ID NO: 465, a VL$_B$ CDR2 of SEQ ID NO: 466, and a VL$_B$ CDR3 of SEQ ID NO: 467 (e.g., those of FIT024a).

In one embodiment, the binding proteins of the present invention bind BTLA and PD-1 and comprise a VL$_A$ and VH$_B$ on the first polypeptide, a VH$_A$ on the second polypeptide, and a VL$_B$ on the third polypeptide, wherein the VL$_A$ of the first polypeptide comprises a VL$_A$ CDR1 of SEQ ID NO: 470, a VL$_A$ CDR2 of SEQ ID NO: 471, and a VL$_A$ CDR3 of SEQ ID NO: 472; wherein the VH$_B$ of the first polypeptide comprises a VH$_B$ CDR1 of SEQ ID NO: 474, a VH$_B$ CDR2 of SEQ ID NO: 475, and a VH$_B$ CDR3 of SEQ ID NO: 476; wherein the VH$_A$ of the second polypeptide comprises a VH$_A$ CDR1 of SEQ ID NO: 479, a VH$_A$ CDR2 of SEQ ID NO: 480, and a VH$_A$ CDR3 of SEQ ID NO: 481; and wherein the VL$_B$ of the third polypeptide comprises a VL$_B$ CDR1 of SEQ ID NO: 484, a VL$_B$ CDR2 of SEQ ID NO: 485, and a VL$_B$ CDR3 of SEQ ID NO: 486 (e.g., those of FIT024b).

In one embodiment, the binding proteins of the present invention bind BTLA and PD-1 and comprise a first polypeptide chain comprising a VL$_A$ having the sequence of SEQ ID NO: 450, and a VH$_B$ having the sequence of SEQ ID NO: 454, wherein the binding protein comprises a second polypeptide chain comprising a VH$_A$ having the sequence of SEQ ID NO: 459, and wherein the binding protein comprises a third polypeptide chain comprising a VL$_B$ having the sequence of SEQ ID NO: 464 (e.g., those of FIT024a).

In one embodiment, the binding proteins of the present invention bind BTLA and PD-1 and comprise a first polypeptide chain comprising a VL$_A$ having the sequence of SEQ ID NO: 469, and a VH$_B$ having the sequence of SEQ ID NO: 473, wherein the binding protein comprises a second polypeptide chain comprising a VH$_A$ having the sequence of SEQ ID NO: 478, and wherein the binding protein comprises a third polypeptide chain comprising a VL$_B$ having the sequence of SEQ ID NO: 483 (e.g., those of FIT024b).

In one embodiment, the binding proteins of the present invention bind BTLA and PD-1 and comprising, consisting essentially of, or consisting of a first polypeptide chain comprising an amino acid sequence of SEQ ID NO: 449; a second polypeptide chain comprising an amino acid sequence of SEQ ID NO: 458; and a third polypeptide chain comprising an amino acid sequence of SEQ ID NO: 463 (those of FIT024a).

In one embodiment, the binding proteins of the present invention bind BTLA and PD-1 and comprising, consisting essentially of, or consisting of a first polypeptide chain comprising an amino acid sequence of SEQ ID NO: 468; a second polypeptide chain comprising an amino acid sequence of SEQ ID NO: 477; and a third polypeptide chain comprising an amino acid sequence of SEQ ID NO: 482 (those of FIT024b).

In one embodiment, the binding proteins of the present invention bind BTLA and PD-1, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding CD20 and CD22. The binding proteins of the present invention, in one embodiment, are capable of binding CD20 and CD22 and comprise variable heavy and light chains derived from the CD20 antibody Ofatumumab and the CD22 antibody Epratuzumab. In some embodiments, polypeptide derived from CD20 antibody is in the upper domain and polypeptide derived from CD22 antibody is in the lower domain. For example, in some embodiments, the binding proteins comprise a first polypeptide of VL$_A$-CL-VH$_B$-CH1-Fc, a second polypeptide of VH$_A$-CH1, and a third polypeptide of VL$_B$-CL, wherein antigen A is CD20, and antigen B is CD22. For another example, in some embodiments, the binding proteins comprise a first polypeptide of VH$_B$-CH1-VL$_A$-CL-Fc, a second polypeptide of VL$_B$-CL, and a third polypeptide of VH$_A$-CH1, wherein antigen B is CD20, and antigen A is CD22. In some embodiments, polypeptide derived from CD20 antibody is in the lower domain and polypeptide derived from CD22 antibody is in the upper domain. For example, in some embodiments, the binding proteins comprise a first polypeptide of VL$_A$-CL-VH$_B$-CH1-Fc, a second polypeptide of VH$_A$-CH1, and a third polypeptide of VL$_B$-CL, wherein antigen A is CD22, and antigen B is CD20. For another example, in some embodiments, the binding proteins comprise a first polypeptide of VH$_B$-CH1-VL$_A$-CL-Fc, a second polypeptide of VL$_B$-CL, and a third polypeptide of VH$_A$-CH1, wherein antigen B is CD22, and antigen A is CD20.

In one embodiment, the binding protein of the present invention is capable of binding the same epitope of CD20 and the same epitope of CD22 as that of bispecific binding protein FIT021b, wherein the bispecific binding protein FIT021b comprises a first polypeptide chain comprising an amino acid sequence of SEQ ID NO: 392; a second polypeptide chain comprising an amino acid sequence of SEQ ID NO: 401; and a third polypeptide chain comprising an amino acid sequence of SEQ ID NO: 406.

In one embodiment, the binding proteins of the present invention bind CD20 and CD22 and comprise a VL$_A$ on the first polypeptide, wherein the VL$_A$ of the first polypeptide comprises a VL$_A$ CDR1 of SEQ ID NO: 394, a VL$_A$ CDR2 of SEQ ID NO: 395, and a VL$_A$ CDR3 of SEQ ID NO: 396.

In one embodiment, the binding proteins of the present invention bind CD20 and CD22 and comprise a VH$_B$ on the first polypeptide, wherein the VH$_B$ of the first polypeptide comprises a VH$_B$ CDR1 of SEQ ID NO: 398, a VH$_B$ CDR2 of SEQ ID NO: 399, and a VH$_B$ CDR3 of SEQ ID NO: 400.

In one embodiment, the binding proteins of the present invention bind CD20 and CD22 and comprise a VH$_A$ on the second polypeptide, wherein the VH$_A$ of the second polypeptide comprises a VH$_A$ CDR1 of SEQ ID NO: 403, a VH$_A$ CDR2 of SEQ ID NO: 404, and a VH$_A$ CDR3 of SEQ ID NO: 405.

In one embodiment, the binding proteins of the present invention bind CD20 and CD22 and comprise a VL$_B$ on the third polypeptide, wherein the VL$_B$ of the third polypeptide comprises a VL$_B$ CDR1 of SEQ ID NO: 408, a VL$_B$ CDR2 of SEQ ID NO: 409, and a VL$_B$ CDR3 of SEQ ID NO: 410.

In one embodiment, the binding proteins of the present invention bind CD20 and CD22 and comprise a VL$_A$ and VH$_B$ on the first polypeptide, a VH$_A$ on the second polypeptide, and a VL$_B$ on the third polypeptide, wherein the VL$_A$ of the first polypeptide comprises a VL$_A$ CDR1 of SEQ ID NO: 394, a VL$_A$ CDR2 of SEQ ID NO: 395, and a VL$_A$ CDR3 of SEQ ID NO: 396; wherein the VH$_B$ of the first polypeptide comprises a VH$_B$ CDR1 of SEQ ID NO: 398, a VH$_B$ CDR2 of SEQ ID NO: 399, and a VH$_B$ CDR3 of SEQ ID NO: 400; wherein the VH$_A$ of the second polypeptide comprises a VH$_A$ CDR1 of SEQ ID NO: 403, a VH$_A$ CDR2 of SEQ ID NO: 404, and a VH$_A$ CDR3 of SEQ ID NO: 405; and wherein the VL$_B$ of the third polypeptide comprises a VL$_B$ CDR1 of SEQ ID NO: 408, a VL$_B$ CDR2 of SEQ ID NO: 409, and a VL$_B$ CDR3 of SEQ ID NO: 410.

In one embodiment, the binding proteins of the present invention bind CD20 and CD22 and comprise a first polypeptide chain comprising a VL$_A$ having the sequence of SEQ ID NO: 393, and a VH$_B$ having the sequence of SEQ ID NO: 397, wherein the binding protein comprises a second polypeptide chain comprising a VH$_A$ having the sequence of SEQ ID NO: 402, and wherein the binding protein comprises a third polypeptide chain comprising a VL$_B$ having the sequence of SEQ ID NO: 407.

In one embodiment, the binding proteins of the present invention bind CD20 and CD22 and comprising, consisting essentially of, or consisting of a first polypeptide chain comprising an amino acid sequence of SEQ ID NO: 392; a second polypeptide chain comprising an amino acid sequence of SEQ ID NO: 401; and a third polypeptide chain comprising an amino acid sequence of SEQ ID NO: 406.

In one embodiment, the binding proteins of the present invention bind CD20 and CD22, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding PD-L1 and TIM3. In some embodiments, polypeptide derived from PD-L1 antibody is in the upper domain and polypeptide derived from TIM3 antibody is in the lower domain. For example, in some embodiments, the binding proteins comprise a first polypeptide of VL$_A$-CL-VH$_B$-CH1-Fc, a second polypeptide of VH$_A$-CH1, and a third polypeptide of VL$_B$-CL, wherein antigen A is PD-L1, and antigen B is TIM3. For another example, in some embodiments, the binding proteins comprise a first polypeptide of VH$_B$-CH1-VL$_A$-CL-Fc, a second polypeptide of VL$_B$-CL, and a third polypeptide of VH$_A$-CH1, wherein antigen B is PD-L1, and antigen A is TIM3. In some embodiments, polypeptide derived from PD-L1 antibody is in the lower domain and polypeptide derived from TIM3 antibody is in the upper domain. For example, in some embodiments, the binding proteins comprise a first polypeptide of VL$_A$-CL-VH$_B$-CH1-Fc, a second polypeptide of VH$_A$-CH1, and a third polypeptide of VL$_B$-CL, wherein antigen A is TIM3, and antigen B is PD-L1. For another example, in some embodiments, the binding proteins comprise a first polypeptide of VH$_B$-CH1-VL$_A$-CL-Fc, a second polypeptide of VL$_B$-CL, and a third polypeptide of VH$_A$-CH1, wherein antigen B is TIM3, and antigen A is PD-L1.

In one embodiment, the binding protein is capable of binding one or more epitopes on one or more immune checkpoint protein on T cells such as, for example, TIM-3, Lag3, ICOS, BTLA, CD160, 2B4, KIR, CD137, CD27, OX40, CD40L, and A2aR. In another embodiment, the binding protein is capable of binding one or more epitopes on one or more tumor cell surface protein that is involved with immune checkpoint pathways, such as, for example, PD-L1, PD-L2, Galectin9, HVEM, CD48, B7-1, B7-2, ICOSL, B7-H3, B7-H4, CD137L, OX40L, CD70, and CD40.

In one aspect, the present invention provides pharmaceutical compositions comprising the binding proteins described herein. In one embodiment, provided herein are pharmaceutical compositions comprising the binding protein of any one of the preceding claims and one or more pharmaceutically acceptable carrier.

In another aspect, the present invention provides methods of treating or preventing an inflammatory disease, autoimmune disease, neurodegenerative disease, cancer, sepsis, or spinal cord injury in a subject in need thereof. In one embodiment, the method comprises administering to a subject an effective amount of one or more of the binding proteins provided herein, or one or more pharmaceutical compositions comprising the binding proteins provided herein and a pharmaceutically acceptable carrier. Uses of the binding proteins described herein in the manufacture of a medicament for treatment or prevention of an inflammatory disease, autoimmune disease, neurodegenerative disease, cancer, spinal cord injury, or other conditions are also provided herein. In one embodiment, the inflammatory disease, autoimmune disease, cancer, neurodegenerative disease, and other conditions include, but are not limited to, asthma, rheumatoid arthritis, systemic lupus erythematosus, multiple sclerosis, Alzheimer's disease, Parkinson's disease, infectious diseases and disorders, such as psoriasis, psoriatic arthritis, dermatitis, systemic sclerosis, inflammatory bowel disease (IBD), Crohn's disease, ulcerative colitis, respiratory distress syndrome, meningitis, encephalitis, uveitis, glomerulonephritis, eczema, asthma, atherosclerosis, leukocyte adhesion deficiency, Raynaud's syndrome, Sjögren's syndrome, juvenile onset diabetes, Reiter's disease, Behçet's disease, immune complex nephritis, IgA nephropathy, IgM polyneuropathies, immune-mediated thrombocytopenias, such as acute idiopathic thrombocytopenic purpura and chronic idiopathic thrombocytopenic purpura, hemolytic anemia, myasthenia gravis, lupus nephritis, atopic dermatitis, pemphigus, Graves' disease, severe acute respiratory distress syndrome, choreoretinitis, Hashimoto's thyroiditis, Wegener's granulomatosis, Omenn's syndrome, chronic renal failure, acute infectious mononucleosis, HIV, herpes virus associated diseases, type 1 diabetes, graft versus host disease (GVHD); immune disorders associated with graft transplantation rejection; T cell lymphoma, T cell acute lymphoblastic leukemia, testicular angiocentric T cell lymphoma, benign lymphocytic angiitis, primary myxedema, pernicious anemia, autoimmune atrophic gastritis, Addison's disease, insulin dependent diabetes mellitus, good pasture's syndrome, sympathetic ophthalmia, idiopathic thrombocytopenia, primary biliary cirrhosis, chronic action hepatitis, ulceratis colitis, Sjogren's syndrome, rheumatoid arthritis, polymyositis, scleroderma, mixed connective tissue disease, pemphigus vulgaris, pemphigoid, ankylosing spondylitis, aplastic anemia, autoimmune hepatitis, coeliac disease, dermatomyositis, Goodpasture's syndrome, Guillain-Barré syndrome, idiopathic leucopenia, idiopathic thrombocytopenic purpura, male infertility, phacogenic uveitis, primary myxoedema, Reiter's syndrome, stiff man syndrome, thyrotoxicosis, ulceritive colitis, breast cancer, ovarian cancer, lung cancer, colorectal cancer, anal cancer, prostate cancer, kidney cancer, bladder cancer, head and neck cancer, pancreatic cancer, skin cancer, oral cancer, esophageal cancer, vaginal cancer, cervical cancer, cancer of the spleen, testicular cancer, cancer of the thymus, squamous cell carcinoma, small cell lung cancer, non-small cell lung cancer, blastoma, sarcom, adenocarcinoma of the lung, squamous cell carcinoma of the lung, peritoneal carcinoma, dermal cancer, dermal or intraocular melanoma, rectal cancer, perianal cancer, esophageal cancer, small intestine cancer, endocrine gland cancer, parathyroid cancer, adrenal gland cancer, soft tissue sarcoma, urethral cancer, male/female genital tract cancer, nerve cancer, chronic or acute leukemia, lymphocyte lymphoma, hepatoma, stomach cancer, glioblastoma, ovarian cancer, liver cancer, hepatic tumor, colon cancer, large intestine cancer, endometrial cancer, uterine cancer, salivary gland cancer, renal cancer, vulvar cancer, thyroid cancer, gestational diabetes, chronic thromboembolic diseases or disorders associated with fibrin formation including vascular disorders such as deep venous thrombosis, arterial thrombosis, stroke, tumor metastasis, thrombolysis, arteriosclerosis and restenosis following angioplasty, septic shock, septicemia, hypotension, adult respiratory distress syndrome (ARDS), disseminated intravascular coagulopathy (DIC), sarcoidosis, arterial arteriosclerosis, peptic ulcers, burns, pancreatitis, polycystic ovarian disease (POD), endometriosis, uterine fibroid, benign prostate hypertrophy, T-cell acute lymphoblastic leukemia (T-ALL), cerebral autosomal dominant arteriopathy with subcortical infarcts and leukoencephalopathy (CADASIL), tetralogy of Fallot (TOF), Alagille syndrome (AS), macular degeneration and age-related macular degeneration diseases, inflammatory fibrosis (e.g., scleroderma, lung fibrosis, and cirrhosis), osteoarthritis, osteoporosis, asthma (including allergic asthma), allergies, chronic obstructive pulmonary disease (COPD), juvenile early-onset Type I diabetes, transplant rejection, and SLE.

In one embodiment, the present disclosure provides methods for treating or preventing rheumatoid arthritis, psoriasis, osteoporosis, stroke, liver disease, or oral cancer to a subject in need thereof, the method comprising administering to the subject a FIT-Ig binding protein described herein, wherein the binding protein is capable of binding IL-17 and IL-20. In a further embodiment, the FIT-Ig binding protein comprises an amino acid sequence selected from SEQ ID NOs: 15, 25, and 27; and amino acid sequence according to SEQ ID NO: 21; and an amino acid sequence according to SEQ ID NO: 23. In another embodiment, the FIT-Ig binding protein comprises an amino acid sequence selected from SEQ ID NOs: 15, 25, and 27; and an amino acid sequence selected from SEQ ID NOs: 29, 30 and 31.

In one embodiment, the present disclosure provides methods for treating or preventing a B cell cancer in a subject in need thereof, the method comprising administering to the subject a FIT-Ig binding protein, wherein the FIT-Ig binding protein is capable of binding one or more B cell antigen. In a further embodiment, the FIT-Ig binding protein is capable of binding CD20. In a further embodiment, the FIT-Ig binding protein is capable of binding CD20 and another antigen. In a further embodiment, the binding protein is capable of binding CD3 and CD20. In a further embodiment, the cancer is a B cell cancer. In a still further embodiment, the B cell cancer is selected from the group consisting of Hodgkin's lymphoma, non-Hodgkin's lymphoma [NHL], precursor B cell lymphoblastic leukemia/lymphoma, mature B cell neoplasms, B cell chronic lymphocytic leukemia/small lymphocytic lymphoma, B cell prolymphocytic leukemia, lymphoplasmacytic lymphoma, mantle cell lymphoma, follicular lymphoma, cutaneous follicle center lymphoma, marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma. In one embodiment, the present disclosure provides methods for treating or preventing a B cell cancer in a subject in need thereof, the method comprising administering to the subject a FIT-Ig binding protein, wherein the FIT-Ig binding protein comprises an amino acid sequence according to SEQ ID NOs: 41 or 48; and amino acid sequence according to SEQ ID NO: 44, and an amino acid sequence according to SEQ ID NO: 46.

In one embodiment, the present disclosure provides methods for treating or preventing an autoimmune disease, inflammatory disease, or infection in a subject in need thereof, the method comprising administering to the subject a FIT-Ig binding protein described herein, wherein the binding protein is capable of binding TNF and IL-17. In a further embodiment, the FIT-Ig binding protein comprises sequences according to SEQ ID NOs: 87, 89, and 91. In another embodiment, the present disclosure provides methods for treating or preventing an autoimmune or inflammatory disease, the method comprising administering to the subject a FIT-Ig binding protein, wherein the binding protein is capable of binding TNF and IL-17, and wherein the autoimmune or inflammatory disease is selected from the group consisting of Crohn's disease, psoriasis (including plaque psoriasis), arthritis (including rheumatoid arthritis, psoratic arthritis, osteoarthritis, or juvenile idiopathic arthritis), multiple sclerosis, ankylosing spondylitis, spondylosing arthropathy, systemic lupus erythematosus, uveitis, sepsis, neurodegenerative diseases, neuronal regeneration, spinal cord injury, primary and metastatic cancers, a respiratory disorder; asthma; allergic and nonallergic asthma; asthma due to infection; asthma due to infection with respiratory syncytial virus (RSV); chronic obstructive pulmonary disease (COPD); a condition involving airway inflammation; eosinophilia; fibrosis and excess mucus production; cystic fibrosis; pulmonary fibrosis; an atopic disorder; atopic dermatitis; urticaria; eczema; allergic rhinitis; allergic enterogastritis; an inflammatory and/or autoimmune condition of the skin; an inflammatory and/or autoimmune condition of gastrointestinal organs; inflammatory bowel diseases (IBD); ulcerative colitis; an inflammatory and/or autoimmune condition of the liver; liver cirrhosis; liver fibrosis; and liver fibrosis caused by hepatitis B and/or C virus; scleroderma. In another embodiment, In another embodiment, the present disclosure provides methods for treating or preventing cancer in a subject in need thereof, the method comprising administering to the subject a FIT-Ig binding protein described herein, wherein the binding protein is capable of binding TNF and IL-17. In a further embodiment, the cancer is hepatocellular carcinoma; glioblastoma; lymphoma; or Hodgkin's lymphoma. In another embodiment, the present disclosure provides methods for treating or preventing and infection in a subject in need thereof, the method comprising administering to the subject a FIT-Ig binding protein described herein, wherein the infection is a viral infection, a bacterial infection, a parasitic infection, HTLV-1 infection. In one embodiment, the present disclosure provides methods for suppression of expression of protective type 1 immune responses, and suppression of expression of a protective type 1 immune response during vaccination.

In one embodiment, the present disclosure provides methods for treating rheumatoid arthritis in a subject in need thereof, the method comprising administering to the subject a FIT-Ig binding protein, wherein the binding protein comprises sequences according to SEQ ID NOs: 87, 89, and 91.

In one embodiment, the present disclosure provides methods for treating or preventing cancer in a subject in need thereof, the method comprising administering to the subject a FIT-Ig binding protein described herein, wherein the binding protein is capable of binding CTLA-4 and PD-1. In a further embodiment, the FIT-Ig binding protein comprises an amino acid sequence comprising SEQ ID NOs: 92, 95, and 97. In another embodiment, the present disclosure provides methods for treating or preventing cancer in a subject in need thereof, wherein the binding protein is capable of binding CTLA-4 and PD-1, and wherein the cancer is a cancer typically responsive to immunotherapy. In another embodiment, the cancer is a cancer that has not been associated with immunotherapy. In another embodiment, the cancer is a cancer that is a refractory or recurring malignancy. In another embodiment, the binding protein inhibits the growth or survival of tumor cells. In another embodiment, the cancer is selected from the group consisting of melanoma (e.g., metastatic malignant melanoma), renal cancer (e.g. clear cell carcinoma), prostate cancer (e.g. hormone refractory prostate adenocarcinoma), pancreatic adenocarcinoma, breast cancer, colon cancer, lung cancer (e.g. non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies.

In one embodiment, the present disclosure provides methods for treating or preventing melanoma in a subject in need thereof, the method comprising administering to the subject a FIT-Ig binding protein described herein, wherein the binding protein is capable of binding CTLA-4 and PD-1. In a further embodiment, the present disclosure provides methods for treating or preventing melanoma in a subject in need thereof, wherein the method comprises administering to the subject a FIT-Ig binding protein comprising amino acid sequences according to SEQ ID NOs: 92, 95, and 97.

In another embodiment, the present disclosure provides methods for treating or preventing infections or infectious disease in a subject in need thereof, the method comprising administering to the subject a FIT-Ig binding protein described herein, wherein the binding protein is capable of binding CTLA-4 and PD-1. In one embodiment, the FIT-Ig binding protein is administered alone, or in combination with vaccines, to stimulate the immune response to pathogens, toxins, and self-antigens. Therefore, in one embodiment, the binding proteins provided herein can be used to stimulate immune response to viruses infectious to humans, such as, but not limited to, human immunodeficiency viruses, hepatitis viruses class A, B and C, Epstein Barr virus, human cytomegalovirus, human papilloma viruses, herpes viruses, bacteria, fungal parasites, or other pathogens.

BRIEF DESCRIPTION OF THE DRAWINGS

FIG. 7a), FIT13a-Ig (cMet/EGFR; FIG. 7b), FIT14-Ig (Factor IXa/Factor X; FIG. 7c), FIT16a-Ig (Her3/IGF-1R; FIG. 7d), FIT17a-Ig (DLL-4/VEGF; FIG. 7e), FIT18a-Ig (CD20/CD3; FIG. 7f), FIT19a-Ig (Her3/EGFR; FIG. 7g), FIT20a-Ig (PD-1/PD-L1; FIG. 7h), and FIT22a-Ig (Her3/PD-1; FIG. 7i).

FIG. 18A (right panel) shows dual binding to MKN-45 cell as measured by a BD FACSVerse flow cytometer. FIG. 18A (left panel) indicates that in MKN-45 cell, membrane expression level c-Met is much higher than EGFR, so c-Met binding cite of FIT013a and FIT013a-Fab can be occupied by membrane c-Met, the free EGFR binding cite of FIT013a and FIT013a-Fab can be detected by biotinylated EGFR. FIG. 18B (right panel) shows dual binding to SGC-7901 cell as measured by a BD FACSVerse flow cytometer. FIG. 18B (left panel) indicates that in SGC-7901 cell, membrane expression level EGFR is much higher than c-Met, so EGFR binding cite of FIT013a and FIT013a-Fab can be occupied by membrane EGFR, the free c-Met binding cite of FIT013a and FIT013a-Fab can be detected by biotinylated c-Met. FIG. 18C (right panel) shows dual binding to NCI-H1975 cell as measured by a BD FACSVerse flow cytometer. FIG. 18C (left panel) indicates that in NCI-H1975 cell, membrane expression level c-Met is equal to EGFR, so c-Met and EGFR binding cites of FIT013a and FIT013a-Fab are occupied simultaneously, and no free EGFR or c-Met binding cite of FIT013a and FIT013a-Fab can be detected.

DETAILED DESCRIPTION

Figure 1A:
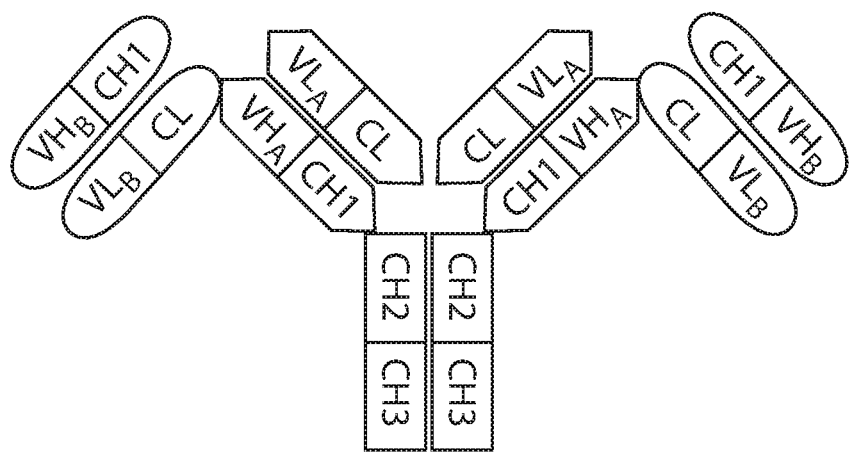
FIG. 1A shows the structure of FIT-Igs that are made up of three constructs, such as FIT1-Ig, FIT2-Ig, and FIT3-Ig.

The present invention relates to multivalent and multi-specific binding proteins, methods of making the binding proteins, and to their uses in the prevention and/or treatment of acute and chronic inflammatory diseases and disorders, cancers, and other diseases. This invention pertains to multivalent and/or multispecific binding proteins capable of binding two or more antigens. Specifically, the invention relates to Fabs-in-tandem immunoglobulins (FIT-Ig), and pharmaceutical compositions thereof, as well as nucleic acids, recombinant expression vectors and host cells for making such FIT-Igs. Methods of using the FIT-Igs of the invention to detect specific antigens, either in vitro or in vivo are also encompassed by the invention.

The novel family of binding proteins provided herein are capable of binding two or more antigens, e.g., with high affinity. Specifically, the present invention provides an approach to construct a bispecific binding protein using 2 parental monoclonal antibodies: mAb A, which binds to antigen a; and mAb B, which binds to antigen b.

In one aspect, the present invention provides a binding protein comprising a variable light chain specific for a first antigen or epitope, a first light chain constant domain, a variable heavy chain specific for a second antigen or epitope, a first heavy chain CH1, a variable heavy chain specific for the first antigen or epitope, a second heavy chain CH1, a variable heavy chain specific for the second antigen or epitope, and a second light chain constant domain. In one embodiment, the binding protein further comprises an Fc region. The binding protein may further comprise one or more amino acid or polypeptide linker linking two or more of the components of the binding protein. For example, the binding protein may comprise a polypeptide linker linking the light chain variable region to the light chain constant region.

In one embodiment, the present disclosure provides a binding protein comprising a polypeptide chain comprising $VL_A$-CL-(X1)n-$VH_B$-CH1-(X2)n, wherein $VL_A$ is the light chain variable domain of mAb A, CL is a light chain constant domain, X1 represents an amino acid or an oligopeptide linker, $VH_B$ is the heavy chain variable domain of mAb B, CH1 is the first constant domain of the heavy chain, X2 represents an Fc region or a different dimerization domain, and n is 0 or 1.

In one embodiment, the invention provides a binding protein comprising three different polypeptide chains (FIG. 1), wherein the first polypeptide chain (construct #1) comprises $VL_A$-CL-(X1)n-$VH_B$-CH1-(X2)n, wherein $VL_A$ is the light chain variable domain of mAb A, CL is a light chain constant domain, X1 represents an amino acid or an oligopeptide linker, $VH_B$ is the heavy chain variable domain of mAb B, CH1 is the first constant domain of the heavy chain, X2 represents an Fc region or a different dimerization domain, and n is 0 or 1. The second polypeptide chain (construct #2) comprises $VH_A$-CH1, wherein $VH_A$ is the heavy chain variable domain of mAb A, and CH1 is the first constant domain of the heavy chain. The third polypeptide chain (construct #3) comprises $VL_B$-CL, wherein $VL_B$ is the light chain variable domain of mAb B, and CL is the constant domain of the light chain.

In another embodiment, the invention provides a binding protein comprising three different polypeptide chains with the overall molecular design similar to the previous embodiment except the order of the variable domains are reversed. In the embodiment the first polypeptide chain comprises $VH_B$-CH1-(X1)n-$VL_A$-CL-(X2)n, wherein $VL_A$ is a light chain variable domain of mAb A, CL is a light chain constant domain, X1 represents an amino acid or an oligopeptide linker, $VH_B$ is the heavy chain variable domain of mAb B, CH1 is the first constant domain of the heavy chain, X2 represents an Fc region or a different dimerization domain, and n is 0 or 1. The second polypeptide chain comprises $VH_A$-CH1, wherein $VH_A$ is the heavy chain variable domain of mAb A and CH1 is the first constant domain of the heavy chain. The third polypeptide chain comprises $VL_B$-CL, wherein $VL_B$ is the light chain variable domain of mAb B and CL is the constant domain of the light chain.

In another embodiment the invention provides a binding protein comprising two different polypeptide chains (FIG. 2), wherein the first polypeptide chain (construct #1) comprises $VL_A$-CL-(X1)n-$VH_B$-CH1-(X2)n, wherein $VL_A$ is a light chain variable domain of mAb A, CL is a light chain constant domain, X1 represents an amino acid or an oligopeptide linker, $VH_B$ is the heavy chain variable domain of mAb B, CH1 is the first constant domain of the heavy chain, X2 represents an Fc region or a different dimerization domain, and n is 0 or 1. The second polypeptide chain (construct #4) comprises $VH_A$-CH1-(X3)n-$VL_B$-CL, wherein $VH_A$ is the heavy chain variable domain of mAb A, CH1 is the first constant domain of the heavy chain, X3 represents an amino acid or polypeptide that is not a constant domain, n is 0 or 1, $VL_B$ is the light chain variable domain of mAb B, and CL is the constant domain of the light chain.

In another embodiment the invention provides a binding protein comprising two polypeptide chains with the overall molecular design similar to the previous embodiment except the order of the variable domains are reversed. In this embodiment the first polypeptide chain comprises $VH_B$-CH1-(X1)n-$VL_A$-CL-(X2)n, wherein $VL_A$ is a light chain variable domain of mAb A, CL is a light chain constant domain, X1 represents an amino acid or an oligopeptide linker, $VH_B$ is the heavy chain variable domain of mAb B, CH1 is the first constant domain of the heavy chain, X2 represents an Fc region or a different dimerization domain, and n is 0 or 1. The second polypeptide chain comprises $VL_B$-CL-(X3)n-$VH_A$-CH1, wherein $VH_A$ is the heavy chain variable domain of mAb A, CH1 is the first constant domain of the heavy chain, X3 represents an amino acid or an oligopeptide linker, n is 0 or 1, $VL_B$ is the light chain variable domain of mAb B, and CL is the constant domain of the light chain.

In one embodiment, the VH and VL domains in the binding protein are selected from the group consisting of murine heavy/light chain variable domains, fully human heavy/light chain variable domains, CDR grafted heavy/light chain variable domains, humanized heavy/light chain variable domains, and mixtures thereof. In a preferred embodiment $VH_A/VL_A$ and $VH_B/VL_B$ are capable of binding the same antigen. In another embodiment $VH_A/VL_A$ and $VH_B/VL_B$ are capable of binding different antigens.

In one embodiment, the first polypeptide chain comprises $VL_A$-CL-$VH_B$-CH1-Fc, and the CL and $VH_B$ of the first polypeptide chain are directly fused together. In another embodiment, the CL and $VH_B$ are linked by an amino acid or an oligopeptide linker. In another embodiment, the first polypeptide chain comprises $VH_B$-CH1-$VL_A$-CL-Fc, and the CH1 and $VL_A$ are directly fused together. In another embodiment, the CH1 and $VL_A$ are linked by an amino acid or an oligopeptide linker. In a further embodiment, the oligo- or poly-peptide linker comprises 1 or more amino acids of any reasonable sequence that provides flexibility. Preferably the linker is selected from the group consisting of G, GS, SG, GGS, GSG, SGG, GGG, GGGS (SEQ ID NO: 489), SGGG (SEQ ID NO: 490), GGGGS (SEQ ID NO: 491), GGGGSGS (SEQ ID NO: 492), GGGGSGGS (SEQ ID NO: 493), GGGGSGGGGS (SEQ ID NO: 494), GGGGSGGGGSGGGGS (SEQ ID NO: 495), AKTTPKLEEGEFSEAR (SEQ ID NO: 496), AKTTPKLEEGEFSEARV (SEQ ID NO: 497), AKTTPKLGG (SEQ ID NO: 498), SAKTTPKLGG (SEQ ID NO: 499), SAKTTP (SEQ ID NO: 500), RADAAP (SEQ ID NO: 501), RADAAPTVS (SEQ ID NO: 502), RADAAAAGGPGS (SEQ ID NO: 503), RADAAAA ($G_4S$)$_4$ (SEQ ID NO: 504), SAKTTPKLEEGEFSEARV (SEQ ID NO: 505), ADAAP (SEQ ID NO: 506), ADAAPTVSIFPP (SEQ ID NO: 507), TVAAP (SEQ ID NO: 508), TVAAPSVFIFPP (SEQ ID NO: 509), QPKAAP (SEQ ID NO: 510), QPKAAPSVTLFPP (SEQ ID NO: 511), AKTTPP (SEQ ID NO: 512), AKTTPPSVTPLAP (SEQ ID NO: 513), AKTTAPSVYPLAP (SEQ ID NO: 514), ASTKGP (SEQ ID NO: 515), ASTKGPSVFPLAP (SEQ ID NO: 516), GENKVEYAPALMALS (SEQ ID NO: 517), GPAKELTPLKEAKVS (SEQ ID NO: 518), GHEAAAVMQVQYPAS (SEQ ID NO: 519), and AKTTAP (SEQ ID NO: 80). In one embodiment, the amino acid sequence of the linker may be selected from the group consisting of SEQ ID NOs. 26, 28, and 49-86. In one embodiment, the linker is GSG (SEQ ID NO: 26) or GGGGSGS (SEQ ID NO: 28). The linkers can also be in vivo cleavable peptide linkers, protease (such as MMPs) sensitive linkers, disulfide bond-based linkers that can be cleaved by reduction, etc., as previously described (Fusion Protein Technologies for Biopharmaceuticals: Applications and Challenges, edited by Stefan R. Schmidt), or any cleavable linkers known in the art. Such cleavable linkers can be used to release the top Fab in vivo for various purposes, in order to improve tissue/cell penetration and distribution, to enhance binding to targets, to reduce potential side effect, as well as to modulate in vivo functional and physical half-life of the 2 different Fab regions. In one embodiment, the binding protein comprises an Fc region. As used herein, the term "Fc region" refers to the C-terminal region of an IgG heavy chain. An example of the amino acid sequence containing the human IgG1 Fc region is SEQ ID NO: 20. The Fc region of an IgG comprises two constant domains, CH2 and CH3.

In one embodiment, the Fc region is a variant Fc region. In one embodiment, the variant Fc region has one or more amino acid modifications, such as substitutions, deletions, or insertions, relative to the parent Fc region. In a further embodiment, amino acid modifications of the Fc region alter the effector function activity relative to the parent Fc region activity. For example, in one embodiment, the variant Fc region may have altered (i.e., increased or decreased) antibody-dependent cytotoxicity (ADCC), complement-mediated cytotoxicity (CDC), phagocytosis, opsonization, or cell binding. In another embodiment, amino acid modifications of the Fc region may alter (i.e., increase or decrease) the affinity of the variant Fc region for an FcγR relative to the parent Fc region. For example, the variant Fc region may alter the affinity for FcγRI, FcγRII, FcγRIII.

In one preferred embodiment, the binding proteins provided herein are capable of binding one or more targets. In one embodiment, the target is selected from the group consisting of cytokines, cell surface proteins, enzymes and receptors. Preferably the binding protein is capable of modulating a biological function of one or more targets. More preferably the binding protein is capable of neutralizing one or more targets.

In one embodiment, the binding protein of the invention is capable of binding cytokines selected from the group consisting of lymphokines, monokines, and polypeptide hormones. In a further embodiment, the binding protein is capable of binding pairs of cytokines selected from the group consisting of IL-1α and IL-1β; IL-12 and IL-18, TNFα and IL-23, TNFα and IL-13; TNF and IL-18; TNF and IL-12; TNF and IL-1beta; TNF and MIF; TNF and IL-6, TNF and IL-6 Receptor, TNF and IL-17; IL-17 and IL-20; IL-17 and IL-23; TNF and IL-15; TNF and VEGF; VEGFR and EGFR; IL-13 and IL-9; IL-13 and IL-4; IL-13 and IL-5; IL-13 and IL-25; IL-13 and TARC; IL-13 and MDC; IL-13 and MIF; IL-13 and TGF-β; IL-13 and LHR agonist; IL-13 and CL25; IL-13 and SPRR2a; IL-13 and SPRR2b; IL-13 and ADAM8; and TNFα and PGE4, IL-13 and PED2, TNF and PEG2.

In another embodiment, the binding protein of the invention is capable of binding pairs of targets selected from the group consisting of CD137 and CD20, CD137 and EGFR, CD137 and Her-2, CD137 and PD-1, CD137 and PDL-1, VEGF and PD-L1, Lag-3 and TIM-3, OX40 and PD-1, TIM-3 and PD-1, TIM-3 and PDL-1, EGFR and DLL-4, VEGF and EGFR, HGF and VEGF, VEGF and VEGF (same or a different epitope), VEGF and Ang2, EGFR and cMet, PDGF and VEGF, VEGF and DLL-4, OX40 and PD-L1, ICOS and PD-1, ICOS and PD-L1, Lag-3 and PD-1, Lag-3 and PD-L1, Lag-3 and CTLA-4, ICOS and CTLA-4, CD138 and CD20; CD138 and CD40; CD19 and CD20; CD20 and CD3; CD3 and CD33; CD3 and CD133; CD38 & CD138; CD38 and CD20; CD20 and CD22; CD38 and CD40; CD40 and CD20; CD47 and CD20, CD-8 and IL-6; CSPGs and RGM A; CTLA-4 and BTNO2; CTLA-4 and PD-1; IGF1 and IGF2; IGF1/2 and Erb2B; IGF-1R and EGFR; EGFR and CD13; IGF-1R and ErbB3; EGFR-2 and IGFR; Her2 and Her2 (same or a different epitope); Factor IXa and Factor X, VEGFR-2 and Met; VEGF-A and Angiopoietin-2 (Ang-2); IL-12 and TWEAK; IL-13 and IL-1beta; MAG and RGM A; NgR and RGM A; NogoA and RGM A; OMGp and RGM A; PDL-1 and CTLA-4; PD-1 and CTLA-4, PD-1 and TIM-3; RGM A and RGM B; Te38 and TNFα; TNFα and Blys; TNFα and CD-22; TNFα and CTLA-4 domain; TNFα and GP130; TNFα and IL-12p40; TNFα and RANK ligand; EGFR and PD-L1; EGFR and cMet; Her3 and IGF-IR; DLL-4 and VEGF; PD-1 and PD-L1; Her3 and PD-1, Her3 and EGFR, cMet and PD-L1, and BTLA and PD-1.

In some embodiments, the binding proteins contain variable regions or CDRs derived from CD20 antibodies including, but not limited to, ofatumumab, rituximab, iodine i 131 tositumomab, obinutuzumab, ibritumomab, and those described in U.S. Pat. Nos. 9,228,008, 8,206,711, 7,682,612, 8,562,992, 7,799,900, 7,422,739, 7,850,962, 8,097,713, 8,057,793, 8,592,156, 6,652,852, 6,893,625, 6,120,767, 8,084,582, 8,778,339, 9,184,781, 7,381,560, 8,101,179, 9,382,327, 7,151,164, 7,435,803, 8,529,902, 9,416,187, 7,812,116, 8,329,181, 8,034,902, 9,289,479, 9,234,045, 4,987,084, 9,173,961, 9,175,086, 6,410,319, each of which is incorporated by reference in its entirety.

In some embodiments, the binding proteins contain variable regions or CDRs derived from CD3 antibodies including, but not limited to, muromonab-CD3, otelixizumab, teplizumab and visilizumab, and those described in U.S. Pat. Nos. 8,569,450, 7,635,472,5585097, 6706265, 5834597, 9056906, 9486475, 7728114, 8551478, 9226962, 9192665, 9505849, 8394926, 6306575, 5795727, 8840888, 5627040, 9249217, 8663634, 6491917, 5877299, each of which is incorporated by reference in its entirety.

In some embodiments, the binding proteins contain variable regions or CDRs derived from CTLA-4 antibodies including, but not limited to, ipilimumab and those described in U.S. Pat. Nos. 5,434,131, 5,968,510, 5,844,095, 7,572,772, 6,090,914, 7,311,910, 5,885,796, 5,885,579, 5,770,197, 5,851,795, 5,977,318, 7,161,058, 6,875,904, 7,504,554, 7,034,121, 6,719,972, 7,592,007, each of which is incorporated by reference in its entirety.

In some embodiments, the binding proteins contain variable regions or CDRs derived from PD-1 antibodies including, but are not limited to, pembrolizumab, nivolumab, atezolizumab, and those described in U.S. Pat. Nos. 8,741,295, 7,029,674, 7,722,868, 9,243,052, 8,927,697, 9,181,342, 8,552,154, 9,102,727, 9,220,776, 9,084,776, 8,008,449, 9,387,247, 9,492,540, 8,779,105, 9,358,289, 9,492,539, 9,205,148, 8,900,587, 8,952,136, 8,460,886, 7,414,171, 8,287,856, 8,580,247, 7,488,802, 7,521,051, 8,088,905, 7,709,214, 8,617,546, 9,381,244, 8,993,731, 8,574,872, 7,432,059, 8,216,996, 9,499,603, 9,102,728, 9,212,224, each of which is incorporated by reference in its entirety.

In some embodiments, the binding proteins contain variable regions or CDRs derived from PD-L1 antibodies including, but not limited to, durvalumab, avelumab, and those described in U.S. Pat. Nos. 8,741,295, 9,102,725, 8,168,179, 8,952,136, 8,552,154, 8,617,546, 9,212,224, 8,217,149, 8,383,796, each of which is incorporated by reference in its entirety.

In some embodiments, the binding proteins contain variable regions or CDRs derived from EGFR antibodies including, but not limited to, gefitinib, erlotinib, lapatinib, cetuximab, panitumumab, vandetanib, necitumumab, osimertinib, and those described in U.S. Pat. Nos. 7,723,484, 9,044,460, 9,226,964, 8,658,175, 7,618,631, 8,748,175, 9,499,622, 9,527,913, 9,493,568, 8,580,263, 7,514,240, 9,314,536, 9,051,370, 9,233,171, 9,029,513, 8,592,152, 8,597,652, 9,327,035, 8,628,773, 9,023,356, 9,132,192, 8,637,026, 9,283,276, 9,540,440, 9,545,442, 8,758,756, 9,120,853, 7,981,605, 8,546,107, 7,598,350, 5,212,290, 8,017,321, 7,589,180, 9,260,524, 8,790,649, 9,125,896, 9,238,690, 8,071,093, each of which is incorporated by reference in its entirety.

In some embodiments, the binding proteins contain variable regions or CDRs derived from TIM3 (CD366) antibodies including, but not limited to, 4C4G3, 7D3, B8.2C12, F38-2E2, and those described in U.S. Pat. Nos. 8,841,418, 8,552,156, 9,556,270, each of which is incorporated by reference in its entirety.

In some embodiments, the binding proteins contain variable regions or CDRs derived from cMet antibodies including, but not limited to, h1332, 71-8000, ab74217, and those described in U.S. Pat. Nos. 8,673,302, 9,120,852, 7,476,724, 7,892,550, 9,249,221, 9,535,055, 9,487,589, 8,329,173, 9,101,610, 8,101,727, 9,068,011, 9,260,531, 9,296,817, 8,481,689, 8,546,544, 8,563,696, 8,871,909, 8,889,832, 8,871,910, 9,107,907, 8,747,850, 9,469,691, 8,765,128, 8,729,249, 8,741,290, 8,637,027, 8,900,582, 9,192,666, 9,201,074, 9,505,843, 8,821,869, 8,163,280, 7,498,420, 8,562,985, 8,545,839, 9,213,031, 9,213,032, 8,217,148, 8,398,974, 9,394,367, 9,364,556, 8,623,359, 9,011,865, 9,375,425, 9,233,155, 9,169,329, 9,150,655, each of which is incorporated by reference in its entirety.

In some embodiments, the binding proteins contain variable regions or CDRs derived from Factor IXa antibodies including, but not limited to, ab97619, ab128048, ab128038, and those described in U.S. Pat. Nos. 7,279,161, 7,033,590, 4,786,726, 6,624,295, 7,049,411, 7,297,336, each of which is incorporated by reference in its entirety.

In some embodiments, the binding proteins contain variable regions or CDRs derived from Factor X antibodies including, but not limited to, PA5-22059, ab97632, B122M.

In some embodiments, the binding proteins contain variable regions or CDRs derived from Her3 (ErbB3) antibodies including, but not limited to, duligotumab, elgemtumab, lumretuzumab, patritumab, seribantumab, and those described in U.S. Pat. Nos. 9,346,883, 9,321,839, 8,859,737, 8,362,215, 8,828,388, 9,220,775, 9,217,039, 9,527,913, 9,085,622, 9,192,663, 8,735,551, 9,011,851, 7,846,440, 9,284,380, 8,791,244, 8,691,225, 9,487,588, 8,961,966, 9,034,328, 5,968,511, 9,346,889, 9,217,039, 9,346,890, each of which is incorporated by reference in its entirety.

In some embodiments, the binding proteins contain variable regions or CDRs derived from IGF-1R (CD221) antibodies including, but not limited to cixutumumab, dalotuzumab, figitumumab, ganitumab, robatumumab, teprotumumab, and those described in U.S. Pat. Nos. 7,572,897, 7,579,157, 7,968,093, 7,638,605, 7,329,745, 7,037,498, 7,982,024, 8,642,037, 7,700,742, 9,234,041, 7,815,907, 8,945,871, 8,361,461, 9,056,907, 8,168,410, 7,241,444, 7,914,784, 9,150,644, 7,985,842, 7,538,195, 8,268,617, 8,034,904, 8,344,112, 7,553,485, 8,101,180, 8,105,598, 7,824,681, 8,124,079, 8,420,085, 7,854,930, each of which is incorporated by reference in its entirety.

In some embodiments, the binding proteins contain variable regions or CDRs derived from DLL4 antibodies including, but not limited to demcizumab, enoticumab, navicixizumab, and those described in U.S. Pat. Nos. 9,469,689, 9,115,195, 8,623,358, 9,132,190, 9,469,688, 9,403,904, 8,663,636, 8,192,738, 750,124, each of which is incorporated by reference in its entirety.

In some embodiments, the binding proteins contain variable regions or CDRs derived from VEGF antibodies including, but not limited to Bevacizumab, Brolucizumab, Ranibizumab, and those described in U.S. Pat. Nos. 8,921,537, 7,910,098, 7,365,166, 7,060,269, 7,169,901, 6,884,879, 7,297,334, 7,375,193, 9,388,239, 8,834,883, 8,287,873, 7,998,931, 8,007,799, 7,785,803, 9,102,720, 8,486,397, 6,730,489, 6,383,484, 9,441,034, 7,097,986, 9,079,953, 8,945,552, 8,236,312, 7,740,844, 6,403,088, 9,018,357, 8,975,381, 7,691,977, 7,758,859, 8,512,699, 8,492,527, 9,353,177, 8,092,797, 7,811,785, 8,101,177, 8,592,563, 9,090,684, 8,349,322, each of which is incorporated by reference in its entirety.

In some embodiments, the binding proteins contain variable regions or CDRs derived from CD22 antibodies including, but not limited to bectumomab, epratuzumab, inotuzumab, moxetumomab, pinatuzumab, and those described in U.S. Pat. Nos. 9,181,343, 5,484,892, 9,279,019, 8,591,889, 9,499,632, 8,481,683, 7,355,012, 7,777,019, 8,809,502, 8,389,688, 7,829,086, each of which is incorporated by reference in its entirety.

In some embodiments, the binding proteins contain variable regions or CDRs derived from BTLA(CD272) antibodies including, but not limited to MIH26, AAP44003, MA5-16843, 6A5, and those described in U.S. Pat. Nos. 8,563,694, 9,346,882, 8,580,259, 8,247,537, each of which is incorporated by reference in its entirety.

In some embodiments, the binding proteins contain antibodies as described in WO2015103072, which is herein incorporated by reference in its entirety.

In one embodiment, the binding protein is capable of binding human IL-17 and human IL-20. In a further embodiment, the binding protein is capable of binding human IL-17 and human IL-20 and comprises a FIT-Ig polypeptide chain #1 sequence that is about 65%, about 70%, about 75%, about 80%, about 85%, about 90%, about 95%, about 99%, or 100% identical to a sequence selected from the group consisting of SEQ ID NO. 15, 25, and 27; a polypeptide chain #2 sequence that is about 65%, about 70%, about 75%, about 80%, about 85%, about 90%, about 95%, about 99%, or 100% identical to SEQ ID NO. 21; and a polypeptide chain #3 sequence that is about 65%, about 70%, about 75%, about 80%, about 85%, about 90%, about 95%, about 99%, or 100% identical to SEQ ID NO. 23. In another embodiment, the binding protein is capable of binding human IL-17 and human IL-20 and comprises FIT-Ig polypeptide chain #1 sequence that is about 65%, about 70%, about 75%, about 80%, about 85%, about 90%, about 95%, about 99%, or 100% identical to a sequence selected from the group consisting of SEQ ID NO. 15, 25, and 27; and a polypeptide chain #4 that is about 65%, about 70%, about 75%, about 80%, about 85%, about 90%, about 95%, about 99%, or 100% identical to a sequence selected from the group consisting of SEQ ID NO. 29, 30, and 31.

In one embodiment, the binding protein is capable of binding human CD3 and human CD20. In a further embodiment, the binding protein comprises a FIT-Ig polypeptide chain #1 sequence that is about 65%, about 70%, about 75%, about 80%, about 85%, about 90%, about 95%, about 99%, or 100% identical to a sequence selected from the group consisting of SEQ ID NO. 41, 48 and 316; a polypeptide chain #2 sequence that is about 65%, about 70%, about 75%, about 80%, about 85%, about 90%, about 95%, about 99%, or 100% identical to SEQ ID NO. 44 or SEQ ID NO. 325; and a polypeptide chain #3 sequence that is about 65%, about 70%, about 75%, about 80%, about 85%, about 90%, about 95%, about 99%, or 100% identical to SEQ ID NO. 46 or SEQ ID NO. 330.

In one embodiment, the binding protein is capable of binding human IL-17 and human TNF. In a further embodiment, the binding protein is capable of binding human IL-17 and human TNF and comprises a FIT-Ig polypeptide chain #1 sequence that is about 65%, about 70%, about 75%, about 80%, about 85%, about 90%, about 95%, about 99%, or 100% identical to SEQ ID NO. 87; a polypeptide chain #2 sequence that is about 65%, about 70%, about 75%, about 80%, about 85%, about 90%, about 95%, about 99%, or 100% identical to SEQ ID NO. 89; and a polypeptide chain #3 sequence that is about 65%, about 70%, about 75%, about 80%, about 85%, about 90%, about 95%, about 99%, or 100% identical to SEQ ID NO. 91.

In one embodiment, the binding protein is capable of binding human CTLA-4 and human PD-1. In a further embodiment, the binding protein is capable of binding human CTLA-4 and human PD-1 and comprises a FIT-Ig polypeptide chain #1 sequence that is about 65%, about 70%, about 75%, about 80%, about 85%, about 90%, about 95%, about 99%, or 100% identical to SEQ ID NO. 92, SEQ ID NO. 126, SEQ ID NO. 145, SEQ ID NO. 164, or SEQ ID NO. 183, a polypeptide chain #2 sequence that is about 65%, about 70%, about 75%, about 80%, about 85%, about 90%, about 95%, about 99%, or 100% identical to SEQ ID NO. 95, SEQ ID NO. 135, SEQ ID NO. 154, SEQ ID NO. 173, or SEQ ID NO. 192; and a polypeptide chain #3 sequence that is about 65%, about 70%, about 75%, about 80%, about 85%, about 90%, about 95%, about 99%, or 100% identical to SEQ ID NO. 97, SEQ ID NO. 140, SEQ ID NO. 159, SEQ ID NO. 178, or SEQ ID NO. 197.

In one embodiment, the binding protein is capable of binding EGFR and PD-L1. In a further embodiment, the binding protein is capable of binding EGFR and PD-L1 and comprises a FIT-Ig polypeptide chain #1 sequence that that is about 65%, about 70%, about 75%, about 80%, about 85%, about 90%, about 95%, about 99%, or 100% identical to SEQ ID NO. 99, SEQ ID NO. 202 or SEQ ID NO. 221; a polypeptide chain #2 sequence that is about 65%, about 70%, about 75%, about 80%, about 85%, about 90%, about 95%, about 99%, or 100% identical to SEQ ID NO. 100, SEQ ID NO. 211, or SEQ ID NO. 230; and a polypeptide chain #3 sequence that is about 65%, about 70%, about 75%, about 80%, about 85%, about 90%, about 95%, about 99%, or 100% identical to SEQ ID NO. 101, SEQ ID NO. 216, or SEQ ID NO. 235.

In one embodiment, the binding protein is capable of binding cMet and EGFR. In a further embodiment, the binding protein is capable of binding cMET and EGFR and comprises a FIT-Ig polypeptide chain #1 sequence that that is about 65%, about 70%, about 75%, about 80%, about 85%, about 90%, about 95%, about 99%, or 100% identical to SEQ ID NO. 102 or SEQ ID NO. 240; a polypeptide chain #2 sequence that is about 65%, about 70%, about 75%, about 80%, about 85%, about 90%, about 95%, about 99%, or 100% identical to SEQ ID NO. 103 or SEQ ID NO. 249; and a polypeptide chain #3 sequence that is about 65%, about 70%, about 75%, about 80%, about 85%, about 90%, about 95%, about 99%, or 100% identical to SEQ ID NO. 104 or SEQ ID NO. 254.

In one embodiment, the binding protein is capable of binding Factor IXa and Factor X. In a further embodiment, the binding protein is capable of binding Factor IXa and Factor X and comprises a FIT-Ig polypeptide chain #1 sequence that that is about 65%, about 70%, about 75%, about 80%, about 85%, about 90%, about 95%, about 99%, or 100% identical to SEQ ID NO. 105, or SEQ ID NO. 259; a polypeptide chain #2 sequence that is about 65%, about 70%, about 75%, about 80%, about 85%, about 90%, about 95%, about 99%, or 100% identical to SEQ ID NO. 106 or SEQ ID NO. 268; and a polypeptide chain #3 sequence that is about 65%, about 70%, about 75%, about 80%, about 85%, about 90%, about 95%, about 99%, or 100% identical to SEQ ID NO. 107 or SEQ ID NO. 273.

In one embodiment, the binding protein is capable of binding Her3 and IGF-1R. In a further embodiment, the binding protein is capable of binding Her3 and IGF-1R and comprises a FIT-Ig polypeptide chain #1 sequence that that is about 65%, about 70%, about 75%, about 80%, about 85%, about 90%, about 95%, about 99%, or 100% identical to SEQ ID NO. 108, SEQ ID NO. 278; a polypeptide chain #2 sequence that is about 65%, about 70%, about 75%, about 80%, about 85%, about 90%, about 95%, about 99%, or 100% identical to SEQ ID NO. 109 or SEQ ID NO. 287; and a polypeptide chain #3 sequence that is about 65%, about 70%, about 75%, about 80%, about 85%, about 90%, about 95%, about 99%, or 100% identical to SEQ ID NO. 110 or SEQ ID NO. 292.

In one embodiment, the binding protein is capable of binding DLL-4 and VEGF. In a further embodiment, the binding protein is capable of binding DLL-4 and VEGF and comprises a FIT-Ig polypeptide chain #1 sequence that that is about 65%, about 70%, about 75%, about 80%, about 85%, about 90%, about 95%, about 99%, or 100% identical to SEQ ID NO. 111, or SEQ ID NO. 297; a polypeptide chain #2 sequence that is about 65%, about 70%, about 75%, about 80%, about 85%, about 90%, about 95%, about 99%, or 100% identical to SEQ ID NO. 112, or SEQ ID NO. 306; and a polypeptide chain #3 sequence that is about 65%, about 70%, about 75%, about 80%, about 85%, about 90%, about 95%, about 99%, or 100% identical to SEQ ID NO. 113 or SEQ ID NO. 311.

In one embodiment, the binding protein is capable of binding CD20 and CD3. In a further embodiment, the binding protein is capable of binding CD20 and CD3 and comprises a FIT-Ig polypeptide chain #1 sequence that that is about 65%, about 70%, about 75%, about 80%, about 85%, about 90%, about 95%, about 99%, or 100% identical to SEQ ID NO. 114 or SEQ ID NO. 316; a polypeptide chain #2 sequence that is about 65%, about 70%, about 75%, about 80%, about 85%, about 90%, about 95%, about 99%, or 100% identical to SEQ ID NO. 115 or SEQ ID NO. 325; and a polypeptide chain #3 sequence that is about 65%, about 70%, about 75%, about 80%, about 85%, about 90%, about 95%, about 99%, or 100% identical to SEQ ID NO. 116 or SEQ ID NO. 330.

In one embodiment, the binding protein is capable of binding Her3 and EGFR. In a further embodiment, the binding protein is capable of binding Her3 and EGFR and comprises a FIT-Ig polypeptide chain #1 sequence that that is about 65%, about 70%, about 75%, about 80%, about 85%, about 90%, about 95%, about 99%, or 100% identical to SEQ ID NO. 117, SEQ ID NO. 335, or SEQ ID NO. 354; a polypeptide chain #2 sequence that is about 65%, about 70%, about 75%, about 80%, about 85%, about 90%, about 95%, about 99%, or 100% identical to SEQ ID NO. 118, SEQ ID NO. 344, or SEQ ID NO. 363; and a polypeptide chain #3 sequence that is about 65%, about 70%, about 75%, about 80%, about 85%, about 90%, about 95%, about 99%, or 100% identical to SEQ ID NO. 119, SEQ ID NO. 349, or SEQ ID NO. 368.

In one embodiment, the binding protein is capable of binding PD-1 and PD-L1. In a further embodiment, the binding protein is capable of binding PD-1 and PD-L1 and comprises a FIT-Ig polypeptide chain #1 sequence that that is about 65%, about 70%, about 75%, about 80%, about 85%, about 90%, about 95%, about 99%, or 100% identical to SEQ ID NO. 120 or SEQ ID NO. 373; a polypeptide chain #2 sequence that is about 65%, about 70%, about 75%, about 80%, about 85%, about 90%, about 95%, about 99%, or 100% identical to SEQ ID NO. 121 or SEQ ID NO. 382; and a polypeptide chain #3 sequence that is about 65%, about 70%, about 75%, about 80%, about 85%, about 90%, about 95%, about 99%, or 100% identical to SEQ ID NO. 122 or SEQ ID NO. 387.

In one embodiment, the binding protein is capable of binding Her3 and PD-1. In a further embodiment, the binding protein is capable of binding Her3 and PD-1 and comprises a FIT-Ig polypeptide chain #1 sequence that that is about 65%, about 70%, about 75%, about 80%, about 85%, about 90%, about 95%, about 99%, or 100% identical to SEQ ID NO. 123 or SEQ ID NO. 411; a polypeptide chain #2 sequence that is about 65%, about 70%, about 75%, about 80%, about 85%, about 90%, about 95%, about 99%, or 100% identical to SEQ ID NO. 124 or SEQ ID NO. 420; and a polypeptide chain #3 sequence that is about 65%, about 70%, about 75%, about 80%, about 85%, about 90%, about 95%, about 99%, or 100% identical to SEQ ID NO. 125 or SEQ ID NO. 425.

In one embodiment, the binding protein is capable of binding cMet and PD-L1. In a further embodiment, the binding protein is capable of binding cMet and PD-L1 and comprises a FIT-Ig polypeptide chain #1 sequence that that is about 65%, about 70%, about 75%, about 80%, about 85%, about 90%, about 95%, about 99%, or 100% identical to SEQ ID NO. 430; a polypeptide chain #2 sequence that is about 65%, about 70%, about 75%, about 80%, about 85%, about 90%, about 95%, about 99%, or 100% identical to SEQ ID NO. 439; and a polypeptide chain #3 sequence that is about 65%, about 70%, about 75%, about 80%, about 85%, about 90%, about 95%, about 99%, or 100% identical to SEQ ID NO. 444.

In one embodiment, the binding protein is capable of binding BTLA and PD-1. In a further embodiment, the binding protein is capable of binding BTLA and PD-1 and comprises a FIT-Ig polypeptide chain #1 sequence that that is about 65%, about 70%, about 75%, about 80%, about 85%, about 90%, about 95%, about 99%, or 100% identical to SEQ ID NO. 449 or SEQ ID NO. 468; a polypeptide chain #2 sequence that is about 65%, about 70%, about 75%, about 80%, about 85%, about 90%, about 95%, about 99%, or 100% identical to SEQ ID NO. 458 or SEQ ID NO. 477; and a polypeptide chain #3 sequence that is about 65%, about 70%, about 75%, about 80%, about 85%, about 90%, about 95%, about 99%, or 100% identical to SEQ ID NO. 463 or SEQ ID NO. 482.

In one embodiment, the binding protein is capable of binding CD20 and CD22. In a further embodiment, the binding protein is capable of binding CD20 and CD22 and comprises a FIT-Ig polypeptide chain #1 sequence that that is about 65%, about 70%, about 75%, about 80%, about 85%, about 90%, about 95%, about 99%, or 100% identical to SEQ ID NO. 392; a polypeptide chain #2 sequence that is about 65%, about 70%, about 75%, about 80%, about 85%, about 90%, about 95%, about 99%, or 100% identical to SEQ ID NO. 401; and a polypeptide chain #3 sequence that is about 65%, about 70%, about 75%, about 80%, about 85%, about 90%, about 95%, about 99%, or 100% identical to SEQ ID NO. 406.

Biologically active variants or functional variants of the exemplary binding proteins described herein are also a part of the present invention. As used herein, the phrase "a biologically active variant" or "functional variant" with respect to a protein refers to an amino acid sequence that is altered by one or more amino acids with respect to a reference sequence, while still maintains substantial biological activity of the reference sequence. The variant can have "conservative" changes, wherein a substituted amino acid has similar structural or chemical properties, e.g., replacement of leucine with isoleucine. The following table shows exemplary conservative amino acid substitutions. In some embodiments, the variant has one or more amino acid substitutions, wherein one or more or all substitutions are acidic amino acid, such as Aspartic acid, Asparagine, Glutamc acid, or Glutamine.

| Original Residue | Very Highly - Conserved Substitutions | Highly Conserved Substitutions (from the Blosum90 Matrix) | Conserved Substitutions (from the Blosum65 Matrix) |
| --- | --- | --- | --- |
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software.

Binding proteins that are capable of binding the same epitopes on a given group of targets as that of an exemplary bispecific binding protein described herein are also a part of the present invention. The epitopes can be linear epitopes, conformational epitopes, or a mixture thereof. In some embodiments, such same epitopes can be identified by a suitable epitope mapping technique, including but not limited to, X-ray co-crystallography, array-based oligo-peptide scanning, site-directed mutagenesis, high throughput mutagenesis mapping, bacteriophage surface display, and hydrogen-deuterium exchange. Additional methods are described in U.S. Pat. Nos. 5,955,264, 65,796,676, 6,984,488, and 8,802,375, each of which is incorporated by reference in its entirety for all purposes.

In another embodiment, the binding protein of the invention is capable of binding one or two cytokines, cytokine-related proteins, and cytokine receptors selected from the group consisting of BMP1, BMP2, BMP3B (GDF10), BMP4, BMP6, BMP8, CSF1 (M-CSF), CSF2 (GM-CSF), CSF3 (G-CSF), EPO, FGF1 (aFGF), FGF2 (bFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, IGF1, IGF2, IFNA1, IFNA2, IFNA4, IFNA5, IFNA6, IFNA7, IFNB1, IFNG, IFNW1, FIL1, FIL1 (EPSILON), FIL1 (ZETA), IL1A, IL1B, IL2, IL3, IL4, IL5, IL6, IL7, IL8, IL9, IL10, IL11, IL12A, IL12B, IL13, IL14, IL15, IL16, IL17, IL17B, IL18, IL19, IL20, IL22, IL23, IL24, IL25, IL26, IL27, IL28A, IL28B, IL29, IL30, PDGFA, FGER1, FGFR2, FGFR3, EGFR, ROR1, 2B4, KIR, CD137, CD27, OX40, CD40L, A2aR, CD48, B7-1, B7-2, ICOSL, B7-H3, B7-H4, CD137L, OX40L, CD70, CD40, PDGFB, TGFA, TGFB1, TGFB2, TGFB3, LTA (TNF-b), LTB, TNF (TNF-a), TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TNFSF10 (TRAIL), TNFSF11 (TRANCE), TNFSF12 (APO3L), TNFSF13 (April), TNFSF13B, TNFSF14 (HVEM-L), TNFSF15 (VEGI), TNFSF18, FIGF (VEGFD), VEGF, VEGFB, VEGFC, IL1R1, IL1R2, IL1RL1, IL1RL2, IL2RA, IL2RB, IL2RG, IL3RA, IL4R, IL5RA, IL6R, IL7R, IL8RA, IL8RB, IL9R, IL10RA, IL10RB, IL11RA, IL12RB1, IL12RB2, IL13RA1, IL13RA2, IL15RA, IL17R, IL18R1, IL20RA, IL21R, IL22R, IL1HY1, IL1RAP, IL1RAPL1, IL1RAPL2, IL1RN, IL6ST, IL18BP, IL18RAP, IL22RA2, AIF1, HGF, LEP (leptin), PTN, and THPO.

The binding protein of the invention is capable of binding one or more chemokines, chemokine receptors, and chemokine-related proteins selected from the group consisting of CCL1 (1-309), CCL2 (MCP-1/MCAF), CCL3 (MIP-1a), CCL4 (MIP-1b), CCL5 (RANTES), CCL7 (MCP-3), CCL8 (mcp-2), CCL11 (eotaxin), CCL13 (MCP-4), CCL15 (MIP-1d), CCL16 (HCC-4), CCL17 (TARC), CCL18 (PARC), CCL19 (MIP-3b), CCL20 (MIP-3a), CCL21 (SLC/exodus-2), CCL22 (MDC/STC-1), CCL23 (MPIF-1), CCL24 (MPIF-2/eotaxin-2), CCL25 (TECK), CCL26 (eotaxin-3), CCL27 (CTACK/ILC), CCL28, CXCL1 (GRO1), CXCL2 (GRO2), CXCL3 (GRO3), CXCL5 (ENA-78), CXCL6 (GCP-2), CXCL9 (MIG), CXCL10 (IP 10), CXCL11 (I-TAC), CXCL12 (SDF1), CXCL13, CXCL14, CXCL16, PF4 (CXCL4), PPBP (CXCL7), CX3CL1 (SCYD1), SCYE1, XCL1 (lymphotactin), XCL2 (SCM-1b), BLR1 (MDR15), CCBP2 (D6/JAB61), CCR1 (CKR1/HM145), CCR2 (mcp-1RB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBI1), CCR8 (CMKBR8/TER1/CKR-L1), CCR9 (GPR-9-6), CCRL1 (VSHK1), CCRL2 (L-CCR), XCR1 (GPR5/CCXCR1), CMKLR1, CMKOR1 (RDC1), CX3CR1 (V28), CXCR4, GPR2 (CCR10), GPR31, GPR81 (FKSG80), CXCR3 (GPR9/CKR-L2), CXCR6 (TYMSTR/STRL33/Bonzo), HM74, IL8RA (IL8Ra), IL8RB (IL8Rb), LTB4R (GPR16), TCP10, CKLFSF2, CKLFSF3, CKLFSF4, CKLFSF5, CKLFSF6, CKLFSF7, CKLFSF8, BDNF, C5R1, CSF3, GRCC10

(CO1), EPO, FY (DARC), GDF5, HIF1A, IL8, PRL, RGS3, RGS13, SDF2, SLIT2, TLR2, TLR4, TREM1, TREM2, and VHL.

In another embodiment, a binding protein of the invention is capable of binding cell surface protein such as, for example, integrins. In another embodiment, the binding protein of the invention is capable of binding enzymes selected from the group consisting of kinases and proteases. In yet another embodiment, the binding protein of the invention is capable of binding receptors selected from the group consisting of lymphokine receptors, monokine receptors, and polypeptide hormone receptors.

In one embodiment, the binding protein is multivalent. In another embodiment, the binding protein is multispecific. The multivalent and or multispecific binding proteins described above have desirable properties particularly from a therapeutic standpoint. For instance, the multivalent and or multispecific binding protein may (1) be internalized (and/or catabolized) faster than a bivalent antibody by a cell expressing an antigen to which the antibodies bind; (2) be an agonist antibody; and/or (3) induce cell death and/or apoptosis of a cell expressing an antigen which the multivalent antibody is capable of binding to. The "parent antibody" which provides at least one antigen binding specificity of the multivalent and or multispecific binding proteins may be one which is internalized (and/or catabolized) by a cell expressing an antigen to which the antibody binds; and/or may be an agonist, cell death-inducing, and/or apoptosis-inducing antibody, and the multivalent and or multispecific binding protein as described herein may display improvement(s) in one or more of these properties. Moreover, the parent antibody may lack any one or more of these properties, but may be endowed with them when constructed as a multivalent binding protein as herein described.

In another embodiment a binding protein of the invention has an on rate constant (Kon) to one or more targets selected from the group consisting of: at least about $10^2 M^{-1}s^{-1}$; at least about $10^3 M^{-1}s^{-1}$; at least about $10^4 M^{-1}s^{-1}$; at least about $10^5 M^{-1}s^{-1}$; and at least about $10^6 M^{-1}s^{-1}$ (inclusive of all values therebetween), as measured by surface plasmon resonance. Preferably, the binding protein of the invention has an on rate constant (Kon) to one or more targets between $10^2 M^{-1}s^{-1}$ to $10^3 M^{-1}s^{-1}$; between $10^3 M^{-1}s^{-1}$ to $10^4 M^{-1}s^{-1}$; between $10^4 M^{-1}s^{-1}$ to $10^5 M^{-1}s^{-1}$; or between $10^5 M^{-1}s^{-1}$ to $10^6 M^{-1}s^{-1}$ (inclusive of all values therebetween), as measured by surface plasmon resonance.

In another embodiment a binding protein has an off rate constant (Koff) for one or more targets selected from the group consisting of: at most about $10^{-3} s^{-1}$; at most about $10^{-4} s^{-1}$; at most about $10^{-5} s^{-1}$; and at most about $10^{-6} s^{-1}$, as measured by surface plasmon resonance (inclusive of all values therebetween). Preferably, the binding protein of the invention has an off rate constant (Koff) to one or more targets of $10^{-3} s^{-1}$ to $10^{-4} s^{-1}$; of $10^{-4} s^{-1}$ to $10^{-5} s^{-1}$; or of $10^{-5} s^{-1}$ to $10^{-6} s^{-1}$, as measured by surface plasmon resonance (inclusive of all values therebetween).

In another embodiment a binding protein has a dissociation constant ($K_D$) to one or more targets selected from the group consisting of: at most about $10^{-7}$ M; at most about $10^{-8}$ M; at most about $10^{-9}$ M; at most about $10^{-10}$ M; at most about $10^{-11}$ M; at most about $10^{-12}$ M; and at most $10^{-13}$ M (inclusive of all values therebetween). Preferably, the binding protein of the invention has a dissociation constant ($K_D$) to IL-12 or IL-23 of $10^{-7}$ M to $10^{-8}$ M; of $10^{-8}$ M to $10^{-9}$ M; of $10^{-9}$ M to $10^{-10}$ M; of $10^{-10}$ to $10^{-11}$ M; of $10^{-11}$ M to $10^{-12}$ M; or of $10^{-12}$ M to $10^{-13}$ M (inclusive of all values therebetween).

In another embodiment a binding protein of the invention has a monomer % of at least about 75%, about 76%, about 77%, about 78%, about 79%, about 80%, about 80%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, or more, or 100% (inclusive of all values therebetween) in a one-step Protein A purification using Size-exclusion chromatography (SEC)-HPLC.

In another embodiment a binding protein of the invention has an expression level at least about 0.01 mg/L, 0.05 mg/L, 0.1 mg/L, about 0.2 mg/L, about 0.3 mg/L, about 0.4 mg/L, about 0.5 mg/L, about 0.6 mg/L, about 0.7 mg/L, about 0.8 mg/L, about 0.9 mg/L, about 1.0 mg/L, about 2 mg/L, about 3 mg/L, about 4 mg/L, about 5 mg/L, about 6 mg/L, about 7 mg/L, about 8 mg/L, about 9 mg/L, about 10 mg/L, about 11 mg/L, about 12 mg/L, about 13 mg/L, about 14 mg/L, about 15 mg/L, about 16 mg/L, about 17 mg/L, about 18 mg/L, about 19 mg/L, about 20 mg/L, about 21 mg/L, about 22 mg/L, about 23 mg/L, about 24 mg/L, about 25 mg/L, about 26 mg/L, about 27 mg/L, about 28 mg/L, about 29 mg/L, about 30 mg/L, about 40 mg/L, about 50 mg/L, about 60 mg/L, about 70 mg/L, about 80 mg/L, about 90 mg/L, about 100 mg/L, about 200 mg/L, about 300 mg/L, about 400 mg/L, about 500 mg/L, about 600 mg/L, about 700 mg/L, about 800 mg/L, about 900 mg/L, about 1000 mg/L (inclusive of all values therebetween) or more, under optimized conditions. In some embodiments, the binding protein of the invention is expressed in 293E cells or in any other cells suitable for the purpose.

In another embodiment a binding protein of the invention has an Tm1 transition temperature as measured by Differential scanning calorimetry (DSC) which is at least about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82, about 82° C., about 83° C., about 84° C., about 85° C., about 86° C., about 87° C., about 88° C., about 89° C., about 90° C., about 95° C., about 99° C. (inclusive of all values therebetween) or more.

A binding protein of the invention has great stability in freeze-thaw test. In some embodiments, when a binding protein sample of the invention is thawed and incubated at 4° C., 25° C. and 40° C. for 1 day, 3 days or 7 days, reduction of intact binding protein due to aggregates is less than about 5%, about 4%, about 3%, about 2%, about 1%, about 0.5%, about 0.1%, about 0.05%, about 0.01% (inclusive of all values therebetween), or less, as measured by SEC-HPLC.

In another embodiment, when a binding protein of the invention is administered intravenously, it has one or more of the following PK parameters (1) an Apparent total body clearance of the drug from plasma (CL, mL/day/kg) of about 0.1, 0.5, 1, 2, 3, 4, 5, 6, 7, 8, 9, 10, 15, 20, 25, 30, 35, 40, 45, 50 (inclusive of all values therebetween) or more; (2) an Apparent volume of distribution at steady state (Vss, mL/kg) of about 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200 (inclusive of all values therebetween), or more; (3) an Apparent volume of the central or plasma compartment in a two-compartment model (V1, mL/kg) of about 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200 (inclusive of all values therebetween), or more; (4) an initial or disposition half-life (Alpha t1/2, day) of about 0.01, 0.05, 0.1, 0.2 0.3, 0.4, 0.5, 0.6, 0.7, 0.8, 0.9, 1, 2, 3, 4, 5, 6, 7, 8, 9, 10, 15, 20, 25, 30 (inclusive of all values therebetween) or more; (5) a Terminal elimination half-life (Beta t1/2, day) of about 0.01, 0.05, 0.1, 0.2 0.3, 0.4, 0.5, 0.6, 0.7, 0.8, 0.9, 1, 2, 3, 4, 5, 6, 7, 8, 9, 10, 15, 20, 25, 30 (inclusive of all values therebetween) or more; (6) an area under the plasma concentration-time curve (AUC, day×μg/mL) of about 10, 20, 30, 40, 50, 60, 70, 80, 90, 100, 200, 300, 400, 500, 600, 700, 800, 900, 1000, 1500, 2000, 2500, 3000 (inclusive of all values therebetween) or more; and (6) a Mean residence time (MRT, day) of about 0.01, 0.05, 0.1, 0.2 0.3, 0.4, 0.5, 0.6, 0.7, 0.8, 0.9, 1, 2, 3, 4, 5, 6, 7, 8, 9, 10, 15, 20, 25, 30 (inclusive of all values therebetween) or more. In some embodiments, the above parameters are associated with a dosage of about 1 mg/kg, 5 mg/kg, 10 mg/kg, 20 mg/kg, 50 mg/kg, 100 mg/kg, 200 mg/kg (inclusive of all values therebetween) or more.

In another embodiment, when a binding protein of the invention is administered subcutaneously, it has one or more of the following PK parameters (1) a Time to reach maximum (peak) plasma concentration following drug administration (Tmax, day) of about 0.05, 0.1, 0.2 0.3, 0.4, 0.5, 0.6, 0.7, 0.8, 0.9, 1, 2, 3, 4, 5, 6, 7, 8, 9, 10, 15, 20, 25, 30 (inclusive of all values therebetween) or more; (2) a Maximum (peak) plasma drug concentration (Cmax, μg/ml) of about 0.1, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500 (inclusive of all values therebetween) or more; (3) an Elimination half-life (Terminal $t_{1/2}$, day) of about 0.01, 0.05, 0.1, 0.2 0.3, 0.4, 0.5, 0.6, 0.7, 0.8, 0.9, 1, 2, 3, 4, 5, 6, 7, 8, 9, 10, 15, 20, 25, 30 (inclusive of all values therebetween) or more; (4) an Area under the plasma concentration-time curve from time zero to time of last measurable concentration (AUClast, day×μg/ml) of about 10, 20, 30, 40, 50, 60, 70, 80, 90, 100, 200, 300, 400, 500, 600, 700, 800, 900, 1000, 1500, 2000, 2500, 3000 (inclusive of all values therebetween) or more; (5) an Area under the plasma concentration-time curve from time zero to infinity ($AUC_{inf}$, day×μg/ml) of about 10, 20, 30, 40, 50, 60, 70, 80, 90, 100, 200, 300, 400, 500, 600, 700, 800, 900, 1000, 1500, 2000, 2500, 3000 (inclusive of all values therebetween) or more; (6) a Formation clearance of drug to metabolite (CL/F, mL/day/kg) of about 0.1, 0.5, 1, 2, 3, 4, 5, 6, 7, 8, 9, 10, 15, 20, 25, 30, 35, 40, 45, 50 (inclusive of all values therebetween) or more; (7) a Bioavailability (F, %) of about 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200 (inclusive of all values therebetween), or more. In some embodiments, the above parameters are associated with a dosage of about 1 mg/kg, 5 mg/kg, 10 mg/kg, 20 mg/kg, 50 mg/kg, 100 mg/kg, 200 mg/kg (inclusive of all values therebetween) or more.

In another embodiment, the binding protein described above is a conjugate further comprising an agent selected from the group consisting of an immunoadhesion molecule, an imaging agent, a therapeutic agent, and a cytotoxic agent. In one embodiment, the imaging agent is selected from the group consisting of a radiolabel, an enzyme, a fluorescent label, a luminescent label, a bioluminescent label, a magnetic label, and biotin. In a further embodiment, the imaging agent is a radiolabel selected from the group consisting of: $^3$H, $^{14}$C, $^{35}$S, $^{90}$Y, $^{99}$Tc, $^{111}$In, $^{125}$I, $^{131}$I, $^{177}$Lu, $^{166}$Ho, and $^{153}$Sm. In one embodiment, the therapeutic or cytotoxic agent is selected from the group consisting of an immunosuppressive agent, an immuno-stimulatory agent, an anti-metabolite, an alkylating agent, an antibiotic, a growth factor, a cytokine, an anti-angiogenic agent, an anti-mitotic agent, an anthracycline, a toxin, and an apoptotic agent. In one embodiment, the binding protein is conjugated directly to the agent. In another embodiment, the binding protein is conjugated to the agent via a linker. Suitable linkers include, but are not limited to, amino acid and polypeptide linkers disclosed herein. Linkers may be cleavable or non-cleavable.

In another embodiment the binding protein described above is a crystallized binding protein and exists as a crystal. Preferably the crystal is a carrier-free pharmaceutical controlled release crystal. More preferably the crystallized binding protein has a greater half life in vivo than the soluble counterpart of said binding protein. Most preferably the crystallized binding protein retains biological activity.

In another embodiment the binding protein described above is glycosylated. Preferably, the glycosylation is a human glycosylation pattern.

One aspect of the invention pertains to an isolated nucleic acid encoding any one of the binding protein disclosed above. A further embodiment provides a vector comprising the isolated nucleic acid disclosed above wherein said vector is selected from the group consisting of pcDNA; pTT (Durocher et al., Nucleic Acids Research 2002, Vol 30, No. 2); pTT3 (pTT with additional multiple cloning site; pEF-BOS (Mizushima, S. and Nagata, S., (1990) Nucleic acids Research Vol 18, No. 17); pBV; pJV; pcDNA3.1 TOPO, pEF6 TOPO and pBJ. The multi-specific binding proteins and methods of making the same are provided. The binding protein can be generated using various techniques. Expression vectors, host cells and methods of generating the binding proteins are provided in this disclosure.

The antigen-binding variable domains of the binding proteins of this disclosure can be obtained from parent binding proteins, including polyclonal Abs, monoclonal Abs, and or receptors capable of binding antigens of interest. These parent binding proteins may be naturally occurring or may be generated by recombinant technology. The person of ordinary skill in the art is well familiar with many methods for producing antibodies and/or isolated receptors, including, but not limited to using hybridoma techniques, selected lymphocyte antibody method (SLAM), use of a phage, yeast, or RNA-protein fusion display or other library, immunizing a non-human animal comprising at least some of the human immunoglobulin locus, and preparation of chimeric, CDR-grafted, and humanized antibodies. See, e.g., US Patent Publication No. 20090311253 A1. Variable domains may also be prepared using affinity maturation techniques. The binding variable domains of the binding proteins can also be obtained from isolated receptor molecules obtained by extraction procedures known in the art (e.g., using solvents, detergents, and/or affinity purifications), or determined by biophysical methods known in the art (e.g., X-ray crystallography, NMR, interferometry, and/or computer modeling).

An embodiment is provided comprising selecting parent binding proteins with at least one or more properties desired in the binding protein molecule. In an embodiment, the desired property is one or more of those used to characterize antibody parameters, such as, for example, antigen specificity, affinity to antigen, potency, biological function, epitope recognition, stability, solubility, production efficiency, immunogenicity, pharmacokinetics, bioavailability, tissue cross reactivity, or orthologous antigen binding. See, e.g., US Patent Publication No. 20090311253.

The multi-specific antibodies may also be designed such that one or more of the antigen binding domain are rendered non-functional. The variable domains may be obtained using recombinant DNA techniques from parent binding proteins generated by any one of the methods described herein. In an embodiment, a variable domain is a murine heavy or light chain variable domain. In another embodiment, a variable domain is a CDR grafted or a humanized variable heavy or light chain domain. In an embodiment, a variable domain is a human heavy or light chain variable domain.

In an embodiment, one or more constant domains are linked to the variable domains using recombinant DNA techniques. In an embodiment, a sequence comprising one or more heavy chain variable domains is linked to a heavy chain constant domain and a sequence comprising one or more light chain variable domains is linked to a light chain constant domain. In an embodiment, the constant domains are human heavy chain constant domains and human light chain constant domains, respectively. In an embodiment, the heavy chain is further linked to an Fc region. The Fc region may be a native sequence Fc region or a variant Fc region. In another embodiment, the Fc region is a human Fc region. In another embodiment, the Fc region includes Fc region from IgG1, IgG2, IgG3, IgG4, IgA, IgM, IgE, or IgD.

Additionally, the binding proteins provided herein can be employed for tissue-specific delivery (target a tissue marker and a disease mediator for enhanced local PK thus higher efficacy and/or lower toxicity), including intracellular delivery (targeting an internalizing receptor and an intracellular molecule), delivering to inside brain (targeting transferrin receptor and a CNS disease mediator for crossing the blood-brain barrier). The binding proteins can also serve as a carrier protein to deliver an antigen to a specific location via binding to a non-neutralizing epitope of that antigen and also to increase the half-life of the antigen. Furthermore, the binding proteins can be designed to either be physically linked to medical devices implanted into patients or target these medical devices (see Burke et al. (2006) Advanced Drug Deliv. Rev. 58(3): 437-446; Hildebrand et al. (2006) Surface and Coatings Technol. 200(22-23): 6318-6324; Drug/device combinations for local drug therapies and infection prophylaxis, Wu (2006) Biomaterials 27(11):2450-2467; Mediation of the cytokine network in the implantation of orthopedic devices, Marques (2005) Biodegradable Systems in Tissue Engineer. Regen. Med. 377-397). Directing appropriate types of cell to the site of medical implant may promote healing and restoring normal tissue function. Alternatively, inhibition of mediators (including but not limited to cytokines), released upon device implantation by a receptor antibody fusion protein coupled to or target to a device is also provided.

In one aspect, a host cell is transformed with the vector disclosed above. In one embodiment, the host cell is a prokaryotic cell. In a further embodiment, the host cell is *Escherecia coli*. In another embodiment, the host cell is an eukaryotic cell. In a further embodiment, the eukaryotic cell is selected from the group consisting of protist cell, animal cell, plant cell and fungal cell. In one embodiment, the host cell is a mammalian cell including, but not limited to, 293, COS, NS0, and CHO and; or a fungal cell such as *Saccharomyces cerevisiae*; or an insect cell such as Sf9.

Another aspect of the invention provides a method of producing a binding protein disclosed above comprising culturing any one of the host cells also disclosed above in a culture medium under conditions sufficient to produce the binding protein. Preferably 50%-75% of the binding protein produced by this method is a dual specific tetravalent binding protein. More preferably 75%-90% of the binding protein produced by this method is a dual specific tetravalent binding protein. Most preferably 90%-95% of the binding protein produced is a dual specific tetravalent binding protein.

Another embodiment provides a binding protein produced according to the method disclosed above.

One embodiment provides a composition for the release of a binding protein wherein the composition comprises a formulation which in turn comprises a crystallized binding protein, as disclosed above and an ingredient; and at least one polymeric carrier. Preferably the polymeric carrier is a polymer selected from one or more of the group consisting of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutryate), poly (caprolactone), poly (dioxanone); poly (ethylene glycol), poly ((hydroxypropyl) methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polyeaccharides, blends and copolymers thereof. Preferably the ingredient is selected from the group consisting of albumin, sucrose, trehalose, lactitol, gelatin, hydroxypropyl-β-cyclodextrin, methoxypolyethylene glycol and polyethylene glycol. Another embodiment provides a method for treating a mammal comprising the step of administering to the mammal an effective amount of the composition disclosed above.

The invention also provides a pharmaceutical composition comprising a binding protein, as disclosed above and a pharmaceutically acceptable carrier. Pharmaceutically acceptable carriers include, but are not limited to, phosphate buffer or saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. The carrier can be a solvent or dispersion medium containing, for example, water, ethanol, polyol (e.g., glycerol, propylene glycol, and liquid polyethylene glycol, and the like), and suitable mixtures thereof. In some cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In a further embodiment the pharmaceutical composition comprises at least one additional therapeutic agent for treating a disorder. In one embodiment, the additional agent is selected from the group consisting of: therapeutic agents, imaging agents, cytotoxic agent, angiogenesis inhibitors (including but not limited to anti-VEGF antibodies or VEGF-trap); kinase inhibitors (including but not limited to KDR and TIE-2 inhibitors); co-stimulation molecule blockers (including but not limited to anti-B7.1, anti-B7.2, CTLA4-Ig, anti-PD-1, anti-CD20); adhesion molecule blockers (including but not limited to anti-LFA-1 Abs, anti-E/L selectin Abs, small molecule inhibitors); anti-cytokine antibody or functional fragment thereof (including but not limited to anti-IL-18, anti-TNF, anti-IL-6/cytokine receptor antibodies); methotrexate; cyclosporin; rapamycin; FK506; detectable label or reporter; a TNF antagonist; an antirheumatic; a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, and a cytokine antagonist.

In another aspect, the invention provides a method for treating a human subject suffering from a disorder in which the target, or targets, capable of being bound by the binding protein disclosed above is detrimental, comprising administering to the human subject a binding protein disclosed above such that the activity of the target or targets in the human subject is inhibited and treatment or preventions of the disorder is achieved. In one embodiment, the disease or disorder is an inflammatory condition, autoimmune disease, or cancer. In one embodiment, the disease or disorder is selected from the group comprising arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjorgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aordic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic ateriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrythmias, HIV infection/HIV neuropathy, Hodgkin's disease, hyperkinetic movement disorders, hypersensitity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, *legionella*, leishmaniasis, leprosy, lesions of the corticospinal system, lipedema, liver transplant rejection, lymphederma, malaria, malignamt Lymphoma, malignant histiocytosis, malignant melanoma, meningitis, meningococcemia, metabolic/idiopathic, migraine headache, mitochondrial multi-system disorder, mixed connective tissue disease, monoclonal gammopathy, multiple myeloma, multiple systems degenerations (Mencel Dejerine-Thomas Shi-Drager and Machado-Joseph), myasthenia gravis, *mycobacterium* avium intracellulare, *Mycobacterium tuberculosis*, myelodyplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-Hodgkin's lymphoma, occlusion of the abdominal aorta and its branches, occlusive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, *Pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynoud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue.

In another aspect the invention provides a method of treating a patient suffering from a disorder comprising the step of administering any one of the binding proteins disclosed above before, concurrent, or after the administration of a second agent, as discussed above. In a preferred embodiment the second agent is selected from the group consisting of budenoside, epidermal growth factor, corticosteroids, cyclosporin, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1β monoclonal antibodies, anti-IL-6 monoclonal antibodies, growth factors, elastase inhibitors, pyridinyl-imidazole compounds, antibodies or agonists of TNF, LT, IL-1, IL-2, IL-6, IL-7, IL-8, IL-12, IL-13, IL-15, IL-16, IL-18, IL-23, EMAP-II, GM-CSF, FGF, and PDGF, antibodies of CD2, CD3, CD4, CD8, CD-19, CD25, CD28, CD30, CD40, CD45, CD69, CD90 or their ligands, methotrexate, cyclosporin, FK506, rapamycin, mycophenolate mofetil, leflunomide, NSAIDs, ibuprofen, corticosteroids, prednisolone, phosphodiesterase inhibitors, adenosine agonists, antithrombotic agents, complement inhibitors, adrenergic agents, IRAK, NIK, IKK, p38, MAP kinase inhibitors, IL-1β converting enzyme inhibitors, TNFα converting enzyme inhibitors, T-cell signalling inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1RI, sIL-1RII, sIL-6R, antiinflammatory cytokines, IL-4, IL-10, IL-11, IL-13 and TGFβ.

In one embodiment, the pharmaceutical compositions disclosed above are administered to the subject by at least one mode selected from parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

One aspect of the invention provides at least one anti-idiotype antibody to at least one binding protein of the present invention. The anti-idiotype antibody includes any protein or peptide containing molecule that comprises at least a portion of an immunoglobulin molecule such as, but not limited to, at least one complementarily determining region (CDR) of a heavy or light chain or a ligand binding portion thereof, a heavy chain or light chain variable region, a heavy chain or light chain constant region, a framework region, or; any portion thereof, that can be incorporated into a binding protein of the present invention.

In another embodiment the binding proteins of the invention are capable of binding one or more targets selected from the group consisting of ABCF1; ACVR1; ACVR1B; ACVR2; ACVR2B; ACVRL1; ADORA2A; Aggrecan; AGR2; AICDA; AIF1; AIG1; AKAP1; AKAP2; AMH; AMHR2; ANGPT1; ANGPT2; ANGPTL3; ANGPTL4; ANPEP; APC; APOC1; AR; AZGP1 (zinc-a-glycoprotein); B7.1; B7.2; BAD; BAFF; BAG1; BAIl; BCL2; BCL6; BDNF; BLNK; BLR1 (MDR15); BlyS; BMP1; BMP2; BMP3B (GDF10); BMP4; BMP6; BMP8; BMPR1A; BMPR1B; BMPR2; BPAG1 (plectin); BRCA1; C19orf10 (IL27w); C3; C4A; C5; C5R1; CANT1; CASP1; CASP4; CAV1; CCBP2 (D6/JAB61); CCL1 (1-309); CCL11 (eotaxin); CCL13 (MCP-4); CCL15 (MIP-1d); CCL16 (HCC-4); CCL17 (TARC); CCL18 (PARC); CCL19 (MIP-3b); CCL2 (MCP-1); MCAF; CCL20 (MIP-3a); CCL21 (MIP-2); SLC; exodus-2; CCL22 (MDC/STC-1); CCL23 (MPIF-1); CCL24 (MPIF-2/eotaxin-2); CCL25 (TECK); CCL26 (eotaxin-3); CCL27 (CTACK/ILC); CCL28; CCL3 (MIP-1a); CCL4 (MIP-1b); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-1RB/RA); CCR3 (CKR3/CMKBR3); CCR4; CCR5 (CMKBR5/ChemR13); CCR6 (CMKBR6/CKR-L3/STRL22/DRY6); CCR7 (CKR7/EBI1); CCR8 (CMKBR8/TER1/CKR-L1); CCR9 (GPR-9-6); CCRL1 (VSHK1); CCRL2 (L-CCR); CD164; CD19; CD1C; CD20; CD200; CD-22; CD24; CD28; CD3; CD37; CD38; CD3E; CD3G; CD3Z; CD4; CD40; CD40L; CD44; CD45RB; CD47; CD48, CD52; CD69; CD70; CD72; CD74; CD79A; CD79B; CD8; CD80; CD81; CD83; CD86; CD137, CD138, B7-1, B7-2, ICOSL, B7-H3, B7-H4, CD137L, OX40L, CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21Wap1/Cip1); CDKN1B (p27Kip1); CDKN1C; CDKN2A (p16INK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); cMet; CMKLR1; CMKOR1 (RDC1); CNR1; COL18A1; COL1A1; COL4A3; COL6A1; CR2; CRP; CSF1 (M-CSF); CSF2 (GM-CSF); CSF3 (GCSF); CTLA-4; CTNNB1 (b-catenin); CTSB (cathepsin B); CX3CL1 (SCYD1); CX3CR1 (V28); CXCL1 (GRO1); CXCL10 (IP-10); CXCL11 (I-TAC/IP-9); CXCL12 (SDF1); CXCL13; CXCL14; CXCL16; CXCL2 (GRO2); CXCL3 (GRO3); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYC1; CYSLTR1; DAB2IP; DES; DKFZp451J0118; DLL-4; DNCL1; DPP4; E2F1; ECGF1; EDG1; EFNA1; EFNA3; EFNB2; EGF; EGFR; ELAC2; ENG; ENO1; ENO2; ENO3; EPHB4; EPO; ERBB2 (Her-2); EREG; ERK8; ESR1; ESR2; F3 (TF); FADD; FasL; FASN; FCER1A; FCER2; FCGR3A; FGF; FGF1 (aFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FIL1 (EPSILON); FIL1 (ZETA); FLJ12584; FLJ25530; FLRT1 (fibronectin); FLT1; FOS; FOSL1 (FRA-1); FY (DARC); GABRP (GABAa); GAGEB1; GAGEC1; GALNAC4S-6ST; GATA3; GDF5; GFI1; GGT1; GM-CSF; GNAS1; GNRH1; GPR2 (CCR10); GPR31; GPR44; GPR81 (FKSG80); GRCC10 (CO1); GRP; GSN (Gelsolin); GSTP1; HAVCR2; HDAC4; HDAC5; HDAC7A; HDAC9; HGF; HIF1A; HIP1; histamine and histamine receptors; Her3; HLA-A; HLA-DRA; HM74; HMOX1; HUMCYT2A; ICEBERG; ICOSL; ID2; IFN-α; IFNA1; IFNA2; IFNA4; IFNA5; IFNA6; IFNA7; IFNB1; IFNgamma; IFNW1; IGBP1; IGF1; IGF1R; IGF2; IGFBP2; IGFBP3; IGFBP6; IL-1; IL10; IL10RA; IL10RB; IL11; IL1 RA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; IL1A; IL1B; IL1F10; IL1F5; IL1F6; IL1F7; IL1F8; IL1F9; IL1HY1; IL1R1; IL1R2; IL1RAP; IL1RAPL1; IL1RAPL2; IL1RL1; IL1RL2 IL1RN; IL2; IL20; IL20RA; IL21R; IL22; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); IL7; IL7R; IL8; IL8RA; IL8RB; IL8RB; IL9; IL9R; ILK; INHA; INHBA; INSL3; INSL4; IRAK1; IRAK2; ITGA1; ITGA2; ITGA3; ITGA6 (a6 integrin); ITGAV; ITGB3; ITGB4 (b 4 integrin); JAG1; JAK1; JAK3; JUN; K6HF; KAI1; KDR; KITLG; KLF5 (GC Box BP); KLF6; KLK10; KLK12; KLK13; KLK14; KLK15; KLK3; KLK4; KLK5; KLK6; KLK9; KRT1; KRT19 (Keratin 19); KRT2A; KRTHB6 (hair-specific type II keratin); LAMA5; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; MIB1; midkine; MIF; MIP-2; MKI67 (Ki-67); MMP2; MMP9; MS4A1; MSMB; MT3 (metallothionectin-III); MTSS1; MUC1 (mucin); MYC; MYD88; NCK2; neurocan; NFKB1; NFKB2; NGFB (NGF); NGFR; NgR-Lingo; NgR-Nogo66 (Nogo); NgR-p75; NgR-Troy; NME1 (NM23A); NOX5; NPPB; NROB1; NROB2; NR1D1; NR1D2; NR1H2; NR1H3; NR1H4; NRII2; NRII3; NR2C1; NR2C2; NR2E1; NR2E3; NR2FI; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRD1; PCSK9; P2RX7; PAP; PART1; PATE; PAWR; PCA3; PCNA; PD-1; PD-L1; alpha4beta7, OX40, GITR, TIM-3, Lag-3, B7-H3, B7-H4, GDF8, CGRP, Lingo-1, Factor IXa, Factor X, ICOS, GARP, BTLA, CD160, ROR1, 2B4, KIR, CD27, OX40, CD40L, A2aR, PDGFA; PDGFB; PECAMi; PF4 (CXCL4); PGF; PGR; phosphacan; PIAS2; PIK3CG; PLAU (uPA); PLG; PLXDC1; PPBP (CXCL7); PPID; PR1; PRKCQ; PRKD1; PRL; PROC; PROK2; PSAP; PSCA; PTAFR; PTEN; PTGS2 (COX-2); PTN; RAC2 (p21Rac2); RARB; RGS1; RGS13; RGS3; RNF110 (ZNF144); ROBO2; S100A2; SCGBiD2 (lipophilin B); SCGB2A1 (mammaglobin 2); SCGB2A2 (mammaglobin 1); SCYE1 (endothelial Monocyte-activating cytokine); SDF2; SERPINA1; SERPINA3; SERPINB5 (maspin); SERPINE1 (PAI-1); SERPINF1; SHBG; SLA2; SLC2A2; SLC33A1; SLC43A1; SLIT2; SPP1; SPRR1B (Spr1); ST6GAL1; STAB1; STAT6; STEAP; STEAP2; TB4R2; TBX21; TCP10; TDGF1; TEK; TGFA; TGFB1; TGFB1II; TGFB2; TGFB3; TGFB1; TGFBR1; TGFBR2; TGFBR3; TH1L; THBS1 (thrombospondin-1); THBS2; THBS4; THPO; TIE (Tie-1); TIMP3; tissue factor; TLR10; TLR2; TLR3; TLR4; TLR5; TLR6; TLR7; TLR8; TLR9; TNF; TNF-α; TNFAIP2 (B94); TNFAIP3; TNFRSF11A; TNFRSF1A; TNFRSF1B; TNFRSF21; TNFRSF5; TNFRSF6 (Fas); TNFRSF7;

TNFRSF8; TNFRSF9; TNFSF10 (TRAIL); TNFSF11 (TRANCE); TNFSF12 (APO3L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1BB ligand); TOLLIP; Toll-like receptors; TOP2A (topoisomerase Iia); TP53; TPM1; TPM2; TRADD; TRAF1; TRAF2; TRAF3; TRAF4; TRAF5; TRAF6; TREM1; TREM2; TRPC6; TSLP; TWEAK; VEGF; VEGFB; VEGFC; versican; VHL C5; $VL_A$-4; XCL1 (lymphotactin); XCL2 (SCM-1b); XCR1 (GPR5/CCXCR1); YY1; and ZFPM2.

Given their ability to bind to two or more antigens, the binding proteins of the present invention can be used to detect the antigens (e.g., in a biological sample, such as serum or plasma), using a conventional immunoassay, such as an enzyme linked immunosorbent assays (ELISA), an radioimmunoassay (RIA) or tissue immunohistochemistry. The FIT-Ig is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include 3H, 14C, 35S, 90Y, 99Tc, 111In, 125I, 131I, 177Lu, 166Ho, or 153Sm.

The binding proteins of the invention, in one embodiment, are capable of neutralizing the activity of the antigens both in vitro and in vivo. Accordingly, such FIT-Igs can be used to inhibit antigen activity, e.g., in a cell culture containing the antigens, in human subjects or in other mammalian subjects having the antigens with which a binding protein of the invention cross-reacts. In another embodiment, the invention provides a method for reducing antigen activity in a subject suffering from a disease or disorder in which the antigen activity is detrimental. A binding protein of the invention can be administered to a human subject for therapeutic purposes.

As used herein, the term "a disorder in which antigen activity is detrimental" is intended to include diseases and other disorders in which the presence of the antigen in a subject suffering from the disorder has been shown to be or is suspected of being either responsible for the pathophysiology of the disorder or a factor that contributes to a worsening of the disorder. Accordingly, a disorder in which antigen activity is detrimental is a disorder in which reduction of antigen activity is expected to alleviate the symptoms and/or progression of the disorder. Such disorders may be evidenced, for example, by an increase in the concentration of the antigen in a biological fluid of a subject suffering from the disorder (e.g., an increase in the concentration of antigen in serum, plasma, synovial fluid, etc. of the subject). Non-limiting examples of disorders that can be treated with the binding proteins of the invention include those disorders discussed below and in the section pertaining to pharmaceutical compositions of the antibodies of the invention.

The FIT-Igs of the invention may bind one antigen or multiple antigens. Such antigens include, but are not limited to, the targets listed in the following databases, which databases are incorporated herein by reference. These target databases include, but are not limited to, the following listings:

Therapeutic targets (http://xin.cz3.nus.edu.sg/group/cjttd/ttd.asp);
Cytokines and cytokine receptors (http://www.cytokinewebfacts.com/, http://www.copewithcytokines.de/cope.cgi, and
http://cmbi.bj mu.edu.cn/cmbidata/cgf/CGF_Database/cytokine.medic.kumamoto-u.ac.jp/CFC/indexR.html);
Chemokines (http://cytokine.medic.kumamoto-u.ac.jp/CFC/CK/Chemokine.html);
Chemokine receptors and GPCRs (http://csp.medic.kumamoto-u.ac.jp/CSP/Receptor.html, http://www.gpcr.org/7tm/);
Olfactory Receptors (http://senselab.med.yale.edu/senselab/ORDB/default.asp);
Receptors (http://www.iuphar-db.org/iuphar-rd/list/index.htm);
Cancer targets (http://cged.hgc.jp/cgi-bin/input.cgi);
Secreted proteins as potential antibody targets (http://spd.cbi.pku.edu.cn/);
Protein kinases (http://spd.cbi.pku.edu.cn/), and
Human CD markers (http://content.labvelocity.com/tools/6/1226/CD_table_final_locked.pdf) and (Zola H, 2005 CD molecules 2005: human cell differentiation molecules Blood, 106:3123-6).

FIT-Igs are useful as therapeutic agents to simultaneously block two different targets to enhance efficacy/safety and/or increase patient coverage. Such targets may include soluble targets (e.g., IL-13 and TNF) and cell surface receptor targets (e.g., VEGFR and EGFR). It can also be used to induce redirected cytotoxicity between tumor cells and T cells (Her2 and CD3) for cancer therapy, or between autoreactive cell and effector cells for autoimmune/transplantation, or between any target cell and effector cell to eliminate disease-causing cells in any given disease.

In addition, FIT-Ig can be used to trigger receptor clustering and activation when it is designed to target two different epitopes on the same receptor. This may have benefit in making agonistic and antagonistic anti-GPCR therapeutics. In this case, FIT-Ig can be used to target two different epitopes on one cell for clustering/signaling (two cell surface molecules) or signaling (on one molecule). Similarly, a FIT-Ig molecule can be designed to trigger CTLA-4 ligation, and a negative signal by targeting two different epitopes (or 2 copies of the same epitope) of CTLA-4 extracellular domain, leading to down regulation of the immune response. CTLA-4 is a clinically validated target for therapeutic treatment of a number of immunological disorders. CTLA-4/B7 interactions negatively regulate T cell activation by attenuating cell cycle progression, IL-2 production, and proliferation of T cells following activation, and CTLA-4 (CD152) engagement can down-regulate T cell activation and promote the induction of immune tolerance. However, the strategy of attenuating T cell activation by agonistic antibody engagement of CTLA-4 has been unsuccessful since CTLA-4 activation requires ligation. The molecular interaction of CTLA-4/B7 is in "skewed zipper" arrays, as demonstrated by crystal structural analysis (Stamper 2001 Nature 410:608). However none of the currently available CTLA-4 binding reagents have ligation properties, including anti-CTLA-4 monoclonal antibodies. There have been several attempts to address this issue. In one case, a cell member-bound single chain antibody was generated, and significantly inhibited allogeneic rejection in mice (Hwang 2002 JI 169:633). In a separate case, artificial APC surface-linked single-chain antibody to CTLA-4 was generated and demonstrated to attenuate T cell responses (Griffin 2000 JI 164:4433). In both cases, CTLA-4 ligation was achieved by closely localized member-bound antibodies in artificial systems. While these experiments provide proof-of-concept for immune down-regulation by triggering CTLA-4 negative signaling, the reagents used in these reports are not suitable for therapeutic use. To this end, CTLA-4 ligation may be achieved by using a FIT-Ig molecule, which target two different epitopes (or 2 copies of the same epitope) of CTLA-4 extracellular domain. The rationale is that the distance spanning two binding sites of an IgG, approximately 150-170 Å, is too large for active ligation of CTLA-4 (30-50 Å between 2 CTLA-4 homodimer). However the distance between the two binding sites on FIT-Ig (one arm) is much shorter, also in the range of 30-50 Å, allowing proper ligation of CTLA-4.

Similarly, FIT-Ig can target two different members of a cell surface receptor complex (e.g. IL-12R alpha and beta). Furthermore, FIT-Ig can target CR1 and a soluble protein/pathogen to drive rapid clearance of the target soluble protein/pathogen.

Additionally, FIT-Igs of the invention can be employed for tissue-specific delivery (target a tissue marker and a disease mediator for enhanced local PK thus higher efficacy and/or lower toxicity), including intracellular delivery (targeting an internalizing receptor and a intracellular molecule), delivering to inside brain (targeting transferrin receptor and a CNS disease mediator for crossing the blood-brain barrier). FIT-Ig can also serve as a carrier protein to deliver an antigen to a specific location via biding to a non-neutralizing epitope of that antigen and also to increase the half-life of the antigen. Furthermore, FIT-Ig can be designed to either be physically linked to medical devices implanted into patients or target these medical devices (Burke, Sandra E.; Kuntz, Richard E.; Schwartz, Lewis B. Zotarolimus (ABT-578) eluting stents. Advanced Drug Delivery Reviews (2006), 58(3), 437-446; Surface coatings for biological activation and functionalization of medical devices. Hildebrand, H. F.; Blanchemain, N.; Mayer, G.; Chai, F.; Lefebvre, M.; Boschin, F. Surface and Coatings Technology (2006), 200(22-23), 6318-6324; Drug/device combinations for local drug therapies and infection prophylaxis. Wu, Peng; Grainger, David W. Biomaterials (2006), 27(11), 2450-2467; Mediation of the cytokine network in the implantation of orthopedic devices. Marques, A. P.; Hunt, J. A.; Reis, Rui L. Biodegradable Systems in Tissue Engineering and Regenerative Medicine (2005), 377-397; Page: 52

Mediation of the cytokine network in the implantation of orthopedic devices. Marques, A. P.; Hunt, J. A.; Reis, Rui L. Biodegradable Systems in Tissue Engineering and Regenerative Medicine (2005), 377-397.) Briefly, directing appropriate types of cell to the site of medical implant may promote healing and restoring normal tissue function. Alternatively, inhibition of mediators (including but not limited to cytokines), released upon device implantation by a FIT-Ig coupled to or target to a device is also provided. For example, Stents have been used for years in interventional cardiology to clear blocked arteries and to improve the flow of blood to the heart muscle. However, traditional bare metal stents have been known to cause restenosis (re-narrowing of the artery in a treated area) in some patients and can lead to blood clots. Recently, an anti-CD34 antibody coated stent has been described which reduced restenosis and prevents blood clots from occurring by capturing endothelial progenitor cells (EPC) circulating throughout the blood. Endothelial cells are cells that line blood vessels, allowing blood to flow smoothly. The EPCs adhere to the hard surface of the stent forming a smooth layer that not only promotes healing but prevents restenosis and blood clots, complications previously associated with the use of stents (Aoji et al. 2005 J Am Coll Cardiol. 45(10):1574-9). In addition to improving outcomes for patients requiring stents, there are also implications for patients requiring cardiovascular bypass surgery. For example, a prosthetic vascular conduit (artificial artery) coated with anti-EPC antibodies would eliminate the need to use arteries from patients legs or arms for bypass surgery grafts. This would reduce surgery and anesthesia times, which in turn will reduce coronary surgery deaths. FIT-Ig are designed in such a way that it binds to a cell surface marker (such as CD34) as well as a protein (or an epitope of any kind, including but not limited to lipids and polysaccharides) that has been coated on the implanted device to facilitate the cell recruitment. Such approaches can also be applied to other medical implants in general. Alternatively, FIT-Igs can be coated on medical devices and upon implantation and releasing all FITs from the device (or any other need which may require additional fresh FIT-Ig, including aging and denaturation of the already loaded FIT-Ig) the device could be reloaded by systemic administration of fresh FIT-Ig to the patient, where the FIT-Ig is designed to binds to a target of interest (a cytokine, a cell surface marker (such as CD34) etc.) with one set of binding sites and to a target coated on the device (including a protein, an epitope of any kind, including but not limited to lipids, polysaccharides and polymers) with the other. This technology has the advantage of extending the usefulness of coated implants.

FIT-Ig molecules of the invention are also useful as therapeutic molecules to treat various diseases. Such FIT-Ig molecules may bind one or more targets involved in a specific disease. Examples of such targets in various diseases are described below.

Many proteins have been implicated in general autoimmune and inflammatory responses, including C5, CCL1 (1-309), CCL11 (eotaxin), CCL13 (mcp-4), CCL15 (MIP-1d), CCL16 (HCC-4), CCL17 (TARC), CCL18 (PARC), CCL19, CCL2 (mcp-1), CCL20 (MIP-3a), CCL21 (MIP-2), CCL23 (MPIF-1), CCL24 (MPIF-2/eotaxin-2), CCL25 (TECK), CCL26, CCL3 (MIP-1a), CCL4 (MIP-1b), CCL5 (RANTES), CCL7 (mcp-3), CCL8 (mcp-2), CXCL1, CXCL10 (IP-10), CXCL11 (I-TAC/IP-9), CXCL12 (SDF1), CXCL13, CXCL14, CXCL2, CXCL3, CXCL5 (ENA-78/LIX), CXCL6 (GCP-2), CXCL9, IL13, IL8, CCL13 (mcp-4), CCR1, CCR2, CCR3, CCR4, CCR5, CCR6, CCR7, CCR8, CCR9, CX3CR1, IL8RA, XCR1 (CCXCR1), IFNA2, IL10, IL13, IL17C, IL1A, IL1B, IL1F10, IL1F5, IL1F6, IL1F7, IL1F8, IL1F9, IL22, IL5, IL8, IL9, LTA, LTB, MIF, SCYE1 (endothelial Monocyte-activating cytokine), SPP1, TNF, TNFSF5, IFNA2, IL10RA, IL10RB, IL13, IL13RA1, IL5RA, IL9, IL9R, ABCF1, BCL6, C3, C4A, CEBPB, CRP, ICEBERG, IL1R1, IL1RN, IL8RB, LTB4R, TOLLIP, FADD, IRAK1, IRAK2, MYD88, NCK2, TNFAIP3, TRADD, TRAF1, TRAF2, TRAF3, TRAF4, TRAF5, TRAF6, ACVR1, ACVR1B, ACVR2, ACVR2B, ACVRL1, CD28, CD3E, CD3G, CD3Z, CD69, CD80, CD86, CNR1, CTLA-4, CYSLTR1, FCER1A, FCER2, FCGR3A, GPR44, HAVCR2, OPRD1, P2RX7, TLR2, TLR3, TLR4, TLR5, TLR6, TLR7, TLR8, TLR9, TLR10, BLR1, CCL1, CCL2, CCL3, CCL4, CCL5, CCL7, CCL8, CCL11, CCL13, CCL15, CCL16, CCL17, CCL18, CCL19, CCL20, CCL21, CCL22, CCL23, CCL24, CCL25, CCR1, CCR2, CCR3, CCR4, CCR5, CCR6, CCR7, CCR8, CCR9, CX3CL1, CX3CR1, CXCL1, CXCL2, CXCL3, CXCL5, CXCL6, CXCL10, CXCL11, CXCL12, CXCL13, CXCR4, GPR2, SCYE1, SDF2, XCL1, XCL2, XCR1, AMH, AMHR2, BMPR1A, BMPR1B, BMPR2, C19orf10 (IL27w), CER1, CSF1, CSF2, CSF3, DKFZp451J0118, FGF2, GFI1, IFNA1, IFNB1, IFNG, IGF1, IL1A, IL1B, IL1R1, IL1R2, IL2, IL2RA, IL2RB, IL2RG, IL3, IL4, IL4R, IL5, IL5RA, IL6, IL6R, IL6ST, IL7, IL8, IL8RA, IL8RB, IL9, IL9R, IL10, IL10RA, IL10RB, IL11, IL11RA, IL12A, IL12B, IL12RB1, IL12RB2, IL13, IL13RA1, IL13RA2, IL15, IL15RA, IL16, IL17, IL17R, IL18, IL18R1, IL19, IL20, KITLG, LEP, LTA, LTB, LTB4R, LTB4R2, LTBR, MIF, NPPB, PDGFB, TBX21, TDGF1, TGFA, TGFB1, TGFBII1, TGFB2, TGFB3, TGFB1, TGFBR1, TGFBR2, TGFBR3, TH1L, TNF, TNFRSF1A, TNFRSF1B, TNFRSF7, TNFRSF8, TNFRSF9, TNFRSF11A, TNFRSF21, TNFSF4, TNFSF5, TNFSF6, TNFSF11, VEGF, ZFPM2, and RNF110 (ZNF144). FIT-Igs capable of binding one or more of the targets listed above are also contemplated.

Allergic asthma is characterized by the presence of eosinophilia, goblet cell metaplasia, epithelial cell alterations, airway hyperreactivity (AHR), and Th2 and Th1 cytokine expression, as well as elevated serum IgE levels. It is now widely accepted that airway inflammation is the key factor underlying the pathogenesis of asthma, involving a complex interplay of inflammatory cells such as T cells, B cells, eosinophils, mast cells and macrophages, and of their secreted mediators including cytokines and chemokines. Corticosteroids are the most important anti-inflammatory treatment for asthma today, however their mechanism of action is non-specific and safety concerns exist, especially in the juvenile patient population. The development of more specific and targeted therapies is therefore warranted. There is increasing evidence that IL-13 in mice mimics many of the features of asthma, including AHR, mucus hypersecretion and airway fibrosis, independently of eosinophilic inflammation (Finotto et al., International Immunology (2005), 17(8), 993-1007; Padilla et al., Journal of Immunology (2005), 174(12), 8097-8105).

IL-13 has been implicated as having a pivotal role in causing pathological responses associated with asthma. The development of anti-IL-13 monoclonal antibody therapy to reduce the effects of IL-13 in the lung is an exciting new approach that offers considerable promise as a novel treatment for asthma. However other mediators of differential immunological pathways are also involved in asthma pathogenesis, and blocking these mediators, in addition to IL-13, may offer additional therapeutic benefit. Such target pairs include, but are not limited to, IL-13 and a pro-inflammatory cytokine, such as tumor necrosis factor-α (TNF-α). TNF-α may amplify the inflammatory response in asthma and may be linked to disease severity (McDonnell, et al., Progress in Respiratory Research (2001), 31(New Drugs for Asthma, Allergy and COPD), 247-250). This suggests that blocking both IL-13 and TNF-α may have beneficial effects, particularly in severe airway disease. In a preferred embodiment the FIT-Ig of the invention binds the targets IL-13 and TNFα and is used for treating asthma.

Animal models such as OVA-induced asthma mouse model, where both inflammation and AHR can be assessed, are known in the art and may be used to determine the ability of various FIT-Ig molecules to treat asthma. Animal models for studying asthma are disclosed in Coffman, et al., Journal of Experimental Medicine (2005), 201(12), 1875-1879; Lloyd, et al., Advances in Immunology (2001), 77, 263-295; Boyce et al., Journal of Experimental Medicine (2005), 201(12), 1869-1873; and Snibson, et al., Journal of the British Society for Allergy and Clinical Immunology (2005), 35(2), 146-52. In addition to routine safety assessments of these target pairs specific tests for the degree of immunosuppression may be warranted and helpful in selecting the best target pairs (see Luster et al., Toxicology (1994), 92(1-3), 229-43; Descotes, et al., Developments in biological standardization (1992), 77 99-102; Hart et al., Journal of Allergy and Clinical Immunology (2001), 108(2), 250-257).

Based on the rationale disclosed above and using the same evaluation model for efficacy and safety other pairs of targets that FIT-Ig molecules can bind and be useful to treat asthma may be determined. Preferably such targets include, but are not limited to, IL-13 and IL-1beta, since IL-1beta is also implicated in inflammatory response in asthma; IL-13 and cytokines and chemokines that are involved in inflammation, such as IL-13 and IL-9; IL-13 and IL-4; IL-13 and IL-5; IL-13 and IL-25; IL-13 and TARC; IL-13 and MDC; IL-13 and MIF; IL-13 and TGF-β; IL-13 and LHR agonist; IL-13 and CL25; IL-13 and SPRR2a; IL-13 and SPRR2b; and IL-13 and ADAM8. The present invention also contemplates FIT-Igs capable of binding one or more targets involved in asthma selected from the group consisting of CSF1 (MCSF), CSF2 (GM-CSF), CSF3 (GCSF), FGF2, IFNA1, IFNB1, IFNG, histamine and histamine receptors, IL1A, IL1B, IL2, IL3, IL4, IL5, IL6, IL7, IL8, IL9, IL10, IL11, IL12A, IL12B, IL13, IL14, IL15, IL16, IL17, IL18, IL19, KITLG, PDGFB, IL2RA, IL4R, IL5RA, IL8RA, IL8RB, IL12RB1, IL12RB2, IL13RA1, IL13RA2, IL18R1, TSLP, CCL1, CCL2, CCL3, CCL4, CCL5, CCL7, CCL8, CCL13, CCL17, CCL18, CCL19, CCL20, CCL22, CCL24, CX3CL1, CXCL1, CXCL2, CXCL3, XCL1, CCR2, CCR3, CCR4, CCR5, CCR6, CCR7, CCR8, CX3CR1, GPR2, XCR1, FOS, GATA3, JAK1, JAK3, STAT6, TBX21, TGFB1, TNFSF6, YY1, CYSLTR1, FCER1A, FCER2, LTB4R, TB4R2, LTBR, and Chitinase.

Rheumatoid arthritis (RA), a systemic disease, is characterized by a chronic inflammatory reaction in the synovium of joints and is associated with degeneration of cartilage and erosion of juxta-articular bone. Many pro-inflammatory cytokines including TNF, chemokines, and growth factors are expressed in diseased joints. Systemic administration of anti-TNF antibody or sTNFR fusion protein to mouse models of RA was shown to be anti-inflammatory and joint protective. Clinical investigations in which the activity of TNF in RA patients was blocked with intravenously administered infliximab (Harriman G, Harper L K, Schaible T F. 1999 Summary of clinical trials in rheumatoid arthritis using infliximab, an anti-TNFalpha treatment. Ann Rheum Dis 58 Suppl 1:161-4), a chimeric anti-TNF monoclonal antibody (mAB), has provided evidence that TNF regulates IL-6, IL-8, MCP-1, and VEGF production, recruitment of immune and inflammatory cells into joints, angiogenesis, and reduction of blood levels of matrix metalloproteinases-1 and -3. A better understanding of the inflammatory pathway in rheumatoid arthritis has led to identification of other therapeutic targets involved in rheumatoid arthritis. Promising treatments such as interleukin-6 antagonists (MRA), CTLA4Ig (abatacept, Genovese Mc et al 2005 Abatacept for rheumatoid arthritis refractory to tumor necrosis factor alpha inhibition. N Engl J Med. 353:1114-23), and anti-B cell therapy (rituximab, Okamoto H, Kamatani N. 2004 Rituximab for rheumatoid arthritis. N Engl J Med. 351:1909) have already been tested in randomized controlled trials over the past year. Other cytokines have been identified and have been shown to be of benefit in animal models, including interleukin-15, interleukin-17, and interleukin-18, and clinical trials of these agents are currently under way. Dual-specific antibody therapy, combining anti-TNF and another mediator, has great potential in enhancing clinical efficacy and/or patient coverage. For example, blocking both TNF and VEGF can potentially eradicate inflammation and angiogenesis, both of which are involved in pathophysiology of RA. Blocking other pairs of targets involved in RA including, but not limited to, TNF and IL-18; TNF and IL-12; TNF and IL-23; TNF and IL-1beta; TNF and MIF; TNF and IL-17; and TNF and IL-15 with specific FIT-Ig Igs is also contemplated. In addition to routine safety assessments of these target pairs, specific tests for the degree of immunosuppression may be warranted and helpful in selecting the best target pairs (see Luster et al., Toxicology (1994), 92(1-3), 229-43; Descotes, et al., Developments in biological standardization (1992), 77 99-102; Hart et al., Journal of Allergy and Clinical Immunology (2001), 108(2), 250-257). Whether a FIT-Ig Ig molecule will be useful for the treatment of rheumatoid arthritis can be assessed using preclinical animal RA models such as the collagen-induced arthritis mouse model. Other useful models are also well known in the art (see Brand D D., Comp Med. (2005) 55(2):114-22).

The immunopathogenic hallmark of systemic lupus erythematosus (SLE) is the polyclonal B cell activation, which leads to hyperglobulinemia, autoantibody production and immune complex formation. The fundamental abnormality appears to be the failure of T cells to suppress the forbidden B cell clones due to generalized T cell dysregulation. In addition, B and T-cell interaction is facilitated by several cytokines such as IL-10 as well as co-stimulatory molecules such as CD40 and CD40L, B7 and CD28 and CTLA-4, which initiate the second signal. These interactions together with impaired phagocytic clearance of immune complexes and apoptotic material, perpetuate the immune response with resultant tissue injury. The following targets may be involved in SLE and can potentially be used for FIT-Ig approach for therapeutic intervention: B cell targeted therapies: CD-20, CD-22, CD-19, CD28, CD4, CD80, HLA-DRA, IL10, IL2, IL4, TNFRSF5, TNFRSF6, TNFSF5, TNFSF6, BLR1, HDAC4, HDAC5, HDAC7A, HDAC9, ICOSL, IGBP1, MS4A1, RGS1, SLA2, CD81, IFNB1, IL10, TNFRSF5, TNFRSF7, TNFSF5, AICDA, BLNK, GALNAC4S-6ST, HDAC4, HDAC5, HDAC7A, HDAC9, IL10, IL11, IL4, INHA, INHBA, KLF6, TNFRSF7, CD28, CD38, CD69, CD80, CD83, CD86, DPP4, FCER2, IL2RA, TNFRSF8, TNFSF7, CD24, CD37, CD40, CD72, CD74, CD79A, CD79B, CR2, IL1R2, ITGA2, ITGA3, MS4A1, ST6GAL1, CD1C, CHST10, HLA-A, HLA-DRA, and NT5E.; co-stimulatory signals: CTLA-4 or B7.1/B7.2; inhibition of B cell survival: BlyS, BAFF; Complement inactivation: C5; Cytokine modulation: the key principle is that the net biologic response in any tissue is the result of a balance between local levels of proinflammatory or anti-inflammatory cytokines (see Sfikakis P P et al 2005 Curr Opin Rheumatol 17:550-7). SLE is considered to be a Th-2 driven disease with documented elevations in serum IL-4, IL-6, IL-10. FIT-Ig Igs capable of binding one or more targets selected from the group consisting of IL-4, IL-6, IL-10, IFN-α, and TNF-α are also contemplated. Combination of targets discussed above will enhance therapeutic efficacy for SLE which can be tested in a number of lupus preclinical models (see Peng S L (2004) Methods Mol Med.; 102:227-72).

Multiple sclerosis (MS) is a complex human autoimmune-type disease with a predominantly unknown etiology. Immunologic destruction of myelin basic protein (MBP) throughout the nervous system is the major pathology of multiple sclerosis. MS is a disease of complex pathologies, which involves infiltration by CD4+ and CD8+ T cells and of response within the central nervous system. Expression in the CNS of cytokines, reactive nitrogen species and costimulator molecules have all been described in MS. Of major consideration are immunological mechanisms that contribute to the development of autoimmunity. In particular, antigen expression, cytokine and leukocyte interactions, and regulatory T-cells, which help balance/modulate other T-cells such as Th1 and Th2 cells, are important areas for therapeutic target identification.

IL-12 is a proinflammatory cytokine that is produced by APC and promotes differentiation of Th1 effector cells. IL-12 is produced in the developing lesions of patients with MS as well as in EAE-affected animals. Previously it was shown that interference in IL-12 pathways effectively prevents EAE in rodents, and that in vivo neutralization of IL-12p40 using a anti-IL-12 mAb has beneficial effects in the myelin-induced EAE model in common marmosets.

TWEAK is a member of the TNF family, constitutively expressed in the central nervous system (CNS), with pro-inflammatory, proliferative or apoptotic effects depending upon cell types. Its receptor, Fn14, is expressed in CNS by endothelial cells, reactive astrocytes and neurons. TWEAK and Fn14 mRNA expression increased in spinal cord during experimental autoimmune encephalomyelitis (EAE). Anti-TWEAK antibody treatment in myelin oligodendrocyte glycoprotein (MOG) induced EAE in C57BL/6 mice resulted in a reduction of disease severity and leukocyte infiltration when mice were treated after the priming phase.

One aspect of the invention pertains to FIT-Ig Ig molecules capable of binding one or more, preferably two, targets selected from the group consisting of IL-12, TWEAK, IL-23, CXCL13, CD40, CD40L, IL-18, VEGF, $VL_A$-4, TNF, CD45RB, CD200, IFNgamma, GM-CSF, FGF, C5, CD52, and CCR2. A preferred embodiment includes a dual-specific anti-IL-12/TWEAK FIT-Ig Ig as a therapeutic agent beneficial for the treatment of MS. Several animal models for assessing the usefulness of the FIT-Ig molecules to treat MS are known in the art (see Steinman L, et al., (2005) Trends Immunol. 26(11):565-71; Lublin F D., et al., (1985) Springer Semin Immunopathol. 8(3):197-208; Genain C P, et al., (1997) J Mol Med. 75(3):187-97; Tuohy V K, et al., (1999) J Exp Med. 189(7):1033-42; Owens T, et al., (1995) Neurol Clin. 13(1):51-73; and 't Hart B A, et al., (2005) J Immunol 175(7):4761-8. In addition to routine safety assessments of these target pairs specific tests for the degree of immunosuppression may be warranted and helpful in selecting the best target pairs (see Luster et al., Toxicology (1994), 92(1-3), 229-43; Descotes, et al., Developments in biological standardization (1992), 77 99-102; Jones R. 2000 Rovelizumab (ICOS Corp). IDrugs. 3(4):442-6).

The pathophysiology of sepsis is initiated by the outer membrane components of both gram-negative organisms (lipopolysaccharide [LPS], lipid A, endotoxin) and gram-positive organisms (lipoteichoic acid, peptidoglycan). These outer membrane components are able to bind to the CD14 receptor on the surface of monocytes. By virtue of the recently described toll-like receptors, a signal is then transmitted to the cell, leading to the eventual production of the proinflammatory cytokines tumor necrosis factor-alpha (TNF-alpha) and interleukin-1 (IL-I). Overwhelming inflammatory and immune responses are essential features of septic shock and play a central part in the pathogenesis of tissue damage, multiple organ failure, and death induced by sepsis. Cytokines, especially tumor necrosis factor (TNF) and interleukin (IL)-1, have been shown to be critical mediators of septic shock. These cytokines have a direct toxic effect on tissues; they also activate phospholipase A2. These and other effects lead to increased concentrations of platelet-activating factor, promotion of nitric oxide synthase activity, promotion of tissue infiltration by neutrophils, and promotion of neutrophil activity.

The treatment of sepsis and septic shock remains a clinical conundrum, and recent prospective trials with biological response modifiers (i.e. anti-TNF, anti-MIF) aimed at the inflammatory response have shown only modest clinical benefit. Recently, interest has shifted toward therapies aimed at reversing the accompanying periods of immune suppression. Studies in experimental animals and critically ill patients have demonstrated that increased apoptosis of lymphoid organs and some parenchymal tissues contribute to this immune suppression, anergy, and organ system dysfunction. During sepsis syndromes, lymphocyte apoptosis can be triggered by the absence of IL-2 or by the release of glucocorticoids, granzymes, or the so-called 'death' cytokines: tumor necrosis factor alpha or Fas ligand. Apoptosis proceeds via auto-activation of cytosolic and/or mitochondrial caspases, which can be influenced by the pro- and anti-apoptotic members of the Bcl-2 family. In experimental animals, not only can treatment with inhibitors of apoptosis prevent lymphoid cell apoptosis; it may also improve outcome. Although clinical trials with anti-apoptotic agents remain distant due in large part to technical difficulties associated with their administration and tissue targeting, inhibition of lymphocyte apoptosis represents an attractive therapeutic target for the septic patient. Likewise, a dual-specific agent targeting both inflammatory mediator and a apoptotic mediator, may have added benefit. One aspect of the invention pertains to FIT-Ig Igs capable of binding one or more targets involved in sepsis, preferably two targets, selected from the group consisting TNF, IL-1, MIF, IL-6, IL-8, IL-18, IL-12, IL-23, FasL, LPS, Toll-like receptors, TLR-4, tissue factor, MIP-2, ADORA2A, CASP1, CASP4, IL10, IL1B, NFKB1, PROC, TNFRSF1A, CSF3, IL10, IL1B, IL6, ADORA2A, CCR3, IL10, IL1B, IL1RN, MIF, NFKB1, PTAFR, TLR2, TLR4, GPR44, HMOX1, midkine, IRAK1, NFKB2, SERPINA1, SERPINE1, and TREM1. The efficacy of such FIT-Ig Igs for sepsis can be assessed in preclinical animal models known in the art (see Buras J A, et al., (2005) Nat Rev Drug Discov. 4(10):854-65 and Calandra T, et al., (2000) Nat Med. 6(2):164-70).

Chronic neurodegenerative diseases are usually age-dependent diseases characterized by progressive loss of neuronal functions (neuronal cell death, demyelination), loss of mobility and loss of memory. Emerging knowledge of the mechanisms underlying chronic neurodegenerative diseases (e.g. Alzheimer's disease) show a complex etiology and a variety of factors have been recognized to contribute to their development and progression e.g. age, glycemic status, amyloid production and multimerization, accumulation of advanced glycation-end products (AGE) which bind to their receptor RAGE (receptor for AGE), increased brain oxidative stress, decreased cerebral blood flow, neuroinflammation including release of inflammatory cytokines and chemokines, neuronal dysfunction and microglial activation. Thus these chronic neurodegenerative diseases represent a complex interaction between multiple cell types and mediators. Treatment strategies for such diseases are limited and mostly constitute either blocking inflammatory processes with non-specific anti-inflammatory agents (e.g., corticosteroids, COX inhibitors) or agents to prevent neuron loss and/or synaptic functions. These treatments fail to stop disease progression. Recent studies suggest that more targeted therapies such as antibodies to soluble A-β peptide (including the A-b oligomeric forms) can not only help stop disease progression but may help maintain memory as well. These preliminary observations suggest that specific therapies targeting more than one disease mediator (e.g. A-β and a pro-inflammatory cytokine such as TNF) may provide even better therapeutic efficacy for chronic neurodegenerative diseases than observed with targeting a single disease mechanism (e.g. soluble A-β alone) (see C. E. Shepherd, et al, Neurobiol Aging. 2005 Oct. 24; Nelson R B., Curr Pharm Des. 2005; 11:3335; William L. Klein; Neurochem Int. 2002; 41:345; Michelle C Janelsins, et al., J Neuroinflammation. 2005; 2:23; Soloman B., Curr Alzheimer Res. 2004; 1:149; Igor Klyubin, et al., Nat Med. 2005; 11:556-61; Arancio O, et al., EMBO Journal (2004) 1-10; Bornemann K D, et al., Am J Pathol. 2001; 158:63; Deane R, et al., Nat Med. 2003; 9:907-13; and Eliezer Masliah, et al., Neuron. 2005; 46:857).

The FIT-Ig molecules of the invention can bind one or more targets involved in Chronic neurodegenerative diseases such as Alzheimer's. Such targets include, but are not limited to, any mediator, soluble or cell surface, implicated in AD pathogenesis e.g. AGE (S100 Å, amphoterin), pro-inflammatory cytokines (e.g. IL-1), chemokines (e.g. MCP 1), molecules that inhibit nerve regeneration (e.g. Nogo, RGM A), molecules that enhance neurite growth (neurotrophins). The efficacy of FIT-Ig molecules can be validated in pre-clinical animal models such as the transgenic mice that over-express amyloid precursor protein or RAGE and develop Alzheimer's disease-like symptoms. In addition, FIT-Ig molecules can be constructed and tested for efficacy in the animal models and the best therapeutic FIT-Ig can be selected for testing in human patients. FIT-Ig molecules can also be employed for treatment of other neurodegenerative diseases such as Parkinson's disease. Alpha-Synuclein is involved in Parkinson's pathology. A FIT-Ig capable of targeting alpha-synuclein and inflammatory mediators such as TNF, IL-1, MCP-1 can prove effective therapy for Parkinson's disease and are contemplated in the invention.

Despite an increase in knowledge of the pathologic mechanisms, spinal cord injury (SCI) is still a devastating condition and represents a medical indication characterized by a high medical need. Most spinal cord injuries are contusion or compression injuries and the primary injury is usually followed by secondary injury mechanisms (inflammatory mediators e.g. cytokines and chemokines) that worsen the initial injury and result in significant enlargement of the lesion area, sometimes more than 10-fold. These primary and secondary mechanisms in SCI are very similar to those in brain injury caused by other means e.g. stroke. No satisfying treatment exists and high dose bolus injection of methylprednisolone (MP) is the only used therapy within a narrow time window of 8 h post injury. This treatment, however, is only intended to prevent secondary injury without causing any significant functional recovery. It is heavily criticized for the lack of unequivocal efficacy and severe adverse effects, like immunosuppression with subsequent infections and severe histopathological muscle alterations. No other drugs, biologics or small molecules, stimulating the endogenous regenerative potential are approved, but promising treatment principles and drug candidates have shown efficacy in animal models of SCI in recent years. To a large extent the lack of functional recovery in human SCI is caused by factors inhibiting neurite growth, at lesion sites, in scar tissue, in myelin as well as on injury-associated cells. Such factors are the myelin-associated proteins NogoA, OMgp and MAG, RGM A, the scar-associated CSPG (Chondroitin Sulfate Proteoglycans) and inhibitory factors on reactive astrocytes (some semaphorins and ephrins). However, at the lesion site not only growth inhibitory molecules are found but also neurite growth stimulating factors like neurotrophins, laminin, L1 and others. This ensemble of neurite growth inhibitory and growth promoting molecules may explain that blocking single factors, like NogoA or RGM A, resulted in significant functional recovery in rodent SCI models, because a reduction of the inhibitory influences could shift the balance from growth inhibition to growth promotion. However, recoveries observed with blocking a single neurite outgrowth inhibitory molecule were not complete. To achieve faster and more pronounced recoveries either blocking two neurite outgrowth inhibitory molecules e.g. Nogo and RGM A, or blocking an neurite outgrowth inhibitory molecule and enhancing functions of a neurite outgrowth enhancing molecule e.g. Nogo and neurotrophins, or blocking a neurite outgrowth inhibitory molecule e.g. Nogo and a pro-inflammatory molecule e.g. TNF, may be desirable (see McGee A W, et al., Trends Neurosci. 2003; 26:193; Marco Domeniconi, et al., J Neurol Sci. 2005; 233:43; Milan Makwanal, et al., FEBS J. 2005; 272:2628; Barry J. Dickson, Science. 2002; 298:1959; Felicia Yu Hsuan Teng, et al., J Neurosci Res. 2005; 79:273; Tara Karnezis, et al., Nature Neuroscience 2004; 7, 736; Gang Xu, et al., J. Neurochem. 2004; 91; 1018).

Other FIT-Igs contemplated are those capable of binding target pairs such as NgR and RGM A; NogoA and RGM A; MAG and RGM A; OMGp and RGM A; RGM A and RGM B; CSPGs and RGM A; aggrecan, midkine, neurocan, versican, phosphacan, Te38 and TNF-α; A13 globulomer-specific antibodies combined with antibodies promoting dendrite & axon sprouting. Dendrite pathology is a very early sign of AD and it is known that NOGO A restricts dendrite growth. One can combine such type of ab with any of the SCI-candidate (myelin-proteins) Ab. Other FIT-Ig targets may include any combination of NgR-p75, NgR-Troy, NgR-Nogo66 (Nogo), NgR-Lingo, Lingo-Troy, Lingo-p75, MAG or Omgp. Additionally, targets may also include any mediator, soluble or cell surface, implicated in inhibition of neurite e.g Nogo, Ompg, MAG, RGM A, semaphorins, ephrins, soluble A-b, pro-inflammatory cytokines (e.g. IL-1), chemokines (e.g. MIP 1a), molecules that inhibit nerve regeneration. The efficacy of anti-nogo/anti-RGM A or similar FIT-Ig molecules can be validated in pre-clinical animal models of spinal cord injury. In addition, these FIT-Ig molecules can be constructed and tested for efficacy in the animal models and the best therapeutic FIT-Ig can be selected for testing in human patients. In addition, FIT-Ig molecules can be constructed that target two distinct ligand binding sites on a single receptor e.g. Nogo receptor which binds three ligand Nogo, Ompg, and MAG and RAGE that binds A-b and S100 A. Furthermore, neurite outgrowth inhibitors e.g. nogo and nogo receptor, also play a role in preventing nerve regeneration in immunological diseases like multiple sclerosis. Inhibition of nogo-nogo receptor interaction has been shown to enhance recovery in animal models of multiple sclerosis. Therefore, FIT-Ig molecules that can block the function of one immune mediator eg a cytokine like IL-12 and a neurite outgrowth inhibitor molecule eg nogo or RGM may offer faster and greater efficacy than blocking either an immune or an neurite outgrowth inhibitor molecule alone.

Monoclonal antibody therapy has emerged as an important therapeutic modality for cancer (von Mehren M, et al 2003 Monoclonal antibody therapy for cancer. Annu Rev Med.; 54:343-69). Antibodies may exert antitumor effects by inducing apoptosis, redirected cytotoxicity, interfering with ligand-receptor interactions, or preventing the expression of proteins that are critical to the neoplastic phenotype. In addition, antibodies can target components of the tumor microenvironment, perturbing vital structures such as the formation of tumor-associated vasculature. Antibodies can also target receptors whose ligands are growth factors, such as the epidermal growth factor receptor. The antibody thus inhibits natural ligands that stimulate cell growth from binding to targeted tumor cells. Alternatively, antibodies may induce an anti-idiotype network, complement-mediated cytotoxicity, or antibody-dependent cellular cytotoxicity (ADCC). The use of dual-specific antibody that targets two separate tumor mediators will likely give additional benefit compared to a mono-specific therapy. FIT-Ig Igs capable of binding the following pairs of targets to treat oncological disease are also contemplated: IGF1 and IGF2; IGF1/2 and Erb2B; VEGFR and EGFR; CD20 and CD3, CD138 and CD20, CD38 and CD20, CD38 & CD138, CD40 and CD20, CD138 and CD40, CD38 and CD40. Other target combinations include one or more members of the EGF/erb-2/erb-3 family. Other targets (one or more) involved in oncological diseases that FIT-Ig Igs may bind include, but are not limited to those selected from the group consisting of: CD52, CD20, CD19, CD3, CD4, CD8, BMP6, IL12A, IL1A, IL1B, IL2, IL24, INHA, TNF, TNFSF10, BMP6, EGF, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, GRP, IGF1, IGF2, IL12A, IL1A, IL1B, IL2, INHA, TGFA, TGFB1, TGFB2, TGFB3, VEGF, CDK2, EGF, FGF10, FGF18, FGF2, FGF4, FGF7, IGF1, IGF1R, IL2, VEGF, BCL2, CD164, CDKN1A, CDKN1B, CDKN1C, CDKN2A, CDKN2B, CDKN2C, CDKN3, GNRH1, IGFBP6, IL1A, IL1B, ODZ1, PAWR, PLG, TGFBII1, AR, BRCA1, CDK3, CDK4, CDK5, CDK6, CDK7, CDK9, E2F1, EGFR, ENO1, ERBB2, ESR1, ESR2, IGFBP3, IGFBP6, IL2, INSL4, MYC, NOX5, NR6A1, PAP, PCNA, PRKCQ, PRKD1, PRL, TP53, FGF22, FGF23, FGF9, IGFBP3, IL2, INHA, KLK6, TP53, CHGB, GNRH1, IGF1, IGF2, INHA, INSL3, INSL4, PRL, KLK6, SHBG, NR1D1, NR1H3, NR1I3, NR2F6, NR4A3, ESR1, ESR2, NROB1, NROB2, NR1D2, NR1H2, NR1H4, NR1I2, NR2C1, NR2C2, NR2E1, NR2E3, NR2F1, NR2F2, NR3C1, NR3C2, NR4A1, NR4A2, NR5A1, NR5A2, NR6A1, PGR, RARB, FGF1, FGF2, FGF6, KLK3, KRT1, APOC1, BRCA1, CHGA, CHGB, CLU, COL1A1, COL6A1, EGF, ERBB2, ERK8, FGF1, FGF10, FGF11, FGF13, FGF14, FGF16, FGF17, FGF18, FGF2, FGF20, FGF21, FGF22, FGF23, FGF3, FGF4, FGF5, FGF6, FGF7, FGF8, FGF9, GNRH1, IGF1, IGF2, IGFBP3, IGFBP6, IL12A, IL1A, IL1B, IL2, IL24, INHA, INSL3, INSL4, KLK10, KLK12, KLK13, KLK14, KLK15, KLK3, KLK4, KLK5, KLK6, KLK9, MMP2, MMP9, MSMB, NTN4, ODZ1, PAP, PLAU, PRL, PSAP, SERPINA3, SHBG, TGFA, TIMP3, CD44, CDH1, CDH10, CDH19, CDH20, CDH7, CDH9, CDH1, CDH10, CDH13, CDH18, CDH19, CDH20, CDH7, CDH8, CDH9, ROBO2, CD44, ILK, ITGA1, APC, CD164, COL6A1, MTSS1, PAP, TGFB1I1, AGR2, AIG1, AKAP1, AKAP2, CANT1, CAV1, CDH12, CLDN3, CLN3, CYB5, CYC1, DAB2IP, DES, DNCL1, ELAC2, ENO2, ENO3, FASN, FLJ12584, FLJ25530, GAGEB1, GAGEC1, GGT1, GSTP1, HIP1, HUMCYT2A, IL29, K6HF, KAI1, KRT2A, MIB1, PART1, PATE, PCA3, PIAS2, PIK3CG, PPID, PR1, PSCA, SLC2A2, SLC33A1, SLC43A1, STEAP, STEAP2, TPM1, TPM2, TRPC6, ANGPT1, ANGPT2, ANPEP, ECGF1, EREG, FGF1, FGF2, FIGF, FLT1, JAG1, KDR, LAMA5, NRP1, NRP2, PGF, PLXDC1, STAB1, VEGF, VEGFC, ANGPTL3, BAIl, COL4A3, IL8, LAMA5, NRP1, NRP2, STAB1, ANGPTL4, PECAMi, PF4, PROK2, SERPINF1, TNFAIP2, CCL11, CCL2, CXCL1, CXCL10, CXCL3, CXCL5, CXCL6, CXCL9, IFNA1, IFNB1, IFNG, IL1B, IL6, MDK, EDG1, EFNA1, EFNA3, EFNB2, EGF, EPHB4, FGFR3, HGF, IGF1, ITGB3, PDGFA, TEK, TGFA, TGFB1, TGFB2, TGFBR1, CCL2, CDH5, COL18A1, EDG1, ENG, ITGAV, ITGB3, THBS1, THBS2, BAD, BAG1, BCL2, CCNA1, CCNA2, CCND1, CCNE1, CCNE2, CDH1 (E-cadherin), CDKN1B (p27Kip1), CDKN2A (p16INK4a), COL6A1, CTNNB1 (b-catenin), CTSB (cathepsin B), ERBB2 (Her-2), ESR1, ESR2, F3 (TF), FOSL1 (FRA-1), GATA3, GSN (Gelsolin), IGFBP2, IL2RA, IL6, IL6R, IL6ST (glycoprotein 130), ITGA6 (a6 integrin), JUN, KLK5, KRT19, MAP2K7 (c-Jun), MK167 (Ki-67), NGFB (NGF), NGFR, NME1 (NM23A), PGR, PLAU (uPA), PTEN, CTLA-4, OX40, GITR, TIM-3, Lag-3, B7-H3, B7-H4, GDF8, CGRP, Lingo-1, ICOS, GARP, BTLA, CD160, ROR1, SERPINB5 (maspin), SERPINE1 (PAI-1), TGFA, THBS1 (thrombospondin-1), TIE (Tie-1), TNFRSF6 (Fas), TNFSF6 (FasL), TOP2A (topoisomerase Iia), TP53, AZGP1 (zinc-a-glycoprotein), BPAG1 (plectin), CDKN A (p2 Wap1/Cip1), CLDN7 (claudin-7), CLU (clusterin), ERBB2 (Her-2), FGF1, FLRT1 (fibronectin), GABRP (GABAa), GNAS1, ID2, ITGA6 (a6 integrin), ITGB4 (b 4 integrin), KLF5 (GC Box BP), KRT19 (Keratin 19), KRTHB6 (hair-specific type II keratin), MACMARCKS, MT3 (metallothionectin-III), MUC1 (mucin), PTGS2 (COX-2), RAC2 (p21Rac2), S100A2, SCGBiD2 (lipophilin B), SCGB2A1 (mammaglobin 2), SCGB2A2 (mammaglobin 1), SPRRiB (Spr1), THBS1, THBS2, THBS4, and TNFAIP2 (B94).

In an embodiment, diseases that can be treated or diagnosed with the compositions and methods provided herein include, but are not limited to, primary and metastatic cancers, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), solid tumors arising from hematopoietic malignancies such as leukemias, and lymphomas (both Hodgkin's and non-Hodgkin's lymphomas).

In an embodiment, the antibodies provided herein or antigen-binding portions thereof, are used to treat cancer or in the prevention of metastases from the tumors described herein either when used alone or in combination with radiotherapy and/or other chemotherapeutic agents.

According to another embodiment of the invention, the human immune effector cell is a member of the human lymphoid cell lineage. In this embodiment, the effector cell may advantageously be a human T cell, a human B cell or a human natural killer (NK) cell. Advantageously, such cells will have either a cytotoxic or an apoptotic effect on the target cell. Especially advantageously, the human lymphoid cell is a cytotoxic T cell which, when activated, exerts a cytotoxic effect on the target cell. According to this embodiment, then, the recruited activity of the human effector cell is this cell's cytotoxic activity.

According to a preferred embodiment, activation of the cytotoxic T cell may occur via binding of the CD3 antigen as effector antigen on the surface of the cytotoxic T cell by a bispecific antibody of this embodiment of the invention. The human CD3 antigen is present on both helper T cells and cytotoxic T cells. Human CD3 denotes an antigen which is expressed on T cells as part of the multimolecular T cell complex and which comprises three different chains: CD3-epsilon, CD3-delta and CD3-gamma.

The activation of the cytotoxic potential of T cells is a complex phenomenon which requires the interplay of multiple proteins. The T cell receptor ("TCR") protein is a membrane bound disulfide-linked heterodimer consisting of two different glycoprotein subunits. The TCR recognizes and binds foreign peptidic antigen which itself has been bound by a member of the highly diverse class of major histocompatibility complex ("MHC") proteins and has been presented, bound to the MHC, on the surface of antigen presenting cells ("APCs").

Although the variable TCR binds foreign antigen as outlined above, signaling to the T cell that this binding has taken place depends on the presence of other, invariant, signaling proteins associated with the TCR. These signaling proteins in associated form are collectively referred to as the CD3 complex, here collectively referred to as the CD3 antigen.

The activation of T cell cytotoxicity, then, normally depends first on the binding of the TCR with an MHC protein, itself bound to foreign antigen, located on a separate cell. Only when this initial TCR-MHC binding has taken place can the CD3-dependent signaling cascade responsible for T cell clonal expansion and, ultimately, T cell cytotoxicity ensue.

However, binding of the human CD3 antigen by the first or second portion of a bispecific antibody of the invention activates T cells to exert a cytotoxic effect on other cells in the absence of independent TCR-MHC binding. This means that T cells may be cytotoxically activated in a clonally independent fashion, i.e., in a manner which is independent of the specific TCR clone carried by the T cell. This allows an activation of the entire T cell compartment rather than only specific T cells of a certain clonal identity.

In light of the foregoing discussion, then, an especially preferred embodiment of the invention provides a bispecific antibody in which the effector antigen is the human CD3 antigen. The bispecific antibody according to this embodiment of the invention may have a total of either two or three antibody variable domains.

According to further embodiments of the invention, other lymphoid cell-associated effector antigens bound by a bispecific antibody of the invention may be the human CD16 antigen, the human NKG2D antigen, the human NKp46 antigen, the human CD2 antigen, the human CD28 antigen or the human CD25 antigen.

According to another embodiment of the invention, the human effector cell is a member of the human myeloid lineage. Advantageously, the effector cell may be a human monocyte, a human neutrophilic granulocyte or a human dendritic cell. Advantageously, such cells will have either a cytotoxic or an apoptotic effect on the target cell. Advantageous antigens within this embodiment which may be bound by a bispecific antibody of the invention may be the human CD64 antigen or the human CD89 antigen.

According to another embodiment of the invention, the target antigen is an antigen which is uniquely expressed on a target cell or effector cell in a disease condition, but which remains either non-expressed, expressed at a low level or non-accessible in a healthy condition. Examples of such target antigens which might be specifically bound by a bispecific antibody of the invention may advantageously be selected from EpCAM, CCR5, CD19, HER-2 neu, HER-3, HER-4, EGFR, PSMA, CEA, MUC-1 (mucin), MUC2, MUC3, MUC4, MUC5AC, MUC5B, MUC7, P3hCG, Lewis-Y, CD20, CD33, CD30, ganglioside GD3, 9-O-Acetyl-GD3, GM2, Globo H, fucosyl GM1, Poly SA, GD2, Carboanhydrase IX (MN/CA IX), CD44v6, Sonic Hedgehog (Shh), Wue-1, Plasma Cell Antigen, (membrane-bound) IgE, Melanoma Chondroitin Sulfate Proteoglycan (MCSP), CCR8, TNF-alpha precursor, STEAP, mesothelin, A33 Antigen, Prostate Stem Cell Antigen (PSCA), Ly-6; desmoglein 4, E-cadherin neoepitope, Fetal Acetylcholine Receptor, CD25, CA19-9 marker, CA-125 marker and Muellerian Inhibitory Substance (MIS) Receptor type II, sTn (sialylated Tn antigen; TAG-72), FAP (fibroblast activation antigen), endosialin, EGFRvIII, LG, SAS and CD63.

According to a specific embodiment, the target antigen specifically bound by a bispecific antibody may be a cancer-related antigen, e.g., an antigen related to a malignant condition. Such an antigen is either expressed or accessible on a malignant cell, whereas the antigen is either not present, not significantly present, or is not accessible on a non-malignant cell. As such, a bispecific antibody according to this embodiment of the invention is a bispecific antibody which recruits the activity of a human immune effector cell against the malignant target cell bearing the target antigen, or rendering the target antigen accessible.

Gene Therapy: In a specific embodiment, nucleic acid sequences encoding a binding protein provided herein or another prophylactic or therapeutic agent provided herein are administered to treat, prevent, manage, or ameliorate a disorder or one or more symptoms thereof by way of gene therapy. Gene therapy refers to therapy performed by the administration to a subject of an expressed or expressible nucleic acid. In this embodiment, the nucleic acids produce their encoded antibody or prophylactic or therapeutic agent provided herein that mediates a prophylactic or therapeutic effect.

Any of the methods for gene therapy available in the art can be used in the methods provided herein. For general reviews of the methods of gene therapy, see Goldspiel et al. (1993) Clin. Pharmacy 12:488-505; Wu and Wu (1991) Biotherapy 3:87-95; Tolstoshev (1993) Ann Rev. Pharmacol. Toxicol. 32:573-596; Mulligan (1993) Science 260:926-932; Morgan and Anderson (1993) Ann Rev. Biochem. 62:191-217; and May (1993) TIBTECH 11(5):155-215. Methods commonly known in the art of recombinant DNA technology which can be used are described in Ausubel et al. (eds.), Current Protocols in Molecular Biology, John Wiley & Sons, N Y (1993); and Kriegler, Gene Transfer and Expression, A Laboratory Manual, Stockton Press, NY (1990). Detailed description of various methods of gene therapy is disclosed in US Patent Publication No. US20050042664.

Diagnostics: The disclosure herein also provides diagnostic applications including, but not limited to, diagnostic assay methods, diagnostic kits containing one or more binding proteins, and adaptation of the methods and kits for use in automated and/or semi-automated systems. The methods, kits, and adaptations provided may be employed in the detection, monitoring, and/or treatment of a disease or disorder in an individual. This is further elucidated below.

A. Method of Assay: The present disclosure also provides a method for determining the presence, amount or concentration of an analyte, or fragment thereof, in a test sample using at least one binding protein as described herein. Any suitable assay as is known in the art can be used in the method. Examples include, but are not limited to, immunoassays and/or methods employing mass spectrometry. Immunoassays provided by the present disclosure may include sandwich immunoassays, radioimmunoassay (RIA), enzyme immunoassay (EIA), enzyme-linked immunosorbent assay (ELISA), competitive-inhibition immunoassays, fluorescence polarization immunoassay (FPIA), enzyme multiplied immunoassay technique (EMIT), bioluminescence resonance energy transfer (BRET), and homogenous chemiluminescent assays, among others. A chemiluminescent microparticle immunoassay, in particular one employing the ARCHITECT® automated analyzer (Abbott Laboratories, Abbott Park, Ill.), is an example of an immunoassay. Methods employing mass spectrometry are provided by the present disclosure and include, but are not limited to MALDI (matrix-assisted laser desorption/ionization) or by SELDI (surface-enhanced laser desorption/ionization).

Methods for collecting, handling, processing, and analyzing biological test samples using immunoassays and mass spectrometry would be well-known to one skilled in the art, are provided for in the practice of the present disclosure (US 2009-0311253 A1).

B. Kit: A kit for assaying a test sample for the presence, amount or concentration of an analyte, or fragment thereof, in a test sample is also provided. The kit comprises at least one component for assaying the test sample for the analyte, or fragment thereof, and instructions for assaying the test sample for the analyte, or fragment thereof. The at least one component for assaying the test sample for the analyte, or fragment thereof, can include a composition comprising a binding protein, as disclosed herein, and/or an anti-analyte binding protein (or a fragment, a variant, or a fragment of a variant thereof), which is optionally immobilized on a solid phase. Optionally, the kit may comprise a calibrator or control, which may comprise isolated or purified analyte. The kit can comprise at least one component for assaying the test sample for an analyte by immunoassay and/or mass spectrometry. The kit components, including the analyte, binding protein, and/or anti-analyte binding protein, or fragments thereof, may be optionally labeled using any art-known detectable label. The materials and methods for the creation provided for in the practice of the present disclosure would be known to one skilled in the art (US 2009-0311253 A1).

C. Adaptation of Kit and Method: The kit (or components thereof), as well as the method of determining the presence, amount or concentration of an analyte in a test sample by an assay, such as an immunoassay as described herein, can be adapted for use in a variety of automated and semi-automated systems (including those wherein the solid phase comprises a microparticle), as described, for example, in U.S. Pat. Nos. 5,089,424 and 5,006,309, and as commercially marketed, for example, by Abbott Laboratories (Abbott Park, Ill.) as ARCHITECT®. Other platforms available from Abbott Laboratories include, but are not limited to, AxSYM®, IMx® (see, for example, U.S. Pat. No. 5,294,404, PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. Nos. 5,063,081, 7,419,821, and 7,682,833; and US Publication Nos. 20040018577, 20060160164 and US 20090311253. It will be readily apparent to those skilled in the art that other suitable modifications and adaptations of the methods described herein are obvious and may be made using suitable equivalents without departing from the scope of the embodiments disclosed herein. Having now described certain embodiments in detail, the same will be more clearly understood by reference to the following examples, which are included for purposes of illustration only and are not intended to be limiting.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of non-critical parameters that could be changed or modified to yield essentially similar results.

EXAMPLES

Example 1. Construction, Expression, Purification, and Analysis of Anti-IL17/IL-20 Fabs-in-Tandem Immunoglobulin (FIT-Ig)

Figure 1B:
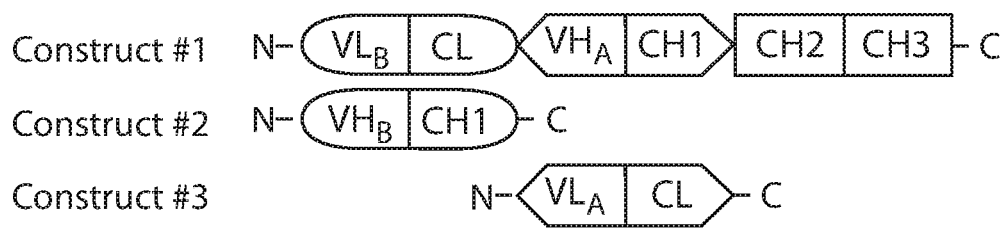
FIG. 1B shows the three constructs used to prepare such FIT1-Igs.

To demonstrate the FIT-Ig technology, we have generated a group of anti-IL-17/IL-20 FIT-Ig molecules: FIT1-Ig, FIT2-Ig, and FIT3-Ig, all of which contains 3 different polypeptides, as shown in FIG. 1, where antigen A is IL-17 and antigen B is IL-20. The DNA construct used to generate FIT-Ig capable of binding IL-17 and IL-20 is illustrated in FIG. 1B. Briefly, parental mAbs included two high affinity antibodies, anti-IL-17 (clone LY) (U.S. Pat. No. 7,838,638) and anti-hIL-20 (clone 15D2) (U.S. Patent Application Publication No. US2014/0194599). To generate FIT-Ig construct #1, the VL-CL of LY was directly (FIT1-Ig), or through a linker of 3 amino acids (FIT2-Ig) or 7 amino acids (FIT3-Ig) fused to the N-terminus of the 15D2 heavy chain (as shown in Table 1). The construct #2 is VH-CH1 of LY, and the 3$^{rd}$ construct is VL-CL of 15D2. The 3 constructs for each FIT-Ig were co-transfected in 293 cells, resulting in the expression and secretion of FIT-Ig protein.

Figure 2A:
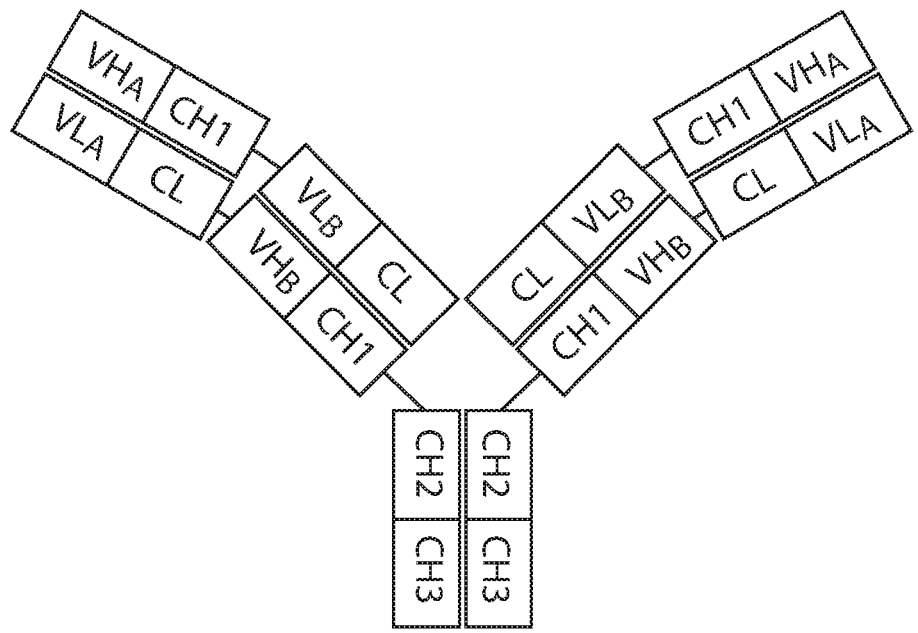
FIG. 2A shows the basic structure of FIT-Igs that are made up of two constructs.
Figure 2B:
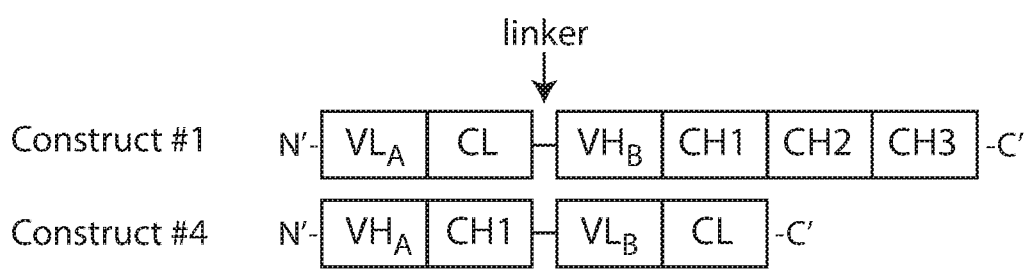
FIG. 2B shows the two constructs used to prepare such FIT-Igs.

We also generated a group of anti-IL-17/IL-20 FIT-Ig molecules: FIT4-Ig, FIT5-Ig, and FIT6-Ig, each of which contains 2 different polypeptides, as shown in FIG. 2. The DNA constructs used to generate FIT-Ig capable of binding IL-17 and IL-20 are illustrated in FIG. 2B, where antigen A is IL-17 and antigen B is IL-20. Briefly, parental mAbs included two high affinity antibodies, anti-IL-17 (clone LY) and anti-hIL-20 (clone 15D2). To generate FIT-Ig construct #1, the VL-CL of LY was directly (FIT4-Ig), or through a linker of 3 amino acids (FIT5-Ig) or 7 amino acids (FIT6-Ig) fused to the N-terminus of the 15D2 heavy chain (as shown in Table 1). To generate FIT-Ig construct #4, the VH-CH1 of LY was directly (FIT4-Ig), or through a linker of 3 amino acids (FIT5-Ig) or 7 amino acids (FIT6-Ig) fused to the N-terminus of the 15D2 light chain. The 2 DNA constructs (construct #1 and #4) for each FIT-Ig were co-transfected in 293 cells, resulting in the expression and secretion of FIT-Ig protein. The detailed procedures of the PCR cloning are described below.

Example 1.1: Molecular Cloning of Anti-IL-17/IL-20 FIT-Ig Molecules

For construct #1 cloning, LY light chain was amplified by PCR using forward primers annealing on light chain signal sequence and reverse primers annealing on C-terminus of the light chain. 15D2 heavy chain was amplified by PCR using forward primers annealing on N-terminus of 15D2 VH and reverse primers annealing on C-terminus of CH. These 2 PCR fragments were gel purified and combined by overlapping PCR using signal peptide and CH primer pair. The combined PCR product was cloned into a 293 expression vector, which already contained the human Fc sequence.

TABLE 1

Anti-IL-17/IL-20 FIT-Ig molecules and DNA constructs.

| FIT-Ig molecule | Construct #1 | Linker | Construct #2 | Construct #3 | Construct #4 |
|---|---|---|---|---|---|
| FIT1-Ig | VL$_{17}$-CL-VH$_{20}$-CH1-Fc | No linker | VH$_{17}$-CH1 | VL$_{20}$-CL | |
| FIT2-Ig | VL$_{17}$-CL-linker-VH$_{20}$-CH1-Fc | GSG | VH$_{17}$-CH1 | VL$_{20}$-CL | |
| FIT3-Ig | VL$_{17}$-CL-linker-VH$_{20}$-CH1-Fc | GGGGSGS | VH$_{17}$-CH1 | VL$_{20}$-CL | |
| FIT4-Ig | VL$_{17}$-CL-VH$_{20}$-CH1-Fc | No linker | | | VH$_{17}$-CH1-VL$_{20}$-CL |
| FIT5-Ig | VL$_{17}$-CL-linker-VH$_{20}$-CH1-Fc | GSG | | | VH$_{17}$-CH1-linker-VL$_{20}$-CL |
| FIT6-Ig | VL$_{17}$-CL-linker-VH$_{20}$-CH1-Fc | GGGGSGS | | | VH$_{17}$-CH1-linker-VL$_{20}$-CL |

For construct #2 cloning, LY VH-CH1 was amplified by PCR using forward primers annealing on heavy chain signal peptide and reverse primer annealing on C-terminal of CH1. The PCR product was gel purified before cloning into 293 expression vector.

For construct #3, 15D2 light chain was amplified by PCR using forward primer annealing on N-terminal of light chain signal peptide and reverse primer annealing on the end of CL. The PCR product was gel purified before cloning into 293 expression vector.

For construct #4 cloning, LY VH-CH1 was amplified by PCR using forward primer annealing on N-terminus of heavy chain signal peptide and reverse primer annealing on the end of CH1. 15D2 VL was amplified using primers annealing on the end of 15D2 VL. Both PCR products were gel purified and combined by overlap PCR. The combined PCR product was gel purified and cloned in 293 expression vector. Table 2 shows sequences of PCR primers used for above molecular cloning.

TABLE 2

PCR primers used for molecular construction of anti-IL-17/anti-CD20 FIT-Igs

| | |
|---|---|
| P1: 5' CAGGTGCAGCTGGTGCAGAGCGGCGCCGAAG 3' | SEQ ID NO. 1 |
| P2: 5'GCTGGACCTGAGAGCCTGAACCGCCACCACCACACTCTCCCCTGTTGAAGC 3' | SEQ ID NO. 2 |
| P3: 5' GGTGGTGGCGGTTCAGGCTCTCAGGTCCAGCTTGTGCAATCTGGCGCCGAGG3' | SEQ ID NO. 3 |
| P4: 5' GTCTGCGGCCGCTCATTTACCCGGAGACAGGGAGAG 3' | SEQ ID NO. 4 |
| P5: 5' TAAGCGTACGGTGGCTGCACCATCTGTCTTC 3' | SEQ ID NO. 5 |
| P6: 5' CGGCGCCAGATTGCACAAGCTGGACCTGGCCTGAACCACACTCTCCCCTGTT-GAAGCTC 3' | SEQ ID NO. 6 |
| P7: 5' GCTGGACCTGAGAGCCTGAACCGCCACCACCACACTCTCCCCTGTTGAAGC3' | SEQ ID NO. 7 |
| P8: 5' GGTGGTGGCGGTTCAGGCTCTCAGGTCCAGCTTGTGCAATCTGGCGCCGAGG3' | SEQ ID NO. 8 |
| P9: 5' TACCTCGGCGCCAGATTGCACAAGCTGGACCTGACACTCTCCCCTGTT-GAAGCTCTTTG 3' | SEQ ID NO. 9 |
| P10: 5' CATGACACCTTAACAGAGGCCCCAGGTCGTTTTACCTCGGCGCCAGATTGCACAAG3' | SEQ ID NO. 10 |
| P11: 5' CAATAAGCTTTACATGACACCTTAACAGAGGCCCCAG3' | SEQ ID NO. 11 |
| P12: 5' TCGAGCGGCCGCTCAACAAGATTTGGGCTCAACTTTCTTG3' | SEQ ID NO. 12 |
| P13: 5'GCTGCTGCTGTGGTTCCCCGGCTCGCGATGCGCTATACAGTTGACACAGTC3' | SEQ ID NO. 13 |
| P14: 5' GAAGATGAAGACAGATGGTGCAGCCACCGTACGCTTGATCTCTACCTTTGTTC 3' | SEQ ID NO. 14 |

The final sequences of hIL-17/hIL-20 FIT1-Ig, FIT2-Ig, FIT3-Ig, FIT4-Ig, FIT5-Ig, and FIT6-Ig are listed in Table 3.

TABLE 3

Amino acid sequences of anti-IL-17/IL-20 FIT-Ig molecules

| Protein | Protein region | Sequence Identifier | Sequence 12345678901234567890 |
|---|---|---|---|
| Anti-IL-17/IL-20 FIT1-Ig POLYPEPTIDE #1 | | SEQ ID NO.: 15 | DIVMTQTPLSLSVTPGQPASISCRSSRSLVHSRGNTYLHWY LQKPGQSPQLLIYKVSNRFIGVPDRFSGSGSGTDFTLKISR VEAEDVGVYYCSQSTHLPFTFGQGTKLEIKRTVAAPSVFIF PPSDEQLKSGTASVVCLLNNFYPREAKVQWKVDNALQSGNS QESVTEQDSKDSTYSLSSTLTLSKADYEKHKVYACEVTHQG LSSPVTKSFNRGECQVQLVQSGAEVKRPGASVKVSCKASGY TFTNDIIHWVRQAPGQRLEWMGWINAGYGNTQYSQNFQDRV SITRDTSASTAYMELISLRSEDTAVYYCAREPLWFGESSPH DYYGMDVWGQGTTVTVSSASTKGPSVFPLAPSSKSTSGGTA ALGCLVKDYFPEPVTVSWNSGALTSGVHTFPAVLQSSGLYS LSSVVTVPSSSLGTQTYICNVNHKPSNTKVDKKVEPKSCDK THTCPPCPAPELLGGPSVFLFPPKPKDTLMISRTPEVTCVV VDVSHEDPEVKFNWYVDGVEVHNAKTKPREEQYNSTYRVVS VLTVLHQDWLNGKEYKCKVSNKALPAPIEKTISKAKGQPRE PQVYTLPPSREEMTKNQVSLTCLVKGFYPSDIAVEWESNGQ PENNYKTTPPVLDSDGSFFLYSKLTVDKSRWQQGNVFSCSV MHEALHNHYTQKSLSLSPGK |
| | LY VL | SEQ ID NO.: 16 | DIVMTQTPLSLSVTPGQPASISCRSSRSLVHSRGNTYLHWY LQKPGQSPQLLIYKVSNRFIGVPDRFSGSGSGTDFTLKISR VEAEDVGVYYCSQSTHLPFTFGQGTKLEIK |
| | CL | SEQ ID NO.: 17 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |

TABLE 3-continued

Amino acid sequences of anti-IL-17/IL-20 FIT-Ig molecules

| Protein | Protein region | Sequence Identifier | Sequence 12345678901234567890 |
|---|---|---|---|
| | Linker | | None |
| | 15D2 VH | SEQ ID NO.: 18 | QVQLVQSGAEVKRPGASVKVSCKASGYTFTNDIIHWVRQAP GQRLEWMGWINAGYGNTQYSQNFQDRVSITRDTSASTAYME LISLRSEDTAVYYCAREPLWFGESSPHDYYGMDVWGQGTTV TVSS |
| | CH1 | SEQ ID NO.: 19 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKKVEPKSC |
| | Fc | SEQ ID NO.: 20 | DKTHTCPPCPAPELLGGPSVFLFPPKPKDTLMISRTPEVTC VVVDVSHEDPEVKFNWYVDGVEVHNAKTKPREEQYNSTYRV VSVLTVLHQDWLNGKEYKCKVSNKALPAPIEKTISKAKGQP REPQVYTLPPSREEMTKNQVSLTCLVKGFYPSDIAVEWESN GQPENNYKTTPPVLDSDGSFFLYSKLTVDKSRWQQGNVFSC SVMHEALHNHYTQKSLSLSPGK |
| Anti-IL-17/IL-20 FIT1-Ig POLYPEPTIDE #2 | | SEQ ID NO.: 21 | QVQLVQSGAEVKKPGSSVKVSCKASGYSFTDYHIHWVRQAP GQGLEWMGVINPMYGTTDYNQRFKGRVTITADESTSTAYME LSSLRSEDTAVYYCARYDYFTGTGVYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKKVEPKSC |
| | LY VH | SEQ ID NO.: 22 | QVQLVQSGAEVKKPGSSVKVSCKASGYSFTDYHIHWVRQAP GQGLEWMGVINPMYGTTDYNQRFKGRVTITADESTSTAYME LSSLRSEDTAVYYCARYDYFTGTGVYWGQGTLVTVSS |
| | CH1 | SEQ ID NO.: 19 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKKVEPKSC |
| Anti-IL-17/IL-20 FIT1-Ig POLYPEPTIDE #3 | | SEQ ID NO.: 23 | AIQLTQSPSSLSASVGDRVTITCRASQGISSALAWYQQKPG KAPKLLIYDASSLESGVPSRFSGSGSGTDFTLTISSLQPED FATYYCQQFNSYPLTFGGGTKVEIKRTVAAPSVFIFPPSDE QLKSGTASVVCLLNNFYPREAKVQWKVDNALQSGNSQESVT EQDSKDSTYSLSSTLTLSKADYEKHKVYACEVTHQGLSSPV TKSFNRGEC |
| | 15D2 VL | SEQ ID NO.: 24 | AIQLTQSPSSLSASVGDRVTITCRASQGISSALAWYQQKPG KAPKLLIYDASSLESGVPSRFSGSGSGTDFTLTISSLQPED FATYYCQQFNSYPLTFGGGTKVEIK |
| | CL | SEQ ID NO.: 17 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| Anti-IL-17/IL-20 FIT2-Ig POLYPEPTIDE #1 | | SEQ ID NO.: 25 | DIVMTQTPLSLSVTPGQPASISCRSSRSLVHSRGNTYLHWY LQKPGQSPQLLIYKVSNRFIGVPDRFSGSGSGTDFTLKISR VEAEDVGVYYCSQSTHLPFTFGQGTKLEIKRTVAAPSVFIF PPSDEQLKSGTASVVCLLNNFYPREAKVQWKVDNALQSGNS QESVTEQDSKDSTYSLSSTLTLSKADYEKHKVYACEVTHQG LSSPVTKSFNRGECGSGQVQLVQSGAEVKRPGASVKVSCKA SGYTFTNDIIHWVRQAPGQRLEWMGWINAGYGNTQYSQNFQ DRVSITRDTSASTAYMELISLRSEDTAVYYCAREPLWFGES SPHDYYGMDVWGQGTTVTVSSASTKGPSVFPLAPSSKSTSG GTAALGCLVKDYFPEPVTVSWNSGALTSGVHTFPAVLQSSG LYSLSSVVTVPSSSLGTQTYICNVNHKPSNTKVDKKVEPKS CDKTHTCPPCPAPELLGGPSVFLFPPKPKDTLMISRTPEVT CVVVDVSHEDPEVKFNWYVDGVEVHNAKTKPREEQYNSTYR VVSVLTVLHQDWLNGKEYKCKVSNKALPAPIEKTISKAKGQ PREPQVYTLPPSREEMTKNQVSLTCLVKGFYPSDIAVEWES NGQPENNYKTTPPVLDSDGSFFLYSKLTVDKSRWQQGNVFS CSVMHEALHNHYTQKSLSLSPGK |
| | LY VL | SEQ ID NO.: 16 | DIVMTQTPLSLSVTPGQPASISCRSSRSLVHSRGNTYLHWY LQKPGQSPQLLIYKVSNRFIGVPDRFSGSGSGTDFTLKISR VEAEDVGVYYCSQSTHLPFTFGQGTKLEIK |
| | CL | SEQ ID NO.: 17 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| | Linker | SEQ ID NO.: 26 | GSG |
| | 15D2 VH | SEQ ID NO.: 18 | QVQLVQSGAEVKRPGASVKVSCKASGYTFTNDIIHWVRQAP GQRLEWMGWINAGYGNTQYSQNFQDRVSITRDTSASTAYME LISLRSEDTAVYYCAREPLWFGESSPHDYYGMDVWGQGTTV TVSS |
| | CH1 | SEQ ID NO.: 19 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKKVEPKSC |
| | Fc | SEQ ID NO.: 20 | DKTHTCPPCPAPELLGGPSVFLFPPKPKDTLMISRTPEVTC VVVDVSHEDPEVKFNWYVDGVEVHNAKTKPREEQYNSTYRV |

TABLE 3-continued

Amino acid sequences of anti-IL-17/IL-20 FIT-Ig molecules

| Protein | Protein region | Sequence Identifier | Sequence<br>12345678901234567890 |
|---|---|---|---|
| | | | VSVLTVLHQDWLNGKEYKCKVSNKALPAPIEKTISKAKGQP<br>REPQVYTLPPSREEMTKNQVSLTCLVKGFYPSDIAVEWESN<br>GQPENNYKTTPPVLDSDGSFFLYSKLTVDKSRWQQGNVFSC<br>SVMHEALHNHYTQKSLSLSPGK |
| Anti-IL-17/IL-20<br>FIT2-Ig<br>POLYPEPTIDE #2 | | SEQ ID<br>NO.: 21 | QVQLVQSGAEVKKPGSSVKVSCKASGYSFTDYHIHWVRQAP<br>GQGLEWMGVINPMYGTTDYNQRFKGRVTITADESTSTAYME<br>LSSLRSEDTAVYYCARYDYFTGTGVYWGQGTLVTVSSASTK<br>GPSVFPLAPSSKSTSGGTAALGCLVKDYFPEPVTVSWNSGA<br>LTSGVHTFPAVLQSSGLYSLSSVVTVPSSSLGTQTYICNVN<br>HKPSNTKVDKKVEPKSC |
| | LY VH | SEQ ID<br>NO.: 22 | QVQLVQSGAEVKKPGSSVKVSCKASGYSFTDYHIHWVRQAP<br>GQGLEWMGVINPMYGTTDYNQRFKGRVTITADESTSTAYME<br>LSSLRSEDTAVYYCARYDYFTGTGVYWGQGTLVTVSS |
| | CH1 | SEQ ID<br>NO.: 19 | ASTKGPSVFPLAPSSKSTSGGTAALGCLVKDYFPEPVTVSW<br>NSGALTSGVHTFPAVLQSSGLYSLSSVVTVPSSSLGTQTYI<br>CNVNHKPSNTKVDKKVEPKSC |
| Anti-IL-17/IL-20<br>FIT2-Ig<br>POLYPEPTIDE #3 | | SEQ ID<br>NO.: 23 | AIQLTQSPSSLSASVGDRVTITCRASQGISSALAWYQQKPG<br>KAPKLLIYDASSLESGVPSRFSGSGSGTDFTLTISSLQPED<br>FATYYCQQFNSYPLTFGGGTKVEIKRTVAAPSVFIFPPSDE<br>QLKSGTASVVCLLNNFYPREAKVQWKVDNALQSGNSQESVT<br>EQDSKDSTYSLSSTLTLSKADYEKHKVYACEVTHQGLSSPV<br>TKSFNRGEC |
| | 15D2 VL | SEQ ID<br>NO.: 24 | AIQLTQSPSSLSASVGDRVTITCRASQGISSALAWYQQKPG<br>KAPKLLIYDASSLESGVPSRFSGSGSGTDFTLTISSLQPED<br>FATYYCQQFNSYPLTFGGGTKVEIK |
| | CL | SEQ ID<br>NO.: 17 | RTVAAPSVFIFPPSDEQLKSGTASVVCLLNNFYPREAKVQW<br>KVDNALQSGNSQESVTEQDSKDSTYSLSSTLTLSKADYEKH<br>KVYACEVTHQGLSSPVTKSFNRGEC |
| Anti-IL-17/IL-20<br>FIT3-Ig<br>POLYPEPTIDE #1 | | SEQ ID<br>NO.: 27 | DIVMTQTPLSLSVTPGQPASISCRSSRSLVHSRGNTYLHWY<br>LQKPGQSPQLLIYKVSNRFIGVPDRFSGSGSGTDFTLKISR<br>VEAEDVGVYYCSQSTHLPFTFGQGTKLEIKRTVAAPSVFIF<br>PPSDEQLKSGTASVVCLLNNFYPREAKVQWKVDNALQSGNS<br>QESVTEQDSKDSTYSLSSTLTLSKADYEKHKVYACEVTHQG<br>LSSPVTKSFNRGECGGGGSGSQVQLVQSGAEVKRPGASVKV<br>SCKASGYTFTNDIIHWVRQAPGQRLEWMGWINAGYGNTQYS<br>QNFQDRVSITRDTSASTAYMELISLRSEDTAVYYCAREPLW<br>FGESSPHDYYGMDVWGQGTTVTVSSASTKGPSVFPLAPSSK<br>STSGGTAALGCLVKDYFPEPVTVSWNSGALTSGVHTFPAVL<br>QSSGLYSLSSVVTVPSSSLGTQTYICNVNHKPSNTKVDKKV<br>EPKSCDKTHTCPPCPAPELLGGPSVFLFPPKPKDTLMISRT<br>PEVTCVVVDVSHEDPEVKFNWYVDGVEVHNAKTKPREEQYN<br>STYRVVSVLTVLHQDWLNGKEYKCKVSNKALPAPIEKTISK<br>AKGQPREPQVYTLPPSREEMTKNQVSLTCLVKGFYPSDIAV<br>EWESNGQPENNYKTTPPVLDSDGSFFLYSKLTVDKSRWQQG<br>NVFSCSVMHEALHNHYTQKSLSLSPGK |
| | LY VL | SEQ ID<br>NO.: 16 | DIVMTQTPLSLSVTPGQPASISCRSSRSLVHSRGNTYLHWY<br>LQKPGQSPQLLIYKVSNRFIGVPDRFSGSGSGTDFTLKISR<br>VEAEDVGVYYCSQSTHLPFTFGQGTKLEIK |
| | CL | SEQ ID<br>NO.: 17 | RTVAAPSVFIFPPSDEQLKSGTASVVCLLNNFYPREAKVQW<br>KVDNALQSGNSQESVTEQDSKDSTYSLSSTLTLSKADYEKH<br>KVYACEVTHQGLSSPVTKSFNRGEC |
| | Linker | SEQ ID<br>NO.: 28 | GGGGSGS |
| | 15D2 VH | SEQ ID<br>NO.: 18 | QVQLVQSGAEVKRPGASVKVSCKASGYTFTNDIIHWVRQAP<br>GQRLEWMGWINAGYGNTQYSQNFQDRVSITRDTSASTAYME<br>LISLRSEDTAVYYCAREPLWFGESSPHDYYGMDVWGQGTTV<br>TVSS |
| | CH1 | SEQ ID<br>NO.: 19 | ASTKGPSVFPLAPSSKSTSGGTAALGCLVKDYFPEPVTVSW<br>NSGALTSGVHTFPAVLQSSGLYSLSSVVTVPSSSLGTQTYI<br>CNVNHKPSNTKVDKKVEPKSC |
| | Fc | SEQ ID<br>NO.: 20 | DKTHTCPPCPAPELLGGPSVFLFPPKPKDTLMISRTPEVTC<br>VVVDVSHEDPEVKFNWYVDGVEVHNAKTKPREEQYNSTYRV<br>VSVLTVLHQDWLNGKEYKCKVSNKALPAPIEKTISKAKGQP<br>REPQVYTLPPSREEMTKNQVSLTCLVKGFYPSDIAVEWESN<br>GQPENNYKTTPPVLDSDGSFFLYSKLTVDKSRWQQGNVFSC<br>SVMHEALHNHYTQKSLSLSPGK |
| Anti-IL-17/IL-<br>20 FIT3-Ig<br>POLYPEPTIDE | | SEQ ID<br>NO.: 21 | QVQLVQSGAEVKKPGSSVKVSCKASGYSFTDYHIHWVRQAP<br>GQGLEWMGVINPMYGTTDYNQRFKGRVTITADESTSTAYME<br>LSSLRSEDTAVYYCARYDYFTGTGVYWGQGTLVTVSSASTK |

TABLE 3-continued

Amino acid sequences of anti-IL-17/IL-20 FIT-Ig molecules

| Protein | Protein region | Sequence Identifier | Sequence |
|---|---|---|---|
| #2 | | | GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKKVEPKSC |
| | LY VH | SEQ ID NO.: 22 | QVQLVQSGAEVKKPGSSVKVSCKASGYSFTDYHIHWVRQAP GQGLEWMGVINPMYGTTDYNQRFKGRVTITADESTSTAYME LSSLRSEDTAVYYCARYDYFTGTGVYWGQGTLVTVSS |
| | CH1 | SEQ ID NO.: 19 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKKVEPKSC |
| Anti-IL-17/IL- 20 FIT3-Ig POLYPEPTIDE #3 | | SEQ ID NO.: 23 | AIQLTQSPSSLSASVGDRVTITCRASQGISSALAWYQQKPG KAPKLLIYDASSLESGVPSRFSGSGSGTDFTLTISSLQPED FATYYCQQFNSYPLTFGGGTKVEIKRTVAAPSVFIFPPSDE QLKSGTASVVCLLNNFYPREAKVQWKVDNALQSGNSQESVT EQDSKDSTYSLSSTLTLSKADYEKHKVYACEVTHQGLSSPV TKSFNRGEC |
| | 15D2 VL | SEQ ID NO.: 24 | AIQLTQSPSSLSASVGDRVTITCRASQGISSALAWYQQKPG KAPKLLIYDASSLESGVPSRFSGSGSGTDFTLTISSLQPED FATYYCQQFNSYPLTFGGGTKVEIK |
| | CL | SEQ ID NO.: 17 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| Anti-IL-17/IL-20 FIT 4-Ig POLYPEPTIDE #1 | | SEQ ID NO.: 15 | DIVMTQTPLSLSVTPGQPASISCRSSRSLVHSRGNTYLHWY LQKPGQSPQLLIYKVSNRFIGVPDRFSGSGSGTDFTLKISR VEAEDVGVYYCSQSTHLPFTFGQGTKLEIKRTVAAPSVFIF PPSDEQLKSGTASVVCLLNNFYPREAKVQWKVDNALQSGNS QESVTEQDSKDSTYSLSSTLTLSKADYEKHKVYACEVTHQG LSSPVTKSFNRGECQVQLVQSGAEVKRPGASVKVSCKASGY TFTNDIIHWVRQAPGQRLEWMGWINAGYGNTQYSQNFQDRV SITRDTSASTAYMELISLRSEDTAVYYCAREPLWFGESSPH DYYGMDVWGQGTTVTVSSASTKGPSVFPLAPSSKSTSGGTA ALGCLVKDYFPEPVTVSWNSGALTSGVHTFPAVLQSSGLYS LSSVVTVPSSSLGTQTYICNVNHKPSNTKVDKKVEPKSCDK THTCPPCPAPELLGGPSVFLFPPKPKDTLMISRTPEVTCVV VDVSHEDPEVKFNWYVDGVEVHNAKTKPREEQYNSTYRVVS VLTVLHQDWLNGKEYKCKVSNKALPAPIEKTISKAKGQPRE PQVYTLPPSREEMTKNQVSLTCLVKGFYPSDIAVEWESNGQ PENNYKTTPPVLDSDGSFFLYSKLTVDKSRWQQGNVFSCSV MHEALHNHYTQKSLSLSPGK |
| | LY VL | SEQ ID NO.: 16 | DIVMTQTPLSLSVTPGQPASISCRSSRSLVHSRGNTYLHWY LQKPGQSPQLLIYKVSNRFIGVPDRFSGSGSGTDFTLKISR VEAEDVGVYYCSQSTHLPFTFGQGTKLEIK |
| | CL | SEQ ID NO.: 17 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| | Linker | | None |
| | 15D2 VH | SEQ ID NO.: 18 | QVQLVQSGAEVKRPGASVKVSCKASGYTFTNDIIHWVRQAP GQRLEWMGWINAGYGNTQYSQNFQDRVSITRDTSASTAYME LISLRSEDTAVYYCAREPLWFGESSPHDYYGMDVWGQGTTV TVSS |
| | CH1 | SEQ ID NO.: 19 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKKVEPKSC |
| | Fc | SEQ ID NO.: 20 | DKTHTCPPCPAPELLGGPSVFLFPPKPKDTLMISRTPEVTC VVVDVSHEDPEVKFNWYVDGVEVHNAKTKPREEQYNSTYRV VSVLTVLHQDWLNGKEYKCKVSNKALPAPIEKTISKAKGQP REPQVYTLPPSREEMTKNQVSLTCLVKGFYPSDIAVEWESN GQPENNYKTTPPVLDSDGSFFLYSKLTVDKSRWQQGNVFSC SVMHEALHNHYTQKSLSLSPGK |
| Anti-IL-17/IL-20 FIT4-Ig POLYPEPTIDE #4 | | SEQ ID NO.: 29 | QVQLVQSGAEVKKPGSSVKVSCKASGYSFTDYHIHWVRQAP GQGLEWMGVINPMYGTTDYNQRFKGRVTITADESTSTAYME LSSLRSEDTAVYYCARYDYFTGTGVYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKKVEPKSCAIQLTQSPSSLSASVGDRVTITCR ASQGISSALAWYQQKPGKAPKLLIYDASSLESGVPSRFSGS GSGTDFTLTISSLQPEDFATYYCQQFNSYPLTFGGGTKVEI KRTVAAPSVFIFPPSDEQLKSGTASVVCLLNNFYPREAKVQ WKVDNALQSGNSQESVTEQDSKDSTYSLSSTLTLSKADYEK HKVYACEVTHQGLSSPVTKSFNRGEC |
| | LY VH | SEQ ID NO.: 22 | QVQLVQSGAEVKKPGSSVKVSCKASGYSFTDYHIHWVRQAP GQGLEWMGVINPMYGTTDYNQRFKGRVTITADESTSTAYME LSSLRSEDTAVYYCARYDYFTGTGVYWGQGTLVTVSS |

TABLE 3-continued

Amino acid sequences of anti-IL-17/IL-20 FIT-Ig molecules

| Protein | Protein region | Sequence Identifier | Sequence |
|---|---|---|---|
| | CH1 | SEQ ID NO.: 19 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKKVEPKSC |
| | Linker | | none |
| | 15D2VL | SEQ ID NO.: 24 | AIQLTQSPSSLSASVGDRVTITCRASQGISSALAWYQQKPG KAPKLLIYDASSLESGVPSRFSGSGSGTDFTLTISSLQPED FATYYCQQFNSYPLTFGGGTKVEIK |
| | CL | SEQ ID NO.: 17 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| Anti-IL-17/IL-20 FIT 5-Ig POLYPEPTIDE #1 | | SEQ ID NO.: 25 | DIVMTQTPLSLSVTPGQPASISCRSSRSLVHSRGNTYLHWY LQKPGQSPQLLIYKVSNRFIGVPDRFSGSGSGTDFTLKISR VEAEDVGVYYCSQSTHLPFTFGQGTKLEIKRTVAAPSVFIF PPSDEQLKSGTASVVCLLNNFYPREAKVQWKVDNALQSGNS QESVTEQDSKDSTYSLSSTLTLSKADYEKHKVYACEVTHQG LSSPVTKSFNRGECGSGQVQLVQSGAEVKRPGASVKVSCKA SGYTFTNDIIHWVRQAPGQRLEWMGWINAGYGNTQYSQNFQ DRVSITRDTSASTAYMELISLRSEDTAVYYCAREPLWFGES SPHDYYGMDVWGQGTTVTVSSASTKGPSVFPLAPSSKSTSG GTAALGCLVKDYFPEPVTVSWNSGALTSGVHTFPAVLQSSG LYSLSSVVTVPSSSLGTQTYICNVNHKPSNTKVDKKVEPKS CDKTHTCPPCPAPELLGGPSVFLFPPKPKDTLMISRTPEVT CVVVDVSHEDPEVKFNWYVDGVEVHNAKTKPREEQYNSTYR VVSVLTVLHQDWLNGKEYKCKVSNKALPAPIEKTISKAKGQ PREPQVYTLPPSREEMTKNQVSLTCLVKGFYPSDIAVEWES NGQPENNYKTTPPVLDSDGSFFLYSKLTVDKSRWQQGNVFS CSVMHEALHNHYTQKSLSLSPGK |
| | LY VL | SEQ ID NO.: 16 | DIVMTQTPLSLSVTPGQPASISCRSSRSLVHSRGNTYLHWY LQKPGQSPQLLIYKVSNRFIGVPDRFSGSGSGTDFTLKISR VEAEDVGVYYCSQSTHLPFTFGQGTKLEIK |
| | CL | SEQ ID NO.: 17 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| | Linker | SEQ ID NO.: 26 | GSG |
| | 15D2 VH | SEQ ID NO.: 18 | QVQLVQSGAEVKRPGASVKVSCKASGYTFTNDIIHWVRQAP GQRLEWMGWINAGYGNTQYSQNFQDRVSITRDTSASTAYME LISLRSEDTAVYYCAREPLWFGESSPHDYYGMDVWGQGTTV TVSS |
| | CH1 | SEQ ID NO.: 19 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKKVEPKSC |
| | Fc | SEQ ID NO.: 20 | DKTHTCPPCPAPELLGGPSVFLFPPKPKDTLMISRTPEVTC VVVDVSHEDPEVKFNWYVDGVEVHNAKTKPREEQYNSTYRV VSVLTVLHQDWLNGKEYKCKVSNKALPAPIEKTISKAKGQP REPQVYTLPPSREEMTKNQVSLTCLVKGFYPSDIAVEWESN GQPENNYKTTPPVLDSDGSFFLYSKLTVDKSRWQQGNVFSC SVMHEALHNHYTQKSLSLSPGK |
| Anti-IL-17/IL-20 FIT5-Ig POLYPEPTIDE #4 | | SEQ ID NO.: 30 | QVQLVQSGAEVKKPGSSVKVSCKASGYSFTDYHIHWVRQAP GQGLEWMGVINPMYGTTDYNQRFKGRVTITADESTSTAYME LSSLRSEDTAVYYCARYDYFTGTGVYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKKVEPKSCGSGAIQLTQSPSSLSASVGDRVTI TCRASQGISSALAWYQQKPGKAPKLLIYDASSLESGVPSRF SGSGSGTDFTLTISSLQPEDFATYYCQQFNSYPLTFGGGTK VEIKRTVAAPSVFIFPPSDEQLKSGTASVVCLLNNFYPREA KVQWKVDNALQSGNSQESVTEQDSKDSTYSLSSTLTLSKAD YEKHKVYACEVTHQGLSSPVTKSFNRGEC |
| | LY VH | SEQ ID NO.: 22 | QVQLVQSGAEVKKPGSSVKVSCKASGYSFTDYHIHWVRQAP GQGLEWMGVINPMYGTTDYNQRFKGRVTITADESTSTAYME LSSLRSEDTAVYYCARYDYFTGTGVYWGQGTLVTVSS |
| | CH1 | SEQ ID NO.: 19 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKKVEPKSC |
| | Linker | SEQ ID NO.: 26 | GSG |
| | 15D2 VL | SEQ ID NO.: 24 | AIQLTQSPSSLSASVGDRVTITCRASQGISSALAWYQQKPG KAPKLLIYDASSLESGVPSRFSGSGSGTDFTLTISSLQPED FATYYCQQFNSYPLTFGGGTKVEIK |
| | CL | SEQ ID NO.: 17 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |

TABLE 3-continued

Amino acid sequences of anti-IL-17/IL-20 FIT-Ig molecules

| Protein | Protein region | Sequence Identifier | Sequence 12345678901234567890 |
|---|---|---|---|
| Anti-IL-17/IL-20 FIT 6-Ig POLYPEPTIDE #1 | | SEQ ID NO.: 27 | DIVMTQTPLSLSVTPGQPASISCRSSRSLVHSRGNTYLHWY LQKPGQSPQLLIYKVSNRFIGVPDRFSGSGSGTDFTLKISR VEAEDVGVYYCSQSTHLPFTFGQGTKLEIKRTVAAPSVFIF PPSDEQLKSGTASVVCLLNNFYPREAKVQWKVDNALQSGNS QESVTEQDSKDSTYSLSSTLTLSKADYEKHKVYACEVTHQG LSSPVTKSFNRGECGGGGSGSQVQLVQSGAEVKRPGASVKV SCKASGYTFTNDIIHWVRQAPGQRLEWMGWINAGYGNTQYS QNFQDRVSITRDTSASTAYMELISLRSEDTAVYYCAREPLW FGESSPHDYYGMDVWGQGTTVTVSSASTKGPSVFPLAPSSK STSGGTAALGCLVKDYFPEPVTVSWNSGALTSGVHTFPAVL QSSGLYSLSSVVTVPSSSLGTQTYICNVNHKPSNTKVDKKV EPKSCDKTHTCPPCPAPELLGGPSVFLFPPKPKDTLMISRT PEVTCVVVDVSHEDPEVKFNWYVDGVEVHNAKTKPREEQYN STYRVVSVLTVLHQDWLNGKEYKCKVSNKALPAPIEKTISK AKGQPREPQVYTLPPSREEMTKNQVSLTCLVKGFYPSDIAV EWESNGQPENNYKTTPPVLDSDGSFFLYSKLTVDKSRWQQG NVFSCSVMHEALHNHYTQKSLSLSPGK |
| | LY VL | SEQ ID NO.: 16 | DIVMTQTPLSLSVTPGQPASISCRSSRSLVHSRGNTYLHWY LQKPGQSPQLLIYKVSNRFIGVPDRFSGSGSGTDFTLKISR VEAEDVGVYYCSQSTHLPFTFGQGTKLEIK |
| | CL | SEQ ID NO.: 17 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| | Linker | | GGGGSGS |
| | 15D2 VH | SEQ ID NO.: 18 | QVQLVQSGAEVKRPGASVKVSCKASGYTFTNDIIHWVRQAP GQRLEWMGWINAGYGNTQYSQNFQDRVSITRDTSASTAYME LISLRSEDTAVYYCAREPLWFGESSPHDYYGMDVWGQGTTV TVSS |
| | CH1 | SEQ ID NO.: 19 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKKVEPKSC |
| | Fc | SEQ ID NO.: 20 | DKTHTCPPCPAPELLGGPSVFLFPPKPKDTLMISRTPEVTC VVVDVSHEDPEVKFNWYVDGVEVHNAKTKPREEQYNSTYRV VSVLTVLHQDWLNGKEYKCKVSNKALPAPIEKTISKAKGQP REPQVYTLPPSREEMTKNQVSLTCLVKGFYPSDIAVEWESN GQPENNYKTTPPVLDSDGSFFLYSKLTVDKSRWQQGNVFSC SVMHEALHNHYTQKSLSLSPGK |
| Anti-IL-17/IL-20 FIT6-Ig POLYPEPTIDE #4 | | SEQ ID NO.: 31 | QVQLVQSGAEVKKPGSSVKVSCKASGYSFTDYHIHWVRQAP GQGLEWMGVINPMYGTTDYNQRFKGRVTITADESTSTAYME LSSLRSEDTAVYYCARYDYFTGTGVYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKKVEPKSCGGGGSGSAIQLTQSPSSLSASVGD RVTITCRASQGISSALAWYQQKPGKAPKLLIYDASSLESGV PSRFSGSGSGTDFTLTISSLQPEDFATYYCQQFNSYPLTFG GGTKVEIKRTVAAPSVFIFPPSDEQLKSGTASVVCLLNNFY PREAKVQWKVDNALQSGNSQESVTEQDSKDSTYSLSSTLTL SKADYEKHKVYACEVTHQGLSSPVTKSFNRGEC |
| | LY VH | SEQ ID NO.: 22 | QVQLVQSGAEVKKPGSSVKVSCKASGYSFTDYHIHWVRQAP GQGLEWMGVINPMYGTTDYNQRFKGRVTITADESTSTAYME LSSLRSEDTAVYYCARYDYFTGTGVYWGQGTLVTVSS |
| | CH1 | SEQ ID NO.: 19 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKKVEPKSC |
| | Linker | SEQ ID NO.: 28 | GGGGSGS |
| | 15D2 VL | SEQ ID NO.: 24 | AIQLTQSPSSLSASVGDRVTITCRASQGISSALAWYQQKPG KAPKLLIYDASSLESGVPSRFSGSGSGTDFTLTISSLQPED FATYYCQQFNSYPLTFGGGTKVEIK |
| | CL | SEQ ID NO.: 17 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |

Example 1.2: Expression, Purification, and Analysis of Anti-IL-17/IL-20 FIT-Ig Proteins All DNA constructs of each FIT-Ig were subcloned into pBOS based vectors, and sequenced to ensure accuracy. Construct #1, #2, and #3 of each FIT-Ig (1, 2, and 3), or construct #1 and #4 of each FIT-Ig (4, 5, and 6) were transiently co-expressed using Polyethyleneimine (PEI) in 293E cells. Briefly, DNA in FreeStyle™ 293 Expression Medium was mixed with the PEI with the final concentration of DNA to PEI ratio of 1:2, incubated for 15 min (no more than 20 min) at room temperature, and then added to the 293E cells (1.0-1.2×10$^6$/ml, cell viability >95%) at 60 µg DNA/120 ml culture. After 6-24 hours culture in shaker, peptone was added to the transfected cells at a final concentration of 5%, with shaking at 125 rpm/min., at 37° C., 8% $CO_2$. On the 6th-7th day, supernatant was harvested by centrifugation and filtration, and FIT-Ig protein was purified using protein A chromatography (Pierce, Rockford, Ill.) according to the manufacturer's instructions. The proteins were analyzed by SDS-PAGE and their concentrations determined by A280 and BCA (Pierce, Rockford, Ill.).

For the expression of FIT1-Ig, FIT2-Ig, and FIT3-Ig, different DNA molar ratios of the 3 constructs were used, including construct #1:#2:#3=1:1:1, construct #1:#2:#3=1:1.5:1.5, and construct #1:#2:#3=1:3:3 (Table 4). FIT-Ig proteins were purified by protein A chromatography. The purification yield (7-16 mg/L) was consistent with hIgG quantification of the expression medium for each protein. The composition and purity of the purified FIT-Igs were analyzed by SDS-PAGE in both reduced and non-reduced conditions. In non-reduced conditions, FIT-Ig migrated as a single band of approximately 250 KDa. In reducing conditions, each of the FIT-Ig proteins yielded two bands, one higher MW band is construct #1 of approximately 75 KDa, and one lower MW band corresponds to both construct #2 and #3 overlapped at approximately 25 KDa. The SDS-PAGE showed that each FIT-Ig is expressed as a single species, and the 3 polypeptide chains are efficiently paired to form an IgG-like molecule. The sizes of the chains as well as the full-length protein of FIT-Ig molecules are consistent with their calculated molecular mass based on amino acid sequences.

TABLE 4

Expression and SEC analysis of hIL-17/IL-20 FIT-Ig proteins

| FIT-Ig protein | DNA ratio: Construct 1:2:3 | Expression level (mg/L) | % Peak monomeric fraction by SEC |
|---|---|---|---|
| FIT1-Ig | 1:1:1 | 15.16 | 92.07 |
|  | 1:1.5:1.5 | 14.73 | 95.49 |
|  | 1:3:3 | 9.87 | 97.92 |
| FIT2-Ig | 1:1:1 | 15.59 | 90.92 |
|  | 1:1.5:1.5 | 12.61 | 94.73 |
|  | 1:3:3 | 7.03 | 97.29 |
| FIT3-Ig | 1:1:1 | 15.59 | 91.47 |
|  | 1:1.5:1.5 | 15.16 | 94.08 |
|  | 1:3:3 | 7.75 | 97.57 |

To further study the physical properties of FIT-Ig in solution, size exclusion chromatography (SEC) was used to analyze each protein. For SEC analysis of the FIT-Ig, purified FIT-Ig, in PBS, was applied on a TSKgel SuperSW3000, 300×4.6 mm column (TOSOH). An HPLC instrument, Model U3000 (DIONEX) was used for SEC. All proteins were determined using UV detection at 280 nm and 214 nm. The elution was isocratic at a flow rate of 0.25 mL/min. All 3 FIT-Ig proteins exhibited a single major peak, demonstrating physical homogeneity as monomeric proteins (Table 4). The ratio of construct #1:#2:#3=1:3:3 showed a better monomeric profile by SEC for all 3 FIT-Ig proteins (Table 4).

Table 4 also shows that the expression levels of all the FIT-Ig proteins are comparable to that of the regular mAbs, indicating that the FIT-Ig can be expressed efficiently in mammalian cells. For the expression of FIT4-Ig, FIT5-Ig, and FIT6-Ig, the DNA ration of construct #1:#4=1:1, and the expression level were in the range of 1-10 mg/L, and the % Peak monomeric fraction as determined by SEC was in the range of 58-76%. Based on this particular mAb combination (LY and 15D2), the 3-polypepide FIT-Ig constructs (FIT1-Ig, FIT2-Ig, and FIT3-Ig) showed better expression profile than that of the 2-polypeptide FIT-Ig constructs (FIT4-Ig, FIT5-Ig, and FIT6-Ig), therefore FIT1-Ig, FIT2-Ig, and FIT3-Ig were further analyzed for functional properties Example 1.3 Determination of Antigen Binding Affinity of Anti-IL-17/IL-20 FIT-Igs The kinetics of FIT-Ig binding to rhIL-17 and rhIL-20 was determined by surface plasmon resonance (Table 5) with a Biacore X100 instrument (Biacore AB, Uppsala, Sweden) using HBS-EP (10 mM HEPES, pH 7.4, 150 mM NaCl, 3 mM EDTA, and 0.005% surfactant P20) at 25° C. Briefly, goat anti-human IgG Fcγ fragment specific polyclonal antibody (Pierce Biotechnology Inc, Rockford, Ill.) was directly immobilized across a CM5 research grade biosensor chip using a standard amine coupling kit according to manufacturer's instructions. Purified FIT-Ig samples were diluted in HEPES-buffered saline for capture across goat anti-human IgG Fc specific reaction surfaces and injected over reaction matrices at a flow rate of 5 µl/min. The association and dissociation rate constants, kon (M−1s−1) and koff (s−1) were determined under a continuous flow rate of 30 µL/min. Rate constants were derived by making kinetic binding measurements at ten different antigen concentrations ranging from 1.25 to 1000 nM. The equilibrium dissociation constant (M) of the reaction between FIT-Ig and the target proteins was then calculated from the kinetic rate constants by the following formula: KD=koff/kon. Aliquots of antigen samples were also simultaneously injected over a blank reference and reaction CM surface to record and subtract any nonspecific binding background to eliminate the majority of the refractive index change and injection noise. Surfaces were regenerated with two subsequent 25 ml injections of 10 mM Glycine (pH 1.5) at a flow rate of 10 µL/min. The anti-Fc antibody immobilized surfaces were completely regenerated and retained their full capture capacity over twelve cycles.

TABLE 5

Functional characterizations of anti-IL-17/IL-20 FIT-Ig molecules

| mAb or FIT-Ig | Antigen | Binding Kinetics by Biacore | | | Neutralization |
|---|---|---|---|---|---|
| | | $k_{on}$ ($M^{-1}s^{-1}$) | $k_{off}$ ($s^{-1}$) | $K_d$ (M) | Potency $IC_{50}$ (pM) |
| LY | hIL-17 | 8.24E+5 | 1.80E−5 | 2.18E−11 | 101 |
| FIT1-Ig | hIL-17 | 1.07E+7 | 3.88E−5 | 3.64E−12 | 102 |
| FIT2-Ig | hIL-17 | 9.24E+6 | 1.53E−5 | 1.65E−12 | 137 |
| FIT3-Ig | hIL-17 | 8.71E+6 | 9.58E−6 | 1.10E−12 | 146 |
| 15D2 | hIL-20 | 1.70E+6 | 8.30E−5 | 5.00E−11 | 50 |
| FIT1-Ig | hIL-20 | 1.40E+6 | 3.82E−5 | 2.73E−11 | 54 |
| FIT2-Ig | hIL-20 | 1.80E+6 | 3.50E−5 | 1.95E−11 | 50 |
| FIT3-Ig | hIL-20 | 1.40E+6 | 3.82E−5 | 2.73E−11 | 72 |

The Biacore analysis indicated the overall binding parameters of the three FIT-Igs to hIL-17 and hIL-20 were similar, with the affinities of the FIT-Igs being very close to that of the parental mAb LY and 15D2, and there was no lose of binding affinities for either antigen binding domains (Table 5).

Figure 3A:
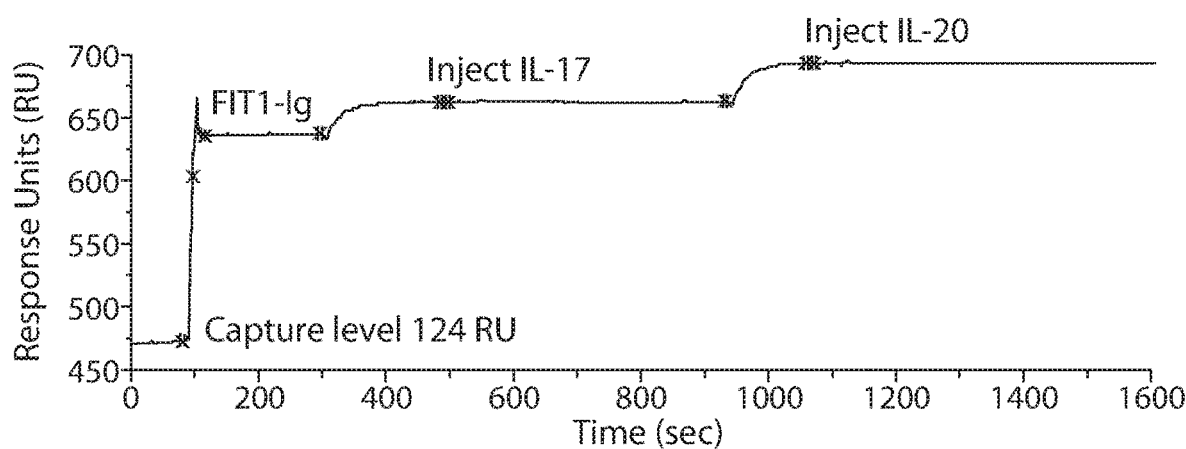
FIG. 3 provides the dual-specific antigen binding of FIT1-Ig as measured by Biacore. The top panel of FIG. 3 shows the results of the Biacore binding assay in which FIT1-Ig was first saturated by IL-17, followed by IL-20. The bottom panel of FIG. 3 shows the results of the Biacore assay in which FIT1-Ig was first saturated by IL-20, followed by IL-17.
Figure 3B:
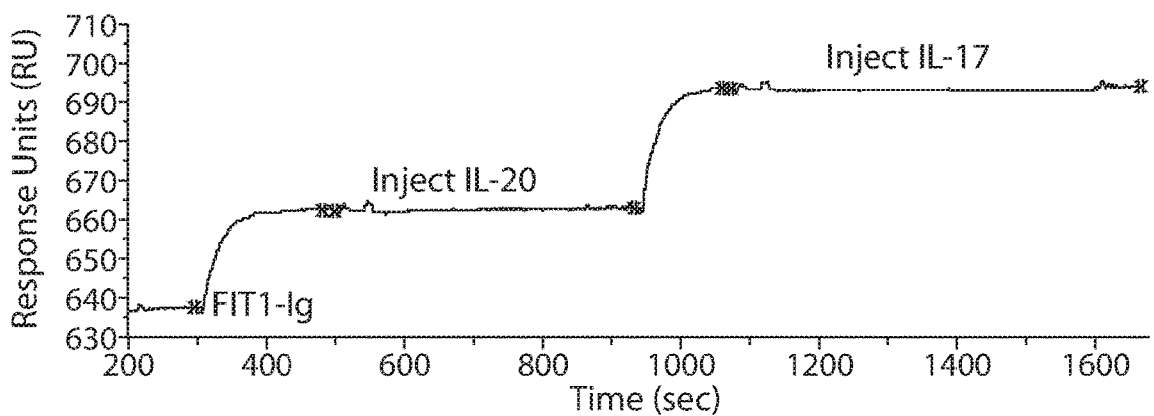

In addition, tetravalent dual-specific antigen binding of FIT-Ig was also analyzed by Biacore. FIT1-Ig was first captured via a goat anti-human Fc antibody on the Biacore sensor chip, and the first antigen was injected and a binding signal observed. As the FIT1-Ig was saturated by the first antigen, the second antigen was then injected and the second signal observed. This was done either by first injecting IL-17 then IL-20 or by first injecting IL-20 followed by IL-17 for FIT2-Ig (FIG. 3). In either sequence, a dual-binding activity was detected, and both antigen binding was saturated at 25-30 RU. Similar results were obtained for FIT2-Ig and FIT3-Ig. Thus each FIT-Ig was able to bind both antigens simultaneously as a dual-specific tetravalent molecule.

The expression profile and dual-binding properties of FIT-Ig clearly demonstrated that, within the FIT-Ig molecule, both VL-CL paired correctly with their corresponding VH-CH1 to form 2 functional binding domains, and expressed as a single monomeric, tetravalent, and bispecific full length FIT-Ig protein. This is in contrast to the multivalent antibody type of molecules (Miller and Presta, U.S. Pat. No. 8,722,859), which displayed tetravalent but monospecific binding activities to one target antigen.

Example 1.4 Determination of Biological Activity of Anti-IL-17/IL-20 FIT-Ig

The biological activity of FIT-Ig to neutralize IL-17 function was measured using GROα bioassay. Briefly, Hs27 cells were seeded at 10000 cells/50 L/well into 96 well plates. FIT-Ig or anti-IL-17 control antibody (25 μL) were added in duplicate wells, with starting concentration at 2.5 nM followed by 1:2 serial dilutions until 5 pM. IL-17A (25 μL) was then added to each well. The final concentration of IL-17A was 0.3 nM. Cells were incubated at 37° C. for 17 h before cell culture supernatant were collected. Concentrations of GRO-α in cell culture supernatants were measured by human CACL1/GRO alpha Quantikine kit according to the manufacturer's protocol (R&D systems).

The biological activity of FIT-Ig to neutralize IL-20 function was measured using IL-20R BAF3 cell proliferation assay. Briefly, 25 μL of recombinant human IL-20 at 0.8 nM was added to each well of 96-well plates (the final concentration of IL-20 is 0.2 nM). Anti-IL20 antibody or FIT-Ig or other control antibody were diluted to 400 nM (working concentration was 100 nM) followed by 5-fold serial dilutions and were added to 96-well assay plates (25 μL per well). BaF3 cells stably transfected with IL-20 receptor were then added to each well at concentration of 10000 cell/well in volume of 50 μL RPMI 1640 plus 10% FBS, Hygromycin B at the concentration of 800 μg/ml, G418 at the concentration of 800 μg/ml. After 48-hr incubation, 100 μL CellTiter-Glo Luminescent buffer were added to each well. Contents were mixed for 2 minutes on an orbital shaker to induce cell lysis and plates were incubated at room temperature for 10 minutes to stabilize luminescent signal. Luminescence was recorded by SpectraMax M5.

As shown in Table 5, all FIT-Igs were able to neutralize both hIL-20 and hIL-17, with affinities similar to that of the paternal antibodies. Based on functional analysis using both Biacore and cell-based neutralization assays, it appears that all 3 FIT-Igs fully retain the activities of the parental mAbs. There was no significant functional difference among the three FIT-Igs, indicating that the linker was optional, and that FIT-Ig construct provided sufficient flexibility and special dimension to allow dual binding in the absence of a peptide spacer between the 2 Fab binding regions. This is in contrast to DVD-Ig type of molecules, where a linker between the 2 variable domains on each of the 2 polypeptide chain is required for retaining activities of the lower ($2^{nd}$) variable domain.

Example 1.5 Stability Study of Anti-IL-17/IL-20 FIT-Ig

FIT1-Ig protein samples in citrate buffer (pH=6.0) were individually incubated at constant 4° C., 25° C. and 40° C. for 1 day, 3 days or 7 days; Similarly, FIT1-Ig protein samples were freeze-thawed once, twice or three times. The fractions of intact full monomeric protein of all samples was detected by SEC-HPLC, with 10 Vag of each protein sample injected into Ultimate 3000 HPLC equipping Superdex200 5/150 GL at flow rate 0.3 mL/min for 15 min, and data was recorded and analyzed using Chromeleon software supplied by the manufacturer. Table 6 shows that FIT1-Ig and FIT3-Ig remained full intact monomeric molecule under these thermo-challenged conditions.

TABLE 6

Stability analysis of FIT-Ig by measuring % full monomeric fractions by SEC

| Temp. (° C.) | Time (day) | FIT1-Ig | FIT3-Ig |
| --- | --- | --- | --- |
| 4 | 0 (Starting) | 98.74 | 98.60 |
|   | 1 | 98.09 | 97.78 |
|   | 3 | 97.81 | 97.45 |
|   | 7 | 97.63 | 97.65 |
| 25 | 1 | 99.00 | 98.26 |
|   | 3 | 99.00 | 98.01 |
|   | 7 | 98.86 | 98.53 |
| 40 | 1 | 98.95 | 98.50 |
|   | 3 | 98.94 | 98.35 |
|   | 7 | 98.82 | 98.37 |
| 1X freeze-thaw | | 98.89 | 98.21 |
| 2X freeze-thaw | | 95.37 | 98.21 |
| 3X freeze-thaw | | 95.24 | 98.35 |

Example 1.6 Solubility Study of Anti-IL-17/IL-20 FIT-Ig

Figure 4A:
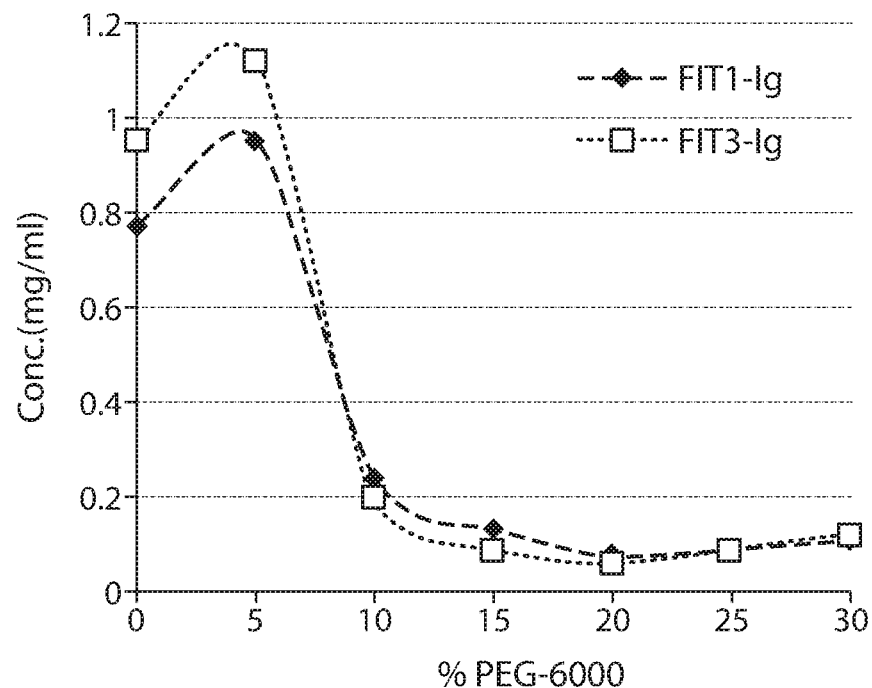
FIG. 4. Shows the solubility at a range of pH of anti-IL-17/IL-20 FIT Ig or monoclonal antibody rituximab, as measured by PEG-induced precipitation.
Figure 4B:
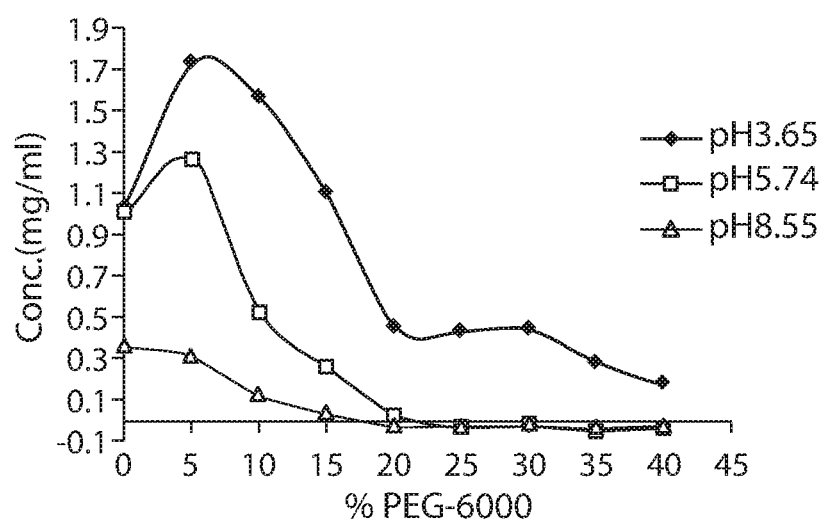

The solubility of FIT1-Ig was analyzed by measuring sign of precipitation in the presence of increasing concentration of PEG6000 (PEG6000 was purchased from Shanghai lingfeng chemical reagent co. Ltd). Briefly, solubility of protein in the presence of PEG6000 was obtained as a function of PEG6000 concentration (0, 5%, 10%, 15%, 20%, 25% and 30%). The solubility studies were conducted at a temperature of 25° C. at a solution pH of 6.0. Briefly, protein was precipitated by mixing appropriate quantities of buffered stock solutions of the protein, PEG and the buffer to get the desired concentration of the components. The final volume was made up to 200 μl and the concentration of protein was set at 1.0 mg/mL. The final solutions were mixed well and equilibrated for 16 h. After equilibration, the solutions were centrifuged at 13000 rpm for 10 min to separate the protein precipitate. Protein solubility was measured at 280 nm using Spectra Max Plus384 (Molecular Device) and obtained from the absorbance of the supernatant, and calculating the concentration based on standard curve of protein concentration (FIG. 4A). We also analyzed a commercial antibody Rituxan using the same experimental method under 3 different pH conditions (FIG. 4B). It appears that the protein solubility is dependent on the pH conditions, and that the predicted solubility of FIT-Ig would be in the range of monoclonal antibodies.

Example 1.7 Pharmacokinetic Study of Anti-IL-17/IL-20 FIT-Ig

Pharmacokinetic properties of FIT1-Ig were assessed in male Sprague-Dawley (SD) rats. FIT-Ig proteins were administered to male SD rats at a single intravenous dose of 5 mg/kg via a jugular cannula or subcutaneously under the dorsal skin. Serum samples were collected at different time points over a period of 28 days with sampling at 0, 5, 15, and 30 min; 1, 2, 4, 8, and 24 hr; and 2, 4, 7, 10, 14, 21, and 28 day serial bleeding via tail vein, and analyzed by human IL-17 capture and/or human IL-20 capture ELISAs. Briefly, ELISA plates were coated with goat anti-biotin antibody (5 μg/ml, 4° C., overnight), blocked with Superblock (Pierce), and incubated with biotinylated human IL-17 (IL-17 capture ELISA) or IL-20 (IL-20 capture ELISA) at 50 ng/ml in 10% Superblock TTBS at room temperature for 2 h. Serum samples were serially diluted (0.5% serum, 10% Superblock in TTBS) and incubated on the plate for 30 min at room temperature. Detection was carried out with HRP-labeled goat anti human antibody and concentrations were determined with the help of standard curves using the four parameter logistic fit. Several animals, especially in the subcutaneous group, showed a sudden drop in FIT-Ig concentrations following day 10, probably due to developing an anti-human response. These animals were eliminated from the final calculations. Values for the pharmacokinetic parameters were determined by non-compartmental model using WinNonlin software (Pharsight Corporation, Mountain View, Calif.).

The rat PK study, FIT1-Ig serum concentrations were very similar when determined by the two different ELISA methods, indicating that the molecule was intact, and capable of binding both antigens in vivo. Upon IV dosing, FIT1-Ig exhibited a bi-phasic pharmacokinetic profile, consisting of a distribution phase followed by an elimination phase, similar to the PK profile of conventional IgG molecules. The pharmacokinetic parameters calculated based on the two different analytical methods were very similar and are shown in Table 7. Clearance of FIT-Ig was low (~12 mL/day/kg), with low volumes of distribution (Vss~130 mL/kg) resulting in a long half-life (T1/2>10 days). Following subcutaneous administration, FIT-Ig absorbed slowly, with maximum serum concentrations of approximately 26.9 μg/ml reached at 4 days post-dose. The terminal half-life was about 11 days and the subcutaneous bioavailability was close to 100%. As demonstrated by these results, the properties of FIT1-Ig are very similar to a conventional IgG molecule in vivo, indicating a potential for therapeutic applications using comparable dosing regimens.

The pharmacokinetics study of FIT-Ig has demonstrated a surprising breakthrough in the field of multi-specific Ig-like biologics development. The rat pharmacokinetic system is commonly used in the pharmaceutical industry for preclinical evaluation of therapeutic mAbs, and it well predicts the pharmacokinetic profile of mAbs in humans. The long half-life and low clearance of FIT-Ig will enable its therapeutic utility for chronic indications with less frequent dosing, similar to a therapeutic mAb. In addition, FIT-Ig, being 100-kDa larger than an IgG, seemed to penetrate efficiently into the tissues based on its IgG-like volume of distribution parameter from the PK study.

TABLE 7

Pharmacokinetics analysis of FIT1-Ig in SD Rats

| | IV PK parameters | | | | |
|---|---|---|---|---|---|
| | CL | Vss | Beta $t_{1/2}$ | AUC | MRT |
| | Unit | | | | |
| | mL/day/kg | mL/kg | Day | Day × μg/mL | Day |
| IL-17 ELISA | 12.2 | 131 | 10.8 | 411 | 10.7 |
| IL-20 ELISA | 11.9 | 128 | 10.8 | 421 | 10.7 |

| | SC PK parameters | | | | |
|---|---|---|---|---|---|
| | $T_{max}$ | $C_{max}$ | $t_{1/2}$ | $AUC_{INF}$ | CL/F | F |
| | Unit | | | | | |
| | Day | ug/mL | Day | Day × ug/mL | mL/day/kg | % |
| IL-17 ELISA | 4.00 | 26.9 | 11.0 | 406 | 12.4 | 103.5 |
| IL-20 ELISA | 4.00 | 23.1 | 10.4 | 350 | 14.3 | 86.4 |

Example 1.8 Stable CHO Cell Line Development Studies of FIT-Ig

It has been observed that FIT-Ig was efficiently expressed in transiently-transfected 293E cells. In order to further determine the manufacturing feasibility of FIT-Ig, stable transfections were carried out in both CHO-DG44 and CHO-S cell lines, and subsequent clone selections as well as productivity analysis were performed. Briefly, CHO cells were transfected by electroporation with $8\times10^6$ cells in 400 μl transfection solution plus 20 ug DNA (for CHO DG44 cells) or 25 μg DNA (for CHO-S cells) subcloned in Freedom pCHO vector (Life Technologies). The stable cell line selection was done using routine procedures. Briefly, for CHO-DG44 selection, upon transfection, stable pool was selected (−HT/2P/400G, where P is g/mL Puromycin, G is g/mL G418), and protein production was analyzed by IgG ELISA. Top pools were selected and proceed to amplification for several rounds with increasing concentration of MTX (50, 100, 200 and 500 nM), followed by analysis of protein production by IgG ELISA. The top pools were then selected for subcloning. For CHO-S cell selection, the first phase selection was performed in medium containing 10P/400G/100M (M is nM MTX), followed by analysis of protein production. Then the top pools were selected and proceed to $2^{nd}$ phase selection in either 30P/400G/500M or 50P/400G/1000M, followed by protein production measurement by ELISA. The top pools were then selected for subcloning. For protein productivity analysis, fully recovered cell pools (viability >90%) were seeded at $5\times10^5$ viable cells/mL (CHO DG44) or $3\times10^5$ viable cells/mL (CHO-S) using 30 mL fresh medium (CD FortiCHO™ medium supplemented with 6 mM L-glutamine) in 125-mL shake flasks. The cells were incubated on a shaking platform at 37° C., 80% relative humidity, 8% CO2, and 130 rpm. Sample cultures daily or at regular intervals (e.g., on day 0, 3, 5, 7, 10, 12, and 14) to determine the cell density, viability, and productivity until culture viability drops below 50% or day 14 of culture is reached. After sampling, feed the cultures with glucose as needed.

The overall process of FIT1-Ig CHO stable cell line development showed features similar to that of a monoclonal antibody development in CHO cells. For example, during DG44 pool analysis under 2P/400G, the VCD continued to increase until day 10-12 up to about 1.3E7, whereas cell viability remained above 80% up to day 13-14, and the productivity reached almost 40 mg/mL on day 14. Upon amplification at 5P/400G/50M, productivity reached above 50 mg/mL on day 14. For CHO-S cell selection, the titer reached above 200 mg/mL during the phase 1 selection, and above 370 mg/mL at the phase 2 selection. These levels of productivity are similar to what have been previously observed for regular human mAb development is our laboratory, suggesting that FIT-Ig display mAb-like manufacturing feasibility for commercial applications.

Example 2: Construction, Expression, and Purification of Anti-CD3/CD20 Fabs-in-Tandem Immunoglobulin (FIT-Ig)

To demonstrate if a FIT-Ig can bind to cell surface antigens, we have generated an anti-CD3/CD20 FIT-Ig molecule FIT7-Ig and FIT8-Ig, which is the 3-polypeptide construct, as shown in FIG. 1. The construct used to generate FIT-Ig capable of binding cell surface CD3 and CD20 is illustrated in FIG. 1B. Briefly, parental mAbs include two high affinity antibodies, anti-CD3 (OKT3) and anti-CD20 (Ofatumumab). To generate FIT7-Ig construct #1, the VL-CL of OKT3 was fused directly (FIT7-Ig) or through a linker of 7 amino acids linker (FIT8-Ig) to the N-terminus of the Ofatumumab heavy chain (as shown in Table 8). The construct #2 is VH-CH1 of OKT3 and the $3^{rd}$ construct is VL-CL of Ofatumumab. The 3 constructs for FIT-Ig were co-transfected in 293 cells, resulting in the expression and secretion of FIT-Ig proteins. The detailed procedures of the PCR cloning are described below:

Example 2.1 Molecular Cloning of Anti-CD3/CD20 FIT-Ig

The molecular cloning method is similar as that for anti-hIL-17/hIL-20 FIT-Ig.

TABLE 8

Anti-CD3/CD20 FIT-Ig molecules and constructs.

| FIT-Ig molecule | Construct #1 | Linker | Construct #2 | Construct #3 |
|---|---|---|---|---|
| FIT7-Ig | $VL_{CD3}$-CL-$VH_{CD20}$-CH1-Fc | No linker | $VH_{CD3}$-CH1 | $VL_{CD20}$-CL |
| FIT8-Ig | $VL_{CD3}$-CL-linker-$VH_{CD20}$-CH1-Fc | GGGGSGS | $VH_{CD3}$-CH1 | $VL_{CD20}$-CL |

Table 9 shows sequences of PCR primers used for molecular construction above.

TABLE 9

PCR primers used for molecular construction of anti-IL-17/IL-20 FIT-Igs

| | SEQ ID NO. |
|---|---|
| P4: GTCTGCGGCCGCTCATTTACCCGGAGACAGGGAGAG | 32 |
| P12: TCGAGCGGCCGCTCAACAAGATTTGGGCTCAACTTTCTTG | 33 |
| P20: CAGGTCCAGCTGCAGCAGTCTG | 34 |
| P22: GCCTGCGAAGTCACCCATCAGGGCCTGAGCTCGCCCGTCACAAAGAGCTTCAACAGGGG | 35 |
| P23: TACGAGAAACACAAAGTCTACGCCTGCGAAGTCACCCATCAGGGCCTGAG | 36 |
| P24: TGACGCTGAGCAAAGCAGACTACGAGAAACACAAAGTCTACGCCTGCGAA | 37 |
| P25: CTCGCCCGTCACAAAGAGCTTCAACAGGGGAGAGTGTGAAGTGCAGCTGGTGGAGTCTG | 38 |
| P28: GCTGCTGCTGTGGTTCCCCGGCTCGCGATGCGAAATTGTGTTGACACAGTC | 39 |
| P29: AAGATGAAGACAGATGGTGCAGCCACCGTACGTTTAATCTCCAGTCGTGTCC | 40 |

The final sequences of anti-CD3/CD20 FIT-Ig are described in Table 10.

TABLE 10

Amino acid sequences of anti-CD3/CD20 FIT-Ig

| Protein | Protein region | Sequence Identifier | Sequence 12345678901234567890 |
|---|---|---|---|
| OKT3/Ofatumumab FIT7-Ig POLYPEPTIDE #1 | | SEQ ID NO.: 41 | QIVLTQSPAIMSASPGEKVTMTCSASSSVSYMNWYQQKS GTSPKRWIYDTSKLASGVPAHFRGSGSGTSYSLTISGME AEDAATYYCQQWSSNPFTFGSGTKLEINRTVAAPSVFIF PPSDEQLKSGTASVVCLLNNFYPREAKVQWKVDNALQSG NSQESVTEQDSKDSTYSLSSTLTLSKADYEKHKVYACEV THQGLSSPVTKSFNRGECEVQLVESGGGLVQPGRSLRLS CAASGFTFNDYAMHWVRQAPGKGLEWVSTISWNSGSIGY ADSVKGRFTISRDNAKKSLYLQMNSLRAEDTALYYCAKD IQYGNYYYGMDVWGQGTTVTVSSASTKGPSVFPLAPSSK STSGGTAALGCLVKDYFPEPVTVSWNSGALTSGVHTFPA VLQSSGLYSLSSVVTVPSSSLGTQTYICNVNHKPSNTKV DKKVEPKSCDKTHTCPPCPAPELLGGPSVFLFPPKPKDT LMISRTPEVTCVVVDVSHEDPEVKFNWYVDGVEVHNAKT KPREEQYNSTYRVVSVLTVLHQDWLNGKEYKCKVSNKAL PAPIEKTISKAKGQPREPQVYTLPPSREEMTKNQVSLTC LVKGFYPSDIAVEWESNGQPENNYKTTPPVLDSDGSFFL YSKLTVDKSRWQQGNVFSCSVMHEALHNHYTQKSLSLSP GK |
| | OKT3 VL | SEQ ID NO.: 42 | QIVLTQSPAIMSASPGEKVTMTCSASSSVSYMNWYQQKS GTSPKRWIYDTSKLASGVPAHFRGSGSGTSYSLTISGME AEDAATYYCQQWSSNPFTFGSGTKLEIN |

TABLE 10-continued

Amino acid sequences of anti-CD3/CD20 FIT-Ig

| Protein | Protein region | Sequence Identifier | Sequence 12345678901234567890 |
|---|---|---|---|
| | CL | SEQ ID NO.: 17 | RTVAAPSVFIFPPSDEQLKSGTASVVCLLNNFYPREAKV QWKVDNALQSGNSQESVTEQDSKDSTYSLSSTLTLSKAD YEKHKVYACEVTHQGLSSPVTKSFNRGEC |
| | Linker | | none |
| | Ofatumumab VH | SEQ ID NO.: 43 | EVQLVESGGGLVQPGRSLRLSCAASGFTFNDYAMHWVRQ APGKGLEWVSTISWNSGSIGYADSVKGRFTISRDNAKKS LYLQMNSLRAEDTALYYCAKDIQYGNYYYGMDVWGQGTT VTVSS |
| | CH1 | SEQ ID NO.: 19 | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSC |
| | Fc | SEQ ID NO.: 20 | DKTHTCPPCPAPELLGGPSVFLFPPKPKDTLMISRTPEV TCVVVDVSHEDPEVKFNWYVDGVEVHNAKTKPREEQYNS TYRVVSVLTVLHQDWLNGKEYKCKVSNKALPAPIEKTIS KAKGQPREPQVYTLPPSREEMTKNQVSLTCLVKGFYPSD IAVEWESNGQPENNYKTTPPVLDSDGSFFLYSKLTVDKS RWQQGNVFSCSVMHEALHNHYTQKSLSLSPGK |
| OKT3/Ofatumumab FIT7-Ig POLYPEPTIDE #2 | | SEQ ID NO.: 44 | QVQLQQSGAELARPGASVKMSCKASGYTFTRYTMHWVKQ RPGQGLEWIGYINPSRGYTNYNQKFKDKATLTTDKSSST AYMQLSSLTSEDSAVYYCARYYDDHYCLDYWGQGTTLTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKKVEPKSC |
| | OKT3 VH | SEQ ID NO.: 45 | QVQLQQSGAELARPGASVKMSCKASGYTFTRYTMHWVKQ RPGQGLEWIGYINPSRGYTNYNQKFKDKATLTTDKSSST AYMQLSSLTSEDSAVYYCARYYDDHYCLDYWGQGTTLTV SS |
| | CH1 | SEQ ID NO.: 19 | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSC |
| OKT3/Ofatumumab FIT7-Ig POLYPEPTIDE #3 | | SEQ ID NO.: 46 | EIVLTQSPATLSLSPGERATLSCRASQSVSSYLAWYQQK PGQAPRLLIYDASNRATGIPARFSGSGSGTDFTLTISSL EPEDFAVYYCQQRSNWPITFGQGTRLEIKRTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC |
| | Ofatumumab VL | SEQ ID NO.: 47 | EIVLTQSPATLSLSPGERATLSCRASQSVSSYLAWYQQK PGQAPRLLIYDASNRATGIPARFSGSGSGTDFTLTISSL EPEDFAVYYCQQRSNWPITFGQGTRLEIK |
| | CL | SEQ ID NO.: 17 | RTVAAPSVFIFPPSDEQLKSGTASVVCLLNNFYPREAKV QWKVDNALQSGNSQESVTEQDSKDSTYSLSSTLTLSKAD YEKHKVYACEVTHQGLSSPVTKSFNRGEC |
| OKT3/Ofatumumab FIT8-Ig POLYPEPTIDE #1 | | SEQ ID NO.: 48 | QIVLTQSPAIMSASPGEKVTMTCSASSSVSYMNWYQQKS GTSPKRWIYDTSKLASGVPAHFRGSGSGTSYSLTISGME AEDAATYYCQQWSSNPFTFGSGTKLEINRTVAAPSVFIF PPSDEQLKSGTASVVCLLNNFYPREAKVQWKVDNALQSG NSQESVTEQDSKDSTYSLSSTLTLSKADYEKHKVYACEV THQGLSSPVTKSFNRGECGGGGSGSEVQLVESGGGLVQP GRSLRLSCAASGFTFNDYAMHWVRQAPGKGLEWVSTISW NSGSIGYADSVKGRFTISRDNAKKSLYLQMNSLRAEDTA LYYCAKDIQYGNYYYGMDVWGQGTTVTVSSASTKGPSVF PLAPSSKSTSGGTAALGCLVKDYFPEPVTVSWNSGALTS GVHTFPAVLQSSGLYSLSSVVTVPSSSLGTQTYICNVNH KPSNTKVDKKVEPKSCDKTHTCPPCPAPELLGGPSVFLF PPKPKDTLMISRTPEVTCVVVDVSHEDPEVKFNWYVDGV EVHNAKTKPREEQYNSTYRVVSVLTVLHQDWLNGKEYKC KVSNKALPAPIEKTISKAKGQPREPQVYTLPPSREEMTK NQVSLTCLVKGFYPSDIAVEWESNGQPENNYKTTPPVLD SDGSFFLYSKLTVDKSRWQQGNVFSCSVMHEALHNHYTQ KSLSLSPGK |
| | OKT3 VL | SEQ ID NO.: 42 | QIVLTQSPAIMSASPGEKVTMTCSASSSVSYMNWYQQKS GTSPKRWIYDTSKLASGVPAHFRGSGSGTSYSLTISGME AEDAATYYCQQWSSNPFTFGSGTKLEIN |
| | CL | SEQ ID NO.: 17 | RTVAAPSVFIFPPSDEQLKSGTASVVCLLNNFYPREAKV QWKVDNALQSGNSQESVTEQDSKDSTYSLSSTLTLSKAD YEKHKVYACEVTHQGLSSPVTKSFNRGEC |
| | Linker | SEQ ID NO.: 28 | GGGGSGS |
| | Ofatumumab VH | | EVQLVESGGGLVQPGRSLRLSCAASGFTFNDYAMHWVRQ APGKGLEWVSTISWNSGSIGYADSVKGRFTISRDNAKKS LYLQMNSLRAEDTALYYCAKDIQYGNYYYGMDVWGQGTT VTVSS |

TABLE 10-continued

Amino acid sequences of anti-CD3/CD20 FIT-Ig

| Protein | Protein region | Sequence Identifier | Sequence 12345678901234567890 |
|---|---|---|---|
| | CH1 | SEQ ID NO.: 19 | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSC |
| | Fc | SEQ ID NO.: 20 | DKTHTCPPCPAPELLGGPSVFLFPPKPKDTLMISRTPEV TCVVVDVSHEDPEVKFNWYVDGVEVHNAKTKPREEQYNS TYRVVSVLTVLHQDWLNGKEYKCKVSNKALPAPIEKTIS KAKGQPREPQVYTLPPSREEMTKNQVSLTCLVKGFYPSD IAVEWESNGQPENNYKTTPPVLDSDGSFFLYSKLTVDKS RWQQGNVFSCSVMHEALHNHYTQKSLSLSPGK |
| OKT3/Ofatumumab FIT8-Ig POLYPEPTIDE #2 | | SEQ ID NO.: 44 | QVQLQQSGAELARPGASVKMSCKASGYTFTRYTMHWVKQ RPGQGLEWIGYINPSRGYTNYNQKFKDKATLTTDKSSST AYMQLSSLTSEDSAVYYCARYYDDHYCLDYWGQGTTLTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKKVEPKSC |
| | OKT3 VH | SEQ ID NO.: 45 | QVQLQQSGAELARPGASVKMSCKASGYTFTRYTMHWVKQ RPGQGLEWIGYINPSRGYTNYNQKFKDKATLTTDKSSST AYMQLSSLTSEDSAVYYCARYYDDHYCLDYWGQGTTLTV SS |
| | CH1 | SEQ ID NO.: 19 | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSC |
| OKT3/Ofatumumab FIT8-Ig POLYPEPTIDE #3 | | SEQ ID NO.: 46 | EIVLTQSPATLSLSPGERATLSCRASQSVSSYLAWYQQK PGQAPRLLIYDASNRATGIPARFSGSGSGTDFTLTISSL EPEDFAVYYCQQRSNWPITFGQGTRLEIKRTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC |
| | Ofatumumab VL | SEQ ID NO.: 47 | EIVLTQSPATLSLSPGERATLSCRASQSVSSYLAWYQQK PGQAPRLLIYDASNRATGIPARFSGSGSGTDFTLTISSL EPEDFAVYYCQQRSNWPITFGQGTRLEIK |
| | CL | SEQ ID NO.: 17 | RTVAAPSVFIFPPSDEQLKSGTASVVCLLNNFYPREAKV QWKVDNALQSGNSQESVTEQDSKDSTYSLSSTLTLSKAD YEKHKVYACEVTHQGLSSPVTKSFNRGEC |

Example 2.2 Expression and Purification of Anti-CD3/CD20 FIT-Ig

All DNA constructs of each FIT-Ig were subcloned into pBOS based vectors, and sequenced to ensure accuracy. Construct #1, #2, and #3 of each FIT-Ig were transiently co-expressed using Polyethyleneimine (PEI) in 293E cells. Briefly, DNA in FreeStyle™ 293 Expression Medium was mixed with the PEI with the final concentration of DNA to PEI ratio of 1:2, incubated for 15 min (no more than 20 min) at room temperature, and then added to the 293E cells ($1.0$-$1.2 \times 10^6$/ml, cell viability >95%) at 60 µg DNA/120 ml culture. After 6-24 hours culture in shaker, add peptone to the transfected cells at a final concentration of 5%, with shaking at 125 rpm/min., at 37° C., 8% CO2. On the 6th-7th day, supernatant was harvested by centrifugation and filtration, and FIT-Ig protein purified using protein A chromatography (Pierce, Rockford, Ill.) according to manufacturer's instructions. The proteins were analyzed by SDS-PAGE and their concentration determined by A280 and BCA (Pierce, Rockford, Ill.) (Table 11).

TABLE 11

Expression and SEC analysis of anti-CD3/CD20 FIT-Ig proteins

| FIT-Ig protein | DNA ratio: Construct 1:2:3 | Expression level (mg/L) | % Peak monomeric fraction by SEC |
|---|---|---|---|
| FIT7-Ig | 1:3:3 | 21.3 | 99.53 |
| FIT8-Ig | 1:3:3 | 25.6 | 99.16 |

Example 2.3 Binding Activities of Anti-CD3/CD20 FIT-Ig Molecules

Binding of anti-CD3/CD20 FIT-Igs to both targets were analyzed by FACS, using Jurkat cells that express CD3 on the cell surface, as well as Raji cells that express CD20 on the cell surface. Briefly, $5 \times 10^5$ cells were washed in ice-cold PBS and blocked with 2% FBS on ice for 1 hr. Cells were incubated with antibody, FIT-Ig (100 nM), or isotype control on ice for 1 hr and washed 3 times with PBS. Secondary antibody (goat anti-human IgG labeled with Alexa Fluor 488, Invitrogen) were added and incubated with cells on ice for 1 hr in dark followed by three times wash with PBS. Samples were analyzed in FACs calibur. The cell surface binding shows that both FIT7-Ig and FIT8-Ig were able to binding to both cell surface antigens CD3 and CD20 in a concentration dependent manner. Compared to the binding activities of the parental mAbs, FIT-Ig showed a reduced binding intensity to CD3 on Jurkat cells, but an enhanced binding intensity to CD20 on Raji cells. In all binding studies, FIT7-Ig and FIT8-Ig showed similar binding activities to both antigens, indicating the linker did not make a significant impact on its binding ability for FIT8-Ig (Table 12).

TABLE 12

Cell surface antigen binding studies of anti-CD3/CD20 FIT-Ig proteins

| FIT-Ig protein | Antigen (cell line) | Binding Intensity by FACS (MFI) |
|---|---|---|
| OKT3 | CD3 (Jurkat) | 399 |
| FIT7-Ig | | 159 |
| FIT8-Ig | | 211 |
| Ofatumumab | CD20 (Raji) | 181 |
| FIT7-Ig | | 291 |
| FIT8-Ig | | 274 |

Example 3: Construction, Expression, and Purification of Anti-TNF/IL-17 Fabs-in-Tandem Immunoglobulin (FIT-Ig)

Another FIT-Ig that can bind to human IL-17 and human TNFα (FIT9-Ig) was also generated using anti-IL-17 mAb clone LY, and anti-TNF mAb Golimumab, in the 3-polypeptide construct, as shown in FIG. 1. To generate FIT-Ig construct #1, the VL-CL of Golimumab was fused directly to the N-terminus of LY heavy chain (as shown in Table 13). The construct #2 is VH-CH1 of Golimumab and the 3$^{rd}$ construct is VL-CL of LY. The 3 constructs for FIT9-Ig were co-transfected in 293 cells, resulting in the expression and secretion of FIT9-Ig proteins. The final sequences of anti-TNF/IL-17 FIT-Ig are described in Table 14.

Example 3.1 Molecular Cloning of Anti-TNF/IL-17 FIT-Ig

The molecular cloning method is similar as that for anti-hIL-17/hIL-20 FIT-Ig.

TABLE 13

Anti-TNF/IL-17 FIT-Ig molecule and constructs.

| FIT-Ig molecule | Construct #1 | Linker | Construct #2 | Construct #3 |
|---|---|---|---|---|
| FIT9-Ig | VL$_{TNF}$-CL-VH$_{IL-17}$-CH1-Fc | No linker | VH$_{TNF}$-CH1 | VL$_{IL-17}$-CL |

TABLE 14

Amino acid sequences of anti-TNF/IL-17 FIT-Ig molecules

| Protein | Protein region | SEQ ID NO: | Sequence |
|---|---|---|---|
| Anti-IL-TNF/IL-17 FIT9-Ig POLYPEPTIDE #1 | | SEQ ID NO.: 87 | EIVLTQSPATLSLSPGERATLSCRASQSVYSYLAWYQQK PGQAPRLLIYDASNRATGIPARFSGSGSGTDFTLTISSL EPEDFAVYYCQQRSNWPPFTFGPGTKVDIKRTVAAPSVF IFPPSDEQLKSGTASVVCLLNNFYPREAKVQWKVDNALQ SGNSQESVTEQDSKDSTYSLSSTLTLSKADYEKHKVYAC EVTHQGLSSPVTKSFNRGECQVQLVQSGAEVKKPGSSVK VSCKASGYSFTDYHIHWVRQAPGQGLEWMGVINPMYGTT DYNQRFKGRVTITADESTSTAYMELSSLRSEDTAVYYCA RYDYFTGTGVYWGQGTLVTVSSASTKGPSVFPLAPSSKS TSGGTAALGCLVKDYFPEPVTVSWNSGALTSGVHTFPAV LQSSGLYSLSSVVTVPSSSLGTQTYICNVNHKPSNTKVD KKVEPKSCDKTHTCPPCPAPELLGGPSVFLFPPKPKDTL MISRTPEVTCVVVDVSHEDPEVKFNWYVDGVEVHNAKTK PREEQYNSTYRVVSVLTVLHQDWLNGKEYKCKVSNKALP APIEKTISKAKGQPREPQVYTLPPSREEMTKNQVSLTCL VKGFYPSDIAVEWESNGQPENNYKTTPPVLDSDGSFFLY SKLTVDKSRWQQGNVFSCSVMHEALHNHYTQKSLSLSPG K |
| | GOLIMUMAB VL | SEQ ID NO.: 88 | EIVLTQSPATLSLSPGERATLSCRASQSVYSYLAWYQQK PGQAPRLLIYDASNRATGIPARFSGSGSGTDFTLTISSL EPEDFAVYYCQQRSNWPPFTFGPGTKVDIK |
| | CL | SEQ ID NO.: 17 | RTVAAPSVFIFPPSDEQLKSGTASVVCLLNNFYPREAKV QWKVDNALQSGNSQESVTEQDSKDSTYSLSSTLTLSKAD YEKHKVYACEVTHQGLSSPVTKSFNRGEC |
| | Linker | | None |
| | LY VH | SEQ ID NO.: 22 | QVQLVQSGAEVKKPGSSVKVSCKASGYSFTDYHIHWVRQ APGQGLEWMGVINPMYGTTDYNQRFKGRVTITADESTST AYMELSSLRSEDTAVYYCARYDYFTGTGVYWGQGTLVTV SS |
| | CH1 | SEQ ID NO.: 19 | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSC |
| | Fc | SEQ ID NO.: 20 | DKTHTCPPCPAPELLGGPSVFLFPPKPKDTLMISRTPEV TCVVVDVSHEDPEVKFNWYVDGVEVHNAKTKPREEQYNS TYRVVSVLTVLHQDWLNGKEYKCKVSNKALPAPIEKTIS KAKGQPREPQVYTLPPSREEMTKNQVSLTCLVKGFYPSD IAVEWESNGQPENNYKTTPPVLDSDGSFFLYSKLTVDKS RWQQGNVFSCSVMHEALHNHYTQKSLSLSPGK |
| Anti-TNF/IL-17 FIT9-Ig POLYPEPTIDE #2 | | SEQ ID NO.: 89 | QVQLVESGGGVVQPGRSLRLSCAASGFIFSSYAMHWVRQ APGNGLEWVAFMSYDGSNKKYADSVKGRFTISRDNSKNT LYLQMNSLRAEDTAVYYCARDRGIAAGGNYYYGMDVWG QGTTVTVSSASTKGPSVFPLAPSSKSTSGGTAALGCLVK DYFPEPVTVSWNSGALTSGVHTFPAVLQSSGLYSLSSVV TVPSSSLGTQTYICNVNHKPSNTKVDKKVEPKSC |

TABLE 14-continued

Amino acid sequences of anti-TNF/IL-17 FIT-Ig molecules

| Protein | Protein region | SEQ ID NO: | Sequence 12345678901234567890 |
|---|---|---|---|
| | GOLIMUMAB VH | SEQ ID NO.: 90 | QVQLVESGGGVVQPGRSLRLSCAASGFIFSSYAMHWVRQ APGNGLEWVAFMSYDGSNKKYADSVKGRFTISRDNSKNT LYLQMNSLRAEDTAVYYCARDRGIAAGGNYYYYGMDVWG QGTTVTVSS |
| | CH1 | SEQ ID NO.: 19 | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSC |
| Anti-IL-TNF/IL-17 FIT9-Ig POLYPEPTIDE #3 | | SEQ ID NO.: 91 | DIVMTQTPLSLSVTPGQPASISCRSSRSLVHSRGNTYLH WYLQKPGQSPQLLIYKVSNRFIGVPDRFSGSGSGTDFTL KISRVEAEDVGVYYCSQSTHLPFTFGQGTKLEIKRTVAA PSVFIFPPSDEQLKSGTASVVCLLNNFYPREAKVQWKVD NALQSGNSQESVTEQDSKDSTYSLSSTLTLSKADYEKHK VYACEVTHQGLSSPVTKSFNRGEC |
| | LY VL | SEQ ID NO.: 16 | DIVMTQTPLSLSVTPGQPASISCRSSRSLVHSRGNTYLH WYLQKPGQSPQLLIYKVSNRFIGVPDRFSGSGSGTDFTL KISRVEAEDVGVYYCSQSTHLPFTFGQGTKLEIK |
| | CL | SEQ ID NO.: 17 | RTVAAPSVFIFPPSDEQLKSGTASVVCLLNNFYPREAKV QWKVDNALQSGNSQESVTEQDSKDSTYSLSSTLTLSKAD YEKHKVYACEVTHQGLSSPVTKSFNRGEC |

Example 3.2 Expression, Purification, and Analysis of Anti-TNF/IL-17 FIT-Ig Proteins All DNA constructs of each FIT-Ig were subcloned into pBOS based vectors, and sequenced to ensure accuracy. Construct #1, #2, and #3 of FIT9-Ig were transiently co-expressed using Polyethyleneimine (PEI) in 293E cells as described previously and FIT9-Ig proteins were purified by protein A chromatography. The expression level was 10-23 mg/L. The purified protein was subjected to functional analysis using cell-based assays for IL-17 (production of GROα by Hs27 cells) and TNF (production of IL-8 by L929 cells). The neutralization potency of FIT9-Ig against human TNF was 11.6 pM (compared to 15.9 pM by Golimumab in the same experiment), as against human IL-17 was 122 pM (compared to 51.5 pM by LY in the same experiment). Overall FIT9-Ig maintained the biological activities of the parental mAbs.

Example 4: Construction, Expression, and Purification of Anti-CTLA-4/PD-1 Fabs-in-Tandem Immunoglobulin (FIT-Ig)

Another FIT-Ig that can bind to human CTLA-4 and human PD-1 (FIT10-Ig) was generated using anti-CTLA-4 mAb Ipilimumab, and anti-PD-1 mAb Nivolumab, in the 3-polypeptide construct, as shown in FIG. 1. To generate FIT10-Ig construct #1, the VL-CL of Ipilimumab was fused directly to the N-terminus of Nivolumab heavy chain (as shown in Table 15). The construct #2 is VH-CH1 of Ipilimumab and the $3^{rd}$ construct is VL-CL of Nivolumab. The 3 constructs for FIT10-Ig were co-transfected in 293 cells, resulting in the expression and secretion of FIT10-Ig proteins.

Example 4.1 Molecular Cloning of Anti-CTLA-4/PD-1 FIT-Ig

The molecular cloning method is similar as that for anti-hIL-17/hIL-20 FIT-Ig. The final sequences of anti-CTLA-4/PD-1 FIT-Ig are described in Table 16.

TABLE 15

Anti-CTLA-4/PD-1 FIT-Ig molecule and constructs.

| FIT-Ig molecule | Construct #1 | Linker | Construct #2 | Construct #3 |
|---|---|---|---|---|
| FIT10-Ig | $VL_{CTLA-4}$-CL-$VH_{PD-1}$-CH1-Fc | No linker | $VH_{CTLA-4}$-CH1 | $VL_{PD-1}$-CL |

TABLE 16

Amino acid sequences of anti-CTLA-4/PD-1 FIT-Ig molecules

| Protein | Protein region | SEQ ID NO: | Sequence 12345678901234567890 |
|---|---|---|---|
| Anti-CTLA-4/PD-1 FIT10-Ig POLYPEPTIDE #1 | | SEQ ID NO.: 92 | EIVLTQSPGTLSLSPGERATLSCRASQSVGSSYLAWYQQKPGQ APRLLIYGAFSRATGIPDRFSGSGSGTDFTLTISRLEPEDFAV YYCQQYGSSPWTFGQGTKVEIKRTVAAPSVFIFPPSDEQLKSG TASVVCLLNNFYPREAKVQWKVDNALQSGNSQESVTEQDSKDS TYSLSSTLTLSKADYEKHKVYACEVTHQGLSSPVTKSFNRGEC QVQLVESGGGVVQPGRSLRLDCKASGITFSNSGMHWVRQAPGK GLEWVAVIWYDGSKRYYADSVKGRFTISRDNSKNTLFLQMNSL RAEDTAVYYCATNDDYWGQGTLVTVSSASTKGPSVFPLAPSSK STSGGTAALGCLVKDYFPEPVTVSWNSGALTSGVHTFPAVLQS SGLYSLSSVVTVPSSSLGTQTYICNVNHKPSNTKVDKKVEPKS CDKTHTCPPCPAPELLGGPSVFLFPPKPKDTLMISRTPEVTCV VVDVSHEDPEVKFNWYVDGVEVHNAKTKPREEQYNSTYRVVSV |

TABLE 16-continued

Amino acid sequences of anti-CTLA-4/PD-1 FIT-Iq molecules

| Protein | Protein region | SEQ ID NO: | Sequence |
|---|---|---|---|
| | | | LTVLHQDWLNGKEYKCKVSNKALPAPIEKTISKAKGQPREPQV YTLPPSREEMTKNQVSLTCLVKGFYPSDIAVEWESNGQPENNY KTTPPVLDSDGSFFLYSKLTVDKSRWQQGNVFSCSVMHEALHN HYTQKSLSLSPGK |
| | IPILIMUMAB VL | SEQ ID NO.: 93 | EIVLTQSPGTLSLSPGERATLSCRASQSVGSSYLAWYQQKPGQ APRLLIYGAFSRATGIPDRFSGSGSGTDFTLTISRLEPEDFAV YYCQQYGSSPWTFGQGTKVEIK |
| | CL | SEQ ID NO.: 17 | RTVAAPSVFIFPPSDEQLKSGTASVVCLLNNFYPREAKVQWKV DNALQSGNSQESVTEQDSKDSTYSLSSTLTLSKADYEKHKVYA CEVTHQGLSSPVTKSFNRGEC |
| | Linker | None | |
| | NIVOLUMAB VH | SEQ ID NO.: 94 | QVQLVESGGGVVQPGRSLRLDCKASGITFSNSGMHWVRQAPGK GLEWVAVIWYDGSKRYYADSVKGRFTISRDNSKNTLFLQMNSL RAEDTAVYYCATNDDYWGQGTLVTVSS |
| | CH1 | SEQ ID NO.: 19 | ASTKGPSVFPLAPSSKSTSGGTAALGCLVKDYFPEPVTVSWNS GALTSGVHTFPPAVLQSSGLYSLSSVVTVPSSSLGTQTYICNVN HKPSNTKVDKKVEPKSC |
| | Fc | SEQ ID NO.: 20 | DKTHTCPPCPAPELLGGPSVFLFPPKPKDTLMISRTPEVTCVV VDVSHEDPEVKFNWYVDGVEVHNAKTKPREEQYNSTYRVVSVL TVLHQDWLNGKEYKCKVSNKALPAPIEKTISKAKGQPREPQV YTLPPSREEMTKNQVSLTCLVKGFYPSDIAVEWESNGQPENNYK TTPPVLDSDGSFFLYSKLTVDKSRWQQGNVFSCSVMHEALHNH YTQKSLSLSPGK |
| Anti-CTLA-4/PD-1 FIT10-Ig POLYPEPTIDE #2 | | SEQ ID NO.: 95 | QVQLVESGGGVVQPGRSLRLSCAASGFTFSSYTMHWVRQAPGK GLEWVTFISYDGNNKYYADSVKGRFTISRDNSKNTLYLQMNSL RAEDTAIYYCARTGWLGPFDYWGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSC |
| | IPILIMUMAB VH | SEQ ID NO.: 96 | QVQLVESGGGVVQPGRSLRLSCAASGFTFSSYTMHWVRQAPGK GLEWVTFISYDGNNKYYADSVKGRFTISRDNSKNTLYLQMNSL RAEDTAIYYCARTGWLGPFDYWGQGTLVTVSS |
| | CH1 | SEQ ID NO.: 19 | ASTKGPSVFPLAPSSKSTSGGTAALGCLVKDYFPEPVTVSWNS GALTSGVHTFPPAVLQSSGLYSLSSVVTVPSSSLGTQTYICNVN HKPSNTKVDKKVEPKSC |
| Anti-CTLA-4/PD-1 FIT10-Ig POLYPEPTIDE #3 | | SEQ ID NO.: 97 | EIVLTQSPATLSLSPGERATLSCRASQSVSSYLAWYQQKPGQA PRLLIYDASNRATGIPARFSGSGSGTDFTLTISSLEPEDFAVY YCQQSSNWPRTFGQGTKVEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| | NivolumabVL | SEQ ID NO.: 98 | EIVLTQSPATLSLSPGERATLSCRASQSVSSYLAWYQQKPGQA PRLLIYDASNRATGIPARFSGSGSGTDFTLTISSLEPEDFAVY YCQQSSNWPRTFGQGTKVEIK |
| | CL | SEQ ID NO.: 17 | RTVAAPSVFIFPPSDEQLKSGTASVVCLLNNFYPREAKVQWKV DNALQSGNSQESVTEQDSKDSTYSLSSTLTLSKADYEKHKVYA CEVTHQGLSSPVTKSFNRGEC |

Figure 5A:
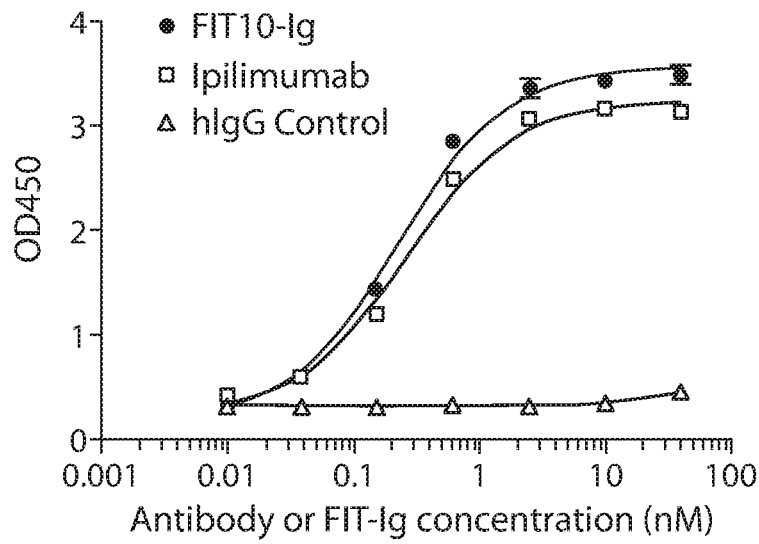
FIG. 5 shows the binding to CTLA-4 (FIG. 5A) or PD-1 (FIG. 5B) by FIT10-Ig or the parental antibodies Ipilimumab and Nivolumab, as assessed by ELISA.
Figure 5B:
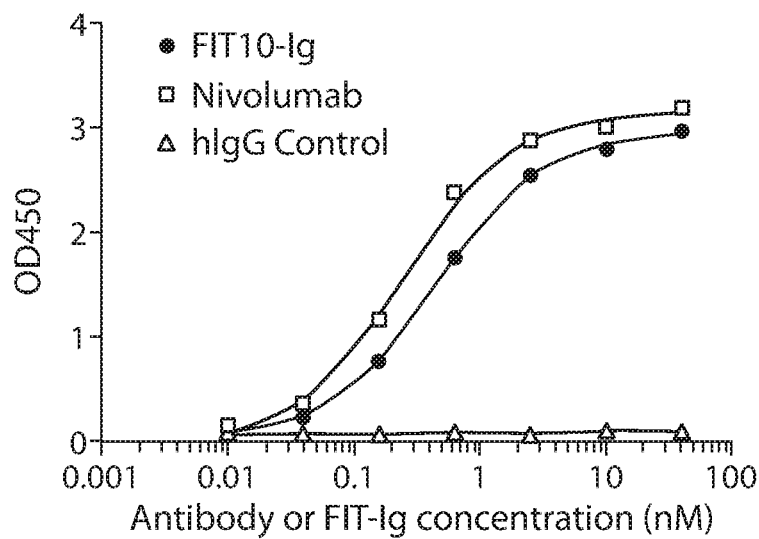

Example 4.2 Expression, Purification, and Functional Analysis of Anti-CTLA-4/PD-1 FIT-Ig Proteins All DNA constructs of each FIT-Ig were subcloned into pBOS based vectors, and sequenced to ensure accuracy. Construct #1, #2, and #3 of FIT10-Ig were transiently co-expressed using Polyethyleneimine (PEI) in 293E cells as described previously and FIT9-Ig proteins were purified by protein A chromatography to 98% monomeric full protein. The expression levels were up to 43 mg/L. The purified protein was subjected to binding analysis using ELISA against recombinant CTLA-4Ig and PD-1. Briefly, for binding to CTLA-4, human CTLA-4Ig (R&D Systems) was immobilized on 96-well plates, followed by routine wash and blocking procedures. Then FIT-10-Ig or Ipilimumab at various concentrations were added to the plate, followed by incubation and multiple wash steps, and detected with anti-human Fab-HRP. For binding to PD-1, human PD-1 (with a his tag) (R&D Systems) was immobilized on 96-well plates, followed by routine wash and blocking procedures. Then FIT-10-Ig or Nivolumab at various concentrations were added to the plate, followed by incubation and multiple wash steps, and detected with anti-human Fc-HRP (FIG. 5). It appears that FIT10-Ig was able to bind both CTLA-4 (A) and PD-1 (B) with similar activities as the parental mAbs Ipilimumab and Nivolumab, respectively.

Figure 6:
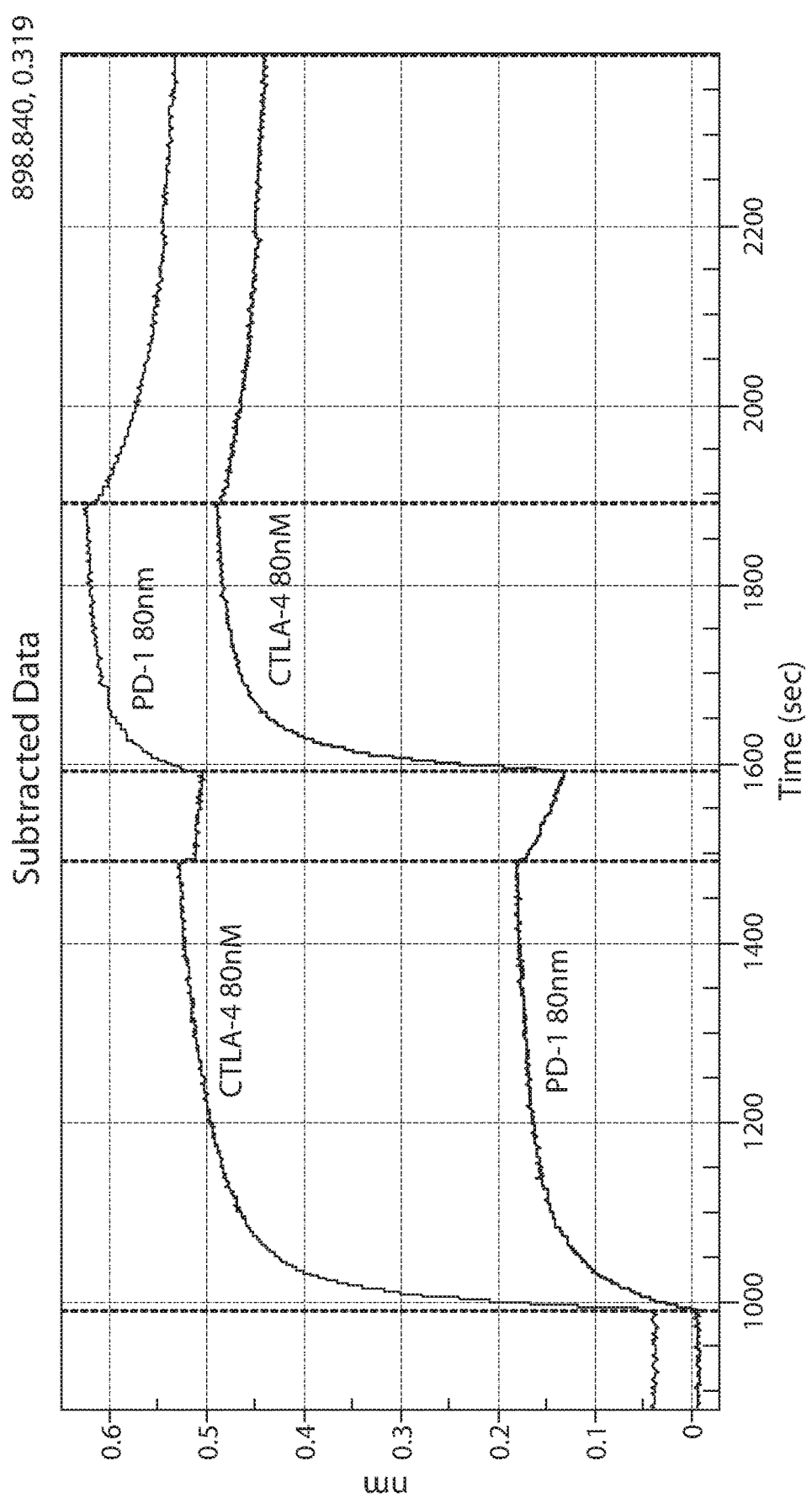
FIG. 6 shows a multiple binding study of FIT10-Ig against both CTLA-4 and PD-1. Binding to CTLA-4 followed by PD-1; and binding by PD-1 followed by CTLA-4 are both shown as indicated in FIG. 6.
Figure 7A:
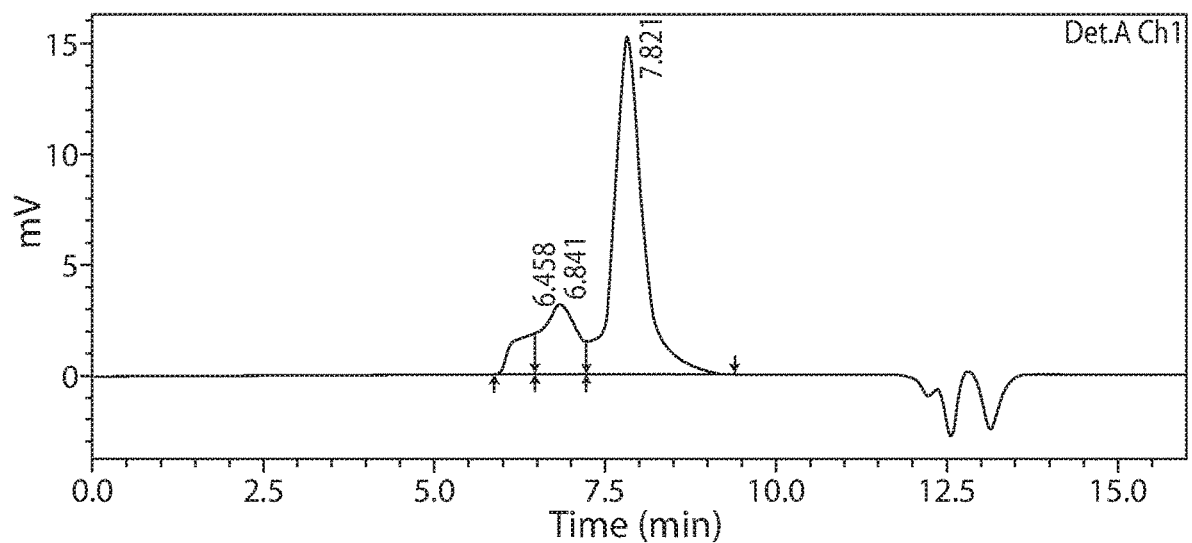
FIGS. 7a-7i show the SEC profiles for FIT12a-Ig (EGFR/PD-L1.
Figure 7B:
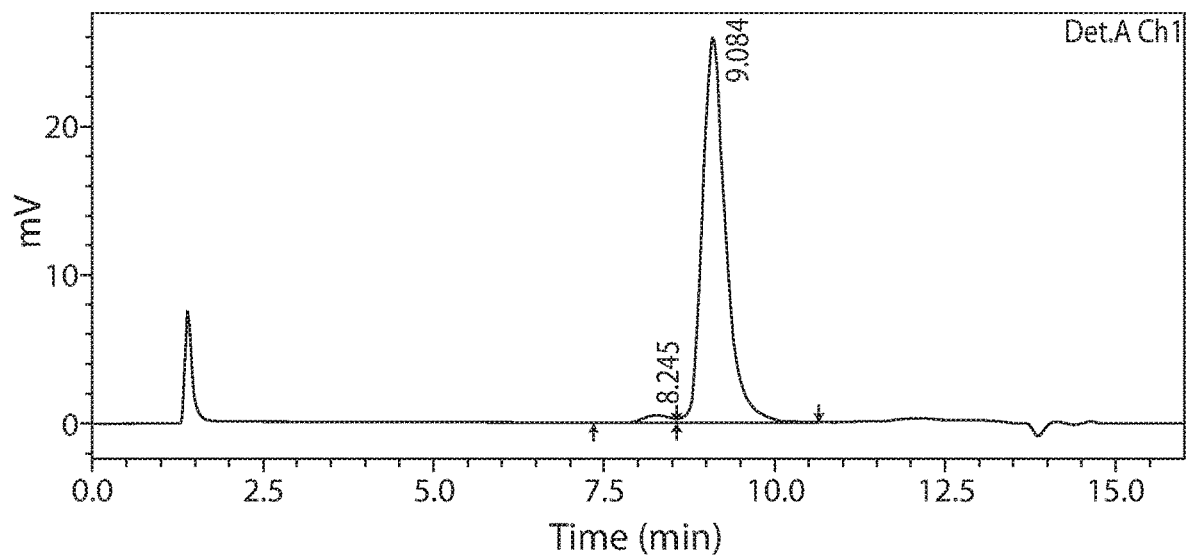
Figure 7C:
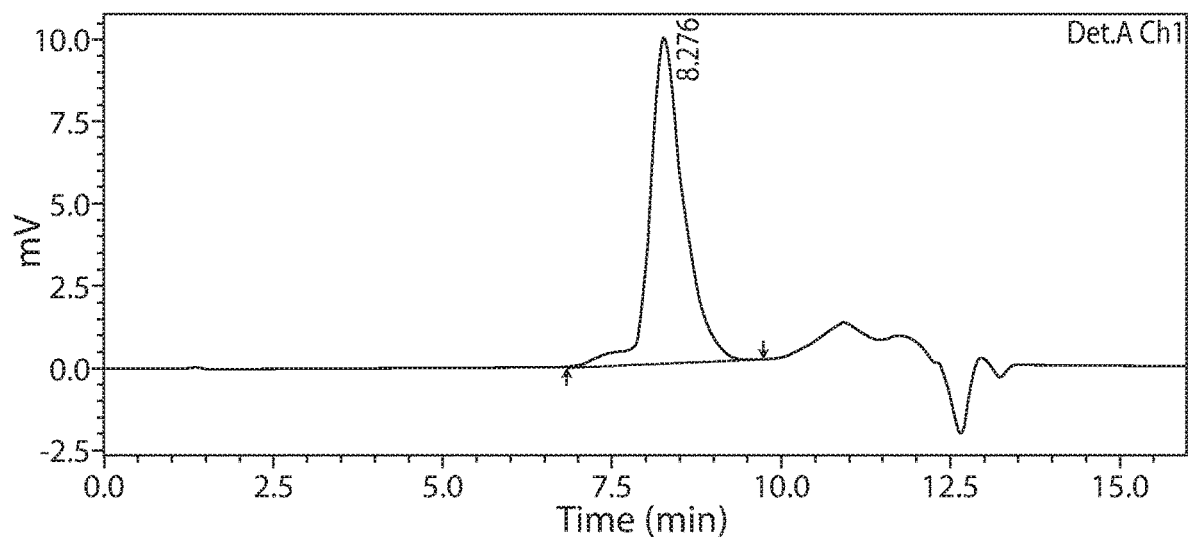
Figure 7D:
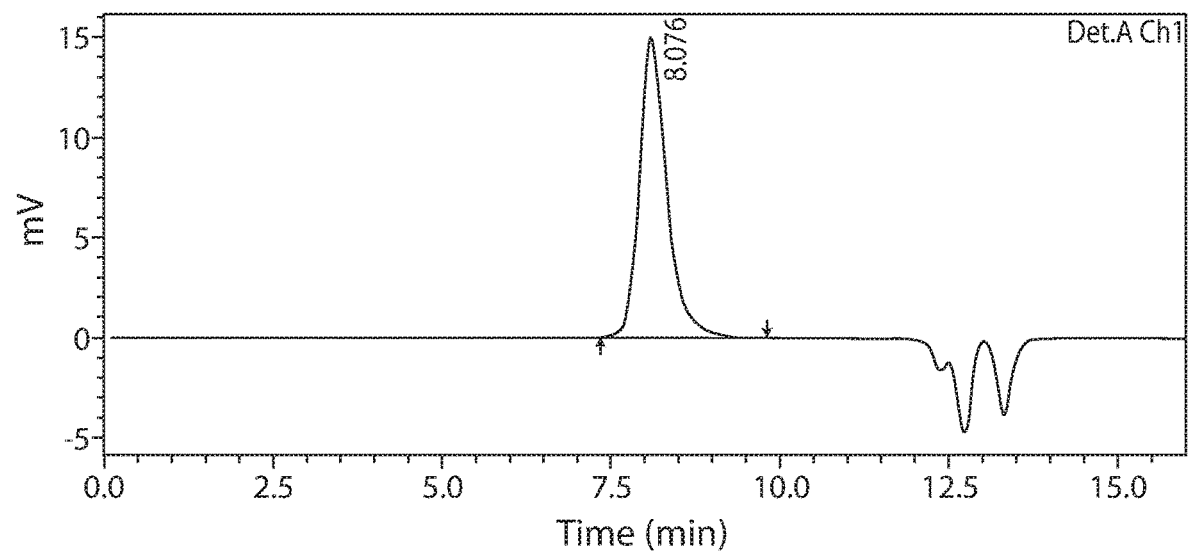
Figure 7E:
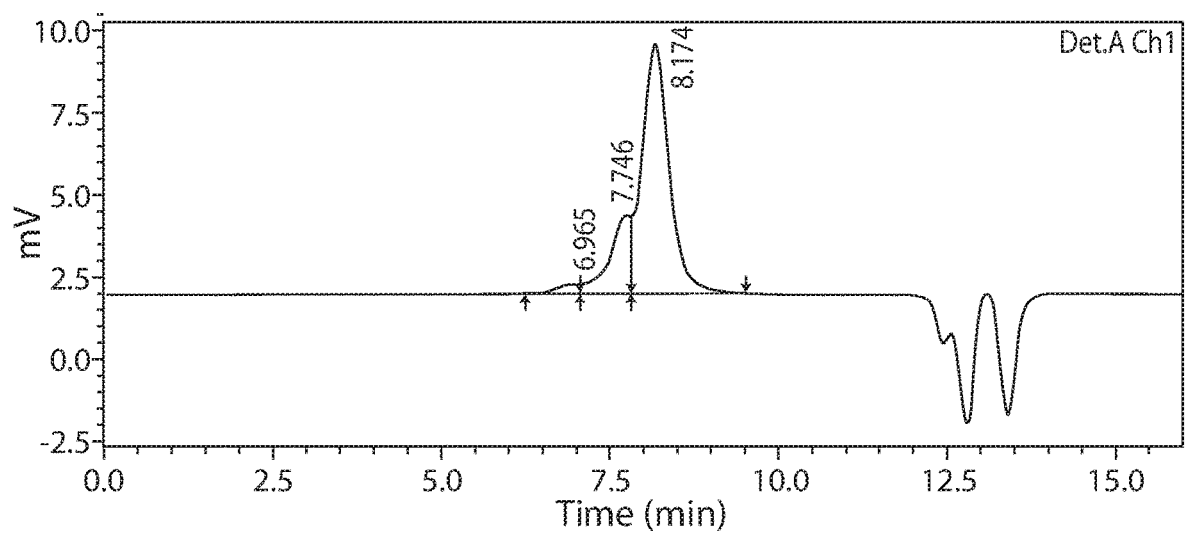
Figure 7F:
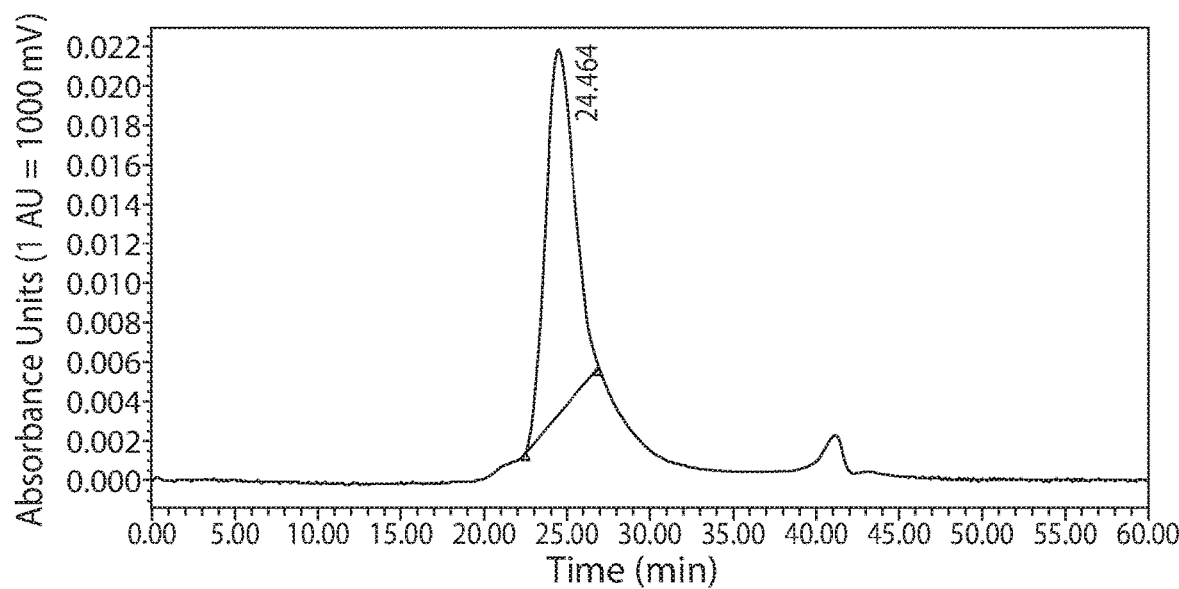
Figure 7G:
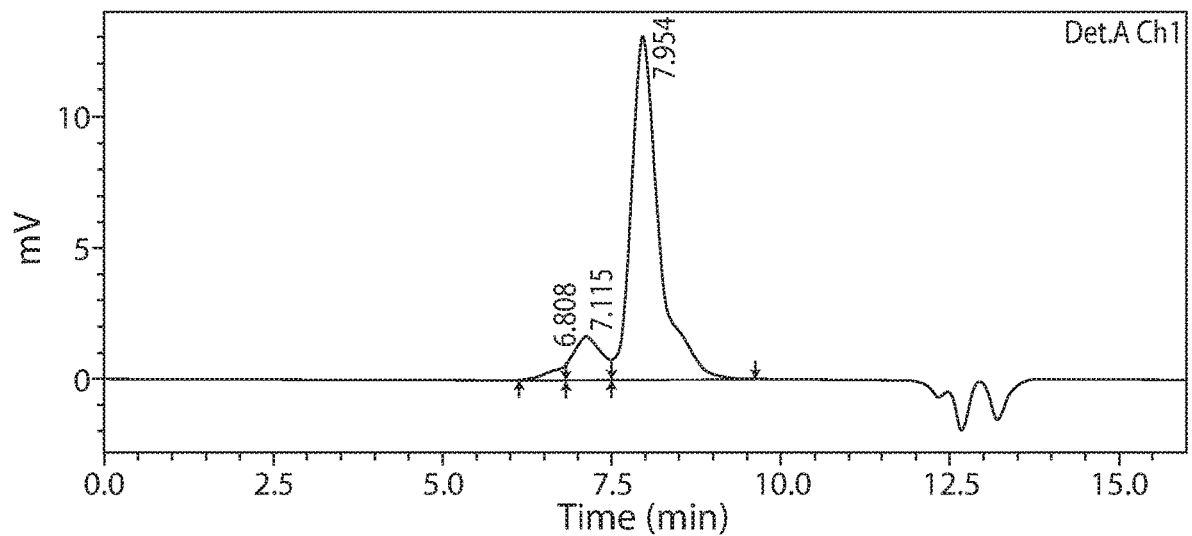
Figure 7H:
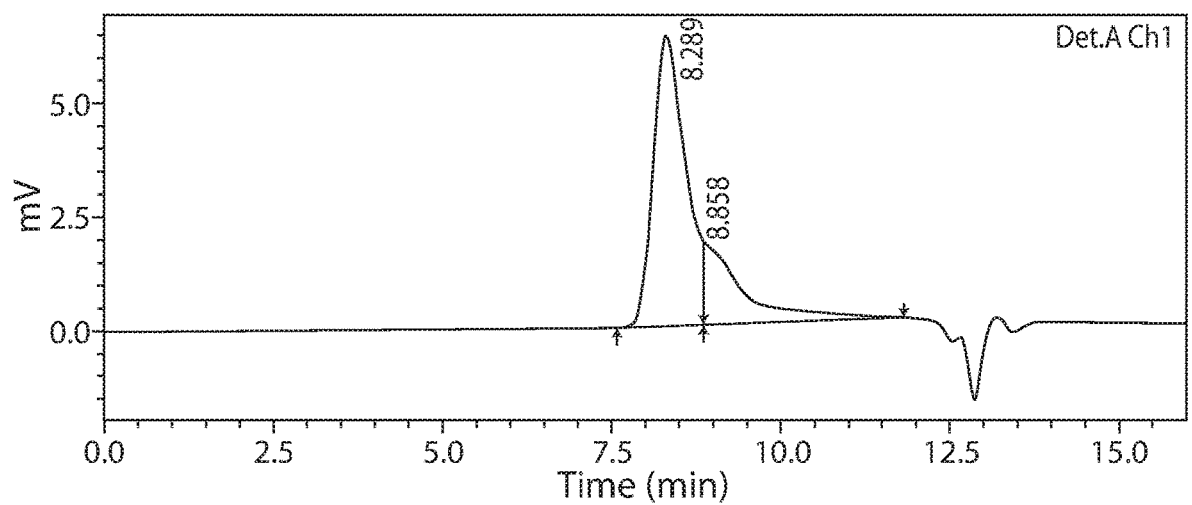
Figure 7I:
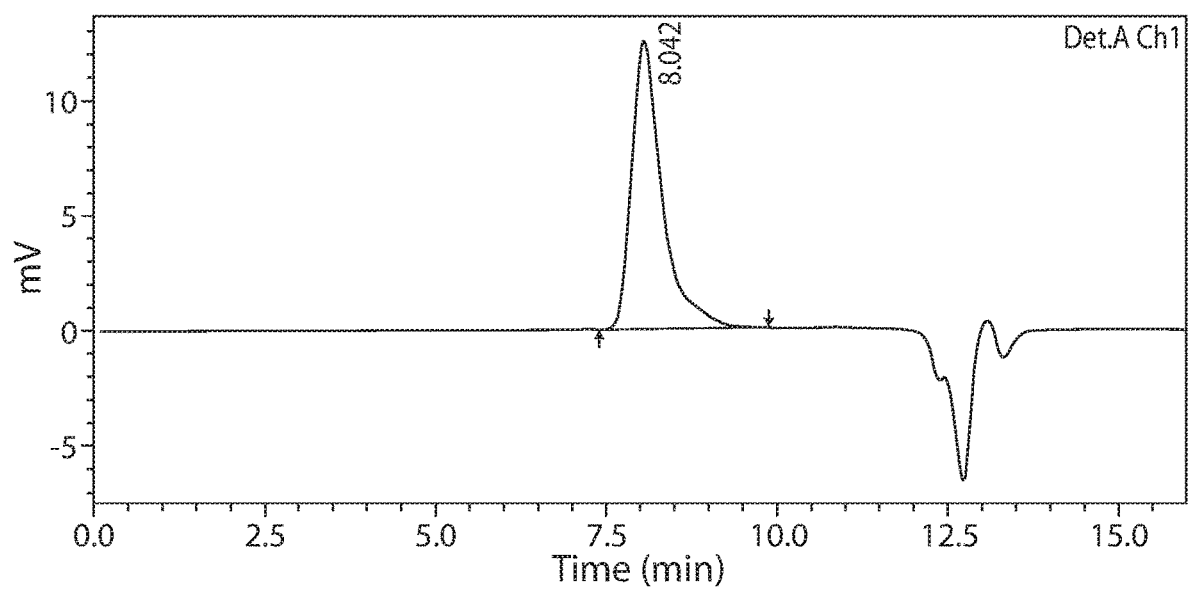

In addition, multiple-antigen binding study was done using OctetRed to determine if FIT10-Ig was able to bind recombinant CTLA-4 and PD-1 simultaneously. Briefly, FIT10-Ig was immobilize on AR2G sensor at concentration of 10 μg/ml, followed by binding of CTLA-4Ig and then PD-1 (or PD-1 first, then CTLA-4Ig) in assay buffer (PBS pH 7.4, 0.1% BSA, 0.02% Tween), with concentration at 80 nM. At the end of the experiment, the surface was regenerated with 10 mM glycine at pH1.5 five times (FIG. 6). This experiment shows that FIT10-Ig was able to bind PD-1 when it had already bound to CTLA-4, and vice versa, indicating that FIT10-Ig was able to bind both CTLA-4Ig and PD-1 simultaneously.

Example 5: Construction, Expression, and Purification of Additional Fabs-in-Tandem Immunoglobulin (FIT-Ig)

FIT-Ig having specificity for EGFR and PD-L1; cMet and EGFR; Factor IXa and Factor X; Her3 and IGF-1R; DLL-4 and VEGF; CD20 and CD3; Her3 and EGFR; PD-1 and PD-L1; and Her3 and PD-1 were constructed as in the foregoing Examples. These exemplary FIT-Ig and their corresponding sequences are provided below in Table 17. Table 18 provides the expression level in 293E cells and the SEC profile for each of the FIT-Ig.

TABLE 17

Amino acid sequences of additional exemplary FIT-Ig

| Name Target (mAb) | Protein region | SEQ ID NO | Sequence |
|---|---|---|---|
| FIT12a-Ig EGFR (panitumumab)/ PD-L1 (1B12) | Pani VL-hCk-1B12VH-hCg1 | 99 | MDMRVPAQLLGLLLLWFPGSRCDIQMTQSPSSLSASVGDRVTI TCQASQDISNYLNWYQQKPGKAPKLLIYDASNLETGVPSRFSG SGSGTDFTFTISSLQPEDIATYFCQHFDHLPLAFGGGTKVEIK RTVAAPSVFIFPPSDEQLKSGTASVVCLLNNFYPREAKVQWKV DNALQSGNSQESVTEQDSKDSTYSLSSTLTLSKADYEKHKVYA CEVTHQGLSSPVTKSFNRGECQVQLVQSGAEVKKPGSSVKVSC KTSGDTFSSYAISWVRQAPGQGLEWMGGIIPIFGRAHYAQKFQ GRVTITADESTSTAYMELSSLRSEDTAVYFCARKFHFVSGSPF GMDVWGQGTTVTVSSASTKGPSVFPLAPSSKSTSGGTAALGCL VKDYFPEPVTVSWNSGALTSGVHTFPAVLQSSGLYSLSSVVTV PSSSLGTQTYICNVNHKPSNTKVDKKVEPKSCDKTHTCPPCPA PELLGGPSVFLFPPKPKDTLMISRTPEVTCVVVDVSHEDPEVK FNWYVDGVEVHNAKTKPREEQYNSTYRVVSVLTVLHQDWLNGK EYKCKVSNKALPAPIEKTISKAKGQPREPQVYTLPPSREEMTK NQVSLTCLVKGFYPSDIAVEWESNGQPENNYKTTPPVLDSDGS FFLYSKLTVDKSRWQQGNVFSCSVMHEALHNHYTQKSLSLSPG K |
| | Pani VH-CH1h | 100 | MEFGLSWLFLVAILKGVQCQVQLQESGPGLVKPSETLSLTCTV SGGSVSSGDYYWTWIRQSPGKGLEWIGHIYYSGNTNYNPSLKS RLTISIDTSKTQFSLKLSSVTAADTAIYYCVRDRVTGAFDIWG QGTMVTVSSASTKGPSVFPLAPSSKSTSGGTAALGCLVKDYFP EPVTVSWNSGALTSGVHTFPAVLQSSGLYSLSSVVTVPSSSLG TQTYICNVNHKPSNTKVDKKVEPKSC |
| | 1B12 VL-hCk | 101 | MDMRVPAQLLGLLLLWFPGSRCEIVLTQSPATLSLSPGERATL SCRASQSVSSYLAWYQQKPGQAPRLLIYDASNRATGIPARFSG SGSGTDFTLTISSLEPEDFAVYYCQQRSNWPTFGQGTKVEIKR TVAAPSVFIFPPSDEQLKSGTASVVCLLNNFYPREAKVQWKVD NALQSGNSQESVTEQDSKDSTYSLSSTLTLSKADYEKHKVYAC EVTHQGLSSPVTKSFNRGEC |
| FIT13a-Ig cMet (h1332)/EGFR (panitumumab) | h1332VL-hCk-PaniVH-hCg1 | 102 | MDMRVPAQLLGLLLLWFPGSRCDIQMTQSPSSVSASVGDRVTI TCRASQGINTWLAWYQQKPGKAPKLLIYAASSLKSGVPSRFSG SGSGTDFTLTISSLQPEDFATYYCQQANSFPLTFGGGTKVEIK RTVAAPSVFIFPPSDEQLKSGTASVVCLLNNFYPREAKVQWKV DNALQSGNSQESVTEQDSKDSTYSLSSTLTLSKADYEKHKVYA CEVTHQGLSSPVTKSFNRGECQVQLQESGPGLVKPSETLSLTC TVSGGSVSSGDYYWTWIRQSPGKGLEWIGHIYYSGNTNYNPSL KSRLTISIDTSKTQFSLKLSSVTAADTAIYYCVRDRVTGAFDI WGQGTMVTVSSASTKGPSVFPLAPSSKSTSGGTAALGCLVKDY FPEPVTVSWNSGALTSGVHTFPAVLQSSGLYSLSSVVTVPSSS LGTQTYICNVNHKPSNTKVDKKVEPKSCDKTHTCPPCPAPELL GGPSVFLFPPKPKDTLMISRTPEVTCVVVDVSHEDPEVKFNWY VDGVEVHNAKTKPREEQYNSTYRVVSVLTVLHQDWLNGKEYKC KVSNKALPAPIEKTISKAKGQPREPQVYTLPPSREEMTKNQVS LTCLVKGFYPSDIAVEWESNGQPENNYKTTPPVLDSDGSFFLY SKLTVDKSRWQQGNVFSCSVMHEALHNHYTQKSLSLSPGK |
| | h1332 VH-CH1h | 103 | MEFGLSWLFLVAILKGVQCQVQLVQSGAEVKKPGASVKVSCKA SGYTFTSYGFSWVRQAPGQGLEWMGWISASNGNTYYAQKLQGR VTMTTDTSTSTAYMELRSLRSDDTAVYYCARVYADYADYWGQG TLVTVSSASTKGPSVFPLAPSSKSTSGGTAALGCLVKDYFPEP VTVSWNSGALTSGVHTFPAVLQSSGLYSLSSVVTVPSSSLGTQ TYICNVNHKPSNTKVDKKVEPKSC |
| | Pani VL-hCk | 104 | MDMRVPAQLLGLLLLWFPGSRCDIQMTQSPSSLSASVGDRVTI TCQASQDISNYLNWYQQKPGKAPKLLIYDASNLETGVPSRFSG SGSGTDFTFTISSLQPEDIATYFCQHFDHLPLAFGGGTKVEIK RTVAAPSVFIFPPSDEQLKSGTASVVCLLNNFYPREAKVQWKV DNALQSGNSQESVTEQDSKDSTYSLSSTLTLSKADYEKHKVYA CEVTHQGLSSPVTKSFNRGEC |
| FIT14-Ig Factor IXa/ FactorX | FIX VL-hCk-FX-VH-hCg4 | 105 | MDMRVPAQLLGLLLLWFPGSRCDIQMTQSPSSLSASVGDRVTI TCKASRNIERQLAWYQQKPGQAPELLIYQASRKESGVPDRFSG SRYGTDFTLTISSLQPEDIATYYCQQYSDPPLTFGGGTKVEIK RTVAAPSVFIFPPSDEQLKSGTASVVCLLNNFYPREAKVQWKV DNALQSGNSQESVTEQDSKDSTYSLSSTLTLSKADYEKHKVYA CEVTHQGLSSPVTKSFNRGECQVQLVQSGSELKKPGASVKVSC KASGYTFTDNNMDWVRQAPGQGLEWMGDINTRSGGSIYNEEFQ |

TABLE 17-continued

Amino acid sequences of additional exemplary FIT-Iq

| Name Target (mAb) | Protein region | SEQ ID NO | Sequence |
|---|---|---|---|
| | | | DRVIMTVDKSTDTAYMELSSLRSEDTATYHCARRKSYGYYLDE WGEGTLVTVSSASTKGPSVFPLAPCSRSTSESTAALGCLVKDY FPEPVTVSWNSGALTSGVHTFPAVLQSSGLYSLSSVVTVPSSS LGTQTYTCNVDHKPSNTKVDKRVESKYGPPCPPCPAPEFLGGP SVFLFPPKPKDTLMISRTPEVTCVVVDVSQEDPEVQFNWYVDG VEVHNAKTKPREEQYNSTYRVVSVLTVLHQDWLNGKEYKCKVS NKGLPSSIEKTISKAKGQPREPQVYTLPPSQEEMTKNQVSLTC LVKGFYPSDIAVEWESNGQPENNYKTTPPVLDSDGSFFLYSKL TVDKSRWQEGNVFSCSVMHEALHNHYTQESLSLSP |
| | F-IX VH-CH1h | 106 | MEFGLSWLFLVAILKGVQCQVQLVESGGGLVQPGGSLRLSCAA SGFTFSYYDIQWVRQAPGKGLEWVSSISPSGQSTYYRREVKGR FTISRDNSKNTLYLQMNSLRAEDTAVYYCARRTGREYGGGWYF DYWGQGTLVTVSSASTKGPSVFPLAPSSKSTSGGTAALGCLVK DYFPEPVTVSWNSGALTSGVHTFPAVLQSSGLYSLSSVVTVPS SSLGTQTYICNVNHKPSNTKVDKKVEPKSC |
| | F-X VL-hCk | 107 | MDMRVPAQLLGLLLLWFPGSRCDIQMTQSPSSLSASVGDRVTI TCKASRNIERQLAWYQQKPGQAPELLIYQASRKESGVPDRFSG SRYGTDFTLTISSLQPEDIATYYCQQYSDPPLTFGGGTKVEIK RTVAAPSVFIFPPSDEQLKSGTASVVCLLNNFYPREAKVQWKV DNALQSGNSQESVTEQDSKDSTYSLSSTLTLSKADYEKHKVYA CEVTHQGLSSPVTKSFNRGEC |
| FIT16a-Ig Her3 (paritumumab)/ IGF-1R (figitumumab) | Paritu VL-hCk-figituVH-hCg1 | 108 | MDMRVPAQLLGLLLLWFPGSRCDIEMTQSPDSLAVSLGERATI NCRSSQSVLYSSSNRNYLAWYQQNPGQPPKLLIYWASTRESGV PDRFSGSGSGTDFTLTISSLQAEDVAVYYCQQYYSTPRTFGQG TKVEIKRTVAAPSVFIFPPSDEQLKSGTASVVCLLNNFYPREA KVQWKVDNALQSGNSQESVTEQDSKDSTYSLSSTLTLSKADYE KHKVYACEVTHQGLSSPVTKSFNRGECEVQLLESGGGLVQPGG SLRLSCTASGFTFSSYAMNWVRQAPGKGLEWVSAISGSGGTTF YADSVKGRFTISRDNSRTTLYLQMNSLRAEDTAVYYCAKDLGW SDSYYYYGMDVWGQGTTVTVSSASTKGPSVFPLAPSSKSTSG GTAALGCLVKDYFPEPVTVSWNSGALTSGVHTFPAVLQSSGLY SLSSVVTVPSSSLGTQTYICNVNHKPSNTKVDKKVEPKSCDKT HTCPPCPAPELLGGPSVFLFPPKPKDTLMISRTPEVTCVVVDV SHEDPEVKFNWYVDGVEVHNAKTKPREEQYNSTYRVVSVLTVL HQDWLNGKEYKCKVSNKALPAPIEKTISKAKGQPREPQVYTLP PSREEMTKNQVSLTCLVKGFYPSDIAVEWESNGQPENNYKTTP PVLDSDGSFFLYSKLTVDKSRWQQGNVFSCSVMHEALHNHYTQ KSLSLSPGK |
| | Patritumab-CH1h | 109 | MEFGLSWLFLVAILKGVQCQVQLQQWGAGLLKPSETLSLTCAV YGGSFSGYYWSWIRQPPGKGLEWIGEINHSGSTNYNPSLKSRV TISVETSKNQFSLKLSSVTAADTAVYYCARDKWTWYFDLWGRG TLVTVSSASTKGPSVFPLAPSSKSTSGGTAALGCLVKDYFPEP VTVSWNSGALTSGVHTFPAVLQSSGLYSLSSVVTVPSSSLGTQ TYICNVNHKPSNTKVDKKVEPKSC |
| | Figitu VL-hCk | 110 | MDMRVPAQLLGLLLLWFPGSRCDIQMTQFPSSLSASVGDRVTI TCRASQGIRNDLGWYQQKPGKAPKRLIYAASRLHRGVPSRFSG SGSGTEFTLTISSLQPEDFATYYCLQHNSYPCSFGQGTKLEIK RTVAAPSVFIFPPSDEQLKSGTASVVCLLNNFYPREAKVQWKV DNALQSGNSQESVTEQDSKDSTYSLSSTLTLSKADYEKHKVYA CEVTHQGLSSPVTKSFNRGEC |
| FIT17a-Ig DLL-4 (demcizumab)/ VEGF (bevicizumab) | Demci VL-hCk-Bevci VH-hCg1 | 111 | MDMRVPAQLLGLLLLWFPGSRCDIVMTQSPDSLAVSLGERATI SCRASESVDNYGISFMKWFQQKPGQPPKLLIYAASNQGSGVPD RFSGSGSGTDFTLTISSLQAEDVAVYYCQQSKEVPWTFGGGTK VEIKRTVAAPSVFIFPPSDEQLKSGTASVVCLLNNFYPREAKV QWKVDNALQSGNSQESVTEQDSKDSTYSLSSTLTLSKADYEKH KVYACEVTHQGLSSPVTKSFNRGECEVQLVESGGGLVQPGGSL RLSCAASGYTFTNYGMNWVRQAPGKGLEWVGWINTYTGEPTYA ADFKRRFTSLDTSKSTAYLQMNSLRAEDTAVYYCAKYPHYYG SSHWYFDVWGQGTLVTVSSASTKGPSVFPLAPSSKSTSGGTAA LGCLVKDYFPEPVTVSWNSGALTSGVHTFPAVLQSSGLYSLSS VVTVPSSSLGTQTYICNVNHKPSNTKVDKKVEPKSCDKTHTCP PCPAPELLGGPSVFLFPPKPKDTLMISRTPEVTCVVVDVSHED PEVKFNWYVDGVEVHNAKTKPREEQYNSTYRVVSVLTVLHQDW LNGKEYKCKVSNKALPAPIEKTISKAKGQPREPQVYTLPPSRE EMTKNQVSLTCLVKGFYPSDIAVEWESNGQPENNYKTTPPVLD SDGSFFLYSKLTVDKSRWQQGNVFSCSVMHEALHNHYTQKSLS LSPGK |
| | Demci-CH1h | 112 | MEFGLSWLFLVAILKGVQCQVQLVQSGAEVKKPGASVKISCKA SGYSFTAYYIHWVKQAPGQGLEWIGYISSYNGATNYNQKFKGR VTFTTDTSTSTAYMELRSLRSDDTAVYYCARDYDYDVGMDYWG |

TABLE 17-continued

Amino acid sequences of additional exemplary FIT-Ig

| Name Target (mAb) | Protein region | SEQ ID NO | Sequence |
|---|---|---|---|
| | | | QGTLVTVSSASTKGPSVFPLAPSSKSTSGGTAALGCLVKDYFP EPVTVSWNSGALTSGVHTFPAVLQSSGLYSLSSVVTVPSSSLG TQTYICNVNHKPSNTKVDKKVEPKSC |
| | Bevci VL-hCk | 113 | MDMRVPAQLLGLLLLWFPGSRCDIQMTQSPSSLSASVGDRVTI TCSASQDISNYLNWYQQKPGKAPKVLIYFTSSLHSGVPSRFSG SGSGTDFTLTISSLQPEDFATYYCQQYSTVPWTFGQGTKVEIK RTVAAPSVFIFPPSDEQLKSGTASVVCLLNNFYPREAKVQWKV DNALQSGNSQESVTEQDSKDSTYSLSSTLTLSKADYEKHKVYA CEVTHQGLSSPVTKSFNRGEC |
| FIT18a-Ig CD20 (ofatumumab)/ CD3 | OfatuVL-hCk-CD3mAb VH-hCg1mut | 114 | MDMRVPAQLLGLLLLWFPGSRCEIVLTQSPATLSLSPGERATL SCRASQSVSSYLAWYQQKPGQAPRLLIYDASNRATGIPARFSG SGSGTDFTLTISSLEPEDFAVYYCQQRSNWPITFGQGTRLEIK RTVAAPSVFIFPPSDEQLKSGTASVVCLLNNFYPREAKVQWKV DNALQSGNSQESVTEQDSKDSTYSLSSTLTLSKADYEKHKVYA CEVTHQGLSSPVTKSFNRGECEVQLLESGGGLVQPGGSLKLSC AASGFTFNTYAMNWVRQAPGKGLEWVARIRSKYNNYATYYADS VKDRFTISRDDSKNTAYLQMNNLKTEDTAVYYCVRHGNFGNSY VSWFAYWGQGTLVTVSSASTKGPSVFPLAPSSKSTSGGTAALG CLVKDYFPEPVTVSWNSGALTSGVHTFPAVLQSSGLYSLSSVV TVPSSSLGTQTYICNVNHKPSNTKVDKKVEPKSCDKTHTCPPC PAPEAAGGPSVFLFPPKPKDTLMISRTPEVTCVVVDVSHEDPE VKFNWYVDGVEVHNAKTKPREEQYNSTYRVVSVLTVLHQDWLN GKEYKCKVSNKALPAPIEKTISKAKGQPREPQVYTLPPSREEM TKNQVSLTCLVKGFYPSDIAVEWESNGQPENNYKTTPPVLDSD GSFFLYSKLTVDKSRWQQGNVFSCSVMHEALHNHYTQKSLSLS PGK |
| | Ofatu VH-CH1 | 115 | MEFGLSWLFLVAILKGVQCEVQLVESGGGLVQPGRSLRLSCAA SGFTFNDYAMHWVRQAPGKGLEWVSTISWNSGSIGYADSVKGR FTISRDNAKKSLYLQMNSLRAEDTALYYCAKDIQYGNYYYGMD VWGQGTTVTVSSASTKGPSVFPLAPSSKSTSGGTAALGCLVKD YFPEPVTVSWNSGALTSGVHTFPAVLQSSGLYSLSSVVTVPSS SLGTQTYICNVNHKPSNTKVDKKVEPKSC |
| | CD3mAb VL-hCL | 116 | MTWTPLLFLTLLLHCTGSLSELVVTQEPSLTVSPGGTVTLTCR SSTGAVTTSNYANWVQQKPGQAPRGLIGGTNKRAPGTPARFSG SLLGGKAALTLSGVQPEDEAEYYCALWYSNLWVFGGGTKLTVL GQPKAAPSVTLFPPSSEELQANKATLVCLISDFYPGAVTVAWK ADSSPVKAGVETTTPSKQSNNKYAASSYLSLTPEQWKSHRSYS CQVTHEGSTVEKTVAPTECS |
| FIT19a-Ig Her3 (patritumab)/ EGFR (panitumumab) | patritu VL-hCk-PaniVH-hCg1 | 117 | MDMRVPAQLLGLLLLWFPGSRCDIEMTQSPDSLAVSLGERATI NCRSSQSVLYSSSNRNYLAWYQQNPGQPPKLLIYWASTRESGV PDRFSGSGSGTDFTLTISSLQAEDVAVYYCQQYYSTPRTFGQG TKVEIKRTVAAPSVFIFPPSDEQLKSGTASVVCLLNNFYPREA KVQWKVDNALQSGNSQESVTEQDSKDSTYSLSSTLTLSKADYE KHKVYACEVTHQGLSSPVTKSFNRGECQVQLQESGPGLVKPSE TLSLTCTVSGGSVSSGDYYWTWIRQSPGKGLEWIGHIYYSGNT NYNPSLKSRLTISIDTSKTQFSLKLSSVTAADTAIYYCVRDRV TGAFDIWGQGTMVTVSSASTKGPSVFPLAPSSKSTSGGTAALG CLVKDYFPEPVTVSWNSGALTSGVHTFPAVLQSSGLYSLSSVV TVPSSSLGTQTYICNVNHKPSNTKVDKKVEPKSCDKTHTCPPC PAPELLGGPSVFLFPPKPKDTLMISRTPEVTCVVVDVSHEDPE VKFNWYVDGVEVHNAKTKPREEQYNSTYRVVSVLTVLHQDWLN GKEYKCKVSNKALPAPIEKTISKAKGQPREPQVYTLPPSREEM TKNQVSLTCLVKGFYPSDIAVEWESNGQPENNYKTTPPVLDSD GSFFLYSKLTVDKSRWQQGNVFSCSVMHEALHNHYTQKSLSLS PGK |
| | Patritumab-CH1 | 118 | MEFGLSWLFLVAILKGVQCQVQLQQWGAGLLKPSETLSLTCAV YGGSFSGYYWSWIRQPPGKGLEWIGEINHSGSTNYNPSLKSRV TISVETSKNQFSLKLSSVTAADTAVYYCARDKWTWYFDLWGRG TLVTVSSASTKGPSVFPLAPSSKSTSGGTAALGCLVKDYFPEP VTVSWNSGALTSGVHTFPAVLQSSGLYSLSSVVTVPSSSLGTQ TYICNVNHKPSNTKVDKKVEPKSC |
| | Pani VL-hCk | 119 | MDMRVPAQLLGLLLLWFPGSRCDIQMTQSPSSLSASVGDRVTI TCQASQDISNYLNWYQQKPGKAPKLLIYDASNLETGVPSRFSG SGSGTDFTFTISSLQPEDIATYFCQHFDHLPLAFGGGTKVEIK RTVAAPSVFIFPPSDEQLKSGTASVVCLLNNFYPREAKVQWKV DNALQSGNSQESVTEQDSKDSTYSLSSTLTLSKADYEKHKVYA CEVTHQGLSSPVTKSFNRGEC |
| FIT20a-Ig PD-1 (nivolumab)/ PD-L1 (1B12) | Nivolu VL-hCk-1B12 VH-hCg1Mut | 120 | MDMRVPAQLLGLLLLWFPGSRCEIVLTQSPATLSLSPGERATL SCRASQSVSSYLAWYQQKPGQAPRLLIYDASNRATGIPARFSG SGSGTDFTLTISSLEPEDFAVYYCQQSSNWPRTFGQGTKVEIK RTVAAPSVFIFPPSDEQLKSGTASVVCLLNNFYPREAKVQWKV DNALQSGNSQESVTEQDSKDSTYSLSSTLTLSKADYEKHKVYA |

TABLE 17-continued

Amino acid sequences of additional exemplary FIT-Ig

| Name Target (mAb) | Protein region | SEQ ID NO | Sequence |
|---|---|---|---|
| | | | CEVTHQGLSSPVTKSFNRGECQVQLVQSGAEVKKPGSSVKVSC KTSGDTFSSYAISWVRQAPGQGLEWMGGIIPIFGRAHYAQKFQ GRVTITADESTSTAYMELSSLRSEDTAVYFCARKFHFVSGSPF GMDVWGQGTTVTVSSASTKGPSVFPLAPSSKSTSGGTAALGCL VKDYFPEPVTVSWNSGALTSGVHTFPAVLQSSGLYSLSSVVTV PSSSLGTQTYICNVNHKPSNTKVDKKVEPKSCDKTHTCPPCPA PELLGGPSVFLFPPKPKDTLMISRTPEVTCVVVDVSHEDPEVK FNWYVDGVEVHNAKTKPREEQYNSTYRVVSVLTVLHQDWLNGK EYKCKVSNKALPAPIEKTISKAKGQPREPQVYTLPPSREEMTK NQVSLTCLVKGFYPSDIAVEWESNGQPENNYKTTPPVLDSDGS FFLYSKLTVDKSRWQQGNVFSCSVMHEALHNHYTQKSLSLSPG K |
| | Nivo VH-CH1 | 121 | MEFGLSWLFLVAILKGVQCQVQLVESGGGVVQPGRSLRLDCKA SGITFSNSGMHWVRQAPGKGLEWVAVIWYDGSKRYYADSVKGR FTISRDNSKNTLFLQMNSLRAEDTAVYYCATNDDYWGQGTLVT VSSASTKGPSVFPLAPSSKSTSGGTAALGCLVKDYFPEPVTVS WNSGALTSGVHTFPAVLQSSGLYSLSSVVTVPSSSLGTQTYIC NVNHKPSNTKVDKKVEPKSC |
| | 1B12 VL-hCk | 122 | MDMRVPAQLLGLLLLWFPGSRCEIVLTQSPATLSLSPGERATL SCRASQSVSSYLAWYQQKPGQAPRLLIYDASNRATGIPARFSG SGSGTDFTLTISSLEPEDFAVYYCQQRSNWPTFGQGTKVEIKR TVAAPSVFIFPPSDEQLKSGTASVVCLLNNFYPREAKVQWKVD NALQSGNSQESVTEQDSKDSTYSLSSTLTLSKADYEKHKVYAC EVTHQGLSSPVTKSFNRGEC |
| FIT22a-Ig Her3 (patritumab)/ PD-1 (nivolumab) | patritu VL-hCk-Nivolu VH-hCg1mut | 123 | MDMRVPAQLLGLLLLWFPGSRCDIEMTQSPDSLAVSLGERATI NCRSSQSVLYSSSNRNYLAWYQQNPGQPPKLLIYWASTRESGV PDRFSGSGSGTDFTLTISSLQAEDVAVYYCQQYYSTPRTFGQG TKVEIKRTVAAPSVFIFPPSDEQLKSGTASVVCLLNNFYPREA KVQWKVDNALQSGNSQESVTEQDSKDSTYSLSSTLTLSKADYE KHKVYACEVTHQGLSSPVTKSFNRGECQVQLVESGGGVVQPGR SLRLDCKASGITFSNSGMHWVRQAPGKGLEWVAVIWYDGSKRY YADSVKGRFTISRDNSKNTLFLQMNSLRAEDTAVYYCATNDDY WGQGTLVTVSSASTKGPSVFPLAPSSKSTSGGTAALGCLVKDY FPEPVTVSWNSGALTSGVHTFPAVLQSSGLYSLSSVVTVPSSS LGTQTYICNVNHKPSNTKVDKKVEPKSCDKTHTCPPCPAPELL GGPSVFLFPPKPKDTLMISRTPEVTCVVVDVSHEDPEVKFNWY VDGVEVHNAKTKPREEQYNSTYRVVSVLTVLHQDWLNGKEYKC KVSNKALPAPIEKTISKAKGQPREPQVYTLPPSREEMTKNQVS LTCLVKGFYPSDIAVEWESNGQPENNYKTTPPVLDSDGSFFLY SKLTVDKSRWQQGNVFSCSVMHEALHNHYTQKSLSLSPGK |
| | Patritumab-CH1 | 124 | MEFGLSWLFLVAILKGVQCQVQLQQWGAGLLKPSETLSLTCAV YGGSFSGYYWSWIRQPPGKGLEWIGEINHSGSTNYNPSLKSRV TISVETSKNQFSLKLSSVTAADTAVYYCARDKWTWYFDLWGRG TLVTVSSASTKGPSVFPLAPSSKSTSGGTAALGCLVKDYFPEP VTVSWNSGALTSGVHTFPAVLQSSGLYSLSSVVTVPSSSLGTQ TYICNVNHKPSNTKVDKKVEPKSC |
| | NivoVL-hCK | 125 | MDMRVPAQLLGLLLLWFPGSRCEIVLTQSPATLSLSPGERATL SCRASQSVSSYLAWYQQKPGQAPRLLIYDASNRATGIPARFSG SGSGTDFTLTISSLEPEDFAVYYCQQSSNWPRTFGQGTKVEIK RTVAAPSVFIFPPSDEQLKSGTASVVCLLNNFYPREAKVQWKV DNALQSGNSQESVTEQDSKDSTYSLSSTLTLSKADYEKHKVYA CEVTHQGLSSPVTKSFNRGEC |

TABLE 18

Expression level in 293E cells and SEC profile for FIT-Igs

| Name Target (mAb) | Expression Level in 293E cells (mg/L) | SEC Profile (% monomeric fraction) |
|---|---|---|
| FIT12a-Ig EGFR (panitumumab)/ PD-L1 (IB12) | 0.26 | 74.72 |
| FIT13a-Ig cMet (h1332)/ EGFR (panitumumab) | 0.705 | 97.70 |
| FIT14-Ig Factor IXa/ Factor X | 0.135 | 100.00 |
| FIT16a-Ig Her3 (paritumumab)/ IGF-1R (figitumumab) | 0.15 | 100.00 |
| FIT17a-Ig DLL-4 (demcizumab)/ VEGF (bevicizumab) | 0.11 | 78.384 |
| FIT18a-Ig CD20 (ofatumumab)/CD3 | 0.39 | 100.00 |

TABLE 18-continued

Expression level in 293E cells and SEC profile for FIT-Igs

| Name Target (mAb) | Expression Level in 293E cells (mg/L) | SEC Profile (% monomeric fraction) |
|---|---|---|
| FIT19a-Ig Her3 (patritumab)/ EGFR (panitumumab) | 0.37 | 86.762 |
| FIT20a-Ig PD-1 (nivolumab)/ PD-L1 (1B12) | 0.51 | 73.721 |
| FIT22a-Ig Her3 (patritumab)/ PD-1 (nivolumab) | 0.098 | 100.00 |

The SEC profiles for each of the FIT-Ig of Tables 17 and 18 are also provided in FIG. 7a-7i.

Figure 8:
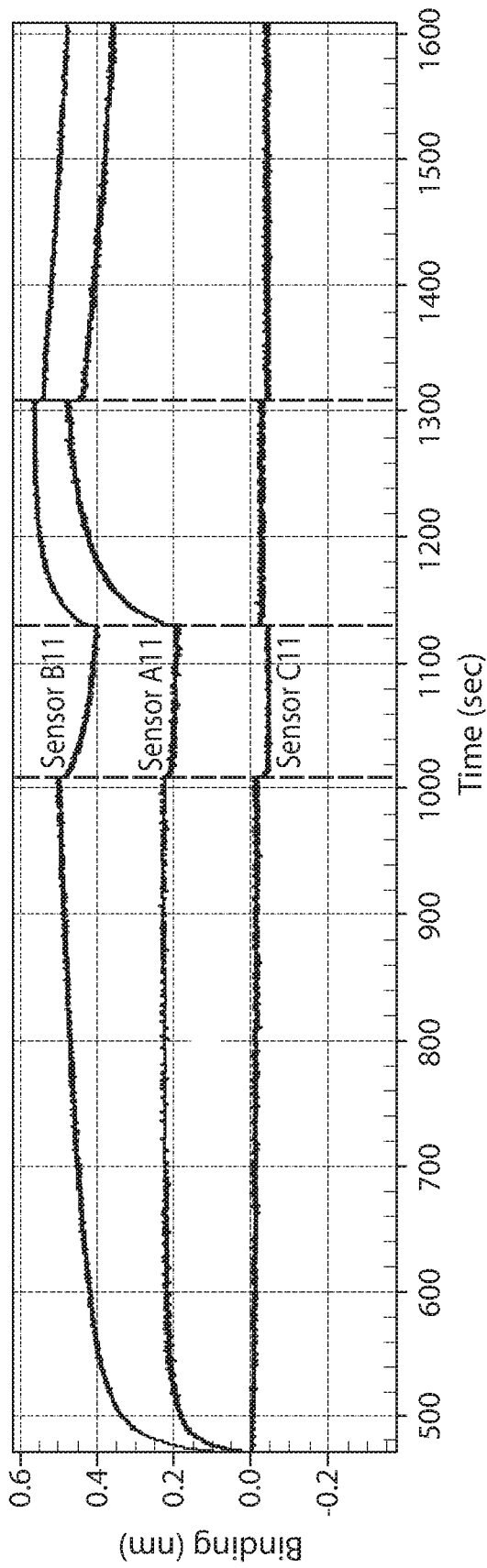
FIG. 8 shows a multiple binding study of FIT13a-Ig against both cMet and EGFR.

Functional binding data for FIT13a-Ig are provided below in Table 19. In addition, a multiple-antigen binding study was performed to determine if FIT13a-Ig was able to bind cMet and EGFR. The results of the study are shown in FIG. 8, and show that FIT13a-Ig was able to bind both cMet and EGFR simultaneously.

TABLE 19

Functional binding data for FIT13a-Ig

| Ig | Target | Kon | Koff | KD |
|---|---|---|---|---|
| mAb-h1332 | c-met | 2.61E+05 | 6.87E−04 | 2.63E−09 |
| FIT-Ig13a | | 2.94E+05 | 7.26E−04 | 2.47E−09 |
| Panitumumab | hEGFR | 3.61E+05 | 5.59E−04 | 1.55E−09 |
| FIT-Ig13a | | 2.69E+05 | 4.07E−04 | 1.52E−09 |

Functional binding data for the Factor IXa binding activity of FIT14-Ig are provided below in Table 20.

TABLE 20

Functional binding data for FIT14-Ig

| Ig | Target | Kon | Koff | KD |
|---|---|---|---|---|
| Factor IXa mAb | Factor IXa | 2.74E+04 | 3.55E−04 | 1.30E−08 |
| FIT-Ig 014 | | 3.35E+04 | 3.32E−04 | 9.90E−09 |
| Factor X mAb | Factor X | | | |
| FIT-Ig 14 | | | | |

The results of the study show that additional FIT-Ig can be constructed, expressed, and purified and will exhibit functional binding to the target proteins.

Example 6: Construction, Expression, and Purification of New Anti-CTLA-4/PD-1 Fabs-in-Tandem Immunoglobulin (FIT-Ig)

New FIT-Ig having specificity for CTLA4 and PD1 were constructed as in the foregoing Examples. These exemplary FIT-Ig and their corresponding sequences are provided below in Table 21. Table 21 provides the expression level in 293E cells and the SEC profile for each of the FIT-Ig.

TABLE 21

Amino acid sequences of additional exemplary FIT-Ig for CTLA4 and PD1

| Name Target (mAb) mAb1 (upper domain)/mAb2 (lower domain) | Protein region | SEQ ID NO | Sequences |
|---|---|---|---|
| NBS3-Ig CTLA4 (ipilimumab)/ PD-1 (nivolumab) | Long chain (IpiliVL-hCk- NivoluVH- hCg1mut) | 126 | MDMRVPAQLLGLLLLWFPGSRCEIVLTQSPGTLSLSPGER ATLSCRASQSVGSSYLAWYQQKPGQAPRLLIYGAFSRATG IPDRFSGSGSGTDFTLTISRLEPEDFAVYYCQQYGSSPWT FGQGTKVEIKRTVAAPSVFIFPPSDEQLKSGTASVVCLLN NFYPREAKVQWKVDNALQSGNSQESVTEQDSKDSTYSLSS TLTLSKADYEKHKVYACEVTHQGLSSPVTKSFNRGECQVQ LVESGGGVVQPGRSLRLDCKASGITFS<u>NSGMH</u>WVRQAPGK GLEWVA<u>VIWYDGSKRYYADSVKG</u>RFTISRDNSKNTLFLQM NSLRAEDTAVYYCAT<u>NDDY</u>WGQGTLVTVSSASTKGPSVFP LAPSSKSTSGGTAALGCLVKDYFPEPVTVSWNSGALTSGV HTFPAVLQSSGLYSLSSVVTVPSSSLGTQTYICNVNHKPS NTKVDKKVEPKSCDKTHTCPPCPAPEAAGGPSVFLFPPKP KDTLMISRTPEVTCVVVDVSHEDPEVKFNWYVDGVEVHNA KTKPREEQYNSTYRVVSVLTVLHQDWLNGKEYKCKVSNKA LPAPIEKTISKAKGQPREPQVYTLPPSREEMTKNQVSLTC LVKGFYPSDIAVEWESNGQPENNYKTTPPVLDSDGSFFLY SKLTVDKSRWQQGNVFSCSVMHEALHNHYTQKSLSLSPGK |
| | Ipili VL | 127 | EIVLTQSPGTLSLSPGERATLSC<u>RASQSVGSSYLA</u>WYQQK PGQAPRLLIY<u>GAFSRAT</u>GIPDRFSGSGSGTDFTLTISRLE PEDFAVYYCQQYGSSPWTFGQGTKVEIK |
| | Ipili VL - CDR1 | 128 | <u>RASQSVGSSYLA</u> |
| | Ipili VL - CDR2 | 129 | <u>GAFSRAT</u> |
| | Ipili VL - CDR3 | 130 | <u>QQYGSSPWT</u> |
| | NivoluVH | 131 | QVQLVESGGGVVQPGRSLRLDCKASGITFS<u>NSGMH</u>WVRQA PGKGLEWVA<u>VIWYDGSKRYYADSVKG</u>RFTISRDNSKNTLF LQMNSLRAEDTAVYYCAT<u>NDDY</u>WGQGTLVTVSS |
| | Nivolu VH - CDR1 | 132 | <u>NSGMH</u> |
| | Nivolu VH - CDR2 | 133 | <u>VIWYDGSKRYYADSVKG</u> |
| | Nivolu VH - CDR3 | 134 | <u>NDDY</u> |

TABLE 21-continued

Amino acid sequences of additional exemplary FIT-Ig for CTLA4 and PD1

| Name Target (mAb) mAb1 (upper domain)/mAb2 (lower domain) | Protein region | SEQ ID NO | Sequences |
|---|---|---|---|
| | Short Chai #1 (Ipili VH-CH1) | 135 | MEFGLSWLFLVAILKGVQCQVQLVESGGGVVQPGRSLRLS CAASGFTFSSYTMHWVRQAPGKGLEWVTFISYDGNNKYYA DSVKGRFTISRDNSKNTLYLQMNSLRAEDTAIYYCARTGW LGPFDYWGQGTLVTVSSASTKGPSVFPLAPSSKSTSGGTA ALGCLVKDYFPEPVTVSWNSGALTSGVHTFPAVLQSSGLY SLSSVVTVPSSSLGTQTYICNVNHKPSNTKVDKKVEPKSC |
| | Ipili VH | 136 | QVQLVESGGGVVQPGRSLRLSCAASGFTFSSYTMHWVRQA PGKGLEWVTFISYDGNNKYYADSVKGRFTISRDNSKNTLY LQMNSLRAEDTAIYYCARTGWLGPFDYWGQGTLVTVSS |
| | Ipili VH - CDR1 | 137 | SYTMH |
| | Ipili VH - CDR2 | 138 | FISYDGNNKYYADSVKG |
| | Ipili VH - CDR3 | 139 | TGWLGPFDY |
| | Short Chain #2 (Nivolu VL-hCK) | 140 | MDMRVPAQLLGLLLLWFPGSRCEIVLTQSPATLSLSPGERA TLSCRASQSVSSYLAWYQQKPGQAPRLLIYDASNRATGIPA RFSGSGSGTDFTLTISSLEPEDFAVYYCQQSSNWPRTFGQG TKVEIKRTVAAPSVFIFPPSDEQLKSGTASVVCLLNNFYPR EAKVQWKVDNALQSGNSQESVTEQDSKDSTYSLSSTLTLSK ADYEKHKVYACEVTHQGLSSPVTKSFNRGEC |
| | Nivolu VL | 141 | EIVLTQSPATLSLSPGERATLSCRASQSVSSYLAWYQQKP GQAPRLLIYDASNRATGIPARFSGSGSGTDFTLTISSLEP EDFAVYYCQQSSNWPRTFGQGTKVE1K |
| | Nivolu VL - CDR1 | 142 | RASQSVSSYLA |
| | Nivolu VL - CDR2 | 143 | DASNRAT |
| | Nivolu VL - CDR3 | 144 | QQSSNWPRT |
| NBS3R - Ig PD-1(nivolumab)/ CTLA4 (ipilimumab) | Long Chain (Nivolu VL-hCk-Ipili VH-hCg1mut) | 145 | MDMRVPAQLLGLLLLWFPGSRCEIVLTQSPATLSLSPGER ATLSCRASQSVSSYLAWYQQKPGQAPRLLIYDASNRATGI PARFSGSGSGTDFTLTISSLEPEDFAVYYCQQSSNWPRTF GQGTKVEIKRTVAAPSVFIFPPSDEQLKSGTASVVCLLNN FYPREAKVQWKVDNALQSGNSQESVTEQDSKDSTYSLSST LTLSKADYEKHKVYACEVTHQGLSSPVTKSFNRGECQVQL VESGGGVVQPGRSLRLSCAASGFTFSSYTMHWVRQAPGKG LEWVTFISYDGNNKYYADSVKGRFTISRDNSKNTLYLQMN SLRAEDTAIYYCARTGWLGPFDYWGQGTLVTVSSASTKGP SVFPLAPSSKSTSGGTAALGCLVKDYFPEPVTVSWNSGAL TSGVHTFPAVLQSSGLYSLSSVVTVPSSSLGTQTYICNVN HKPSNTKVDKKVEPKSCDKTHTCPPCPAPEAAGGPSVFLF PPKPKDTLMISRTPEVTCVVVDVSHEDPEVKFNWYVDGVE VHNAKTKPREEQYNSTYRVVSVLTVLHQDWLNGKEYKCKV SNKALPAPIEKTISKAKGQPREPQVYTLPPSREEMTKNQV SLTCLVKGFYPSDIAVEWESNGQPENNYKTTPPVLDSDGS FFLYSKLTVDKSRWQQGNVFSCSVMHEALHNHYTQKSLSL SPGK |
| | Nivolu VL | 146 | EIVLTQSPATLSLSPGERATLSCRASQSVSSYLAWYQQKP GQAPRLLIYDASNRATGIPARFSGSGSGTDFTLTISSLEP EDFAVYYCQQSSNWPRTFGQGTKVE1K |
| | Nivolu VL - CDR1 | 147 | RASQSVSSYLA |
| | Nivolu VL - CDR2 | 148 | DASNRAT |
| | Nivolu VL - CDR3 | 149 | QQSSNWPRT |
| | Ipili VH | 150 | QVQLVESGGGVVQPGRSLRLSCAASGFTFSSYTMHWVRQA PGKGLEWVTFISYDGNNKYYADSVKGRFTISRDNSKNTLY LQMNSLRAEDTAIYYCARTGWLGPFDYWGQGTLVTVSS |
| | Ipili VH - CDR1 | 151 | SYTMH |
| | Ipili VH - CDR2 | 152 | FISYDGNNKYYADSVKG |
| | Ipili VH - CDR3 | 153 | TGWLGPFDY |
| | Short Chain #1 (Nivolu VH-CH1) | 154 | MEFGLSWLFLVAILKGVQCQVQLVESGGGVVQPGRSLRLD CKASGITFSNSGMHWVRQAPGKGLEWVAIWYDGSKRYYA DSVKGRFTISRDNSKNTLFLQMNSLRAEDTAVYYCATNDD YWGQGTLVTVSSASTKGPSVFPLAPSSKSTSGGTAALGCL VKDYFPEPVTVSWNSGALTSGVHTFPAVLQSSGLYSLSSV VTVPSSSLGTQTYICNVNHKPSNTKVDKKVEPKSC |
| | Nivolu VH | 155 | QVQLVESGGGVVQPGRSLRLDCKASGITFSNSGMHWVRQA PGKGLEWVAVIWYDGSKRYYADSVKGRFTISRDNSKNTLF LQMNSLRAEDTAVYYCATNDDYWGQGTLVTVSS |
| | Nivolu VH - CDR1 | 156 | GMH |
| | Nivolu VH - CDR2 | 157 | VIWYDGSKRYYADSVKG |
| | Nivolu VH - CDR3 | 158 | NDDY |
| | Short Chain #2 (Ipili VL-hCK) | 159 | MDMRVPAQLLGLLLLWFPGSRCEIVLTQSPGTLSLSPGER ATLSCRASQSVGSSYLAWYQQKPGQAPRLLIYGAFSRATG IPDRFSGSGSGTDFTLTISRLEPEDFAVYYCQQYGSSPWT FGQGTKVEIKRTVAAPSVFIFPPSDEQLKSGTASVVCLLN |

TABLE 21-continued

Amino acid sequences of additional exemplary FIT-Ig for CTLA4 and PD1

| Name Target (mAb) mAb1 (upper domain)/mAb2 (lower domain) | Protein region | SEQ ID NO | Sequences |
|---|---|---|---|
| | | | NFYPREAKVQWKVDNALQSGNSQESVTEQDSKDSTYSLSSTLTLSKADYEKHKVYACEVTHQGLSSPVTKSFNRGEC |
| | Ipili VL | 160 | EIVLTQSPGTLSLSPGERATLSC<u>RASQSVGSSYLA</u>WYQQKPGQAPRLLIY<u>GAFSRAT</u>GIPDRFSGSGSGTDFTLTISRLEPEDFAVYYC<u>QQYGSSPWT</u>FGQGTKVEIK |
| | Ipili VL - CDR1 | 161 | <u>RASQSVGSSYLA</u> |
| | Ipili VL - CDR2 | 162 | <u>GAFSRAT</u> |
| | Ipili VL - CDR3 | 163 | <u>YGSSPWT</u> |
| NBS3-C-Ig CTLA4 (ipilimumab)/ PD-1(nivolumab) | LongChain (IpiliVL-hCk-NivoluVH-hCg4): | 164 | <u>MDMRVPAQLLGLLLLWFPGSRC</u>EIVLTQSPGTLSLSPGERATLSC<u>RASQSVGSSYLA</u>WYQQKPGQAPRLLIY<u>GAFSRAT</u>GIPDRFSGSGSGTDFTLTISRLEPEDFAVYYC<u>QQYGSSPWT</u>FGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECQVQLVESGGGVVQPGRSLRLDCKASGIITS<u>NSGMH</u>WVRQAPGKGLEWVA<u>VIWYDGSKRYYADSVKG</u>RFTISRDNSKNTLFLQMNSLRAEDTAVYYCAT<u>NDDY</u>WGQGTLVTVSSASTKGPSVFPLAPCSRSTSESTAALGCLVKDYFPEPVTVSWNSGALTSGVHTPPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| | IpiliVL | 165 | EIVLTQSPGTLSLSPGERATLSC<u>RASQSVGSSYLA</u>WYQQKPGQAPRLLIY<u>GAFSRAT</u>GIPDRFSGSGSGTDFTLTISRLEPEDFAVYYC<u>QQYGSSPWT</u>FGQGTKVEIK |
| | IpiliVL - CDR1 | 166 | <u>RASQSVGSSYLA</u> |
| | IpiliVL - CDR2 | 167 | <u>GAFSRAT</u> |
| | IpiliVL - CDR3 | 168 | <u>QQYGSS</u> |
| | NivoluVH | 169 | QVQLVESGGGVVQPGRSLRLDCKASGITFS<u>NSGMH</u>WVRQAPGKGLEWVA<u>VIWYDGSKRYYADSVKG</u>RFTISRDNSKNTLFLQMNSLRAEDTAVYYCAT<u>NDDY</u>WGQGTLVTVSS |
| | NivoluVH - CDR1 | 170 | <u>NSGMH</u> |
| | NivoluVH - CDR2 | 171 | <u>VIWYDGSKRYYADSVKG</u> |
| | NivoluVH - CDR3 | 172 | <u>NDDY</u> |
| | Short Chain #1 (Ipili VH-CH1) | 173 | <u>MEFGLSWLFLVAILKGVQC</u>QVQLVESGGGVVQPGRSLRLSCAASGFTFS<u>SYTMH</u>WVRQAPGKGLEWVT<u>FISYDGNNKYYADSVKG</u>RFTISRDNSKNTLYLQMNSLRAEDTAIYYCAR<u>TGWLGPFDY</u>WGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | Ipili VH | 174 | QVQLVESGGGVVQPGRSLRLSCAASGFTFS<u>SYTMH</u>WVRQAPGKGLEWVT<u>FISYDGNNKYYADSVKG</u>RFTISRDNSKNTLYLQMNSLRAEDTAIYYCAR<u>TGWLGPFDY</u>WGQGTLVTVSS |
| | Ipili VH - CDR1 | 175 | <u>SYTMH</u> |
| | Ipili VH - CDR2 | 176 | <u>FISYDGNNKYYADSVKG</u> |
| | Ipili VH - CDR3 | 177 | <u>TGWLGPFDY</u> |
| | Short Chain #2 (Nivolu VL-hCK) | 178 | <u>MDMRVPAQLLGLLLLWFPGSRC</u>EIVLTQSPATLSLSPGERATLSC<u>RASQSVSSYLA</u>WYQQKPGQAPRLLIY<u>DASNRAT</u>GIPARFSGSGSGTDFTLTISSLEPEDFAVYYC<u>QQSSNWPRT</u>FGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | Nivolu VL | 179 | EIVLTQSPATLSLSPGERATLSC<u>RASQSVSSYLA</u>WYQQKPGQAPRLLIY<u>DASNRAT</u>GIPARFSGSGSGTDFTLTISSLEPEDFAVYYC<u>QQSSNWPRT</u>FGQGTKVEIK |
| | Nivolu VL - CDR1 | 180 | <u>RASQSVSSYLA</u> |
| | Nivolu VL - CDR2 | 181 | <u>DASNRAT</u> |
| | Nivolu VL - CDR3 | 182 | <u>QQSSNWPRT</u> |
| NBS3R-C-Ig PD-1(nivolumab)/ CTLA4 (ipilimumab) | Long Chain (Nivolu VL-hCk-Ipili VH-hCg1mut) | 183 | <u>MDMRVPAQLLGLLLLWFPGSRC</u>EIVLTQSPATLSLSPGERATLSC<u>RASQSVSSYLA</u>WYQQKPGQAPRLLIY<u>DASNRAT</u>GIPARESGSGSGTDFTLTISSLEPEDFAVYYC<u>QQSSNWPRT</u>FGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECQVQLVESGGGVVQPGRSLRLSCAASGFITS<u>SYTMH</u>WVRQAPGKGLEWVT<u>FISYDGNNKYYADSVKG</u>RFTISRDNSKNTLYLQMN |

TABLE 21-continued

Amino acid sequences of additional exemplary FIT-Ig for CTLA4 and PD1

| Name Target (mAb) mAb1 (upper domain)/mAb2 (lower domain) | Protein region | SEQ ID NO | Sequences |
|---|---|---|---|
| | | | SLRAEDTAIYYCART<u>GWLGPFDY</u>WGQGTLVTVSSASTKGP SVFPLAPSSKSTSGGTAALGCLVKDYFPEPVTVSWNSGAL TSGVHTFPAVLQSSGLYSLSSVVTVPSSSLGTQTYICNVN HKPSNTKVDKKVEPKSCDKTHTCPPCPAPEAAGGPSVFLF PPKPKDTLMISRTPEVTCVVVDVSHEDPEVKFNWYVDGVE VHNAKTKPREEQYNSTYRVVSVLTVLHQDWLNGKEYKCKV SNKALPAPIEKTISKAKGQPREPQVYTLPPSREEMTKNQV SLTCLVKGFYPSDIAVEWESNGQPENNYKTTPPVLDSDGS FFLYSKLTVDKSRWQQGNVFSCSVMHEALHNHYTQKSLSL SPGK |
| Nivolu VL | | 184 | EIVLTQSPATLSLSPGERATLSC<u>RASQSVSSYLA</u>WYQQKP GQAPRLLIY<u>DASNRAT</u>GIPARFSGSGSGTDFTLTISSLEP EDFAVYYC<u>QQSSNWPRT</u>FGQGTKVE1K |
| Nivolu VL - CDR1 | | 185 | <u>RASQSVSSYLA</u> |
| Nivolu VL - CDR2 | | 186 | <u>DASNRAT</u> |
| Nivolu VL - CDR3 | | 187 | <u>QQSSNWPRT</u> |
| Ipili VH | | 188 | QVQLVESGGGVVQPGRSLRLSCAASGFTFS<u>SYTMH</u>WVRQA PGKGLEWVT<u>FISYDGNNKYYADSVKG</u>RFTISRDNSKNTLY LQMNSLRAEDTAIYYCART<u>GWLGPFDY</u>WGQGTLVTVSS |
| Ipili VH - CDR1 | | 189 | <u>SYTMH</u> |
| Ipili VH - CDR2 | | 190 | <u>FISYDGNNKYYADSVKG</u> |
| Ipili VH - CDR3 | | 191 | <u>TGWLGPFDY</u> |
| Short Chain #1 (Nivolu VH-IgG4-CH1) | | 192 | <u>MEFGLSWLFLVAILKGVQC</u>QVQLVESGGGVVQPGRSLRLD CKASGITFSNSGMHWVRQAPGKGLEWVA<u>VIWYDGSKRYYA DSVKG</u>RFTISRDNSKNTLFLQMNSLRAEDTAVYYCAT<u>NDD YWGQGTLVTVSS</u>ASTKGPSVFPLAPCSRSTSESTAALGCL VKDYFPEPVTVSWNSGALTSGVHTFPAVLQSSGLYSLSSV VTVPSSSLGTKTYTCNVDHKPSNTKVDKRVES |
| Nivolu VH | | 193 | QVQLVESGGGVVQPGRSLRLDCKASGITFS<u>NSGMH</u>WVRQA PGKGLEWVA<u>VIWYDGSKRYYADSVKG</u>RFTISRDNSKNTLF LQMNSLRAEDTAVYYCAT<u>NDDY</u>WGQGTLVTVSS |
| Nivolu VH - CDR1 | | 194 | <u>NSGMH</u> |
| Nivolu VH - CDR2 | | 195 | <u>VIWYDGSKRYYADSVKG</u> |
| Nivolu VH - CDR3 | | 196 | <u>NDDY</u> |
| Short Chain #2 (Ipili VL-hCK) | | 197 | <u>MDMRVPAQLLGLLLLWFPGSRC</u>EIVLTQSPGTLSLSPGER ATLSC<u>RASQSVGSSYLA</u>WYQQKPGQAPRLLIY<u>GAFSRATG</u> IPDRFSGSGSGTDFTLTISRLEPEDFAVYYC<u>QQYGSSPWT</u> FGQGTKVEIKRTVAAPSVFIFPPSDEQLKSGTASVVCLLN NFYPREAKVQWKVDNALQSGNSQESVTEQDSKDSTYSLSS TLTLSKADYEKHKVYACEVTHQGLSSPVTKSFNRGEC |
| Ipili VL | | 198 | EIVLTQSPGTLSLSPGERATLSC<u>RASQSVGSSYLA</u>WYQQK PGQAPRLLIY<u>GAFSRAT</u>GIPDRFSGSGSGTDFTLTISRLE PEDFAVYYC<u>QQYGSSPWT</u>FGQGTKVEIK |
| Ipili VL - CDR1 | | 199 | <u>RASQSVGSSYLA</u> |
| Ipili VL - CDR2 | | 200 | <u>GAFSRAT</u> |
| Ipili VL - CDR3 | | 201 | <u>QQYGSSPWT</u> |

The long chain and short chain comprise a leader sequence, which can be either MDMRVPAQLLGLLLL-WFPGSRC (SEQ ID NO: 487), or MEFGLSWLFLVAILKGVQC (SEQ ID NO: 488).

TABLE 22

SEC Profile/Expression level in 293E cells:

| FIT-Ig | Monomer % in SEC | Expression level(mg/L) |
|---|---|---|
| NBS3 | >95% | 24.6 |
| NBS3R | 100% | 6.3 |
| NBS3-C | 98.28 | 9.6 |
| NBS3R-C | 100% | 4.0 |

Expression level was evaluated in small scale production without any optimization, except NBS3. All SEC samples are under one step Protein A purification. FIT-Ig in both IgG1 and IgG4 format can be produced as homogeneous protein from 293 cells.

Functional Studies

Functional binding data for these antibodies is provided below in Table 23. The data suggests that the affinity was not affected by changing IgG constant sequences, but can be improved by place certain Fab in upper domain.

TABLE 23

Functional binding data

| Captured Antibody | Antigen | ka (1/Ms) | kd (1/s) | KD (M) |
|---|---|---|---|---|
| NBS3R-C | PD1-his | 3.412E+5 | 0.001407 | 4.123E−9 |
| NBS3R | | 3.315E+5 | 0.001402 | 4.228E−9 |
| NBS3-C | | 1.746E+5 | 0.002457 | 1.408E−8 |
| NBS3 | | 1.868E+5 | 0.002605 | 1.395E−8 |

TABLE 23-continued

Functional binding data

| Captured Antibody | Antigen | ka (1/Ms) | kd (1/s) | KD (M) |
|---|---|---|---|---|
| NBS3R-C | CTLA-4, his | 7.79E+04 | 0.001573 | 2.02E−08 |
| NBS3R | | 9.85E+04 | 0.001166 | 1.18E−08 |
| NBS3-C | | 1.93E+05 | 0.001123 | 5.82E−09 |
| NBS3 | | 2.05E+05 | 0.001096 | 5.34E−09 |

Figure 9A:
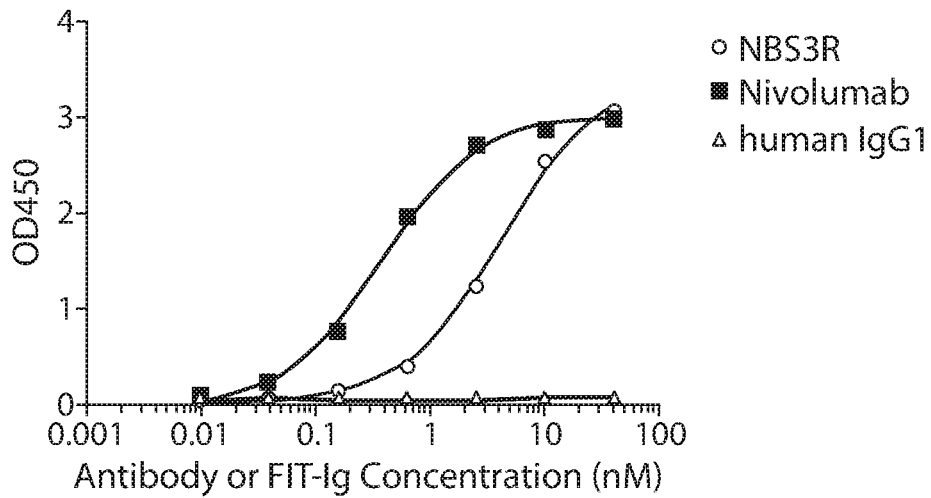
FIG. 9A and FIG. 9B show the binding of NBSR or the parental antibody Nivolumab to PD-1 (FIG. 9A) or CTLA-4 (FIG. 9B), as assessed by ELISA. Human IgG1 was included as a control.
Figure 9B:
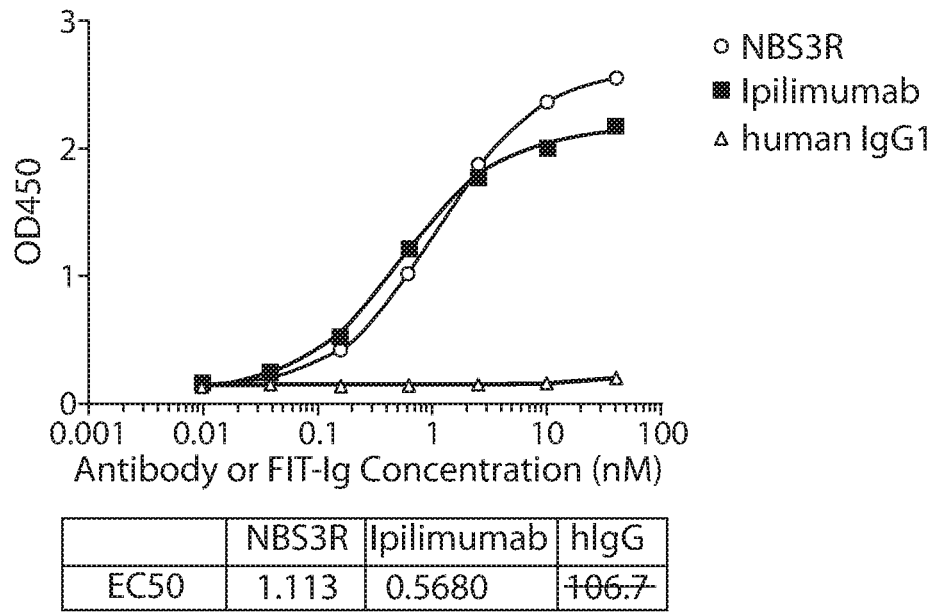

ELISA Binding Study:

ELISA binding of NBS3R was tested. Briefly, for binding to CTLA-4, human CTLA-4Ig (R&D Systems) was immobilized on 96-well plates, followed by routine wash and blocking procedures. Then FIT-Ig or related monoclonal antibodies at various concentrations were added to the plate, followed by incubation and multiple wash steps, and detected with anti-human Fab-HRP. For binding to PD-1, human PD-1 (with a his tag) (R&D Systems) was immobilized on 96-well plates, followed by routine wash and blocking procedures. Then NBS3R or Nivolumab at various concentrations was added to the plate, followed by incubation and multiple wash steps, and detected with anti-human Fc-HRP. It appears that NBS3R was able to bind both CTLA-4 (A) and PD-1 (B), respectively. The result is shown in FIG. 9A and Figure. 9B.

Figure 10:
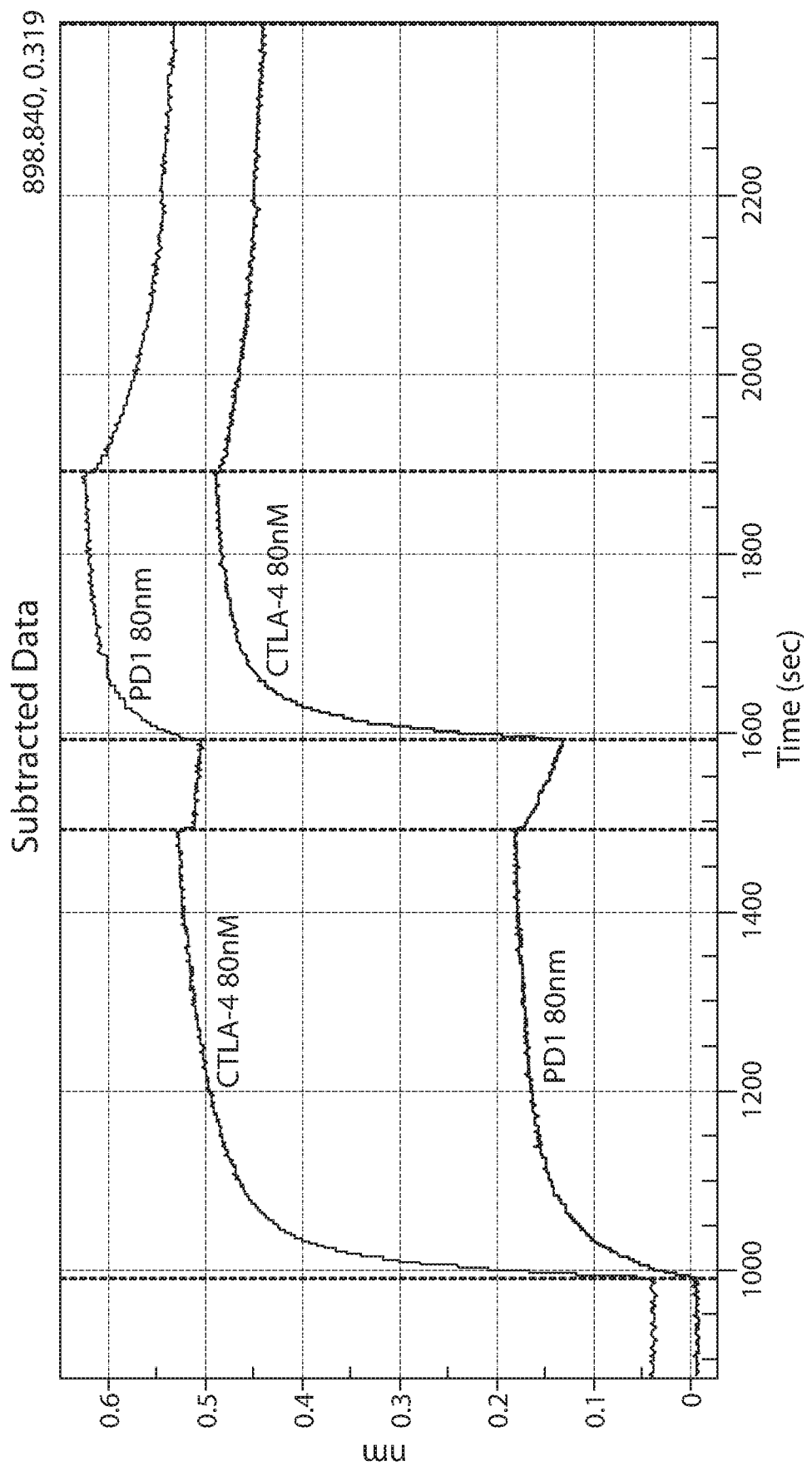
FIG. 10 shows a multiple binding study of NBS3 against both CTLA-4 and PD-1. Binding to CTLA-4 followed by PD-1; and binding by PD-1 followed by CTLA-4 are both shown as indicated.

Multiple Binding Study:

A multiple binding study of NBS3 was also carried out. The result is shown in Figure. 10.

Thermo Stability Study:

Thermo stability test was also performed on these antibodies, the result of which is shown in Table 24. The melting temperature was measured by DSC.

TABLE 24

Thermo stability test

| Antibody Code | $T_{m1}$ (° C.) | $T_{m2}$ (° C.) | $T_{m3}$ (° C.) | $T_{m4}$ (° C.) |
|---|---|---|---|---|
| NBS3R-c | 57.38 | 70.24 | 74.42 | 82.38 |
| NBS3R | 69.78 | 75.54 | 82.75 | |
| NBS3-c | 68.4 | 75.03 | | |
| NBS3 | 69.38 | 75.01 | 82.52 | |

Storage Stability Study:

The storage stability of NBS3 was assessed by SEC-HPLC method, and result is shown in Table 25. Samples were treated by freeze/thaw cycle for one time, two times or three times, no aggregation or degradation was observed by SEC-HPLC profile. Samples was treated at 4° C., 25° C. or 40° C. for 1 day, 3 days or 7 days, no aggregation or degradation was observed by SEC-HPLC profile.

TABLE 25

Storage stability of NBS3

| Sample Name | Rel. Area % 1 | Rel. Area % 2 | Rel. Area % 3 |
|---|---|---|---|
| NBS3_D0 | 0.77 | 99.23 | n.a. |
| NBS3_F/T1 | 1.23 | 98.77 | n.a. |
| NBS3_F/T2 | 1.32 | 98.68 | n.a. |
| NBS3_F/T3 | 1.39 | 98.61 | n.a. |
| NBS3_4C-D1 | 1.45 | 98.55 | n.a. |
| NBS3_25C-D1 | 1.45 | 98.55 | n.a. |
| NBS3_40C-D1 | 1.44 | 98.56 | n.a. |
| NBS3_4C-D3 | 1.49 | 98.51 | n.a. |
| NBS3_25C-D3 | 1.50 | 98.50 | n.a. |
| NBS3_40C-D3 | 1.62 | 97.85 | 0.53 |
| NBS3_4C-D7 | 1.61 | 98.39 | n.a. |
| NBS3_25C-D7 | 1.67 | 98.33 | n.a. |
| NBS3_40C-D7 | 1.76 | 97.70 | 0.55 |

Figures 11A, 11B:
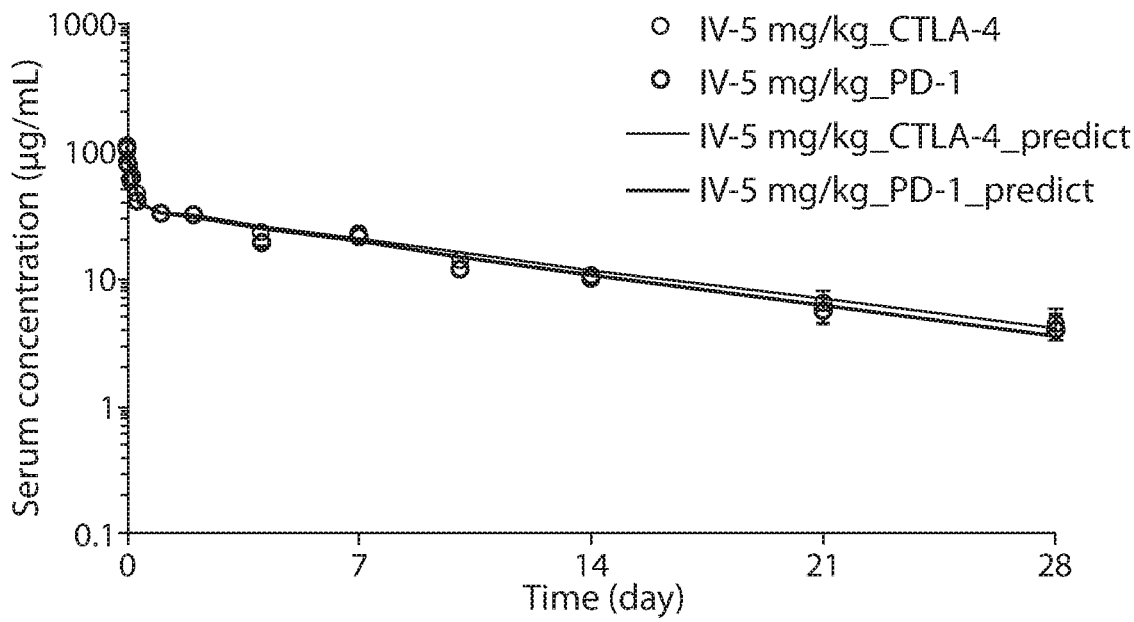
FIG. 11A shows mean serum concentration-time profiles of 5 mg/kg NBS3 administered intravenously (IV) or subcutaneously (SC).
FIG. 11B provides the detail PK parameters of this study.

NBS3 was further tested in rat PK study, and the result is shown in FIG. 11A and FIG. 11B. The purpose of this study was to evaluate the pharmacokinetic of NBS3 following single intravenous (IV) or subcutaneous (SC) administrations in SD rats. The IV dose was administered via foot dorsal vein injection and SC dose was administered via subcutaneous injection. At the designated time-points, the animals were restrained manually, and approximately 240 μL blood/time point was collected via tail vein puncture or cardiac puncture into tubes. The blood samples were placed at room temperature for 0.5 hr. Then blood samples were centrifuged (10000 g, 5 min under 4° C.) to obtain the serum samples. The serum samples were immediately stored at −80° C. until analysis. Samples were analyzed together with dosing solution via ELISA. The measured dosing concentration was used for the PK parameter calculation.

Figure 12:
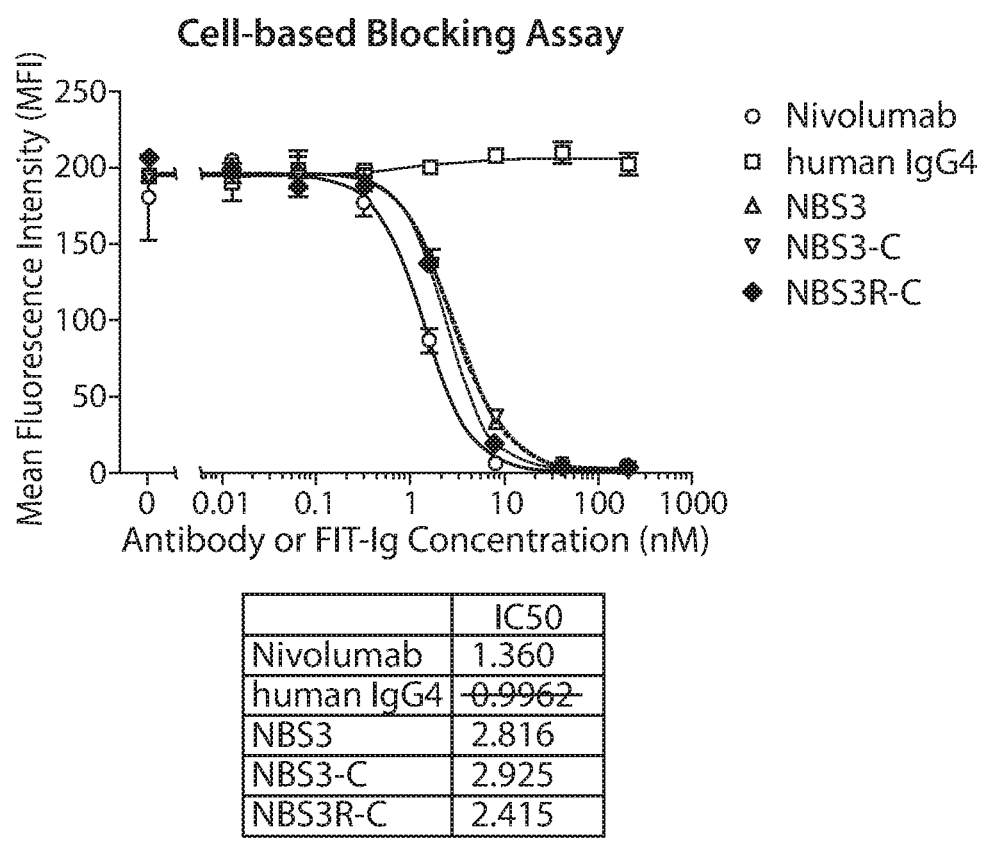
FIG. 12 shows cell-based receptor blocking assay of NBS3, NBS3-C, NBS3R-C compared to the parental antibody Nivolumab. Human IgG4 was included as a control.

NBS3, NBS3-C, and NBS3R-C were tested in cell-based receptor blocking assay. Briefly, PD1-Fc was immobilized on 96-well plates, followed by routine wash and blocking procedures. Then diluted FIT-Ig and biotinylated PD-L1-Fc was added to each well, followed by incubation and multiple wash steps, and detected with Streptavidin-HRP. The result is shown in FIG. 12.

NBS3, NBS3-C, and NBS3R-C were further tested in MLR (Mixed Lymphocyte Reaction) assays and PBMC SEB-stimulation assay for their functional activity.

Figure 13A:
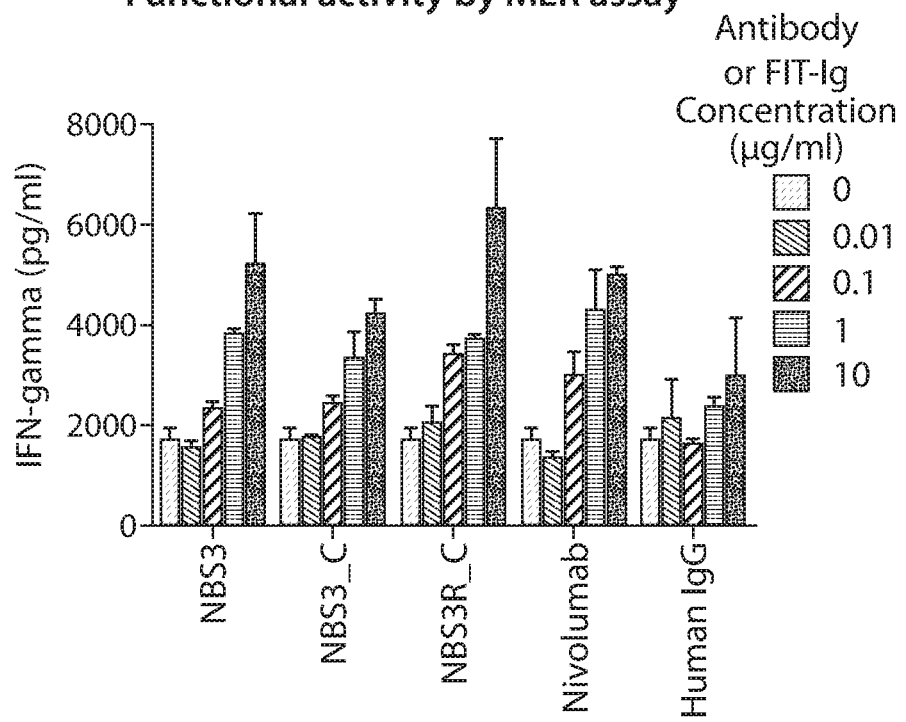
FIG. 13A shows functional activity of NBS3, NBS3-C, and NBS3R-C in MLR assays, when compared to the parental antibody Nivolumab at a concentration of 0, 0.01, 0.1, 1, or 10 μg/ml. The induction of IFN-γ was measured for each antibody. Human IgG was included as a control.
Figure 13B:
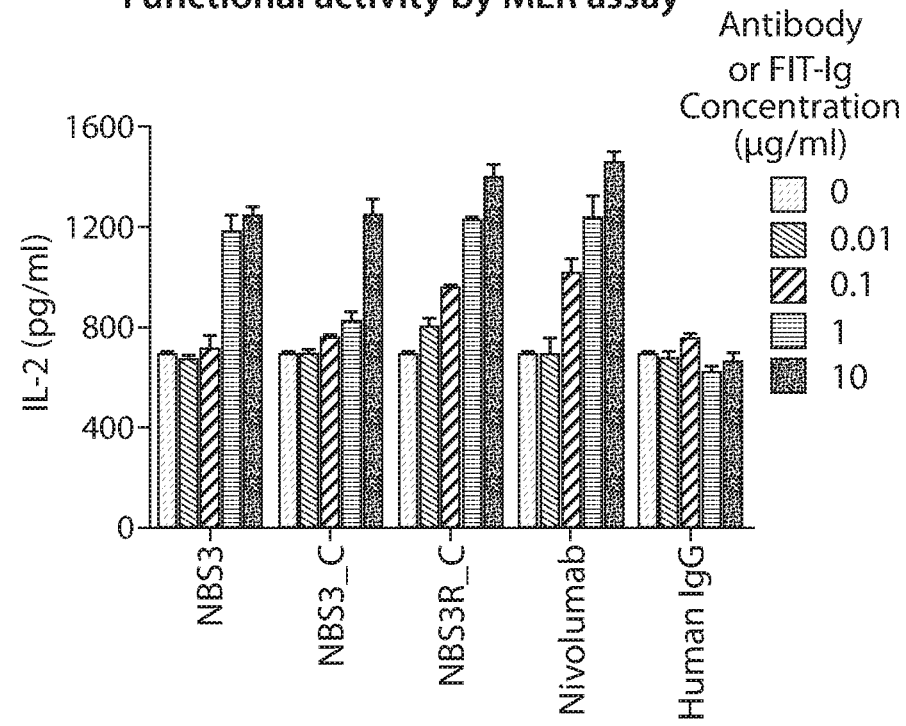
FIG. 13B shows the induction of IL-2 by these antibodies.

In the MLR assays, mixed lymphocyte reaction was performed using monocyte-derived dendritic cells from one donor and allogeneic CD4 T cells from another donor. The whole blood samples were collected from healthy donors, and PBMC were isolated from whole blood using Ficoll-Pague gradient centrifugation. On day 1, PBMC from one donor was isolated and diluted with serum-free RPMI 1640 at 1×10⁶/ml. The diluted PBMC was seeded into 6-well tissue culture plate at 3 ml/well and incubated for 3 h. Supernatant was removed and unattached cells were washed off. The attached monocyte were polarized into dendritic cells with 250 U/ml IL-4 and 500 U/ml GM-CSF in RPMI1640 with 10% FBS. The medium was replaced with fresh IL-4 and GM-CSF at day 4. At day 7, immature DC was collected and treated with 1 μg/ml LPS in RPMI 1640 with 10% FBS for additional 24 h for maturation. At Day 8, CD4 T cells were isolated from another donor PBMC by negative selection and adjusted to final concentration at 2×10⁶ cells/ml. Mature DC were treated with mitomycin C at 37° C. for 1.5 hr. Then DC were washed with PBS and adjusted to final concentration at 1×10⁶ cells/ml. CD4 T cells (Responder cells) were added into 96 well plate at 100 l/well and pre-treated with test antibody at diluted concentration for 30 minutes. Then mature DC (Stimulator cells) were added into the well at 100 l/well. The final volume of each well is 200p1. The MLR were incubated at 37 degree for 72 hr for IL-2 test and 120 hr for IFN-gamma test respectively using ELISA. The result is shown in FIG. 13A and FIG. 13B.

Figure 14:
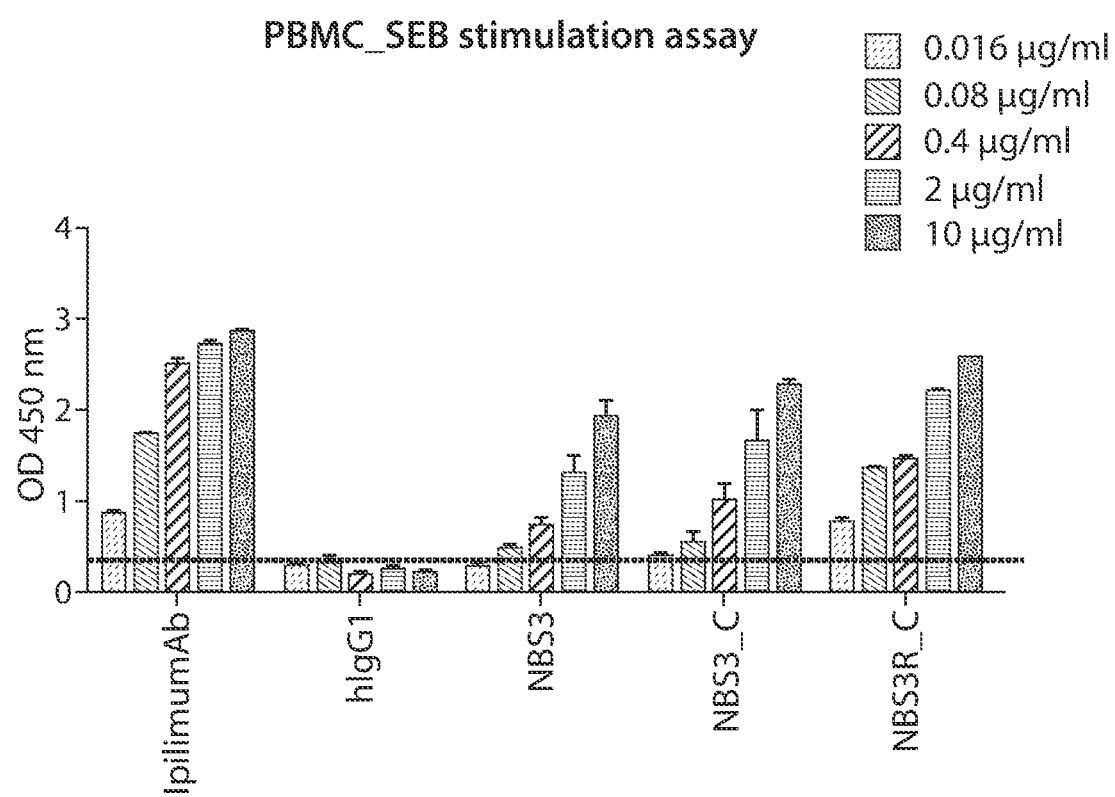
FIG. 14 shows functional activity of NBS3, NBS3-C, and NBS3R-C in PBMC SEB-stimulation assays when compared to the parental antibody lpilimumab, at a concentration of 0.016. 0.08, 0.4, 2, or 10 μg/ml. The IL-2 cytokine production in the supernatant was detected by ELISA.

In the PBMC SEB-stimulation assays, PBMC were isolated from healthy donor blood by Ficoll-Pague gradient centrifugation. The isolated PBMC were seeded into 96-well tissue culture plate at 1×10⁵ cells/well. Then the PBMC were pre-treated with diluted test antibodies for 30 min. *Staphylococcus* enterotoxin B (SEB) was added into cell culture medium with final concentration at 100 ng/ml. The final assay volume was 200l1/well. The cells were cultured for 96 hr and the culture supernatant was collected. IL-2 cytokine production in the supernatant was detected by ELISA. The result is shown in FIG. 14.

Example 7: Construction, Expression, and Purification of Additional Anti-EGFR/PD-L1 Fabs-in-Tandem Immunoglobulin (FIT-Ig)

New FIT-Igs having specificity for EGFR and PD-L1 were constructed as in the foregoing Examples. These exemplary FIT-Igs and their corresponding sequences are provided below in Table 26. Table 27 provides the expression level in 293E cells and the SEC profile for each of the FIT-Ig.

TABLE 26

Amino acid sequences of additional exemplary FIT-Ig for EGFR and PD-L1

| Name Target (mAb) mAb1 (upper domain)/mAb2 (lower domain) | Protein region | SEQ ID NO | Sequences |
|---|---|---|---|
| FIT012b - Ig EGFR (panitumumab)/ PD-L1 (1B12) | Long Chain (Pani VL-hCk-1B12VH-hCg1) | 202 | MDMRVPAQLLGLLLLWFPGSRCDIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECQVQLVQSGAEVKKPGSSVKVSCKTSGDTFSSYAISWVRQAPGQGLEWMGGIIPIFGRAHYAQKFQGRVTITADESTSTAYMELSSLRSEDTAVYFCARKFHFVSGSPFGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | Pani VL | 203 | DIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIK |
| | Pani VL - CDR1 | 204 | QASQDISNYL |
| | Pani VL - CDR2 | 205 | DASNLET |
| | Pani VL - CDR3 | 206 | QHFDHLPLA |
| | 1B12VH | 207 | QVQLVQSGAEVKKPGSSVKVSCKTSGDTFSSYAISWVRQAPGQGLEWMGGIIPIFGRAHYAQKFQGRVTITADESTSTAYMELSSLRSEDTAVYFCARKFHFVSGSPFGMDVWGQGTTVTVSS |
| | 1B12VH - CDR1 | 208 | SYAIS |
| | 1B12VH - CDR2 | 209 | GIIPIFGRAHYAQKFQG |
| | 1B12VH - CDR3 | 210 | KFHFVSGSPFGMDV |
| | Short Chain #1 (Pani VH-CH1h) | 211 | MEFGLSWLFLVAILKGVQCQVQLQESGPGLVKPSETLSLTCTVSGGSVSSGDYYWTWIRQSPGKGLEWIGHIYYSGNTNYNPSLKSRLTISIDTSKTQFSLKLSSVTAADTAIYYCVRDRVTGAFDIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | Pani VH | 212 | QVQLQESGPGLVKPSETLSLTCTVSGGSVSSGDYYWTWIRQSPGKGLEWIGHIYYSGNTNYNPSLKSRLTISIDTSKTQFSLKLSSVTAADTAIYYCVRDRVTGAFDIWGQGTMVTVSS |
| | Pani VH - CDR1 | 213 | SGDYYWT |
| | Pani VH - CDR2 | 214 | HIYYSGNTNYNPSLKS |
| | Pani VH - CDR3 | 215 | DRVTGAFDI |
| | Short Chain #2 (1B12 VL-hCk) | 216 | MDMRVPAQLLGLLLLWFPGSRCEIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | 1B12 VL | 217 | EIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIK |

TABLE 26-continued

Amino acid sequences of additional exemplary FIT-Ig for EGFR and PD-L1

| Name Target (mAb) mAb1 (upper domain)/mAb2 (lower domain) | Protein region | SEQ ID NO | Sequences |
|---|---|---|---|
| | 1B12 VL - CDR1 | 218 | RASQSVSSYLA |
| | 1B12 VL - CDR2 | 219 | DASNRAT |
| | 1B12 VL - CDR3 | 220 | QQRSNWPT |
| | Long Chain (Pani VL-hCk-10A5VH-hCg1) | 221 | MDMRVPAQLLGLLLLWFPGSRCDIQMTQSPSSLSASVGDR VTITCQASQDISNYLNWYQQKPGKAPKLLIYDASNLETGV PSRFSGSGSGTDFTFTISSLQPEDIATYFCQHFDHLPLAF GGGTKVEIKRTVAAPSVFIFPPSDEQLKSGTASVVCLLNN FYPREAKVQWKVDNALQSGNSQESVTEQDSKDSTYSLSST LTLSKADYEKHKVYACEVTHQGLSSPVTKSFNRGECQVQL VQSGAEVKKPGASVKVSCKASGYTFTSYDVHWVRQAPGQR LEWMGWLHADTGITKFSQKFQGRVTITRDTSASTAYMELS SLRSEDTAVYYCARERIQLWFDYWGQGTLVTVSSASTKGP SVFPLAPSSKSTSGGTAALGCLVKDYFPEPVTVSWNSGAL TSGVHTFPAVLQSSGLYSLSSVVTVPSSSLGTQTYICNVN HKPSNTKVDKKVEPKSCDKTHTCPPCPAPELLGGPSVFLF PPKPKDTLMISRTPEVTCVVVDVSHEDPEVKFNWYVDGVE VHNAKTKPREEQYNSTYRVVSVLTVLHQDWLNGKEYKCKV SNKALPAPIEKTISKAKGQPREPQVYTLPPSREEMTKNQV SLTCLVKGFYPSDIAVEWESNGQPENNYKTTPPVLDSDGS FFLYSKLTVDKSRWQQGNVFSCSVMHEALHNHYTQKSLSL SPGK |
| | Pani VL | 222 | DIQMTQSPSSLSASVGDRVTITCQASQDISNYLNWYQQKP GKAPKLLIYDASNLETGVPSRFSGSGSGTDFTFTISSLQP EDIATYFCQHFDHLPLAFGGGTKVEIK |
| | Pani VL - CDR1 | 223 | QASQDISNYLN |
| | Pani VL - CDR2 | 224 | DASNLET |
| | Pani VL - CDR3 | 225 | QHFDHLPLA |
| | 10A5VH | 226 | QVQLVQSGAEVKKPGASVKVSCKASGYTFTSYDVHWVRQA PGQRLEWMGWLHADTGITKFSQKFQGRVTITRDTSASTAY MELSSLRSEDTAVYYCARERIQLWFDYWGQGTLVTVSS |
| | 10A5VH - CDR1 | 227 | SYDVH |
| | 10A5VH - CDR2 | 228 | WLHADTGITKFSQKFQG |
| | 10A5VH - CDR3 | 229 | ERIQLWFDY |
| | Short Chain #1 (Pani VH-CH1h) | 230 | MEFGLSWLFLVAILKGVQCQVQLQESGPGLVKPSETLSLT CTVSGGSVSSGDYYWTWIRQSPGKGLEWIGHIYYSGNTNY NPSLKSRLTISIDTSKTQFSLKLSSVTAADTAIYYCVRDR VTGAFDIWGQGTMVTVSSASTKGPSVFPLAPSSKSTSGGT AALGCLVKDYFPEPVTVSWNSGALTSGVHTFPAVLQSSGL YSLSSVVTVPSSSLGTQTYICNVNHKPSNTKVDKKVEPKS C |
| | Pani VH | 231 | QVQLQESGPGLVKPSETLSLTCTVSGGSVSSGDYYWTWIR QSPGKGLEWIGHIYYSGNTNYNPSLKSRLTISIDTSKTQF SLKLSSVTAADTAIYYCVRDRVTGAFDIWGQGTMVTVSS |
| | Pani VH - CDR1 | 232 | SGDYYWT |
| | Pani VH - CDR2 | 233 | HIYYSGNTNYNPSLKS |
| | Pani VH - CDR3 | 234 | DRVTGAFDI |
| | Short Chain #2 (10A5 VL-hCk) | 235 | MDMRVPAQLLGLLLLWFPGSRCDIQMTQSPSSLSASVGDR VTITCRASQGISSWLAWYQQKPEKAPKSLIYAASSLQSGV PSRFSGSGSGTDFTLTISSLQPEDFATYYCQQYNSYPYTF GQGTKLEIKRTVAAPSVFIFPPSDEQLKSGTASVVCLLNN FYPREAKVQWKVDNALQSGNSQESVTEQDSKDSTYSLSST LTLSKADYEKHKVYACEVTHQGLSSPVTKSFNRGEC |
| | 10A5 VL | 236 | DIQMTQSPSSLSASVGDRVTITCRASQGISSWLAWYQQKP EKAPKSLIYAASSLQSGVPSRFSGSGSGTDFTLTISSLQP EDFATYYCQQYNSYPYTFGQGTKLEIK |
| | 10A5 VL - CDR1 | 237 | RASQGISSWLA |
| | 10A5 VL - CDR2 | 238 | AASSLQS |
| | 10A5 VL - CDR3 | 239 | QQYNSYPYT |

TABLE 27

| | SEC Profile/Expression level in 293E cells: | |
|---|---|---|
| FIT-Ig | Monomer % in SEC | Expression level(mg/L) |
| FIT012b - Ig | 74.72% | 5.3 |
| FIT012d - Ig | >87% | 1.05 |

The SEC profile and expression data suggest that FIT012d exhibited better purity than FIT012b by changing PD-L1 antibody sequences.

Functional binding data for these two antibodies is provided below in Table 28 and Table 29. The data suggests that the affinity was not affected by changing IgG constant sequences, but can be improved by place certain Fab in upper domain.

TABLE 28

| | Functional binding data of FIT012b | | | |
|---|---|---|---|---|
| Ig | Target | Kon | Koff | KD IC50 |
| Panitumumab | 1(EGFR) | 2.42E+05 | 4.48E-04 | 1.85E-09 |
| FIT012b | | 3.08E+05 | 7.83E-04 | 2.54E-09 |
| 1B12 | 2(PD-L1) | 2.35E+05 | 2.14E-03 | 9.08E-09 |
| FIT012b | | 6.97E+05 | 2.71E-03 | 3.89E-09 |

TABLE 29

| | Functional binding data of FIT012d | | | | |
|---|---|---|---|---|---|
| Ig | Target | Kon | Koff | KD | IC50 |
| Panitumumab | 1(EGFR) | 1.05E+05 | 4.91E-05 | 4.66E-10 | |
| FIT012d | | 1.03E+05 | 4.92E-05 | 4.76E-10 | |
| 10A5 | 2(PD-L1) | 8.91E+05 | 6.54E-04 | 7.35E-10 | |
| FIT012d | | 1.03E+06 | 6.00E-04 | 5.80E-10 | |

Figure 15:
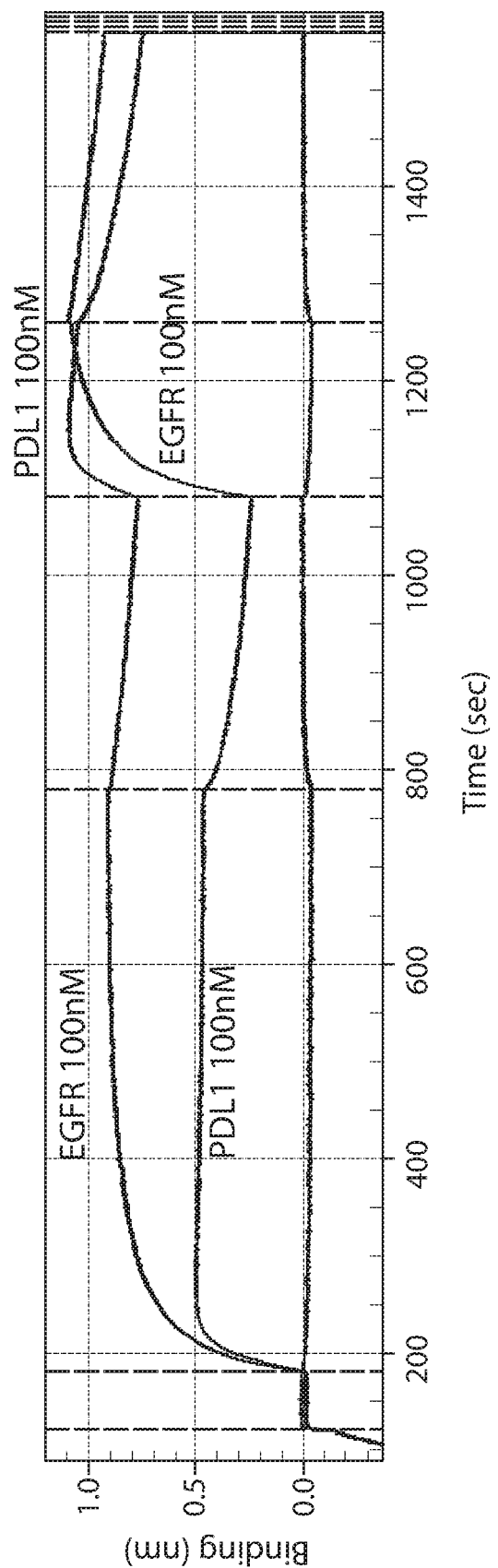
FIG. 15 shows a multiple binding study of FIT012b against both EGFR and PD-L1. Binding to human EGFR followed by human PD-L1; and binding by human PD-L1 followed by human EGFR are both shown as indicated.
Figure 16A:
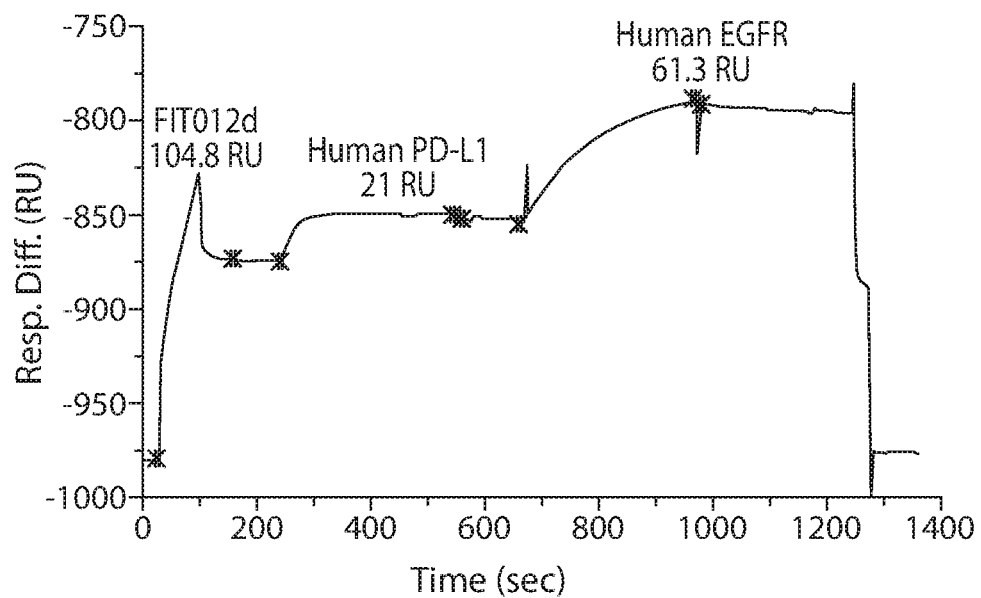
FIG. 16A and FIG. 16B show a multiple binding study of FIT012d against both human EGFR and human PD-L1. Binding to human EGFR followed by human PD-L1 (FIG. 16A); and binding by human PD-L1 followed by human EGFR (FIG. 16B) are both shown as indicated.
Figure 16B:
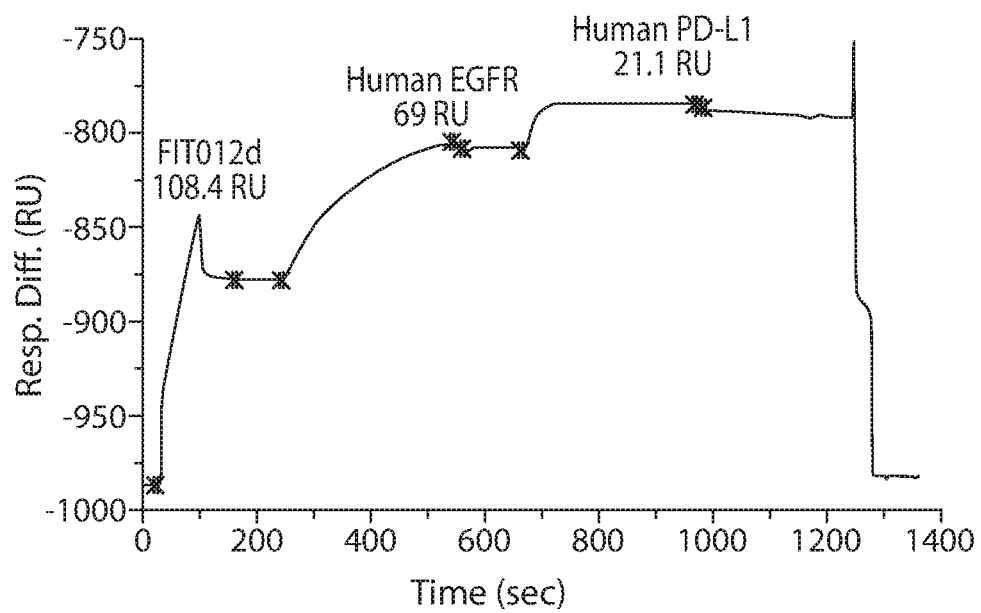

A multiple binding study of FIT012b and FIT012d was also carried out. The result is shown in FIG. 15 (FIT012b) and FIG. 16A to FIG. 16B (FIT012d).

Example 8: Construction, Expression, and Purification of Anti-cMet/EGFR Fabs-in-Tandem Immunoglobulin (FIT-Ig)

New FIT-Ig having specificity for cMet and EGFR was constructed as in the foregoing Examples. This exemplary FIT-Ig and its corresponding sequences are provided below in Table 30. Table 31 provides the expression level in 293E cells and the SEC profile for each of the FIT-Ig.

TABLE 30

Amino acid sequences of additional exemplary FIT-Ig for cMet and EGFR

| Name Target (mAb) mAb1 (upper domain)/mAb2 (lower domain) | Protein region | SEQ ID NO | Sequences |
|---|---|---|---|
| FIT013a cMet (h1332 (13.3.2L-A91T,H-42K,S97T)) | Long Chain (h1332 VL-hCk-Pani VH-hCg1) | 240 | MDMRVPAQLLGLLLLWFPGSRCDIQMTQSPSSVSASVGDR VTITCRASQGINTWLAWYQQKPGKAPKLLIYAASSLKSGV PSRFSGSGSGTDFTLTISSLQPEDFATYYCQQANSFPLTF GGGTKVEIKRTVAAPSVFIFPPSDEQLKSGTASVVCLLNN FYPREAKVQWKVDNALQSGNSQESVTEQDSKDSTYSLSST LTLSKADYEKHKVYACEVTHQGLSSPVTKSFNRGECQVQL QESGPGLVKPSETLSLTCTVSGGVSSGDYYWTWIRQSPG KGLEWIGHIYYSGNTNYNPSLKSRLTISIDTSKTQFSLKL SSVTAADTAIYYCVRDRVTGAFDIWGQGTMVTVSSASTKG PSVFPLAPSSKSTSGGTAALGCLVKDYFPEPVTVSWNSGA LTSGVHTFPAVLQSSGLYSLSSVVTVPSSSLGTQTYICNV NHKPSNTKVDKKVEPKSCDKTHTCPPCPAPELLGGPSVFL FPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVYTLPPSREEMTKNQ VSLTCLVKGFYPSDIAVEWESNGQPENNYKTTPPVLDSDG SFFLYSKLTVDKSRWQQGNVFSCSVMHEALHNHYTQKSLS LSPGK |
| | h1332 VL | 241 | DIQMTQSPSSVSASVGDRVTITCRASQGINTWLAWYQQKP GKAPKLLIYAASSLKSGVPSRFSGSGSGTDFTLTISSLQP EDFATYYCQQANSFPLTFGGGTKVEIK |
| | h1332 VL - CDR1 | 242 | RASQGINTWLA |
| | h1332 VL - CDR2 | 243 | AASSLKS |
| | h1332 VL - CDR3 | 244 | QQANSFPLT |
| | Pani VH | 245 | QVQLQESGPGLVKPSETLSLTCTVSGGVSSGDYYWTWIR QSPGKGLEWIGHIYYSGNTNYNPSLKSRLTISIDTSKTQF SLKLSSVTAADTAIYYCVRDRVTGAFDIWGQGTMVTVSS |
| | Pani VH - CDR1 | 246 | SGDYYWT |
| | Pani VH - CDR2 | 247 | HIYYSGNTNYNPSLKS |
| | Pani VH - CDR3 | 248 | DRVTGAFDI |
| | Short Chain #1 (h1332 VH-CH1) | 249 | MEFGLSWLFLVAILKGVQCQVQLVQSGAEVKKPGASVKVS CKASGYTFTSYGFSWVRQAPGQGLEWMGWISASNGNTYYA QKLQGRVTMTTDTSTSTAYMELRSLRSDDTAVYYCARVYA DYADYWGQGTLVTVSSASTKGPSVFPLAPSSKSTSGGTAA LGCLVKDYFPEPVTVSWNSGALTSGVHTFPAVLQSSGLYS LSSVVTVPSSSLGTQTYICNVNHKPSNTKVDKKVEPKSC |

TABLE 30-continued

Amino acid sequences of additional exemplary FIT-Ig for cMet and EGFR

| Name Target (mAb) mAb1 (upper domain)/mAb2 (lower domain) | Protein region | SEQ ID NO | Sequences |
|---|---|---|---|
| | h1332 VH | 250 | QVQLVQSGAEVKKPGASVKVSCKASGYTFT<u>SYGFS</u>WVRQA PGQGLEWMG<u>WISASNGNTYYAQKLQG</u>RVTMTTDTSTSTAY MELRSLRSDDTAVYYCAR<u>VYADYADY</u>WGQGTLVTVSS |
| | h1332 VH - CDR1 | 251 | <u>SYGFS</u> |
| | h1332 VH - CDR2 | 252 | <u>WISASNGNTYYAQKLQG</u> |
| | h1332 VH - CDR3 | 253 | <u>VYADYADY</u> |
| | Short Chain #2 (Pani VL-hCk) | 254 | MDMRVPAQLLGLLLLWFPGSRCDIQMTQSPSSLSASVGDR VTITC<u>QASQDISNYLN</u>WYQQKPGKAPKLLIY<u>DASNLET</u>GV PSRFSGSGSGTDFTFTISSLQPEDIATYFC<u>QHFDHLPLA</u>F GGGTKVEIKRTVAAPSVFIFPPSDEQLKSGTASVVCLLNN FYPREAKVQWKVDNALQSGNSQESVTEQDSKDSTYSLSST LTLSKADYEKHKVYACEVTHQGLSSPVTKSFNRGEC |
| | Pani VL | 255 | DIQMTQSPSSLSASVGDRVTITC<u>QASQDISNYLN</u>WYQQKP GKAPKLLIY<u>DASNLET</u>GVPSRFSGSGSGTDFTFTISSLQP EDIATYFC<u>QHFDHLPLA</u>FGGGTKVEIK |
| | Pani VL - CDR1 | 256 | <u>QASQDISNYLN</u> |
| | Pani VL - CDR2 | 257 | <u>DASNLET</u> |
| | Pani VL - CDR3 | 258 | <u>QHFDHLPLA</u> |

TABLE 31

SEC Profile/Expression level in 293E cells:

| FIT-Ig | Monomer % in SEC | Expression level(mg/L) |
|---|---|---|
| FIT013a | 98.48% | 22 |

Stability Data

The storage stability of FIT013a was assessed by SEC-HPLC method, and result is shown in Table 32. Samples were treated by freeze/thaw cycle for one time, two times or three times, no aggregation or degradation was observed by SEC-HPLC profile. Samples was treated at 4° C., 25° C. or 40° C. for 1 day, 3 days or 7 days, no aggregation or degradation was observed by SEC-HPLC profile.

TABLE 32

Storage stability of FIT013a

| Sample Name | Rel. Area % agg | Rel. Area % mono | Rel. Area % clip |
|---|---|---|---|
| FIT013a_D0 | 2.95 | 97.05 | n.a. |
| FIT013a_F/T1 | 3.26 | 96.74 | n.a. |
| FIT013a_F/T2 | 3.38 | 96.62 | n.a. |
| FIT013a_F/T3 | 3.47 | 96.53 | n.a. |
| FIT013a_4C-D1 | 3.56 | 96.44 | n.a. |
| FIT013a_25C-D1 | 3.66 | 96.34 | n.a. |
| FIT013a_40C-D1 | 3.72 | 96.22 | 0.06 |
| FIT013a_4C-D3 | 3.63 | 96.37 | n.a. |
| FIT013a_25C-D3 | 3.65 | 96.35 | n.a. |
| FIT013a_40C-D3 | 3.76 | 96.16 | 0.08 |
| FIT013a_4C-D7 | 3.64 | 96.36 | n.a. |
| FIT013a_25C-D7 | 3.72 | 96.28 | n.a. |
| FIT013a_40C-D7 | 3.95 | 95.92 | 0.12 |

Functional Study:

Protein based binding data for FIT013a is provided below in Table 33 and Table 34.

TABLE 33

Functional binding data of FIT013a (human cMet/human EGFR)

| Ig | Target | Kon | Koff | KD | IC50 |
|---|---|---|---|---|---|
| H1332 | 1 (human cMet) | 4.14E+05 | 5.27E−04 | 1.27E−09 | |
| FIT013a | | 4.75E+05 | 5.02E−04 | 1.06E−09 | |
| Panitumumab | 2 (human EGFR) | 8.43E+04 | 5.10E−05 | 6.05E−10 | |
| FIT013a | | 1.09E+05 | 5.84E−05 | 5.34E−10 | |

TABLE 34

Functional binding data of FIT013a (Cyno cMEt/Cyno EGFR)

| Ig | Target | Kon | Koff | KD | IC50 |
|---|---|---|---|---|---|
| H1332 | 1 (Cyno cMet) | 2.21E+05 | 1.00E−03 | 4.53E−09 | |
| FIT013a | | 2.86E+05 | 9.74E−04 | 3.40E−09 | |
| Panitumumab | 2 (Cyno EGFR) | 5.87E+05 | 2.12E−04 | 3.62E−10 | |
| FIT013a | | 2.66E+05 | 1.54E−04 | 5.77E−10 | |

Figure 17:
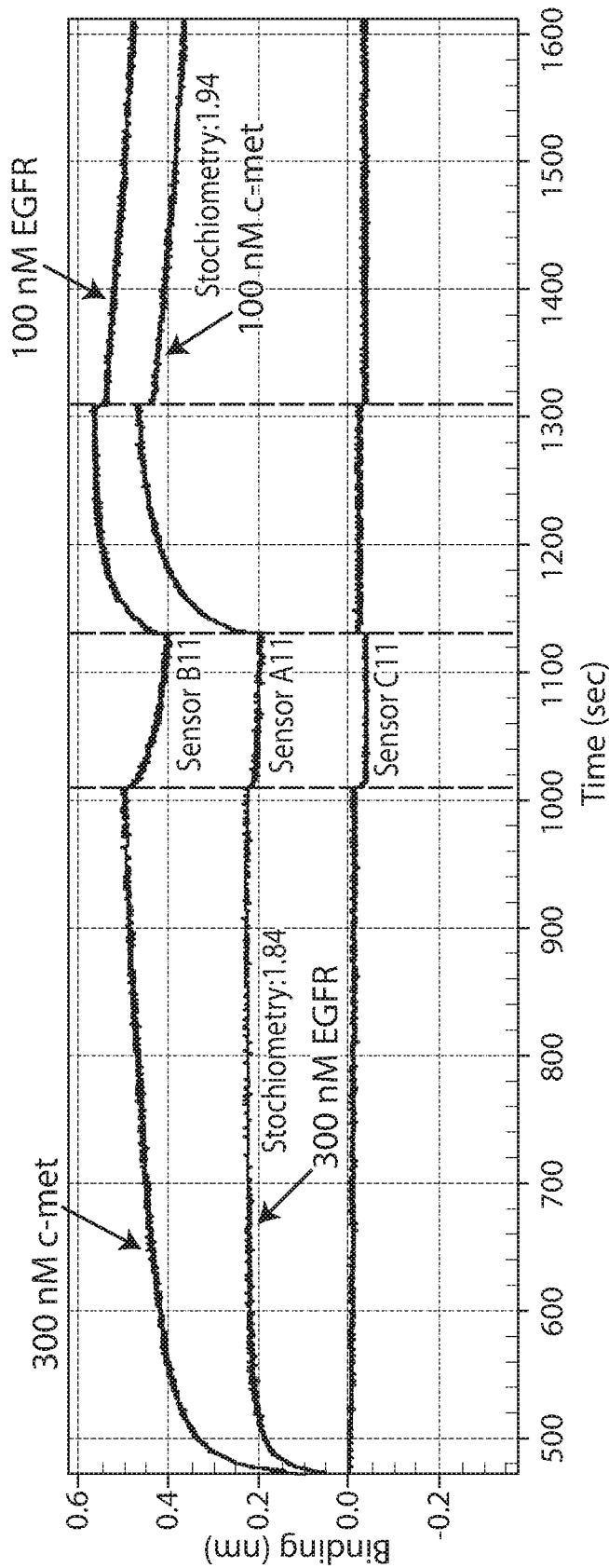
FIG. 17 shows a multiple binding study of FIT013a against both cMet and EGFR. Binding to cMet followed by EGFR; and binding by EGFR followed by cMet are both shown as indicated.

A multiple binding study of FIT013a was also carried out. The result is shown in FIG. 17.

Further, the binding activity of FIT013a in cancer cell lines was determined by flow cytometry using BD FACSVerse. Cells grown in culture were detached from flask with trypsin-free medium and collected. The collected cells were washed in PBS buffer containing 2% FBS. Cells were then aliquot and incubated with 1:5 serially diluted FIT013a on ice for 1 hr. The starting working concentration of FTI013a was 20 µg/ml. Cells were washed, resuspended and incubated with 1:100 diluted Alexa Fluor® 488 labeled mouse anti-human IgG1 (Invitrogen, Cat. No. A-10631) on ice protected from light for 1 hr. Cells were washed and signal was detected with a BD FACSVerse flow cytometer according to manufacture's protocols.

These experiments demonstrate that FIT013a can bind to many cancer cell lines, like NCI-H1993, HCC827, MKN-45, SGC-7901, EBC-1, A549, KP4, NCI-H292, NCI-H1975, etc. Geometric mean fluorescence intensity (MFI) and EC50 for each cell lines are listed in the Table 35.

TABLE 35

Cell based binding data for FIT013a

| Cell lines | MFI | EC50 (nM) |
|---|---|---|
| NCI-H1993 | 447 | 37.14 |
| HCC827 | 2000 | 41.33 |
| MKN-45 | 2050 | 8.89 |
| SGC-7901 | 590 | 2.53 |
| EBC-1 | 6000 | 1.5 |
| A549 | 1000 | 0.62 |
| KP4 | 345 | 0.31 |
| NCI-H292 | 920 | 0.58 |
| HCI-H1975 | 507 | — |

In addition, FACS assays were conducted to measure FIT013a's dual binding to membrane c-Met and EGFR to show its multiple binding activity.

Several cell lines were used n this assay. MKN-45 (human gastric adenocarcinoma cells) expressed high level of c-Met and low level of EGFR. SGC-7901 (human gastric cancer) expressed high level of EGFR and low level of c-Met. NCI-H1975 (human non-small cell lung cancer) expressed equal level of c-Met and EGFR.

Cells grown in culture were detached from flask with trypsin-free medium and collected. The collected cells were washed in PBS buffer containing 2% FBS. Cells were aliquot and incubated with serially diluted FIT013a or FIT013a-Fab on ice for 1 hr. Cells were then washed and incubated with lpg/ml biotinylated human c-MET or biotinylated EGFR on ice for 1 hr. Cells were resuspended and incubated with 4 μg/ml Alexa Fluor® 488 labeled Streptavidin (Invitrogen, Cat. No S32354) on ice protected from light for 1 hr. Cells were washed and signal was detected with a BD FACSVerse flow cytometer according to manufacture's protocols.

Figure 18A:
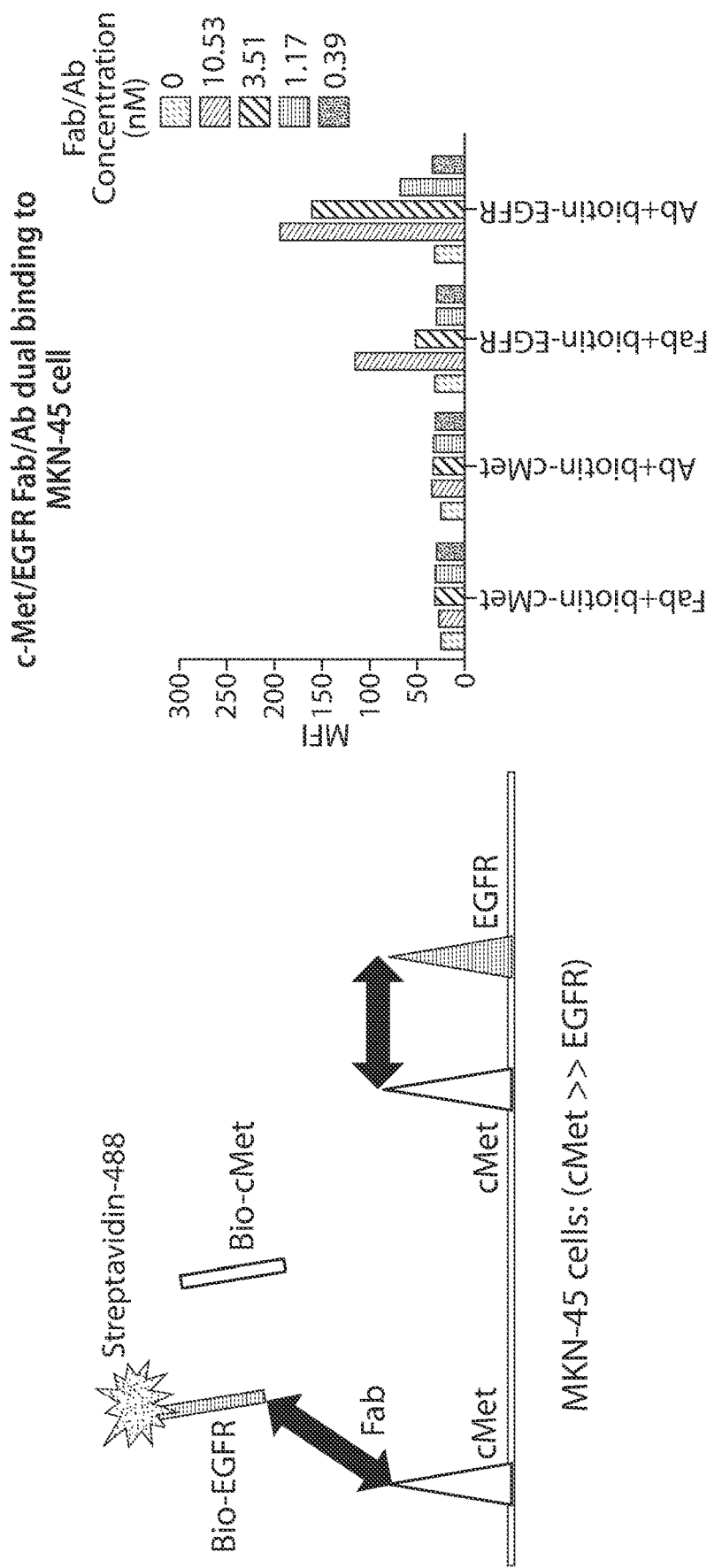
FIG. 18A to FIG. 18C show FACS assays in which FIT013a's binding activity to membrane c-Met and EGFR was tested.
Figure 18B:
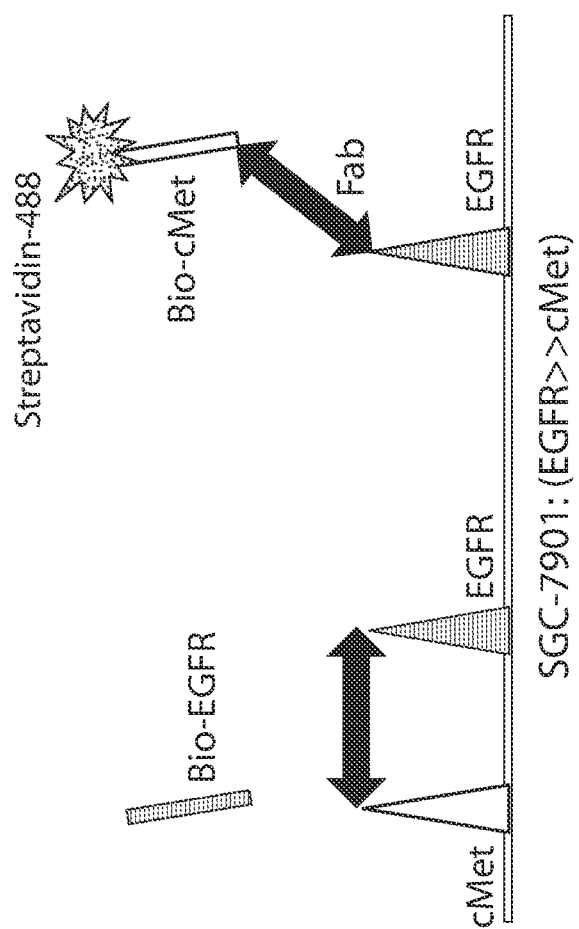
Figure 18B:
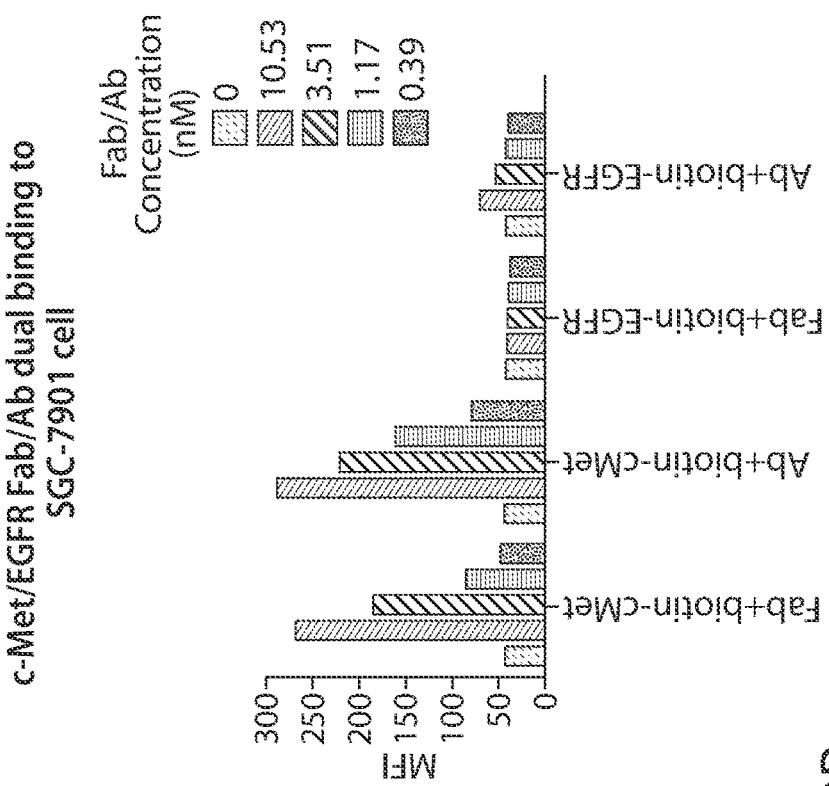
Figure 18C:
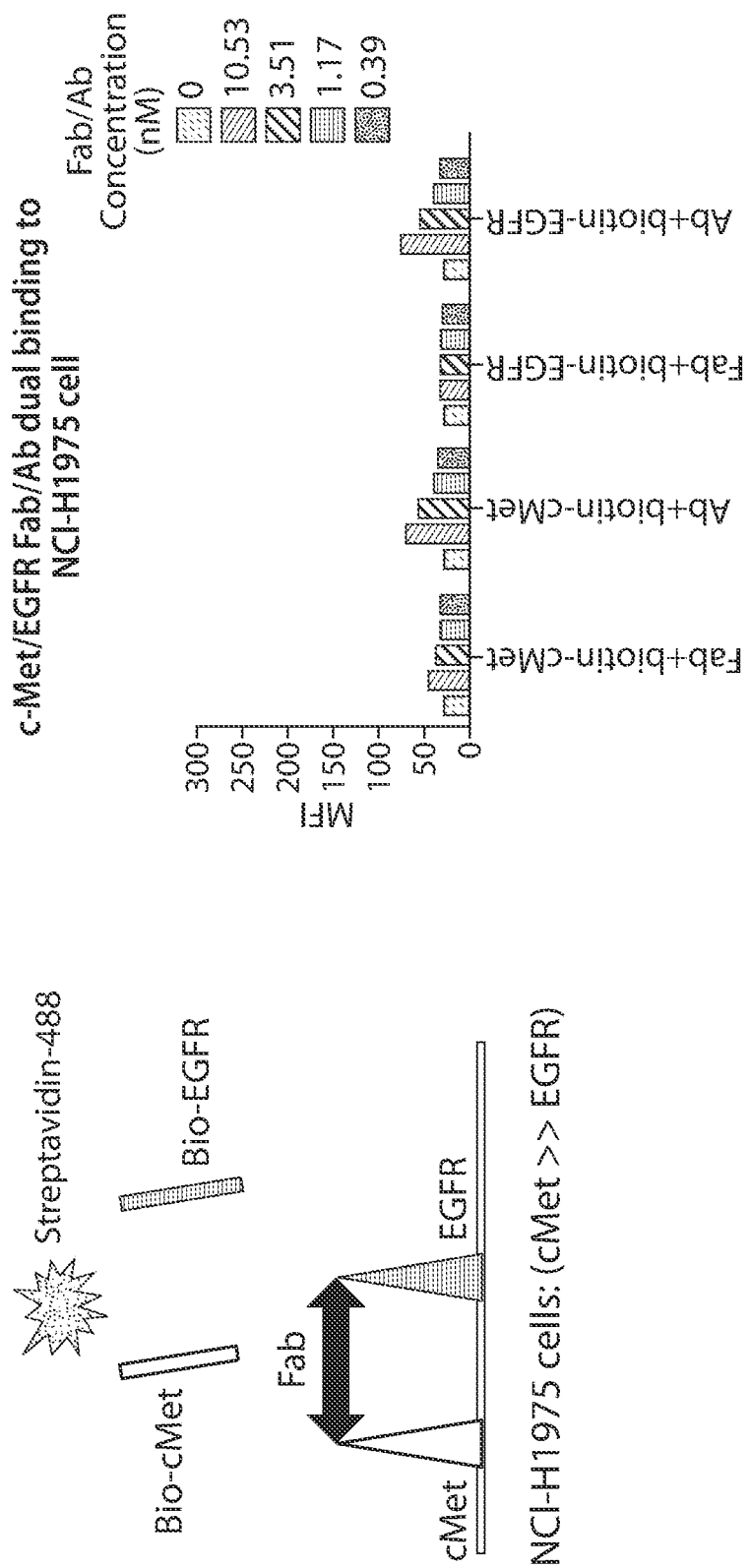

When cell membrane expression level c-Met is much higher than EGFR (e.g., on MKN-45 cell), c-Met binding cite of FIT013a and FIT013a-Fab can be occupied by membrane c-Met, the free EGFR binding cite of FIT013a and FIT013a-Fab can be detected by biotinylated EGFR. When cell membrane expression level EGFR is much higher than c-Met (e.g., on SGC-7901), EGFR binding cite of FIT013a and FIT013a-Fab can be occupied by membrane EGFR, the free c-Met binding cite of FIT013a and FIT013a-Fab can be detected by biotinylated c-Met. When cell membrane expression level c-Met is equal to EGFR (e.g., on NCI-H1975 cell), c-Met and EGFR binding cites of FIT013a and FIT013a-Fab are occupied simultaneously, no free EGFR or c-Met binding cite of FIT013a and FIT013a-Fab can be detected. As demonstrated in FIG. 18A to FIG. 18C, FIT013a and FIT013a-Fab can simultaneously bind to two receptors c-Met and EGFR on the cell surface.

Figure 19:
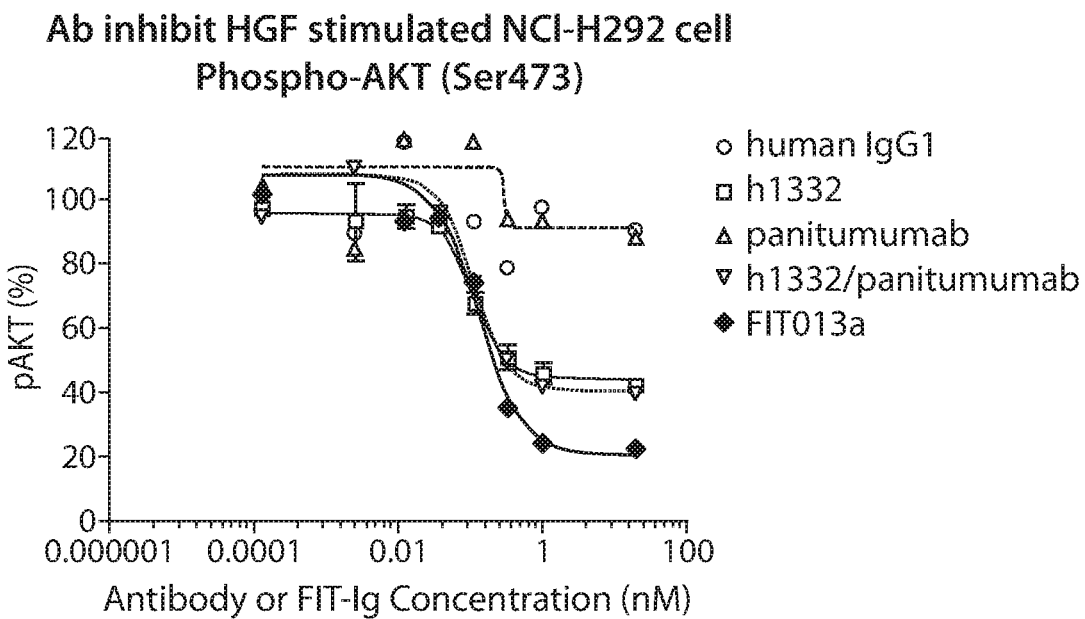
FIG. 19 shows FIT013a's ability of inhibiting HGF induced AKT phosphorylation in NCI-H292 cells. FIT013a, h1332, panitumumab, a combination of h1332/panitumumab, and human IgG1 were added to cells and incubated for 30 mins and then 40 ng/ml HGF was added to the assay plate for 5 mins. The cells were lysed and AKT phosphorylation was detected by ERK phospho-T202/Y204 kit.

Signaling Assay:

Next, FIT013a was used to inhibit HGF induced AKT phosphorylation in cells. NCI-H292 cells were plated at $2\times10^5$ per well in 96-well plate and serum starved overnight. Serially diluted FIT013a or other related Abs were added to plate and incubate for 30 mins and then 40 ng/ml HGF was added to the assay plate for 5 mins. The cells were lysed and AKT phosphorylation was detected by ERK phospho-T202/Y204 kit (Cisbio, Cat: 64AKSPEG). The experiment demonstrates that FIT013a shows superior activity than mAbs combo in neutralizing HGF induced AKT phosphorylation in NCI-H292 cell. FIT013a inhibited 80% of AKT phosphorylation while EGFR and c-Met antibody combo inhibit 60% of AKT phosphorylation, see FIG. 19.

Figure 20:
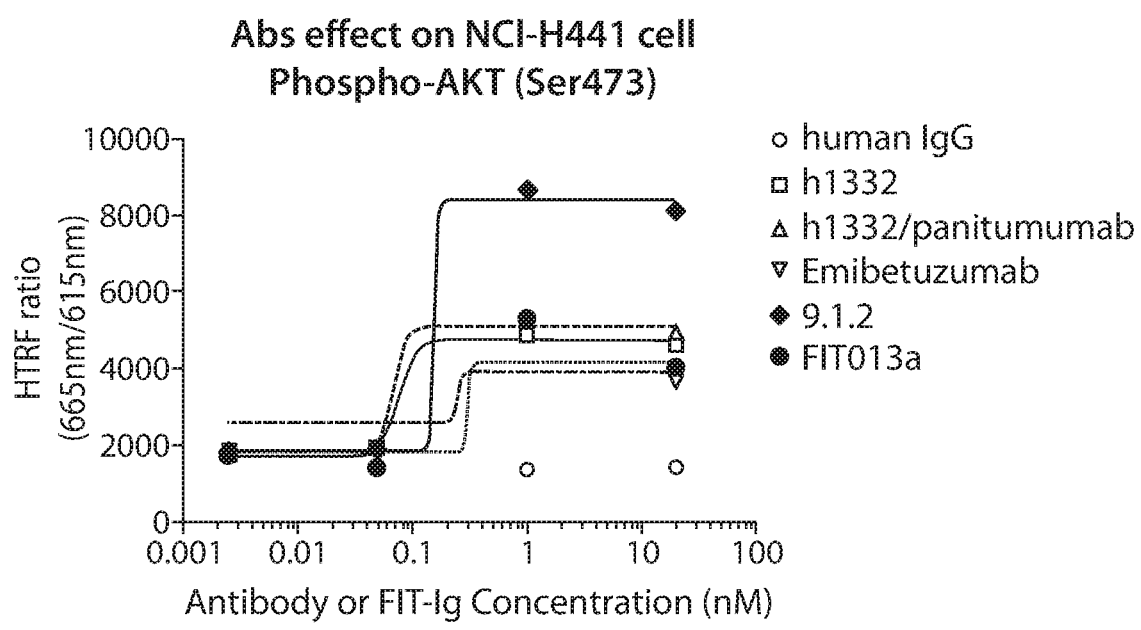
FIG. 20 shows FIT013a's agonist effect in the absence of HGF as measured by AKT phosphorylation. Serially diluted FIT013a or other Abs (h1332, a combination of h1332/panitumumab, emibetuzumab, 9.1.2, and human IgG1) were added to cells and incubate for 30 mins. The cells were lysed and AKT phosphorylation was detected by ERK phospho-T202/Y204 kit.
Figure 21A:
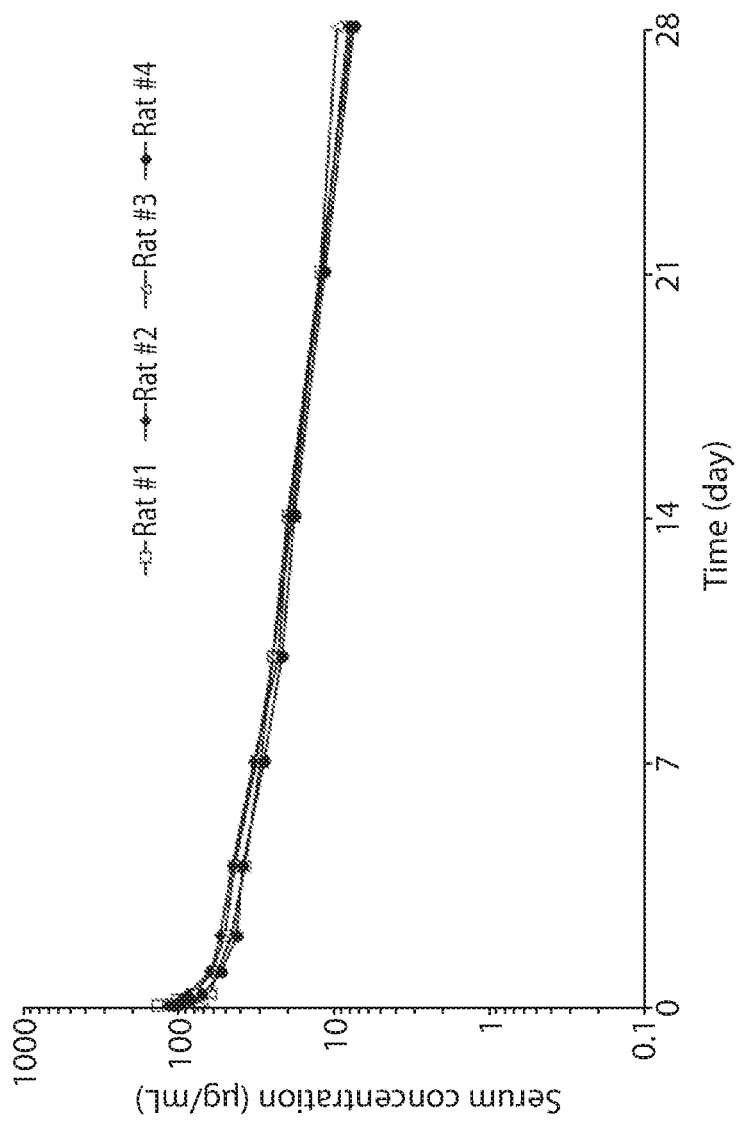
FIG. 21A shows individual serum concentration-time profiles of FIT013a (c-met/EGFR) after an IV dose of 5 mg/kg in male SD rats (N=4/time point, c-met plate).
Figure 21B:
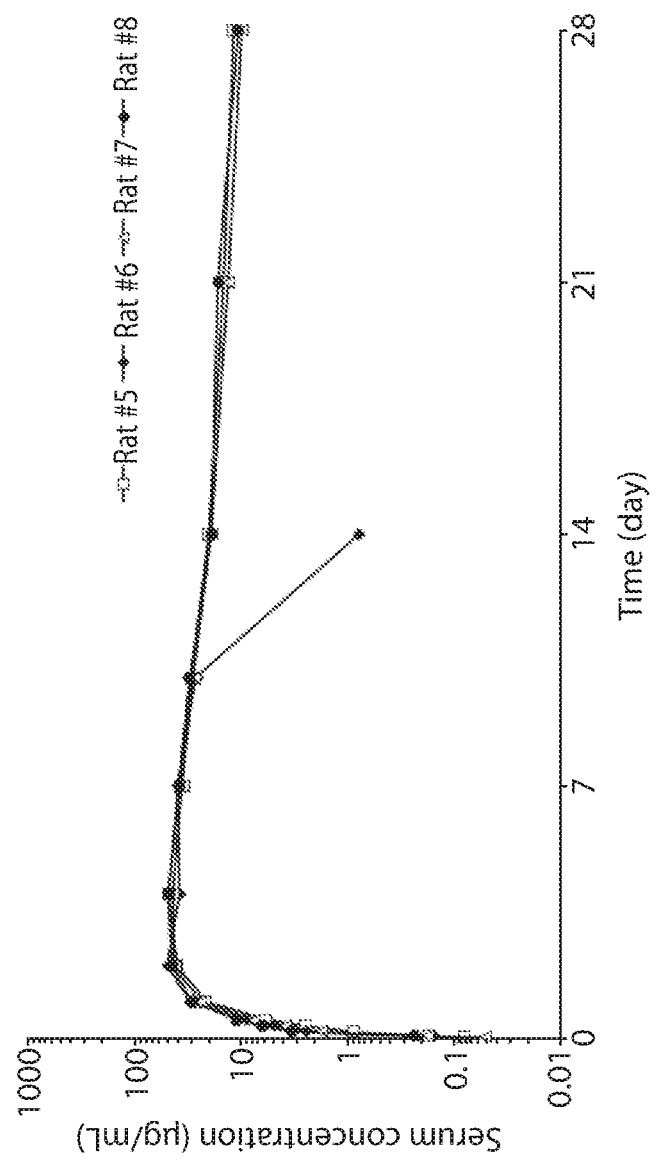
FIG. 21B shows individual serum concentration-time profiles of FIT013a (c-met/EGFR) after a SC dose of 5 mg/kg in male SD rats (N=4/time point, c-met plate).
Figure 21C:
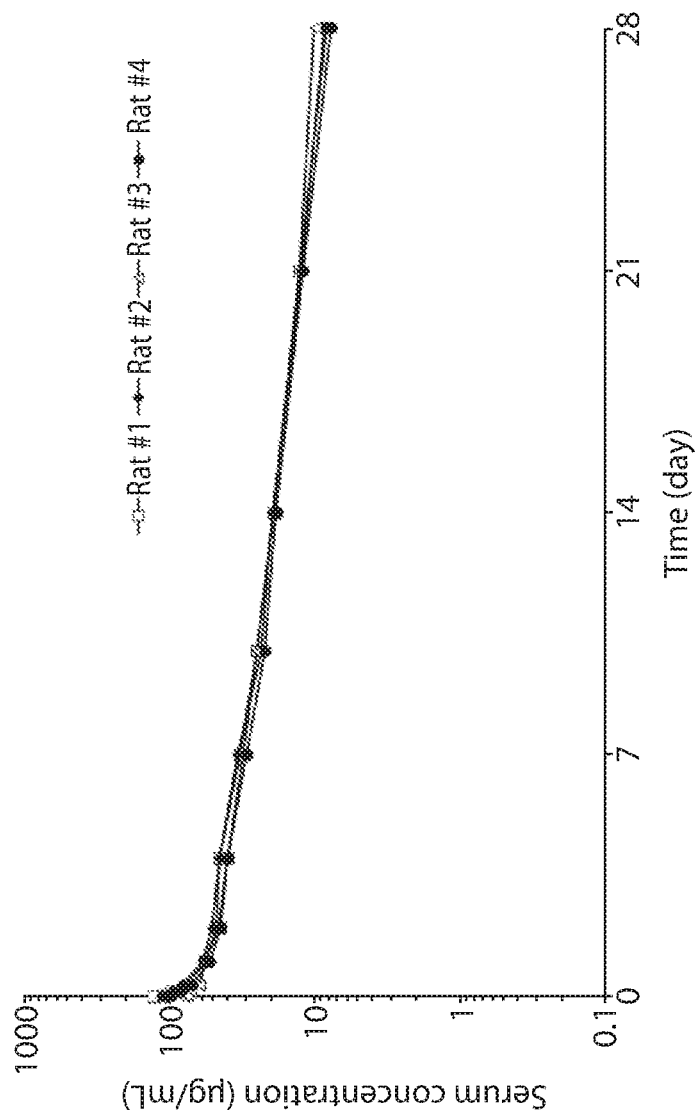
FIG. 21C shows individual serum concentration-time profiles of FIT013a (c-Met/EGFR) after an IV dose of 5 mg/kg in male SD rats (N=4/time point, EGFR plate).
Figure 21D:
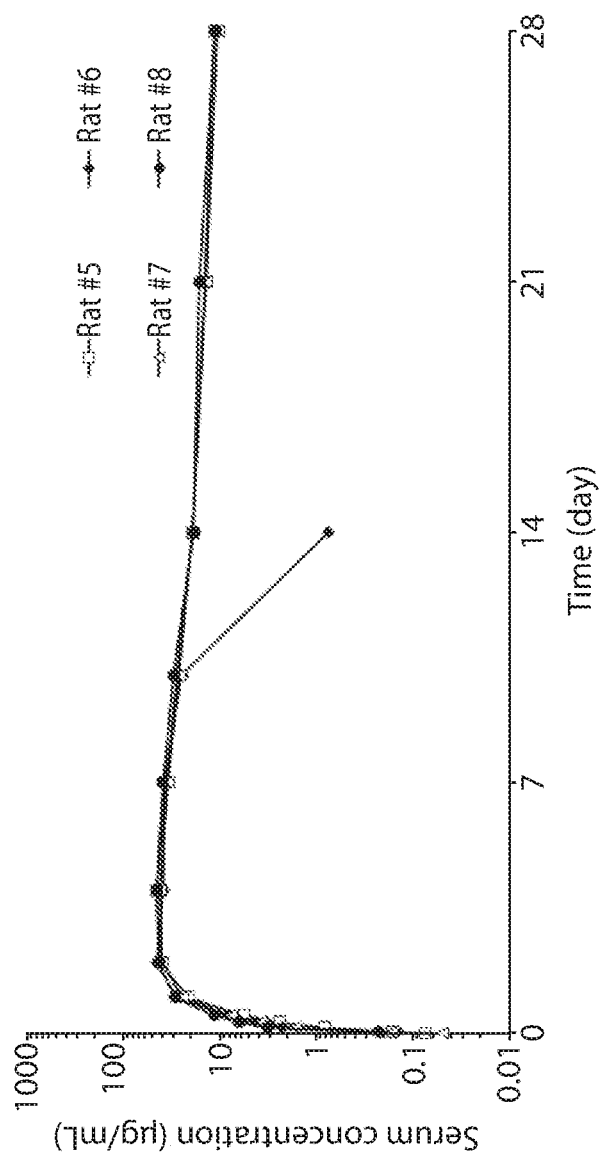
FIG. 21D shows individual serum concentration-time profiles of FIT013a (c-met/EGFR) after a SC dose of 5 mg/kg in male SD rats (N=4/time point, EGFR plate).

Agonist Assay:

Agonist effect of c-Met, EGFR antibody in FIT013a was tested by AKT phosphorylation. NCI-H441 cells were plated at 2×10 per well in 96-well plate and serum starved overnight. Serially diluted FIT013a or other related Abs were added to plate and incubate for 30 mins. The cells were lysed and AKT phosphorylation was detected by ERK phospho-T202/Y204 kit (Cisbio, Cat: 64AKSPEG). As shown in FIG. 20, the experiment demonstrates that FIT013a showed weak agonist effect in absence of HGF.

Receptor Depletion Study:

FIT013a was tested to see if it can deplete both c-Met and EGFR on cell membrane. The c-Met antibody, EGFR antibody and FIT013a were incubated with H441 cell for more than 16 hrs at 37° C. and then EGFR and c-Met remaining on the cell surface was detected by FACS. The result indicates that FIT013a can deplete near 70% of cell membrane c-Met and EGFR, higher than the c-Met antibody or the EGFR antibody, see Table 36.

TABLE 36

Receptor depletion by FIT013a

| H441 cell | EGFR Depletion (%) | c-Met Depletion (%) |
|---|---|---|
| h1332 | 0.0 | 54.0 |
| Panitumumab | 56.6 | 0.0 |
| FIT013a | 65.9 | 64.5 |

Rat PK Study:

The purpose of this study was to evaluate the pharmacokinetic of FIT013a (c-met/EGFR) following single intravenous (IV) or subcutaneous (SC) administrations in SD rats. For IV and SC dosing, the test article FIT013a (c-met/EGFR) was dissolved (in 10 mM sodium citrate, 50 mM NaCl, pH 6.0) at 2.3 mg/mL (lot: 160408001). A total of 8 male SD rats, approximately 195-208 g of body weight, purchased from SLAC Laboratory Animal Co. LTD. with Qualification No.: SCXK (SH) 2008001659659, were used in this study. The dosing and sampling is designed as Table 37.

TABLE 37

Dosing and Sampling Design

| Treatment Group | Treatment | No. of animals | Route of admin. | Dose Level (mg/kg) | Solution Conc. (mg/mL) | Dose Volume (mL/kg) | Time points |
|---|---|---|---|---|---|---|---|
| 1 | FIT013a (c-met/EGFR) | 4 | IV | 5 | 2 | 2.5 | Sampling at 0, 10 min, 1, 4, 8, 24 hr, 2, 4, 7, 10, 14, 21, 28 d, serial bleeding via tail vein for serum only. ~240 uL blood per time point. |

TABLE 37-continued

Dosing and Sampling Design

| Treatment Group | Treatment | No. of animals | Route of admin. | Dose Level (mg/kg) | Solution Conc. (mg/mL) | Dose Volume (mL/kg) | Time points |
|---|---|---|---|---|---|---|---|
| 2 | FIT013a (c-met/EGFR) | 4 | SC | 5 | 2 | 2.5 | Sampling at 0, 30 min, 1, 4, 8, 12, 24 hr, 2, 4, 7, 10, 14, 21, 28 d, serial bleeding via tail vein for serum only. ~240 uL blood per time point. |

The IV dose was administered via foot dorsal vein injection and SC dose was administered via subcutaneous injection. At the designated time-points, the animals were restrained manually, and approximately 240 ptL blood/time point was collected via tail vein puncture or cardiac puncture into tubes. The blood samples were placed at room temperature for 0.5 hr. Then blood samples were centrifuged (10000 g, 5 min under 4° C.) to obtain the serum samples. The serum samples were immediately stored at −80° C. until analysis. The samples were detected by ELISA using c-Met and EGFR protein respectively. The concentration-time data of FIT013a (c-met/EGFR) in rat serum for IV and SC studies are listed in Table 38 to Table 41, and are illustrated in FIG. 21A to FIG. 21D.

TABLE 38

Serum concentration-time data and pharmacokinetic parameters of FIT013a (c-met/EGFR) after an IV dose at 5 mg/kg in male SD rats (c-met plate)

| Dose (mg/kg) | Dose route | Sampling time (Day) | Concentration (μg/mL) | | | | Mean (μg/mL) | SD | CV (%) |
|---|---|---|---|---|---|---|---|---|---|
| | | | Rat #1 | Rat #2 | Rat #3 | Rat #4 | | | |
| 5 | IV | 0 | BQL | BQL | BQL | BQL | BQL | NA | NA |
| | c-met plate | 0.00694 | 138 | 118 | 82.0 | 108 | 112 | 23.3 | 20.9 |
| | | 0.0417 | 114 | 105 | 74.3 | 99.3 | 98.2 | 17.0 | 17.4 |
| | | 0.167 | 103 | 97.8 | 71.7 | 83.8 | 89.0 | 14.0 | 15.8 |
| | | 0.333 | 79.1 | 87.9 | 62.8 | 70.9 | 75.2 | 10.8 | 14.4 |
| | | 1 | 60.8 | 62.8 | 56.3 | 53.6 | 58.4 | 4.17 | 7.14 |
| | | 2 | 51.0 | 54.2 | 45.4 | 42.6 | 48.3 | 5.27 | 10.9 |
| | | 4 | 44.0 | 45.5 | 37.7 | 39.0 | 41.5 | 3.81 | 9.17 |
| | | 7 | 31.9 | 33.1 | 29.6 | 28.6 | 30.8 | 2.06 | 6.68 |
| | | 10 | 24.7 | 22.7 | 24.4 | 21.8 | 23.4 | 1.40 | 5.97 |
| | | 14 | 20.0 | 19.7 | 18.5 | 18.0 | 19.1 | 0.946 | 4.96 |
| | | 21 | 12.3 | 11.9 | 12.1 | 11.5 | 12.0 | 0.319 | 2.67 |
| | | 28 | 7.68 | 8.12 | 9.53 | 7.43 | 8.19 | 0.938 | 11.5 |

| PK parameters | Unit | Rat #1 | Rat #2 | Rat #3 | Rat #4 | Mean | SD | CV (%) |
|---|---|---|---|---|---|---|---|---|
| CL | mL/day/kg | 6.24 | 6.14 | 6.21 | 6.86 | 6.36 | 0.335 | 5.27 |
| Vss | mL/kg | 82.5 | 82.7 | 105 | 97.6 | 91.8 | 11.0 | 12.0 |
| V1 | mL/kg | 38.2 | 44.4 | 65.3 | 47.6 | 48.9 | 11.6 | 23.8 |
| Alpha $t_{1/2}$ | day | 0.235 | 0.491 | 0.879 | 0.309 | 0.478 | 0.288 | 60.2 |
| Beta $t_{1/2}$ | day | 9.46 | 9.80 | 12.3 | 10.21 | 10.4 | 1.26 | 12.1 |
| AUC | Day × μg/mL | 802 | 815 | 805 | 729 | 788 | 39.5 | 5.02 |
| MRT | day | 13.2 | 13.5 | 16.8 | 14.2 | 14.4 | 1.65 | 11.4 |

TABLE 39

Serum concentration-time data and pharmacokinetic parameters of FIT013a (c-met/EGFR) after a SC dose of 5 mg/kg in male SD rats (c-met plate)

| Dose (mg/kg) | Dose route | Sampling time (Day) | Concentration (µg/mL) | | | | Mean (µg/mL) | SD | CV (%) |
|---|---|---|---|---|---|---|---|---|---|
| | | | Rat #5 | Rat #6 | Rat #7 | Rat #8 | | | |
| 5 | SC | 0 | BQL | BQL | BQL | BQL | BQL | NA | NA |
| c-Met plate | | 0.00694 | 0.0780 | BQL | 0.0500 | BQL | 0.0640 | NA | NA |
| | | 0.0417 | 0.167 | 0.150 | 0.172 | 0.228 | 0.179 | 0.0338 | 18.9 |
| | | 0.167 | 0.865 | 2.38 | 1.70 | 3.28 | 2.06 | 1.03 | 49.9 |
| | | 0.333 | 2.44 | 4.89 | 3.66 | 6.17 | 4.29 | 1.60 | 37.4 |
| | | 0.5 | 5.69 | 8.74 | 7.37 | 10.8 | 8.16 | 2.18 | 26.7 |
| | | 1 | 21.3 | 29.5 | 23.6 | 28.3 | 25.7 | 3.85 | 15.0 |
| | | 2 | 39.4 | 47.9 | 40.9 | 43.7 | 43.0 | 3.73 | 8.69 |
| | | 4 | 47.4 | 36.8 | 42.3 | 47.2 | 43.4 | 5.01 | 11.5 |
| | | 7 | 36.8 | 38.5 | 34.4 | 37.7 | 36.9 | 1.76 | 4.78 |
| | | 10 | 28.8 | 25.7 | 27.0 | 29.9 | 27.9 | 1.85 | 6.64 |
| | | 14 | 19.8 | *0.753 | 18.5 | 18.6 | 19.0 | 0.748 | 3.94 |
| | | 21 | 14.2 | BQL | 12.8 | 16.2 | 14.4 | 1.67 | 11.6 |
| | | 28 | 11.6 | BQL | 9.52 | 10.5 | 10.5 | 1.03 | 9.74 |

| PK parameters | Unit | Rat #5 | Rat #6 | Rat #7 | Rat #8 | Mean | SD | CV (%) |
|---|---|---|---|---|---|---|---|---|
| $T_{max}$ | day | 4.00 | 2.00 | 4.00 | 4.00 | 3.50 | 1.00 | 28.6 |
| $C_{max}$ | µg/ml | 47.4 | 47.9 | 42.3 | 47.2 | 46.2 | 2.63 | 5.70 |
| Terminal $t_{1/2}$ | day | 11.6 | 11.6 | 11.4 | 12.0 | 11.7 | 0.262 | 2.24 |
| $AUC_{last}$ | Day × µg/ml | 656 | 344 | 611 | 680 | 573 | 155 | 27.1 |
| $AUC_{INF}$ | Day × µg/ml | 850 | 775 | 767 | 863 | 814 | 49.8 | 6.12 |
| CL/F | mL/day/kg | 5.88 | 6.45 | 6.52 | 5.79 | 6.16 | 0.376 | 6.11 |
| F | % | 108 | 98.4 | 97.4 | 110 | 103 | 6.32 | 6.12 |

*The serum concentration of these time point were excluded from mean value and PK parameters calculation due to the posibility of anti-drug antibody.

TABLE 40

Serum concentration-time data and pharmacokinetic parameters of FIT013a (c-met/EGFR) after an IV dose at 5 mg/kg in male SD rats (EGFR plate)

| Dose (mg/kg) | Dose route | Sampling time (Day) | Concentration (µg/mL) | | | | Mean (µg/mL) | SD | CV (%) |
|---|---|---|---|---|---|---|---|---|---|
| | | | Rat #1 | Rat #2 | Rat #3 | Rat #4 | | | |
| 5 | IV | 0 | BQL | BQL | BQL | BQL | BQL | NA | NA |
| EGFR plate | | 0.00694 | 130 | 115 | 80.0 | 105 | 107 | 21.0 | 19.6 |
| | | 0.0417 | 111 | 103 | 75.8 | 97.3 | 96.9 | 15.2 | 15.7 |
| | | 0.167 | 98.0 | 95.5 | 72.3 | 83.4 | 87.3 | 11.9 | 13.6 |
| | | 0.333 | 76.2 | 83.6 | 62.1 | 70.8 | 73.2 | 9.06 | 12.4 |
| | | 1 | 57.0 | 59.3 | 56.6 | 53.1 | 56.5 | 2.59 | 4.58 |
| | | 2 | 47.6 | 50.9 | 45.6 | 44.6 | 47.2 | 2.79 | 5.92 |
| | | 4 | 45.6 | 45.3 | 39.9 | 39.8 | 42.6 | 3.27 | 7.67 |
| | | 7 | 32.7 | 33.8 | 31.1 | 29.5 | 31.8 | 1.88 | 5.90 |
| | | 10 | 25.1 | 23.6 | 25.2 | 22.3 | 24.0 | 1.37 | 5.69 |
| | | 14 | 19.2 | 19.7 | 19.1 | 18.4 | 19.1 | 0.524 | 2.75 |
| | | 21 | 12.8 | 12.2 | 12.8 | 12.1 | 12.5 | 0.365 | 2.92 |
| | | 28 | 8.38 | 8.62 | 10.0 | 7.71 | 8.68 | 0.973 | 11.2 |

| PK parameters | Unit | Rat #1 | Rat #2 | Rat #3 | Rat #4 | Mean | SD | CV (%) |
|---|---|---|---|---|---|---|---|---|
| CL | mL/day/kg | 6.14 | 6.09 | 5.98 | 6.66 | 6.22 | 0.302 | 4.86 |
| Vss | mL/kg | 86.3 | 85.2 | 102 | 96.0 | 92.3 | 7.94 | 8.61 |
| V1 | mL/kg | 39.7 | 44.8 | 65.3 | 48.7 | 49.6 | 11.1 | 22.3 |
| Alpha $t_{1/2}$ | day | 0.222 | 0.368 | 0.795 | 0.306 | 0.423 | 0.255 | 60.3 |
| Beta $t_{1/2}$ | day | 10.0 | 10.0 | 12.3 | 10.3 | 10.7 | 1.09 | 10.2 |
| AUC | Day × µg/mL | 815 | 821 | 836 | 751 | 806 | 37.6 | 4.67 |
| MRT | day | 14.1 | 14.0 | 17.0 | 14.4 | 14.9 | 1.44 | 9.70 |

TABLE 41

Serum concentration-time data and pharmacokinetic parameters of FIT013a
(c-met/EGFR) after a SC dose at 5 mg/kg in male SD rats (EGFRplate)

| Dose (mg/kg) | Dose route | Sampling time (Day) | Concentration (µg/mL) | | | | Mean (µg/mL) | SD | CV(%) |
|---|---|---|---|---|---|---|---|---|---|
| | | | Rat #5 | Rat #6 | Rat #7 | Rat #8 | | | |
| 5 | SC | 0 | BQL | BQL | BQL | BQL | BQL | NA | NA |
| | EGFR plate | 0.00694 | 0.0760 | BQL | 0.0490 | BQL | 0.0625 | NA | NA |
| | | 0.0417 | 0.164 | 0.144 | 0.167 | 0.231 | 0.177 | 0.0377 | 21.4 |
| | | 0.167 | 0.836 | 2.32 | 1.66 | 3.30 | 2.03 | 1.04 | 51.4 |
| | | 0.333 | 2.45 | 4.45 | 3.74 | 6.37 | 4.25 | 1.64 | 38.5 |
| | | 0.5 | 5.85 | 8.61 | 7.69 | 11.6 | 8.45 | 2.42 | 28.6 |
| | | 1 | 21.6 | 27.7 | 24.5 | 29.8 | 25.9 | 3.61 | 14.0 |
| | | 2 | 41.5 | 45.3 | 40.0 | 43.8 | 42.6 | 2.39 | 5.60 |
| | | 4 | 46.2 | 38.9 | 41.9 | 46.2 | 43.3 | 3.56 | 8.22 |
| | | 7 | 35.9 | 37.3 | 34.7 | 39.6 | 36.9 | 2.13 | 5.77 |
| | | 10 | 28.5 | 25.0 | 26.8 | 30.6 | 27.7 | 2.40 | 8.65 |
| | | 14 | 19.3 | *0.768 | 19.4 | 19.0 | 19.2 | 0.183 | 0.950 |
| | | 21 | 14.7 | BQL | 13.9 | 16.5 | 15.0 | 1.33 | 8.84 |
| | | 28 | 11.7 | BQL | 10.5 | 11.4 | 11.2 | 0.601 | 5.37 |

| PK parameters | Unit | Rat #5 | Rat #6 | Rat #7 | Rat #8 | Mean | SD | CV (%) |
|---|---|---|---|---|---|---|---|---|
| $T_{max}$ | day | 4.00 | 2.00 | 4.00 | 4.00 | 3.50 | 1.00 | 28.6 |
| $C_{max}$ | µg/ml | 46.2 | 45.3 | 41.9 | 46.2 | 44.9 | 2.03 | 4.51 |
| Terminal $t_{1/2}$ | day | 13.1 | 9.38 | 12.4 | 12.3 | 11.8 | 1.66 | 14.0 |
| $AUC_{last}$ | Day × µg/ml | 653 | 339 | 625 | 694 | 578 | 162 | 28.0 |
| $AUC_{INF}$ | Day × µg/ml | 875 | 677 | 813 | 896 | 815 | 98.8 | 12.1 |
| CL/F | mL/day/kg | 5.72 | 7.39 | 6.15 | 5.58 | 6.21 | 0.823 | 13.3 |
| F | % | 109 | 84.0 | 101 | 111 | 101 | 12.3 | 12.1 |

*The serum concentration of these time point were excluded from mean value and PK parameters calculation due to the posibility of anti-drug antibody.

NCI-H1975-HGF Xenograft Model Tumor Distribution Study

In this study, serum and tumor concentration of FIT013a was measured 24 hrs after single IP dose in NCI-H1975-HGF tumor bearing nude BALB/c Mice.

NCI-H1975-HGF cells were subcutaneously inoculated to nude BALB/c mice. When the average tumor volume reached to 200-250 mm³, the mice were randomly allocated to four groups, FIT013a, H1332, Panitumumab and vehicle group. FIT013a group was single IP dose, 16 mg/kg; H1332 or Panitumumab was single IP dose, 10 mg/kg. Vehicle group was dosed with formulation buffer 10 mM sodium citrate, 50 mM NaCl, pH 6.0. 24 hrs after dosing, tumor and serum were collect. Tumors were homogenized and the supernatant was collected for the following ELISA study. FIT013a, Panitumumab, and H1332 were quantified by using generic hIgG ELISA method for both serum and tumor.

Figure 22:
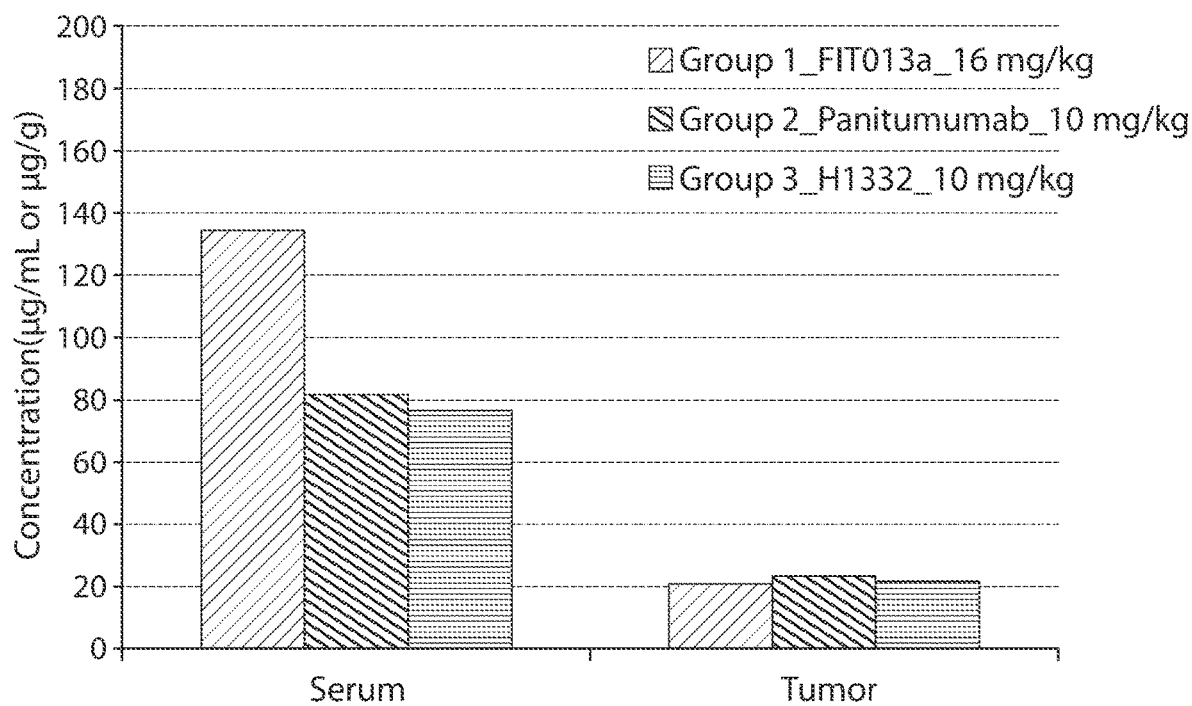
FIG. 22 shows distributions of FIT013a, panitumumab, and H1332 in the serum and tumor in nude BALB/c mice (N=3 animal/group) inoculated with NCI-H1975-HGF tumor cells.

The experiment demonstrates that FIT013a showed comparable distribution activity in serum and tumor with monoclonal antibodies, see FIG. 22.

NCI-H1975-HGF Xenograft Model Efficacy Study

In this study, the efficacy of FIT013a was measured in NCI-H1975-HGF xenograft model.

NCI-H1975-HGF cells were subcutaneously inoculated to nude BALB/c mice. When the average tumor volume reached to 100-130 mm³, and the largest tumor volume was less than 140 mm³. The mice were randomly allocated to four groups, FIT013a, H1332, Panitumumab and vehicle group. The antibodies were dosed two times/week i.p. for three weeks. The dosing for FIT013a was 16 mg/kg, for H1332 or Panitumumab was 10 mg/kg. Vehicle group was dosed with formulation buffer, 10 mM sodium citrate, 50 mM NaCl, pH 6.0. The tumor volume and mouse body weight was measured twice/week. Percentage tumor growth inhibition (% TGI) was defined as the difference between the control-treated group mean tumor volume (MTV) and the test antibody-treated group MTV.

Figure 23:
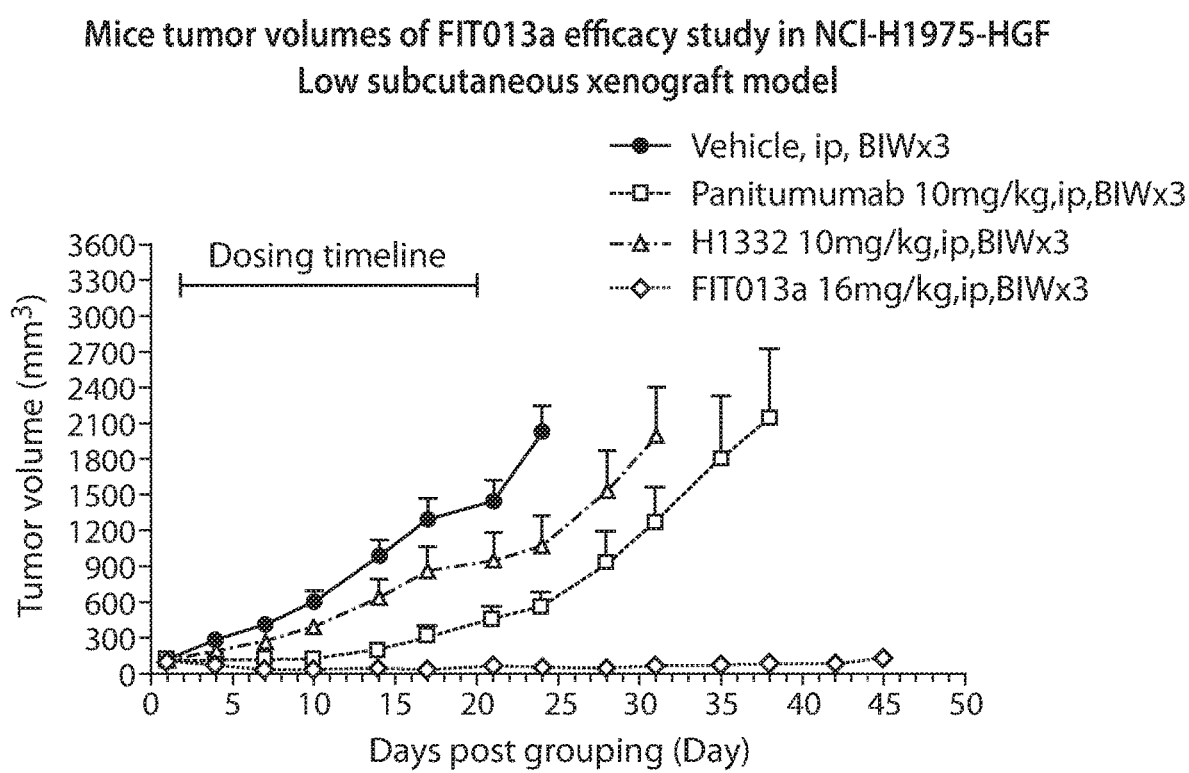
FIG. 23 shows the efficacy of FIT013a, panitumumab, H1332, vehicle in inhibiting tumor size in nude BALB/c mice (N=8 animal/group) inoculated with NCI-H1975-HGF tumor cells. The antibodies were dosed two times/week i.p. for three weeks. The dosing for FIT013a was 16 mg/kg, for H1332 or Panitumumab was 10 mg/kg.

The experiment demonstrates that FIT013a showed FIT013a showed better efficacy than EGFR or c-Met monoclonal Ab, see FIG. 23.

Example 9: Study of Anti-Factor IXa/Factor X Fabs-in-Tandem Immunoglobulin (FIT-Ig)

FIT-Ig having specificity for Factor IXa and Factor X was constructed as in the foregoing Examples. This exemplary FIT-Ig and its corresponding sequences are provided below in Table 42. Table 43 provides the expression level in 293E cells and the SEC profile for each of the FIT-Ig.

TABLE 42

Amino acid sequences of additional exemplary FIT-Ig for cMEt and EGFR

| Name<br>Target (mAb)<br>mAb1 (upper domain)/mAb2 (lower domain) | Protein region | SEQ ID NO | Sequences |
|---|---|---|---|
| FIT014a<br>Factor IX<br>(Factor IX Ab)/Factor X<br>(Factor X Ab) | Long Chain (FIX VL-hCk-FX-VH-hCg4) | 259 | MDMRVPAQLLGLLLLWFPGSRCDIQMTQSPSSLSASVGDR VTITCKASRNIERQLAWYQQKPGQAPELLIYQASRKESGV PDRFSGSRYGTDFTLTISSLQPEDIATYYCQQYSDPPLTF GGGTKVEIKRTVAAPSVFIFPPSDEQLKSGTASVVCLLNN FYPREAKVQWKVDNALQSGNSQESVTEQDSKDSTYSLSST LTLSKADYEKHKVYACEVTHQGLSSPVTKSFNRGECQVQL VQSGSELKKPGASVKVSCKASGYTFTDNNMDWVRQAPGQG LEWMGDINTRSGGSIYNEEFQDRVIMTVDKSTDTAYMELS SLRSEDTATYHCARRKSYGYYLDEWGEGTLVTVSSASTKG PSVFPLAPCSRSTSESTAALGCLVKDYFPEPVTVSWNSGA LTSGVHTFPAVLQSSGLYSLSSVVTVPSSSLGTQTYTCNV DHKPSNTKVDKRVESKYGPPCPPCPAPEFLGGPSVFLFPP KPKDTLMISRTPEVTCVVVDVSQEDPEVQFNWYVDGVEVH NAKTKPREEQYNSTYRVVSVLTVLHQDWLNGKEYKCKVSN KGLPSSIEKTISKAKGQPREPQVYTLPPSQEEMTKNQVSL TCLVKGFYPSDIAVEWESNGQPENNYKTTPPVLDSDGSFF LYSKLTVDKSRWQEGNVFSCSVMHEALHNHYTQESLSLSP |
| | FIX VL | 260 | DIQMTQSPSSLSASVGDRVTITCKASRNIERQLAWYQQKP GQAPELLIYQASRKESGVPDRFSGSRYGTDFTLTISSLQP EDIATYYCQQYSDPPLTFGGGTKVEIK |
| | FIX VL - CDR1 | 261 | KASRNIERQLA |
| | FIX VL - CDR2 | 262 | QASRKES |
| | FIX VL - CDR3 | 263 | QQYSDPPLT |
| | FX-VH | 264 | QVQLVQSGSELKKPGASVKVSCKASGYTFTDNNMDWVRQA PGQGLEWMGDINTRSGGSIYNEEFQDRVIMTVDKSTDTAY MELSSLRSEDTATYHCARRKSYGYYLDEWGEGTLVTVSS |
| | FX-VH - CDR1 | 265 | DNNMD |
| | FX-VH - CDR2 | 266 | DINTRSGGSIYNEEFQD |
| | FX-VH - CDR3 | 267 | RKSYGYYLDE |
| | Short Chain #1 (F-IX VH-CH1h) | 268 | MEFGLSWLFLVAILKGVQCQVQLVESGGGLVQPGGSLRLS CAASGFTFSYYDIQWVRQAPGKGLEWVSSISPSGQSTYYR REVKGRFTISRDNSKNTLYLQMNSLRAEDTAVYYCARRTG REYGGGWYFDYWGQGTLVTVSSASTKGPSVFPLAPSSKST SGGTAALGCLVKDYFPEPVTVSWNSGALTSGVHTFPAVLQ SSGLYSLSSVVTVPSSSLGTQTYICNVNHKPSNTKVDKKV EPKSC |
| | F-IX VH | 269 | QVQLVESGGGLVQPGGSLRLSCAASGFTFSYYDIQWVRQA PGKGLEWVSSISPSGQSTYYRREVKGRFTISRDNSKNTLY LQMNSLRAEDTAVYYCARRTGREYGGGWYFDYWGQGTLVT VSS |
| | F-IX VH - CDR1 | 270 | SYYDIQ |
| | F-IX VH - CDR2 | 271 | SISPSGQSTYYRREVKG |
| | F-IX VH - CDR3 | 272 | RTGREYGGGWYFDY |
| | Short Chain #2 (F-X VL-hCk) | 273 | MDMRVPAQLLGLLLLWFPGSRCDIQMTQSPSSLSASVGDR VTITCKASRNIERQLAWYQQKPGQAPELLIYQASRKESGV PDRFSGSRYGTDFTLTISSLQPEDIATYYCQQYSDPPLTF GGGTKVEIKRTVAAPSVFIFPPSDEQLKSGTASVVCLLNN FYPREAKVQWKVDNALQSGNSQESVTEQDSKDSTYSLSST LTLSKADYEKHKVYACEVTHQGLSSPVTKSFNRGEC |
| | F-X VL | 274 | DIQMTQSPSSLSASVGDRVTITCKASRNIERQLAWYQQKP GQAPELLIYQASRKESGVPDRFSGSRYGTDFTLTISSLQP EDIATYYCQQYSDPPLTFGGGTKVEIK |
| | F-X VL - CDR1 | 275 | KASRNIERQLA |
| | F-X VL - CDR2 | 276 | QASRKES |
| | F-X VL - CDR3 | 277 | QQYSDPPLT |

TABLE 43

SEC Profile/Expression level in 293E cells:

| FIT-Ig | Monomer % in SEC | Expression level (mg/L) |
|---|---|---|
| FIT014a | 98.8% | 10.5 |

Functional Study

Affinity Measurement by Surface Plasmon Resonance:

The kinetics of FIT-Ig binding to hFactor IX and hFactor X (Enzyme Research Laboratory) was determined by surface plasmon resonance with a Biacore X100 instrument (Biacore AB, Uppsala, Sweden) using HBS-EP (10 mM HEPES, pH 7.4, 150 mM NaCl, 3 mM EDTA, and 0.005% surfactant P20) at 25° C. Briefly, goat anti-human IgG Fc fragment specific polyclonal antibody (Pierce Biotechnology Inc, Rockford, Ill.) was directly immobilized across a CM5 research grade biosensor chip using a standard amine coupling kit according to manufacturer's instructions. Purified FIT-Ig samples were diluted in HEPES-buffered saline for capture across goat anti-human IgG Fc specific reaction surfaces and injected over reaction matrices at a flow rate of 5 µl/min. The association and dissociation rate constants, kon (M−1s−1) and koff (s−1) were determined under a continuous flow rate of 30 μL/min. Rate constants were derived by making kinetic binding measurements at 500 nM antigen concentrations. The equilibrium dissociation constant (M) of the reaction between FIT-Ig and the target proteins was then calculated from the kinetic rate constants by the following formula: KD=koff/kon. Aliquots of antigen samples were also simultaneously injected over a blank reference and reaction CM surface to record and subtract any nonspecific binding background to eliminate the majority of the refractive index change and injection noise. Surfaces were regenerated with two subsequent 25 ml injections of 10 mM Glycine (pH 1.5) at a flow rate of 10 μL/min. The anti-Fc antibody immobilized surfaces were completely regenerated and retained their full capture capacity over twelve cycles. Protein based binding data for FIT014a is provided below in Table 44.

TABLE 44

Functional binding data of FIT014

| Ig | Target | Kon | Koff | KD |
|---|---|---|---|---|
| Factor IX mAb | Factor IX | 2.74E+04 | 3.55E−04 | 1.30E−08 |
| FIT-Ig 014a | | 3.35E+04 | 3.32E−04 | 9.91E−09 |
| Factor X mAb | Factor X | 3.15E+04 | 1.42E−03 | 4.51E−08 |
| FIT-Ig 014a | | 7.75E+04 | 7.76E−04 | 1.00E−08 |

Figure 24:
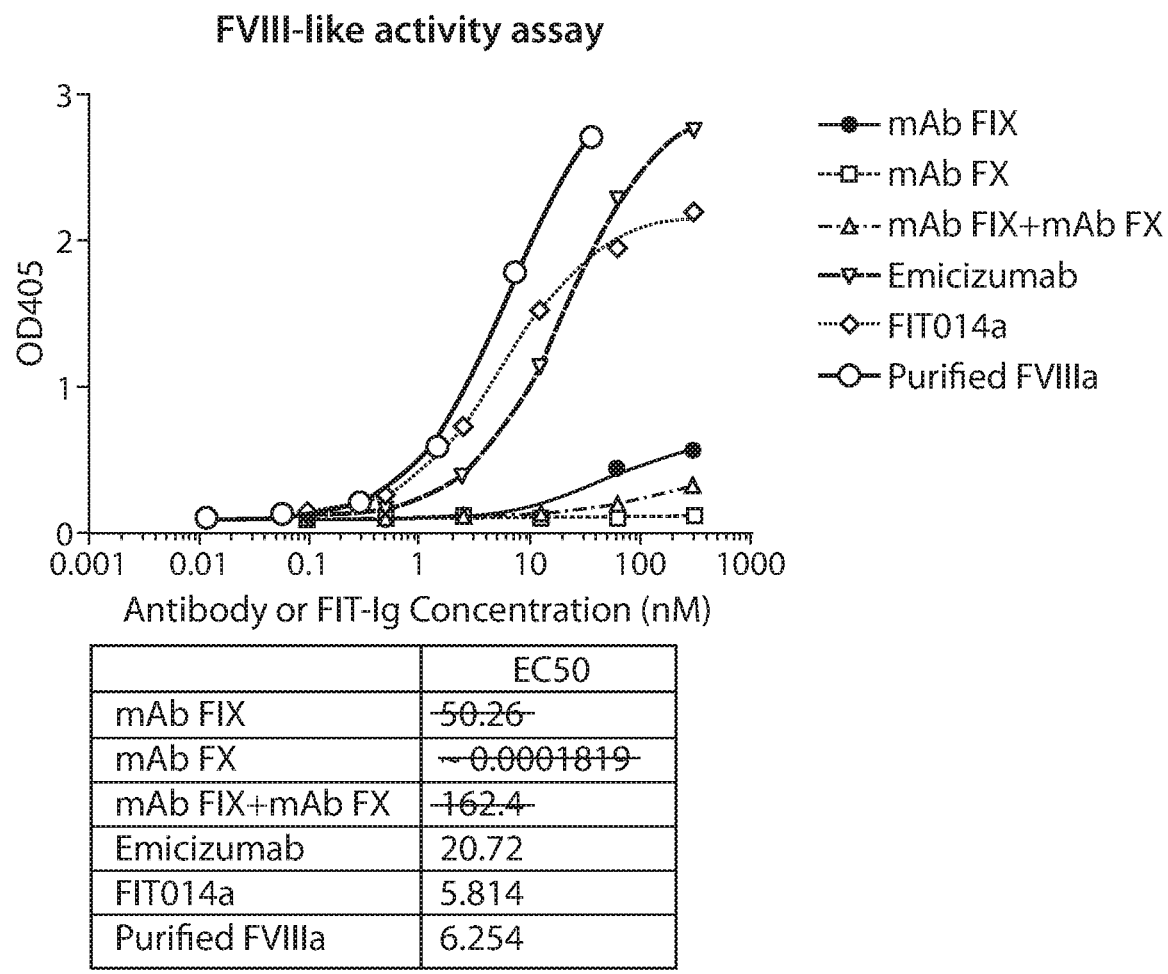
FIG. 24 shows enzyme assay for Factor VIIIa-like activity using BIOPHEN FVIII:C kit (Hyphen-Biomed). Samples containing mAb FIX, mAb FX, a combination of mAb FIX and mAb FX, Emicizumab, FIT014a, and purified FVIIIa were analyzed.

Factor VIIIa-Like Activity Assay:

FVIIIa-like activity of the FIT-Ig was evaluated by an enzyme assay according to manufacturer's instructions of BIOPHEN FVIII:C kit (Hyphen-Biomed, 221402-RUO). The result indicates that FIT014a has comparable FVIIIa like activity with Emicizumab and purified FVIIIa, while monoclonal antibody of Factor IX and Factor X, as well as a combination of them, has no activity, see FIG. 24.

Figure 25:
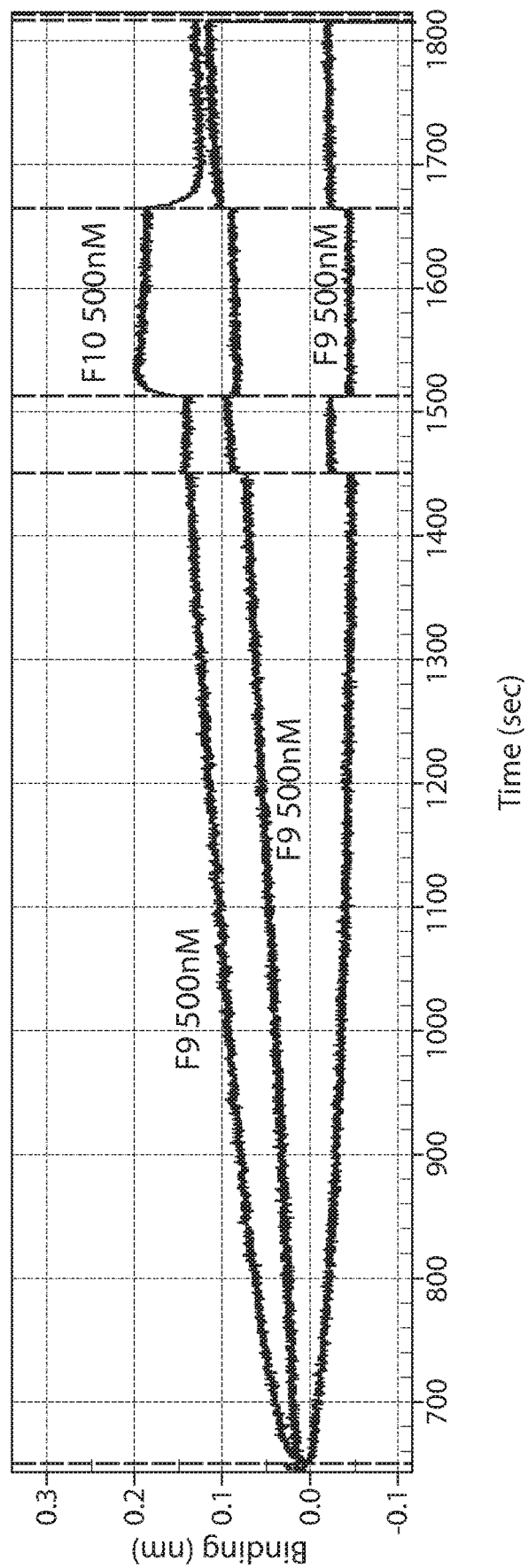
FIG. 25 shows a multiple binding study of FIT014a against both FIX and FX. Binding to FIX followed by FX; and binding by FX followed by FIX are both shown as indicated.

Multiple-Antigen Binding Study:

this study was done using OctetRed to determine if FIT014a is able to bind hFactor IX and hFactor X simultaneously. Briefly, FIT014a was immobilize on AR2G sensor at concentration of 10 μg/ml, followed by binding of hFactor IX and then hFactor X (Enzyme Research Laboratory) in assay buffer (PBS pH 7.4, 0.1% BSA, 0.02% Tween), with concentration at 500 nM. At the end of the experiment, the surface was regenerated with 10 mM glycine at pH1.5 five times. This experiment shows that FIT014a is able to bind hFactor X when it had already bound to hFactor IX, indicating that FIT014a is able to bind both hFactor IX and hFactor X simultaneously, see FIG. 25.

Stability Study:

FIT014a protein samples in citrate buffer (pH=6.0) were individually incubated at constant 4° C., 25° C. and 40° C. for 1 day, 3 days or 7 days. Similarly, FIT014a protein samples were freeze-thawed once, twice or three times. The fractions of intact full monomeric protein of all samples was detected by SEC-HPLC, with 10 μg of each protein sample injected into Ultimate 3000 HPLC equipping Superdex200 5/150 GL at flow rate 0.3 mL/min for 15 min, and data was recorded and analyzed using Chromeleon software supplied by the manufacturer. Table 45 shows that FIT014a remained full intact monomeric molecule under these thermo-challenged conditions.

TABLE 45

Storage stability of FIT014

| Sample Name | Rel. Area % 1 | Rel. Area % 2 | Rel. Area % 3 |
|---|---|---|---|
| FIT014_D0 | 6.28 | 93.32 | 0.40 |
| FIT014_F/T1 | 6.86 | 92.25 | 0.89 |
| FIT014-F/T2 | 6.72 | 92.36 | 0.93 |
| FIT014_F/T3 | 6.80 | 92.03 | 1.16 |
| FIT014_4C-D1 | 6.19 | 93.51 | 0.30 |
| FIT014_25C-D1 | 6.81 | 92.24 | 0.95 |
| FIT014_40C-D1 | 6.60 | 92.36 | 1.04 |
| FIT014_4C-D3 | 6.63 | 92.42 | 0.95 |
| FIT014_25C-D3 | 6.92 | 92.02 | 1.07 |
| FIT014_40C-D3 | 6.60 | 92.15 | 1.25 |
| FIT014_4C-D7 | 6.68 | 92.45 | 0.87 |
| FIT014_25C-D7 | 6.58 | 92.39 | 1.03 |
| FIT014_40C-D7 | 6.94 | 91.74 | 1.32 |

Figure 26:
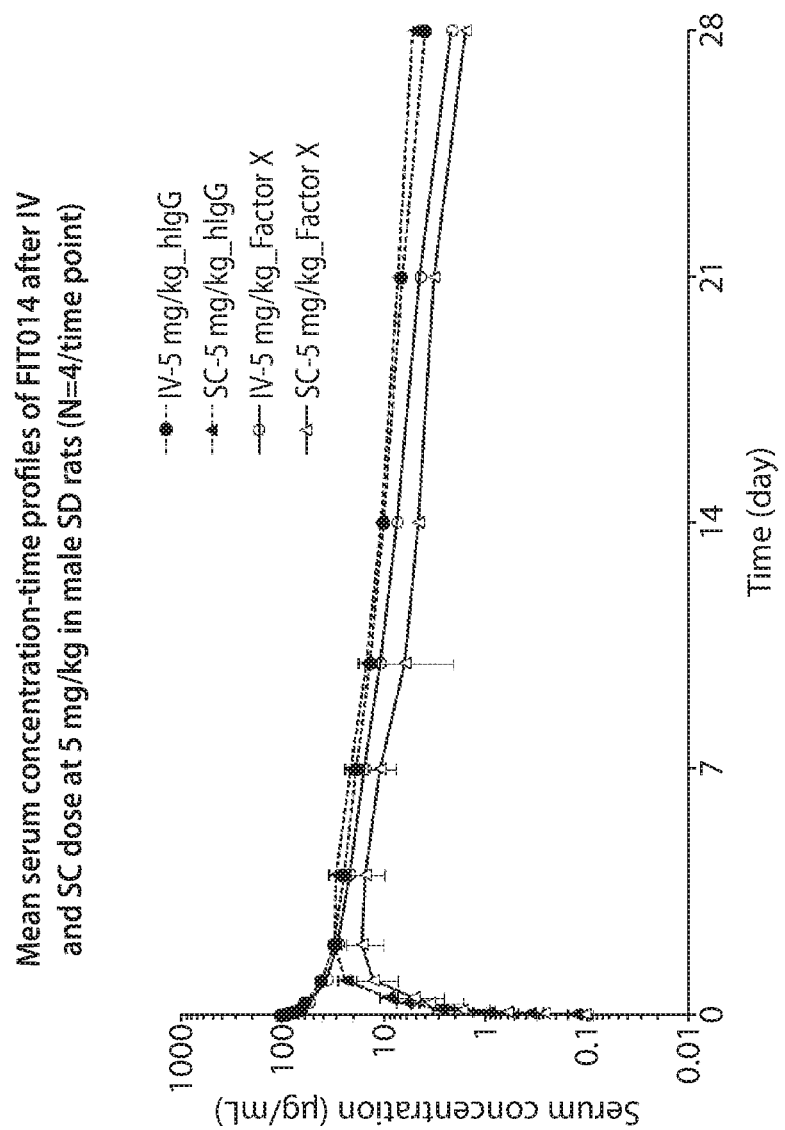
FIG. 26 shows mean serum concentration-time profiles of 5 mg/kg FIT014a administered intravenously (IV) or subcutaneously (SC) on either hIgG plate or Factor X plate. Antibody concentrations in rat serum samples were detected by ELISA with LLOQ of 62.5 ng/mL. On hIgG plate, the coating protein is anti-hIgG Fc, and the detection antibody is anti-hIgG Fab. On Factor X plate, the coating protein is Factor X, while the detection antibody is anti-human-IgG Fc.

Rat PK Study:

FIT014a was subjected to PK study in rat, and the result is shown in FIG. 26 and Table 46. Antibody concentrations in rat serum samples were detected by ELISA with LLOQ of 62.5 ng/mL. On hIgG plate, the coating protein is anti-hIgG Fc, and the detection antibody is anti-hIgG Fab. On Factor X plate, the coating protein is hFactor X, while the detection antibody is anti-human-IgG Fc.

TABLE 46

Rat PK data for FIT014a

| PK parameters | hIgG plate | | Factor X plate | |
|---|---|---|---|---|
| | IV, 5 mg/kg | SC, 5 mg/kg | IV, 5 mg/kg | SC, 5 mg/kg |
| CL, mL/day/kg | 11.2 | NA | 14.5 | NA |
| Alpha $t_{1/2}$, Day | 0.329 | NA | 0.233 | NA |
| Beta $t_{1/2}$, day | 8.79 | 6.90 | 7.03 | 5.76 |
| V1, mL/kg | 54.0 | NA | 52.6 | NA |
| $T_{max}$, day | 0.00347 | 3.00 | 0.00347 | 2.50 |
| $C_{max}$, μg/mL | 104 | 30.7 | 105 | 16.3 |
| F (%) | NA | 73.8 | NA | 48.3 |

Example 10: Study of Anti-HER3/IGF-1R Fabs-in-Tandem Immunoglobulin (FIT-Ig)

FIT-Ig having specificity for HER3 and IGF-1R was constructed as in the foregoing Examples. This exemplary FIT-Ig and its corresponding sequences are provided below in Table 47. Table 48 provides the expression level in 293E cells and the SEC profile for the FIT-Ig.

TABLE 47

Amino acid sequences of additional exemplary FIT-Ig for HER3 and IGF-1R

| Name Target (mAb) mAb1 (upper domain)/mAb2 (lower domain) | Protein region | SEQ ID NO | Sequences |
|---|---|---|---|
| FIT016a HER3 (Patritumab)/IGF 1R (Figitumumab) | Long Chain (paritu VL-hCk-FigituVH-hCg1) | 278 | MDMRVPAQLLGLLLLWFPGSRCDIEMTQSPDSLAVSL GERATINCRSSQSVLYSSSNRNYLAWYQQNPGQPPKL LIYWASTRESGVPDRFSGSGSGTDFTLTISSLQAEDV AVYYCQQYYSTPRTFGQGTKVEIKRTVAAPSVFIFPP SDEQLKSGTASVVCLLNNFYPREAKVQWKVDNALQSG NSQESVTEQDSKDSTYSLSSTLTLSKADYEKHKVYAC EVTHQGLSSPVTKSFNRGECEVQLLESGGGLVQPGGS LRLSCTASGFTSSYAMNWVRQAPGKGLEWVSAISGS GGTTFYADSVKGRFTISRDNSRTTLYLQMNSLRAEDT AVYYCAKDLGWSDSYYYYYGMDVWGQGTTVTVSSASTKGPSVFPLAPSSKSTSGGTAALGCLVKDYFPEPVTVS WNSGALTSGVHTFPAVLQSSGLYSLSSVVTVPSSSLG TQTYICNVNHKPSNTKVDKKVEPKSCDKTHTCPPCPA PELLGGPSVFLFPPKPKDTLMISRTPEVTCVVVDVSH EDPEVKFNWYVDGVEVHNAKTKPREEQYNSTYRVVSV LTVLHQDWLNGKEYKCKVSNKALPAPIEKTISKAKGQ PREPQVYTLPPSREEMTKNQVSLTCLVKGFYPSDIAV EWESNGQPENNYKTTPPVLDSDGSFFLYSKLTVDKSR WQQGNVFSCSVMHEALHNHYTQKSLSLSPGK |
| | paritu VL | 279 | DIEMTQSPDSLAVSLGERATINCRSSQSVLYSSSNRN YLAWYQQNPGQPPKLLIYWASTRESGVPDRFSGSGSG TDFTLTISSLQAEDVAVYYCQQYYSTPRTFGQGTKVE IK |
| | paritu VL - CDR1 | 280 | RSSQSVLYSSSNRNYLA |
| | paritu VL - CDR2 | 281 | WASTRES |
| | paritu VL - CDR3 | 282 | QQYYSTPRT |
| | FigituVH | 283 | EVQLLESGGGLVQPGGSLRLSCTASGFTSSYAMNWV RQAPGKGLEWVSAISGSGGTTFYADSVKGRFTISRDN SRTTLYLQMNSLRAEDTAVYYCAKDLGWSDSYYYYYG MDVWGQGTTVTVSS |
| | FigituVH - CDR1 | 284 | SYAMN |
| | FigituVH - CDR2 | 285 | AISGSGGTTFYADSVKG |
| | FigituVH - CDR3 | 286 | DLGWSDSYYYYYGMDV |
| | Short Chain #1 (PatritumabVH - CH1) | 287 | MEFGLSWLFLVAILKGVQCQVQLQQWGAGLLKPSETL SLTCAVYGGSFSGYYWSWIRQPPGKGLEWIGEINHSG STNYNPSLKSRVTISVETSKNQFSLKLSSVTAADTAV YYCARDKWTWYFDLWGRGTLVTVSSASTKGPSVFPLA PSSKSTSGGTAALGCLVKDYFPEPVTVSWNSGALTSG VHTFPAVLQSSGLYSLSSVVTVPSSSLGTQTYICNVN HKPSNTKVDKKVEPKSC |
| | PatritumabVH | 288 | QVQLQQWGAGLLKPSETLSLTCAVYGGSFSGYYWSWI RQPPGKGLEWIGEINHSGSTNYNPSLKSRVTISVETS KNQFSLKLSSVTAADTAVYYCARDKWTWYFDLWGRGT LVTVSS |
| | PatritumabVH - CDR1 | 289 | GYYWS |
| | PatritumabVH - CDR2 | 290 | EINHSGSTNYNPSLKS |
| | PatritumabVH - CDR3 | 291 | DKWTWYFDL |
| | Short Chain #2 (Figitu VL-hCk) | 292 | MDMRVPAQLLGLLLLWFPGSRCDIQMTQFPSSLSASV GDRVTITCRASQGIRNDLGWYQQKPGKAPKRLIYAAS RLHRGVPSRFSGSGSGTEFTLTISSLQPEDFATYYCL QHNSYPCSFGQGTKLEIKRTVAAPSVFIFPPSDEQLK SGTASVVCLLNNFYPREAKVQWKVDNALQSGNSQESV TEQDSKDSTYSLSSTLTLSKADYEKHKVYACEVTHQG LSSPVTKSFNRGEC |
| | Figitu VL | 293 | DIQMTQFPSSLSASVGDRVTITCRASQGIRNDLGWYQ QKPGKAPKRLIYAASRLHRGVPSRFSGSGSGTEFTLT ISSLQPEDFATYYCLQHNSYPCSFGQGTKLEIK |
| | Figitu VL - CDR1 | 294 | RASQGIRNDLG |
| | Figitu VL - CDR2 | 295 | AASRLHR |
| | Figitu VL - CDR3 | 296 | LQHNSYPCS |

TABLE 48

SEC Profile/Expression level in 293E cells:

| FIT-Ig | Monomer % in SEC | Expression level(mg/L) |
|---|---|---|
| FIT016a | 99.54% | 16 |

Functional Studies

Functional Binding Study:

Functional binding data for FIT016a is provided below in Table 49.

TABLE 49

Functional binding data

| Ig | Target | Kon | Koff | KD | IC50 |
|---|---|---|---|---|---|
| Patritumab | 1 (HER3) | 3.17E+05 | 2.85E-04 | 9.00E-10 | |
| FIT016a | | 3.19E+05 | 3.19E-04 | 1.00E-09 | |

TABLE 49-continued

Functional binding data

| Ig | Target | Kon | Koff | KD | IC50 |
|---|---|---|---|---|---|
| Figitumumab | 2 (IGF1R) | 1.30E+05 | 9.48E-05 | 7.29E-10 | |
| FIT016a | | 3.38E+04 | 9.19E-05 | 2.72E-09 | |

Figure 27:
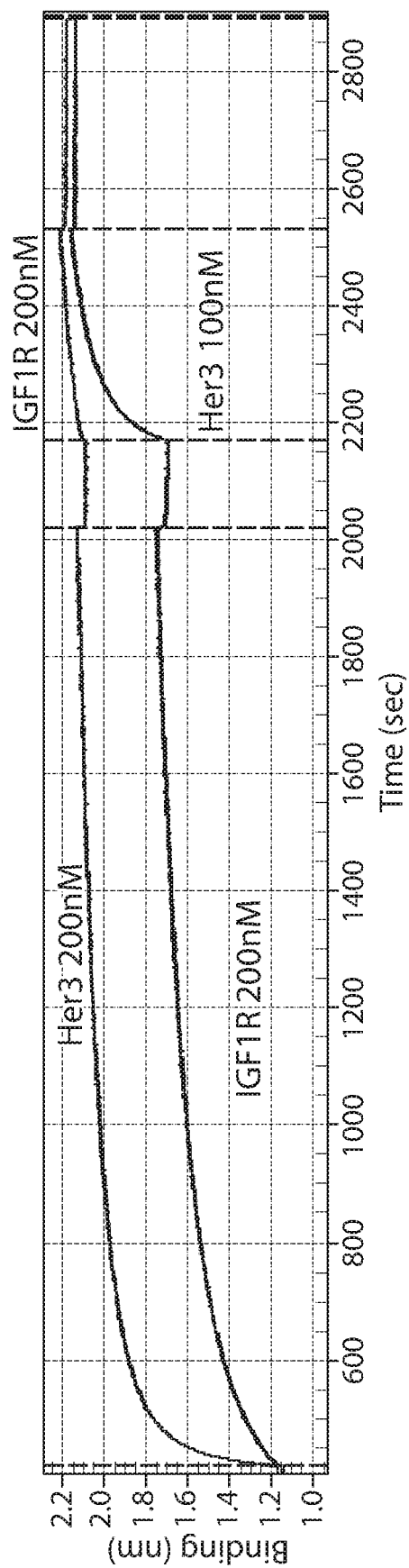
FIG. 27 shows a multiple binding study of FIT016a against both Her3 and IGF1R Binding to Her3 followed by IGF1R; and binding by IGF1R followed by Her3 are both shown as indicated.

Multiple-Antigen Binding Study:

this study was done using OctetRed to determine if FIT016a is able to bind Her3 and IGF1R simultaneously. This experiment shows that FIT016a is able to bind Her3 when it had already bound to IGF1R, indicating that FIT016a is able to bind both Her3 and IGF-1R simultaneously, see FIG. 27.

Example 11: Study of Anti-DLL4/VEGF Fabs-in-Tandem Immunoglobulin (FIT-Ig)

FIT-Ig having specificity for DLL4 and IGF1R was constructed as in the foregoing Examples. This exemplary FIT-Ig and its corresponding sequences are provided below in Table 50. Table 51 provides the expression level in 293E cells and the SEC profile for the FIT-Ig.

TABLE 50

Amino acid sequences of additional exemplary FIT-Ig for HER3 and IGF-IR

| Name Target (mAb) mAb1 (upper domain)/mAb2 (lower domain) | Protein region | SEQ ID NO | Sequences |
|---|---|---|---|
| FIT017a DLL4 (demcizumab)/ VEGF (bevcizumab) | Long Chain (Demci VL-hCk-Bevci VH-hCg1) | 297 | MDMRVPAQLLGLLLLWFPGSRCDIVMTQSPDSLAVSLGE RATISCRASESVDNYGISFMKWFQQKPGQPPKLLIYAAS NQGSGVPDRFSGSGSGTDFTLTISSLQAEDVAVYYCQQS KEVPWTFGGGTKVEIKRTVAAPSVFIFPPSDEQLKSGTA SVVCLLNNFYPREAKVQWKVDNALQSGNSQESVTEQDSK DSTYSLSSTLTLSKADYEKHKVYACEVTHQGLSSPVTKS FNRGECEVQLVESGGGLVQPGGSLRLSCAASGYTFTNYG MNWVRQAPGKGLEWVGWINTYTGEPTYAADFKRRFTFSL DTSKSTAYLQMNSLRAEDTAVYYCAKYPHYYGSSHWYFD VWGQGTLVTVSSASTKGPSVFPLAPSSKSTSGGTAALGC LVKDYFPEPVTVSWNSGALTSGVHTFPAVLQSSGLYSLS SVVTVPSSSLGTQTYICNVNHKPSNTKVDKKVEPKSCDK THTCPPCPAPELLGGPSVFLFPPKPKDTLMISRTPEVTC VVVDVSHEDPEVKFNWYVDGVEVHNAKTKPREEQYNSTY RVVSVLTVLHQDWLNGKEYKCKVSNKALPAPIEKTISKA KGQPREPQVYTLPPSREEMTKNQVSLTCLVKGFYPSDIA VEWESNGQPENNYKTTPPVLDSDGSFFLYSKLTVDKSRW QQGNVFSCSVMHEALHNHYTQKSLSLSPGK |
| | Demci VL | 298 | DIVMTQSPDSLAVSLGERATISCRASESVDNYGISFMKW FQQKPGQPPKLLIYAASNQGSGVPDRFSGSGSGTDFTLT ISSLQAEDVAVYYCQQSKEVPWTFGGGTKVEIK |
| | Demci VL - CDR1 | 299 | RASESVDNYGISFMK |
| | Demci VL - CDR2 | 300 | AASNQGS |
| | Demci VL - CDR3 | 301 | QQSKEVPWT |
| | Bevci VH | 302 | EVQLVESGGGLVQPGGSLRLSCAASGYTFTNYGMNWVRQ APGKGLEWVGWINTYTGEPTYAADFKRRFTFSLDTSKST AYLQMNSLRAEDTAVYYCAKYPHYYGSSHWYFDVWGQGT LVTVSS |
| | Bevci VH - CDR1 | 303 | NYGMN |
| | Bevci VH - CDR2 | 304 | WINTYTGEPTYAADFKR |
| | Bevci VH - CDR3 | 305 | YPHYYGSSHWYFDV |
| | Short Chain #1 (Demci VH-CH1h) | 306 | MEFGLSWLFLVAILKGVQCQVQLVQSGAEVKKPGASVKI SCKASGYSFTAYYIHWVKQAPGQGLEWIGYISSYNGATN YNQKFKGRVTFTTDTSTSTAYMELRSLRSDDTAVYYCAR DYDYDVGMDYWGQGTLVTVSSASTKGPSVFPLAPSSKST SGGTAALGCLVKDYFPEPVTVSWNSGALTSGVHTFPAVL QSSGLYSLSSVVTVPSSSLGTQTYICNVNHKPSNTKVDK KVEPKSC |
| | Demci VH | 307 | QVQLVQSGAEVKKPGASVKISCKASGYSFTAYYIHWVKQ APGQGLEWIGYISSYNGATNYNQKFKGRVTFTTDTSTST AYMELRSLRSDDTAVYYCARDYDYDVGMDYWGQGTLVTV SS |

TABLE 50-continued

Amino acid sequences of additional exemplary FIT-Ig for HER3 and IGF-IR

| Name Target (mAb) mAb1 (upper domain)/mAb2 (lower domain) | Protein region | SEQ ID NO | Sequences |
|---|---|---|---|
| | Demci VH - CDR1 | 308 | AYYIH |
| | Demci VH - CDR2 | 309 | YISSYNGATNYNQKFKG |
| | Demci VH - CDR3 | 310 | DYDYDVGMDY |
| | Short Chain #2 (Bevci VL-hCk)) | 311 | MDMRVPAQLLGLLLLWFPGSRCDIQMTQSPSSLSASVGD RVTITCSASQDISNYLNWYQQKPGKAPKVLIYFTSSLHS GVPSRFSGSGSGTDFTLTISSLQPEDFATYYCQQYSTVP WTFGQGTKVEIKRTVAAPSVFIFPPSDEQLKSGTASVVC LLNNFYPREAKVQWKVDNALQSGNSQESVTEQDSKDSTY SLSSTLTLSKADYEKHKVYACEVTHQGLSSPVTKSFNRG EC |
| | Bevci VL | 312 | DIQMTQSPSSLSASVGDRVTITCSASQDISNYLNWYQQK PGKAPKVLIYFTSSLHSGVPSRFSGSGSGTDFTLTISSL QPEDFATYYCQQYSTVPWTFGQGTKVEIK |
| | Bevci VL - CDR1 | 313 | SASQDISNYLN |
| | Bevci VL - CDR2 | 314 | FTSSLHS |
| | Bevci VL - CDR3 | 315 | QQYSTVPWT |

TABLE 51

SEC Profile/Expression level in 293E cells:

| FIT-Ig | Monomer % in SEC | Expression level (mg/L) |
|---|---|---|
| FIT017a | >82% | 2.2 |

Functional Studies

Functional Binding Study:

Functional binding data for FIT017a is provided below in Table 52.

TABLE 52

Functional binding data

| Ig | Target | Kon | Koff | KD | IC50 |
|---|---|---|---|---|---|
| demcizumab | 1 (DLL4) | 1.74E+05 | 1.28E-04 | 7.36E-09 | |
| FIT017a | | 1.88E+05 | 1.28E-04 | 6.81E-09 | |

TABLE 52-continued

Functional binding data

| Ig | Target | Kon | Koff | KD | IC50 |
|---|---|---|---|---|---|
| bevcizumab | 2 (VEGF) | 3.46E+05 | 2.43E-06 | 7.04E-12 | |
| FIT017a | | 3.50E+05 | 1.28E-05 | 3.65E-11 | |

Figure 28:
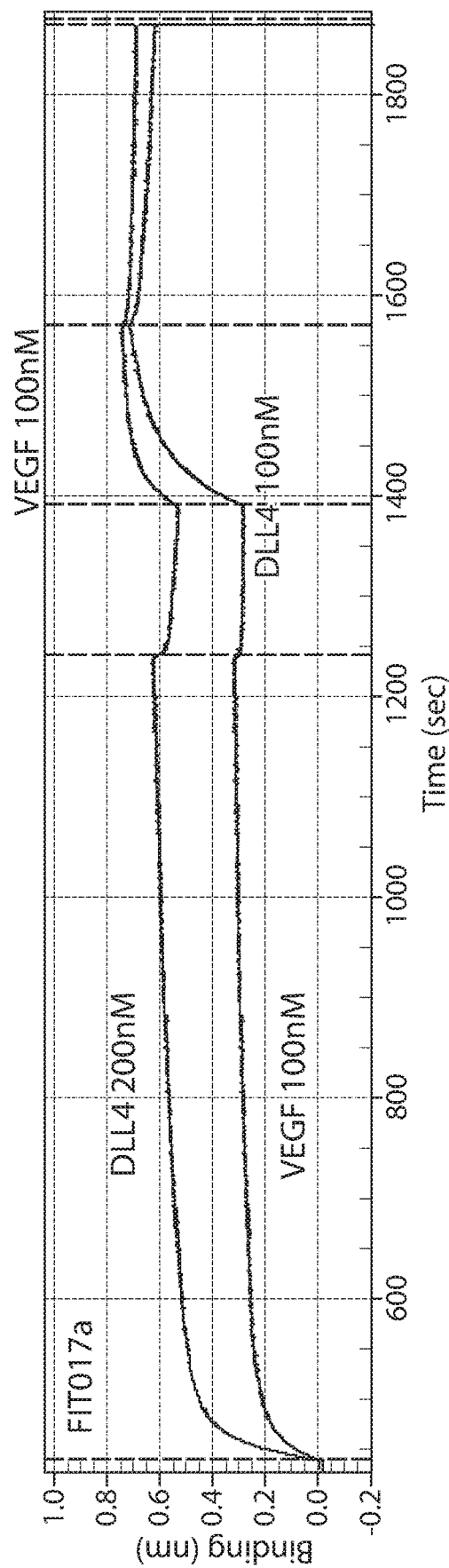
FIG. 28 shows a multiple binding study of FIT017a against both DLL4 and VEGF Binding to DLL4 followed by VEGF; and binding by VEGF followed by DLL4 are both shown as indicated.

Multiple-Antigen Binding Study:

this study was done using OctetRed to determine if FIT017a is able to bind DLL4 and VEGF simultaneously. This experiment shows that FIT017a is able to bind DLL4 when it had already bound to VEGF, indicating that FIT017a is able to bind both DLL4 and VEGF simultaneously, see FIG. 28.

Example 12: Study of Anti-CD20/CD3 Fabs-in-Tandem Immunoglobulin (FIT-Ig)

FIT-Ig having specificity for CD20 and CD3 was constructed as in the foregoing Examples. This exemplary FIT-Ig and its corresponding sequences are provided below in Table 53. Table 54 provides the expression level in 293E cells and the SEC profile for the FIT-Ig.

TABLE 53

Amino acid sequences of additional exemplary FIT-Ig for CD20 and CD3

| Name Target (mAb) mAb1 (upper domain)/mAb2 (lower domain) | Protein region | SEQ ID NO | Sequences |
|---|---|---|---|
| FIT018a CD20(Ofatumumab)/ CD3 mAb (described in US2009/0252683, incorporated by reference) | Long Chain (OfatuVL-hCk-CD3mAb VH-hCg1mut) | 316 | MDMRVFAQLLGLLLLWFPGSRCEIVLTQSPATLSLSPG ERATLSCRASQSVSSYLAWYQQKPGQAPRLLIYDASNR ATGIPARFSGSGSGTDFTLTISSLEPEDFAVYYCQQRS NWPITFGQGTRLEIKRTVAAPSVFIFPPSDEQLKSGTA SVVCLLNNFYPREAKVQWKVDNALQSGNSQESVTEQDS KDSTYSLSSTLTLSKADYEKHKVYACEVTHQGLSSPVT KSFNRGECEVQLLESGGGLVQPGGSLKLSCAASGFTFN TYAMNWVRQAPGKGLEWVARIRSKYNNYATYYADSVKD RFTISRDDSKNTAYLQMNNLKTEDTAVYYCVRHGNFGN SYVSWFAYWGQGTLVTVSSASTKGPSVFPLAPSSKSTS GGTAALGCLVKDYFPEPVTVSWNSGALTSGVHTFPAVL QSSGLYSLSSVVTVPSSSLGTQTYICNVNHKPSNTKVD KKVEPKSCDKTHTCPPCPAPEAAGGPSVFLFPPKPKDT LMISRTPEVTCVVVDVSHEDPEVKFNWYVDGVEVHNAK |

TABLE 53-continued

Amino acid sequences of additional exemplary FIT-Ig for CD20 and CD3

| Name Target (mAb) mAb1 (upper domain)/mAb2 (lower domain) | Protein region | SEQ ID NO | Sequences |
|---|---|---|---|
| | | | TKPREEQYNSTYRVVSVLTVLHQDWLNGKEYKCKVSNK ALPAPIEKTISKAKGQPREPQVYTLPPSREEMTKNQVS LTCLVKGFYPSDIAVEWESNGQPENNYKTTPPVLDSDG SFFLYSKLTVDKSRWQQGNVFSCSVMHEALHNHYTQKS LSLSPGK |
| | Ofatu VL | 317 | EIVLTQSPATLSLSPGERATLSCRASQSVSSYLAWYQQ KPGQAPRLLIYDASNRATGIPARFSGSGSGTDFTLTIS SLEPEDFAVYYCQQRSNWPITFGQGTRLEIK |
| | OfatuVL - CDR1 | 318 | RASQSVSSYLA |
| | OfatuVL - CDR2 | 319 | DASNRAT |
| | OfatuVL - CDR3 | 320 | QQRSNWPIT |
| | CD3mAb VH | 321 | EVQLLESGGGLVQPGGSLKLSCAASGFTFNTYAMNWVR QAPGKGLEWVARIRSKYNNYATYYADSVKDRFTISRDD SKNTAYLQMNNLKTEDTAVYYCVRHGNFGNSYVSWFAY WGQGTLVTVSS |
| | CD3mAb VH - CDR1 | 322 | TYAMN |
| | CD3mAb VH - CDR2 | 323 | RIRSKYNNYATYYADSVKD |
| | CD3mAb VH - CDR3 | 324 | HGNFGNSYVSWFAY |
| | Short Chain #1 (Ofatu VH-CH1) | 325 | MEFGLSWLFLVAILKGVQCEVQLVESGGGLVQPGRSLR LSCAASGETFNDYAMHWVRQAPGKGLEWVSTISWNSGS IGYADSVKGRFTISRDNAKKSLYLQMNSLRAEDTALYY CAKDIQYGNYYYGMDVWGQGTTVTVSS**ASTKGPSVFPL APSSKSTSGGTAALGCLVKDYFPEPVTVSWNSGALTSG VHTFPAVLQSSGLYSLSSVVTVPSSSLGTQTYICNVNH KPSNTKVDKKVEPKSC |
| | Ofatu VH | 326 | EVQLVESGGGLVQPGRSLRLSCAASGFTFNDYAMHWVR QAPGKGLEWVSTISWNSGSIGYADSVKGRFTISRDNAK KSLYLQMNSLRAEDTALYYCAKDIQYGNYYYGMDVWGQ GTTVTVSS |
| | Ofatu VH - CDR1 | 327 | DYAMH |
| | Ofatu VH - CDR2 | 328 | TISWNSGSIGYADSVKG |
| | Ofatu VH - CDR3 | 329 | DIQYGNYYYGMDV |
| | Short Chain #2 (CD3mAb VL-hCL) | 330 | MTWTPLLFLTLLLHCTGSLSELVVTQEPSLTVSPGGTV TLTCRSSTGAVTTSNYANWVQQKPGQAPRGLIGGTNKR APGTPARFSGSLLGGKAALTLSGVQPEDEAEYYCALWY SNLWVFGGGTKLTVLGQPKAAPSVTLFPPSSEELQANK ATLVCLISDFYPGAVTVAWKADSSPVKAGVETTTPSKQ SNNKYAASSYLSLTPEQWKSHRSYSCQVTHEGSTVEKT VAPTECS |
| | CD3mAb VL | 331 | ELVVTQEPSLTVSPGGTVTLTCRSSTGAVTTSNYANWV QQKPGQAPRGLIGGTNKRAPGTPARFSGSLLGGKAALT LSGVQPEDEAEYYCALWYSNLWVFGGGTKLTVL |
| | CD3mAb VL - CDR1 | 332 | RSSTGAVTTSNYAN |
| | CD3mAb VL - CDR2 | 333 | GTNKRAP |
| | CD3mAb VL - CDR3 | 334 | ALWYSNLWV |

TABLE 54

| SEC Profile/Expression level in 293E cells: | | |
|---|---|---|
| FIT-Ig | Monomer % in SEC | Expression level (mg/L) |
| FIT017a | 97.03% | 7.8 |

Functional Studies

Functional Binding Study:

Functional binding data for FIT018a is provided below in Table 55.

TABLE 55

| Functional binding data | | | | |
|---|---|---|---|---|
| Ig | Target | Kon | Koff | KD IC50 |
| Ofatumumab FIT018a | 1 (CD20) | | | |
| CD3 mAb | 2 (CD3e) | 6.69E+05 | 8.86E-05 | 1.32E-10 |
| FIT018a | | 7.79E+05 | 1.22E-04 | 1.57E-10 |

Figure 29A:
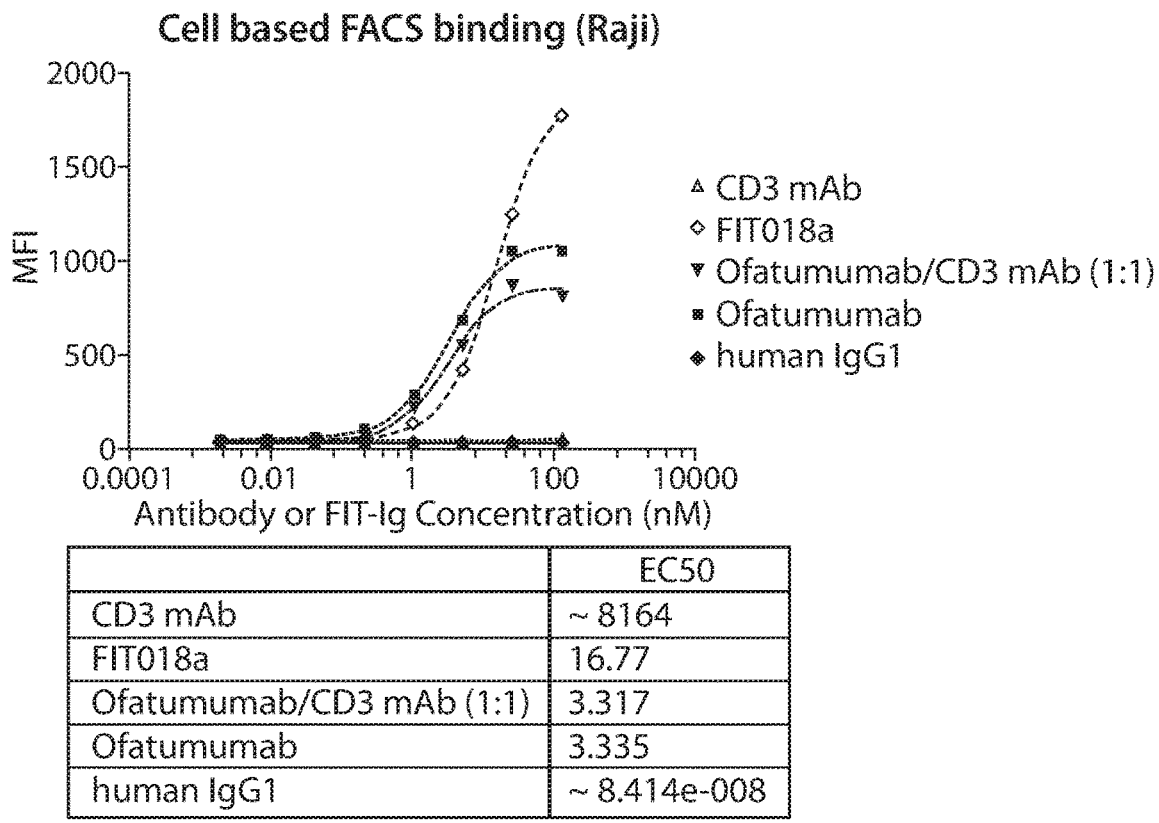
FIG. 29A and FIG. 29B show cell based FACS binding assays of FIT018a compared to its related parental antibodies (CD3 mAb, Ofatumumab, and a combination of CD3 mAb and Ofatumumab), and human IgG1 for their ability of binding to CD20 and CD3 on human B cells and human T cells. In the assay of FIG. 29A, human B cell line Raji was used. In the assay of FIG. 29B, human T cell line Jurkat was used.
Figure 29B:
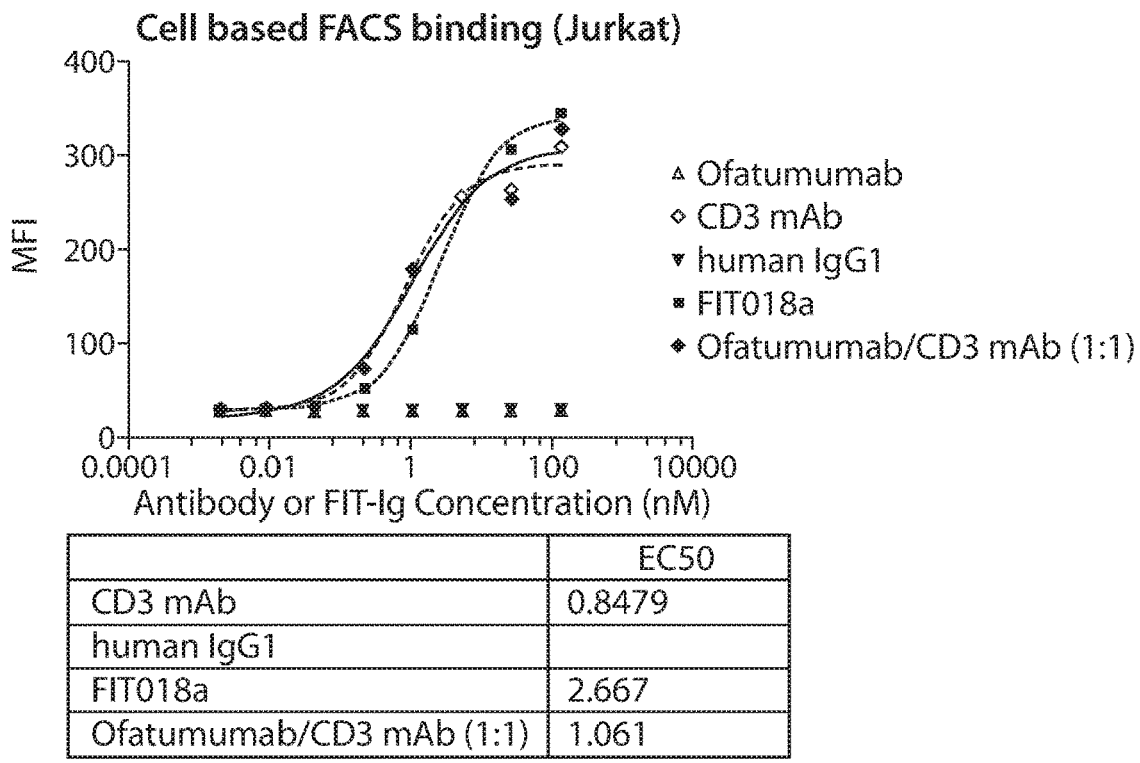
Figure 30A:
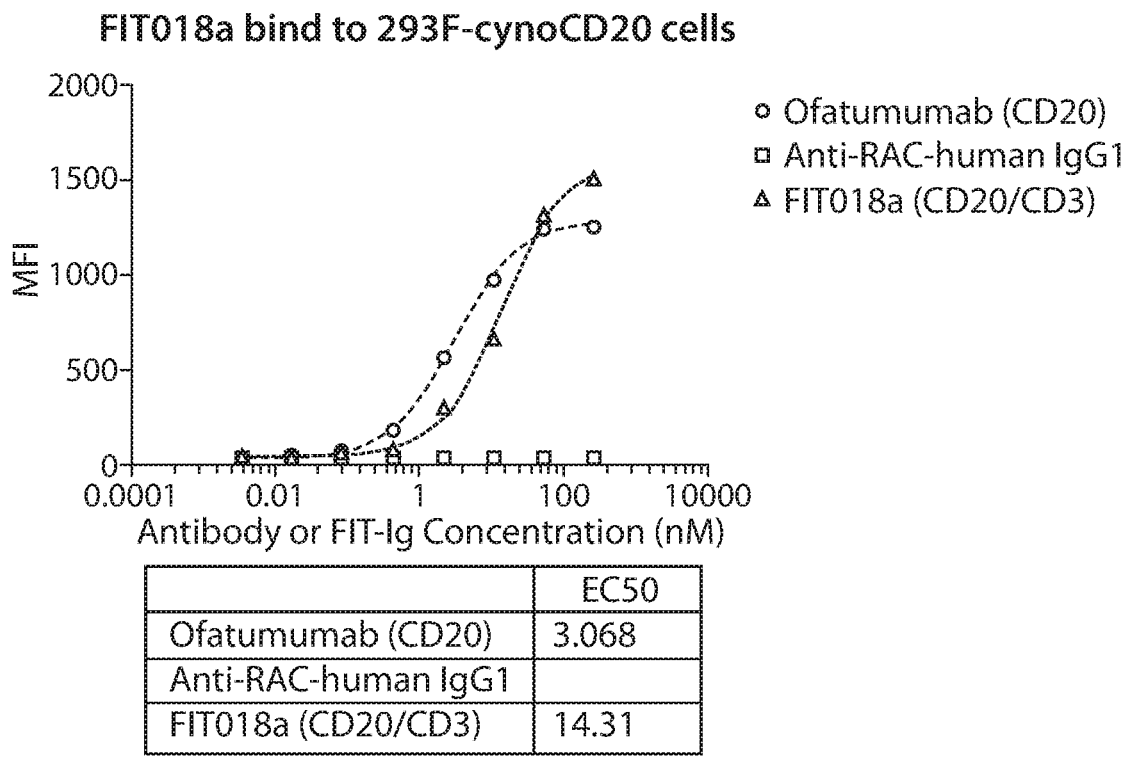
FIG. 30A shows cell based FACS binding assays of FIT018a compared to ofatumumab (CD20) and anti-RAC-human IgG1 for their ability of binding to cynomologus CD20 cells.
Figure 30B:
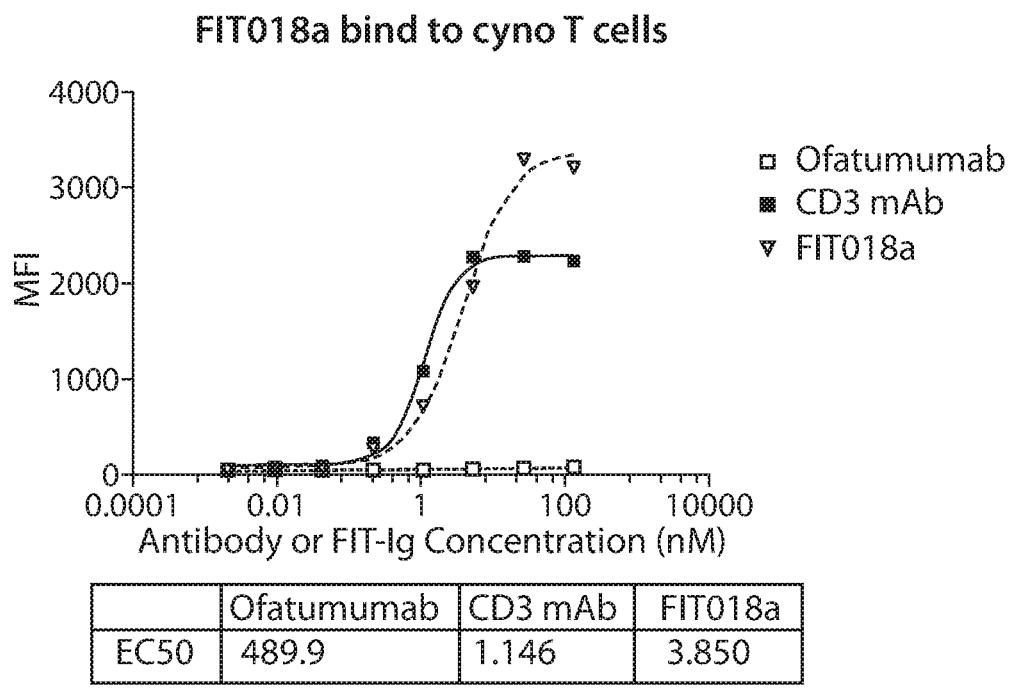
FIG. 30B shows cell based FACS binding assays of FIT018a compared to ofatumumab (CD20), CD3 mAb for their ability of binding to cynomolgus T cells.

Cell Based Binding Study:

The binding activity of FIT018a to human or cynomolgus B cell and T cell were determined by flow cytometry using BD FACSVerse. Raji cell was used for detecting human B cell binding. Jurakt cell was used for detecting human T cell binding. Primary cynomolgus T cell was used for detecting cynomolgus T cell binding. HEK 293 cell transit transfected with cynoCD20 was used for detecting cynomolgus B cell binding. Cells were washed in PBS buffer containing 2% FBS. Cells were then aliquot and incubated with 1:5 serially diluted FIT018a on ice for 1 hr. The starting working concentration of FIT018a was 20 µg/ml. Cells were washed, resuspended and incubated with 1:100 diluted Alexa Fluor® 488 labeled mouse anti-human IgG1 (Invitrogen, Cat. No. A-10631) on ice protected from light for 1 hr. Cells were washed and signal was detected with a BD FACSVerse flow cytometer according to manufacture's protocols. These experiments demonstrate that FIT018a can bind to human B cell and T cell (Raji is human B cell line and Jurkat is human T cell line), see FIG. 29A and FIG. 29B. FIT018a can also bind to cynomolgus CD20 and CD3, see FIG. 30A and FIG. 30B.

Figure 31A:
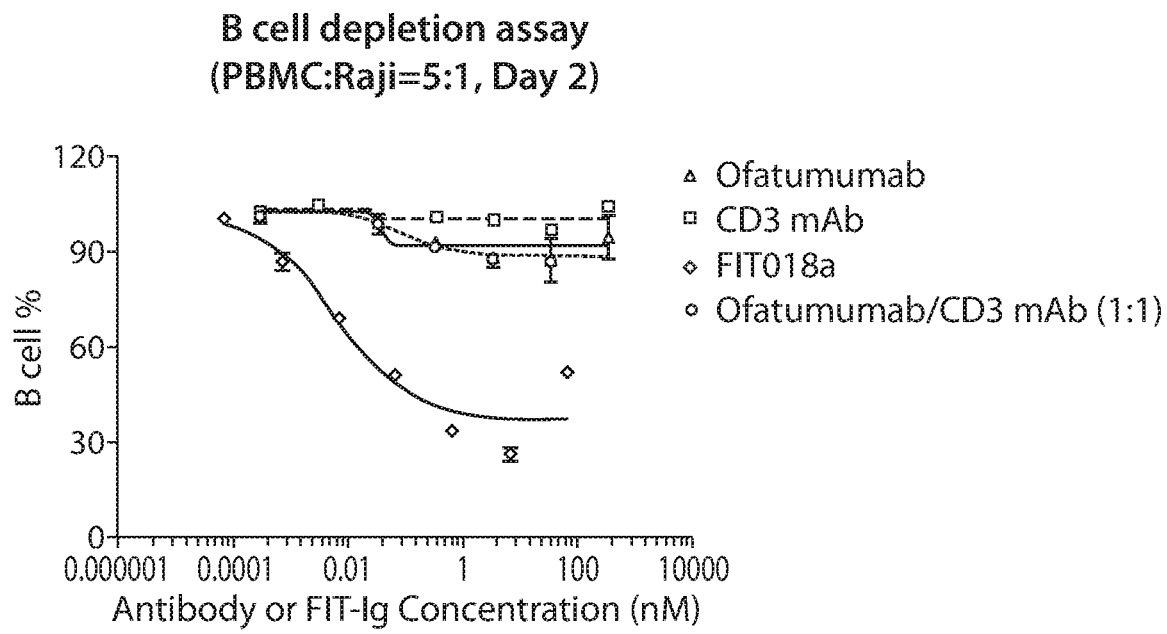
FIG. 31A and FIG. 31B show the ability of FIT018a, Ofatumumab, CD3 mAb, and a combination ofatumumab and CD3 mAb (1:1) in inducing apoptosis of human B cell (Raji) at day 2 (FIG. 31A) and day 3 (FIG. 31B), as measured in B-cell depletion assays.
Figure 31B:
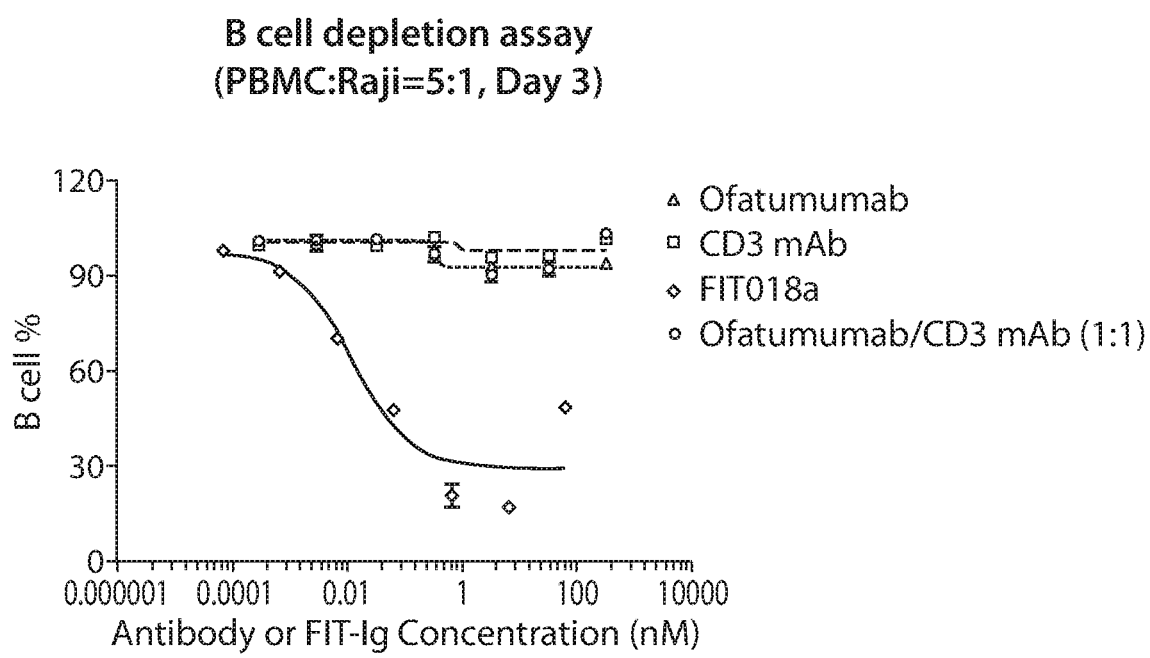

B-Cell Depletion Assay:

The in vitro activity of FIT018a was measured by B-cell depletion assay. Human PBMCs were isolated by Ficoll Paque Plus (GE HEALTHCARE, cat: GE17144002) according to manufacture's instruction. Target cell Raji was harvested and seeded to assay plate at $5 \times 10^4$ per well. Antibodies were serially diluted and added to assay plate. $2.5 \times 10^5$ per well PBMCs were added to assay plate and incubate for 2 days or 3 days. After incubation, B cell was detected by anti-CD19 antibody using FACS machine. The experiments demonstrate that FIT018a can induce B cell apoptosis, see FIG. 31A and FIG. 31B.

Example 13: Study of Anti-HER3/EGFR Fabs-in-Tandem Immunoglobulin (FIT-Ig)

FIT-Ig having specificity for HER3 and EGFR was constructed as in the foregoing Examples. This exemplary FIT-Ig and corresponding sequences are provided below in Table 56. Table 57 provides the expression level in 293E cells and the SEC profile for the FIT-Ig.

TABLE 56

| Amino acid sequences of additional exemplary FIT-Ig for HER3 and EGFR | | | |
|---|---|---|---|
| Name Target (mAb) mAb1 (upper domain)/mAb2 (lower domain) | Protein region | SEQ ID NO | Sequences |
| FIT019a - Ig HER3 (patritumab/ EGFR (Panitumumab) | Long Chain (patritu VL-hCk-PaniVH-hCg1) | 335 | MDMRVPAQLLGLLLLWFPGSRCDIEMTQSPDSLAVSLGE RATINC<u>RSSQSVLYSSSNRNYLA</u>WYQQNPGQPPKLLIYW <u>ASTRES</u>GVPDRFSGSGSGTDFTLTISSLQAEDVAVYYC<u>Q</u> <u>QYYSTPRT</u>FGQGTKVEIKRTVAAPSVFIFPPSDEQLKSG TASVVCLLNNFYPREAKVQWKVDNALQSGNSQESVTEQD SKDSTYSLSSTLTLSKADYEKHKVYACEVTHQGLSSPVT KSFNRGECQVQLQESGPGLVKPSETLSLTCTVSGGSVS<u>S</u> <u>GDYYWTW</u>IRQSPGKGLEWIG<u>HIYYSGNTNYNPSLKS</u>RLT ISIDTSKTQFSLKLSSVTAADTAIYYCVR<u>DRVTGAFDIW</u> GQGTMVTVSSASTKGPSVFPLAPSSKSTSGGTAALGCLV KDYFPEPVTVSWNSGALTSGVHTFPAVLQSSGLYSLSSV VTVPSSSLGTQTYICNVNHKPSNTKVDKKVEPKSCDKTH TCPPCPAPELLGGPSVFLFPPKPKDTLMISRTPEVTCVV VDVSHEDPEVKFNWYVDGVEVHNAKTKPREEQYNSTYRV VSVLTVLHQDWLNGKEYKCKVSNKALPAPIEKTISKAKG QPREPQVYTLPPSREEMTKNQVSLTCLVKGFYPSDIAVE WESNGQPENNYKTTPPVLDSDGSFFLYSKLTVDKSRWQQ GNVFSCSVMHEALHNHYTQKSLSLSPGK |
| | patritu VL | 336 | DIEMTQSPDSLAVSLGERATINC<u>RSSQSVLYSSSNRNYL</u> <u>A</u>WYQQNPGQPPKLLIY<u>WASTRES</u>GVPDRFSGSGSGTDFT LTISSLQAEDVAVYYC<u>QQYYSTPRT</u>FGQGTKVEIK |
| | patritu VL - CDR1 | 337 | <u>RSSQSVLYSSSNRNYLA</u> |
| | patritu VL - CDR2 | 338 | <u>WASTRES</u> |
| | patritu VL - CDR3 | 339 | <u>QQYYSTPRT</u> |
| | PaniVH | 340 | QVQLQESGPGLVKPSETLSLTCTVSGGSVS<u>SGDYYWTW</u>I RQSPGKGLEWIG<u>HIYYSGNTNYNPSLKS</u>RLTISIDTSKT QFSLKLSSVTAADTAIYYCVR<u>DRVTGAFDIW</u>GQGTMVTV SS |

TABLE 56-continued

Amino acid sequences of additional exemplary FIT-Ig for HER3 and EGFR

| Name Target (mAb) mAb1 (upper domain)/mAb2 (lower domain) | Protein region | SEQ ID NO | Sequences |
|---|---|---|---|
| | Pani VH - CDR1 | 341 | SGDYYWT |
| | Pani VH - CDR2 | 342 | HIYYSGNTNYNPSLKS |
| | Pani VH - CDR3 | 343 | DRVTGAFDI |
| | Short Chain #1 (Patritumab VH-CH1) | 344 | MEFGLSWLFLVAILKGVQCQVQLQQWGAGLLKPSETLSLTCAVYGGSFSGYYWSWIRQPPGKGLEWIGEINHSGSTNYNPSLKSRVTISVETSKNQFSLKLSSVTAADTAVYYCARDKWTWYFDLWGRGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | Patritumab VH | 345 | QVQLQQWGAGLLKPSETLSLTCAVYGGSFSGYYWSWIRQPPGKGLEWIGEINHSGSTNYNPSLKSRVTISVETSKNQFSLKLSSVTAADTAVYYCARDKWTWYFDLWGRGTLVTVSS |
| | Patritumab VH - CDR1 | 346 | GYYWS |
| | Patritumab VH - CDR2 | 347 | EINHSGSTNYNPSLKS |
| | Patritumab VH - CDR3 | 348 | DKWTWYFDL |
| | Short Chain #2 (Pani VL-hCk) | 349 | MDMRVPAQLLGLLLLWFPGSRCDIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | Pani VL | 350 | DIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIK |
| | Pani VL - CDR1 | 351 | QASQDISNYLN |
| | Pani VL - CDR2 | 352 | DASNLET |
| | Pani VL - CDR3 | 353 | QHFDHLPLA |
| FIT019b - Ig EGFR (Panitumumab)/ HER3 (patritumab) | Long Chain (Panitu VL-hCk-Patritu-hCg1) | 354 | MDMRVPAQLLGLLLLWFPGSRCDIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECQVQLQQWGAGLLKPSETLSLTCAVYGGSFSGYYWSWIRQPPGKGLEWIGEINHSGSTNYNPSLKSRVTISVETSKNQFSLKLSSVTAADTAVYYCARDKWTWYFDLWGRGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | Panitu VL | 355 | DIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIK |
| | Panitu VL - CDR1 | 356 | QASQDISNYLN |
| | Panitu VL - CDR2 | 357 | DASNLET |
| | Panitu VL - CDR3 | 358 | QHFDHLPLA |
| | PatrituVH | 359 | QVQLQQWGAGLLKPSETLSLTCAVYGGSFSGYYWSWIRQPPGKGLEWIGEINHSGSTNYNPSLKSRVTISVETSKNQFSLKLSSVTAADTAVYYCARDKWTWYFDLWGRGTLVTVSS |
| | Patritu VH - CDR1 | 360 | GYYWS |
| | Patritu VH - CDR2 | 361 | EINHSGSTNYNPSLKS |
| | Patritu VH - CDR3 | 362 | DKWTWYFDL |
| | Short Chain #1 (Panitu VH-CH1) | 363 | MEFGLSWLFLVAILKGVQCQVQLQESGPGLVKPSETLSLTCTVSGGSVSSGDYYWTWIRQSPGKGLEWIGHIYYSGNTNYNPSLKSRLTISIDTSKTQFSLKLSSVTAADTAIYYCVRDRVTGAFDIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |

TABLE 56-continued

Amino acid sequences of additional exemplary FIT-Ig for HER3 and EGFR

| Name Target (mAb) mAb1 (upper domain)/mAb2 (lower domain) | Protein region | SEQ ID NO | Sequences |
|---|---|---|---|
| | Panitu VH | 364 | QVQLQESGPGLVKPSETLSLTCTVSGGSVSSGDYYWTI RQSPGKGLEWIGHIYYSGNTNYNPSLKSRLTISIDTSKT QFSLKLSSVTAADTAIYYCVRDRVTGAFDIWGQGTMVTV SS |
| | Panitu VH - CDR1 | 365 | DYYWT |
| | Panitu VH - CDR2 | 366 | HIYYSGNTNYNPSLKS |
| | Panitu VH - CDR3 | 367 | DRVTGAFDI |
| | Short Chain #2 (Patritu VL-hCk) | 368 | MDMRVPAQLLGLLLLWFPGSRCDIEMTQSPDSLAVSLGE RATINCRSSQSVLYSSSNRNYLAWYQQNPGQPPKLLIYW ASTRESGVPDRFSGSGSGTDFTLTISSLQAEDVAVYYCQ QYYSTPRTFGQGTKVEIKRTVAAPSVFIFPPSDEQLKSG TASVVCLLNNFYPREAKVQWKVDNALQSGNSQESVTEQD SKDSTYSLSSTLTLSKADYEKHKVYACEVTHQGLSSPVT KSFNRGEC |
| | Patritu VL | 369 | DIEMTQSPDSLAVSLGERATINCRSSQSVLYSSSNRNYL AWYQQNPGQPPKLLIYWASTRESGVPDRFSGSGSGTDFT LTISSLQAEDVAVYYCQQYYSTPRTFGQGTKVEIK |
| | Patritu VL - CDR1 | 370 | RSSQSVLYSSSNRNYLA |
| | Patritu VL - CDR2 | 371 | WASTRES |
| | Patritu VL - CDR3 | 372 | QQYYSTPRT |

TABLE 57

SEC Profile/Expression level in 293E cells:

| FIT-Ig | Monomer % in SEC | Expression level (mg/L) |
|---|---|---|
| FIT019a | >86% | 15.6 |
| FIT019b | 96.7% | 10.2 |

Functional Studies

Functional Binding Study:

Functional binding data for FIT019a and FIT019b is provided below in Table 58 and Table 59, respectively.

TABLE 58

Functional binding data of FIT019a

| Ig | Target | Kon | Koff | KD | IC50 |
|---|---|---|---|---|---|
| Patritumab | 1(Her3) | 1.59E+05 | 4.80E−06 | 3.02E−11 | |
| FIT019a | | 1.57E+05 | 5.05E−06 | 3.21E−11 | |
| Panitumumab | 2(EGFR) | 4.45E+05 | 4.92E−04 | 1.10E−09 | |
| FIT019a | | 2.86E+05 | 3.91E−04 | 1.37E−09 | |

TABLE 59

Functional binding data of FIT019b

| Ig | Target | Kon | Koff | KD | IC50 |
|---|---|---|---|---|---|
| Panitumumab | 1(EGFR) | 8.43E+04 | 5.10E−05 | 6.05E−10 | |
| FIT019b | | 2.84E+05 | 9.60E−05 | 3.38E−10 | |
| Patritumab | 2(Her3) | 3.17E+05 | 2.85E−04 | 9.00E−10 | |
| FIT019b | | 1.20E+05 | 2.37E−04 | 1.98E−09 | |

Figure 32:
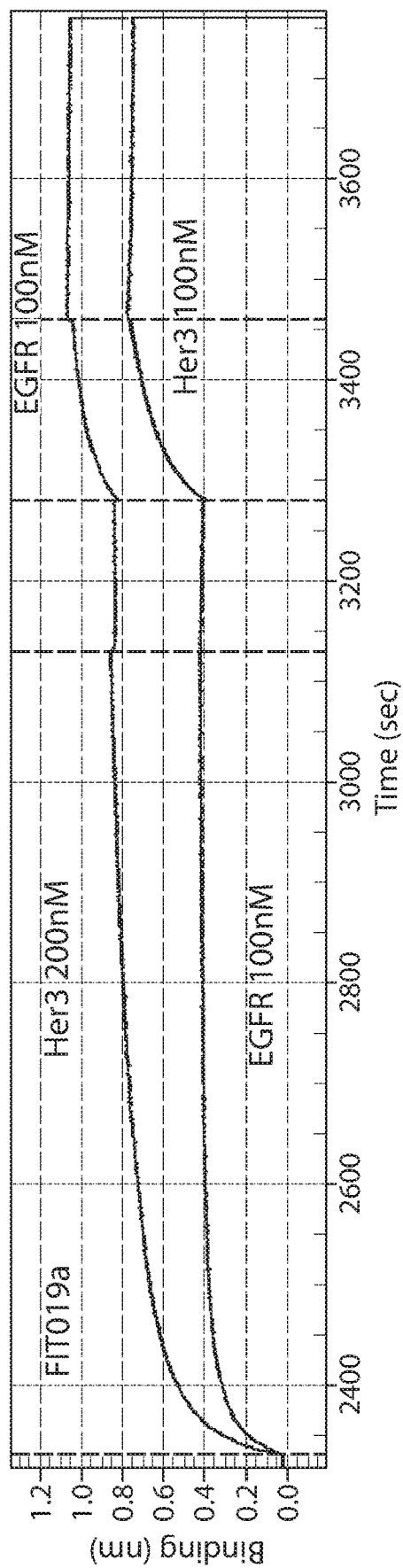
FIG. 32 shows a multiple binding study of FIT019a against both Her3 and EGFR. Binding to Her3 followed by EGFR, and binding by EGFR followed by Her3 are both shown as indicated.
Figure 33A:
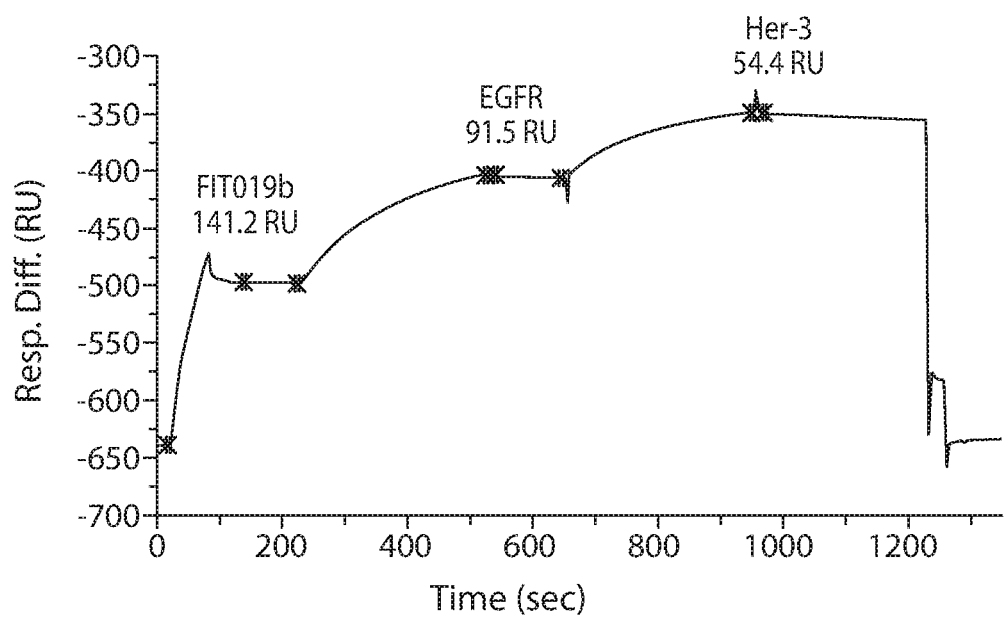
FIG. 33A and FIG. 33B show a multiple binding study of FIT019b against both Her3 and hEGFR. Binding to EGFR followed by Her3 (FIG. 33A); and binding by Her3 followed by EGFR (FIG. 33B) are both shown as indicated.
Figure 33B:
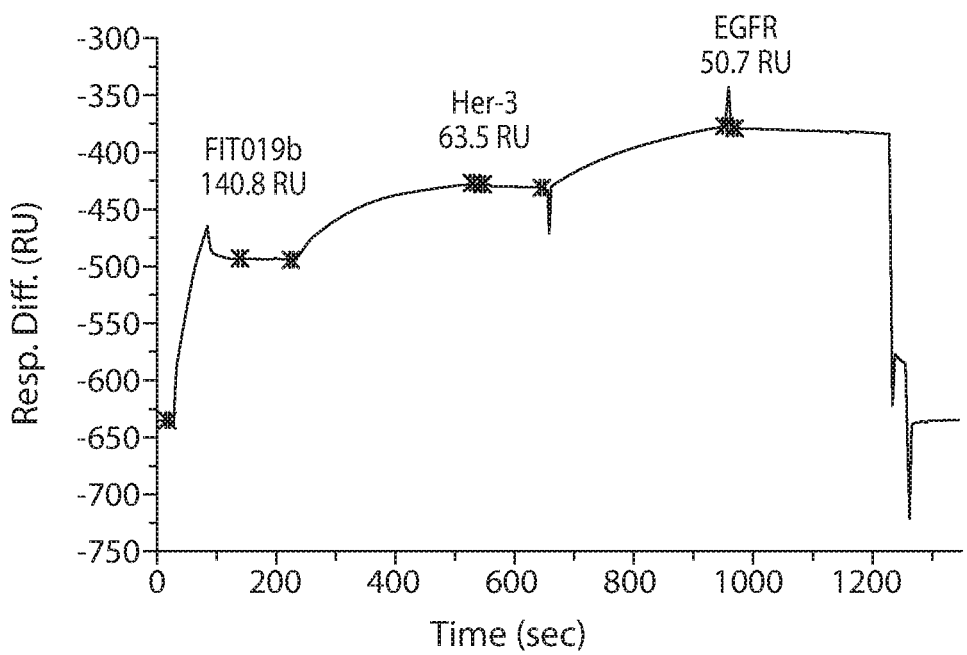

Multiple Binding Study:

A multiple binding study of FIT019a and FIT019b was carried out. The result is shown in FIG. 32 (FIT019a) and FIG. 33A to FIG. 33B (FIT019b), respectively. The result indicates that both FIT019a and FIT019b can bind to HER3 and EGFR simultaneously.

Example 14: Study of Anti-PD-L1/PD-1 Fabs-in-Tandem Immunoglobulin (FIT-Ig)

FIT-Ig having specificity for PD-L1 and PD-1 was constructed as in the foregoing Examples. This exemplary FIT-Ig and its corresponding sequences are provided below in Table 60. Table 61 provides the expression level in 293E cells and the SEC profile for the FIT-Ig.

TABLE 60

Amino acid sequences of additional exemplary FIT-Ig for PD-L1 and PD-1

| Name Target (mAb) mAb1 (upper domain)/mAb2 (lower domain) | Protein region | SEQ ID NO | Sequences |
|---|---|---|---|
| FIT020b PD-L1 (1B12)/PD-1 (nivolumab) | Long Chain (1B12 VL-hCk-Nivolu VH-hCg1Mut) | 373 | MDMRVPAQLLGLLLLWFPGSRCEIVLTQSPATLSLSPGE RATLSCRASQSVSSYLAWYQQKPGQAPRLLIYDASNRAT GIPARFSGSGSGTDFTLTISSLEPEDFAVYYCQQRSNWP TFGQGTKVEIKRTVAAPSVFIFPPSDEQLKSGTASVVCL LNNFYPREAKVQWKVDNALQSGNSQESVTEQDSKDSTYS LSSTLTLSKADYEKHKVYACEVTHQGLSSPVTKSFNRGE CQVQLVESGGGVVQPGRSLRLDCKASGITFSNSGMHWVR QAPGKGLEWVAVIWYDGSKRYYADSVKGRFTISRDNSKN |

TABLE 60-continued

Amino acid sequences of additional exemplary FIT-Ig for PD-L1 and PD-1

| Name Target (mAb) mAb1 (upper domain)/mAb2 (lower domain) | Protein region | SEQ ID NO | Sequences |
|---|---|---|---|
| | | | TLFLQMNSLRAEDTAVYYCATNDDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | 1B12 VL | 374 | EIVLTQSPATLSLSPGERATLSC<u>RASQSVSSYLA</u>WYQQKPGQAPRLLIY<u>DASNRAT</u>GIPARFSGSGSGTDFTLTISSLEPEDFAVYYC<u>QQRSNWPT</u>FGQGTKVEIK |
| | 1B12 VL – CDR1 | 375 | <u>RASQSVSSYLA</u> |
| | 1B12 VL – CDR2 | 376 | <u>DASNRAT</u> |
| | 1B12 VL – CDR3 | 377 | <u>QQRSNWPT</u> |
| | NivoluVH | 378 | QVQLVESGGGVVQPGRSLRLDCKASGITFS<u>NSGMH</u>WVRQAPGKGLEWVA<u>VIWYDGSKRYYADSVKG</u>RFTISRDNSKNTLFLQMNSLRAEDTAVYYCAT<u>NDDY</u>WGQGTLVTVSS |
| | NivoluVH – CDR1 | 379 | <u>NSGMH</u> |
| | NivoluVH – CDR2 | 380 | <u>VIWYDGSKRYYADSVKG</u> |
| | NivoluVH – CDR3 | 381 | <u>NDDY</u> |
| | Short Chain #1 (1B12 VH-CH1) | 382 | <u>MEFGLSWLFLVAILKGVQC</u>QVQLVQSGAEVEKPGSSVKVSCKTSGDIFS<u>SYAIS</u>WVRQAPGQGLEWMGG<u>IIPIFGRAH YAQKFQG</u>RVTITADESTSTAYMELSSLRSEDTAVYFCAR<u>KFHFVSGSPFGMDV</u>WGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | 1B12 VH | 383 | QVQLVQSGAEVKKPGSSVKVSCKTSGDTFS<u>SYAIS</u>WVRQAPGQGLEWMGG<u>IIPIFGRAHYAQKFQG</u>RVTITADESTSTAYMELSSLRSEDTAVYFCAR<u>KFHFVSGSPFGMDV</u>WGQGTTVTVSS |
| | 1B12 VH – CDR1 | 384 | <u>SYAIS</u> |
| | 1B12 VH – CDR2 | 385 | <u>GIIPIFGRAHYAQKFQG</u> |
| | 1B12 VH – CDR3 | 386 | <u>KFHFVSGSPFGMDV</u> |
| | Short Chain #2 (Nivolu VL-hCK) | 387 | <u>MDMRVPAQLLGLLLLWFPGSRC</u>EIVLTQSPATLSLSPGERATLSC<u>RASQSVSSYLA</u>WYQQKPGQAPRLLIY<u>DASNRAT</u>GIPARFSGSGSGTDFTLTISSLEPEDFAVYYC<u>QQSSNWPRT</u>FGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | Nivolu VL | 388 | EIVLTQSPATLSLSPGERATLSC<u>RASQSVSSYLA</u>WYQQKPGQAPRLLIY<u>DASNRAT</u>GIPARFSGSGSGTDFTLTISSLEPEDFAVYYC<u>QQSSNWPRT</u>FGQGTKVEIK |
| | Nivolu VL – CDR1 | 389 | <u>RASQSVSSYLA</u> |
| | Nivolu VL – CDR2 | 390 | <u>DASNRAT</u> |
| | Nivolu VL – CDR3 | 391 | <u>QQSSNWPRT</u> |

TABLE 61

SEC Profile/Expression level in 293E cells:

| FIT-Ig | Monomer % in SEC | Expression level (mg/L) |
|---|---|---|
| FIT020b | 100% | 6.2 |

Functional Studies

Affinity Measurement by Surface Plasmon Resonance:

The kinetics of FIT-Ig binding to rhPD-L1 and rhPD-1 was determined by surface plasmon resonance with a Biacore X100 instrument (Biacore AB, Uppsala, Sweden) using HBS-EP (10 mM HEPES, pH 7.4, 150 mM NaCl, 3 mM EDTA, and 0.005% surfactant P20) at 25° C. Briefly, for rhPD-L1 and rhPD-1 was directly immobilized at 40 RU across a CM5 research grade biosensor chip using a standard amine coupling kit according to manufacturer's instructions. Rate constants were derived by making kinetic binding measurements at seven different antigen concentrations ranging from 1 to 40 nM. The equilibrium dissociation constant (M) of the reaction between FIT-Ig and the target proteins was then calculated from the kinetic rate constants by the following formula: KD=koff/kon. Aliquots of FIT-Ig/Ab samples were also simultaneously injected over a blank reference and reaction CM surface to record and subtract any nonspecific binding background to eliminate the majority of the refractive index change and injection noise. Surfaces were regenerated with two subsequent 25 ml injections of 10 mM Glycine (pH 1.5) at a flow rate of 10 μL/min. Functional binding data for FIT020b is provided below in Table 62.

TABLE 62

Functional binding data

| Ig | Target | Kon | Koff | KD | IC50 |
|---|---|---|---|---|---|
| 1B12 | 1(PD-L1) | 6.77E+05 | 2.72E-04 | 4.02E-10 | |
| FIT020b | | 2.92E+05 | 1.85E-04 | 6.34E-10 | |
| Nivolumab | 2(PD1) | 5.00E+05 | 1.76E-04 | 3.52E-10 | |
| FIT020b | | 8.89E+04 | 3.02E-04 | 3.39E-09 | |

Figure 34A:
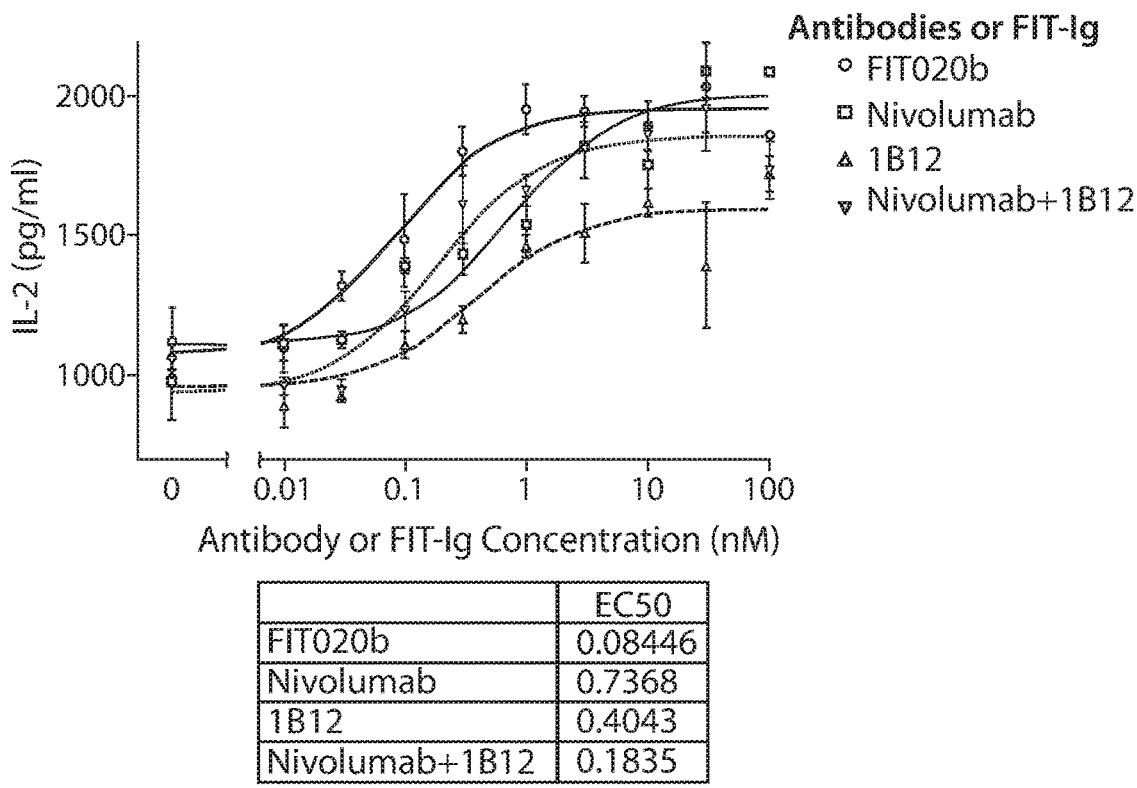
FIG. 34A shows functional activity of FIT020b in MLR assays, when compared to the parental antibody Nivolumab, 1B12 and a combination of Nivolumab and 1B12 (1:1) at a concentration of 0, 0.01, 0.1, 1, 10, or 100 nM, as measured by the level of induced IL-2.
Figure 34B:
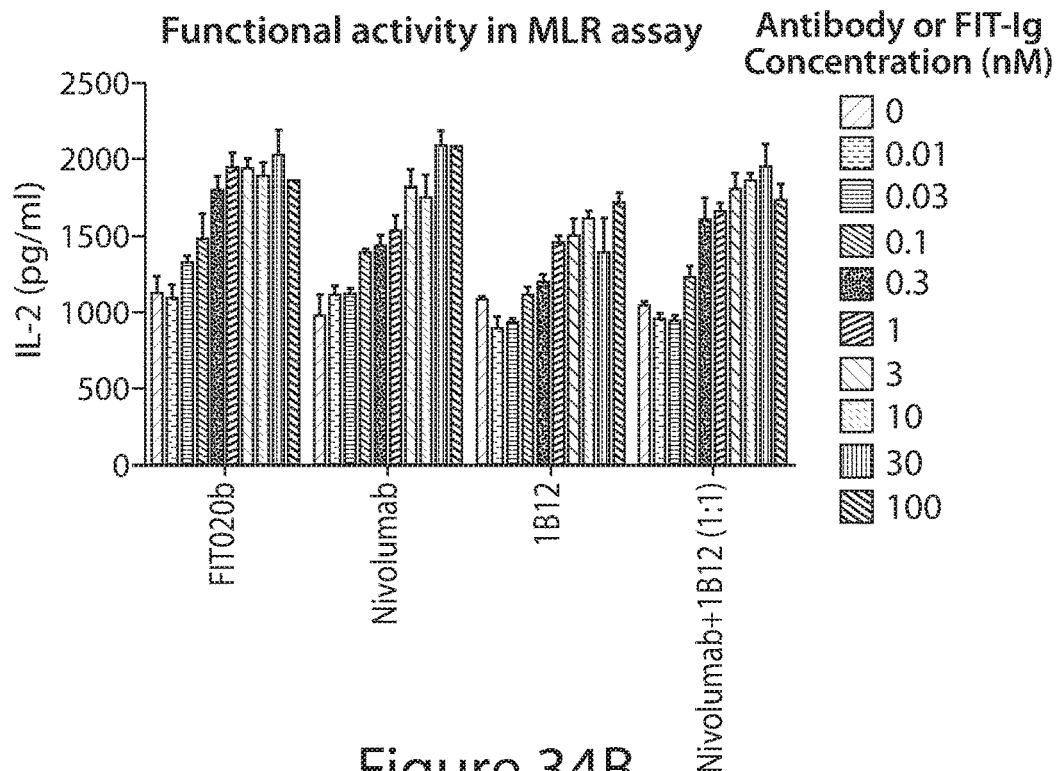
FIG. 34B shows the induction of IL-2 at a concentration of 0, 0.01, 0.03, 0.1, 0.3, 1, 3, 10, 30, and 100 nM by these antibodies.

Functional Activity Test by MLR Assay:

Mixed lymphocyte reaction was performed using monocyte-derived dendritic cells from one donor and allogeneic CD4 T cells from another donor. The whole blood samples were collected from healthy donors, and PBMC were isolated from whole blood using Ficoll-Pague gradient centrifugation. On day 1, PBMC from one donor was isolated and diluted with serum-free RPMI 1640 at $1\times10^6$/ml. The diluted PBMC was seeded into 6-well tissue culture plate at 3 ml/well and incubated for 3 h. Supernatant was removed and unattached cells were washed off. The attached monocyte were polarized into dendritic cells with 250 U/ml IL-4 and 500 U/ml GM-CSF in RPMI1640 with 10% FBS. The medium was replaced with fresh IL-4 and GM-CSF at day 4. At day 7, immature DC was collected and treated with Ipg/ml LPS in RPMI 1640 with 10% FBS for additional 24 h for maturation. At Day 8, CD4 T cells were isolated from another donor PBMC by negative selection and adjusted to final concentration at $2\times10^6$ cells/ml. Mature DC were treated with mitomycin C at 37° C. for 1.5 hr. Then DC were washed with PBS and adjusted to final concentration at $1\times10^6$ cells/ml. CD4 T cells (Responder cells) were added into 96 well plate at 100 μl/well and pre-treated with test antibody at diluted concentration for 30 minutes. Then mature DC (Stimulator cells) were added into the well at 100 μl/well. The final volume of each well is 200p1. The MLR were incubated at 37 degree for 72 hr for IL-2 test. The result is shown in FIG. 34A and FIG. 34B.

Figure 35:
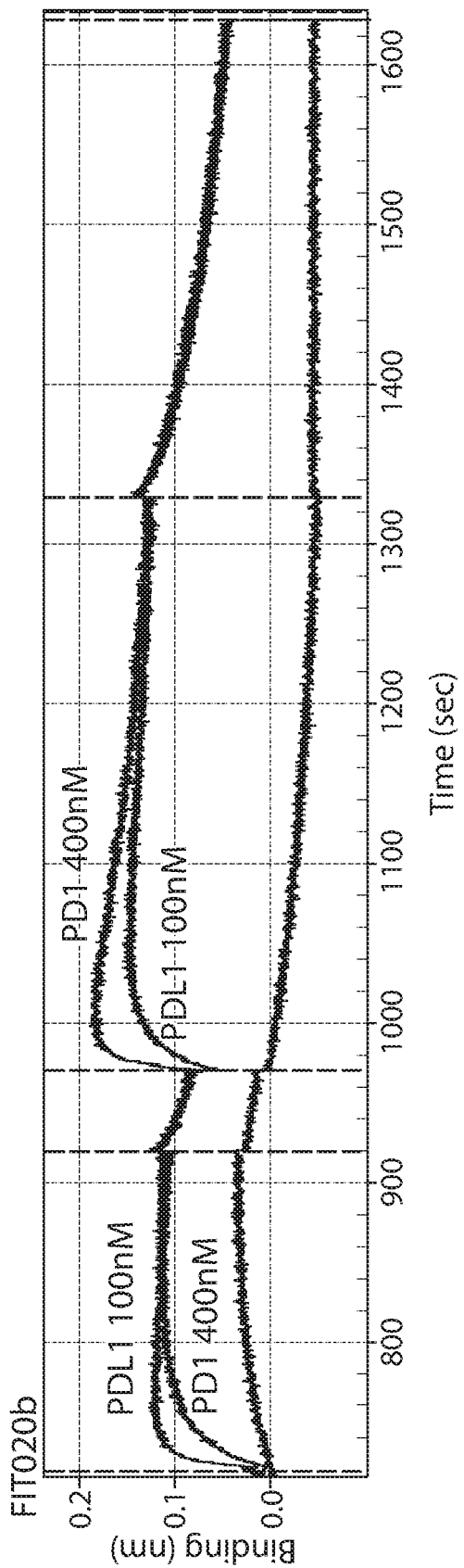
FIG. 35 shows a multiple binding study of FIT020b against both PD-L1 and PD-1. Binding to PD-L1 followed by PD-1; and binding by PD-1 followed by PD-L1 are both shown as indicated.

Multiple Binding Study:

A multiple binding study of FIT020b was carried out. The result is shown in FIG. 35. The result indicates that FIT020b can bind to PD-L1 and PD-1 simultaneously.

Example 15: Study of Anti-CD20/CD-22 Fabs-in-Tandem Immunoglobulin (FIT-Ig)

FIT-Ig having specificity for CD20 and CD22 was constructed as in the foregoing Examples. This exemplary FIT-Ig and its corresponding sequences are provided below in Table 63. Table 64 provides the expression level in 293E cells and the SEC profile for the FIT-Ig.

TABLE 63

Amino acid sequences of additional exemplary FIT-Ig for CD20 and CD22

| Name Target (mAb) mAb1 (upper domain)/mAb2 (lower domain) | Protein region | SEQ ID NO | Sequences |
|---|---|---|---|
| FIT021b CD20 (Ofatumumab)/ CD22 (Epratuzumab) | Long Chain (Ofatu VL-hCk-Epratu VH-hCg1) | 392 | MDMRVPAQLLGLLLLWFPGSRCEIVLTQSPATLSLSPGE RATLSC<u>RASQSVSSYLA</u>WYQQKPGQAPRLLIY<u>DASNRAT</u> GIPARFSGSGSGTDFTLTISSLEPEDFAVYYC<u>QQRSNWP</u> <u>IT</u>FGQGTRLEIKRTVAAPSVFIFPPSDEQLKSGTASVVC LLNNFYPREAKVQWKVDNALQSGNSQESVTEQDSKDSTY SLSSTLTLSKADYEKHKVYACEVTHQGLSSPVTKSFNRG ECQVQLVQSGAEVKKPGSSVKVSCKASGYTFT<u>SYWLH</u>WV RQAPGQGLEWIGYINPRNDYTEYNQNFKDKATITADEST NTAYMELSSLRSEDTAFYFCARR<u>DITTFY</u>FWGQGTTVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKKVEPKSCDKTHTCPPCPAPE LLGGPSVFLFPPKPKDTLMISRTPEVTCVVVDVSHEDPE VKFNWYVDGVEVHNAKTKPREEQYNSTYRVVSVLTVLHQ DWLNGKEYKCKVSNKALPAPIEKTISKAKGQPREPQVYT LPPSREEMTKNQVSLTCLVKGFYPSDIAVEWESNGQPEN NYKTTPPVLDSDGSFFLYSKLTVDKSRWQQGNVFSCSVM HEALHNHYTQKSLSLSPGK |
| | OfatuVL | 393 | EIVLTQSPATLSLSPGERATLSC<u>RASQSVSSYLA</u>WYQQK PGQAPRLLIY<u>DASNRAT</u>GIPARFSGSGSGTDFTLTISSL EPEDFAVYYC<u>QQRSNWPIT</u>FGQGTRLEIK |
| | Ofatu VL - CDR1 | 394 | <u>RASQSVSSYLA</u> |
| | Ofatu VL - CDR2 | 395 | <u>DASNRAT</u> |
| | Ofatu VL - CDR3 | 396 | <u>QQRSNWPIT</u> |
| | Epratu VH | 397 | QVQLVQSGAEVKKPGSSVKVSCKASGYTFT<u>SYWLH</u>WVRQ APGQGLEWIG<u>YINPRNDYTEYNQNFKD</u>KATITADESTNT AYMELSSLRSEDTAFYFCARR<u>DITTFY</u>WGQGTTVTVSS |
| | Epratu VH - CDR1 | 398 | <u>SYWLH</u> |
| | Epratu VH - CDR2 | 399 | <u>YINPRNDYTEYNQNFKD</u> |
| | Epratu VH - CDR3 | 400 | <u>RDITTFY</u> |
| | Short Chain #1 (Ofatu VH-CH1) | 401 | MEFGLSWLFLVAILKGVQCEVQLVESGGGLVQPGRSLRL SCAASGFTFN<u>DYAMH</u>WVRQAPGKGLEWVS<u>TISWNSGSIG</u> <u>YADSVKGRF</u>TISRDNAKKSLYLQMNSLRAEDTALYYCAK <u>DIQYGNYYYGMDV</u>WGQGTTVTVSSASTKGPSVFPLAPSS KSTSGGTAALGCLVKDYFPEPVTVSWNSGALTSGVHTFP AVLQSSGLYSLSSVVTVPSSSLGTQTYICNVNHKPSNTK VDKKVEPKSC |

TABLE 63-continued

Amino acid sequences of additional exemplary FIT-Ig for CD20 and CD22

| Name Target (mAb) mAb1 (upper domain)/mAb2 (lower domain) | Protein region | SEQ ID NO | Sequences |
|---|---|---|---|
| | Ofatu VH | 402 | EVQLVESGGGLVQPGRSLRLSCAASGFTFN<u>DYAMH</u>WVRQ APGKGLEWVS<u>TISWNSGSIGYADSVK</u>GRFTISRDNAKKS LYLQMNSLRAEDTALYYCAK<u>DIQYGNYYYGMDV</u>WGQGTT VTVSS |
| | Ofatu VH - CDR1 | 403 | <u>DYAMH</u> |
| | Ofatu VH - CDR2 | 404 | <u>TISWNSGSIGYADSVK</u> |
| | Ofatu VH - CDR3 | 405 | <u>DIQYGNYYYGMDV</u> |
| | Short Chain #2 (Epratu VL-hCk) | 406 | MDMRVPAQLLGLLLLWFPGSRCDIQLTQSPSSLSASVGD RVTMSCKSSQSVLYSANHKNYLAWYQQKPGKAPKLLIYW ASTRESGVPSRFSGSGSGTDFTFTISSLQPEDIATYYCH QYLSSWTFGGGTKLEIKRTVAAPSVFIFPPSDEQLKSGT ASVVCLLNNFYPREAKVQWKVDNALQSGNSQESVTEQDS KDSTYSLSSTLTLSKADYEKHKVYACEVTHQGLSSPVTK SFNRGEC |
| | Epratu VL | 407 | DIQLTQSPSSLSASVGDRVTMSC<u>KSSQSVLYSANHKNYL A</u>WYQQKPGKAPKLLIY<u>WASTRES</u>GVPSRFSGSGSGTDFT FTISSLQPEDIATYYC<u>HQYLSSWT</u>FGGGTKLEIK |
| | Epratu VL - CDR1 | 408 | <u>KSSQSVLYSANHKNYLA</u> |
| | Epratu VL - CDR2 | 409 | <u>WASTRES</u> |
| | Epratu VL - CDR3 | 410 | <u>HQYLSSWT</u> |

TABLE 64

SEC Profile/Expression level in 293E cells:

| FIT-Ig | Monomer % in SEC | Expression level (mg/L) |
|---|---|---|
| FIT021b | 100% | 4.9 |

Functional Studies

Figure 36A:
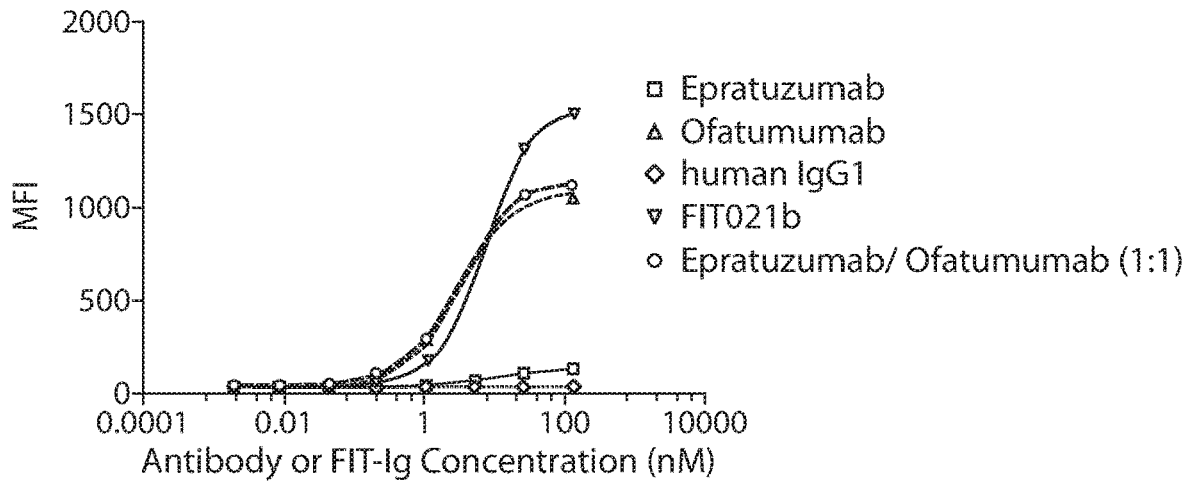
FIG. 36A and FIG. 36B show cell based FACS binding assays of FIT021b compared to its related parental antibodies (Ofatumumab, Epratuzumab, and a combination ofatumumab and Epratuzumab (1:1)), and human IgG1 for its ability of binding to human B cells. In the assay of FIG. 36A, human B cell line Raji was used. In the assay of FIG. 36B, human B cell line Daudi was used.
Figure 36B:
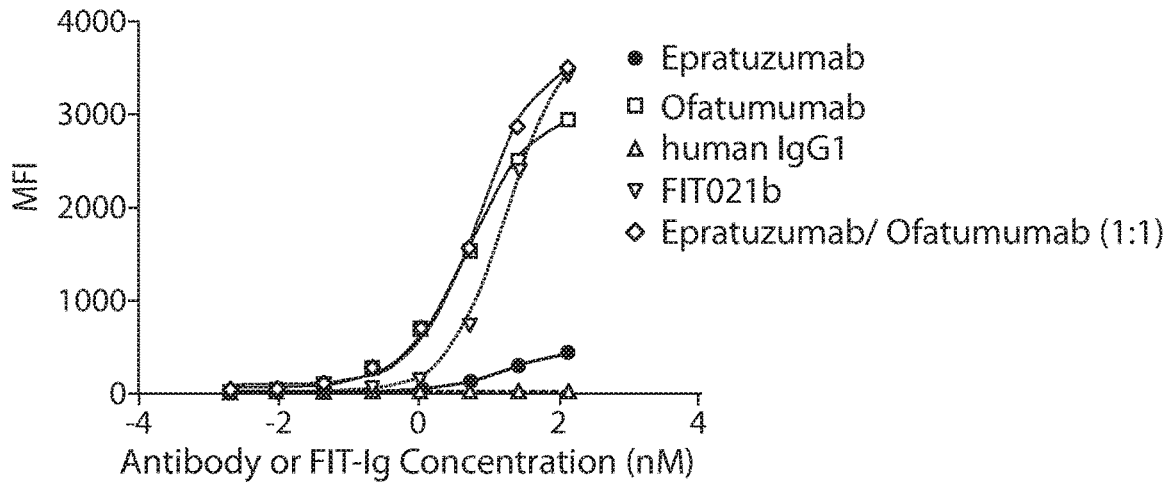

Cell Based Binding Study:

The binding activity of FIT021b to B lymphoma cell lines Raji or Daudi were determined by flow cytometry using BD FACSVerse. Cells were washed in PBS buffer containing 2% FBS. Cells were then aliquot and incubated with 1:5 serially diluted FIT021b on ice for 1 hr. The starting working concentration of FIT021b was 20 µg/ml. Cells were washed, resuspended and incubated with 1:100 diluted Alexa Fluor® 488 labeled mouse anti-human IgG1 (Invitrogen, Cat. No. A-10631) on ice protected from light for 1 hr. Cells were washed and signal was detected with a BD FACSVerse flow cytometer according to manufacture's protocols. These experiments demonstrate that FIT021b can bind to B lymphoma cell lines Raji or Daudi, see FIG. 36A and FIG. 36B.

Example 16: Study of Anti-HER3/PD-1 Fabs-in-Tandem Immunoglobulin (FIT-Ig)

FIT-Ig having specificity for HER3 and PD1 was constructed as in the foregoing Examples. This exemplary FIT-Ig and its corresponding sequences are provided below in Table 65. Table 66 provides the expression level in 293E cells and the SEC profile for the FIT-Ig.

TABLE 65

Amino acid sequences of additional exemplary FIT-Ig for HER3 and PD-1

| Name Target (mAb) mAb1 (upper domain)/mAb2 (lower domain) | Protein region | SEQ ID NO | Sequences |
|---|---|---|---|
| FIT022a HER3 (patritumab)/ PD-1 (nivolumab) | Long Chain (patritu VL-hCk-Nivolu VH-hCg1mut) | 411 | MDMRVPAQLLGLLLLWFPGSRCDIEMTQSPDSLAVSLGE RATINCRSSQSVLYSSSNRNYLAWYQQNPGQPPKLLIYW ASTRESGVPDRFSGSGSGTDFTLTISSLQAEDVAVYYCQ QYYSTPRTFGQGTKVEIKRTVAAPSVFIFPPSDEQLKSG TASVVCLLNNFYPREAKVQWKVDNALQSGNSQESVTEQD SKDSTYSLSSTLTLSKADYEKHKVYACEVTHQGLSSPVT KSFNRGECQVQLVESGGGVVQPGRSLRLDCKASGITFSN SGMHWVRQAPGKGLEWVAVIWYDGSKRYYADSVKGRFTI SRDNSKNTLFLQMNSLRAEDTAVYYCATNDDYWGQGTLV TVSSASTKGPSVFPLAPSSKSTSGGTAALGCLVKDYFPE PVTVSWNSGALTSGVHTFPAVLQSSGLYSLSSVVTVPSS SLGTQTYICNVNHKPSNTKVDKKVEPKSCDKTHTCPPCP APELLGGPSVFLFPPKPKDTLMISRTPEVTCVVVDVSHE DPEVKFNWYVDGVEVHNAKTKPREEQYNSTYRVVSVLTV LHQDWLNGKEYKCKVSNKALPAPIEKTISKAKGQPREPQ VYTLPPSREEMTKNQVSLTCLVKGFYPSDIAVEWESNGQ PENNYKTTPPVLDSDGSFFLYSKLTVDKSRWQQGNVFSC SVMHEALHNHYTQKSLSLSPGK |

TABLE 65-continued

Amino acid sequences of additional exemplary FIT-Ig for HER3 and PD-1

| Name Target (mAb) mAb1 (upper domain)/mAb2 (lower domain) | Protein region | SEQ ID NO | Sequences |
|---|---|---|---|
| | patrituVL | 412 | DIEMTQSPDSLAVSLGERATINCRSSQSVLYSSSNRNYLAWYQQNPGQPPKLLIYWASTRESGVPDRFSGSGSGTDFTLTISSLQAEDVAVYYCQQYYSTPRTFGQGTKVEIK |
| | patritu VL - CDR1 | 413 | RSSQSVLYSSSNRNYLA |
| | patritu VL - CDR2 | 414 | WASTRES |
| | patritu VL - CDR3 | 415 | QQYYSTPRT |
| | Nivolu VH | 416 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS |
| | Nivolu VH - CDR1 | 417 | NSGMH |
| | Nivolu VH - CDR2 | 418 | VIWYDGSKRYYADSVKG |
| | Nivolu VH - CDR3 | 419 | NDDY |
| | Short Chain #1 (Patritumab-CH1) | 420 | MEFGLSWLFLVAILKGVQCQVQLQQWGAGLLKPSETLSLTCAVYGGSFSGYYWSWIRQPPGKGLEWIGEINHSGSTNYNPSLKSRVTISVETSKNQFSLKLSSVTAADTAVYYCARDKWTWYFDLWGRGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | Patritumab VH | 421 | QVQLQQWGAGLLKPSETLSLTCAVYGGSFSGYYWSWIRQPPGKGLEWIGEINHSGSTNYNPSLKSRVTISVETSKNQFSLKLSSVTAADTAVYYCARDKWTWYFDLWGRGTLVTVSS |
| | Patritumab VH - CDR1 | 422 | GYYWS |
| | Patritumab VH - CDR2 | 423 | EINHSGSTNYNPSLKS |
| | Patritumab VH - CDR3 | 424 | DKWTWYFDL |
| | Short Chain#2 (NivoVL-hCK) | 425 | MDMRVPAQLLGLLLLWFPGSRCEIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | Nivo VL | 426 | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK |
| | Nivo VL - CDR1 | 427 | RASQSVSSYLA |
| | Nivo VL - CDR2 | 428 | DASNRAT |
| | Nivo VL - CDR3 | 429 | QQSSNWPRT |

TABLE 66

SEC Profile/Expression level in 293E cells:

| FIT-Ig | Monomer % in SEC | Expression level (mg/L) |
|---|---|---|
| FIT022a | 100% | 1.6 |

Functional Studies

Affinity Measurement by Surface Plasmon Resonance:

The kinetics of FIT022a-Ig binding to Her3-his and hPD-1-Fc was determined by surface plasmon resonance. The result is shown in Table 67.

TABLE 67

Functional binding data for FIT022a

| Ig | Target | Kon | Koff | KD | IC50 |
|---|---|---|---|---|---|
| Patritumab | Her3-his | 2.43E+05 | 3.12E-04 | 1.28E-09 | |
| FIT022a | | 2.68E+05 | 3.23E-04 | 1.21E-09 | |
| Nivolumab | hPD1-Fc | 5.00E+05 | 1.76E-04 | 3.52E-10 | |
| FIT022a | | 1.29E+05 | 3.01E-04 | 2.34E-09 | |

Figure 37:
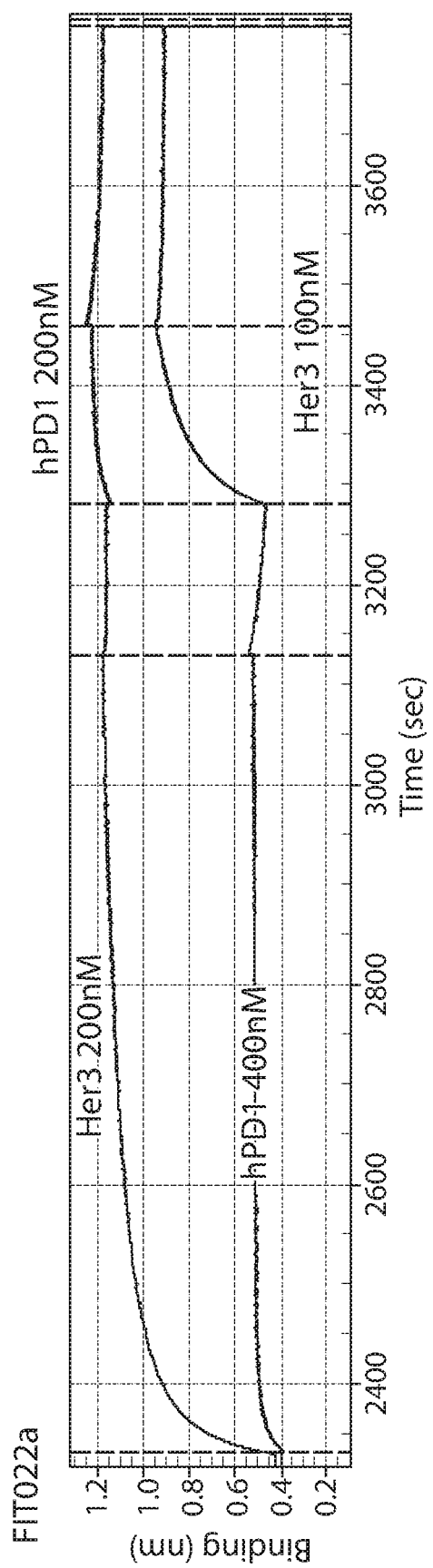
FIG. 37 shows a multiple binding study of FIT022a against both Her3 and human PD-1. Binding to Her3 followed by human PD-1; and binding by human PD-1 followed by Her3 are both shown as indicated

Multiple Binding Study:

A multiple binding study of FIT022a was carried out. The result is shown in FIG. 37. The result indicates that FIT022a can bind to PD-L1 and PD-1 simultaneously.

Figure 38A:
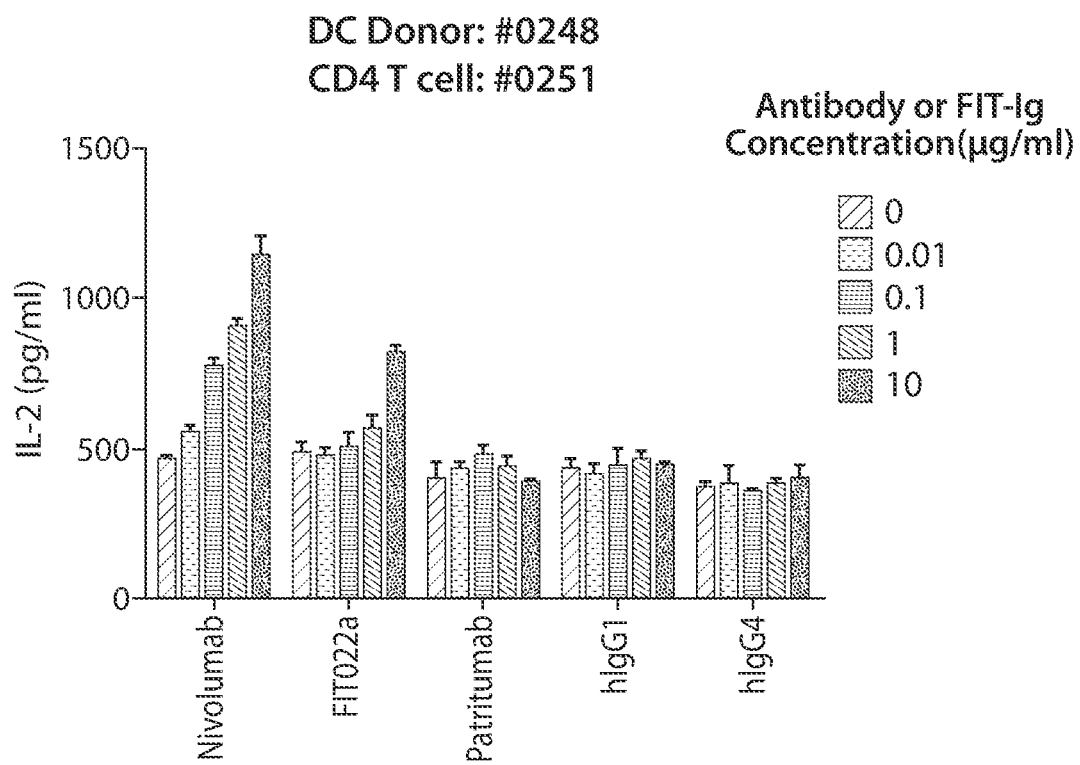
FIG. 38A shows functional activity of FIT022a in MLR assays, when compared to the parental antibody Nivolumab and Patritumab at a concentration of 0, 0.01, 0.1, 1, or 10 μg/ml. The induction of LI-2 was measured for each antibody. Human IgG1 and human IgG4 were included as controls.
Figure 38B:
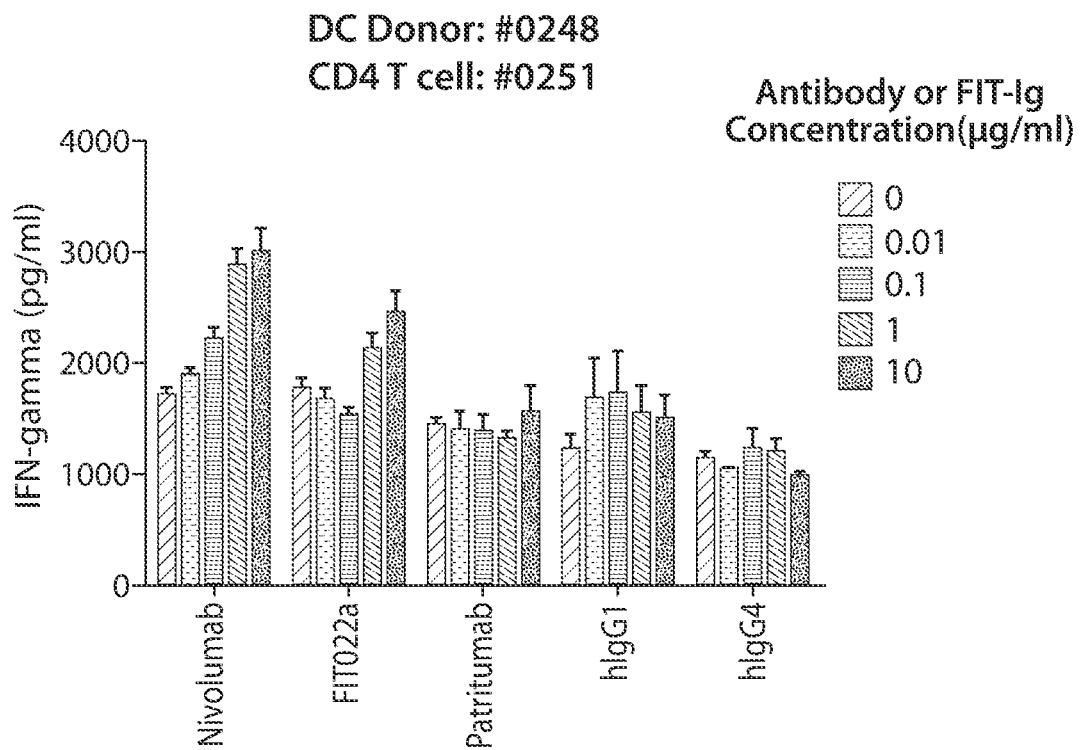
FIG. 38B shows the induction of IFN-γ by these antibodies.

MLR Functional Assay:

Mixed lymphocyte reaction was performed using monocyte-derived dendritic cells from one donor and allogeneic CD4 T cells from another donor. The whole blood samples were collected from healthy donors, and PBMC were isolated from whole blood using Ficoll-Pague gradient centrifugation. On day 1, PBMC from one donor was isolated and diluted with serum-free RPMI 1640 at 1×10$^6$/ml. The diluted PBMC was seeded into 6-well tissue culture plate at 3 ml/well and incubated for 3 h. Supernatant was removed and unattached cells were washed off. The attached monocyte were polarized into dendritic cells with 250 U/ml IL-4 and 500 U/ml GM-CSF in RPMI1640 with 10% FBS. The medium was replaced with fresh IL-4 and GM-CSF at day 4. At day 7, immature DC was collected and treated with 11 µg/ml LPS in RPMI 1640 with 10% FBS for additional 24 h for maturation. At Day 8, CD4 T cells were isolated from another donor PBMC by negative selection and adjusted to final concentration at 2×10e6 cells/ml. Mature DC were treated with mitomycin C at 37° C. for 1.5 hr. Then DC were washed with PBS and adjusted to final concentration at 1×10$^6$ cells/ml. CD4 T cells (Responder cells) were added into 96 well plate at 100 µl/well and pre-treated with test antibody at diluted concentration for 30 minutes. Then mature DC (Stimulator cells) were added into the well at 100 µl/well. The final volume of each well is 200pl. The MLR were incubated at 37 degree for 72 hr for IL-2 test and 120 hr for IFN-gamma test respectively using ELISA. The result is shown in FIG. 38A and FIG. 38B.

Example 17: Study of Anti-cMet/PD-L1 Fabs-in-Tandem Immunoglobulin (FIT-Ig)

FIT-Ig having specificity for cMet and PD-L1 was constructed as in the foregoing Examples. This exemplary FIT-Ig and its corresponding sequences are provided below in Table 68. Table 69 provides the expression level in 293E cells and the SEC profile for the FIT-Ig.

TABLE 68

Amino acid sequences of additional exemplary FIT-Ig for cMet and PD-L1

| Name<br>Target (mAb)<br>mAb1 (upper<br>domain)/mAb2<br>(lower domain) | Protein region | SEQ<br>ID<br>NO | Sequences |
|---|---|---|---|
| FIT023a<br>cMet (h1332)/<br>PD-L1 (1B12) | Long Chain(h1332<br>VL-hCk-1B12 VH-<br>hCg1) | 430 | MDMRVPAQLLGLLLLWFPGSRCDIQMTQSPSSVSASVGD<br>RVTITC<u>RASQGINTWLA</u>WYQQKPGKAPKLLIY<u>AASSLKS</u><br>GVPSRFSGSGSGTDFTLTISSLQPEDFATYYC<u>QQANSFP</u><br><u>LT</u>FGGGTKVEIKRTVAAPSVFIFPPSDEQLKSGTASVVC<br>LLNNFYPREAKVQWKVDNALQSGNSQESVTEQDSKDSTY<br>SLSSTLTLSKADYEKHKVYACEVTHQGLSSPVTKSFNRG<br>ECQVQLVQSGAEVKKPGSSVKVSCKTSGDTFS<u>SYAIS</u>WV<br>RQAPGQGLEWMGG<u>IIPIFGRAHYAQKFQ</u>GRVTITADEST<br>STAYMELSSLRSEDTAVYFCAR<u>KFHFVSGSPFGMDV</u>WGQ<br>GTTVTVSSASTKGPSVFPLAPSSKSTSGGTAALGCLVKD<br>YFPEPVTVSWNSGALTSGVHTFPAVLQSSGLYSLSSVVT<br>VPSSSLGTQTYICNVNHKPSNTKVDKKVEPKSCDKTHTC<br>PPCPAPELLGGPSVFLFPPKPKDTLMISRTPEVTCVVVD<br>VSHEDPEVKFNWYVDGVEVHNAKTKPREEQYNSTYRVVS<br>VLTVLHQDWLNGKEYKCKVSNKALPAPIEKTISKAKGQP<br>REPQVYTLPPSREEMTKNQVSLTCLVKGFYPSDIAVEWE<br>SNGQPENNYKTTPPVLDSDGSFFLYSKLTVDKSRWQQGN<br>VFSCSVMHEALHNHYTQKSLSLSPGK |
| | h1332 VL | 431 | DIQMTQSPSSVSASVGDRVTITC<u>RASQGINTWLA</u>WYQQK<br>PGKAPKLLIY<u>AASSLKS</u>GVPSRFSGSGSGTDFTLTISSL<br>QPEDFATYYC<u>QQANSFPLT</u>FGGGTKVEIK |
| | h1332 VL - CDR1 | 432 | <u>RASQGINTWLA</u> |
| | h1332 VL - CDR2 | 433 | <u>AASSLKS</u> |
| | h1332 VL - CDR3 | 434 | <u>QQANSFPLT</u> |
| | 1B12 VH | 435 | QVQLVQSGAEVKKPGSSVKVSCKTSGDTFS<u>SYAIS</u>WVRQ<br>APGQGLEWMGG<u>IIPIFGRAHYAQKFQ</u>GRVTITADESTST<br>AYMELSSLRSEDTAVYFCAR<u>KFHFVSGSPFGMDV</u>WGQGT<br>TVTVSS |
| | 1B12 VH-CDR1 | 436 | <u>SYAIS</u> |
| | 1B12 VH-CDR2 | 437 | <u>GIIPIFGRAHY</u> |
| | 1B12 VH-CDR3 | 438 | <u>KFHFVSGSPFGMDV</u> |
| | Short Chain #1<br>(h1332 VH-CH1) | 439 | MEFGLSWLFLVAILKGVQCQVQLVQSGAEVKKPGASVKV<br>SCKASGYTFT<u>SYGFS</u>WVRQAPGQGLEWMG<u>WISASNGNTY</u><br><u>YAQKLQG</u>RVTMTTDTSTSTAYMELRSLRSDDTAVYYCAR<br><u>VYADYADY</u>WGQGTLVTVSSASTKGPSVFPLAPSSKSTSG<br>GTAALGCLVKDYFPEPVTVSWNSGALTSGVHTFPAVLQS<br>SGLYSLSSVVTVPSSSLGTQTYICNVNHKPSNTKVDKKV<br>EPKSC |
| | h1332 VH | 440 | QVQLVQSGAEVKKPGASVKVSCKASGYTFT<u>SYGFS</u>WVRQ<br>APGQGLEWMG<u>WISASNGNTYYAQKLQG</u>RVTMTTDTSTST<br>AYMELRSLRSDDTAVYYCAR<u>VYADYADY</u>WGQGTLVTVSS |
| | h1332 VH - CDR1 | 441 | <u>SYGFS</u> |
| | h1332 VH - CDR2 | 442 | <u>WISASNGNTYYAQKLQG</u> |
| | h1332 VH - CDR3 | 443 | <u>VYADYADY</u> |
| | Short Chain #2<br>(1B12 VL-hCK) | 444 | MDMRVPAQLLGLLLLWFPGSRCEIVLTQSPATLSLSPGE<br>RATLSC<u>RASQSVSSYLA</u>WYQQKPGQAPRLLIY<u>DASNRAT</u><br>GIPARFSGSGSGTDFTLTISSLEPEDFAVYYC<u>QQRSNWP</u><br><u>T</u>FGQGTKVEIKRTVAAPSVFIFPPSDEQLKSGTAVVCL<br>LNNFYPREAKVQWKVDNALQSGNSQESVTEQDSKDSTYS<br>LSSTLTLSKADYEKHKVYACEVTHQGLSSPVTKSFNRGE<br>C |

TABLE 68-continued

Amino acid sequences of additional exemplary FIT-Ig for cMet and PD-L1

Name
Target (mAb)
mAb1 (upper
domain)/mAb2
(lower domain) Protein region

| | | SEQ ID NO | Sequences |
|---|---|---|---|
| | 1B12 VL | 445 | EIVLTQSPATLSLSPGERATLSC<u>RASQSVSSYLA</u>WYQQK PGQAPRLLIY<u>DASNRAT</u>GIPARFSGSGSGTDFTLTISSL EPEDFAVYYC<u>QQRSNWPT</u>FGQGTKVEIK |
| | 1B12 VL-CDR1 | 446 | <u>RASQSVSSYLA</u> |
| | 1B12 VL-CDR2 | 447 | <u>DASNRAT</u> |
| | 1B12 VL-CDR3 | 448 | <u>QQRSNWPT</u> |

TABLE 69

SEC Profile/Expression level in 293E cells:

| FIT-Ig | Monomer % in SEC | Expression level (mg/L) |
|---|---|---|
| FIT023a | 97.49% | 5.94 |

Functional Studies

Affinity Measurement by Surface Plasmon Resonance:

The kinetics of FIT023a-Ig binding to cMet and PD-L1 was determined by surface plasmon resonance. The result is shown in Table 70.

TABLE 70

Functional binding data for FIT023a

| Ig | Target | Kon | Koff | KD |
|---|---|---|---|---|
| H1332 | 1(cMet) | 2.47E+05 | 5.39E-04 | 2.19E-09 |
| FIT023a | | 3.42E+05 | 5.10E-04 | 1.49E-09 |

TABLE 70-continued

Functional binding data for FIT023a

| Ig | Target | Kon | Koff | KD |
|---|---|---|---|---|
| 1B12 | 2(PD-L1) | 3.21E+06 | 2.28E-03 | 7.08E-10 |
| FIT023a | | 2.84E+06 | 2.08E-03 | 7.31E-10 |

Figure 39A:
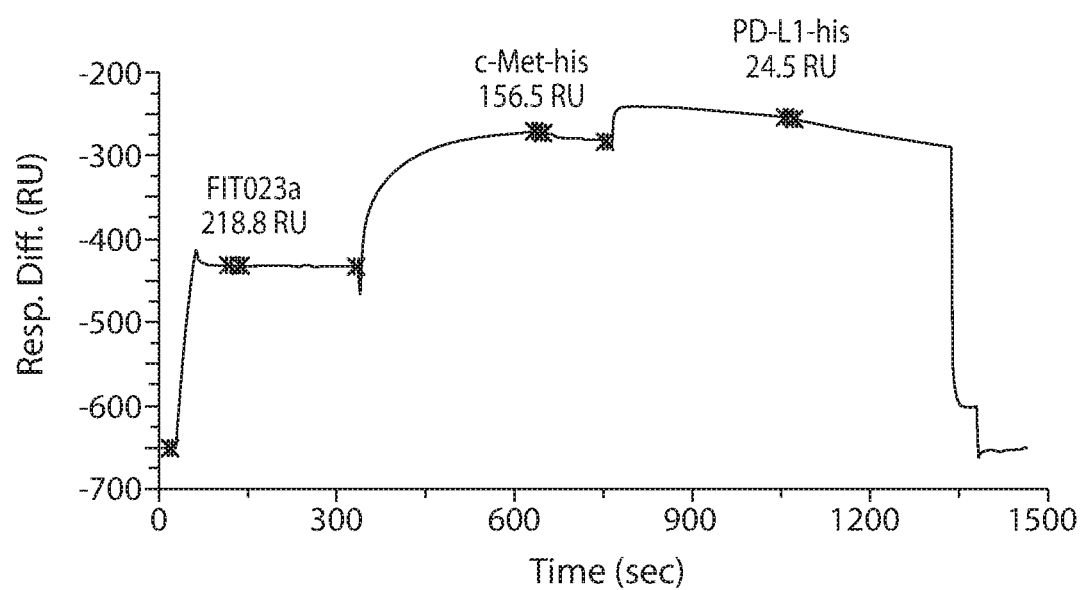
FIG. 39A and FIG. 39B show a multiple binding study of FIT023a against both cMet-his and PD-L-his. Binding to cMet-his followed by PD-L-his (FIG. 39A); and binding by PD-L-his followed by cMet-his (FIG. 39B) are both shown as indicated.
Figure 39B:
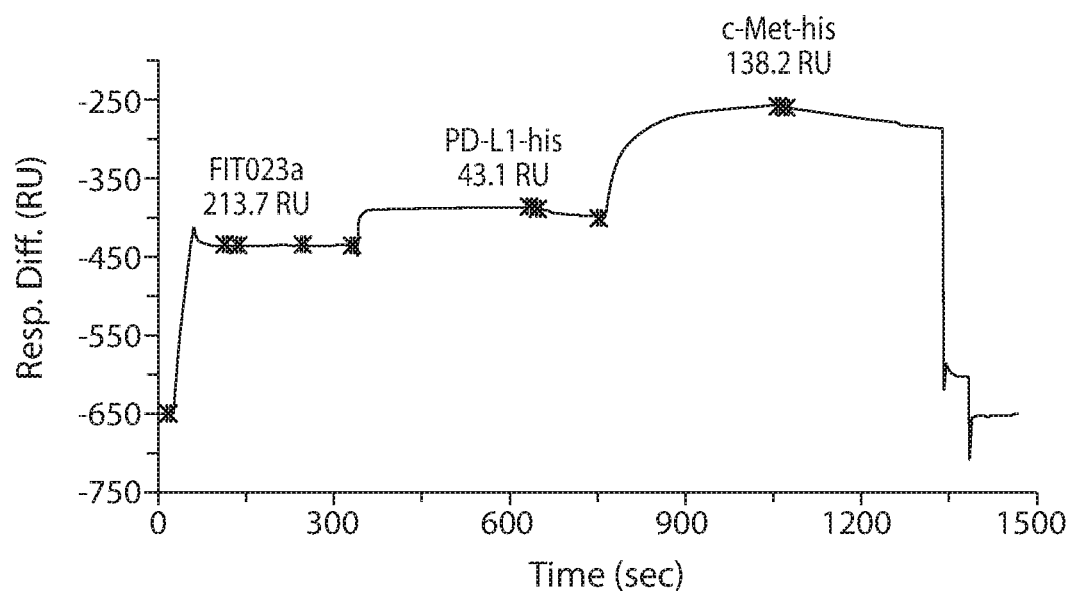
Figure 40A:
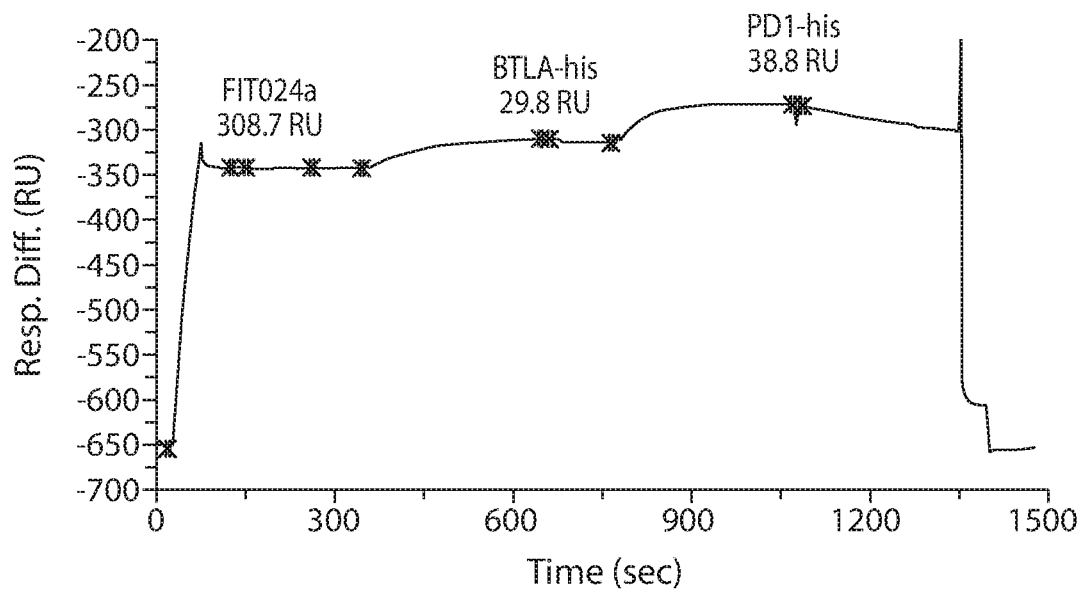
FIG. 40A and FIG. 40B show a multiple binding study of FIT024a against both BTLA-his and PD1-his. Binding to BTLA-his followed by PD1-his (FIG. 40A); and binding by PD1-his followed by BTLA-his (FIG. 40B) are both shown as indicated.
Figure 40B:
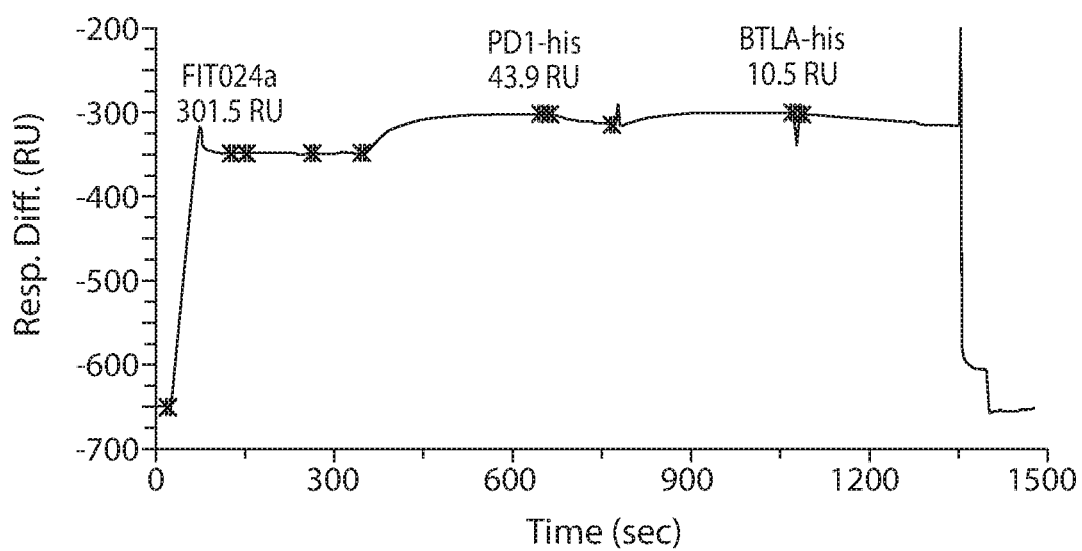
Figure 41A:
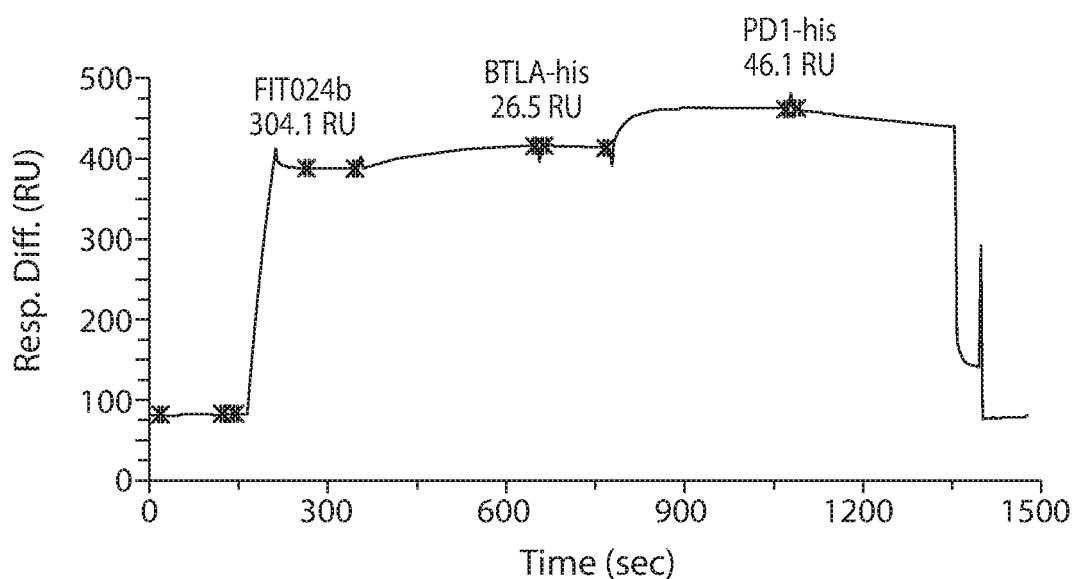
FIG. 41A and FIG. 41B show a multiple binding study of FIT024b against both BTLA-his and PD1-his. Binding to BT:A-his followed by PD1-his (FIG. 41A); and binding by PD1-his followed by BTLA-his (FIG. 41B) are both shown as indicated.
Figure 41B:
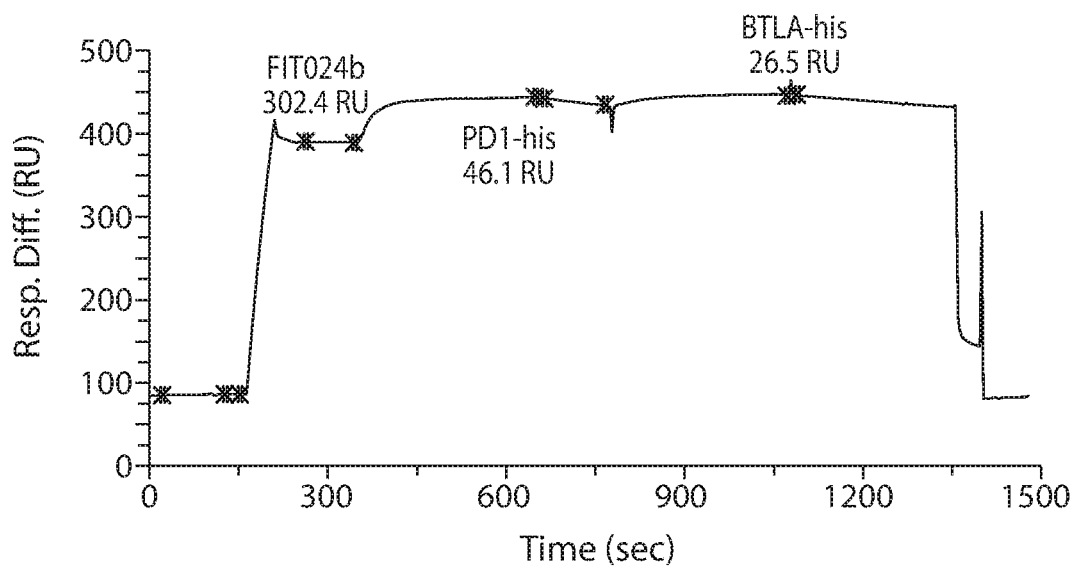

Multiple Binding Study:

A multiple binding study of FIT023a was carried out. The result is shown in FIG. 39A and FIG. 39B. The result indicates that FIT023a can bind to cMet and PD-L1 simultaneously.

Example 18: Study of Anti-BTLA/PD-1 Fabs-in-Tandem Immunoglobulin (FIT-Ig)

FIT-Ig having specificity for BTLA and PD-L1 were constructed as in the foregoing Examples. This exemplary FIT-Ig and their corresponding sequences are provided below in Table 71. Table 72 provides the expression level in 293E cells and the SEC profile for the FIT-Ig. Both FIT024a and FIT024b have good purity after one-step Protein A purification.

TABLE 71

Amino acid sequences of additional exemplary FIT-Ig for BTLA and PD-1

Name
Target (mAb)
mAb1 (upper
domain)/mAb2
(lower domain) Protein region

| | | SEQ ID NO | Sequences |
|---|---|---|---|
| FIT024a-Ig BTLA (6A5)/ PD-1 (Nivolumab) | Long Chain (6A5 VL-hCk-Nivolu VH-hCg1mut) | 449 | <u>MDMRVPAQLLGLLLLWFPGSRC</u>EIVLTQSPGTLSLSPGE RATLSC<u>RASQSVSSTYLA</u>WYQQKPGQAPRLLIY<u>GASSRA</u> TGIPDRFSGSGSGTDFTLTISRLEPEDFAVYYC<u>QQYGSS PPIT</u>FGQGTRLEIKRTVAAPSVFIFPPSDEQLKSGTASV VCLLNNFYPREAKVQWKVDNALQSGNSQESVTEQDSKDS TYSLSSTLTLSKADYEKHKVYACEVTHQGLSSPVTKSFN RGECQVQLVESGGGVVQPGRSLRLDCKASGITF<u>SNSGMH</u> WVRQAPGKGLEWVA<u>VIWYDGSKRYYADSVKGR</u>FTISRDN SKNTLFLQMNSLRAEDTAVYYCAT<u>NDDYW</u>GQGTLVTVSSA STKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSCDKTHTCPPCPAPEA AGGPSVFLFPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSREEMTKNQVSLTCLVKGFYPSDIAVEWESNGQPENN YKTTPPVLDSDGSFFLYSKLTVDKSRWQQGNVFSCSVMH EALHNHYTQKSLSLSPGK |
| | 6A5 VL | 450 | EIVLTQSPGTLSLSPGERATLSC<u>RASQSVSSTYLA</u>WYQQ KPGQAPRLLIY<u>GASSRAT</u>GIPDRFSGSGSGTDFTLTISR LEPEDFAVYYC<u>QQYGSSPPIT</u>FGQGTRLEIK |

TABLE 71-continued

Amino acid sequences of additional exemplary FIT-Ig for BTLA and PD-1

| Name Target (mAb) mAb1 (upper domain)/mAb2 (lower domain) | Protein region | SEQ ID NO | Sequences |
|---|---|---|---|
| | 6A5 VL - CDR1 | 451 | RASQSVSSTYLA |
| | 6A5 VL - CDR2 | 452 | GASSRAT |
| | 6A5 VL - CDR3 | 453 | QQYGSSPPIT |
| | Nivolu VH | 454 | QVQLVESGGGVVQPGRSLRLDCKASGITFSNSGMHWVRQ APGKGLEWVAVIWYDGSKRYYADSVKGRFTISRDNSKNT LFLQMNSLRAEDTAVYYCATNDDYWGQGTLVTVSS |
| | Nivolu VH - CDR1 | 455 | NSGMH |
| | Nivolu VH - CDR2 | 456 | VIWYDGSKRYYADSVKG |
| | Nivolu VH - CDR3 | 457 | NDDY |
| | Short Chain #1 (6A5 VH-CH1) | 458 | MEFGLSWLFLVAILKGVQCQITLKESGPTLVKPTQTLTL TCTFSGFSLSTSGVGVGWIRQPPGKALEWLALIYWDDDK RYSPSLKSRLTITKDTSKNQVVLTMANMDPVDTATYYCA HIRITEVRGVIISYYGMDVWGQGTTVTVSSASTKGPSVF PLAPSSKSTSGGTAALGCLVKDYFPEPVTVSWNSGALTS GVHTFPAVLQSSGLYSLSSVVTVPSSSLGTQTYICNVNH KPSNTKVDKKVEPKSC |
| | 6A5 VH | 459 | QITLKESGPTLVKPTQTLTLTCTFSGFSLSTSGVGVGWI RQPPGKALEWLALIYWDDDKRYSPSLKSRLTITKDTSKN QVVLTMANMDPVDTATYYCAHIRITEVRGVIISYYGMDV WGQGTTVTVSS |
| | 6A5 VH - CDR1 | 460 | TSGVGVG |
| | 6A5 VH - CDR2 | 461 | LIYWDDDKRYSPSLKS |
| | 6A5 VH - CDR3 | 462 | IRITEVRGVIISYYGMDV |
| | Short Chain #2 (Nivolu VL-hCK) | 463 | MDMRVPAQLLGLLLLWFPGSRCEIVLTQSPATLSLSPGE RATLSCRASQSVSSYLAWYQQKPGQAPRLLIYDASNRAT GIPARFSGSGSGTDFTLTISSLEPEDFAVYYCQQSSNWP RTFGQGTKVEIKRTVAAPSVFIFPPSDEQLKSGTASVVC LLNNFYPREAKVQWKVDNALQSGNSQESVTEQDSKDSTY SLSSTLTLSKADYEKHKVYACEVTHQGLSSPVTKSFNRG EC |
| | Nivolu VL | 464 | EIVLTQSPATLSLSPGERATLSCRASQSVSSYLAWYQQK PGQAPRLLIYDASNRATGIPARFSGSGSGTDFTLTISSL EPEDFAVYYCQQSSNWPRTFGQGTKVEIK |
| | Nivolu VL-CDR1 | 465 | RASQSVSSYLA |
| | Nivolu VL-CDR2 | 466 | DASNRAT |
| | Nivolu VL-CDR3 | 467 | QQSSNWPRT |
| FIT024b-Ig PD-1 (Nivolumab)/ BTLA (6A5) | Long Chain (Nivolu VL-hCk-6A5 VH-hCg1mut) | 468 | MDMRVPAQLLGLLLLWFPGSRCEIVLTQSPATLSLSPGE RATLSCRASQSVSSYLAWYQQKPGQAPRLLIYDASNRAT GIPARFSGSGSGTDFTLTISSLEPEDFAVYYCQQSSNWP RTFGQGTKVEIKRTVAAPSVFIFPPSDEQLKSGTASVVC LLNNFYPREAKVQWKVDNALQSGNSQESVTEQDSKDSTY SLSSTLTLSKADYEKHKVYACEVTHQGLSSPVTKSFNRG ECQITLKESGPTLVKPTQTLTLTCTFSGESLSTSGVGVG WIRQPPGKALEWLALIYWDDDKRYSPSLKSRLTITKDTS KNQVVLTMANMDPVDTATYYCAHIRITEVRGVIISYYGM DVWGQGTTVTVSSASTKGPSVFPLAPSSKSTSGGTAALG CLVKDYFPEPVTVSWNSGALTSGVHTFPAVLQSSGLYSL SSVVTVPSSSLGTQTYICNVNHKPSNTKVDKKVEPKSCD KTHTCPPCPAPEAAGGPSVFLFPPKPKDTLMISRTPEVT CVVVDVSHEDPEVKFNWYVDGVEVHNAKTKPREEQYNST YRVVSVLTVLHQDWLNGKEYKCKVSNKALPAPIEKTISK AKGQPREPQVYTLPPSREEMTKNQVSLTCLVKGFYPSDI AVEWESNGQPENNYKTTPPVLDSDGSFFLYSKLTVDKSR WQQGNVFSCSVMHEALHNHYTQKSLSLSPGK |
| | Nivolu VL | 469 | EIVLTQSPATLSLSPGERATLSCRASQSVSSYLAWYQQK PGQAPRLLIYDASNRATGIPARFSGSGSGTDFTLTISSL EPEDFAVYYCQQSSNWPRTFGQGTKVEIK |
| | Nivolu VL - CDR1 | 470 | RASQSVSSYLA |
| | Nivolu VL - CDR2 | 471 | DASNRAT |
| | Nivolu VL - CDR3 | 472 | QQSSNWPRT |
| | 6A5 VH | 473 | QITLKESGPTLVKPTQTLTLTCTFSGFSLSTSGVGVGWI RQPPGKALEWLALIYWDDDKRYSPSLKSRLTITKDTSKN QVVLTMANMDPVDTATYYCAHIRITEVRGVIISYYGMDV WGQGTTVTVSS |
| | 6A5 VH - CDR1 | 474 | TSGVGVG |
| | 6A5 VH - CDR2 | 475 | LIYWDDDKRYSPSLKS |
| | 6A5 VH - CDR3 | 476 | IRITEVRGVIISYYGMDV |
| | Short Chain #1 (Nivolu VH-CH1) | 477 | MEFGLSWLFLVAILKGVQCQVQLVESGGGVVQPGRSLRL DCKASGITFSNSGMHWVRQAPGKGLEWVAVIWYDGSKRY YADSVKGRFTISRDNSKNTLFLQMNSLRAEDTAVYYCAT NDDYWGQGTLVTVSSASTKGPSVFPLAPSSKSTSGGTAA |

TABLE 71-continued

Amino acid sequences of additional exemplary FIT-Ig for BTLA and PD-1

| Name Target (mAb) mAb1 (upper domain)/mAb2 (lower domain) | Protein region | SEQ ID NO | Sequences |
|---|---|---|---|
| | | | LGCLVKDYFPEPVTVSWNSGALTSGVHTFPAVLQSSGLY SLSSVVTVPSSSLGTQTYICNVNHKPSNTKVDKKVEPKS C |
| | Nivolu VH | 478 | QVQLVESGGGVVQPGRSLRLDCKASGITFS<u>NSGMH</u>WVRQ APGKGLEWVA<u>VIWYDGSKRYYADSVKG</u>RFTISRDNSKNT LFLQMNSLRAEDTAVYYCAT<u>NDDY</u>WGQGTLVTVSS |
| | Nivolu VH - CDR1 | 479 | <u>NSGMH</u> |
| | Nivolu VH - CDR2 | 480 | <u>VIWYDGSKRYYADSVKG</u> |
| | Nivolu VH - CDR3 | 481 | <u>NDDY</u> |
| | Short Chain #2 (6A5 VL-hCK) | 482 | MDMRVPAQLLGLLLLWFPGSRCEIVLTQSPGTLSLSPGE RATLSCRASQSVSSTYLAWYQQKPGQAPRLLIYGASSRA TGIPDRFSGSGSGTDFTLTISRLEPEDFAVYYCQQYGSS PPITFGQGTRLEIKRTVAAPSVFIFPPSDEQLKSGTASV VCLLNNFYPREAKVQWKVDNALQSGNSQESVTEQDSKDS TYSLSSTLTLSKADYEKHKVYACEVTHQGLSSPVTKSFN RGEC |
| | 6A5 VL | 483 | EIVLTQSPGTLSLSPGERATLSC<u>RASQSVSSTYLA</u>WYQQ KPGQAPRLLIY<u>GASSRAT</u>GIPDRFSGSGSGTDFTLTISR LEPEDFAVYYC<u>QQYGSSPPIT</u>FGQGTRLEIK |
| | 6A5 VL - CDR1 | 484 | <u>RASQSVSSTYLA</u> |
| | 6A5 VL - CDR2 | 485 | <u>GASSRAT</u> |
| | 6A5 VL - CDR3 | 486 | <u>QQYGSSPPIT</u> |

TABLE 72

SEC Profile/Expression level in 293E cells:

| FIT-Ig | Monomer % in SEC | Expression level (mg/L) |
|---|---|---|
| FIT024a | 99.68% | 9.3 |
| FIT024b | 98.61% | 13.0 |

Functional Studies

Affinity Measurement by Surface Plasmon Resonance:

The kinetics of FIT024a-Ig and FIT024b-Ig binding to BTLA4 and PD-1 was determined by surface plasmon resonance. The result is shown in Table 73.

TABLE 73

Functional binding data for FIT024a and FIT024b

| Ig | Target | Kon | Koff | KD |
|---|---|---|---|---|
| 6A5 | BTLA-his | 6.68E+04 | 7.34E−04 | 1.10E−08 |
| FIT024a | | 6.16E+04 | 8.05E−04 | 1.31E−08 |
| FIT024b | | 4.45E+04 | 8.14E−04 | 1.83E−08 |
| Nivolumab | hPD1-his | 3.76E+05 | 1.39E−03 | 3.70E−09 |
| FIT024a | | 1.76E+05 | 2.58E−03 | 1.46E−08 |
| FIT024b | | 3.53E+05 | 1.48E−03 | 4.20E−09 |

Multiple Binding Study:

A multiple binding study of FIT024a and FIT024b was carried out. The result is shown in FIG. 40A to FIG. 40B and FIG. 41A to FIG. 41B. The result indicates that both FIT024a and FIT024b can bind to BTLA4 and PD-1 simultaneously.

Figure 42A:
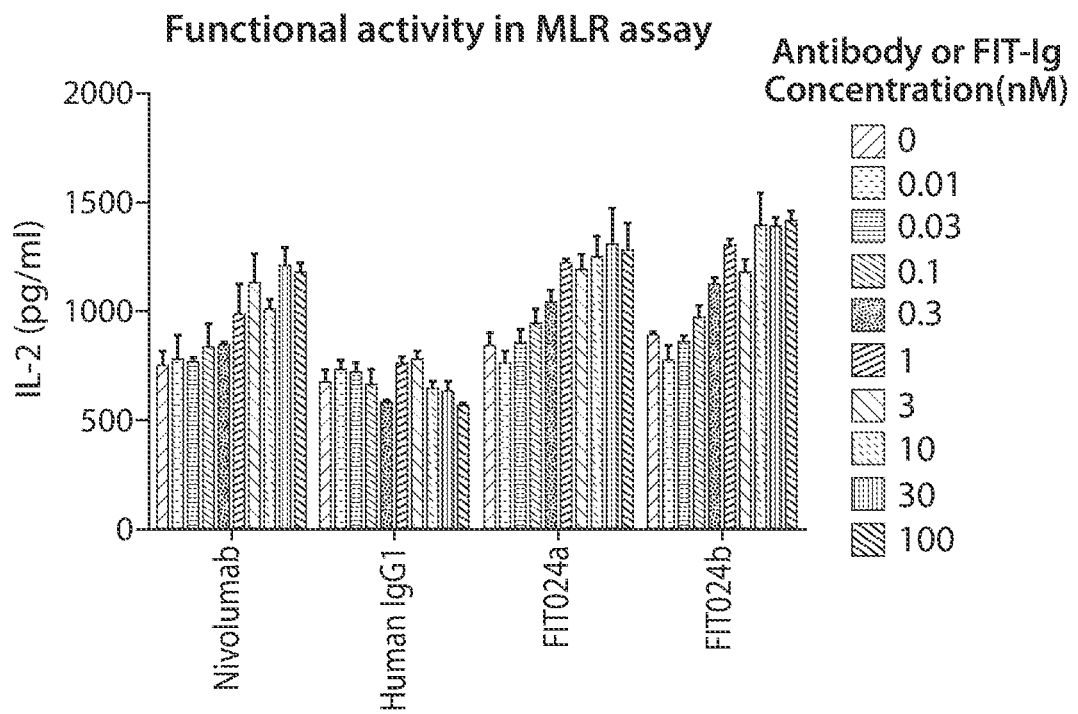
FIG. 42A shows functional activity of FIT024a and FIT024b in MLR assays, when compared to the parental antibody Nivolumab at a concentration of 0, 0.01, 0.03, 0.1, 0.3, 1, 3, 10, 30, or 100 nM, as measured by the level of induced IL-2. Human IgG1 was included as a control.
Figure 42B:
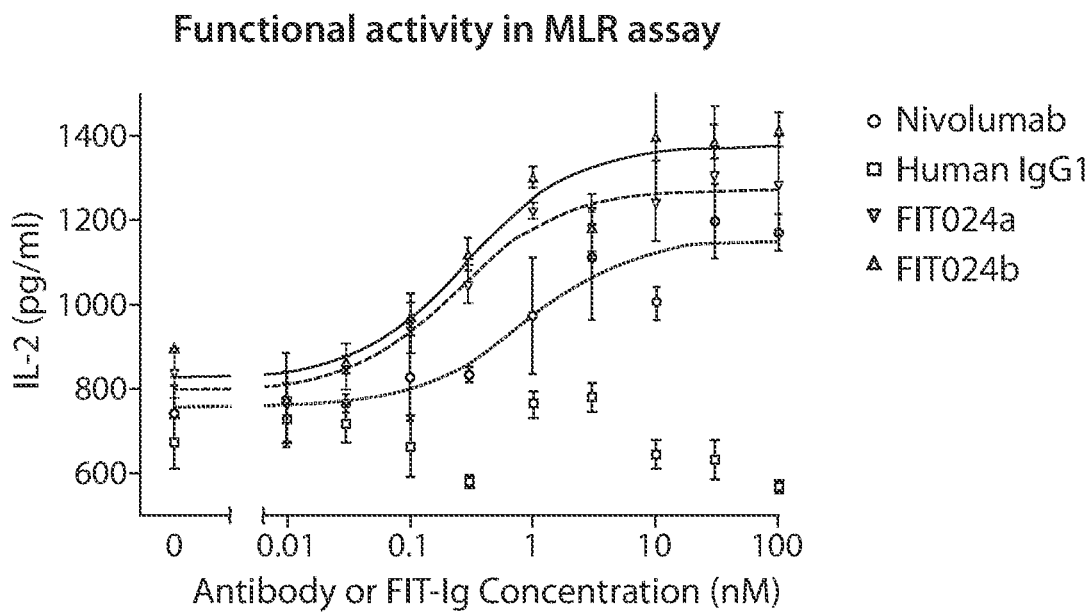
FIG. 42B shows the induction of IL-2 at a concentration of 0, 0.01, 0.1, 1, 10, or 100 by these antibodies.

MLR Functional Assay:

Mixed lymphocyte reaction was performed using monocyte-derived dendritic cells from one donor and allogeneic CD4 T cells from another donor. The whole blood samples were collected from healthy donors, and PBMC were isolated from whole blood using Ficoll-Pague gradient centrifugation. On day 1, PBMC from one donor was isolated and diluted with serum-free RPMI 1640 at $1 \times 10^6$/ml. The diluted PBMC was seeded into 6-well tissue culture plate at 3 ml/well and incubated for 3 h. Supernatant was removed and unattached cells were washed off. The attached monocyte were polarized into dendritic cells with 250 U/ml IL-4 and 500 U/ml GM-CSF in RPMI1640 with 10% FBS. The medium was replaced with fresh IL-4 and GM-CSF at day 4. At day 7, immature DC was collected and treated with 1 μg/ml LPS in RPMI 1640 with 10% FBS for additional 24 h for maturation. At Day 8, CD4 T cells were isolated from another donor PBMC by negative selection and adjusted to final concentration at 2×10e6 cells/ml. Mature DC were treated with mitomycin C at 37° C. for 1.5 hr. Then DC were washed with PBS and adjusted to final concentration at $1 \times 10^6$ cells/ml. CD4 T cells (Responder cells) were added into 96 well plate at 100 μl/well and pre-treated with test antibody at diluted concentration for 30 minutes. Then mature DC (Stimulator cells) were added into the well at 100 μl/well. The final volume of each well is 200 μl. The MLR were incubated at 37 degree for 72 hr for IL-2 test. The result is shown in FIG. 42A and FIG. 42B. Both FIT024a and FIT024b have higher activity to enhance T cell activation in MLR study compared to Nivolumab.

All publications, patent applications, and issued patents cited in this specification are herein incorporated by reference as if each individual publication, patent application, or issued patent were specifically and individually indicated to be incorporated by reference in its entirety.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A bispecific binding protein that binds antigen A and antigen B comprising three polypeptide chains, wherein: the first polypeptide chain comprises, from amino terminus to carboxy terminus, either (1) VLA-CL-VHB-CH1-Fc or (2) VHB-CH1-VLA-CL-Fc, wherein VLA is an antibody light chain variable domain of a first parental antibody that binds antigen A, CL is an antibody light chain constant domain, VHB is an antibody heavy chain variable domain from a second parental antibody that binds antigen B, and CH1 is a first constant domain of an antibody heavy chain; the second polypeptide chain comprises, from amino terminus to carboxy terminus, VHA-CH1 wherein VHA is a heavy chain variable domain of said first parental antibody that binds antigen A and CH1 is a first constant domain of an antibody heavy chain; and the third polypeptide chain comprises, from amino terminus to carboxy terminus, VLB-CL, wherein VLB is a light chain variable domain of said second parental antibody that binds antigen B and CL is an antibody light chain constant domain; wherein said bispecific binding protein binds antigens A and B, wherein A is cMet and B is EGFR, and wherein variable domain VLA comprises VLA CDR1 having amino acid sequence SEQ ID NO:242, VLA CDR2 having amino acid sequence SEQ ID NO:243, and VLA CDR3 having amino acid sequence SEQ ID NO:244; variable domain VHA comprises VHA CDR1 having amino acid sequence SEQ ID NO:251, VHA CDR2 having amino acid sequence SEQ ID NO:252, and VHA CDR3 having amino acid sequence SEQ ID NO:253; variable domain VLB comprises VLB CDR1 having amino acid sequence SEQ ID NO:256, VLB CDR2 having amino acid sequence SEQ ID NO:257, and VLB CDR3 having amino acid sequence SEQ ID NO:258; and variable domain VHB comprises VHB CDR1 having amino acid sequence SEQ ID NO:246, VHB CDR2 having amino acid sequence SEQ ID NO:247, and VHB CDR3 having amino acid sequence SEQ ID NO:248.

2. The bispecific binding protein according to claim 1, wherein said bispecific binding protein binds antigens A and B, wherein A is cMet and B is EGFR, and wherein said bispecific binding protein comprises VLA having amino acid sequence SEQ ID NO:241, VHA having amino acid sequence SEQ ID NO:250, VLB having amino acid sequence SEQ ID NO:255, and VHB having amino acid sequence SEQ ID NO:245.

3. The bispecific binding protein according to claim 2, wherein said bispecific binding protein binds antigen A and B, wherein A is cMet and B is EGFR, and wherein said bispecific binding protein comprises first polypeptide chain having amino acid sequence residues 23-685 of SEQ ID NO:240, second polypeptide chain having amino acid sequence residues 20-239 of SEQ ID NO:249, and third polypeptide chain having amino acid sequence residues 23-236 of SEQ ID NO:254.

4. A pharmaceutical composition comprising the binding protein of any one of claims 1-3 and a pharmaceutically acceptable carrier.

5. A method of treating a condition in a subject in need thereof, the method comprising administering to the subject an effective amount of the pharmaceutical composition of claim 4.

6. The method of claim 5, wherein the condition is an inflammatory disease, autoimmune disease, neurodegenerative disease, cancer, or spinal cord injury.

* * * * *

UNITED STATES PATENT AND TRADEMARK OFFICE
CERTIFICATE OF CORRECTION

PATENT NO. : 11,421,028 B2
APPLICATION NO. : 16/075922
DATED : August 23, 2022
INVENTOR(S) : Chengbin Wu Page 1 of 2

It is certified that error appears in the above-identified patent and that said Letters Patent is hereby corrected as shown below:

In the Claims

Claim 1, Column 587, Line 20, "VLA-CL-VHB-CH1-Fc" should read as —$VL_A$-CL-$VH_B$-CH1-$F_C$—.

Claim 1, Column 587, Line 21, "VHB-CH1-VLA-CL-Fc," should read as —$VH_B$-CH1-$VL_A$-CL-$F_C$,—.

Claim 1, Column 587, Line 21, "VLA" should read as —$VL_A$—.

Claim 1, Column 587, Line 24, "VHB" should read as —$VH_B$—.

Claim 1, Column 587, Line 28, "VHA-CH1" should read as —$VH_A$-CH1—.

Claim 1, Column 587, Line 28, "VHA" should read as —$VH_A$—.

Claim 1, Column 587, Line 32, "VLB-CL" should read as —$VL_B$-CL—.

Claim 1, Column 587, Line 33, "VLB" should read as —$VL_B$—.

Claim 1, Column 587, Line 37, "VLA" should read as —$VL_A$—.

Claim 1, Column 587, Line 38, "VLA" should read as —$VL_A$—.

Claim 1, Column 587, Line 40, "VLA" should read as —$VL_A$—.

Claim 1, Column 587, Line 41, "VHA" should read as —$VH_A$—.

Claim 1, Column 587, Line 41, "VHA" should read as —$VH_A$—.

Claim 1, Column 587, Line 42, "VHA" should read as —$VH_A$—.

Signed and Sealed this
Twenty-fifth Day of October, 2022

Katherine Kelly Vidal
*Director of the United States Patent and Trademark Office*

CERTIFICATE OF CORRECTION (continued)
U.S. Pat. No. 11,421,028 B2

Claim 1, Column 587, Line 43, "VHA" should read as —$VH_A$—.

Claim 1, Column 587, Line 45, "VLB" should read as —$VL_B$—.

Claim 1, Column 587, Line 45, "VLB" should read as —$VL_B$—.

Claim 1, Column 587, Line 46, "VLB" should read as —$VL_B$—.

Claim 1, Column 587, Line 48, "VHB" should read as —$VH_B$—.

Claim 1, Column 588, Line 16, "VHB" should read as —$VH_B$—.

Claim 1, Column 588, Line 17, "VHB" should read as —$VH_B$—.

Claim 1, Column 588, Line 18, "VHB" should read as —$VH_B$—.

Claim 2, Column 588, Line 23, "VLA" should read as —$VL_A$—.

Claim 2, Column 588, Line 24, "VHA" should read as —$VH_A$—.

Claim 2, Column 588, Line 25, "VLB" should read as —$VL_B$—.

Claim 2, Column 588, Line 26, "VHB" should read as —$VH_B$—.

```
                             SEQUENCE LISTING

<160> NUMBER OF SEQ ID NOS: 519

<210> SEQ ID NO 1
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 1
caggtgcagc tggtgcagag cggcgccgaa g                                 31

<210> SEQ ID NO 2
<211> LENGTH: 51
<212> TYPE: DNA
<213> ORGANISM: Artificial Sequence
<220> FEATURE:
<223> OTHER INFORMATION: Oligonucleotide primer

<400> SEQUENCE: 2
gctggacctg agagcctgaa ccgccaccac cacactctcc cctgttgaag c            51

<210> SEQ ID NO 3
<211> LENGTH: 52
<212> TYPE: DNA
<213> ORGANISM: Artificial Sequence
<220> FEATURE:
<223> OTHER INFORMATION: Oligonucleotide primer

<400> SEQUENCE: 3
ggtggtggcg gttcaggctc tcaggtccag cttgtgcaat ctggcgccga gg           52

<210> SEQ ID NO 4
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 4
gtctgcggcc gctcatttac ccggagacag ggagag                            36

<210> SEQ ID NO 5
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 5
taagcgtacg gtggctgcac catctgtctt c                                 31

<210> SEQ ID NO 6
<211> LENGTH: 59
<212> TYPE: DNA
<213> ORGANISM: Artificial Sequence
<220> FEATURE:
<223> OTHER INFORMATION: Oligonucleotide primer

<400> SEQUENCE: 6
```
cggcgccaga ttgcacaagc tggacctggc ctgaaccaca ctctcccctg ttgaagctc    59

<210> SEQ ID NO 7
<211> LENGTH: 51
<212> TYPE: DNA
<213> ORGANISM: Artificial Sequence
<220> FEATURE:
<223> OTHER INFORMATION: Oligonucleotide primer

<400> SEQUENCE: 7
gctggacctg agagcctgaa ccgccaccac cacactctcc cctgttgaag c    51

<210> SEQ ID NO 8
<211> LENGTH: 52
<212> TYPE: DNA
<213> ORGANISM: Artificial Sequence
<220> FEATURE:
<223> OTHER INFORMATION: Oligonucleotide primer

<400> SEQUENCE: 8
ggtggtggcg gttcaggctc tcaggtccag cttgtgcaat ctggcgccga gg    52

<210> SEQ ID NO 9
<211> LENGTH: 59
<212> TYPE: DNA
<213> ORGANISM: Artificial Sequence
<220> FEATURE:
<223> OTHER INFORMATION: Oligonucleotide primer

<400> SEQUENCE: 9
tacctcggcg ccagattgca caagctggac ctgacactct ccctgttga agctctttg    59

<210> SEQ ID NO 10
<211> LENGTH: 56
<212> TYPE: DNA
<213> ORGANISM: Artificial Sequence
<220> FEATURE:
<223> OTHER INFORMATION: Oligonucleotide primer

<400> SEQUENCE: 10
catgacacct taacagaggc cccaggtcgt tttacctcgg cgccagattg cacaag    56

<210> SEQ ID NO 11
<211> LENGTH: 37
<212> TYPE: DNA
<213> ORGANISM: Artificial Sequence
<220> FEATURE:
<223> OTHER INFORMATION: Oligonucleotide primer

<400> SEQUENCE: 11
caataagctt tacatgacac cttaacagag gccccag    37

<210> SEQ ID NO 12
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 12
tcgagcggcc gctcaacaag atttgggctc aactttcttg    40

<210> SEQ ID NO 13
<211> LENGTH: 51
<212> TYPE: DNA
<213> ORGANISM: Artificial Sequence

```
<220> FEATURE:
<223> OTHER INFORMATION: Oligonucleotide primer

<400> SEQUENCE: 13
gctgctgctg tggttccccg gctcgcgatg cgctatacag ttgacacagt c          51

<210> SEQ ID NO 14
<211> LENGTH: 53
<212> TYPE: DNA
<213> ORGANISM: Artificial Sequence
<220> FEATURE:
<223> OTHER INFORMATION: Oligonucleotide primer

<400> SEQUENCE: 14
gaagatgaag acagatggtg cagccaccgt acgcttgatc tctacctttg ttc        53

<210> SEQ ID NO 15
<211> LENGTH: 676
<212> TYPE: PRT
<213> ORGANISM: Artificial Sequence
<220> FEATURE:
<223> OTHER INFORMATION: Anti-IL-17/IL-20 FIT1-Ig polypeptide

<400> SEQUENCE: 15
```

Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gln Val Gln Leu Val
    210                 215                 220

Gln Ser Gly Ala Glu Val Lys Arg Pro Gly Ala Ser Val Lys Val Ser
225                 230                 235                 240

Cys Lys Ala Ser Gly Tyr Thr Phe Thr Asn Asp Ile Ile His Trp Val
                245                 250                 255

Arg Gln Ala Pro Gly Gln Arg Leu Glu Trp Met Gly Trp Ile Asn Ala
            260                 265                 270

```
Gly Tyr Gly Asn Thr Gln Tyr Ser Gln Asn Phe Gln Asp Arg Val Ser
            275                 280                 285

Ile Thr Arg Asp Thr Ser Ala Ser Thr Ala Tyr Met Glu Leu Ile Ser
        290                 295                 300

Leu Arg Ser Glu Asp Thr Ala Val Tyr Tyr Cys Ala Arg Glu Pro Leu
305                 310                 315                 320

Trp Phe Gly Glu Ser Ser Pro His Asp Tyr Tyr Gly Met Asp Val Trp
                325                 330                 335

Gly Gln Gly Thr Thr Val Thr Val Ser Ser Ala Ser Thr Lys Gly Pro
                340                 345                 350

Ser Val Phe Pro Leu Ala Pro Ser Ser Lys Ser Thr Ser Gly Gly Thr
            355                 360                 365

Ala Ala Leu Gly Cys Leu Val Lys Asp Tyr Phe Pro Glu Pro Val Thr
        370                 375                 380

Val Ser Trp Asn Ser Gly Ala Leu Thr Ser Gly Val His Thr Phe Pro
385                 390                 395                 400

Ala Val Leu Gln Ser Ser Gly Leu Tyr Ser Leu Ser Ser Val Val Thr
                405                 410                 415

Val Pro Ser Ser Ser Leu Gly Thr Gln Thr Tyr Ile Cys Asn Val Asn
            420                 425                 430

His Lys Pro Ser Asn Thr Lys Val Asp Lys Lys Val Glu Pro Lys Ser
        435                 440                 445

Cys Asp Lys Thr His Thr Cys Pro Pro Cys Pro Ala Pro Glu Leu Leu
    450                 455                 460

Gly Gly Pro Ser Val Phe Leu Phe Pro Pro Lys Pro Lys Asp Thr Leu
465                 470                 475                 480

Met Ile Ser Arg Thr Pro Glu Val Thr Cys Val Val Val Asp Val Ser
                485                 490                 495

His Glu Asp Pro Glu Val Lys Phe Asn Trp Tyr Val Asp Gly Val Glu
            500                 505                 510

Val His Asn Ala Lys Thr Lys Pro Arg Glu Glu Gln Tyr Asn Ser Thr
        515                 520                 525

Tyr Arg Val Val Ser Val Leu Thr Val Leu His Gln Asp Trp Leu Asn
    530                 535                 540

Gly Lys Glu Tyr Lys Cys Lys Val Ser Asn Lys Ala Leu Pro Ala Pro
545                 550                 555                 560

Ile Glu Lys Thr Ile Ser Lys Ala Lys Gly Gln Pro Arg Glu Pro Gln
                565                 570                 575

Val Tyr Thr Leu Pro Pro Ser Arg Glu Glu Met Thr Lys Asn Gln Val
            580                 585                 590

Ser Leu Thr Cys Leu Val Lys Gly Phe Tyr Pro Ser Asp Ile Ala Val
        595                 600                 605

Glu Trp Glu Ser Asn Gly Gln Pro Glu Asn Asn Tyr Lys Thr Thr Pro
    610                 615                 620

Pro Val Leu Asp Ser Asp Gly Ser Phe Phe Leu Tyr Ser Lys Leu Thr
625                 630                 635                 640

Val Asp Lys Ser Arg Trp Gln Gln Gly Asn Val Phe Ser Cys Ser Val
                645                 650                 655

Met His Glu Ala Leu His Asn His Tyr Thr Gln Lys Ser Leu Ser Leu
            660                 665                 670

Ser Pro Gly Lys
            675
```

-continued

<210> SEQ ID NO 16
<211> LENGTH: 112
<212> TYPE: PRT
<213> ORGANISM: Homo sapiens

<400> SEQUENCE: 16

Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110

<210> SEQ ID NO 17
<211> LENGTH: 107
<212> TYPE: PRT
<213> ORGANISM: Homo sapiens

<400> SEQUENCE: 17

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 18
<211> LENGTH: 127
<212> TYPE: PRT
<213> ORGANISM: Mus sp.

<400> SEQUENCE: 18

Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Asn Asp
            20                  25                  30

Ile Ile His Trp Val Arg Gln Ala Pro Gly Gln Arg Leu Glu Trp Met
        35                  40                  45

Gly Trp Ile Asn Ala Gly Tyr Gly Asn Thr Gly Tyr Ser Gln Asn Phe
    50                  55                  60

Gln Asp Arg Val Ser Ile Thr Arg Asp Thr Ser Ala Ser Thr Ala Tyr

```
                65                  70                  75                  80
Met Glu Leu Ile Ser Leu Arg Ser Glu Asp Thr Ala Val Tyr Tyr Cys
                    85                  90                  95

Ala Arg Glu Pro Leu Trp Phe Gly Ser Ser Pro His Asp Tyr Tyr
                100                 105                 110

Gly Met Asp Val Trp Gly Gln Gly Thr Thr Val Thr Val Ser Ser
            115                 120                 125

<210> SEQ ID NO 19
<211> LENGTH: 103
<212> TYPE: PRT
<213> ORGANISM: Homo sapiens

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 20
<211> LENGTH: 227
<212> TYPE: PRT
<213> ORGANISM: Homo sapiens

<400> SEQUENCE: 20

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
```

```
                165                 170                 175
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 21
<211> LENGTH: 222
<212> TYPE: PRT
<213> ORGANISM: Artificial Sequence
<220> FEATURE:
<223> OTHER INFORMATION: Anti-IL-17/IL-20 FIT1-Ig polypeptide

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 22
<211> LENGTH: 119
<212> TYPE: PRT
<213> ORGANISM: Homo sapiens

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30
```

His Ile His Trp Val Arg Gln Ala Pro Gly Gln Gly Leu Glu Trp Met
            35                  40                  45

Gly Val Ile Asn Pro Met Tyr Gly Thr Thr Asp Tyr Asn Gln Arg Phe
 50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Tyr Phe Thr Gly Thr Gly Val Tyr Trp Gly Gln Gly
            100                 105                 110

Thr Leu Val Thr Val Ser Ser
            115

<210> SEQ ID NO 23
<211> LENGTH: 214
<212> TYPE: PRT
<213> ORGANISM: Artificial Sequence
<220> FEATURE:
<223> OTHER INFORMATION: Anti-IL-17/IL-20 FIT1-Ig polypeptide

<400> SEQUENCE: 23

Ala Ile Gln Leu Thr Gln Ser Pro Ser Ser Leu Ser Ala Ser Val Gly
 1                5                  10                  15

Asp Arg Val Thr Ile Thr Cys Arg Ala Ser Gln Gly Ile Ser Ser Ala
                 20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 24
<211> LENGTH: 107
<212> TYPE: PRT
<213> ORGANISM: Mus sp.

<400> SEQUENCE: 24

-continued

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 25
<211> LENGTH: 679
<212> TYPE: PRT
<213> ORGANISM: Artificial Sequence
<220> FEATURE:
<223> OTHER INFORMATION: Anti-IL-17/IL-20 FIT2-Ig polypeptide

<400> SEQUENCE: 25

Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
                20                  25                  30

Arg Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys Gly Ser Gly Gln Val
    210                 215                 220

Gln Leu Val Gln Ser Gly Ala Glu Val Lys Arg Pro Gly Ala Ser Val
225                 230                 235                 240

Lys Val Ser Cys Lys Ala Ser Gly Tyr Thr Phe Thr Asn Asp Ile Ile
                245                 250                 255

```
His Trp Val Arg Gln Ala Pro Gly Gln Arg Leu Glu Trp Met Gly Trp
                260                 265                 270

Ile Asn Ala Gly Tyr Gly Asn Thr Gln Tyr Ser Gln Asn Phe Gln Asp
            275                 280                 285

Arg Val Ser Ile Thr Arg Asp Thr Ser Ala Ser Thr Ala Tyr Met Glu
        290                 295                 300

Leu Ile Ser Leu Arg Ser Glu Asp Thr Ala Val Tyr Tyr Cys Ala Arg
305                 310                 315                 320

Glu Pro Leu Trp Phe Gly Glu Ser Ser Pro His Asp Tyr Tyr Gly Met
                325                 330                 335

Asp Val Trp Gly Gln Gly Thr Thr Val Thr Val Ser Ser Ala Ser Thr
            340                 345                 350

Lys Gly Pro Ser Val Phe Pro Leu Ala Pro Ser Ser Lys Ser Thr Ser
        355                 360                 365

Gly Gly Thr Ala Ala Leu Gly Cys Leu Val Lys Asp Tyr Phe Pro Glu
        370                 375                 380

Pro Val Thr Val Ser Trp Asn Ser Gly Ala Leu Thr Ser Gly Val His
385                 390                 395                 400

Thr Phe Pro Ala Val Leu Gln Ser Ser Gly Leu Tyr Ser Leu Ser Ser
                405                 410                 415

Val Val Thr Val Pro Ser Ser Ser Leu Gly Thr Gln Thr Tyr Ile Cys
            420                 425                 430

Asn Val Asn His Lys Pro Ser Asn Thr Lys Val Asp Lys Lys Val Glu
        435                 440                 445

Pro Lys Ser Cys Asp Lys Thr His Thr Cys Pro Pro Cys Pro Ala Pro
450                 455                 460

Glu Leu Leu Gly Gly Pro Ser Val Phe Leu Phe Pro Pro Lys Pro Lys
465                 470                 475                 480

Asp Thr Leu Met Ile Ser Arg Thr Pro Glu Val Thr Cys Val Val Val
                485                 490                 495

Asp Val Ser His Glu Asp Pro Glu Val Lys Phe Asn Trp Tyr Val Asp
            500                 505                 510

Gly Val Glu Val His Asn Ala Lys Thr Lys Pro Arg Glu Glu Gln Tyr
        515                 520                 525

Asn Ser Thr Tyr Arg Val Val Ser Val Leu Thr Val Leu His Gln Asp
530                 535                 540

Trp Leu Asn Gly Lys Glu Tyr Lys Cys Lys Val Ser Asn Lys Ala Leu
545                 550                 555                 560

Pro Ala Pro Ile Glu Lys Thr Ile Ser Lys Ala Lys Gly Gln Pro Arg
                565                 570                 575

Glu Pro Gln Val Tyr Thr Leu Pro Pro Ser Arg Glu Glu Met Thr Lys
            580                 585                 590

Asn Gln Val Ser Leu Thr Cys Leu Val Lys Gly Phe Tyr Pro Ser Asp
        595                 600                 605

Ile Ala Val Glu Trp Glu Ser Asn Gly Gln Pro Glu Asn Asn Tyr Lys
        610                 615                 620

Thr Thr Pro Pro Val Leu Asp Ser Asp Gly Ser Phe Phe Leu Tyr Ser
625                 630                 635                 640

Lys Leu Thr Val Asp Lys Ser Arg Trp Gln Gln Gly Asn Val Phe Ser
                645                 650                 655

Cys Ser Val Met His Glu Ala Leu His Asn His Tyr Thr Gln Lys Ser
            660                 665                 670

Leu Ser Leu Ser Pro Gly Lys
```

-continued

```
                675

<210> SEQ ID NO 26
<211> LENGTH: 3
<212> TYPE: PRT
<213> ORGANISM: Artificial Sequence
<220> FEATURE:
<223> OTHER INFORMATION: peptide linker sequence

<400> SEQUENCE: 26

Gly Ser Gly
1

<210> SEQ ID NO 27
<211> LENGTH: 683
<212> TYPE: PRT
<213> ORGANISM: Artificial Sequence
<220> FEATURE:
<223> OTHER INFORMATION: Anti-IL-17/IL-20 FIT3-Ig polypeptide

<400> SEQUENCE: 27

Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Ser Gln Val Gln Leu Val Gln Ser Gly Ala Glu Val Lys Arg Pro
225                 230                 235                 240

Gly Ala Ser Val Lys Val Ser Cys Lys Ala Ser Gly Tyr Thr Phe Thr
                245                 250                 255

Asn Asp Ile Ile His Trp Val Arg Gln Ala Pro Gly Gln Arg Leu Glu
            260                 265                 270

Trp Met Gly Trp Ile Asn Ala Gly Tyr Gly Asn Thr Gln Tyr Ser Gln
        275                 280                 285
```

```
Asn Phe Gln Asp Arg Val Ser Ile Thr Arg Asp Thr Ser Ala Ser Thr
    290                 295                 300

Ala Tyr Met Glu Leu Ile Ser Leu Arg Ser Glu Asp Thr Ala Val Tyr
305                 310                 315                 320

Tyr Cys Ala Arg Glu Pro Leu Trp Phe Gly Glu Ser Ser Pro His Asp
                325                 330                 335

Tyr Tyr Gly Met Asp Val Trp Gly Gln Gly Thr Thr Val Thr Val Ser
            340                 345                 350

Ser Ala Ser Thr Lys Gly Pro Ser Val Phe Pro Leu Ala Pro Ser Ser
        355                 360                 365

Lys Ser Thr Ser Gly Gly Thr Ala Ala Leu Gly Cys Leu Val Lys Asp
370                 375                 380

Tyr Phe Pro Glu Pro Val Thr Val Ser Trp Asn Ser Gly Ala Leu Thr
385                 390                 395                 400

Ser Gly Val His Thr Phe Pro Ala Val Leu Gln Ser Ser Gly Leu Tyr
                405                 410                 415

Ser Leu Ser Ser Val Val Thr Val Pro Ser Ser Ser Leu Gly Thr Gln
            420                 425                 430

Thr Tyr Ile Cys Asn Val Asn His Lys Pro Ser Asn Thr Lys Val Asp
        435                 440                 445

Lys Lys Val Glu Pro Lys Ser Cys Asp Lys Thr His Thr Cys Pro Pro
450                 455                 460

Cys Pro Ala Pro Glu Leu Leu Gly Gly Pro Ser Val Phe Leu Phe Pro
465                 470                 475                 480

Pro Lys Pro Lys Asp Thr Leu Met Ile Ser Arg Thr Pro Glu Val Thr
                485                 490                 495

Cys Val Val Val Asp Val Ser His Glu Asp Pro Glu Val Lys Phe Asn
            500                 505                 510

Trp Tyr Val Asp Gly Val Glu Val His Asn Ala Lys Thr Lys Pro Arg
        515                 520                 525

Glu Glu Gln Tyr Asn Ser Thr Tyr Arg Val Val Ser Val Leu Thr Val
530                 535                 540

Leu His Gln Asp Trp Leu Asn Gly Lys Glu Tyr Lys Cys Lys Val Ser
545                 550                 555                 560

Asn Lys Ala Leu Pro Ala Pro Ile Glu Lys Thr Ile Ser Lys Ala Lys
                565                 570                 575

Gly Gln Pro Arg Glu Pro Gln Val Tyr Thr Leu Pro Pro Ser Arg Glu
            580                 585                 590

Glu Met Thr Lys Asn Gln Val Ser Leu Thr Cys Leu Val Lys Gly Phe
        595                 600                 605

Tyr Pro Ser Asp Ile Ala Val Glu Trp Glu Ser Asn Gly Gln Pro Glu
610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Gln Gly
                645                 650                 655

Asn Val Phe Ser Cys Ser Val Met His Glu Ala Leu His Asn His Tyr
            660                 665                 670

Thr Gln Lys Ser Leu Ser Leu Ser Pro Gly Lys
        675                 680

<210> SEQ ID NO 28
<211> LENGTH: 7
<212> TYPE: PRT
```

```
<213> ORGANISM: Artificial Sequence
<220> FEATURE:
<223> OTHER INFORMATION: peptide linker sequence

<400> SEQUENCE: 28

Gly Gly Gly Gly Ser Gly Ser
1               5

<210> SEQ ID NO 29
<211> LENGTH: 436
<212> TYPE: PRT
<213> ORGANISM: Artificial Sequence
<220> FEATURE:
<223> OTHER INFORMATION: Anti-IL-17/IL-20 FIT4-Ig polypeptide

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
        35                  40                  45

Gly Val Ile Asn Pro Met Tyr Gly Thr Thr Asp Tyr Asn Gln Arg Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Ala Ile
    210                 215                 220

Gln Leu Thr Gln Ser Pro Ser Ser Leu Ser Ala Ser Val Gly Asp Arg
225                 230                 235                 240

Val Thr Ile Thr Cys Arg Ala Ser Gln Gly Ile Ser Ser Ala Leu Ala
                245                 250                 255

Trp Tyr Gln Gln Lys Pro Gly Lys Ala Pro Lys Leu Leu Ile Tyr Asp
            260                 265                 270

Ala Ser Ser Leu Glu Ser Gly Val Pro Ser Arg Phe Ser Gly Ser Gly
        275                 280                 285

Ser Gly Thr Asp Phe Thr Leu Thr Ile Ser Ser Leu Gln Pro Glu Asp
    290                 295                 300

Phe Ala Thr Tyr Tyr Cys Gln Gln Phe Asn Ser Tyr Pro Leu Thr Phe
305                 310                 315                 320
```

```
Gly Gly Gly Thr Lys Val Glu Ile Lys Arg Thr Val Ala Ala Pro Ser
            325                 330                 335

Val Phe Ile Phe Pro Pro Ser Asp Glu Gln Leu Lys Ser Gly Thr Ala
            340                 345                 350

Ser Val Val Cys Leu Leu Asn Asn Phe Tyr Pro Arg Glu Ala Lys Val
            355                 360                 365

Gln Trp Lys Val Asp Asn Ala Leu Gln Ser Gly Asn Ser Gln Glu Ser
            370                 375                 380

Val Thr Glu Gln Asp Ser Lys Asp Ser Thr Tyr Ser Leu Ser Ser Thr
385                 390                 395                 400

Leu Thr Leu Ser Lys Ala Asp Tyr Glu Lys His Lys Val Tyr Ala Cys
            405                 410                 415

Glu Val Thr His Gln Gly Leu Ser Ser Pro Val Thr Lys Ser Phe Asn
            420                 425                 430

Arg Gly Glu Cys
            435

<210> SEQ ID NO 30
<211> LENGTH: 439
<212> TYPE: PRT
<213> ORGANISM: Artificial Sequence
<220> FEATURE:
<223> OTHER INFORMATION: Anti-IL-17/IL-20 FIT5-Ig polypeptide

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

His Ile His Trp Val Arg Gln Ala Pro Gly Gln Gly Leu Glu Trp Met
            35                  40                  45

Gly Val Ile Asn Pro Met Tyr Gly Thr Thr Asp Tyr Asn Gln Arg Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Tyr Asp Tyr Phe Thr Gly Thr Gly Val Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Gly Ser
            210                 215                 220

Gly Ala Ile Gln Leu Thr Gln Ser Pro Ser Ser Leu Ser Ala Ser Val
225                 230                 235                 240
```

Gly Asp Arg Val Thr Ile Thr Cys Arg Ala Ser Gln Gly Ile Ser Ser
                245                 250                 255

Ala Leu Ala Trp Tyr Gln Gln Lys Pro Gly Lys Ala Pro Lys Leu Leu
        260                 265                 270

Ile Tyr Asp Ala Ser Ser Leu Glu Ser Gly Val Pro Ser Arg Phe Ser
            275                 280                 285

Gly Ser Gly Ser Gly Thr Asp Phe Thr Leu Thr Ile Ser Ser Leu Gln
        290                 295                 300

Pro Glu Asp Phe Ala Thr Tyr Tyr Cys Gln Gln Phe Asn Ser Tyr Pro
305                 310                 315                 320

Leu Thr Phe Gly Gly Gly Thr Lys Val Glu Ile Lys Arg Thr Val Ala
                325                 330                 335

Ala Pro Ser Val Phe Ile Phe Pro Pro Ser Asp Glu Gln Leu Lys Ser
            340                 345                 350

Gly Thr Ala Ser Val Val Cys Leu Leu Asn Asn Phe Tyr Pro Arg Glu
        355                 360                 365

Ala Lys Val Gln Trp Lys Val Asp Asn Ala Leu Gln Ser Gly Asn Ser
    370                 375                 380

Gln Glu Ser Val Thr Glu Gln Asp Ser Lys Asp Ser Thr Tyr Ser Leu
385                 390                 395                 400

Ser Ser Thr Leu Thr Leu Ser Lys Ala Asp Tyr Glu Lys His Lys Val
                405                 410                 415

Tyr Ala Cys Glu Val Thr His Gln Gly Leu Ser Ser Pro Val Thr Lys
            420                 425                 430

Ser Phe Asn Arg Gly Glu Cys
            435

<210> SEQ ID NO 31
<211> LENGTH: 443
<212> TYPE: PRT
<213> ORGANISM: Artificial Sequence
<220> FEATURE:
<223> OTHER INFORMATION: Anti-IL-17/IL-20 FIT6-Ig polypeptide

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
                20                  25                  30

His Ile His Trp Val Arg Gln Ala Pro Gly Gln Gly Leu Glu Trp Met
            35                  40                  45

Gly Val Ile Asn Pro Met Tyr Gly Thr Thr Asp Tyr Asn Gln Arg Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Phe Thr Gly Thr Gly Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

```
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220

Gly Gly Ser Gly Ser Ala Ile Gln Leu Thr Gln Ser Pro Ser Ser Leu
225                 230                 235                 240

Ser Ala Ser Val Gly Asp Arg Val Thr Ile Thr Cys Arg Ala Ser Gln
                245                 250                 255

Gly Ile Ser Ser Ala Leu Ala Trp Tyr Gln Gln Lys Pro Gly Lys Ala
            260                 265                 270

Pro Lys Leu Leu Ile Tyr Asp Ala Ser Ser Leu Glu Ser Gly Val Pro
        275                 280                 285

Ser Arg Phe Ser Gly Ser Gly Ser Gly Thr Asp Phe Thr Leu Thr Ile
    290                 295                 300

Ser Ser Leu Gln Pro Glu Asp Phe Ala Thr Tyr Tyr Cys Gln Gln Phe
305                 310                 315                 320

Asn Ser Tyr Pro Leu Thr Phe Gly Gly Gly Thr Lys Val Glu Ile Lys
                325                 330                 335

Arg Thr Val Ala Ala Pro Ser Val Phe Ile Phe Pro Pro Ser Asp Glu
            340                 345                 350

Gln Leu Lys Ser Gly Thr Ala Ser Val Val Cys Leu Leu Asn Asn Phe
        355                 360                 365

Tyr Pro Arg Glu Ala Lys Val Gln Trp Lys Val Asp Asn Ala Leu Gln
    370                 375                 380

Ser Gly Asn Ser Gln Glu Ser Val Thr Glu Gln Asp Ser Lys Asp Ser
385                 390                 395                 400

Thr Tyr Ser Leu Ser Ser Thr Leu Thr Leu Ser Lys Ala Asp Tyr Glu
                405                 410                 415

Lys His Lys Val Tyr Ala Cys Glu Val Thr His Gln Gly Leu Ser Ser
            420                 425                 430

Pro Val Thr Lys Ser Phe Asn Arg Gly Glu Cys
        435                 440

<210> SEQ ID NO 32
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 32
gtctgcggcc gctcatttac ccggagacag ggagag                              36

<210> SEQ ID NO 33
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 33
tcgagcggcc gctcaacaag atttgggctc aactttcttg                          40
```

<210> SEQ ID NO 34
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 34
caggtccagc tgcagcagtc tg                                            22

<210> SEQ ID NO 35
<211> LENGTH: 59
<212> TYPE: DNA
<213> ORGANISM: Artificial Sequence
<220> FEATURE:
<223> OTHER INFORMATION: Oligonucleotide primer

<400> SEQUENCE: 35
gcctgcgaag tcacccatca gggcctgagc tcgcccgtca caaagagctt caacagggg    59

<210> SEQ ID NO 36
<211> LENGTH: 50
<212> TYPE: DNA
<213> ORGANISM: Artificial Sequence
<220> FEATURE:
<223> OTHER INFORMATION: Oligonucleotide primer

<400> SEQUENCE: 36
tacgagaaac acaaagtcta cgcctgcgaa gtcacccatc agggcctgag               50

<210> SEQ ID NO 37
<211> LENGTH: 50
<212> TYPE: DNA
<213> ORGANISM: Artificial Sequence
<220> FEATURE:
<223> OTHER INFORMATION: Oligonucleotide primer

<400> SEQUENCE: 37
tgacgctgag caaagcagac tacgagaaac acaaagtcta cgcctgcgaa               50

<210> SEQ ID NO 38
<211> LENGTH: 59
<212> TYPE: DNA
<213> ORGANISM: Artificial Sequence
<220> FEATURE:
<223> OTHER INFORMATION: Oligonucleotide primer

<400> SEQUENCE: 38
ctcgcccgtc acaaagagct tcaacagggg agagtgtgaa gtgcagctgg tggagtctg     59

<210> SEQ ID NO 39
<211> LENGTH: 51
<212> TYPE: DNA
<213> ORGANISM: Artificial Sequence
<220> FEATURE:
<223> OTHER INFORMATION: Oligonucleotide primer

<400> SEQUENCE: 39
gctgctgctg tggttccccg gctcgcgatg cgaaattgtg ttgacacagt c             51

<210> SEQ ID NO 40
<211> LENGTH: 52
<212> TYPE: DNA
<213> ORGANISM: Artificial Sequence
<220> FEATURE:
<223> OTHER INFORMATION: Oligonucleotide primer

<400> SEQUENCE: 40
aagatgaaga cagatggtgc agccaccgta cgtttaatct ccagtcgtgt cc    52

<210> SEQ ID NO 41
<211> LENGTH: 665
<212> TYPE: PRT
<213> ORGANISM: Artificial Sequence
<220> FEATURE:
<223> OTHER INFORMATION: OKT3/Ofatumumab FIT7-Ig polypeptide

<400> SEQUENCE: 41

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Glu Val Gln Leu Val Glu Ser Gly Gly Gly Leu
    210                 215                 220

Val Gln Pro Gly Arg Ser Leu Arg Leu Ser Cys Ala Ala Ser Gly Phe
225                 230                 235                 240

Thr Phe Asn Asp Tyr Ala Met His Trp Val Arg Gln Ala Pro Gly Lys
                245                 250                 255

Gly Leu Glu Trp Val Ser Thr Ile Ser Trp Asn Ser Gly Ser Ile Gly
            260                 265                 270

Tyr Ala Asp Ser Val Lys Gly Arg Phe Thr Ile Ser Arg Asp Asn Ala
        275                 280                 285

Lys Lys Ser Leu Tyr Leu Gln Met Asn Ser Leu Arg Ala Glu Asp Thr
    290                 295                 300

Ala Leu Tyr Tyr Cys Ala Lys Asp Ile Gln Tyr Gly Asn Tyr Tyr Tyr
305                 310                 315                 320

Gly Met Asp Val Trp Gly Gln Gly Thr Thr Val Thr Val Ser Ser Ala
                325                 330                 335

Ser Thr Lys Gly Pro Ser Val Phe Pro Leu Ala Pro Ser Ser Lys Ser
            340                 345                 350

```
Thr Ser Gly Gly Thr Ala Ala Leu Gly Cys Leu Val Lys Asp Tyr Phe
            355                 360                 365

Pro Glu Pro Val Thr Val Ser Trp Asn Ser Gly Ala Leu Thr Ser Gly
        370                 375                 380

Val His Thr Phe Pro Ala Val Leu Gln Ser Ser Gly Leu Tyr Ser Leu
385                 390                 395                 400

Ser Ser Val Val Thr Val Pro Ser Ser Ser Leu Gly Thr Gln Thr Tyr
                405                 410                 415

Ile Cys Asn Val Asn His Lys Pro Ser Asn Thr Lys Val Asp Lys Lys
            420                 425                 430

Val Glu Pro Lys Ser Cys Asp Lys Thr His Thr Cys Pro Pro Cys Pro
        435                 440                 445

Ala Pro Glu Leu Leu Gly Gly Pro Ser Val Phe Leu Phe Pro Pro Lys
    450                 455                 460

Pro Lys Asp Thr Leu Met Ile Ser Arg Thr Pro Glu Val Thr Cys Val
465                 470                 475                 480

Val Val Asp Val Ser His Glu Asp Pro Glu Val Lys Phe Asn Trp Tyr
                485                 490                 495

Val Asp Gly Val Glu Val His Asn Ala Lys Thr Lys Pro Arg Glu Glu
            500                 505                 510

Gln Tyr Asn Ser Thr Tyr Arg Val Val Ser Val Leu Thr Val Leu His
        515                 520                 525

Gln Asp Trp Leu Asn Gly Lys Glu Tyr Lys Cys Lys Val Ser Asn Lys
    530                 535                 540

Ala Leu Pro Ala Pro Ile Glu Lys Thr Ile Ser Lys Ala Lys Gly Gln
545                 550                 555                 560

Pro Arg Glu Pro Gln Val Tyr Thr Leu Pro Pro Ser Arg Glu Glu Met
                565                 570                 575

Thr Lys Asn Gln Val Ser Leu Thr Cys Leu Val Lys Gly Phe Tyr Pro
            580                 585                 590

Ser Asp Ile Ala Val Glu Trp Glu Ser Asn Gly Gln Pro Glu Asn Asn
        595                 600                 605

Tyr Lys Thr Thr Pro Pro Val Leu Asp Ser Asp Gly Ser Phe Phe Leu
    610                 615                 620

Tyr Ser Lys Leu Thr Val Asp Lys Ser Arg Trp Gln Gln Gly Asn Val
625                 630                 635                 640

Phe Ser Cys Ser Val Met His Glu Ala Leu His Asn His Tyr Thr Gln
                645                 650                 655

Lys Ser Leu Ser Leu Ser Pro Gly Lys
            660                 665

<210> SEQ ID NO 42
<211> LENGTH: 106
<212> TYPE: PRT
<213> ORGANISM: Mus sp.

<400> SEQUENCE: 42

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
```

```
                        50                  55                  60
Gly Ser Gly Thr Ser Tyr Ser Leu Thr Ile Ser Gly Met Glu Ala Glu
 65                  70                  75                  80

Asp Ala Ala Thr Tyr Tyr Cys Gln Gln Trp Ser Ser Asn Pro Phe Thr
                 85                  90                  95

Phe Gly Ser Gly Thr Lys Leu Glu Ile Asn
            100                 105

<210> SEQ ID NO 43
<211> LENGTH: 122
<212> TYPE: PRT
<213> ORGANISM: Homo sapiens

<400> SEQUENCE: 43

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asn Asp Tyr
                20                  25                  30

Ala Met His Trp Val Arg Gln Ala Pro Gly Lys Gly Leu Glu Trp Val
            35                  40                  45

Ser Thr Ile Ser Trp Asn Ser Gly Ser Ile Gly Tyr Ala Asp Ser Val
 50                  55                  60

Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
        115                 120

<210> SEQ ID NO 44
<211> LENGTH: 222
<212> TYPE: PRT
<213> ORGANISM: Artificial Sequence
<220> FEATURE:
<223> OTHER INFORMATION: OKT3/Ofatumumab FIT7-Ig polypeptide

<400> SEQUENCE: 44

Gln Val Gln Leu Gln Gln Ser Gly Ala Glu Leu Ala Arg Pro Gly Ala
 1               5                  10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
 50                  55                  60

Lys Asp Lys Ala Thr Leu Thr Thr Asp Lys Ser Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 45
<211> LENGTH: 119
<212> TYPE: PRT
<213> ORGANISM: Mus sp.

<400> SEQUENCE: 45

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 46
<211> LENGTH: 214
<212> TYPE: PRT
<213> ORGANISM: Artificial Sequence
<220> FEATURE:
<223> OTHER INFORMATION: OKT3/Ofatumumab FIT7-Ig polypeptide

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys Arg Thr Val Ala Ala
            100                 105                 110

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 47
<211> LENGTH: 107
<212> TYPE: PRT
<213> ORGANISM: Homo sapiens

<400> SEQUENCE: 47

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 48
<211> LENGTH: 672
<212> TYPE: PRT
<213> ORGANISM: Artificial Sequence
<220> FEATURE:
<223> OTHER INFORMATION: OKT3/Ofatumumab FIT8-Ig polypeptide

<400> SEQUENCE: 48

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Thr Val Ala Ala Pro
```

```
                100                 105                 110
Ser Val Phe Ile Phe Pro Pro Ser Asp Glu Gln Leu Lys Ser Gly Thr
            115                 120                 125
Ala Ser Val Val Cys Leu Leu Asn Asn Phe Tyr Pro Arg Glu Ala Lys
            130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
            165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
            195                 200                 205
Asn Arg Gly Glu Cys Gly Gly Gly Gly Ser Gly Ser Glu Val Gln Leu
            210                 215                 220
Val Glu Ser Gly Gly Gly Leu Val Gln Pro Gly Arg Ser Leu Arg Leu
225                 230                 235                 240
Ser Cys Ala Ala Ser Gly Phe Thr Phe Asn Asp Tyr Ala Met His Trp
            245                 250                 255
Val Arg Gln Ala Pro Gly Lys Gly Leu Glu Trp Val Ser Thr Ile Ser
            260                 265                 270
Trp Asn Ser Gly Ser Ile Gly Tyr Ala Asp Ser Val Lys Gly Arg Phe
            275                 280                 285
Thr Ile Ser Arg Asp Asn Ala Lys Lys Ser Leu Tyr Leu Gln Met Asn
            290                 295                 300
Ser Leu Arg Ala Glu Asp Thr Ala Leu Tyr Tyr Cys Ala Lys Asp Ile
305                 310                 315                 320
Gln Tyr Gly Asn Tyr Tyr Tyr Gly Met Asp Val Trp Gly Gln Gly Thr
            325                 330                 335
Thr Val Thr Val Ser Ser Ala Ser Thr Lys Gly Pro Ser Val Phe Pro
            340                 345                 350
Leu Ala Pro Ser Ser Lys Ser Thr Ser Gly Gly Thr Ala Ala Leu Gly
            355                 360                 365
Cys Leu Val Lys Asp Tyr Phe Pro Glu Pro Val Thr Val Ser Trp Asn
370                 375                 380
Ser Gly Ala Leu Thr Ser Gly Val His Thr Phe Pro Ala Val Leu Gln
385                 390                 395                 400
Ser Ser Gly Leu Tyr Ser Leu Ser Ser Val Val Thr Val Pro Ser Ser
            405                 410                 415
Ser Leu Gly Thr Gln Thr Tyr Ile Cys Asn Val Asn His Lys Pro Ser
            420                 425                 430
Asn Thr Lys Val Asp Lys Lys Val Glu Pro Lys Ser Cys Asp Lys Thr
            435                 440                 445
His Thr Cys Pro Pro Cys Pro Ala Pro Glu Leu Leu Gly Gly Pro Ser
            450                 455                 460
Val Phe Leu Phe Pro Pro Lys Pro Lys Asp Thr Leu Met Ile Ser Arg
465                 470                 475                 480
Thr Pro Glu Val Thr Cys Val Val Val Asp Val Ser His Glu Asp Pro
            485                 490                 495
Glu Val Lys Phe Asn Trp Tyr Val Asp Gly Val Glu Val His Asn Ala
            500                 505                 510
Lys Thr Lys Pro Arg Glu Glu Gln Tyr Asn Ser Thr Tyr Arg Val Val
            515                 520                 525
```

Ser Val Leu Thr Val Leu His Gln Asp Trp Leu Asn Gly Lys Glu Tyr
            530                 535                 540

Lys Cys Lys Val Ser Asn Lys Ala Leu Pro Ala Pro Ile Glu Lys Thr
545                 550                 555                 560

Ile Ser Lys Ala Lys Gly Gln Pro Arg Glu Pro Gln Val Tyr Thr Leu
                565                 570                 575

Pro Pro Ser Arg Glu Glu Met Thr Lys Asn Gln Val Ser Leu Thr Cys
            580                 585                 590

Leu Val Lys Gly Phe Tyr Pro Ser Asp Ile Ala Val Glu Trp Glu Ser
            595                 600                 605

Asn Gly Gln Pro Glu Asn Asn Tyr Lys Thr Thr Pro Pro Val Leu Asp
            610                 615                 620

Ser Asp Gly Ser Phe Phe Leu Tyr Ser Lys Leu Thr Val Asp Lys Ser
625                 630                 635                 640

Arg Trp Gln Gln Gly Asn Val Phe Ser Cys Ser Val Met His Glu Ala
                645                 650                 655

Leu His Asn His Tyr Thr Gln Lys Ser Leu Ser Leu Ser Pro Gly Lys
            660                 665                 670

<210> SEQ ID NO 49
<211> LENGTH: 3
<212> TYPE: PRT
<213> ORGANISM: Artificial Sequence
<220> FEATURE:
<223> OTHER INFORMATION: peptide linker sequence

<400> SEQUENCE: 49

Gly Gly Ser
1

<210> SEQ ID NO 50
<211> LENGTH: 3
<212> TYPE: PRT
<213> ORGANISM: Artificial Sequence
<220> FEATURE:
<223> OTHER INFORMATION: peptide linker sequence

<400> SEQUENCE: 50

Ser Gly Gly
1

<210> SEQ ID NO 51
<211> LENGTH: 3
<212> TYPE: PRT
<213> ORGANISM: Artificial Sequence
<220> FEATURE:
<223> OTHER INFORMATION: peptide linker sequence

<400> SEQUENCE: 51

Gly Gly Gly
1

<210> SEQ ID NO 52
<211> LENGTH: 4
<212> TYPE: PRT
<213> ORGANISM: Artificial Sequence
<220> FEATURE:
<223> OTHER INFORMATION: peptide linker sequence

<400> SEQUENCE: 52

Gly Gly Gly Ser
1

```
<210> SEQ ID NO 53
<211> LENGTH: 4
<212> TYPE: PRT
<213> ORGANISM: Artificial Sequence
<220> FEATURE:
<223> OTHER INFORMATION: peptide linker sequence

<400> SEQUENCE: 53

Ser Gly Gly Gly
1

<210> SEQ ID NO 54
<211> LENGTH: 5
<212> TYPE: PRT
<213> ORGANISM: Artificial Sequence
<220> FEATURE:
<223> OTHER INFORMATION: peptide linker sequence

<400> SEQUENCE: 54

Gly Gly Gly Gly Ser
1               5

<210> SEQ ID NO 55
<211> LENGTH: 8
<212> TYPE: PRT
<213> ORGANISM: Artificial Sequence
<220> FEATURE:
<223> OTHER INFORMATION: peptide linker sequence

<400> SEQUENCE: 55

Gly Gly Gly Gly Ser Gly Gly Ser
1               5

<210> SEQ ID NO 56
<211> LENGTH: 10
<212> TYPE: PRT
<213> ORGANISM: Artificial Sequence
<220> FEATURE:
<223> OTHER INFORMATION: peptide linker sequence

<400> SEQUENCE: 56

Gly Gly Gly Gly Ser Gly Gly Gly Gly Ser
1               5                   10

<210> SEQ ID NO 57
<211> LENGTH: 15
<212> TYPE: PRT
<213> ORGANISM: Artificial Sequence
<220> FEATURE:
<223> OTHER INFORMATION: peptide linker sequence

<400> SEQUENCE: 57

Gly Gly Gly Gly Ser Gly Gly Gly Ser Gly Gly Gly Gly Ser
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: peptide linker sequence

<400> SEQUENCE: 58

Ala Lys Thr Thr Pro Lys Leu Glu Glu Gly Glu Phe Ser Glu Ala Arg
1               5                   10                  15
```

<210> SEQ ID NO 59
<211> LENGTH: 17
<212> TYPE: PRT
<213> ORGANISM: Artificial Sequence
<220> FEATURE:
<223> OTHER INFORMATION: peptide linker sequence

<400> SEQUENCE: 59

Ala Lys Thr Thr Pro Lys Leu Glu Glu Gly Glu Phe Ser Glu Ala Arg
1               5                   10                  15

Val

<210> SEQ ID NO 60
<211> LENGTH: 9
<212> TYPE: PRT
<213> ORGANISM: Artificial Sequence
<220> FEATURE:
<223> OTHER INFORMATION: peptide linker sequence

<400> SEQUENCE: 60

Ala Lys Thr Thr Pro Lys Leu Gly Gly
1               5

<210> SEQ ID NO 61
<211> LENGTH: 10
<212> TYPE: PRT
<213> ORGANISM: Artificial Sequence
<220> FEATURE:
<223> OTHER INFORMATION: peptide linker sequence

<400> SEQUENCE: 61

Ser Ala Lys Thr Thr Pro Lys Leu Gly Gly
1               5                   10

<210> SEQ ID NO 62
<211> LENGTH: 16
<212> TYPE: PRT
<213> ORGANISM: Artificial Sequence
<220> FEATURE:
<223> OTHER INFORMATION: peptide linker sequence

<400> SEQUENCE: 62

Lys Thr Thr Pro Lys Leu Glu Glu Gly Glu Phe Ser Glu Ala Arg Val
1               5                   10                  15

<210> SEQ ID NO 63
<211> LENGTH: 6
<212> TYPE: PRT
<213> ORGANISM: Artificial Sequence
<220> FEATURE:
<223> OTHER INFORMATION: peptide linker sequence

<400> SEQUENCE: 63

Ser Ala Lys Thr Thr Pro
1               5

<210> SEQ ID NO 64
<211> LENGTH: 10
<212> TYPE: PRT
<213> ORGANISM: Artificial Sequence
<220> FEATURE:
<223> OTHER INFORMATION: peptide linker sequence

<400> SEQUENCE: 64

Ser Ala Lys Thr Thr Pro Lys Leu Gly Gly
1               5                   10

<210> SEQ ID NO 65
<211> LENGTH: 6
<212> TYPE: PRT
<213> ORGANISM: Artificial Sequence
<220> FEATURE:
<223> OTHER INFORMATION: peptide linker sequence

<400> SEQUENCE: 65

Arg Ala Asp Ala Ala Pro
1               5

<210> SEQ ID NO 66
<211> LENGTH: 9
<212> TYPE: PRT
<213> ORGANISM: Artificial Sequence
<220> FEATURE:
<223> OTHER INFORMATION: peptide linker sequence

<400> SEQUENCE: 66

Arg Ala Asp Ala Ala Pro Thr Val Ser
1               5

<210> SEQ ID NO 67
<211> LENGTH: 12
<212> TYPE: PRT
<213> ORGANISM: Artificial Sequence
<220> FEATURE:
<223> OTHER INFORMATION: peptide linker sequence

<400> SEQUENCE: 67

Arg Ala Asp Ala Ala Ala Ala Gly Gly Pro Gly Ser
1               5                   10

<210> SEQ ID NO 68
<211> LENGTH: 27
<212> TYPE: PRT
<213> ORGANISM: Artificial Sequence
<220> FEATURE:
<223> OTHER INFORMATION: peptide linker sequence

<400> SEQUENCE: 68

Arg Ala Asp Ala Ala Ala Ala Gly Gly Gly Gly Ser Gly Gly Gly Gly
1               5                   10                  15

Ser Gly Gly Gly Gly Ser Gly Gly Gly Gly Ser
            20                  25

<210> SEQ ID NO 69
<211> LENGTH: 6
<212> TYPE: PRT
<213> ORGANISM: Artificial Sequence
<220> FEATURE:
<223> OTHER INFORMATION: peptide linker sequence

<400> SEQUENCE: 69

Ser Ala Lys Thr Thr Pro
1               5

<210> SEQ ID NO 70
<211> LENGTH: 10
<212> TYPE: PRT
<213> ORGANISM: Artificial Sequence
<220> FEATURE:
<223> OTHER INFORMATION: peptide linker sequence

<400> SEQUENCE: 70

```
Ser Ala Lys Thr Thr Pro Lys Leu Gly Gly
1               5                   10
```

<210> SEQ ID NO 71
<211> LENGTH: 18
<212> TYPE: PRT
<213> ORGANISM: Artificial Sequence
<220> FEATURE:
<223> OTHER INFORMATION: peptide linker sequence

<400> SEQUENCE: 71

```
Ser Ala Lys Thr Thr Pro Lys Leu Glu Glu Gly Glu Phe Ser Glu Ala
1               5                   10                  15

Arg Val
```

<210> SEQ ID NO 72
<211> LENGTH: 5
<212> TYPE: PRT
<213> ORGANISM: Artificial Sequence
<220> FEATURE:
<223> OTHER INFORMATION: peptide linker sequence

<400> SEQUENCE: 72

```
Ala Asp Ala Ala Pro
1               5
```

<210> SEQ ID NO 73
<211> LENGTH: 12
<212> TYPE: PRT
<213> ORGANISM: Artificial Sequence
<220> FEATURE:
<223> OTHER INFORMATION: peptide linker sequence

<400> SEQUENCE: 73

```
Ala Asp Ala Ala Pro Thr Val Ser Ile Phe Pro Pro
1               5                   10
```

<210> SEQ ID NO 74
<211> LENGTH: 5
<212> TYPE: PRT
<213> ORGANISM: Artificial Sequence
<220> FEATURE:
<223> OTHER INFORMATION: peptide linker sequence

<400> SEQUENCE: 74

```
Thr Val Ala Ala Pro
1               5
```

<210> SEQ ID NO 75
<211> LENGTH: 12
<212> TYPE: PRT
<213> ORGANISM: Artificial Sequence
<220> FEATURE:
<223> OTHER INFORMATION: peptide linker sequence

<400> SEQUENCE: 75

```
Thr Val Ala Ala Pro Ser Val Phe Ile Phe Pro Pro
1               5                   10
```

<210> SEQ ID NO 76
<211> LENGTH: 6
<212> TYPE: PRT
<213> ORGANISM: Artificial Sequence
<220> FEATURE:
<223> OTHER INFORMATION: peptide linker sequence

<400> SEQUENCE: 76

```
Gln Pro Lys Ala Ala Pro
1               5

<210> SEQ ID NO 77
<211> LENGTH: 13
<212> TYPE: PRT
<213> ORGANISM: Artificial Sequence
<220> FEATURE:
<223> OTHER INFORMATION: peptide linker sequence

<400> SEQUENCE: 77

Gln Pro Lys Ala Ala Pro Ser Val Thr Leu Phe Pro Pro
1               5                   10

<210> SEQ ID NO 78
<211> LENGTH: 6
<212> TYPE: PRT
<213> ORGANISM: Artificial Sequence
<220> FEATURE:
<223> OTHER INFORMATION: peptide linker sequence

<400> SEQUENCE: 78

Ala Lys Thr Thr Pro Pro
1               5

<210> SEQ ID NO 79
<211> LENGTH: 13
<212> TYPE: PRT
<213> ORGANISM: Artificial Sequence
<220> FEATURE:
<223> OTHER INFORMATION: peptide linker sequence

<400> SEQUENCE: 79

Ala Lys Thr Thr Pro Pro Ser Val Thr Pro Leu Ala Pro
1               5                   10

<210> SEQ ID NO 80
<211> LENGTH: 6
<212> TYPE: PRT
<213> ORGANISM: Artificial Sequence
<220> FEATURE:
<223> OTHER INFORMATION: peptide linker sequence

<400> SEQUENCE: 80

Ala Lys Thr Thr Ala Pro
1               5

<210> SEQ ID NO 81
<211> LENGTH: 13
<212> TYPE: PRT
<213> ORGANISM: Artificial Sequence
<220> FEATURE:
<223> OTHER INFORMATION: peptide linker sequence

<400> SEQUENCE: 81

Ala Lys Thr Thr Ala Pro Ser Val Tyr Pro Leu Ala Pro
1               5                   10

<210> SEQ ID NO 82
<211> LENGTH: 6
<212> TYPE: PRT
<213> ORGANISM: Artificial Sequence
<220> FEATURE:
<223> OTHER INFORMATION: peptide linker sequence

<400> SEQUENCE: 82
```

```
Ala Ser Thr Lys Gly Pro
1               5
```

<210> SEQ ID NO 83
<211> LENGTH: 13
<212> TYPE: PRT
<213> ORGANISM: Artificial Sequence
<220> FEATURE:
<223> OTHER INFORMATION: peptide linker sequence

<400> SEQUENCE: 83

```
Ala Ser Thr Lys Gly Pro Ser Val Phe Pro Leu Ala Pro
1               5                   10
```

<210> SEQ ID NO 84
<211> LENGTH: 15
<212> TYPE: PRT
<213> ORGANISM: Artificial Sequence
<220> FEATURE:
<223> OTHER INFORMATION: peptide linker sequence

<400> SEQUENCE: 84

```
Gly Glu Asn Lys Val Glu Tyr Ala Pro Ala Leu Met Ala Leu Ser
1               5                   10                  15
```

<210> SEQ ID NO 85
<211> LENGTH: 15
<212> TYPE: PRT
<213> ORGANISM: Artificial Sequence
<220> FEATURE:
<223> OTHER INFORMATION: peptide linker sequence

<400> SEQUENCE: 85

```
Gly Pro Ala Lys Glu Leu Thr Pro Leu Lys Glu Ala Lys Val Ser
1               5                   10                  15
```

<210> SEQ ID NO 86
<211> LENGTH: 15
<212> TYPE: PRT
<213> ORGANISM: Artificial Sequence
<220> FEATURE:
<223> OTHER INFORMATION: peptide linker sequence

<400> SEQUENCE: 86

```
Gly His Glu Ala Ala Ala Val Met Gln Val Gln Tyr Pro Ala Ser
1               5                   10                  15
```

<210> SEQ ID NO 87
<211> LENGTH: 664
<212> TYPE: PRT
<213> ORGANISM: Artificial Sequence
<220> FEATURE:
<223> OTHER INFORMATION: TNF/IL-17 FIT9-Ig polypeptide

<400> SEQUENCE: 87

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

-continued

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gln Val Gln Leu Val Gln Ser Gly Ala
    210                 215                 220

Glu Val Lys Lys Pro Gly Ser Ser Val Lys Val Ser Cys Lys Ala Ser
225                 230                 235                 240

Gly Tyr Ser Phe Thr Asp Tyr His Ile His Trp Val Arg Gln Ala Pro
                245                 250                 255

Gly Gln Gly Leu Glu Trp Met Gly Val Ile Asn Pro Met Tyr Gly Thr
            260                 265                 270

Thr Asp Tyr Asn Gln Arg Phe Lys Gly Arg Val Thr Ile Thr Ala Asp
        275                 280                 285

Glu Ser Thr Ser Thr Ala Tyr Met Glu Leu Ser Ser Leu Arg Ser Glu
    290                 295                 300

Asp Thr Ala Val Tyr Tyr Cys Ala Arg Tyr Asp Tyr Phe Thr Gly Thr
305                 310                 315                 320

Gly Val Tyr Trp Gly Gln Gly Thr Leu Val Thr Val Ser Ser Ala Ser
                325                 330                 335

Thr Lys Gly Pro Ser Val Phe Pro Leu Ala Pro Ser Ser Lys Ser Thr
            340                 345                 350

Ser Gly Gly Thr Ala Ala Leu Gly Cys Leu Val Lys Asp Tyr Phe Pro
        355                 360                 365

Glu Pro Val Thr Val Ser Trp Asn Ser Gly Ala Leu Thr Ser Gly Val
    370                 375                 380

His Thr Phe Pro Ala Val Leu Gln Ser Ser Gly Leu Tyr Ser Leu Ser
385                 390                 395                 400

Ser Val Val Thr Val Pro Ser Ser Ser Leu Gly Thr Gln Thr Tyr Ile
                405                 410                 415

Cys Asn Val Asn His Lys Pro Ser Asn Thr Lys Val Asp Lys Lys Val
            420                 425                 430

Glu Pro Lys Ser Cys Asp Lys Thr His Thr Cys Pro Pro Cys Pro Ala
        435                 440                 445

Pro Glu Leu Leu Gly Gly Pro Ser Val Phe Leu Phe Pro Pro Lys Pro
    450                 455                 460

Lys Asp Thr Leu Met Ile Ser Arg Thr Pro Glu Val Thr Cys Val Val
465                 470                 475                 480

Val Asp Val Ser His Glu Asp Pro Glu Val Lys Phe Asn Trp Tyr Val
                485                 490                 495

Asp Gly Val Glu Val His Asn Ala Lys Thr Lys Pro Arg Glu Gln
            500                 505                 510

Tyr Asn Ser Thr Tyr Arg Val Val Ser Val Leu Thr Val Leu His Gln
        515                 520                 525

Asp Trp Leu Asn Gly Lys Glu Tyr Lys Cys Lys Val Ser Asn Lys Ala
    530                 535                 540

Leu Pro Ala Pro Ile Glu Lys Thr Ile Ser Lys Ala Lys Gly Gln Pro
545                 550                 555                 560

Arg Glu Pro Gln Val Tyr Thr Leu Pro Pro Ser Arg Glu Glu Met Thr
                565                 570                 575

Lys Asn Gln Val Ser Leu Thr Cys Leu Val Lys Gly Phe Tyr Pro Ser
            580                 585                 590

Asp Ile Ala Val Glu Trp Glu Ser Asn Gly Gln Pro Glu Asn Asn Tyr
        595                 600                 605

Lys Thr Thr Pro Pro Val Leu Asp Ser Asp Gly Ser Phe Phe Leu Tyr
    610                 615                 620

Ser Lys Leu Thr Val Asp Lys Ser Arg Trp Gln Gln Gly Asn Val Phe
625                 630                 635                 640

Ser Cys Ser Val Met His Glu Ala Leu His Asn His Tyr Thr Gln Lys
                645                 650                 655

Ser Leu Ser Leu Ser Pro Gly Lys
            660

<210> SEQ ID NO 88
<211> LENGTH: 108
<212> TYPE: PRT
<213> ORGANISM: Homo sapiens

<400> SEQUENCE: 88

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105

<210> SEQ ID NO 89
<211> LENGTH: 229
<212> TYPE: PRT
<213> ORGANISM: Artificial Sequence
<220> FEATURE:
<223> OTHER INFORMATION: TNF/IL-17 FIT9-Ig polypeptide

<400> SEQUENCE: 89

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val

```
                35                  40                  45

Ala Phe Met Ser Tyr Asp Gly Ser Asn Lys Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gly Ile Ala Ala Gly Gly Asn Tyr Tyr Tyr Tyr Gly
                100                 105                 110

Met Asp Val Trp Gly Gln Gly Thr Thr Val Thr Val Ser Ser Ala Ser
                115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Ser Leu Gly Thr Gln Thr Tyr Ile
                195                 200                 205

Cys Asn Val Asn His Lys Pro Ser Asn Thr Lys Val Asp Lys Lys Val
                210                 215                 220

Glu Pro Lys Ser Cys
225

<210> SEQ ID NO 90
<211> LENGTH: 126
<212> TYPE: PRT
<213> ORGANISM: Homo sapiens

<400> SEQUENCE: 90

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Ile Phe Ser Ser Tyr
                 20                  25                  30

Ala Met His Trp Val Arg Gln Ala Pro Gly Asn Gly Leu Glu Trp Val
                 35                  40                  45

Ala Phe Met Ser Tyr Asp Gly Ser Asn Lys Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gly Ile Ala Ala Gly Gly Asn Tyr Tyr Tyr Tyr Gly
                100                 105                 110

Met Asp Val Trp Gly Gln Gly Thr Thr Val Thr Val Ser Ser
                115                 120                 125

<210> SEQ ID NO 91
<211> LENGTH: 219
<212> TYPE: PRT
<213> ORGANISM: Artificial Sequence
<220> FEATURE:
<223> OTHER INFORMATION: TNF/IL-17 FIT9-Ig polypeptide

<400> SEQUENCE: 91
```

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Arg Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ile Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Leu Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 92
<211> LENGTH: 658
<212> TYPE: PRT
<213> ORGANISM: Artificial Sequence
<220> FEATURE:
<223> OTHER INFORMATION: CTLA-4/PD-1 FIT10-Ig polypeptide

<400> SEQUENCE: 92

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140
```

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
    195                 200                 205

Ser Phe Asn Arg Gly Glu Cys Gln Val Gln Leu Val Glu Ser Gly Gly
210                 215                 220

Gly Val Val Gln Pro Gly Arg Ser Leu Arg Leu Asp Cys Lys Ala Ser
225                 230                 235                 240

Gly Ile Thr Phe Ser Asn Ser Gly Met His Trp Val Arg Gln Ala Pro
            245                 250                 255

Gly Lys Gly Leu Glu Trp Val Ala Val Ile Trp Tyr Asp Gly Ser Lys
            260                 265                 270

Arg Tyr Tyr Ala Asp Ser Val Lys Gly Arg Phe Thr Ile Ser Arg Asp
        275                 280                 285

Asn Ser Lys Asn Thr Leu Phe Leu Gln Met Asn Ser Leu Arg Ala Glu
        290                 295                 300

Asp Thr Ala Val Tyr Tyr Cys Ala Thr Asn Asp Asp Tyr Trp Gly Gln
305                 310                 315                 320

Gly Thr Leu Val Thr Val Ser Ser Ala Ser Thr Lys Gly Pro Ser Val
            325                 330                 335

Phe Pro Leu Ala Pro Ser Ser Lys Ser Thr Ser Gly Gly Thr Ala Ala
            340                 345                 350

Leu Gly Cys Leu Val Lys Asp Tyr Phe Pro Glu Pro Val Thr Val Ser
        355                 360                 365

Trp Asn Ser Gly Ala Leu Thr Ser Gly Val His Thr Phe Pro Ala Val
370                 375                 380

Leu Gln Ser Ser Gly Leu Tyr Ser Leu Ser Ser Val Val Thr Val Pro
385                 390                 395                 400

Ser Ser Ser Leu Gly Thr Gln Thr Tyr Ile Cys Asn Val Asn His Lys
            405                 410                 415

Pro Ser Asn Thr Lys Val Asp Lys Lys Val Glu Pro Lys Ser Cys Asp
            420                 425                 430

Lys Thr His Thr Cys Pro Pro Cys Pro Ala Pro Glu Leu Leu Gly Gly
        435                 440                 445

Pro Ser Val Phe Leu Phe Pro Pro Lys Pro Lys Asp Thr Leu Met Ile
    450                 455                 460

Ser Arg Thr Pro Glu Val Thr Cys Val Val Val Asp Val Ser His Glu
465                 470                 475                 480

Asp Pro Glu Val Lys Phe Asn Trp Tyr Val Asp Gly Val Glu Val His
            485                 490                 495

Asn Ala Lys Thr Lys Pro Arg Glu Glu Gln Tyr Asn Ser Thr Tyr Arg
            500                 505                 510

Val Val Ser Val Leu Thr Val Leu His Gln Asp Trp Leu Asn Gly Lys
        515                 520                 525

Glu Tyr Lys Cys Lys Val Ser Asn Lys Ala Leu Pro Ala Pro Ile Glu
    530                 535                 540

Lys Thr Ile Ser Lys Ala Lys Gly Gln Pro Arg Glu Pro Gln Val Tyr
545                 550                 555                 560
```

```
Thr Leu Pro Pro Ser Arg Glu Glu Met Thr Lys Asn Gln Val Ser Leu
                565                 570                 575
Thr Cys Leu Val Lys Gly Phe Tyr Pro Ser Asp Ile Ala Val Glu Trp
            580                 585                 590
Glu Ser Asn Gly Gln Pro Glu Asn Asn Tyr Lys Thr Thr Pro Pro Val
        595                 600                 605
Leu Asp Ser Asp Gly Ser Phe Phe Leu Tyr Ser Lys Leu Thr Val Asp
    610                 615                 620
Lys Ser Arg Trp Gln Gln Gly Asn Val Phe Ser Cys Ser Val Met His
625                 630                 635                 640
Glu Ala Leu His Asn His Tyr Thr Gln Lys Ser Leu Ser Leu Ser Pro
                645                 650                 655
Gly Lys

<210> SEQ ID NO 93
<211> LENGTH: 108
<212> TYPE: PRT
<213> ORGANISM: Homo sapiens

<400> SEQUENCE: 93

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Gly Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Phe Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Trp Thr Phe Gly Gln Gly Thr Lys Val Glu Ile Lys
            100                 105

<210> SEQ ID NO 94
<211> LENGTH: 113
<212> TYPE: PRT
<213> ORGANISM: Homo sapiens

<400> SEQUENCE: 94

Gln Val Gln Leu Val Glu Ser Gly Gly Val Val Gln Pro Gly Arg
1               5                   10                  15
Ser Leu Arg Leu Asp Cys Lys Ala Ser Gly Ile Thr Phe Ser Asn Ser
            20                  25                  30
Gly Met His Trp Val Arg Gln Ala Pro Gly Lys Gly Leu Glu Trp Val
        35                  40                  45
Ala Val Ile Trp Tyr Asp Gly Ser Lys Arg Tyr Tyr Ala Asp Ser Val
    50                  55                  60
Lys Gly Arg Phe Thr Ile Ser Arg Asp Asn Ser Lys Asn Thr Leu Phe
65                  70                  75                  80
Leu Gln Met Asn Ser Leu Arg Ala Glu Asp Thr Ala Val Tyr Tyr Cys
                85                  90                  95
Ala Thr Asn Asp Asp Tyr Trp Gly Gln Gly Thr Leu Val Thr Val Ser
            100                 105                 110
Ser
```

<210> SEQ ID NO 95
<211> LENGTH: 221
<212> TYPE: PRT
<213> ORGANISM: Artificial Sequence
<220> FEATURE:
<223> OTHER INFORMATION: CTLA-4/PD-1 FIT10-Ig polypeptide

<400> SEQUENCE: 95

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220
```

<210> SEQ ID NO 96
<211> LENGTH: 118
<212> TYPE: PRT
<213> ORGANISM: Homo sapiens

<400> SEQUENCE: 96

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95
```

Ala Arg Thr Gly Trp Leu Gly Pro Phe Asp Tyr Trp Gly Gln Gly Thr
            100                 105                 110

Leu Val Thr Val Ser Ser
            115

<210> SEQ ID NO 97
<211> LENGTH: 214
<212> TYPE: PRT
<213> ORGANISM: Artificial Sequence
<220> FEATURE:
<223> OTHER INFORMATION: CTLA-4/PD-1 FIT10-Ig polypeptide

<400> SEQUENCE: 97

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 98
<211> LENGTH: 107
<212> TYPE: PRT
<213> ORGANISM: Homo sapiens

<400> SEQUENCE: 98

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro

```
                65                  70                  75                  80
Glu Asp Phe Ala Val Tyr Tyr Cys Gln Gln Ser Ser Asn Trp Pro Arg
                    85                  90                  95

Thr Phe Gly Gln Gly Thr Lys Val Glu Ile Lys
                100                 105

<210> SEQ ID NO 99
<211> LENGTH: 689
<212> TYPE: PRT
<213> ORGANISM: Artificial Sequence
<220> FEATURE:
<223> OTHER INFORMATION: EGFR/PD-L1 FIT12a (Pani VL-hCk-1B12VH-hCg1)

<400> SEQUENCE: 99

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
                20                  25                  30

Leu Ser Ala Ser Val Gly Asp Arg Val Thr Ile Thr Cys Gln Ala Ser
            35                  40                  45

Gln Asp Ile Ser Asn Tyr Leu Asn Trp Tyr Gln Gln Lys Pro Gly Lys
50                  55                  60

Ala Pro Lys Leu Leu Ile Tyr Asp Ala Ser Asn Leu Glu Thr Gly Val
65                  70                  75                  80

Pro Ser Arg Phe Ser Gly Ser Gly Ser Gly Thr Asp Phe Thr Phe Thr
                85                  90                  95

Ile Ser Ser Leu Gln Pro Glu Asp Ile Ala Thr Tyr Phe Cys Gln His
                100                 105                 110

Phe Asp His Leu Pro Leu Ala Phe Gly Gly Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys Gln Val Gln Leu
225                 230                 235                 240

Val Gln Ser Gly Ala Glu Val Lys Lys Pro Gly Ser Ser Val Lys Val
                245                 250                 255

Ser Cys Lys Thr Ser Gly Asp Thr Phe Ser Ser Tyr Ala Ile Ser Trp
                260                 265                 270

Val Arg Gln Ala Pro Gly Gln Gly Leu Glu Trp Met Gly Gly Ile Ile
            275                 280                 285

Pro Ile Phe Gly Arg Ala His Tyr Ala Gln Lys Phe Gln Gly Arg Val
            290                 295                 300

Thr Ile Thr Ala Asp Glu Ser Thr Ser Thr Ala Tyr Met Glu Leu Ser
305                 310                 315                 320

Ser Leu Arg Ser Glu Asp Thr Ala Val Tyr Phe Cys Ala Arg Lys Phe
```

```
                    325                 330                 335
        His Phe Val Ser Gly Ser Pro Phe Gly Met Asp Val Trp Gly Gln Gly
                    340                 345                 350
        Thr Thr Val Thr Val Ser Ser Ala Ser Thr Lys Gly Pro Ser Val Phe
                    355                 360                 365
        Pro Leu Ala Pro Ser Ser Lys Ser Thr Ser Gly Gly Thr Ala Ala Leu
                    370                 375                 380
        Gly Cys Leu Val Lys Asp Tyr Phe Pro Glu Pro Val Thr Val Ser Trp
        385                 390                 395                 400
        Asn Ser Gly Ala Leu Thr Ser Gly Val His Thr Phe Pro Ala Val Leu
                        405                 410                 415
        Gln Ser Ser Gly Leu Tyr Ser Leu Ser Ser Val Val Thr Val Pro Ser
                        420                 425                 430
        Ser Ser Leu Gly Thr Gln Thr Tyr Ile Cys Asn Val Asn His Lys Pro
                        435                 440                 445
        Ser Asn Thr Lys Val Asp Lys Lys Val Glu Pro Lys Ser Cys Asp Lys
                        450                 455                 460
        Thr His Thr Cys Pro Pro Cys Pro Ala Pro Glu Leu Leu Gly Gly Pro
        465                 470                 475                 480
        Ser Val Phe Leu Phe Pro Pro Lys Pro Lys Asp Thr Leu Met Ile Ser
                        485                 490                 495
        Arg Thr Pro Glu Val Thr Cys Val Val Val Asp Val Ser His Glu Asp
                        500                 505                 510
        Pro Glu Val Lys Phe Asn Trp Tyr Val Asp Gly Val Glu Val His Asn
                        515                 520                 525
        Ala Lys Thr Lys Pro Arg Glu Glu Gln Tyr Asn Ser Thr Tyr Arg Val
                        530                 535                 540
        Val Ser Val Leu Thr Val Leu His Gln Asp Trp Leu Asn Gly Lys Glu
        545                 550                 555                 560
        Tyr Lys Cys Lys Val Ser Asn Lys Ala Leu Pro Ala Pro Ile Glu Lys
                        565                 570                 575
        Thr Ile Ser Lys Ala Lys Gly Gln Pro Arg Glu Pro Gln Val Tyr Thr
                        580                 585                 590
        Leu Pro Pro Ser Arg Glu Glu Met Thr Lys Asn Gln Val Ser Leu Thr
                        595                 600                 605
        Cys Leu Val Lys Gly Phe Tyr Pro Ser Asp Ile Ala Val Glu Trp Glu
                        610                 615                 620
        Ser Asn Gly Gln Pro Glu Asn Asn Tyr Lys Thr Thr Pro Pro Val Leu
        625                 630                 635                 640
        Asp Ser Asp Gly Ser Phe Phe Leu Tyr Ser Lys Leu Thr Val Asp Lys
                        645                 650                 655
        Ser Arg Trp Gln Gln Gly Asn Val Phe Ser Cys Ser Val Met His Glu
                        660                 665                 670
        Ala Leu His Asn His Tyr Thr Gln Lys Ser Leu Ser Leu Ser Pro Gly
                        675                 680                 685
        Lys

<210> SEQ ID NO 100
<211> LENGTH: 241
<212> TYPE: PRT
<213> ORGANISM: Homo Sapiens

<400> SEQUENCE: 100

Met Glu Phe Gly Leu Ser Trp Leu Phe Leu Val Ala Ile Leu Lys Gly
```

```
             1               5                  10                 15
         Val Gln Cys Gln Val Gln Leu Gln Glu Ser Gly Pro Gly Leu Val Lys
                         20                 25                 30
         Pro Ser Glu Thr Leu Ser Leu Thr Cys Thr Val Ser Gly Gly Ser Val
                         35                 40                 45
         Ser Ser Gly Asp Tyr Tyr Trp Thr Trp Ile Arg Gln Ser Pro Gly Lys
          50                 55                 60
         Gly Leu Glu Trp Ile Gly His Ile Tyr Tyr Ser Gly Asn Thr Asn Tyr
          65                 70                 75                 80
         Asn Pro Ser Leu Lys Ser Arg Leu Thr Ile Ser Ile Asp Thr Ser Lys
                         85                 90                 95
         Thr Gln Phe Ser Leu Lys Leu Ser Ser Val Thr Ala Ala Asp Thr Ala
                         100                105                110
         Ile Tyr Tyr Cys Val Arg Asp Arg Val Thr Gly Ala Phe Asp Ile Trp
                         115                120                125
         Gly Gln Gly Thr Met Val Thr Val Ser Ser Ala Ser Thr Lys Gly Pro
          130                135                140
         Ser Val Phe Pro Leu Ala Pro Ser Ser Lys Ser Thr Ser Gly Gly Thr
          145                150                155                160
         Ala Ala Leu Gly Cys Leu Val Lys Asp Tyr Phe Pro Glu Pro Val Thr
                         165                170                175
         Val Ser Trp Asn Ser Gly Ala Leu Thr Ser Gly Val His Thr Phe Pro
                         180                185                190
         Ala Val Leu Gln Ser Ser Gly Leu Tyr Ser Leu Ser Ser Val Val Thr
                         195                200                205
         Val Pro Ser Ser Ser Leu Gly Thr Gln Thr Tyr Ile Cys Asn Val Asn
          210                215                220
         His Lys Pro Ser Asn Thr Lys Val Asp Lys Lys Val Glu Pro Lys Ser
          225                230                235                240
         Cys

<210> SEQ ID NO 101
<211> LENGTH: 235
<212> TYPE: PRT
<213> ORGANISM: Homo Sapiens

<400> SEQUENCE: 101

Met Asp Met Arg Val Pro Ala Gln Leu Leu Gly Leu Leu Leu Leu Trp
 1               5                  10                 15
Phe Pro Gly Ser Arg Cys Glu Ile Val Leu Thr Gln Ser Pro Ala Thr
                 20                 25                 30
Leu Ser Leu Ser Pro Gly Glu Arg Ala Thr Leu Ser Cys Arg Ala Ser
             35                 40                 45
Gln Ser Val Ser Ser Tyr Leu Ala Trp Tyr Gln Gln Lys Pro Gly Gln
         50                 55                 60
Ala Pro Arg Leu Leu Ile Tyr Asp Ala Ser Asn Arg Ala Thr Gly Ile
 65                 70                 75                 80
Pro Ala Arg Phe Ser Gly Ser Gly Ser Gly Thr Asp Phe Thr Leu Thr
                 85                 90                 95
Ile Ser Ser Leu Glu Pro Glu Asp Phe Ala Val Tyr Tyr Cys Gln Gln
                 100                105                110
Arg Ser Asn Trp Pro Thr Phe Gly Gln Gly Thr Lys Val Glu Ile Lys
                 115                120                125
Arg Thr Val Ala Ala Pro Ser Val Phe Ile Phe Pro Pro Ser Asp Glu
```

```
                130                 135                 140
Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
                180                 185                 190

Thr Tyr Ser Leu Ser Ser Thr Leu Thr Leu Ser Lys Ala Asp Tyr Glu
                195                 200                 205

Lys His Lys Val Tyr Ala Cys Glu Val Thr His Gln Gly Leu Ser Ser
                210                 215                 220

Pro Val Thr Lys Ser Phe Asn Arg Gly Glu Cys
225                 230                 235

<210> SEQ ID NO 102
<211> LENGTH: 685
<212> TYPE: PRT
<213> ORGANISM: Artificial Sequence
<220> FEATURE:
<223> OTHER INFORMATION: cMET/EGFR FIT13a polypeptide 1 (h1332 VL-hCk-
      PaniVH-hCg1)

<400> SEQUENCE: 102

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
                20                  25                  30

Val Ser Ala Ser Val Gly Asp Arg Val Thr Ile Thr Cys Arg Ala Ser
                35                  40                  45

Gln Gly Ile Asn Thr Trp Leu Ala Trp Tyr Gln Gln Lys Pro Gly Lys
                50                  55                  60

Ala Pro Lys Leu Leu Ile Tyr Ala Ala Ser Ser Leu Lys Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
                100                 105                 110

Ala Asn Ser Phe Pro Leu Thr Phe Gly Gly Gly Thr Lys Val Glu Ile
                115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
                210                 215                 220

Ser Pro Val Thr Lys Ser Phe Asn Arg Gly Glu Cys Gln Val Gln Leu
225                 230                 235                 240

Gln Glu Ser Gly Pro Gly Leu Val Lys Pro Ser Glu Thr Leu Ser Leu
                245                 250                 255
```

-continued

```
Thr Cys Thr Val Ser Gly Gly Ser Val Ser Gly Asp Tyr Tyr Trp
            260                 265                 270
Thr Trp Ile Arg Gln Ser Pro Gly Lys Gly Leu Glu Trp Ile Gly His
        275                 280                 285
Ile Tyr Tyr Ser Gly Asn Thr Asn Tyr Asn Pro Ser Leu Lys Ser Arg
    290                 295                 300
Leu Thr Ile Ser Ile Asp Thr Ser Lys Thr Gln Phe Ser Leu Lys Leu
305                 310                 315                 320
Ser Ser Val Thr Ala Ala Asp Thr Ala Ile Tyr Tyr Cys Val Arg Asp
                325                 330                 335
Arg Val Thr Gly Ala Phe Asp Ile Trp Gly Gln Gly Thr Met Val Thr
            340                 345                 350
Val Ser Ser Ala Ser Thr Lys Gly Pro Ser Val Phe Pro Leu Ala Pro
        355                 360                 365
Ser Ser Lys Ser Thr Ser Gly Gly Thr Ala Ala Leu Gly Cys Leu Val
    370                 375                 380
Lys Asp Tyr Phe Pro Glu Pro Val Thr Val Ser Trp Asn Ser Gly Ala
385                 390                 395                 400
Leu Thr Ser Gly Val His Thr Phe Pro Ala Val Leu Gln Ser Ser Gly
                405                 410                 415
Leu Tyr Ser Leu Ser Ser Val Val Thr Val Pro Ser Ser Ser Leu Gly
            420                 425                 430
Thr Gln Thr Tyr Ile Cys Asn Val Asn His Lys Pro Ser Asn Thr Lys
        435                 440                 445
Val Asp Lys Lys Val Glu Pro Lys Ser Cys Asp Lys Thr His Thr Cys
    450                 455                 460
Pro Pro Cys Pro Ala Pro Glu Leu Leu Gly Gly Pro Ser Val Phe Leu
465                 470                 475                 480
Phe Pro Pro Lys Pro Lys Asp Thr Leu Met Ile Ser Arg Thr Pro Glu
                485                 490                 495
Val Thr Cys Val Val Val Asp Val Ser His Glu Asp Pro Glu Val Lys
            500                 505                 510
Phe Asn Trp Tyr Val Asp Gly Val Glu Val His Asn Ala Lys Thr Lys
        515                 520                 525
Pro Arg Glu Glu Gln Tyr Asn Ser Thr Tyr Arg Val Val Ser Val Leu
    530                 535                 540
Thr Val Leu His Gln Asp Trp Leu Asn Gly Lys Glu Tyr Lys Cys Lys
545                 550                 555                 560
Val Ser Asn Lys Ala Leu Pro Ala Pro Ile Glu Lys Thr Ile Ser Lys
                565                 570                 575
Ala Lys Gly Gln Pro Arg Glu Pro Gln Val Tyr Thr Leu Pro Pro Ser
            580                 585                 590
Arg Glu Glu Met Thr Lys Asn Gln Val Ser Leu Thr Cys Leu Val Lys
        595                 600                 605
Gly Phe Tyr Pro Ser Asp Ile Ala Val Glu Trp Glu Ser Asn Gly Gln
    610                 615                 620
Pro Glu Asn Asn Tyr Lys Thr Thr Pro Pro Val Leu Asp Ser Asp Gly
625                 630                 635                 640
Ser Phe Phe Leu Tyr Ser Lys Leu Thr Val Asp Lys Ser Arg Trp Gln
                645                 650                 655
Gln Gly Asn Val Phe Ser Cys Ser Val Met His Glu Ala Leu His Asn
            660                 665                 670
His Tyr Thr Gln Lys Ser Leu Ser Leu Ser Pro Gly Lys
```

<210> SEQ ID NO 103
<211> LENGTH: 239
<212> TYPE: PRT
<213> ORGANISM: Homo Sapiens

<400> SEQUENCE: 103

Met Glu Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Phe Ser Trp Val Arg Gln Ala Pro Gly Gln Gly Leu
    50                  55                  60

Glu Trp Met Gly Trp Ile Ser Ala Ser Asn Gly Asn Thr Tyr Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Val Tyr Ala Asp Tyr Ala Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys
225                 230                 235

<210> SEQ ID NO 104
<211> LENGTH: 236
<212> TYPE: PRT
<213> ORGANISM: Homo Sapiens

<400> SEQUENCE: 104

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Gln Ala Ser
        35                  40                  45

Gln Asp Ile Ser Asn Tyr Leu Asn Trp Tyr Gln Gln Lys Pro Gly Lys
    50                  55                  60

Ala Pro Lys Leu Leu Ile Tyr Asp Ala Ser Asn Leu Glu Thr Gly Val
65                  70                  75                  80

Pro Ser Arg Phe Ser Gly Ser Gly Ser Gly Thr Asp Phe Thr Phe Thr

```
                     85                  90                  95

Ile Ser Ser Leu Gln Pro Glu Asp Ile Ala Thr Tyr Phe Cys Gln His
                100                 105                 110

Phe Asp His Leu Pro Leu Ala Phe Gly Gly Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 105
<211> LENGTH: 680
<212> TYPE: PRT
<213> ORGANISM: Artificial Sequence
<220> FEATURE:
<223> OTHER INFORMATION: Factor IX/Factor X FIT14 polypeptide 1 (FIX VL-
      hCk-FX-VH-hCg4)

<400> SEQUENCE: 105

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
                20                  25                  30

Leu Ser Ala Ser Val Gly Asp Arg Val Thr Ile Thr Cys Lys Ala Ser
            35                  40                  45

Arg Asn Ile Glu Arg Gln Leu Ala Trp Tyr Gln Gln Lys Pro Gly Gln
        50                  55                  60

Ala Pro Glu Leu Leu Ile Tyr Gln Ala Ser Arg Lys Glu Ser Gly Val
65                  70                  75                  80

Pro Asp Arg Phe Ser Gly Ser Arg Tyr Gly Thr Asp Phe Thr Leu Thr
                85                  90                  95

Ile Ser Ser Leu Gln Pro Glu Asp Ile Ala Thr Tyr Tyr Cys Gln Gln
                100                 105                 110

Tyr Ser Asp Pro Pro Leu Thr Phe Gly Gly Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205
```

-continued

```
Glu Lys His Lys Val Tyr Ala Cys Glu Val Thr His Gln Gly Leu Ser
    210                 215                 220
Ser Pro Val Thr Lys Ser Phe Asn Arg Gly Glu Cys Gln Val Gln Leu
225                 230                 235                 240
Val Gln Ser Gly Ser Glu Leu Lys Lys Pro Gly Ala Ser Val Lys Val
                245                 250                 255
Ser Cys Lys Ala Ser Gly Tyr Thr Phe Thr Asp Asn Met Asp Trp
    260                 265                 270
Val Arg Gln Ala Pro Gly Gln Gly Leu Glu Trp Met Gly Asp Ile Asn
            275                 280                 285
Thr Arg Ser Gly Gly Ser Ile Tyr Asn Glu Glu Phe Gln Asp Arg Val
    290                 295                 300
Ile Met Thr Val Asp Lys Ser Thr Asp Thr Ala Tyr Met Glu Leu Ser
305                 310                 315                 320
Ser Leu Arg Ser Glu Asp Thr Ala Thr Tyr His Cys Ala Arg Arg Lys
                325                 330                 335
Ser Tyr Gly Tyr Tyr Leu Asp Glu Trp Gly Gly Thr Leu Val Thr
    340                 345                 350
Val Ser Ser Ala Ser Thr Lys Gly Pro Ser Val Phe Pro Leu Ala Pro
            355                 360                 365
Cys Ser Arg Ser Thr Ser Glu Ser Thr Ala Ala Leu Gly Cys Leu Val
    370                 375                 380
Lys Asp Tyr Phe Pro Glu Pro Val Thr Val Ser Trp Asn Ser Gly Ala
385                 390                 395                 400
Leu Thr Ser Gly Val His Thr Phe Pro Ala Val Leu Gln Ser Ser Gly
                405                 410                 415
Leu Tyr Ser Leu Ser Ser Val Val Thr Val Pro Ser Ser Ser Leu Gly
            420                 425                 430
Thr Gln Thr Tyr Thr Cys Asn Val Asp His Lys Pro Ser Asn Thr Lys
    435                 440                 445
Val Asp Lys Arg Val Glu Ser Lys Tyr Gly Pro Pro Cys Pro Pro Cys
450                 455                 460
Pro Ala Pro Glu Phe Leu Gly Gly Pro Ser Val Phe Leu Phe Pro Pro
465                 470                 475                 480
Lys Pro Lys Asp Thr Leu Met Ile Ser Arg Thr Pro Glu Val Thr Cys
                485                 490                 495
Val Val Val Asp Val Ser Gln Glu Asp Pro Glu Val Gln Phe Asn Trp
            500                 505                 510
Tyr Val Asp Gly Val Glu Val His Asn Ala Lys Thr Lys Pro Arg Glu
    515                 520                 525
Glu Gln Tyr Asn Ser Thr Tyr Arg Val Val Ser Val Leu Thr Val Leu
530                 535                 540
His Gln Asp Trp Leu Asn Gly Lys Glu Tyr Lys Cys Lys Val Ser Asn
545                 550                 555                 560
Lys Gly Leu Pro Ser Ser Ile Glu Lys Thr Ile Ser Lys Ala Lys Gly
                565                 570                 575
Gln Pro Arg Glu Pro Gln Val Tyr Thr Leu Pro Pro Ser Gln Glu Glu
            580                 585                 590
Met Thr Lys Asn Gln Val Ser Leu Thr Cys Leu Val Lys Gly Phe Tyr
    595                 600                 605
Pro Ser Asp Ile Ala Val Glu Trp Glu Ser Asn Gly Gln Pro Glu Asn
610                 615                 620
Asn Tyr Lys Thr Thr Pro Pro Val Leu Asp Ser Asp Gly Ser Phe Phe
```

```
                625                 630                 635                 640
Leu Tyr Ser Lys Leu Thr Val Asp Lys Ser Arg Trp Gln Glu Gly Asn
                    645                 650                 655

Val Phe Ser Cys Ser Val Met His Glu Ala Leu His Asn His Tyr Thr
                660                 665                 670

Gln Glu Ser Leu Ser Leu Ser Pro
                675                 680

<210> SEQ ID NO 106
<211> LENGTH: 245
<212> TYPE: PRT
<213> ORGANISM: Homo Sapiens

<400> SEQUENCE: 106

Met Glu Phe Gly Leu Ser Trp Leu Phe Leu Val Ala Ile Leu Lys Gly
1               5                   10                  15

Val Gln Cys Gln Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Tyr Tyr Asp Ile Gln Trp Val Arg Gln Ala Pro Gly Lys Gly Leu
        50                  55                  60

Glu Trp Val Ser Ser Ile Ser Pro Ser Gly Gln Ser Thr Tyr Tyr Arg
65                  70                  75                  80

Arg Glu Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Arg Thr Gly Arg Glu Tyr Gly Gly Gly Trp Tyr
        115                 120                 125

Phe Asp Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys
                245

<210> SEQ ID NO 107
<211> LENGTH: 236
<212> TYPE: PRT
<213> ORGANISM: Homo Sapiens

<400> SEQUENCE: 107

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
```

```
                    20                  25                  30
Leu Ser Ala Ser Val Gly Asp Arg Val Thr Ile Thr Cys Lys Ala Ser
                35                  40                  45
Arg Asn Ile Glu Arg Gln Leu Ala Trp Tyr Gln Gln Lys Pro Gly Gln
            50                  55                  60
Ala Pro Glu Leu Leu Ile Tyr Gln Ala Ser Arg Lys Glu Ser Gly Val
 65                 70                  75                  80
Pro Asp Arg Phe Ser Gly Ser Arg Tyr Gly Thr Asp Phe Thr Leu Thr
                85                  90                  95
Ile Ser Ser Leu Gln Pro Glu Asp Ile Ala Thr Tyr Tyr Cys Gln Gln
            100                 105                 110
Tyr Ser Asp Pro Pro Leu Thr Phe Gly Gly Gly Thr Lys Val Glu Ile
        115                 120                 125
Lys Arg Thr Val Ala Ala Pro Ser Val Phe Ile Phe Pro Pro Ser Asp
    130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235

<210> SEQ ID NO 108
<211> LENGTH: 697
<212> TYPE: PRT
<213> ORGANISM: Artificial Sequence
<220> FEATURE:
<223> OTHER INFORMATION: Her3/IGF1R FIT16a polypeptide 1(paritu VL-hCk-
      FigituVH-hCg1)

<400> SEQUENCE: 108

Met Asp Met Arg Val Pro Ala Gln Leu Leu Gly Leu Leu Leu Leu Trp
 1               5                  10                  15
Phe Pro Gly Ser Arg Cys Asp Ile Glu Met Thr Gln Ser Pro Asp Ser
                20                  25                  30
Leu Ala Val Ser Leu Gly Glu Arg Ala Thr Ile Asn Cys Arg Ser Ser
            35                  40                  45
Gln Ser Val Leu Tyr Ser Ser Asn Arg Asn Tyr Leu Ala Trp Tyr
        50                  55                  60
Gln Gln Asn Pro Gly Gln Pro Pro Lys Leu Leu Ile Tyr Trp Ala Ser
 65                 70                  75                  80
Thr Arg Glu Ser Gly Val Pro Asp Arg Phe Ser Gly Ser Gly Ser Gly
                85                  90                  95
Thr Asp Phe Thr Leu Thr Ile Ser Ser Leu Gln Ala Glu Asp Val Ala
            100                 105                 110
Val Tyr Tyr Cys Gln Gln Tyr Tyr Ser Thr Pro Arg Thr Phe Gly Gln
        115                 120                 125
Gly Thr Lys Val Glu Ile Lys Arg Thr Val Ala Ala Pro Ser Val Phe
    130                 135                 140
```

```
Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

Leu Ser Lys Ala Asp Tyr Glu Lys His Lys Val Tyr Ala Cys Glu Val
    210                 215                 220

Thr His Gln Gly Leu Ser Ser Pro Val Thr Lys Ser Phe Asn Arg Gly
225                 230                 235                 240

Glu Cys Glu Val Gln Leu Leu Glu Ser Gly Gly Leu Val Gln Pro
                245                 250                 255

Gly Gly Ser Leu Arg Leu Ser Cys Thr Ala Ser Gly Phe Thr Phe Ser
            260                 265                 270

Ser Tyr Ala Met Asn Trp Val Arg Gln Ala Pro Gly Lys Gly Leu Glu
        275                 280                 285

Trp Val Ser Ala Ile Ser Gly Ser Gly Gly Thr Thr Phe Tyr Ala Asp
    290                 295                 300

Ser Val Lys Gly Arg Phe Thr Ile Ser Arg Asp Asn Ser Arg Thr Thr
305                 310                 315                 320

Leu Tyr Leu Gln Met Asn Ser Leu Arg Ala Glu Asp Thr Ala Val Tyr
                325                 330                 335

Tyr Cys Ala Lys Asp Leu Gly Trp Ser Asp Ser Tyr Tyr Tyr Tyr Tyr
            340                 345                 350

Gly Met Asp Val Trp Gly Gln Gly Thr Thr Val Thr Val Ser Ser Ala
        355                 360                 365

Ser Thr Lys Gly Pro Ser Val Phe Pro Leu Ala Pro Ser Ser Lys Ser
    370                 375                 380

Thr Ser Gly Gly Thr Ala Ala Leu Gly Cys Leu Val Lys Asp Tyr Phe
385                 390                 395                 400

Pro Glu Pro Val Thr Val Ser Trp Asn Ser Gly Ala Leu Thr Ser Gly
                405                 410                 415

Val His Thr Phe Pro Ala Val Leu Gln Ser Ser Gly Leu Tyr Ser Leu
            420                 425                 430

Ser Ser Val Val Thr Val Pro Ser Ser Ser Leu Gly Thr Gln Thr Tyr
        435                 440                 445

Ile Cys Asn Val Asn His Lys Pro Ser Asn Thr Lys Val Asp Lys Lys
    450                 455                 460

Val Glu Pro Lys Ser Cys Asp Lys Thr His Thr Cys Pro Pro Cys Pro
465                 470                 475                 480

Ala Pro Glu Leu Leu Gly Gly Pro Ser Val Phe Leu Phe Pro Pro Lys
                485                 490                 495

Pro Lys Asp Thr Leu Met Ile Ser Arg Thr Pro Glu Val Thr Cys Val
            500                 505                 510

Val Val Asp Val Ser His Glu Asp Pro Glu Val Lys Phe Asn Trp Tyr
        515                 520                 525

Val Asp Gly Val Glu Val His Asn Ala Lys Thr Lys Pro Arg Glu Glu
    530                 535                 540

Gln Tyr Asn Ser Thr Tyr Arg Val Val Ser Val Leu Thr Val Leu His
545                 550                 555                 560

Gln Asp Trp Leu Asn Gly Lys Glu Tyr Lys Cys Lys Val Ser Asn Lys
```

565                 570                 575
Ala Leu Pro Ala Pro Ile Glu Lys Thr Ile Ser Lys Ala Lys Gly Gln
            580                 585                 590

Pro Arg Glu Pro Gln Val Tyr Thr Leu Pro Pro Ser Arg Glu Glu Met
        595                 600                 605

Thr Lys Asn Gln Val Ser Leu Thr Cys Leu Val Lys Gly Phe Tyr Pro
    610                 615                 620

Ser Asp Ile Ala Val Glu Trp Glu Ser Asn Gly Gln Pro Glu Asn Asn
625                 630                 635                 640

Tyr Lys Thr Thr Pro Pro Val Leu Asp Ser Asp Gly Ser Phe Phe Leu
                645                 650                 655

Tyr Ser Lys Leu Thr Val Asp Lys Ser Arg Trp Gln Gln Gly Asn Val
            660                 665                 670

Phe Ser Cys Ser Val Met His Glu Ala Leu His Asn His Tyr Thr Gln
        675                 680                 685

Lys Ser Leu Ser Leu Ser Pro Gly Lys
    690                 695

<210> SEQ ID NO 109
<211> LENGTH: 239
<212> TYPE: PRT
<213> ORGANISM: Homo Sapiens

<400> SEQUENCE: 109

Met Glu Phe Gly Leu Ser Trp Leu Phe Leu Val Ala Ile Leu Lys Gly
1               5                   10                  15

Val Gln Cys Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Pro Pro Gly Lys Gly Leu
    50                  55                  60

Glu Trp Ile Gly Glu Ile Asn His Ser Gly Ser Thr Asn Tyr Asn Pro
65                  70                  75                  80

Ser Leu Lys Ser Arg Val Thr Ile Ser Val Glu Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Lys Trp Thr Trp Tyr Phe Asp Leu Trp Gly Arg
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys
225                 230                 235

<210> SEQ ID NO 110
<211> LENGTH: 236
<212> TYPE: PRT
<213> ORGANISM: Homo Sapiens

<400> SEQUENCE: 110

```
Met Asp Met Arg Val Pro Ala Gln Leu Leu Gly Leu Leu Leu Leu Trp
  1               5                  10                  15

Phe Pro Gly Ser Arg Cys Asp Ile Gln Met Thr Gln Phe Pro Ser Ser
             20                  25                  30

Leu Ser Ala Ser Val Gly Asp Arg Val Thr Ile Thr Cys Arg Ala Ser
         35                  40                  45

Gln Gly Ile Arg Asn Asp Leu Gly Trp Tyr Gln Gln Lys Pro Gly Lys
     50                  55                  60

Ala Pro Lys Arg Leu Ile Tyr Ala Ala Ser Arg Leu His Arg Gly Val
 65                  70                  75                  80

Pro Ser Arg Phe Ser Gly Ser Gly Ser Gly Thr Glu Phe Thr Leu Thr
                 85                  90                  95

Ile Ser Ser Leu Gln Pro Glu Asp Phe Ala Thr Tyr Tyr Cys Leu Gln
            100                 105                 110

His Asn Ser Tyr Pro Cys Ser Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 111
<211> LENGTH: 693
<212> TYPE: PRT
<213> ORGANISM: Artificial Sequence
<220> FEATURE:
<223> OTHER INFORMATION: DLL4/VEGF FIT17a polypeptide 1 (Demci VL-hCk-Bevci VH-hCg1)

<400> SEQUENCE: 111

```
Met Asp Met Arg Val Pro Ala Gln Leu Leu Gly Leu Leu Leu Leu Trp
  1               5                  10                  15

Phe Pro Gly Ser Arg Cys Asp Ile Val Met Thr Gln Ser Pro Asp Ser
             20                  25                  30

Leu Ala Val Ser Leu Gly Glu Arg Ala Thr Ile Ser Cys Arg Ala Ser
         35                  40                  45

Glu Ser Val Asp Asn Tyr Gly Ile Ser Phe Met Lys Trp Phe Gln Gln
     50                  55                  60

Lys Pro Gly Gln Pro Pro Lys Leu Leu Ile Tyr Ala Ala Ser Asn Gln
 65                  70                  75                  80
```

```
Gly Ser Gly Val Pro Asp Arg Phe Ser Gly Ser Gly Thr Asp
            85                  90                  95
Phe Thr Leu Thr Ile Ser Ser Leu Gln Ala Glu Asp Val Ala Val Tyr
            100                 105                 110
Tyr Cys Gln Gln Ser Lys Glu Val Pro Trp Thr Phe Gly Gly Gly Thr
            115                 120                 125
Lys Val Glu Ile Lys Arg Thr Val Ala Ala Pro Ser Val Phe Ile Phe
130                 135                 140
Pro Pro Ser Asp Glu Gln Leu Lys Ser Gly Thr Ala Ser Val Val Cys
145                 150                 155                 160
Leu Leu Asn Asn Phe Tyr Pro Arg Glu Ala Lys Val Gln Trp Lys Val
                165                 170                 175
Asp Asn Ala Leu Gln Ser Gly Asn Ser Gln Glu Ser Val Thr Glu Gln
            180                 185                 190
Asp Ser Lys Asp Ser Thr Tyr Ser Leu Ser Ser Thr Leu Thr Leu Ser
            195                 200                 205
Lys Ala Asp Tyr Glu Lys His Lys Val Tyr Ala Cys Glu Val Thr His
210                 215                 220
Gln Gly Leu Ser Ser Pro Val Thr Lys Ser Phe Asn Arg Gly Glu Cys
225                 230                 235                 240
Glu Val Gln Leu Val Glu Ser Gly Gly Gly Leu Val Gln Pro Gly Gly
                245                 250                 255
Ser Leu Arg Leu Ser Cys Ala Ala Ser Gly Tyr Thr Phe Thr Asn Tyr
            260                 265                 270
Gly Met Asn Trp Val Arg Gln Ala Pro Gly Lys Gly Leu Glu Trp Val
            275                 280                 285
Gly Trp Ile Asn Thr Tyr Thr Gly Glu Pro Thr Tyr Ala Ala Asp Phe
            290                 295                 300
Lys Arg Arg Phe Thr Phe Ser Leu Asp Thr Ser Lys Ser Thr Ala Tyr
305                 310                 315                 320
Leu Gln Met Asn Ser Leu Arg Ala Glu Asp Thr Ala Val Tyr Tyr Cys
                325                 330                 335
Ala Lys Tyr Pro His Tyr Tyr Gly Ser Ser His Trp Tyr Phe Asp Val
            340                 345                 350
Trp Gly Gln Gly Thr Leu Val Thr Val Ser Ser Ala Ser Thr Lys Gly
            355                 360                 365
Pro Ser Val Phe Pro Leu Ala Pro Ser Ser Lys Ser Thr Ser Gly Gly
            370                 375                 380
Thr Ala Ala Leu Gly Cys Leu Val Lys Asp Tyr Phe Pro Glu Pro Val
385                 390                 395                 400
Thr Val Ser Trp Asn Ser Gly Ala Leu Thr Ser Gly Val His Thr Phe
                405                 410                 415
Pro Ala Val Leu Gln Ser Ser Gly Leu Tyr Ser Leu Ser Ser Val Val
            420                 425                 430
Thr Val Pro Ser Ser Ser Leu Gly Thr Gln Thr Tyr Ile Cys Asn Val
            435                 440                 445
Asn His Lys Pro Ser Asn Thr Lys Val Asp Lys Lys Val Glu Pro Lys
450                 455                 460
Ser Cys Asp Lys Thr His Thr Cys Pro Pro Cys Pro Ala Pro Glu Leu
465                 470                 475                 480
Leu Gly Gly Pro Ser Val Phe Leu Phe Pro Pro Lys Pro Lys Asp Thr
                485                 490                 495
Leu Met Ile Ser Arg Thr Pro Glu Val Thr Cys Val Val Val Asp Val
```

```
                          500                 505                 510
Ser His Glu Asp Pro Glu Val Lys Phe Asn Trp Tyr Val Asp Gly Val
            515                 520                 525

Glu Val His Asn Ala Lys Thr Lys Pro Arg Glu Glu Gln Tyr Asn Ser
        530                 535                 540

Thr Tyr Arg Val Val Ser Val Leu Thr Val Leu His Gln Asp Trp Leu
545                 550                 555                 560

Asn Gly Lys Glu Tyr Lys Cys Lys Val Ser Asn Lys Ala Leu Pro Ala
                565                 570                 575

Pro Ile Glu Lys Thr Ile Ser Lys Ala Lys Gly Gln Pro Arg Glu Pro
            580                 585                 590

Gln Val Tyr Thr Leu Pro Pro Ser Arg Glu Glu Met Thr Lys Asn Gln
        595                 600                 605

Val Ser Leu Thr Cys Leu Val Lys Gly Phe Tyr Pro Ser Asp Ile Ala
    610                 615                 620

Val Glu Trp Glu Ser Asn Gly Gln Pro Glu Asn Asn Tyr Lys Thr Thr
625                 630                 635                 640

Pro Pro Val Leu Asp Ser Asp Gly Ser Phe Phe Leu Tyr Ser Lys Leu
                645                 650                 655

Thr Val Asp Lys Ser Arg Trp Gln Gln Gly Asn Val Phe Ser Cys Ser
            660                 665                 670

Val Met His Glu Ala Leu His Asn His Tyr Thr Gln Lys Ser Leu Ser
        675                 680                 685

Leu Ser Pro Gly Lys
    690

<210> SEQ ID NO 112
<211> LENGTH: 241
<212> TYPE: PRT
<213> ORGANISM: Homo Sapiens

<400> SEQUENCE: 112

Met Glu Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ala Ser Val Lys Ile Ser Cys Lys Ala Ser Gly Tyr Ser Phe
        35                  40                  45

Thr Ala Tyr Tyr Ile His Trp Val Lys Gln Ala Pro Gly Gln Gly Leu
    50                  55                  60

Glu Trp Ile Gly Tyr Ile Ser Ser Tyr Asn Gly Ala Thr Asn Tyr Asn
65                  70                  75                  80

Gln Lys Phe Lys Gly Arg Val Thr Phe Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asp Tyr Asp Tyr Asp Val Gly Met Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175
```

```
Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys

<210> SEQ ID NO 113
<211> LENGTH: 236
<212> TYPE: PRT
<213> ORGANISM: Homo Sapiens

<400> SEQUENCE: 113

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Ser Ala Ser
        35                  40                  45

Gln Asp Ile Ser Asn Tyr Leu Asn Trp Tyr Gln Gln Lys Pro Gly Lys
    50                  55                  60

Ala Pro Lys Val Leu Ile Tyr Phe Thr Ser Ser Leu His Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Ser Thr Val Pro Trp Thr Phe Gly Gln Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 114
<211> LENGTH: 691
<212> TYPE: PRT
<213> ORGANISM: Artificial Sequence
<220> FEATURE:
<223> OTHER INFORMATION: CD20/CD3 FIT18a polypeptide 1 (OfatuVL-hCk-
      CD3mAb VH-hCg1mut)

<400> SEQUENCE: 114

Met Asp Met Arg Val Pro Ala Gln Leu Leu Gly Leu Leu Leu Leu Trp
```

```
1               5                    10                   15
Phe Pro Gly Ser Arg Cys Glu Ile Val Leu Thr Gln Ser Pro Ala Thr
                20                   25                  30
Leu Ser Leu Ser Pro Gly Glu Arg Ala Thr Leu Ser Cys Arg Ala Ser
                35                   40                  45
Gln Ser Val Ser Ser Tyr Leu Ala Trp Tyr Gln Gln Lys Pro Gly Gln
                50                   55                  60
Ala Pro Arg Leu Leu Ile Tyr Asp Ala Ser Asn Arg Ala Thr Gly Ile
65                   70                  75                  80
Pro Ala Arg Phe Ser Gly Ser Gly Ser Gly Thr Asp Phe Thr Leu Thr
                85                   90                  95
Ile Ser Ser Leu Glu Pro Glu Asp Phe Ala Val Tyr Tyr Cys Gln Gln
                100                  105                 110
Arg Ser Asn Trp Pro Ile Thr Phe Gly Gln Gly Thr Arg Leu Glu Ile
                115                  120                 125
Lys Arg Thr Val Ala Ala Pro Ser Val Phe Ile Phe Pro Pro Ser Asp
                130                  135                 140
Glu Gln Leu Lys Ser Gly Thr Ala Ser Val Val Cys Leu Leu Asn Asn
145                  150                 155                 160
Phe Tyr Pro Arg Glu Ala Lys Val Gln Trp Lys Val Asp Asn Ala Leu
                165                  170                 175
Gln Ser Gly Asn Ser Gln Glu Ser Val Thr Glu Gln Asp Ser Lys Asp
                180                  185                 190
Ser Thr Tyr Ser Leu Ser Ser Thr Leu Thr Leu Ser Lys Ala Asp Tyr
                195                  200                 205
Glu Lys His Lys Val Tyr Ala Cys Glu Val Thr His Gln Gly Leu Ser
210                  215                 220
Ser Pro Val Thr Lys Ser Phe Asn Arg Gly Glu Cys Glu Val Gln Leu
225                  230                 235                 240
Leu Glu Ser Gly Gly Gly Leu Val Gln Pro Gly Gly Ser Leu Lys Leu
                245                  250                 255
Ser Cys Ala Ala Ser Gly Phe Thr Phe Asn Thr Tyr Ala Met Asn Trp
                260                  265                 270
Val Arg Gln Ala Pro Gly Lys Gly Leu Glu Trp Val Ala Arg Ile Arg
                275                  280                 285
Ser Lys Tyr Asn Asn Tyr Ala Thr Tyr Tyr Ala Asp Ser Val Lys Asp
                290                  295                 300
Arg Phe Thr Ile Ser Arg Asp Asp Ser Lys Asn Thr Ala Tyr Leu Gln
305                  310                 315                 320
Met Asn Asn Leu Lys Thr Glu Asp Thr Ala Val Tyr Tyr Cys Val Arg
                325                  330                 335
His Gly Asn Phe Gly Asn Ser Tyr Val Ser Trp Phe Ala Tyr Trp Gly
                340                  345                 350
Gln Gly Thr Leu Val Thr Val Ser Ser Ala Ser Thr Lys Gly Pro Ser
                355                  360                 365
Val Phe Pro Leu Ala Pro Ser Ser Lys Ser Thr Ser Gly Gly Thr Ala
                370                  375                 380
Ala Leu Gly Cys Leu Val Lys Asp Tyr Phe Pro Glu Pro Val Thr Val
385                  390                 395                 400
Ser Trp Asn Ser Gly Ala Leu Thr Ser Gly Val His Thr Phe Pro Ala
                405                  410                 415
Val Leu Gln Ser Ser Gly Leu Tyr Ser Leu Ser Ser Val Val Thr Val
                420                  425                 430
```

```
Pro Ser Ser Ser Leu Gly Thr Gln Thr Tyr Ile Cys Asn Val Asn His
        435                 440                 445

Lys Pro Ser Asn Thr Lys Val Asp Lys Lys Val Glu Pro Lys Ser Cys
    450                 455                 460

Asp Lys Thr His Thr Cys Pro Pro Cys Pro Ala Pro Glu Ala Ala Gly
465                 470                 475                 480

Gly Pro Ser Val Phe Leu Phe Pro Pro Lys Pro Lys Asp Thr Leu Met
            485                 490                 495

Ile Ser Arg Thr Pro Glu Val Thr Cys Val Val Val Asp Val Ser His
                500                 505                 510

Glu Asp Pro Glu Val Lys Phe Asn Trp Tyr Val Asp Gly Val Glu Val
            515                 520                 525

His Asn Ala Lys Thr Lys Pro Arg Glu Glu Gln Tyr Asn Ser Thr Tyr
        530                 535                 540

Arg Val Val Ser Val Leu Thr Val Leu His Gln Asp Trp Leu Asn Gly
545                 550                 555                 560

Lys Glu Tyr Lys Cys Lys Val Ser Asn Lys Ala Leu Pro Ala Pro Ile
                565                 570                 575

Glu Lys Thr Ile Ser Lys Ala Lys Gly Gln Pro Arg Glu Pro Gln Val
            580                 585                 590

Tyr Thr Leu Pro Pro Ser Arg Glu Glu Met Thr Lys Asn Gln Val Ser
        595                 600                 605

Leu Thr Cys Leu Val Lys Gly Phe Tyr Pro Ser Asp Ile Ala Val Glu
    610                 615                 620

Trp Glu Ser Asn Gly Gln Pro Glu Asn Asn Tyr Lys Thr Thr Pro Pro
625                 630                 635                 640

Val Leu Asp Ser Asp Gly Ser Phe Phe Leu Tyr Ser Lys Leu Thr Val
                645                 650                 655

Asp Lys Ser Arg Trp Gln Gln Gly Asn Val Phe Ser Cys Ser Val Met
            660                 665                 670

His Glu Ala Leu His Asn His Tyr Thr Gln Lys Ser Leu Ser Leu Ser
        675                 680                 685

Pro Gly Lys
    690

<210> SEQ ID NO 115
<211> LENGTH: 244
<212> TYPE: PRT
<213> ORGANISM: Homo Sapiens

<400> SEQUENCE: 115

Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asn Asp Tyr Ala Met His Trp Val Arg Gln Ala Pro Gly Lys Gly Leu
    50                  55                  60

Glu Trp Val Ser Thr Ile Ser Trp Asn Ser Gly Ser Ile Gly Tyr Ala
65                  70                  75                  80

Asp Ser Val Lys Gly Arg Phe Thr Ile Ser Arg Asp Asn Ala Lys Lys
                85                  90                  95

Ser Leu Tyr Leu Gln Met Asn Ser Leu Arg Ala Glu Asp Thr Ala Leu
```

```
                    100                 105                 110
Tyr Tyr Cys Ala Lys Asp Ile Gln Tyr Gly Asn Tyr Tyr Gly Met
            115                 120                 125

Asp Val Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Leu Gly Thr Gln Thr Tyr Ile Cys
            210                 215                 220

Asn Val Asn His Lys Pro Ser Asn Thr Lys Val Asp Lys Lys Val Glu
225                 230                 235                 240

Pro Lys Ser Cys

<210> SEQ ID NO 116
<211> LENGTH: 235
<212> TYPE: PRT
<213> ORGANISM: Homo Sapiens

<400> SEQUENCE: 116

Met Thr Trp Thr Pro Leu Leu Phe Leu Thr Leu Leu His Cys Thr
1               5                   10                  15

Gly Ser Leu Ser Glu Leu Val Val Thr Gln Glu Pro Ser Leu Thr Val
            20                  25                  30

Ser Pro Gly Gly Thr Val Thr Leu Thr Cys Arg Ser Ser Thr Gly Ala
        35                  40                  45

Val Thr Thr Ser Asn Tyr Ala Asn Trp Val Gln Gln Lys Pro Gly Gln
    50                  55                  60

Ala Pro Arg Gly Leu Ile Gly Gly Thr Asn Lys Arg Ala Pro Gly Thr
65                  70                  75                  80

Pro Ala Arg Phe Ser Gly Ser Leu Leu Gly Gly Lys Ala Ala Leu Thr
                85                  90                  95

Leu Ser Gly Val Gln Pro Glu Asp Glu Ala Glu Tyr Tyr Cys Ala Leu
            100                 105                 110

Trp Tyr Ser Asn Leu Trp Val Phe Gly Gly Gly Thr Lys Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
```

<210> SEQ ID NO 117
<211> LENGTH: 691
<212> TYPE: PRT
<213> ORGANISM: Artificial Sequence
<220> FEATURE:
<223> OTHER INFORMATION: Her3/EGFR FIT19a polypeptide 1 (patritu VL-hCk-PaniVH-hCg1)

<400> SEQUENCE: 117

```
Met Asp Met Arg Val Pro Ala Gln Leu Leu Gly Leu Leu Leu Leu Trp
1               5                   10                  15

Phe Pro Gly Ser Arg Cys Asp Ile Glu Met Thr Gln Ser Pro Asp Ser
            20                  25                  30

Leu Ala Val Ser Leu Gly Glu Arg Ala Thr Ile Asn Cys Arg Ser Ser
        35                  40                  45

Gln Ser Val Leu Tyr Ser Ser Asn Arg Asn Tyr Leu Ala Trp Tyr
    50                  55                  60

Gln Gln Asn Pro Gly Gln Pro Pro Lys Leu Leu Ile Tyr Trp Ala Ser
65                  70                  75                  80

Thr Arg Glu Ser Gly Val Pro Asp Arg Phe Ser Gly Ser Gly Ser Gly
                85                  90                  95

Thr Asp Phe Thr Leu Thr Ile Ser Ser Leu Gln Ala Glu Asp Val Ala
            100                 105                 110

Val Tyr Tyr Cys Gln Gln Tyr Tyr Ser Thr Pro Arg Thr Phe Gly Gln
        115                 120                 125

Gly Thr Lys Val Glu Ile Lys Arg Thr Val Ala Ala Pro Ser Val Phe
    130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

Leu Ser Lys Ala Asp Tyr Glu Lys His Lys Val Tyr Ala Cys Glu Val
    210                 215                 220

Thr His Gln Gly Leu Ser Ser Pro Val Thr Lys Ser Phe Asn Arg Gly
225                 230                 235                 240

Glu Cys Gln Val Gln Leu Gln Glu Ser Gly Pro Gly Leu Val Lys Pro
                245                 250                 255

Ser Glu Thr Leu Ser Leu Thr Cys Thr Val Ser Gly Gly Ser Val Ser
            260                 265                 270

Ser Gly Asp Tyr Tyr Trp Thr Trp Ile Arg Gln Ser Pro Gly Lys Gly
        275                 280                 285

Leu Glu Trp Ile Gly His Ile Tyr Tyr Ser Gly Asn Thr Asn Tyr Asn
    290                 295                 300

Pro Ser Leu Lys Ser Arg Leu Thr Ile Ser Ile Asp Thr Ser Lys Thr
305                 310                 315                 320

Gln Phe Ser Leu Lys Leu Ser Ser Val Thr Ala Ala Asp Thr Ala Ile
                325                 330                 335

Tyr Tyr Cys Val Arg Asp Arg Val Thr Gly Ala Phe Asp Ile Trp Gly
            340                 345                 350
```

```
Gln Gly Thr Met Val Thr Val Ser Ser Ala Ser Thr Lys Gly Pro Ser
            355                 360                 365

Val Phe Pro Leu Ala Pro Ser Ser Lys Ser Thr Ser Gly Gly Thr Ala
    370                 375                 380

Ala Leu Gly Cys Leu Val Lys Asp Tyr Phe Pro Glu Pro Val Thr Val
385                 390                 395                 400

Ser Trp Asn Ser Gly Ala Leu Thr Ser Gly Val His Thr Phe Pro Ala
            405                 410                 415

Val Leu Gln Ser Ser Gly Leu Tyr Ser Leu Ser Ser Val Val Thr Val
                420                 425                 430

Pro Ser Ser Ser Leu Gly Thr Gln Thr Tyr Ile Cys Asn Val Asn His
            435                 440                 445

Lys Pro Ser Asn Thr Lys Val Asp Lys Lys Val Glu Pro Lys Ser Cys
    450                 455                 460

Asp Lys Thr His Thr Cys Pro Pro Cys Pro Ala Pro Glu Leu Leu Gly
465                 470                 475                 480

Gly Pro Ser Val Phe Leu Phe Pro Pro Lys Pro Lys Asp Thr Leu Met
            485                 490                 495

Ile Ser Arg Thr Pro Glu Val Thr Cys Val Val Val Asp Val Ser His
                500                 505                 510

Glu Asp Pro Glu Val Lys Phe Asn Trp Tyr Val Asp Gly Val Glu Val
            515                 520                 525

His Asn Ala Lys Thr Lys Pro Arg Glu Glu Gln Tyr Asn Ser Thr Tyr
    530                 535                 540

Arg Val Val Ser Val Leu Thr Val Leu His Gln Asp Trp Leu Asn Gly
545                 550                 555                 560

Lys Glu Tyr Lys Cys Lys Val Ser Asn Lys Ala Leu Pro Ala Pro Ile
            565                 570                 575

Glu Lys Thr Ile Ser Lys Ala Lys Gly Gln Pro Arg Glu Pro Gln Val
                580                 585                 590

Tyr Thr Leu Pro Pro Ser Arg Glu Glu Met Thr Lys Asn Gln Val Ser
            595                 600                 605

Leu Thr Cys Leu Val Lys Gly Phe Tyr Pro Ser Asp Ile Ala Val Glu
    610                 615                 620

Trp Glu Ser Asn Gly Gln Pro Glu Asn Asn Tyr Lys Thr Thr Pro Pro
625                 630                 635                 640

Val Leu Asp Ser Asp Gly Ser Phe Phe Leu Tyr Ser Lys Leu Thr Val
            645                 650                 655

Asp Lys Ser Arg Trp Gln Gln Gly Asn Val Phe Ser Cys Ser Val Met
                660                 665                 670

His Glu Ala Leu His Asn His Tyr Thr Gln Lys Ser Leu Ser Leu Ser
            675                 680                 685

Pro Gly Lys
    690

<210> SEQ ID NO 118
<211> LENGTH: 239
<212> TYPE: PRT
<213> ORGANISM: Homo Sapiens

<400> SEQUENCE: 118

Met Glu Phe Gly Leu Ser Trp Leu Phe Leu Val Ala Ile Leu Lys Gly
1               5                   10                  15

Val Gln Cys Gln Val Gln Leu Gln Gln Trp Gly Ala Gly Leu Leu Lys
            20                  25                  30
```

```
Pro Ser Glu Thr Leu Ser Leu Thr Cys Ala Val Tyr Gly Gly Ser Phe
            35                  40                  45

Ser Gly Tyr Tyr Trp Ser Trp Ile Arg Gln Pro Pro Gly Lys Gly Leu
    50                  55                  60

Glu Trp Ile Gly Glu Ile Asn His Ser Gly Ser Thr Asn Tyr Asn Pro
65                  70                  75                  80

Ser Leu Lys Ser Arg Val Thr Ile Ser Val Glu Thr Ser Lys Asn Gln
                85                  90                  95

Phe Ser Leu Lys Leu Ser Ser Val Thr Ala Ala Asp Thr Ala Val Tyr
               100                 105                 110

Tyr Cys Ala Arg Asp Lys Trp Thr Trp Tyr Phe Asp Leu Trp Gly Arg
           115                 120                 125

Gly Thr Leu Val Thr Val Ser Ser Ala Ser Thr Lys Gly Pro Ser Val
       130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
               165                 170                 175

Trp Asn Ser Gly Ala Leu Thr Ser Gly Val His Thr Phe Pro Ala Val
           180                 185                 190

Leu Gln Ser Ser Gly Leu Tyr Ser Leu Ser Ser Val Val Thr Val Pro
       195                 200                 205

Ser Ser Ser Leu Gly Thr Gln Thr Tyr Ile Cys Asn Val Asn His Lys
   210                 215                 220

Pro Ser Asn Thr Lys Val Asp Lys Lys Val Glu Pro Lys Ser Cys
225                 230                 235

<210> SEQ ID NO 119
<211> LENGTH: 236
<212> TYPE: PRT
<213> ORGANISM: Homo Sapiens

<400> SEQUENCE: 119

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Gln Ala Ser
        35                  40                  45

Gln Asp Ile Ser Asn Tyr Leu Asn Trp Tyr Gln Gln Lys Pro Gly Lys
    50                  55                  60

Ala Pro Lys Leu Leu Ile Tyr Asp Ala Ser Asn Leu Glu Thr Gly Val
65                  70                  75                  80

Pro Ser Arg Phe Ser Gly Ser Gly Ser Gly Thr Asp Phe Thr Phe Thr
                85                  90                  95

Ile Ser Ser Leu Gln Pro Glu Asp Ile Ala Thr Tyr Phe Cys Gln His
               100                 105                 110

Phe Asp His Leu Pro Leu Ala Phe Gly Gly Gly Thr Lys Val Glu Ile
           115                 120                 125

Lys Arg Thr Val Ala Ala Pro Ser Val Phe Ile Phe Pro Pro Ser Asp
       130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
```

-continued

```
                165                 170                 175
Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 120
<211> LENGTH: 689
<212> TYPE: PRT
<213> ORGANISM: Artificial Sequence
<220> FEATURE:
<223> OTHER INFORMATION: PD-1/PD-L1 FIT20a polypeptide 1 (Nivolu VL-hCk-
      1B12 VH-hCg1Mut)

<400> SEQUENCE: 120

Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Ala Thr
            20                  25                  30

Leu Ser Leu Ser Pro Gly Glu Arg Ala Thr Leu Ser Cys Arg Ala Ser
        35                  40                  45

Gln Ser Val Ser Ser Tyr Leu Ala Trp Tyr Gln Gln Lys Pro Gly Gln
    50                  55                  60

Ala Pro Arg Leu Leu Ile Tyr Asp Ala Ser Asn Arg Ala Thr Gly Ile
65                  70                  75                  80

Pro Ala Arg Phe Ser Gly Ser Gly Ser Gly Thr Asp Phe Thr Leu Thr
                85                  90                  95

Ile Ser Ser Leu Glu Pro Glu Asp Phe Ala Val Tyr Tyr Cys Gln Gln
            100                 105                 110

Ser Ser Asn Trp Pro Arg Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Gln Val Gln Leu
225                 230                 235                 240

Val Gln Ser Gly Ala Glu Val Lys Lys Pro Gly Ser Ser Val Lys Val
                245                 250                 255

Ser Cys Lys Thr Ser Gly Asp Thr Phe Ser Ser Tyr Ala Ile Ser Trp
            260                 265                 270

Val Arg Gln Ala Pro Gly Gln Gly Leu Glu Trp Met Gly Gly Ile Ile
        275                 280                 285
```

```
Pro Ile Phe Gly Arg Ala His Tyr Ala Gln Lys Phe Gln Gly Arg Val
    290                 295                 300
Thr Ile Thr Ala Asp Glu Ser Thr Ser Thr Ala Tyr Met Glu Leu Ser
305                 310                 315                 320
Ser Leu Arg Ser Glu Asp Thr Ala Val Tyr Phe Cys Ala Arg Lys Phe
                325                 330                 335
His Phe Val Ser Gly Ser Pro Phe Gly Met Asp Val Trp Gly Gln Gly
            340                 345                 350
Thr Thr Val Thr Val Ser Ser Ala Ser Thr Lys Gly Pro Ser Val Phe
        355                 360                 365
Pro Leu Ala Pro Ser Ser Lys Ser Thr Ser Gly Gly Thr Ala Ala Leu
370                 375                 380
Gly Cys Leu Val Lys Asp Tyr Phe Pro Glu Pro Val Thr Val Ser Trp
385                 390                 395                 400
Asn Ser Gly Ala Leu Thr Ser Gly Val His Thr Phe Pro Ala Val Leu
                405                 410                 415
Gln Ser Ser Gly Leu Tyr Ser Leu Ser Ser Val Val Thr Val Pro Ser
            420                 425                 430
Ser Ser Leu Gly Thr Gln Thr Tyr Ile Cys Asn Val Asn His Lys Pro
        435                 440                 445
Ser Asn Thr Lys Val Asp Lys Lys Val Glu Pro Lys Ser Cys Asp Lys
450                 455                 460
Thr His Thr Cys Pro Pro Cys Pro Ala Pro Glu Leu Leu Gly Gly Pro
465                 470                 475                 480
Ser Val Phe Leu Phe Pro Pro Lys Pro Lys Asp Thr Leu Met Ile Ser
                485                 490                 495
Arg Thr Pro Glu Val Thr Cys Val Val Val Asp Val Ser His Glu Asp
            500                 505                 510
Pro Glu Val Lys Phe Asn Trp Tyr Val Asp Gly Val Glu Val His Asn
        515                 520                 525
Ala Lys Thr Lys Pro Arg Glu Glu Gln Tyr Asn Ser Thr Tyr Arg Val
530                 535                 540
Val Ser Val Leu Thr Val Leu His Gln Asp Trp Leu Asn Gly Lys Glu
545                 550                 555                 560
Tyr Lys Cys Lys Val Ser Asn Lys Ala Leu Pro Ala Pro Ile Glu Lys
                565                 570                 575
Thr Ile Ser Lys Ala Lys Gly Gln Pro Arg Glu Pro Gln Val Tyr Thr
            580                 585                 590
Leu Pro Pro Ser Arg Glu Glu Met Thr Lys Asn Gln Val Ser Leu Thr
        595                 600                 605
Cys Leu Val Lys Gly Phe Tyr Pro Ser Asp Ile Ala Val Glu Trp Glu
610                 615                 620
Ser Asn Gly Gln Pro Glu Asn Asn Tyr Lys Thr Thr Pro Pro Val Leu
625                 630                 635                 640
Asp Ser Asp Gly Ser Phe Phe Leu Tyr Ser Lys Leu Thr Val Asp Lys
                645                 650                 655
Ser Arg Trp Gln Gln Gly Asn Val Phe Ser Cys Ser Val Met His Glu
            660                 665                 670
Ala Leu His Asn His Tyr Thr Gln Lys Ser Leu Ser Leu Ser Pro Gly
        675                 680                 685
Lys

<210> SEQ ID NO 121
```

```
<211> LENGTH: 235
<212> TYPE: PRT
<213> ORGANISM: Homo Sapiens

<400> SEQUENCE: 121

Met Glu Phe Gly Leu Ser Trp Leu Phe Leu Val Ala Ile Leu Lys Gly
1               5                   10                  15

Val Gln Cys Gln Val Gln Leu Val Glu Ser Gly Gly Val Val Gln
            20                  25                  30

Pro Gly Arg Ser Leu Arg Leu Asp Cys Lys Ala Ser Ile Thr Phe
        35                  40                  45

Ser Asn Ser Gly Met His Trp Val Arg Gln Ala Pro Gly Lys Gly Leu
50                  55                  60

Glu Trp Val Ala Val Ile Trp Tyr Asp Gly Ser Lys Arg Tyr Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Arg Ala Glu Asp Thr Ala Val
            100                 105                 110

Tyr Tyr Cys Ala Thr Asn Asp Asp Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
210                 215                 220

Lys Val Asp Lys Lys Val Glu Pro Lys Ser Cys
225                 230                 235

<210> SEQ ID NO 122
<211> LENGTH: 235
<212> TYPE: PRT
<213> ORGANISM: Homo Sapiens

<400> SEQUENCE: 122

Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Ala Thr
            20                  25                  30

Leu Ser Leu Ser Pro Gly Glu Arg Ala Thr Leu Ser Cys Arg Ala Ser
        35                  40                  45

Gln Ser Val Ser Ser Tyr Leu Ala Trp Tyr Gln Gln Lys Pro Gly Gln
50                  55                  60

Ala Pro Arg Leu Leu Ile Tyr Asp Ala Ser Asn Arg Ala Thr Gly Ile
65                  70                  75                  80

Pro Ala Arg Phe Ser Gly Ser Gly Ser Gly Thr Asp Phe Thr Leu Thr
                85                  90                  95

Ile Ser Ser Leu Glu Pro Glu Asp Phe Ala Val Tyr Tyr Cys Gln Gln
            100                 105                 110
```

```
Arg Ser Asn Trp Pro Thr Phe Gly Gln Gly Thr Lys Val Glu Ile Lys
            115                 120                 125

Arg Thr Val Ala Ala Pro Ser Val Phe Ile Phe Pro Pro Ser Asp Glu
        130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 123
<211> LENGTH: 685
<212> TYPE: PRT
<213> ORGANISM: Artificial Sequence
<220> FEATURE:
<223> OTHER INFORMATION: Her3/PD-1 FIT22a polypeptide 1 (patritu VL-hCk-
      Nivolu VH-hCg1mut)

<400> SEQUENCE: 123

Met Asp Met Arg Val Pro Ala Gln Leu Leu Gly Leu Leu Leu Leu Trp
1               5                   10                  15

Phe Pro Gly Ser Arg Cys Asp Ile Glu Met Thr Gln Ser Pro Asp Ser
            20                  25                  30

Leu Ala Val Ser Leu Gly Glu Arg Ala Thr Ile Asn Cys Arg Ser Ser
        35                  40                  45

Gln Ser Val Leu Tyr Ser Ser Asn Arg Asn Tyr Leu Ala Trp Tyr
    50                  55                  60

Gln Gln Asn Pro Gly Gln Pro Pro Lys Leu Leu Ile Tyr Trp Ala Ser
65                  70                  75                  80

Thr Arg Glu Ser Gly Val Pro Asp Arg Phe Ser Gly Ser Gly Ser Gly
                85                  90                  95

Thr Asp Phe Thr Leu Thr Ile Ser Ser Leu Gln Ala Glu Asp Val Ala
            100                 105                 110

Val Tyr Tyr Cys Gln Gln Tyr Tyr Ser Thr Pro Arg Thr Phe Gly Gln
        115                 120                 125

Gly Thr Lys Val Glu Ile Lys Arg Thr Val Ala Ala Pro Ser Val Phe
    130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

Leu Ser Lys Ala Asp Tyr Glu Lys His Lys Val Tyr Ala Cys Glu Val
    210                 215                 220

Thr His Gln Gly Leu Ser Ser Pro Val Thr Lys Ser Phe Asn Arg Gly
```

-continued

```
                225                 230                 235                 240
Glu Cys Gln Val Gln Leu Val Glu Ser Gly Gly Val Val Gln Pro
                    245                 250                 255
Gly Arg Ser Leu Arg Leu Asp Cys Lys Ala Ser Gly Ile Thr Phe Ser
        260                 265                 270
Asn Ser Gly Met His Trp Val Arg Gln Ala Pro Gly Lys Gly Leu Glu
            275                 280                 285
Trp Val Ala Val Ile Trp Tyr Asp Gly Ser Lys Arg Tyr Tyr Ala Asp
290                 295                 300
Ser Val Lys Gly Arg Phe Thr Ile Ser Arg Asp Asn Ser Lys Asn Thr
305                 310                 315                 320
Leu Phe Leu Gln Met Asn Ser Leu Arg Ala Glu Asp Thr Ala Val Tyr
                325                 330                 335
Tyr Cys Ala Thr Asn Asp Asp Tyr Trp Gly Gln Gly Thr Leu Val Thr
            340                 345                 350
Val Ser Ser Ala Ser Thr Lys Gly Pro Ser Val Phe Pro Leu Ala Pro
        355                 360                 365
Ser Ser Lys Ser Thr Ser Gly Gly Thr Ala Ala Leu Gly Cys Leu Val
    370                 375                 380
Lys Asp Tyr Phe Pro Glu Pro Val Thr Val Ser Trp Asn Ser Gly Ala
385                 390                 395                 400
Leu Thr Ser Gly Val His Thr Phe Pro Ala Val Leu Gln Ser Ser Gly
                405                 410                 415
Leu Tyr Ser Leu Ser Ser Val Val Thr Val Pro Ser Ser Ser Leu Gly
            420                 425                 430
Thr Gln Thr Tyr Ile Cys Asn Val Asn His Lys Pro Ser Asn Thr Lys
        435                 440                 445
Val Asp Lys Lys Val Glu Pro Lys Ser Cys Asp Lys Thr His Thr Cys
    450                 455                 460
Pro Pro Cys Pro Ala Pro Glu Leu Leu Gly Gly Pro Ser Val Phe Leu
465                 470                 475                 480
Phe Pro Pro Lys Pro Lys Asp Thr Leu Met Ile Ser Arg Thr Pro Glu
                485                 490                 495
Val Thr Cys Val Val Val Asp Val Ser His Glu Asp Pro Glu Val Lys
            500                 505                 510
Phe Asn Trp Tyr Val Asp Gly Val Glu Val His Asn Ala Lys Thr Lys
        515                 520                 525
Pro Arg Glu Glu Gln Tyr Asn Ser Thr Tyr Arg Val Val Ser Val Leu
    530                 535                 540
Thr Val Leu His Gln Asp Trp Leu Asn Gly Lys Glu Tyr Lys Cys Lys
545                 550                 555                 560
Val Ser Asn Lys Ala Leu Pro Ala Pro Ile Glu Lys Thr Ile Ser Lys
                565                 570                 575
Ala Lys Gly Gln Pro Arg Glu Pro Gln Val Tyr Thr Leu Pro Pro Ser
            580                 585                 590
Arg Glu Glu Met Thr Lys Asn Gln Val Ser Leu Thr Cys Leu Val Lys
        595                 600                 605
Gly Phe Tyr Pro Ser Asp Ile Ala Val Glu Trp Glu Ser Asn Gly Gln
    610                 615                 620
Pro Glu Asn Asn Tyr Lys Thr Thr Pro Pro Val Leu Asp Ser Asp Gly
625                 630                 635                 640
Ser Phe Phe Leu Tyr Ser Lys Leu Thr Val Asp Lys Ser Arg Trp Gln
                645                 650                 655
```

Gln Gly Asn Val Phe Ser Cys Ser Val Met His Glu Ala Leu His Asn
                660                 665                 670

His Tyr Thr Gln Lys Ser Leu Ser Leu Ser Pro Gly Lys
            675                 680                 685

<210> SEQ ID NO 124
<211> LENGTH: 239
<212> TYPE: PRT
<213> ORGANISM: Homo Sapiens

<400> SEQUENCE: 124

Met Glu Phe Gly Leu Ser Trp Leu Phe Leu Val Ala Ile Leu Lys Gly
1               5                   10                  15

Val Gln Cys Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Pro Pro Gly Lys Gly Leu
    50                  55                  60

Glu Trp Ile Gly Glu Ile Asn His Ser Gly Ser Thr Asn Tyr Asn Pro
65                  70                  75                  80

Ser Leu Lys Ser Arg Val Thr Ile Ser Val Glu Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Lys Trp Thr Trp Tyr Phe Asp Leu Trp Gly Arg
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys
225                 230                 235

<210> SEQ ID NO 125
<211> LENGTH: 236
<212> TYPE: PRT
<213> ORGANISM: Homo Sapiens

<400> SEQUENCE: 125

Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Ala Thr
            20                  25                  30

Leu Ser Leu Ser Pro Gly Glu Arg Ala Thr Leu Ser Cys Arg Ala Ser
        35                  40                  45

Gln Ser Val Ser Ser Tyr Leu Ala Trp Tyr Gln Gln Lys Pro Gly Gln
    50                  55                  60

```
Ala Pro Arg Leu Leu Ile Tyr Asp Ala Ser Asn Arg Ala Thr Gly Ile
 65                  70                  75                  80

Pro Ala Arg Phe Ser Gly Ser Gly Ser Gly Thr Asp Phe Thr Leu Thr
                 85                  90                  95

Ile Ser Ser Leu Glu Pro Glu Asp Phe Ala Val Tyr Tyr Cys Gln Gln
            100                 105                 110

Ser Ser Asn Trp Pro Arg Thr Phe Gly Gln Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 126
<211> LENGTH: 680
<212> TYPE: PRT
<213> ORGANISM: Artificial Sequence
<220> FEATURE:
<223> OTHER INFORMATION: Long chain (IpiliVL-hCk-NivoluVH-hCg1mut)

<400> SEQUENCE: 126

Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Gly Thr
                20                  25                  30

Leu Ser Leu Ser Pro Gly Glu Arg Ala Thr Leu Ser Cys Arg Ala Ser
            35                  40                  45

Gln Ser Val Gly Ser Ser Tyr Leu Ala Trp Tyr Gln Gln Lys Pro Gly
        50                  55                  60

Gln Ala Pro Arg Leu Leu Ile Tyr Gly Ala Phe Ser Arg Ala Thr Gly
 65                 70                  75                  80

Ile Pro Asp Arg Phe Ser Gly Ser Gly Ser Gly Thr Asp Phe Thr Leu
                85                  90                  95

Thr Ile Ser Arg Leu Glu Pro Glu Asp Phe Ala Val Tyr Tyr Cys Gln
            100                 105                 110

Gln Tyr Gly Ser Ser Pro Trp Thr Phe Gly Gln Gly Thr Lys Val Glu
        115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190
```

-continued

```
Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys Gln Val Gln
225                 230                 235                 240

Leu Val Glu Ser Gly Gly Val Val Gln Pro Gly Arg Ser Leu Arg
                245                 250                 255

Leu Asp Cys Lys Ala Ser Gly Ile Thr Phe Ser Asn Ser Gly Met His
                260                 265                 270

Trp Val Arg Gln Ala Pro Gly Lys Gly Leu Glu Trp Val Ala Val Ile
                275                 280                 285

Trp Tyr Asp Gly Ser Lys Arg Tyr Tyr Ala Asp Ser Val Lys Gly Arg
        290                 295                 300

Phe Thr Ile Ser Arg Asp Asn Ser Lys Asn Thr Leu Phe Leu Gln Met
305                 310                 315                 320

Asn Ser Leu Arg Ala Glu Asp Thr Ala Val Tyr Tyr Cys Ala Thr Asn
                325                 330                 335

Asp Asp Tyr Trp Gly Gln Gly Thr Leu Val Thr Val Ser Ser Ala Ser
                340                 345                 350

Thr Lys Gly Pro Ser Val Phe Pro Leu Ala Pro Ser Ser Lys Ser Thr
                355                 360                 365

Ser Gly Gly Thr Ala Ala Leu Gly Cys Leu Val Lys Asp Tyr Phe Pro
        370                 375                 380

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
                405                 410                 415

Ser Val Val Thr Val Pro Ser Ser Ser Leu Gly Thr Gln Thr Tyr Ile
                420                 425                 430

Cys Asn Val Asn His Lys Pro Ser Asn Thr Lys Val Asp Lys Lys Val
        435                 440                 445

Glu Pro Lys Ser Cys Asp Lys Thr His Thr Cys Pro Pro Cys Pro Ala
    450                 455                 460

Pro Glu Ala Ala Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
                485                 490                 495

Val Asp Val Ser His Glu Asp Pro Glu Val Lys Phe Asn Trp Tyr Val
                500                 505                 510

Asp Gly Val Glu Val His Asn Ala Lys Thr Lys Pro Arg Glu Glu Gln
        515                 520                 525

Tyr Asn Ser Thr Tyr Arg Val Val Ser Val Leu Thr Val Leu His Gln
    530                 535                 540

Asp Trp Leu Asn Gly Lys Glu Tyr Lys Cys Lys Val Ser Asn Lys Ala
545                 550                 555                 560

Leu Pro Ala Pro Ile Glu Lys Thr Ile Ser Lys Ala Lys Gly Gln Pro
                565                 570                 575

Arg Glu Pro Gln Val Tyr Thr Leu Pro Pro Ser Arg Glu Glu Met Thr
                580                 585                 590

Lys Asn Gln Val Ser Leu Thr Cys Leu Val Lys Gly Phe Tyr Pro Ser
        595                 600                 605
```

```
Asp Ile Ala Val Glu Trp Glu Ser Asn Gly Gln Pro Glu Asn Asn Tyr
        610                 615                 620

Lys Thr Thr Pro Pro Val Leu Asp Ser Asp Gly Ser Phe Phe Leu Tyr
625                 630                 635                 640

Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
                660                 665                 670

Ser Leu Ser Leu Ser Pro Gly Lys
        675                 680

<210> SEQ ID NO 127
<211> LENGTH: 108
<212> TYPE: PRT
<213> ORGANISM: Artificial Sequence
<220> FEATURE:
<223> OTHER INFORMATION: Ipili VL

<400> SEQUENCE: 127

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 128
<211> LENGTH: 12
<212> TYPE: PRT
<213> ORGANISM: Artificial Sequence
<220> FEATURE:
<223> OTHER INFORMATION: Ipili VL - CDR1

<400> SEQUENCE: 128

Arg Ala Ser Gln Ser Val Gly Ser Ser Tyr Leu Ala
1               5                   10

<210> SEQ ID NO 129
<211> LENGTH: 7
<212> TYPE: PRT
<213> ORGANISM: Artificial Sequence
<220> FEATURE:
<223> OTHER INFORMATION: Ipili VL - CDR2

<400> SEQUENCE: 129

Gly Ala Phe Ser Arg Ala Thr
1               5

<210> SEQ ID NO 130
<211> LENGTH: 9
<212> TYPE: PRT
<213> ORGANISM: Artificial Sequence
<220> FEATURE:
<223> OTHER INFORMATION: Ipili VL - CDR3
```

<400> SEQUENCE: 130

Gln Gln Tyr Gly Ser Ser Pro Trp Thr
1               5

<210> SEQ ID NO 131
<211> LENGTH: 113
<212> TYPE: PRT
<213> ORGANISM: Artificial Sequence
<220> FEATURE:
<223> OTHER INFORMATION: NivoluVH

<400> SEQUENCE: 131

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 132
<211> LENGTH: 5
<212> TYPE: PRT
<213> ORGANISM: Artificial Sequence
<220> FEATURE:
<223> OTHER INFORMATION: Nivolu VH - CDR1

<400> SEQUENCE: 132

Asn Ser Gly Met His
1               5

<210> SEQ ID NO 133
<211> LENGTH: 17
<212> TYPE: PRT
<213> ORGANISM: Artificial Sequence
<220> FEATURE:
<223> OTHER INFORMATION: Nivolu VH - CDR2

<400> SEQUENCE: 133

Val Ile Trp Tyr Asp Gly Ser Lys Arg Tyr Tyr Ala Asp Ser Val Lys
1               5                   10                  15

Gly

<210> SEQ ID NO 134
<211> LENGTH: 4
<212> TYPE: PRT
<213> ORGANISM: Artificial Sequence
<220> FEATURE:
<223> OTHER INFORMATION: Nivolu VH - CDR3

<400> SEQUENCE: 134

Asn Asp Asp Tyr
1

<210> SEQ ID NO 135
<211> LENGTH: 240
<212> TYPE: PRT
<213> ORGANISM: Artificial Sequence
<220> FEATURE:
<223> OTHER INFORMATION: Short Chain 1 (Ipili VH-CH1)

<400> SEQUENCE: 135

Met Glu Phe Gly Leu Ser Trp Leu Phe Leu Val Ala Ile Leu Lys Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Thr Met His Trp Val Arg Gln Ala Pro Gly Lys Gly Leu
    50                  55                  60

Glu Trp Val Thr Phe Ile Ser Tyr Asp Gly Asn Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Ile
            100                 105                 110

Tyr Tyr Cys Ala Arg Thr Gly Trp Leu Gly Pro Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

<210> SEQ ID NO 136
<211> LENGTH: 118
<212> TYPE: PRT
<213> ORGANISM: Artificial Sequence
<220> FEATURE:
<223> OTHER INFORMATION: Ipili VH

<400> SEQUENCE: 136

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Ile Tyr Tyr Cys
                    85                  90                  95

Ala Arg Thr Gly Trp Leu Gly Pro Phe Asp Tyr Trp Gly Gln Gly Thr
                100                 105                 110

Leu Val Thr Val Ser Ser
        115

<210> SEQ ID NO 137
<211> LENGTH: 5
<212> TYPE: PRT
<213> ORGANISM: Artificial Sequence
<220> FEATURE:
<223> OTHER INFORMATION: Ipili VH - CDR1

<400> SEQUENCE: 137

Ser Tyr Thr Met His
1               5

<210> SEQ ID NO 138
<211> LENGTH: 17
<212> TYPE: PRT
<213> ORGANISM: Artificial Sequence
<220> FEATURE:
<223> OTHER INFORMATION: Ipili VH - CDR2

<400> SEQUENCE: 138

Phe Ile Ser Tyr Asp Gly Asn Asn Lys Tyr Tyr Ala Asp Ser Val Lys
1               5                   10                  15

Gly

<210> SEQ ID NO 139
<211> LENGTH: 9
<212> TYPE: PRT
<213> ORGANISM: Artificial Sequence
<220> FEATURE:
<223> OTHER INFORMATION: Ipili VH - CDR3

<400> SEQUENCE: 139

Thr Gly Trp Leu Gly Pro Phe Asp Tyr
1               5

<210> SEQ ID NO 140
<211> LENGTH: 236
<212> TYPE: PRT
<213> ORGANISM: Artificial Sequence
<220> FEATURE:
<223> OTHER INFORMATION: Short Chain 2 (Nivolu VL-hCK)

<400> SEQUENCE: 140

Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Ala Thr
                20                  25                  30

Leu Ser Leu Ser Pro Gly Glu Arg Ala Thr Leu Ser Cys Arg Ala Ser
            35                  40                  45

Gln Ser Val Ser Ser Tyr Leu Ala Trp Tyr Gln Gln Lys Pro Gly Gln
        50                  55                  60

Ala Pro Arg Leu Leu Ile Tyr Asp Ala Ser Asn Arg Ala Thr Gly Ile
65                  70                  75                  80

Pro Ala Arg Phe Ser Gly Ser Gly Ser Gly Thr Asp Phe Thr Leu Thr
                85                  90                  95
```

```
Ile Ser Ser Leu Glu Pro Glu Asp Phe Ala Val Tyr Tyr Cys Gln Gln
            100                 105                 110

Ser Ser Asn Trp Pro Arg Thr Phe Gly Gln Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 141
<211> LENGTH: 107
<212> TYPE: PRT
<213> ORGANISM: Artificial Sequence
<220> FEATURE:
<223> OTHER INFORMATION: Nivolu VL

<400> SEQUENCE: 141

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 142
<211> LENGTH: 11
<212> TYPE: PRT
<213> ORGANISM: Artificial Sequence
<220> FEATURE:
<223> OTHER INFORMATION: Nivolu VL - CDR1

<400> SEQUENCE: 142

Arg Ala Ser Gln Ser Val Ser Ser Tyr Leu Ala
1               5                   10

<210> SEQ ID NO 143
<211> LENGTH: 7
<212> TYPE: PRT
<213> ORGANISM: Artificial Sequence
<220> FEATURE:
<223> OTHER INFORMATION: Nivolu VL - CDR2
```

<400> SEQUENCE: 143

Asp Ala Ser Asn Arg Ala Thr
1               5

<210> SEQ ID NO 144
<211> LENGTH: 9
<212> TYPE: PRT
<213> ORGANISM: Artificial Sequence
<220> FEATURE:
<223> OTHER INFORMATION: Nivolu VL - CDR3

<400> SEQUENCE: 144

Gln Gln Ser Ser Asn Trp Pro Arg Thr
1               5

<210> SEQ ID NO 145
<211> LENGTH: 684
<212> TYPE: PRT
<213> ORGANISM: Artificial Sequence
<220> FEATURE:
<223> OTHER INFORMATION: Long Chain (Nivolu VL-hCk-Ipili VH-hCg1mut)

<400> SEQUENCE: 145

Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Ala Thr
            20                  25                  30

Leu Ser Leu Ser Pro Gly Glu Arg Ala Thr Leu Ser Cys Arg Ala Ser
        35                  40                  45

Gln Ser Val Ser Ser Tyr Leu Ala Trp Tyr Gln Gln Lys Pro Gly Gln
    50                  55                  60

Ala Pro Arg Leu Leu Ile Tyr Asp Ala Ser Asn Arg Ala Thr Gly Ile
65                  70                  75                  80

Pro Ala Arg Phe Ser Gly Ser Gly Ser Gly Thr Asp Phe Thr Leu Thr
                85                  90                  95

Ile Ser Ser Leu Glu Pro Glu Asp Phe Ala Val Tyr Tyr Cys Gln Gln
            100                 105                 110

Ser Ser Asn Trp Pro Arg Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Gln Val Gln Leu
225                 230                 235                 240

Val Glu Ser Gly Gly Gly Val Val Gln Pro Gly Arg Ser Leu Arg Leu
                245                 250                 255

Ser Cys Ala Ala Ser Gly Phe Thr Phe Ser Ser Tyr Thr Met His Trp
            260                 265                 270

```
Val Arg Gln Ala Pro Gly Lys Gly Leu Glu Trp Val Thr Phe Ile Ser
            275                 280                 285

Tyr Asp Gly Asn Asn Lys Tyr Tyr Ala Asp Ser Val Lys Gly Arg Phe
    290                 295                 300

Thr Ile Ser Arg Asp Asn Ser Lys Asn Thr Leu Tyr Leu Gln Met Asn
305                 310                 315                 320

Ser Leu Arg Ala Glu Asp Thr Ala Ile Tyr Tyr Cys Ala Arg Thr Gly
                325                 330                 335

Trp Leu Gly Pro Phe Asp Tyr Trp Gly Gln Gly Thr Leu Val Thr Val
                340                 345                 350

Ser Ser Ala Ser Thr Lys Gly Pro Ser Val Phe Pro Leu Ala Pro Ser
            355                 360                 365

Ser Lys Ser Thr Ser Gly Gly Thr Ala Ala Leu Gly Cys Leu Val Lys
    370                 375                 380

Asp Tyr Phe Pro Glu Pro Val Thr Val Ser Trp Asn Ser Gly Ala Leu
385                 390                 395                 400

Thr Ser Gly Val His Thr Phe Pro Ala Val Leu Gln Ser Ser Gly Leu
                405                 410                 415

Tyr Ser Leu Ser Ser Val Val Thr Val Pro Ser Ser Ser Leu Gly Thr
                420                 425                 430

Gln Thr Tyr Ile Cys Asn Val Asn His Lys Pro Ser Asn Thr Lys Val
            435                 440                 445

Asp Lys Lys Val Glu Pro Lys Ser Cys Asp Lys Thr His Thr Cys Pro
    450                 455                 460

Pro Cys Pro Ala Pro Glu Ala Ala Gly Gly Pro Ser Val Phe Leu Phe
465                 470                 475                 480

Pro Pro Lys Pro Lys Asp Thr Leu Met Ile Ser Arg Thr Pro Glu Val
                485                 490                 495

Thr Cys Val Val Val Asp Val Ser His Glu Asp Pro Glu Val Lys Phe
                500                 505                 510

Asn Trp Tyr Val Asp Gly Val Glu Val His Asn Ala Lys Thr Lys Pro
            515                 520                 525

Arg Glu Glu Gln Tyr Asn Ser Thr Tyr Arg Val Val Ser Val Leu Thr
    530                 535                 540

Val Leu His Gln Asp Trp Leu Asn Gly Lys Glu Tyr Lys Cys Lys Val
545                 550                 555                 560

Ser Asn Lys Ala Leu Pro Ala Pro Ile Glu Lys Thr Ile Ser Lys Ala
                565                 570                 575

Lys Gly Gln Pro Arg Glu Pro Gln Val Tyr Thr Leu Pro Pro Ser Arg
                580                 585                 590

Glu Glu Met Thr Lys Asn Gln Val Ser Leu Thr Cys Leu Val Lys Gly
            595                 600                 605

Phe Tyr Pro Ser Asp Ile Ala Val Glu Trp Glu Ser Asn Gly Gln Pro
    610                 615                 620

Glu Asn Asn Tyr Lys Thr Thr Pro Pro Val Leu Asp Ser Asp Gly Ser
625                 630                 635                 640

Phe Phe Leu Tyr Ser Lys Leu Thr Val Asp Lys Ser Arg Trp Gln Gln
                645                 650                 655

Gly Asn Val Phe Ser Cys Ser Val Met His Glu Ala Leu His Asn His
                660                 665                 670

Tyr Thr Gln Lys Ser Leu Ser Leu Ser Pro Gly Lys
            675                 680
```

<210> SEQ ID NO 146
<211> LENGTH: 107
<212> TYPE: PRT
<213> ORGANISM: Artificial Sequence
<220> FEATURE:
<223> OTHER INFORMATION: Nivolu VL

<400> SEQUENCE: 146

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 147
<211> LENGTH: 11
<212> TYPE: PRT
<213> ORGANISM: Artificial Sequence
<220> FEATURE:
<223> OTHER INFORMATION: Nivolu VL - CDR1

<400> SEQUENCE: 147

Arg Ala Ser Gln Ser Val Ser Ser Tyr Leu Ala
1               5                   10

<210> SEQ ID NO 148
<211> LENGTH: 7
<212> TYPE: PRT
<213> ORGANISM: Artificial Sequence
<220> FEATURE:
<223> OTHER INFORMATION: Nivolu VL - CDR2

<400> SEQUENCE: 148

Asp Ala Ser Asn Arg Ala Thr
1               5

<210> SEQ ID NO 149
<211> LENGTH: 9
<212> TYPE: PRT
<213> ORGANISM: Artificial Sequence
<220> FEATURE:
<223> OTHER INFORMATION: Nivolu VL - CDR3

<400> SEQUENCE: 149

Gln Gln Ser Ser Asn Trp Pro Arg Thr
1               5

<210> SEQ ID NO 150
<211> LENGTH: 118
<212> TYPE: PRT
<213> ORGANISM: Artificial Sequence
<220> FEATURE:
<223> OTHER INFORMATION: Ipili VH

<400> SEQUENCE: 150

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
            115

<210> SEQ ID NO 151
<211> LENGTH: 5
<212> TYPE: PRT
<213> ORGANISM: Artificial Sequence
<220> FEATURE:
<223> OTHER INFORMATION: Ipili VH - CDR1

<400> SEQUENCE: 151

Ser Tyr Thr Met His
1               5

<210> SEQ ID NO 152
<211> LENGTH: 17
<212> TYPE: PRT
<213> ORGANISM: Artificial Sequence
<220> FEATURE:
<223> OTHER INFORMATION: Ipili VH - CDR2

<400> SEQUENCE: 152

Phe Ile Ser Tyr Asp Gly Asn Asn Lys Tyr Tyr Ala Asp Ser Val Lys
1               5                   10                  15

Gly

<210> SEQ ID NO 153
<211> LENGTH: 9
<212> TYPE: PRT
<213> ORGANISM: Artificial Sequence
<220> FEATURE:
<223> OTHER INFORMATION: Ipili VH - CDR3

<400> SEQUENCE: 153

Thr Gly Trp Leu Gly Pro Phe Asp Tyr
1               5

<210> SEQ ID NO 154
<211> LENGTH: 235
<212> TYPE: PRT
<213> ORGANISM: Artificial Sequence
<220> FEATURE:
<223> OTHER INFORMATION: Short Chain 1 (Nivolu VH-CH1)

<400> SEQUENCE: 154

Met Glu Phe Gly Leu Ser Trp Leu Phe Leu Val Ala Ile Leu Lys Gly
1               5                   10                  15

```
Val Gln Cys Gln Val Gln Leu Val Glu Ser Gly Gly Gly Val Val Gln
             20                  25                  30

Pro Gly Arg Ser Leu Arg Leu Asp Cys Lys Ala Ser Gly Ile Thr Phe
         35                  40                  45

Ser Asn Ser Gly Met His Trp Val Arg Gln Ala Pro Gly Lys Gly Leu
     50                  55                  60

Glu Trp Val Ala Val Ile Trp Tyr Asp Gly Ser Lys Arg Tyr Tyr Ala
 65                  70                  75                  80

Asp Ser Val Lys Gly Arg Phe Thr Ile Ser Arg Asp Asn Ser Lys Asn
                 85                  90                  95

Thr Leu Phe Leu Gln Met Asn Ser Leu Arg Ala Glu Asp Thr Ala Val
            100                 105                 110

Tyr Tyr Cys Ala Thr Asn Asp Asp Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys
225                 230                 235

<210> SEQ ID NO 155
<211> LENGTH: 113
<212> TYPE: PRT
<213> ORGANISM: Artificial Sequence
<220> FEATURE:
<223> OTHER INFORMATION: Nivolu VH

<400> SEQUENCE: 155

Gln Val Gln Leu Val Glu Ser Gly Gly Gly Val Val Gln Pro Gly Arg
 1               5                  10                  15

Ser Leu Arg Leu Asp Cys Lys Ala Ser Gly Ile Thr Phe Ser Asn Ser
             20                  25                  30

Gly Met His Trp Val Arg Gln Ala Pro Gly Lys Gly Leu Glu Trp Val
         35                  40                  45

Ala Val Ile Trp Tyr Asp Gly Ser Lys Arg Tyr Tyr Ala Asp Ser Val
     50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
            100                 105                 110

Ser

<210> SEQ ID NO 156
<211> LENGTH: 3
<212> TYPE: PRT
```

<213> ORGANISM: Artificial Sequence
<220> FEATURE:
<223> OTHER INFORMATION: Nivolu VH - CDR1

<400> SEQUENCE: 156

Gly Met His
1

<210> SEQ ID NO 157
<211> LENGTH: 17
<212> TYPE: PRT
<213> ORGANISM: Artificial Sequence
<220> FEATURE:
<223> OTHER INFORMATION: Nivolu VH - CDR2

<400> SEQUENCE: 157

Val Ile Trp Tyr Asp Gly Ser Lys Arg Tyr Tyr Ala Asp Ser Val Lys
1               5                   10                  15

Gly

<210> SEQ ID NO 158
<211> LENGTH: 4
<212> TYPE: PRT
<213> ORGANISM: Artificial Sequence
<220> FEATURE:
<223> OTHER INFORMATION: Nivolu VH - CDR3

<400> SEQUENCE: 158

Asn Asp Asp Tyr
1

<210> SEQ ID NO 159
<211> LENGTH: 237
<212> TYPE: PRT
<213> ORGANISM: Artificial Sequence
<220> FEATURE:
<223> OTHER INFORMATION: Short Chain 2 (Ipili VL-hCK)

<400> SEQUENCE: 159

Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Gly Thr
                20                  25                  30

Leu Ser Leu Ser Pro Gly Glu Arg Ala Thr Leu Ser Cys Arg Ala Ser
            35                  40                  45

Gln Ser Val Gly Ser Ser Tyr Leu Ala Trp Tyr Gln Gln Lys Pro Gly
        50                  55                  60

Gln Ala Pro Arg Leu Leu Ile Tyr Gly Ala Phe Ser Arg Ala Thr Gly
65                  70                  75                  80

Ile Pro Asp Arg Phe Ser Gly Ser Gly Ser Gly Thr Asp Phe Thr Leu
                85                  90                  95

Thr Ile Ser Arg Leu Glu Pro Glu Asp Phe Ala Val Tyr Tyr Cys Gln
            100                 105                 110

Gln Tyr Gly Ser Ser Pro Trp Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

```
Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 160
<211> LENGTH: 108
<212> TYPE: PRT
<213> ORGANISM: Artificial Sequence
<220> FEATURE:
<223> OTHER INFORMATION: Ipili VL

<400> SEQUENCE: 160

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 161
<211> LENGTH: 12
<212> TYPE: PRT
<213> ORGANISM: Artificial Sequence
<220> FEATURE:
<223> OTHER INFORMATION: Ipili VL - CDR1

<400> SEQUENCE: 161

Arg Ala Ser Gln Ser Val Gly Ser Ser Tyr Leu Ala
1               5                   10

<210> SEQ ID NO 162
<211> LENGTH: 7
<212> TYPE: PRT
<213> ORGANISM: Artificial Sequence
<220> FEATURE:
<223> OTHER INFORMATION: Ipili VL - CDR2

<400> SEQUENCE: 162

Gly Ala Phe Ser Arg Ala Thr
1               5

<210> SEQ ID NO 163
<211> LENGTH: 7
<212> TYPE: PRT
<213> ORGANISM: Artificial Sequence
<220> FEATURE:
<223> OTHER INFORMATION: Ipili VL - CDR3

<400> SEQUENCE: 163
```

Tyr Gly Ser Ser Pro Trp Thr
1               5

<210> SEQ ID NO 164
<211> LENGTH: 677
<212> TYPE: PRT
<213> ORGANISM: Artificial Sequence
<220> FEATURE:
<223> OTHER INFORMATION: Long Chain (IpiliVL-hCk-NivoluVH-hCg4)

<400> SEQUENCE: 164

Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Gly Thr
            20                  25                  30

Leu Ser Leu Ser Pro Gly Glu Arg Ala Thr Leu Ser Cys Arg Ala Ser
        35                  40                  45

Gln Ser Val Gly Ser Ser Tyr Leu Ala Trp Tyr Gln Gln Lys Pro Gly
    50                  55                  60

Gln Ala Pro Arg Leu Leu Ile Tyr Gly Ala Phe Ser Arg Ala Thr Gly
65                  70                  75                  80

Ile Pro Asp Arg Phe Ser Gly Ser Gly Ser Gly Thr Asp Phe Thr Leu
                85                  90                  95

Thr Ile Ser Arg Leu Glu Pro Glu Asp Phe Ala Val Tyr Tyr Cys Gln
            100                 105                 110

Gln Tyr Gly Ser Ser Pro Trp Thr Phe Gly Gln Gly Thr Lys Val Glu
        115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys Gln Val Gln
225                 230                 235                 240

Leu Val Glu Ser Gly Gly Gly Val Val Gln Pro Gly Arg Ser Leu Arg
                245                 250                 255

Leu Asp Cys Lys Ala Ser Gly Ile Thr Phe Ser Asn Ser Gly Met His
            260                 265                 270

Trp Val Arg Gln Ala Pro Gly Lys Gly Leu Glu Trp Val Ala Val Ile
        275                 280                 285

Trp Tyr Asp Gly Ser Lys Arg Tyr Tyr Ala Asp Ser Val Lys Gly Arg
    290                 295                 300

Phe Thr Ile Ser Arg Asp Asn Ser Lys Asn Thr Leu Phe Leu Gln Met
305                 310                 315                 320

Asn Ser Leu Arg Ala Glu Asp Thr Ala Val Tyr Tyr Cys Ala Thr Asn
                325                 330                 335

Asp Asp Tyr Trp Gly Gln Gly Thr Leu Val Thr Val Ser Ser Ala Ser
            340                 345                 350

```
Thr Lys Gly Pro Ser Val Phe Pro Leu Ala Pro Cys Ser Arg Ser Thr
        355                 360                 365

Ser Glu Ser Thr Ala Ala Leu Gly Cys Leu Val Lys Asp Tyr Phe Pro
    370                 375                 380

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
                405                 410                 415

Ser Val Val Thr Val Pro Ser Ser Ser Leu Gly Thr Lys Thr Tyr Thr
            420                 425                 430

Cys Asn Val Asp His Lys Pro Ser Asn Thr Lys Val Asp Lys Arg Val
        435                 440                 445

Glu Ser Lys Tyr Gly Pro Pro Cys Pro Pro Cys Pro Ala Pro Glu Phe
    450                 455                 460

Leu Gly Gly Pro Ser Val Phe Leu Phe Pro Pro Lys Pro Lys Asp Thr
465                 470                 475                 480

Leu Met Ile Ser Arg Thr Pro Glu Val Thr Cys Val Val Val Asp Val
                485                 490                 495

Ser Gln Glu Asp Pro Glu Val Gln Phe Asn Trp Tyr Val Asp Gly Val
            500                 505                 510

Glu Val His Asn Ala Lys Thr Lys Pro Arg Glu Glu Gln Phe Asn Ser
        515                 520                 525

Thr Tyr Arg Val Val Ser Val Leu Thr Val Leu His Gln Asp Trp Leu
    530                 535                 540

Asn Gly Lys Glu Tyr Lys Cys Lys Val Ser Asn Lys Gly Leu Pro Ser
545                 550                 555                 560

Ser Ile Glu Lys Thr Ile Ser Lys Ala Lys Gly Gln Pro Arg Glu Pro
                565                 570                 575

Gln Val Tyr Thr Leu Pro Pro Ser Gln Glu Glu Met Thr Lys Asn Gln
            580                 585                 590

Val Ser Leu Thr Cys Leu Val Lys Gly Phe Tyr Pro Ser Asp Ile Ala
        595                 600                 605

Val Glu Trp Glu Ser Asn Gly Gln Pro Glu Asn Asn Tyr Lys Thr Thr
    610                 615                 620

Pro Pro Val Leu Asp Ser Asp Gly Ser Phe Phe Leu Tyr Ser Arg Leu
625                 630                 635                 640

Thr Val Asp Lys Ser Arg Trp Gln Glu Gly Asn Val Phe Ser Cys Ser
                645                 650                 655

Val Met His Glu Ala Leu His Asn His Tyr Thr Gln Lys Ser Leu Ser
            660                 665                 670

Leu Ser Leu Gly Lys
        675

<210> SEQ ID NO 165
<211> LENGTH: 108
<212> TYPE: PRT
<213> ORGANISM: Artificial Sequence
<220> FEATURE:
<223> OTHER INFORMATION: IpiliVL

<400> SEQUENCE: 165

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30
```

```
Tyr Leu Ala Trp Tyr Gln Gln Lys Pro Gly Gln Ala Pro Arg Leu Leu
            35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65              70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
                100                 105

<210> SEQ ID NO 166
<211> LENGTH: 12
<212> TYPE: PRT
<213> ORGANISM: Artificial Sequence
<220> FEATURE:
<223> OTHER INFORMATION: IpiliVL - CDR1

<400> SEQUENCE: 166

Arg Ala Ser Gln Ser Val Gly Ser Ser Tyr Leu Ala
1               5                   10

<210> SEQ ID NO 167
<211> LENGTH: 7
<212> TYPE: PRT
<213> ORGANISM: Artificial Sequence
<220> FEATURE:
<223> OTHER INFORMATION: IpiliVL - CDR2

<400> SEQUENCE: 167

Gly Ala Phe Ser Arg Ala Thr
1               5

<210> SEQ ID NO 168
<211> LENGTH: 6
<212> TYPE: PRT
<213> ORGANISM: Artificial Sequence
<220> FEATURE:
<223> OTHER INFORMATION: IpiliVL - CDR3

<400> SEQUENCE: 168

Gln Gln Tyr Gly Ser Ser
1               5

<210> SEQ ID NO 169
<211> LENGTH: 113
<212> TYPE: PRT
<213> ORGANISM: Artificial Sequence
<220> FEATURE:
<223> OTHER INFORMATION: NivoluVH

<400> SEQUENCE: 169

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80
```

```
Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 170
<211> LENGTH: 5
<212> TYPE: PRT
<213> ORGANISM: Artificial Sequence
<220> FEATURE:
<223> OTHER INFORMATION: NivoluVH - CDR1

<400> SEQUENCE: 170

Asn Ser Gly Met His
1               5

<210> SEQ ID NO 171
<211> LENGTH: 17
<212> TYPE: PRT
<213> ORGANISM: Artificial Sequence
<220> FEATURE:
<223> OTHER INFORMATION: NivoluVH - CDR2

<400> SEQUENCE: 171

Val Ile Trp Tyr Asp Gly Ser Lys Arg Tyr Tyr Ala Asp Ser Val Lys
1               5                   10                  15

Gly

<210> SEQ ID NO 172
<211> LENGTH: 4
<212> TYPE: PRT
<213> ORGANISM: Artificial Sequence
<220> FEATURE:
<223> OTHER INFORMATION: NivoluVH - CDR3

<400> SEQUENCE: 172

Asn Asp Asp Tyr
1

<210> SEQ ID NO 173
<211> LENGTH: 240
<212> TYPE: PRT
<213> ORGANISM: Artificial Sequence
<220> FEATURE:
<223> OTHER INFORMATION: Short Chain 1 (Ipili VH-CH1)

<400> SEQUENCE: 173

Met Glu Phe Gly Leu Ser Trp Leu Phe Leu Val Ala Ile Leu Lys Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Ser Tyr Thr Met His Trp Val Arg Gln Ala Pro Gly Lys Gly Leu
        50                  55                  60

Glu Trp Val Thr Phe Ile Ser Tyr Asp Gly Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Ile
```

```
              100                 105                 110
Tyr Tyr Cys Ala Arg Thr Gly Trp Leu Gly Pro Phe Asp Tyr Trp Gly
        115                 120                 125

Gln Gly Thr Leu Val Thr Val Ser Ser Ala Ser Thr Lys Gly Pro Ser
        130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

<210> SEQ ID NO 174
<211> LENGTH: 118
<212> TYPE: PRT
<213> ORGANISM: Artificial Sequence
<220> FEATURE:
<223> OTHER INFORMATION: Ipili VH

<400> SEQUENCE: 174

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115

<210> SEQ ID NO 175
<211> LENGTH: 5
<212> TYPE: PRT
<213> ORGANISM: Artificial Sequence
<220> FEATURE:
<223> OTHER INFORMATION: Ipili VH - CDR1

<400> SEQUENCE: 175

Ser Tyr Thr Met His
1               5

<210> SEQ ID NO 176
<211> LENGTH: 17
<212> TYPE: PRT
<213> ORGANISM: Artificial Sequence
<220> FEATURE:
```

<223> OTHER INFORMATION: Ipili VH - CDR2

<400> SEQUENCE: 176

Phe Ile Ser Tyr Asp Gly Asn Asn Lys Tyr Tyr Ala Asp Ser Val Lys
1               5                   10                  15
Gly

<210> SEQ ID NO 177
<211> LENGTH: 9
<212> TYPE: PRT
<213> ORGANISM: Artificial Sequence
<220> FEATURE:
<223> OTHER INFORMATION: Ipili VH - CDR3

<400> SEQUENCE: 177

Thr Gly Trp Leu Gly Pro Phe Asp Tyr
1               5

<210> SEQ ID NO 178
<211> LENGTH: 236
<212> TYPE: PRT
<213> ORGANISM: Artificial Sequence
<220> FEATURE:
<223> OTHER INFORMATION: Short Chain 2 (Nivolu VL-hCK)

<400> SEQUENCE: 178

Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Ala Thr
                20                  25                  30

Leu Ser Leu Ser Pro Gly Glu Arg Ala Thr Leu Ser Cys Arg Ala Ser
            35                  40                  45

Gln Ser Val Ser Ser Tyr Leu Ala Trp Tyr Gln Gln Lys Pro Gly Gln
    50                  55                  60

Ala Pro Arg Leu Leu Ile Tyr Asp Ala Ser Asn Arg Ala Thr Gly Ile
65                  70                  75                  80

Pro Ala Arg Phe Ser Gly Ser Gly Ser Gly Thr Asp Phe Thr Leu Thr
                85                  90                  95

Ile Ser Ser Leu Glu Pro Glu Asp Phe Ala Val Tyr Tyr Cys Gln Gln
            100                 105                 110

Ser Ser Asn Trp Pro Arg Thr Phe Gly Gln Gly Thr Lys Val Glu Ile
    115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
    195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 179

```
<211> LENGTH: 107
<212> TYPE: PRT
<213> ORGANISM: Artificial Sequence
<220> FEATURE:
<223> OTHER INFORMATION: Nivolu VL

<400> SEQUENCE: 179

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 180
<211> LENGTH: 11
<212> TYPE: PRT
<213> ORGANISM: Artificial Sequence
<220> FEATURE:
<223> OTHER INFORMATION: Nivolu VL - CDR1

<400> SEQUENCE: 180

Arg Ala Ser Gln Ser Val Ser Ser Tyr Leu Ala
1               5                   10

<210> SEQ ID NO 181
<211> LENGTH: 7
<212> TYPE: PRT
<213> ORGANISM: Artificial Sequence
<220> FEATURE:
<223> OTHER INFORMATION: Nivolu VL - CDR2

<400> SEQUENCE: 181

Asp Ala Ser Asn Arg Ala Thr
1               5

<210> SEQ ID NO 182
<211> LENGTH: 9
<212> TYPE: PRT
<213> ORGANISM: Artificial Sequence
<220> FEATURE:
<223> OTHER INFORMATION: Nivolu VL - CDR3

<400> SEQUENCE: 182

Gln Gln Ser Ser Asn Trp Pro Arg Thr
1               5

<210> SEQ ID NO 183
<211> LENGTH: 684
<212> TYPE: PRT
<213> ORGANISM: Artificial Sequence
<220> FEATURE:
<223> OTHER INFORMATION: Long Chain (Nivolu VL-hCk-Ipili VH-hCg1mut)

<400> SEQUENCE: 183

Met Asp Met Arg Val Pro Ala Gln Leu Leu Gly Leu Leu Leu Leu Trp
```

-continued

```
1               5                   10                  15
Phe Pro Gly Ser Arg Cys Glu Ile Val Leu Thr Gln Ser Pro Ala Thr
                20                  25                  30
Leu Ser Leu Ser Pro Gly Glu Arg Ala Thr Leu Ser Cys Arg Ala Ser
                35                  40                  45
Gln Ser Val Ser Ser Tyr Leu Ala Trp Tyr Gln Gln Lys Pro Gly Gln
        50                  55                  60
Ala Pro Arg Leu Leu Ile Tyr Asp Ala Ser Asn Arg Ala Thr Gly Ile
65                  70                  75                  80
Pro Ala Arg Phe Ser Gly Ser Gly Ser Gly Thr Asp Phe Thr Leu Thr
                85                  90                  95
Ile Ser Ser Leu Glu Pro Glu Asp Phe Ala Val Tyr Tyr Cys Gln Gln
                100                 105                 110
Ser Ser Asn Trp Pro Arg Thr Phe Gly Gln Gly Thr Lys Val Glu Ile
                115                 120                 125
Lys Arg Thr Val Ala Ala Pro Ser Val Phe Ile Phe Pro Pro Ser Asp
        130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
                180                 185                 190
Ser Thr Tyr Ser Leu Ser Ser Thr Leu Thr Leu Ser Lys Ala Asp Tyr
                195                 200                 205
Glu Lys His Lys Val Tyr Ala Cys Glu Val Thr His Gln Gly Leu Ser
        210                 215                 220
Ser Pro Val Thr Lys Ser Phe Asn Arg Gly Glu Cys Gln Val Gln Leu
225                 230                 235                 240
Val Glu Ser Gly Gly Gly Val Val Gln Pro Gly Arg Ser Leu Arg Leu
                245                 250                 255
Ser Cys Ala Ala Ser Gly Phe Thr Phe Ser Ser Tyr Thr Met His Trp
                260                 265                 270
Val Arg Gln Ala Pro Gly Lys Gly Leu Glu Trp Val Thr Phe Ile Ser
                275                 280                 285
Tyr Asp Gly Asn Asn Lys Tyr Tyr Ala Asp Ser Val Lys Gly Arg Phe
        290                 295                 300
Thr Ile Ser Arg Asp Asn Ser Lys Asn Thr Leu Tyr Leu Gln Met Asn
305                 310                 315                 320
Ser Leu Arg Ala Glu Asp Thr Ala Ile Tyr Tyr Cys Ala Arg Thr Gly
                325                 330                 335
Trp Leu Gly Pro Phe Asp Tyr Trp Gly Gln Gly Thr Leu Val Thr Val
                340                 345                 350
Ser Ser Ala Ser Thr Lys Gly Pro Ser Val Phe Pro Leu Ala Pro Ser
                355                 360                 365
Ser Lys Ser Thr Ser Gly Gly Thr Ala Ala Leu Gly Cys Leu Val Lys
        370                 375                 380
Asp Tyr Phe Pro Glu Pro Val Thr Val Ser Trp Asn Ser Gly Ala Leu
385                 390                 395                 400
Thr Ser Gly Val His Thr Phe Pro Ala Val Leu Gln Ser Ser Gly Leu
                405                 410                 415
Tyr Ser Leu Ser Ser Val Val Thr Val Pro Ser Ser Ser Leu Gly Thr
                420                 425                 430
```

```
Gln Thr Tyr Ile Cys Asn Val Asn His Lys Pro Ser Asn Thr Lys Val
            435                 440                 445

Asp Lys Lys Val Glu Pro Lys Ser Cys Asp Lys Thr His Thr Cys Pro
    450                 455                 460

Pro Cys Pro Ala Pro Glu Ala Ala Gly Gly Pro Ser Val Phe Leu Phe
465                 470                 475                 480

Pro Pro Lys Pro Lys Asp Thr Leu Met Ile Ser Arg Thr Pro Glu Val
                485                 490                 495

Thr Cys Val Val Val Asp Val Ser His Glu Asp Pro Glu Val Lys Phe
            500                 505                 510

Asn Trp Tyr Val Asp Gly Val Glu Val His Asn Ala Lys Thr Lys Pro
        515                 520                 525

Arg Glu Glu Gln Tyr Asn Ser Thr Tyr Arg Val Val Ser Val Leu Thr
    530                 535                 540

Val Leu His Gln Asp Trp Leu Asn Gly Lys Glu Tyr Lys Cys Lys Val
545                 550                 555                 560

Ser Asn Lys Ala Leu Pro Ala Pro Ile Glu Lys Thr Ile Ser Lys Ala
                565                 570                 575

Lys Gly Gln Pro Arg Glu Pro Gln Val Tyr Thr Leu Pro Pro Ser Arg
            580                 585                 590

Glu Glu Met Thr Lys Asn Gln Val Ser Leu Thr Cys Leu Val Lys Gly
        595                 600                 605

Phe Tyr Pro Ser Asp Ile Ala Val Glu Trp Glu Ser Asn Gly Gln Pro
    610                 615                 620

Glu Asn Asn Tyr Lys Thr Thr Pro Pro Val Leu Asp Ser Asp Gly Ser
625                 630                 635                 640

Phe Phe Leu Tyr Ser Lys Leu Thr Val Asp Lys Ser Arg Trp Gln Gln
                645                 650                 655

Gly Asn Val Phe Ser Cys Ser Val Met His Glu Ala Leu His Asn His
            660                 665                 670

Tyr Thr Gln Lys Ser Leu Ser Leu Ser Pro Gly Lys
        675                 680

<210> SEQ ID NO 184
<211> LENGTH: 107
<212> TYPE: PRT
<213> ORGANISM: Artificial Sequence
<220> FEATURE:
<223> OTHER INFORMATION: Nivolu VL

<400> SEQUENCE: 184

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105
```

<210> SEQ ID NO 185
<211> LENGTH: 11
<212> TYPE: PRT
<213> ORGANISM: Artificial Sequence
<220> FEATURE:
<223> OTHER INFORMATION: Nivolu VL - CDR1

<400> SEQUENCE: 185

Arg Ala Ser Gln Ser Val Ser Ser Tyr Leu Ala
1               5                   10

<210> SEQ ID NO 186
<211> LENGTH: 7
<212> TYPE: PRT
<213> ORGANISM: Artificial Sequence
<220> FEATURE:
<223> OTHER INFORMATION: Nivolu VL - CDR2

<400> SEQUENCE: 186

Asp Ala Ser Asn Arg Ala Thr
1               5

<210> SEQ ID NO 187
<211> LENGTH: 9
<212> TYPE: PRT
<213> ORGANISM: Artificial Sequence
<220> FEATURE:
<223> OTHER INFORMATION: Nivolu VL - CDR3

<400> SEQUENCE: 187

Gln Gln Ser Ser Asn Trp Pro Arg Thr
1               5

<210> SEQ ID NO 188
<211> LENGTH: 118
<212> TYPE: PRT
<213> ORGANISM: Artificial Sequence
<220> FEATURE:
<223> OTHER INFORMATION: Ipili VH

<400> SEQUENCE: 188

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115

<210> SEQ ID NO 189
<211> LENGTH: 5
<212> TYPE: PRT
<213> ORGANISM: Artificial Sequence
<220> FEATURE:
<223> OTHER INFORMATION: Ipili VH - CDR1

<400> SEQUENCE: 189

Ser Tyr Thr Met His
1               5

<210> SEQ ID NO 190
<211> LENGTH: 17
<212> TYPE: PRT
<213> ORGANISM: Artificial Sequence
<220> FEATURE:
<223> OTHER INFORMATION: Ipili VH - CDR2

<400> SEQUENCE: 190

Phe Ile Ser Tyr Asp Gly Asn Asn Lys Tyr Tyr Ala Asp Ser Val Lys
1               5                   10                  15

Gly

<210> SEQ ID NO 191
<211> LENGTH: 9
<212> TYPE: PRT
<213> ORGANISM: Artificial Sequence
<220> FEATURE:
<223> OTHER INFORMATION: Ipili VH - CDR3

<400> SEQUENCE: 191

Thr Gly Trp Leu Gly Pro Phe Asp Tyr
1               5

<210> SEQ ID NO 192
<211> LENGTH: 232
<212> TYPE: PRT
<213> ORGANISM: Artificial Sequence
<220> FEATURE:
<223> OTHER INFORMATION: Short Chain 1 (Nivolu VH-IgG4-CH1)

<400> SEQUENCE: 192

Met Glu Phe Gly Leu Ser Trp Leu Phe Leu Val Ala Ile Leu Lys Gly
1               5                   10                  15

Val Gln Cys Gln Val Gln Leu Val Glu Ser Gly Gly Gly Val Val Gln
            20                  25                  30

Pro Gly Arg Ser Leu Arg Leu Asp Cys Lys Ala Ser Gly Ile Thr Phe
        35                  40                  45

Ser Asn Ser Gly Met His Trp Val Arg Gln Ala Pro Gly Lys Gly Leu
    50                  55                  60

Glu Trp Val Ala Val Ile Trp Tyr Asp Gly Ser Lys Arg Tyr Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Arg Ala Glu Asp Thr Ala Val
            100                 105                 110

Tyr Tyr Cys Ala Thr Asn Asp Asp Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

```
Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser
225                 230

<210> SEQ ID NO 193
<211> LENGTH: 113
<212> TYPE: PRT
<213> ORGANISM: Artificial Sequence
<220> FEATURE:
<223> OTHER INFORMATION: Nivolu VH

<400> SEQUENCE: 193

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 194
<211> LENGTH: 5
<212> TYPE: PRT
<213> ORGANISM: Artificial Sequence
<220> FEATURE:
<223> OTHER INFORMATION: Nivolu VH - CDR1

<400> SEQUENCE: 194

Asn Ser Gly Met His
1               5

<210> SEQ ID NO 195
<211> LENGTH: 17
<212> TYPE: PRT
<213> ORGANISM: Artificial Sequence
<220> FEATURE:
<223> OTHER INFORMATION: Nivolu VH - CDR2

<400> SEQUENCE: 195

Val Ile Trp Tyr Asp Gly Ser Lys Arg Tyr Tyr Ala Asp Ser Val Lys
1               5                   10                  15

Gly

<210> SEQ ID NO 196
<211> LENGTH: 4
<212> TYPE: PRT
<213> ORGANISM: Artificial Sequence
<220> FEATURE:
```

<223> OTHER INFORMATION: Nivolu VH - CDR3

<400> SEQUENCE: 196

Asn Asp Asp Tyr
1

<210> SEQ ID NO 197
<211> LENGTH: 237
<212> TYPE: PRT
<213> ORGANISM: Artificial Sequence
<220> FEATURE:
<223> OTHER INFORMATION: Short Chain 2 (Ipili VL-hCK)

<400> SEQUENCE: 197

Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Gly Thr
            20                  25                  30

Leu Ser Leu Ser Pro Gly Glu Arg Ala Thr Leu Ser Cys Arg Ala Ser
        35                  40                  45

Gln Ser Val Gly Ser Ser Tyr Leu Ala Trp Tyr Gln Gln Lys Pro Gly
    50                  55                  60

Gln Ala Pro Arg Leu Leu Ile Tyr Gly Ala Phe Ser Arg Ala Thr Gly
65                  70                  75                  80

Ile Pro Asp Arg Phe Ser Gly Ser Gly Ser Gly Thr Asp Phe Thr Leu
                85                  90                  95

Thr Ile Ser Arg Leu Glu Pro Glu Asp Phe Ala Val Tyr Tyr Cys Gln
            100                 105                 110

Gln Tyr Gly Ser Ser Pro Trp Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 198
<211> LENGTH: 108
<212> TYPE: PRT
<213> ORGANISM: Artificial Sequence
<220> FEATURE:
<223> OTHER INFORMATION: Ipili VL

<400> SEQUENCE: 198

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu

```
              35                  40                  45
Ile Tyr Gly Ala Phe Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys
            100                 105

<210> SEQ ID NO 199
<211> LENGTH: 12
<212> TYPE: PRT
<213> ORGANISM: Artificial Sequence
<220> FEATURE:
<223> OTHER INFORMATION: Ipili VL - CDR1

<400> SEQUENCE: 199

Arg Ala Ser Gln Ser Val Gly Ser Ser Tyr Leu Ala
 1               5                  10

<210> SEQ ID NO 200
<211> LENGTH: 7
<212> TYPE: PRT
<213> ORGANISM: Artificial Sequence
<220> FEATURE:
<223> OTHER INFORMATION: Ipili VL - CDR2

<400> SEQUENCE: 200

Gly Ala Phe Ser Arg Ala Thr
 1               5

<210> SEQ ID NO 201
<211> LENGTH: 9
<212> TYPE: PRT
<213> ORGANISM: Artificial Sequence
<220> FEATURE:
<223> OTHER INFORMATION: Ipili VL - CDR3

<400> SEQUENCE: 201

Gln Gln Tyr Gly Ser Ser Pro Trp Thr
 1               5

<210> SEQ ID NO 202
<211> LENGTH: 689
<212> TYPE: PRT
<213> ORGANISM: Artificial Sequence
<220> FEATURE:
<223> OTHER INFORMATION: Long Chain (Pani VL-hCk-1B12VH-hCg1)

<400> SEQUENCE: 202

Met Asp Met Arg Val Pro Ala Gln Leu Leu Gly Leu Leu Leu Leu Trp
 1               5                  10                  15

Phe Pro Gly Ser Arg Cys Asp Ile Gln Met Thr Gln Ser Pro Ser Ser
                 20                  25                  30

Leu Ser Ala Ser Val Gly Asp Arg Val Thr Ile Thr Cys Gln Ala Ser
             35                  40                  45

Gln Asp Ile Ser Asn Tyr Leu Asn Trp Tyr Gln Gln Lys Pro Gly Lys
         50                  55                  60

Ala Pro Lys Leu Leu Ile Tyr Asp Ala Ser Asn Leu Glu Thr Gly Val
 65                  70                  75                  80

Pro Ser Arg Phe Ser Gly Ser Gly Ser Gly Thr Asp Phe Thr Phe Thr
```

```
                85                  90                  95
Ile Ser Ser Leu Gln Pro Glu Asp Ile Ala Thr Tyr Phe Cys Gln His
            100                 105                 110
Phe Asp His Leu Pro Leu Ala Phe Gly Gly Thr Lys Val Glu Ile
            115                 120                 125
Lys Arg Thr Val Ala Ala Pro Ser Val Phe Ile Phe Pro Pro Ser Asp
            130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
                180                 185                 190
Ser Thr Tyr Ser Leu Ser Ser Thr Leu Thr Leu Ser Lys Ala Asp Tyr
                195                 200                 205
Glu Lys His Lys Val Tyr Ala Cys Glu Val Thr His Gln Gly Leu Ser
            210                 215                 220
Ser Pro Val Thr Lys Ser Phe Asn Arg Gly Glu Cys Gln Val Gln Leu
225                 230                 235                 240
Val Gln Ser Gly Ala Glu Val Lys Lys Pro Gly Ser Ser Val Lys Val
                245                 250                 255
Ser Cys Lys Thr Ser Gly Asp Thr Phe Ser Ser Tyr Ala Ile Ser Trp
            260                 265                 270
Val Arg Gln Ala Pro Gly Gln Gly Leu Glu Trp Met Gly Gly Ile Ile
            275                 280                 285
Pro Ile Phe Gly Arg Ala His Tyr Ala Gln Lys Phe Gln Gly Arg Val
    290                 295                 300
Thr Ile Thr Ala Asp Glu Ser Thr Ser Thr Ala Tyr Met Glu Leu Ser
305                 310                 315                 320
Ser Leu Arg Ser Glu Asp Thr Ala Val Tyr Phe Cys Ala Arg Lys Phe
                325                 330                 335
His Phe Val Ser Gly Ser Pro Phe Gly Met Asp Val Trp Gly Gln Gly
            340                 345                 350
Thr Thr Val Thr Val Ser Ser Ala Ser Thr Lys Gly Pro Ser Val Phe
            355                 360                 365
Pro Leu Ala Pro Ser Ser Lys Ser Thr Ser Gly Gly Thr Ala Ala Leu
    370                 375                 380
Gly Cys Leu Val Lys Asp Tyr Phe Pro Glu Pro Val Thr Val Ser Trp
385                 390                 395                 400
Asn Ser Gly Ala Leu Thr Ser Gly Val His Thr Phe Pro Ala Val Leu
                405                 410                 415
Gln Ser Ser Gly Leu Tyr Ser Leu Ser Ser Val Val Thr Val Pro Ser
            420                 425                 430
Ser Ser Leu Gly Thr Gln Thr Tyr Ile Cys Asn Val Asn His Lys Pro
            435                 440                 445
Ser Asn Thr Lys Val Asp Lys Lys Val Glu Pro Lys Ser Cys Asp Lys
    450                 455                 460
Thr His Thr Cys Pro Pro Cys Pro Ala Pro Glu Leu Leu Gly Gly Pro
465                 470                 475                 480
Ser Val Phe Leu Phe Pro Pro Lys Pro Lys Asp Thr Leu Met Ile Ser
                485                 490                 495
Arg Thr Pro Glu Val Thr Cys Val Val Val Asp Val Ser His Glu Asp
            500                 505                 510
```

```
Pro Glu Val Lys Phe Asn Trp Tyr Val Asp Gly Val Glu Val His Asn
            515                 520                 525

Ala Lys Thr Lys Pro Arg Glu Glu Gln Tyr Asn Ser Thr Tyr Arg Val
        530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Pro Ala Pro Ile Glu Lys
                565                 570                 575

Thr Ile Ser Lys Ala Lys Gly Gln Pro Arg Glu Pro Gln Val Tyr Thr
            580                 585                 590

Leu Pro Pro Ser Arg Glu Glu Met Thr Lys Asn Gln Val Ser Leu Thr
        595                 600                 605

Cys Leu Val Lys Gly Phe Tyr Pro Ser Asp Ile Ala Val Glu Trp Glu
610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
            660                 665                 670

Ala Leu His Asn His Tyr Thr Gln Lys Ser Leu Ser Leu Ser Pro Gly
        675                 680                 685

Lys

<210> SEQ ID NO 203
<211> LENGTH: 107
<212> TYPE: PRT
<213> ORGANISM: Artificial Sequence
<220> FEATURE:
<223> OTHER INFORMATION: Pani VL

<400> SEQUENCE: 203

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105

<210> SEQ ID NO 204
<211> LENGTH: 11
<212> TYPE: PRT
<213> ORGANISM: Artificial Sequence
<220> FEATURE:
<223> OTHER INFORMATION: Pani VL - CDR1

<400> SEQUENCE: 204

Gln Ala Ser Gln Asp Ile Ser Asn Tyr Leu Asn
1               5                   10
```

<210> SEQ ID NO 205
<211> LENGTH: 7
<212> TYPE: PRT
<213> ORGANISM: Artificial Sequence
<220> FEATURE:
<223> OTHER INFORMATION: Pani VL - CDR2

<400> SEQUENCE: 205

Asp Ala Ser Asn Leu Glu Thr
1               5

<210> SEQ ID NO 206
<211> LENGTH: 9
<212> TYPE: PRT
<213> ORGANISM: Artificial Sequence
<220> FEATURE:
<223> OTHER INFORMATION: Pani VL - CDR3

<400> SEQUENCE: 206

Gln His Phe Asp His Leu Pro Leu Ala
1               5

<210> SEQ ID NO 207
<211> LENGTH: 123
<212> TYPE: PRT
<213> ORGANISM: Artificial Sequence
<220> FEATURE:
<223> OTHER INFORMATION: 1B12VH

<400> SEQUENCE: 207

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Arg Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120

<210> SEQ ID NO 208
<211> LENGTH: 5
<212> TYPE: PRT
<213> ORGANISM: Artificial Sequence
<220> FEATURE:
<223> OTHER INFORMATION: 1B12VH - CDR1

<400> SEQUENCE: 208

Ser Tyr Ala Ile Ser
1               5

<210> SEQ ID NO 209
<211> LENGTH: 17
<212> TYPE: PRT
<213> ORGANISM: Artificial Sequence

```
<220> FEATURE:
<223> OTHER INFORMATION: 1B12VH - CDR2

<400> SEQUENCE: 209

Gly Ile Ile Pro Ile Phe Gly Arg Ala His Tyr Ala Gln Lys Phe Gln
1               5                   10                  15

Gly

<210> SEQ ID NO 210
<211> LENGTH: 14
<212> TYPE: PRT
<213> ORGANISM: Artificial Sequence
<220> FEATURE:
<223> OTHER INFORMATION: 1B12VH - CDR3

<400> SEQUENCE: 210

Lys Phe His Phe Val Ser Gly Ser Pro Phe Gly Met Asp Val
1               5                   10

<210> SEQ ID NO 211
<211> LENGTH: 241
<212> TYPE: PRT
<213> ORGANISM: Artificial Sequence
<220> FEATURE:
<223> OTHER INFORMATION: Short Chain 1 (Pani VH-CH1h)

<400> SEQUENCE: 211

Met Glu Phe Gly Leu Ser Trp Leu Phe Leu Val Ala Ile Leu Lys Gly
1               5                   10                  15

Val Gln Cys Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Val
        35                  40                  45

Ser Ser Gly Asp Tyr Tyr Trp Thr Trp Ile Arg Gln Ser Pro Gly Lys
    50                  55                  60

Gly Leu Glu Trp Ile Gly His Ile Tyr Tyr Ser Gly Asn Thr Asn Tyr
65                  70                  75                  80

Asn Pro Ser Leu Lys Ser Arg Leu Thr Ile Ser Ile Asp Thr Ser Lys
                85                  90                  95

Thr Gln Phe Ser Leu Lys Leu Ser Ser Val Thr Ala Ala Asp Thr Ala
            100                 105                 110

Ile Tyr Tyr Cys Val Arg Asp Arg Val Thr Gly Ala Phe Asp Ile Trp
        115                 120                 125

Gly Gln Gly Thr Met Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys
```

<210> SEQ ID NO 212
<211> LENGTH: 119
<212> TYPE: PRT
<213> ORGANISM: Artificial Sequence
<220> FEATURE:
<223> OTHER INFORMATION: Pani VH

<400> SEQUENCE: 212

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser
        115

<210> SEQ ID NO 213
<211> LENGTH: 7
<212> TYPE: PRT
<213> ORGANISM: Artificial Sequence
<220> FEATURE:
<223> OTHER INFORMATION: Pani VH - CDR1

<400> SEQUENCE: 213

Ser Gly Asp Tyr Tyr Trp Thr
1               5

<210> SEQ ID NO 214
<211> LENGTH: 16
<212> TYPE: PRT
<213> ORGANISM: Artificial Sequence
<220> FEATURE:
<223> OTHER INFORMATION: Pani VH - CDR2

<400> SEQUENCE: 214

His Ile Tyr Tyr Ser Gly Asn Thr Asn Tyr Asn Pro Ser Leu Lys Ser
1               5                   10                  15

<210> SEQ ID NO 215
<211> LENGTH: 9
<212> TYPE: PRT
<213> ORGANISM: Artificial Sequence
<220> FEATURE:
<223> OTHER INFORMATION: Pani VH - CDR3

<400> SEQUENCE: 215

Asp Arg Val Thr Gly Ala Phe Asp Ile
1               5

<210> SEQ ID NO 216
<211> LENGTH: 235
<212> TYPE: PRT
<213> ORGANISM: Artificial Sequence

```
<220> FEATURE:
<223> OTHER INFORMATION: Short Chain 2 (1B12 VL-hCk)

<400> SEQUENCE: 216

Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Ala Thr
                20                  25                  30

Leu Ser Leu Ser Pro Gly Glu Arg Ala Thr Leu Ser Cys Arg Ala Ser
            35                  40                  45

Gln Ser Val Ser Ser Tyr Leu Ala Trp Tyr Gln Gln Lys Pro Gly Gln
50                  55                  60

Ala Pro Arg Leu Leu Ile Tyr Asp Ala Ser Asn Arg Ala Thr Gly Ile
65                  70                  75                  80

Pro Ala Arg Phe Ser Gly Ser Gly Ser Gly Thr Asp Phe Thr Leu Thr
                85                  90                  95

Ile Ser Ser Leu Glu Pro Glu Asp Phe Ala Val Tyr Tyr Cys Gln Gln
            100                 105                 110

Arg Ser Asn Trp Pro Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 217
<211> LENGTH: 106
<212> TYPE: PRT
<213> ORGANISM: Artificial Sequence
<220> FEATURE:
<223> OTHER INFORMATION: 1B12 VL

<400> SEQUENCE: 217

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
```

<210> SEQ ID NO 218
<211> LENGTH: 11
<212> TYPE: PRT
<213> ORGANISM: Artificial Sequence
<220> FEATURE:
<223> OTHER INFORMATION: 1B12 VL - CDR1

<400> SEQUENCE: 218

Arg Ala Ser Gln Ser Val Ser Ser Tyr Leu Ala
1               5                   10

<210> SEQ ID NO 219
<211> LENGTH: 7
<212> TYPE: PRT
<213> ORGANISM: Artificial Sequence
<220> FEATURE:
<223> OTHER INFORMATION: 1B12 VL - CDR2

<400> SEQUENCE: 219

Asp Ala Ser Asn Arg Ala Thr
1               5

<210> SEQ ID NO 220
<211> LENGTH: 8
<212> TYPE: PRT
<213> ORGANISM: Artificial Sequence
<220> FEATURE:
<223> OTHER INFORMATION: 1B12 VL - CDR3

<400> SEQUENCE: 220

Gln Gln Arg Ser Asn Trp Pro Thr
1               5

<210> SEQ ID NO 221
<211> LENGTH: 684
<212> TYPE: PRT
<213> ORGANISM: Artificial Sequence
<220> FEATURE:
<223> OTHER INFORMATION: Long Chain (Pani VL-hCk-10A5VH-hCg1)

<400> SEQUENCE: 221

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Gln Ala Ser
        35                  40                  45

Gln Asp Ile Ser Asn Tyr Leu Asn Trp Tyr Gln Gln Lys Pro Gly Lys
    50                  55                  60

Ala Pro Lys Leu Leu Ile Tyr Asp Ala Ser Asn Leu Glu Thr Gly Val
65                  70                  75                  80

Pro Ser Arg Phe Ser Gly Ser Gly Ser Gly Thr Asp Phe Thr Phe Thr
            85                  90                  95

Ile Ser Ser Leu Gln Pro Glu Asp Ile Ala Thr Tyr Phe Cys Gln His
            100                 105                 110

Phe Asp His Leu Pro Leu Ala Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn

```
                145                 150                 155                 160
        Phe Tyr Pro Arg Glu Ala Lys Val Gln Trp Lys Val Asp Asn Ala Leu
                        165                 170                 175
        Gln Ser Gly Asn Ser Gln Glu Ser Val Thr Glu Gln Asp Ser Lys Asp
                        180                 185                 190
        Ser Thr Tyr Ser Leu Ser Ser Thr Leu Thr Leu Ser Lys Ala Asp Tyr
                        195                 200                 205
        Glu Lys His Lys Val Tyr Ala Cys Glu Val Thr His Gln Gly Leu Ser
                        210                 215                 220
        Ser Pro Val Thr Lys Ser Phe Asn Arg Gly Glu Cys Gln Val Gln Leu
        225                 230                 235                 240
        Val Gln Ser Gly Ala Glu Val Lys Lys Pro Gly Ala Ser Val Lys Val
                        245                 250                 255
        Ser Cys Lys Ala Ser Gly Tyr Thr Phe Thr Ser Tyr Asp Val His Trp
                        260                 265                 270
        Val Arg Gln Ala Pro Gly Gln Arg Leu Glu Trp Met Gly Trp Leu His
                        275                 280                 285
        Ala Asp Thr Gly Ile Thr Lys Phe Ser Gln Lys Phe Gln Gly Arg Val
                        290                 295                 300
        Thr Ile Thr Arg Asp Thr Ser Ala Ser Thr Ala Tyr Met Glu Leu Ser
        305                 310                 315                 320
        Ser Leu Arg Ser Glu Asp Thr Ala Val Tyr Tyr Cys Ala Arg Glu Arg
                        325                 330                 335
        Ile Gln Leu Trp Phe Asp Tyr Trp Gly Gln Gly Thr Leu Val Thr Val
                        340                 345                 350
        Ser Ser Ala Ser Thr Lys Gly Pro Ser Val Phe Pro Leu Ala Pro Ser
                        355                 360                 365
        Ser Lys Ser Thr Ser Gly Gly Thr Ala Ala Leu Gly Cys Leu Val Lys
                        370                 375                 380
        Asp Tyr Phe Pro Glu Pro Val Thr Val Ser Trp Asn Ser Gly Ala Leu
        385                 390                 395                 400
        Thr Ser Gly Val His Thr Phe Pro Ala Val Leu Gln Ser Ser Gly Leu
                        405                 410                 415
        Tyr Ser Leu Ser Ser Val Val Thr Val Pro Ser Ser Ser Leu Gly Thr
                        420                 425                 430
        Gln Thr Tyr Ile Cys Asn Val Asn His Lys Pro Ser Asn Thr Lys Val
                        435                 440                 445
        Asp Lys Lys Val Glu Pro Lys Ser Cys Asp Lys Thr His Thr Cys Pro
        450                 455                 460
        Pro Cys Pro Ala Pro Glu Leu Leu Gly Gly Pro Ser Val Phe Leu Phe
        465                 470                 475                 480
        Pro Pro Lys Pro Lys Asp Thr Leu Met Ile Ser Arg Thr Pro Glu Val
                        485                 490                 495
        Thr Cys Val Val Val Asp Val Ser His Glu Asp Pro Glu Val Lys Phe
                        500                 505                 510
        Asn Trp Tyr Val Asp Gly Val Glu Val His Asn Ala Lys Thr Lys Pro
                        515                 520                 525
        Arg Glu Glu Gln Tyr Asn Ser Thr Tyr Arg Val Val Ser Val Leu Thr
                        530                 535                 540
        Val Leu His Gln Asp Trp Leu Asn Gly Lys Glu Tyr Lys Cys Lys Val
        545                 550                 555                 560
        Ser Asn Lys Ala Leu Pro Ala Pro Ile Glu Lys Thr Ile Ser Lys Ala
                        565                 570                 575
```

```
Lys Gly Gln Pro Arg Glu Pro Gln Val Tyr Thr Leu Pro Pro Ser Arg
            580                 585                 590

Glu Glu Met Thr Lys Asn Gln Val Ser Leu Thr Cys Leu Val Lys Gly
        595                 600                 605

Phe Tyr Pro Ser Asp Ile Ala Val Glu Trp Glu Ser Asn Gly Gln Pro
    610                 615                 620

Glu Asn Asn Tyr Lys Thr Thr Pro Pro Val Leu Asp Ser Asp Gly Ser
625                 630                 635                 640

Phe Phe Leu Tyr Ser Lys Leu Thr Val Asp Lys Ser Arg Trp Gln Gln
                645                 650                 655

Gly Asn Val Phe Ser Cys Ser Val Met His Glu Ala Leu His Asn His
            660                 665                 670

Tyr Thr Gln Lys Ser Leu Ser Leu Ser Pro Gly Lys
            675                 680

<210> SEQ ID NO 222
<211> LENGTH: 107
<212> TYPE: PRT
<213> ORGANISM: Artificial Sequence
<220> FEATURE:
<223> OTHER INFORMATION: Pani VL

<400> SEQUENCE: 222

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105

<210> SEQ ID NO 223
<211> LENGTH: 11
<212> TYPE: PRT
<213> ORGANISM: Artificial Sequence
<220> FEATURE:
<223> OTHER INFORMATION: Pani VL - CDR1

<400> SEQUENCE: 223

Gln Ala Ser Gln Asp Ile Ser Asn Tyr Leu Asn
1               5                   10

<210> SEQ ID NO 224
<211> LENGTH: 7
<212> TYPE: PRT
<213> ORGANISM: Artificial Sequence
<220> FEATURE:
<223> OTHER INFORMATION: Pani VL - CDR2

<400> SEQUENCE: 224

Asp Ala Ser Asn Leu Glu Thr
1               5
```

```
<210> SEQ ID NO 225
<211> LENGTH: 9
<212> TYPE: PRT
<213> ORGANISM: Artificial Sequence
<220> FEATURE:
<223> OTHER INFORMATION: Pani VL - CDR3

<400> SEQUENCE: 225

Gln His Phe Asp His Leu Pro Leu Ala
1               5

<210> SEQ ID NO 226
<211> LENGTH: 118
<212> TYPE: PRT
<213> ORGANISM: Artificial Sequence
<220> FEATURE:
<223> OTHER INFORMATION: 10A5VH

<400> SEQUENCE: 226

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Val His Trp Val Arg Gln Ala Pro Gly Gln Arg Leu Glu Trp Met
        35                  40                  45

Gly Trp Leu His Ala Asp Thr Gly Ile Thr Lys Phe Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Ile Gln Leu Trp Phe Asp Tyr Trp Gly Gln Gly Thr
            100                 105                 110

Leu Val Thr Val Ser Ser
        115

<210> SEQ ID NO 227
<211> LENGTH: 5
<212> TYPE: PRT
<213> ORGANISM: Artificial Sequence
<220> FEATURE:
<223> OTHER INFORMATION: 10A5VH - CDR1

<400> SEQUENCE: 227

Ser Tyr Asp Val His
1               5

<210> SEQ ID NO 228
<211> LENGTH: 17
<212> TYPE: PRT
<213> ORGANISM: Artificial Sequence
<220> FEATURE:
<223> OTHER INFORMATION: 10A5VH - CDR2

<400> SEQUENCE: 228

Trp Leu His Ala Asp Thr Gly Ile Thr Lys Phe Ser Gln Lys Phe Gln
1               5                   10                  15

Gly

<210> SEQ ID NO 229
<211> LENGTH: 9
<212> TYPE: PRT
```

<213> ORGANISM: Artificial Sequence
<220> FEATURE:
<223> OTHER INFORMATION: 10A5VH - CDR3

<400> SEQUENCE: 229

Glu Arg Ile Gln Leu Trp Phe Asp Tyr
1               5

<210> SEQ ID NO 230
<211> LENGTH: 241
<212> TYPE: PRT
<213> ORGANISM: Artificial Sequence
<220> FEATURE:
<223> OTHER INFORMATION: Short Chain 1 (Pani VH-CH1h)

<400> SEQUENCE: 230

Met Glu Phe Gly Leu Ser Trp Leu Phe Leu Val Ala Ile Leu Lys Gly
1               5                   10                  15

Val Gln Cys Gln Val Gln Leu Gln Glu Ser Gly Pro Gly Leu Val Lys
                20                  25                  30

Pro Ser Glu Thr Leu Ser Leu Thr Cys Thr Val Ser Gly Gly Ser Val
            35                  40                  45

Ser Ser Gly Asp Tyr Tyr Trp Thr Trp Ile Arg Gln Ser Pro Gly Lys
    50                  55                  60

Gly Leu Glu Trp Ile Gly His Ile Tyr Tyr Ser Gly Asn Thr Asn Tyr
65                  70                  75                  80

Asn Pro Ser Leu Lys Ser Arg Leu Thr Ile Ser Ile Asp Thr Ser Lys
                85                  90                  95

Thr Gln Phe Ser Leu Lys Leu Ser Ser Val Thr Ala Ala Asp Thr Ala
            100                 105                 110

Ile Tyr Tyr Cys Val Arg Asp Arg Val Thr Gly Ala Phe Asp Ile Trp
        115                 120                 125

Gly Gln Gly Thr Met Val Thr Val Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys

<210> SEQ ID NO 231
<211> LENGTH: 119
<212> TYPE: PRT
<213> ORGANISM: Artificial Sequence
<220> FEATURE:
<223> OTHER INFORMATION: Pani VH

<400> SEQUENCE: 231

Gln Val Gln Leu Gln Glu Ser Gly Pro Gly Leu Val Lys Pro Ser Glu
1               5                   10                  15

```
Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
            35                  40                  45

Trp Ile Gly His Ile Tyr Tyr Ser Gly Asn Thr Asn Tyr Asn Pro Ser
        50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser
            115

<210> SEQ ID NO 232
<211> LENGTH: 7
<212> TYPE: PRT
<213> ORGANISM: Artificial Sequence
<220> FEATURE:
<223> OTHER INFORMATION: Pani VH - CDR1

<400> SEQUENCE: 232

Ser Gly Asp Tyr Tyr Trp Thr
1               5

<210> SEQ ID NO 233
<211> LENGTH: 16
<212> TYPE: PRT
<213> ORGANISM: Artificial Sequence
<220> FEATURE:
<223> OTHER INFORMATION: Pani VH - CDR2

<400> SEQUENCE: 233

His Ile Tyr Tyr Ser Gly Asn Thr Asn Tyr Asn Pro Ser Leu Lys Ser
1               5                   10                  15

<210> SEQ ID NO 234
<211> LENGTH: 9
<212> TYPE: PRT
<213> ORGANISM: Artificial Sequence
<220> FEATURE:
<223> OTHER INFORMATION: Pani VH - CDR3

<400> SEQUENCE: 234

Asp Arg Val Thr Gly Ala Phe Asp Ile
1               5

<210> SEQ ID NO 235
<211> LENGTH: 236
<212> TYPE: PRT
<213> ORGANISM: Artificial Sequence
<220> FEATURE:
<223> OTHER INFORMATION: Short Chain 2 (10A5 VL-hCk)

<400> SEQUENCE: 235

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
            35                  40                  45
```

```
Gln Gly Ile Ser Ser Trp Leu Ala Trp Tyr Gln Gln Lys Pro Glu Lys
            50                  55                  60
Ala Pro Lys Ser Leu Ile Tyr Ala Ala Ser Ser Leu Gln Ser Gly Val
 65                  70                  75                  80
Pro Ser Arg Phe Ser Gly Ser Gly Ser Gly Thr Asp Phe Thr Leu Thr
                85                  90                  95
Ile Ser Ser Leu Gln Pro Glu Asp Phe Ala Thr Tyr Tyr Cys Gln Gln
               100                 105                 110
Tyr Asn Ser Tyr Pro Tyr Thr Phe Gly Gln Gly Thr Lys Leu Glu Ile
               115                 120                 125
Lys Arg Thr Val Ala Ala Pro Ser Val Phe Ile Phe Pro Pro Ser Asp
130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
               180                 185                 190
Ser Thr Tyr Ser Leu Ser Ser Thr Leu Thr Leu Ser Lys Ala Asp Tyr
               195                 200                 205
Glu Lys His Lys Val Tyr Ala Cys Glu Val Thr His Gln Gly Leu Ser
210                 215                 220
Ser Pro Val Thr Lys Ser Phe Asn Arg Gly Glu Cys
225                 230                 235

<210> SEQ ID NO 236
<211> LENGTH: 107
<212> TYPE: PRT
<213> ORGANISM: Artificial Sequence
<220> FEATURE:
<223> OTHER INFORMATION: 10A5 VL

<400> SEQUENCE: 236

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Ser Ser Trp
                20                  25                  30
Leu Ala Trp Tyr Gln Gln Lys Pro Glu Lys Ala Pro Lys Ser Leu Ile
            35                  40                  45
Tyr Ala Ala Ser Ser Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Tyr Asn Ser Tyr Pro Tyr
                85                  90                  95
Thr Phe Gly Gln Gly Thr Lys Leu Glu Ile Lys
               100                 105

<210> SEQ ID NO 237
<211> LENGTH: 11
<212> TYPE: PRT
<213> ORGANISM: Artificial Sequence
<220> FEATURE:
<223> OTHER INFORMATION: 10A5 VL - CDR1

<400> SEQUENCE: 237

Arg Ala Ser Gln Gly Ile Ser Ser Trp Leu Ala
1               5                   10
```

<210> SEQ ID NO 238
<211> LENGTH: 7
<212> TYPE: PRT
<213> ORGANISM: Artificial Sequence
<220> FEATURE:
<223> OTHER INFORMATION: 10A5 VL - CDR2

<400> SEQUENCE: 238

Ala Ala Ser Ser Leu Gln Ser
1               5

<210> SEQ ID NO 239
<211> LENGTH: 9
<212> TYPE: PRT
<213> ORGANISM: Artificial Sequence
<220> FEATURE:
<223> OTHER INFORMATION: 10A5 VL - CDR3

<400> SEQUENCE: 239

Gln Gln Tyr Asn Ser Tyr Pro Tyr Thr
1               5

<210> SEQ ID NO 240
<211> LENGTH: 685
<212> TYPE: PRT
<213> ORGANISM: Artificial Sequence
<220> FEATURE:
<223> OTHER INFORMATION: Long Chain (h1332 VL-hCk-Pani VH-hCg1)

<400> SEQUENCE: 240

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Asn Thr Trp Leu Ala Trp Tyr Gln Gln Lys Pro Gly Lys
    50                  55                  60

Ala Pro Lys Leu Leu Ile Tyr Ala Ala Ser Ser Leu Lys Ser Gly Val
65                  70                  75                  80

Pro Ser Arg Phe Ser Gly Ser Gly Ser Gly Thr Asp Phe Thr Leu Thr
            85                  90                  95

Ile Ser Ser Leu Gln Pro Glu Asp Phe Ala Thr Tyr Tyr Cys Gln Gln
        100                 105                 110

Ala Asn Ser Phe Pro Leu Thr Phe Gly Gly Gly Thr Lys Val Glu Ile
    115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
        180                 185                 190

Ser Thr Tyr Ser Leu Ser Ser Thr Leu Thr Leu Ser Lys Ala Asp Tyr
    195                 200                 205

Glu Lys His Lys Val Tyr Ala Cys Glu Val Thr His Gln Gly Leu Ser
210                 215                 220

```
Ser Pro Val Thr Lys Ser Phe Asn Arg Gly Glu Cys Gln Val Gln Leu
225                 230                 235                 240

Gln Glu Ser Gly Pro Gly Leu Val Lys Pro Ser Glu Thr Leu Ser Leu
            245                 250                 255

Thr Cys Thr Val Ser Gly Gly Ser Val Ser Ser Gly Asp Tyr Tyr Trp
                260                 265                 270

Thr Trp Ile Arg Gln Ser Pro Gly Lys Gly Leu Glu Trp Ile Gly His
        275                 280                 285

Ile Tyr Tyr Ser Gly Asn Thr Asn Tyr Asn Pro Ser Leu Lys Ser Arg
    290                 295                 300

Leu Thr Ile Ser Ile Asp Thr Ser Lys Thr Gln Phe Ser Leu Lys Leu
305                 310                 315                 320

Ser Ser Val Thr Ala Ala Asp Thr Ala Ile Tyr Tyr Cys Val Arg Asp
                325                 330                 335

Arg Val Thr Gly Ala Phe Asp Ile Trp Gly Gln Gly Thr Met Val Thr
                340                 345                 350

Val Ser Ser Ala Ser Thr Lys Gly Pro Ser Val Phe Pro Leu Ala Pro
                355                 360                 365

Ser Ser Lys Ser Thr Ser Gly Gly Thr Ala Ala Leu Gly Cys Leu Val
370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
                405                 410                 415

Leu Tyr Ser Leu Ser Ser Val Val Thr Val Pro Ser Ser Ser Leu Gly
            420                 425                 430

Thr Gln Thr Tyr Ile Cys Asn Val Asn His Lys Pro Ser Asn Thr Lys
            435                 440                 445

Val Asp Lys Lys Val Glu Pro Lys Ser Cys Asp Lys Thr His Thr Cys
450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                485                 490                 495

Val Thr Cys Val Val Val Asp Val Ser His Glu Asp Pro Glu Val Lys
                500                 505                 510

Phe Asn Trp Tyr Val Asp Gly Val Glu Val His Asn Ala Lys Thr Lys
            515                 520                 525

Pro Arg Glu Glu Gln Tyr Asn Ser Thr Tyr Arg Val Val Ser Val Leu
            530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                565                 570                 575

Ala Lys Gly Gln Pro Arg Glu Pro Gln Val Tyr Thr Leu Pro Pro Ser
            580                 585                 590

Arg Glu Glu Met Thr Lys Asn Gln Val Ser Leu Thr Cys Leu Val Lys
            595                 600                 605

Gly Phe Tyr Pro Ser Asp Ile Ala Val Glu Trp Glu Ser Asn Gly Gln
            610                 615                 620

Pro Glu Asn Asn Tyr Lys Thr Thr Pro Val Leu Asp Ser Asp Gly
625                 630                 635                 640

Ser Phe Phe Leu Tyr Ser Lys Leu Thr Val Asp Lys Ser Arg Trp Gln
```

```
                    645                 650                 655
Gln Gly Asn Val Phe Ser Cys Ser Val Met His Glu Ala Leu His Asn
            660                 665                 670
His Tyr Thr Gln Lys Ser Leu Ser Leu Ser Pro Gly Lys
            675                 680                 685

<210> SEQ ID NO 241
<211> LENGTH: 107
<212> TYPE: PRT
<213> ORGANISM: Artificial Sequence
<220> FEATURE:
<223> OTHER INFORMATION: h1332 VL

<400> SEQUENCE: 241

Asp Ile Gln Met Thr Gln Ser Pro Ser Ser Val Ser Ala Ser Val Gly
1               5                   10                  15
Asp Arg Val Thr Ile Thr Cys Arg Ala Ser Gln Gly Ile Asn Thr Trp
            20                  25                  30
Leu Ala Trp Tyr Gln Gln Lys Pro Gly Lys Ala Pro Lys Leu Leu Ile
        35                  40                  45
Tyr Ala Ala Ser Ser Leu Lys Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Asn Ser Phe Pro Leu
                85                  90                  95
Thr Phe Gly Gly Gly Thr Lys Val Glu Ile Lys
            100                 105

<210> SEQ ID NO 242
<211> LENGTH: 11
<212> TYPE: PRT
<213> ORGANISM: Artificial Sequence
<220> FEATURE:
<223> OTHER INFORMATION: h1332 VL - CDR1

<400> SEQUENCE: 242

Arg Ala Ser Gln Gly Ile Asn Thr Trp Leu Ala
1               5                   10

<210> SEQ ID NO 243
<211> LENGTH: 7
<212> TYPE: PRT
<213> ORGANISM: Artificial Sequence
<220> FEATURE:
<223> OTHER INFORMATION: h1332 VL - CDR2

<400> SEQUENCE: 243

Ala Ala Ser Ser Leu Lys Ser
1               5

<210> SEQ ID NO 244
<211> LENGTH: 9
<212> TYPE: PRT
<213> ORGANISM: Artificial Sequence
<220> FEATURE:
<223> OTHER INFORMATION: h1332 VL - CDR3

<400> SEQUENCE: 244

Gln Gln Ala Asn Ser Phe Pro Leu Thr
1               5
```

```
<210> SEQ ID NO 245
<211> LENGTH: 119
<212> TYPE: PRT
<213> ORGANISM: Artificial Sequence
<220> FEATURE:
<223> OTHER INFORMATION: Pani VH

<400> SEQUENCE: 245

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser
        115

<210> SEQ ID NO 246
<211> LENGTH: 7
<212> TYPE: PRT
<213> ORGANISM: Artificial Sequence
<220> FEATURE:
<223> OTHER INFORMATION: Pani VH - CDR1

<400> SEQUENCE: 246

Ser Gly Asp Tyr Tyr Trp Thr
1               5

<210> SEQ ID NO 247
<211> LENGTH: 16
<212> TYPE: PRT
<213> ORGANISM: Artificial Sequence
<220> FEATURE:
<223> OTHER INFORMATION: Pani VH - CDR2

<400> SEQUENCE: 247

His Ile Tyr Tyr Ser Gly Asn Thr Asn Tyr Asn Pro Ser Leu Lys Ser
1               5                   10                  15

<210> SEQ ID NO 248
<211> LENGTH: 9
<212> TYPE: PRT
<213> ORGANISM: Artificial Sequence
<220> FEATURE:
<223> OTHER INFORMATION: Pani VH - CDR3

<400> SEQUENCE: 248

Asp Arg Val Thr Gly Ala Phe Asp Ile
1               5

<210> SEQ ID NO 249
<211> LENGTH: 239
<212> TYPE: PRT
<213> ORGANISM: Artificial Sequence
<220> FEATURE:
<223> OTHER INFORMATION: Short Chain 1 (h1332 VH-CH1)
```

<400> SEQUENCE: 249

Met Glu Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Phe Ser Trp Val Arg Gln Ala Pro Gly Gln Gly Leu
    50                  55                  60

Glu Trp Met Gly Trp Ile Ser Ala Ser Asn Gly Asn Thr Tyr Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Val Tyr Ala Asp Tyr Ala Asp Tyr Trp Gly Gln
        115                 120                 125

Gly Thr Leu Val Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys
225                 230                 235

<210> SEQ ID NO 250
<211> LENGTH: 117
<212> TYPE: PRT
<213> ORGANISM: Artificial Sequence
<220> FEATURE:
<223> OTHER INFORMATION: h1332 VH

<400> SEQUENCE: 250

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Phe Ser Trp Val Arg Gln Ala Pro Gly Gln Gly Leu Glu Trp Met
        35                  40                  45

Gly Trp Ile Ser Ala Ser Asn Gly Asn Thr Tyr Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Tyr Ala Asp Tyr Ala Asp Tyr Trp Gly Gln Gly Thr Leu
            100                 105                 110

```
Val Thr Val Ser Ser
        115

<210> SEQ ID NO 251
<211> LENGTH: 5
<212> TYPE: PRT
<213> ORGANISM: Artificial Sequence
<220> FEATURE:
<223> OTHER INFORMATION: h1332 VH - CDR1

<400> SEQUENCE: 251

Ser Tyr Gly Phe Ser
1               5

<210> SEQ ID NO 252
<211> LENGTH: 17
<212> TYPE: PRT
<213> ORGANISM: Artificial Sequence
<220> FEATURE:
<223> OTHER INFORMATION: h1332 VH - CDR2

<400> SEQUENCE: 252

Trp Ile Ser Ala Ser Asn Gly Asn Thr Tyr Tyr Ala Gln Lys Leu Gln
1               5                   10                  15

Gly

<210> SEQ ID NO 253
<211> LENGTH: 8
<212> TYPE: PRT
<213> ORGANISM: Artificial Sequence
<220> FEATURE:
<223> OTHER INFORMATION: h1332 VH - CDR3

<400> SEQUENCE: 253

Val Tyr Ala Asp Tyr Ala Asp Tyr
1               5

<210> SEQ ID NO 254
<211> LENGTH: 236
<212> TYPE: PRT
<213> ORGANISM: Artificial Sequence
<220> FEATURE:
<223> OTHER INFORMATION: Short Chain 2 (Pani VL-hCk)

<400> SEQUENCE: 254

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
                20                  25                  30

Leu Ser Ala Ser Val Gly Asp Arg Val Thr Ile Thr Cys Gln Ala Ser
            35                  40                  45

Gln Asp Ile Ser Asn Tyr Leu Asn Trp Tyr Gln Gln Lys Pro Gly Lys
        50                  55                  60

Ala Pro Lys Leu Leu Ile Tyr Asp Ala Ser Asn Leu Glu Thr Gly Val
65                  70                  75                  80

Pro Ser Arg Phe Ser Gly Ser Gly Ser Gly Thr Asp Phe Thr Phe Thr
                85                  90                  95

Ile Ser Ser Leu Gln Pro Glu Asp Ile Ala Thr Tyr Phe Cys Gln His
            100                 105                 110

Phe Asp His Leu Pro Leu Ala Phe Gly Gly Gly Thr Lys Val Glu Ile
        115                 120                 125

Lys Arg Thr Val Ala Ala Pro Ser Val Phe Ile Phe Pro Pro Ser Asp
```

```
                130                 135                 140
Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 255
<211> LENGTH: 107
<212> TYPE: PRT
<213> ORGANISM: Artificial Sequence
<220> FEATURE:
<223> OTHER INFORMATION: Pani VL

<400> SEQUENCE: 255

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105

<210> SEQ ID NO 256
<211> LENGTH: 11
<212> TYPE: PRT
<213> ORGANISM: Artificial Sequence
<220> FEATURE:
<223> OTHER INFORMATION: Pani VL - CDR1

<400> SEQUENCE: 256

Gln Ala Ser Gln Asp Ile Ser Asn Tyr Leu Asn
1               5                   10

<210> SEQ ID NO 257
<211> LENGTH: 7
<212> TYPE: PRT
<213> ORGANISM: Artificial Sequence
<220> FEATURE:
<223> OTHER INFORMATION: Pani VL - CDR2

<400> SEQUENCE: 257

Asp Ala Ser Asn Leu Glu Thr
1               5

<210> SEQ ID NO 258
```

-continued

```
<211> LENGTH: 9
<212> TYPE: PRT
<213> ORGANISM: Artificial Sequence
<220> FEATURE:
<223> OTHER INFORMATION: Pani VL - CDR3

<400> SEQUENCE: 258

Gln His Phe Asp His Leu Pro Leu Ala
1               5

<210> SEQ ID NO 259
<211> LENGTH: 680
<212> TYPE: PRT
<213> ORGANISM: Artificial Sequence
<220> FEATURE:
<223> OTHER INFORMATION: Long Chain (FIX VL-hCk-FX-VH-hCg4)

<400> SEQUENCE: 259

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Arg Asn Ile Glu Arg Gln Leu Ala Trp Tyr Gln Gln Lys Pro Gly Gln
    50                  55                  60

Ala Pro Glu Leu Leu Ile Tyr Gln Ala Ser Arg Lys Glu Ser Gly Val
65                  70                  75                  80

Pro Asp Arg Phe Ser Gly Ser Arg Tyr Gly Thr Asp Phe Thr Leu Thr
                85                  90                  95

Ile Ser Ser Leu Gln Pro Glu Asp Ile Ala Thr Tyr Tyr Cys Gln Gln
            100                 105                 110

Tyr Ser Asp Pro Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Gln Val Gln Leu
225                 230                 235                 240

Val Gln Ser Gly Ser Glu Leu Lys Lys Pro Gly Ala Ser Val Lys Val
                245                 250                 255

Ser Cys Lys Ala Ser Gly Tyr Thr Phe Thr Asp Asn Asn Met Asp Trp
            260                 265                 270

Val Arg Gln Ala Pro Gly Gln Gly Leu Glu Trp Met Gly Asp Ile Asn
        275                 280                 285

Thr Arg Ser Gly Gly Ser Ile Tyr Asn Glu Glu Phe Gln Asp Arg Val
    290                 295                 300

Ile Met Thr Val Asp Lys Ser Thr Asp Thr Ala Tyr Met Glu Leu Ser
```

```
              305                 310                 315                 320
        Ser Leu Arg Ser Glu Asp Thr Ala Thr Tyr His Cys Ala Arg Arg Lys
                        325                 330                 335

Ser Tyr Gly Tyr Tyr Leu Asp Glu Trp Gly Glu Gly Thr Leu Val Thr
                        340                 345                 350

Val Ser Ser Ala Ser Thr Lys Gly Pro Ser Val Phe Pro Leu Ala Pro
                        355                 360                 365

Cys Ser Arg Ser Thr Ser Glu Ser Thr Ala Ala Leu Gly Cys Leu Val
                370                 375                 380

Lys Asp Tyr Phe Pro Glu Pro Val Thr Val Ser Trp Asn Ser Gly Ala
        385                 390                 395                 400

Leu Thr Ser Gly Val His Thr Phe Pro Ala Val Leu Gln Ser Ser Gly
                                405                 410                 415

Leu Tyr Ser Leu Ser Ser Val Val Thr Val Pro Ser Ser Ser Leu Gly
                        420                 425                 430

Thr Gln Thr Tyr Thr Cys Asn Val Asp His Lys Pro Ser Asn Thr Lys
                        435                 440                 445

Val Asp Lys Arg Val Glu Ser Lys Tyr Gly Pro Pro Cys Pro Pro Cys
        450                 455                 460

Pro Ala Pro Glu Phe Leu Gly Gly Pro Ser Val Phe Leu Phe Pro Pro
        465                 470                 475                 480

Lys Pro Lys Asp Thr Leu Met Ile Ser Arg Thr Pro Glu Val Thr Cys
                        485                 490                 495

Val Val Val Asp Val Ser Gln Glu Asp Pro Glu Val Gln Phe Asn Trp
                        500                 505                 510

Tyr Val Asp Gly Val Glu Val His Asn Ala Lys Thr Lys Pro Arg Glu
                        515                 520                 525

Glu Gln Tyr Asn Ser Thr Tyr Arg Val Val Ser Val Leu Thr Val Leu
                        530                 535                 540

His Gln Asp Trp Leu Asn Gly Lys Glu Tyr Lys Cys Lys Val Ser Asn
        545                 550                 555                 560

Lys Gly Leu Pro Ser Ser Ile Glu Lys Thr Ile Ser Lys Ala Lys Gly
                        565                 570                 575

Gln Pro Arg Glu Pro Gln Val Tyr Thr Leu Pro Pro Ser Gln Glu Glu
                        580                 585                 590

Met Thr Lys Asn Gln Val Ser Leu Thr Cys Leu Val Lys Gly Phe Tyr
                        595                 600                 605

Pro Ser Asp Ile Ala Val Glu Trp Glu Ser Asn Gly Gln Pro Glu Asn
        610                 615                 620

Asn Tyr Lys Thr Thr Pro Pro Val Leu Asp Ser Asp Gly Ser Phe Phe
        625                 630                 635                 640

Leu Tyr Ser Lys Leu Thr Val Asp Lys Ser Arg Trp Gln Glu Gly Asn
                        645                 650                 655

Val Phe Ser Cys Ser Val Met His Glu Ala Leu His Asn His Tyr Thr
                        660                 665                 670

Gln Glu Ser Leu Ser Leu Ser Pro
                        675                 680

<210> SEQ ID NO 260
<211> LENGTH: 107
<212> TYPE: PRT
<213> ORGANISM: Artificial Sequence
<220> FEATURE:
<223> OTHER INFORMATION: FIX VL
```

<400> SEQUENCE: 260

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys
            100                 105

<210> SEQ ID NO 261
<211> LENGTH: 11
<212> TYPE: PRT
<213> ORGANISM: Artificial Sequence
<220> FEATURE:
<223> OTHER INFORMATION: FIX VL - CDR1

<400> SEQUENCE: 261

Lys Ala Ser Arg Asn Ile Glu Arg Gln Leu Ala
1               5                   10

<210> SEQ ID NO 262
<211> LENGTH: 7
<212> TYPE: PRT
<213> ORGANISM: Artificial Sequence
<220> FEATURE:
<223> OTHER INFORMATION: FIX VL - CDR2

<400> SEQUENCE: 262

Gln Ala Ser Arg Lys Glu Ser
1               5

<210> SEQ ID NO 263
<211> LENGTH: 9
<212> TYPE: PRT
<213> ORGANISM: Artificial Sequence
<220> FEATURE:
<223> OTHER INFORMATION: FIX VL - CDR3

<400> SEQUENCE: 263

Gln Gln Tyr Ser Asp Pro Pro Leu Thr
1               5

<210> SEQ ID NO 264
<211> LENGTH: 119
<212> TYPE: PRT
<213> ORGANISM: Artificial Sequence
<220> FEATURE:
<223> OTHER INFORMATION: FX-VH

<400> SEQUENCE: 264

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met

```
                 35                  40                  45

Gly Asp Ile Asn Thr Arg Ser Gly Gly Ser Ile Tyr Asn Glu Glu Phe
         50                  55                  60

Gln Asp Arg Val Ile Met Thr Val Asp Lys Ser Thr Asp Thr Ala Tyr
 65                  70                  75                  80

Met Glu Leu Ser Ser Leu Arg Ser Glu Asp Thr Ala Thr Tyr His Cys
                 85                  90                  95

Ala Arg Arg Lys Ser Tyr Gly Tyr Tyr Leu Asp Glu Trp Gly Glu Gly
            100                 105                 110

Thr Leu Val Thr Val Ser Ser
        115

<210> SEQ ID NO 265
<211> LENGTH: 5
<212> TYPE: PRT
<213> ORGANISM: Artificial Sequence
<220> FEATURE:
<223> OTHER INFORMATION: FX-VH - CDR1

<400> SEQUENCE: 265

Asp Asn Asn Met Asp
1               5

<210> SEQ ID NO 266
<211> LENGTH: 17
<212> TYPE: PRT
<213> ORGANISM: Artificial Sequence
<220> FEATURE:
<223> OTHER INFORMATION: FX-VH - CDR2

<400> SEQUENCE: 266

Asp Ile Asn Thr Arg Ser Gly Gly Ser Ile Tyr Asn Glu Glu Phe Gln
1               5                   10                  15

Asp

<210> SEQ ID NO 267
<211> LENGTH: 10
<212> TYPE: PRT
<213> ORGANISM: Artificial Sequence
<220> FEATURE:
<223> OTHER INFORMATION: FX-VH - CDR3

<400> SEQUENCE: 267

Arg Lys Ser Tyr Gly Tyr Tyr Leu Asp Glu
1               5                   10

<210> SEQ ID NO 268
<211> LENGTH: 245
<212> TYPE: PRT
<213> ORGANISM: Artificial Sequence
<220> FEATURE:
<223> OTHER INFORMATION: Short Chain 1 (F-IX VH-CH1h)

<400> SEQUENCE: 268

Met Glu Phe Gly Leu Ser Trp Leu Phe Leu Val Ala Ile Leu Lys Gly
1               5                   10                  15

Val Gln Cys Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Tyr Tyr Asp Ile Gln Trp Val Arg Gln Ala Pro Gly Lys Gly Leu
    50                  55                  60
```

```
Glu Trp Val Ser Ser Ile Ser Pro Ser Gly Gln Ser Thr Tyr Tyr Arg
 65                  70                  75                  80

Arg Glu Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Arg Thr Gly Arg Glu Tyr Gly Gly Gly Trp Tyr
        115                 120                 125

Phe Asp Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys
                245

<210> SEQ ID NO 269
<211> LENGTH: 123
<212> TYPE: PRT
<213> ORGANISM: Artificial Sequence
<220> FEATURE:
<223> OTHER INFORMATION: F-IX VH

<400> SEQUENCE: 269

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Tyr Tyr
                 20                  25                  30

Asp Ile Gln Trp Val Arg Gln Ala Pro Gly Lys Gly Leu Glu Trp Val
             35                  40                  45

Ser Ser Ile Ser Pro Ser Gly Gln Ser Thr Tyr Tyr Arg Arg Glu Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Thr Gly Arg Glu Tyr Gly Gly Gly Trp Tyr Phe Asp Tyr
            100                 105                 110

Trp Gly Gln Gly Thr Leu Val Thr Val Ser Ser
        115                 120

<210> SEQ ID NO 270
<211> LENGTH: 6
<212> TYPE: PRT
<213> ORGANISM: Artificial Sequence
<220> FEATURE:
<223> OTHER INFORMATION: F-IX VH - CDR1
```

<400> SEQUENCE: 270

Ser Tyr Tyr Asp Ile Gln
1               5

<210> SEQ ID NO 271
<211> LENGTH: 17
<212> TYPE: PRT
<213> ORGANISM: Artificial Sequence
<220> FEATURE:
<223> OTHER INFORMATION: F-IX VH - CDR2

<400> SEQUENCE: 271

Ser Ile Ser Pro Ser Gly Gln Ser Thr Tyr Tyr Arg Arg Glu Val Lys
1               5                   10                  15

Gly

<210> SEQ ID NO 272
<211> LENGTH: 14
<212> TYPE: PRT
<213> ORGANISM: Artificial Sequence
<220> FEATURE:
<223> OTHER INFORMATION: F-IX VH - CDR3

<400> SEQUENCE: 272

Arg Thr Gly Arg Glu Tyr Gly Gly Gly Trp Tyr Phe Asp Tyr
1               5                   10

<210> SEQ ID NO 273
<211> LENGTH: 236
<212> TYPE: PRT
<213> ORGANISM: Artificial Sequence
<220> FEATURE:
<223> OTHER INFORMATION: Short Chain 2 (F-X VL-hCk)

<400> SEQUENCE: 273

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
                20                  25                  30

Leu Ser Ala Ser Val Gly Asp Arg Val Thr Ile Thr Cys Lys Ala Ser
            35                  40                  45

Arg Asn Ile Glu Arg Gln Leu Ala Trp Tyr Gln Gln Lys Pro Gly Gln
        50                  55                  60

Ala Pro Glu Leu Leu Ile Tyr Gln Ala Ser Arg Lys Glu Ser Gly Val
65                  70                  75                  80

Pro Asp Arg Phe Ser Gly Ser Arg Tyr Gly Thr Asp Phe Thr Leu Thr
                85                  90                  95

Ile Ser Ser Leu Gln Pro Glu Asp Ile Ala Thr Tyr Tyr Cys Gln Gln
            100                 105                 110

Tyr Ser Asp Pro Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

```
Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 274
<211> LENGTH: 107
<212> TYPE: PRT
<213> ORGANISM: Artificial Sequence
<220> FEATURE:
<223> OTHER INFORMATION: F-X VL

<400> SEQUENCE: 274

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys
            100                 105

<210> SEQ ID NO 275
<211> LENGTH: 11
<212> TYPE: PRT
<213> ORGANISM: Artificial Sequence
<220> FEATURE:
<223> OTHER INFORMATION: F-X VL - CDR1

<400> SEQUENCE: 275

Lys Ala Ser Arg Asn Ile Glu Arg Gln Leu Ala
1               5                   10

<210> SEQ ID NO 276
<211> LENGTH: 7
<212> TYPE: PRT
<213> ORGANISM: Artificial Sequence
<220> FEATURE:
<223> OTHER INFORMATION: F-X VL - CDR2

<400> SEQUENCE: 276

Gln Ala Ser Arg Lys Glu Ser
1               5

<210> SEQ ID NO 277
<211> LENGTH: 9
<212> TYPE: PRT
<213> ORGANISM: Artificial Sequence
<220> FEATURE:
<223> OTHER INFORMATION: F-X VL - CDR3

<400> SEQUENCE: 277

Gln Gln Tyr Ser Asp Pro Pro Leu Thr
1               5
```

```
<210> SEQ ID NO 278
<211> LENGTH: 697
<212> TYPE: PRT
<213> ORGANISM: Artificial Sequence
<220> FEATURE:
<223> OTHER INFORMATION: Long Chain (paritu VL-hCk-FigituVH-hCg1)

<400> SEQUENCE: 278

Met Asp Met Arg Val Pro Ala Gln Leu Leu Gly Leu Leu Leu Leu Trp
1               5                   10                  15

Phe Pro Gly Ser Arg Cys Asp Ile Glu Met Thr Gln Ser Pro Asp Ser
            20                  25                  30

Leu Ala Val Ser Leu Gly Glu Arg Ala Thr Ile Asn Cys Arg Ser Ser
        35                  40                  45

Gln Ser Val Leu Tyr Ser Ser Asn Arg Asn Tyr Leu Ala Trp Tyr
    50                  55                  60

Gln Gln Asn Pro Gly Gln Pro Pro Lys Leu Leu Ile Tyr Trp Ala Ser
65                  70                  75                  80

Thr Arg Glu Ser Gly Val Pro Asp Arg Phe Ser Gly Ser Gly Ser Gly
                85                  90                  95

Thr Asp Phe Thr Leu Thr Ile Ser Ser Leu Gln Ala Glu Asp Val Ala
            100                 105                 110

Val Tyr Tyr Cys Gln Gln Tyr Tyr Ser Thr Pro Arg Thr Phe Gly Gln
        115                 120                 125

Gly Thr Lys Val Glu Ile Lys Arg Thr Val Ala Ala Pro Ser Val Phe
    130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

Leu Ser Lys Ala Asp Tyr Glu Lys His Lys Val Tyr Ala Cys Glu Val
    210                 215                 220

Thr His Gln Gly Leu Ser Ser Pro Val Thr Lys Ser Phe Asn Arg Gly
225                 230                 235                 240

Glu Cys Glu Val Gln Leu Leu Glu Ser Gly Gly Gly Leu Val Gln Pro
                245                 250                 255

Gly Gly Ser Leu Arg Leu Ser Cys Thr Ala Ser Gly Phe Thr Phe Ser
            260                 265                 270

Ser Tyr Ala Met Asn Trp Val Arg Gln Ala Pro Gly Lys Gly Leu Glu
        275                 280                 285

Trp Val Ser Ala Ile Ser Gly Ser Gly Gly Thr Thr Phe Tyr Ala Asp
    290                 295                 300

Ser Val Lys Gly Arg Phe Thr Ile Ser Arg Asp Asn Ser Arg Thr Thr
305                 310                 315                 320

Leu Tyr Leu Gln Met Asn Ser Leu Arg Ala Glu Asp Thr Ala Val Tyr
                325                 330                 335

Tyr Cys Ala Lys Asp Leu Gly Trp Ser Asp Ser Tyr Tyr Tyr Tyr Tyr
            340                 345                 350

Gly Met Asp Val Trp Gly Gln Gly Thr Thr Val Thr Val Ser Ser Ala
        355                 360                 365
```

```
Ser Thr Lys Gly Pro Ser Val Phe Pro Leu Ala Pro Ser Ser Lys Ser
    370                 375                 380

Thr Ser Gly Gly Thr Ala Ala Leu Gly Cys Leu Val Lys Asp Tyr Phe
385                 390                 395                 400

Pro Glu Pro Val Thr Val Ser Trp Asn Ser Gly Ala Leu Thr Ser Gly
                405                 410                 415

Val His Thr Phe Pro Ala Val Leu Gln Ser Ser Gly Leu Tyr Ser Leu
                420                 425                 430

Ser Ser Val Val Thr Val Pro Ser Ser Leu Gly Thr Gln Thr Tyr
            435                 440                 445

Ile Cys Asn Val Asn His Lys Pro Ser Asn Thr Lys Val Asp Lys Lys
    450                 455                 460

Val Glu Pro Lys Ser Cys Asp Lys Thr His Thr Cys Pro Pro Cys Pro
465                 470                 475                 480

Ala Pro Glu Leu Leu Gly Gly Pro Ser Val Phe Leu Phe Pro Pro Lys
                485                 490                 495

Pro Lys Asp Thr Leu Met Ile Ser Arg Thr Pro Glu Val Thr Cys Val
                500                 505                 510

Val Val Asp Val Ser His Glu Asp Pro Glu Val Lys Phe Asn Trp Tyr
            515                 520                 525

Val Asp Gly Val Glu Val His Asn Ala Lys Thr Lys Pro Arg Glu Glu
    530                 535                 540

Gln Tyr Asn Ser Thr Tyr Arg Val Val Ser Val Leu Thr Val Leu His
545                 550                 555                 560

Gln Asp Trp Leu Asn Gly Lys Glu Tyr Lys Cys Lys Val Ser Asn Lys
                565                 570                 575

Ala Leu Pro Ala Pro Ile Glu Lys Thr Ile Ser Lys Ala Lys Gly Gln
                580                 585                 590

Pro Arg Glu Pro Gln Val Tyr Thr Leu Pro Pro Ser Arg Glu Glu Met
            595                 600                 605

Thr Lys Asn Gln Val Ser Leu Thr Cys Leu Val Lys Gly Phe Tyr Pro
    610                 615                 620

Ser Asp Ile Ala Val Glu Trp Glu Ser Asn Gly Gln Pro Glu Asn Asn
625                 630                 635                 640

Tyr Lys Thr Thr Pro Pro Val Leu Asp Ser Asp Gly Ser Phe Phe Leu
                645                 650                 655

Tyr Ser Lys Leu Thr Val Asp Lys Ser Arg Trp Gln Gln Gly Asn Val
                660                 665                 670

Phe Ser Cys Ser Val Met His Glu Ala Leu His Asn His Tyr Thr Gln
            675                 680                 685

Lys Ser Leu Ser Leu Ser Pro Gly Lys
    690                 695

<210> SEQ ID NO 279
<211> LENGTH: 113
<212> TYPE: PRT
<213> ORGANISM: Artificial Sequence
<220> FEATURE:
<223> OTHER INFORMATION: paritu VL

<400> SEQUENCE: 279

Asp Ile Glu Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
                20                  25                  30
```

```
Ser Ser Asn Arg Asn Tyr Leu Ala Trp Tyr Gln Gln Asn Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys

<210> SEQ ID NO 280
<211> LENGTH: 17
<212> TYPE: PRT
<213> ORGANISM: Artificial Sequence
<220> FEATURE:
<223> OTHER INFORMATION: paritu VL - CDR1

<400> SEQUENCE: 280

Arg Ser Ser Gln Ser Val Leu Tyr Ser Ser Asn Arg Asn Tyr Leu
 1               5                  10                  15

Ala

<210> SEQ ID NO 281
<211> LENGTH: 7
<212> TYPE: PRT
<213> ORGANISM: Artificial Sequence
<220> FEATURE:
<223> OTHER INFORMATION: paritu VL - CDR2

<400> SEQUENCE: 281

Trp Ala Ser Thr Arg Glu Ser
 1               5

<210> SEQ ID NO 282
<211> LENGTH: 9
<212> TYPE: PRT
<213> ORGANISM: Artificial Sequence
<220> FEATURE:
<223> OTHER INFORMATION: paritu VL - CDR3

<400> SEQUENCE: 282

Gln Gln Tyr Tyr Ser Thr Pro Arg Thr
 1               5

<210> SEQ ID NO 283
<211> LENGTH: 125
<212> TYPE: PRT
<213> ORGANISM: Artificial Sequence
<220> FEATURE:
<223> OTHER INFORMATION: FigituVH

<400> SEQUENCE: 283

Glu Val Gln Leu Leu Glu Ser Gly Gly Gly Leu Val Gln Pro Gly Gly
 1               5                  10                  15

Ser Leu Arg Leu Ser Cys Thr Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Ala Ile Ser Gly Ser Gly Thr Thr Phe Tyr Ala Asp Ser Val
        50                  55                  60
```

```
Lys Gly Arg Phe Thr Ile Ser Arg Asp Asn Ser Arg Thr Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu Gly Trp Ser Asp Ser Tyr Tyr Tyr Tyr Gly Met
            100                 105                 110

Asp Val Trp Gly Gln Gly Thr Thr Val Thr Val Ser Ser
        115                 120                 125

<210> SEQ ID NO 284
<211> LENGTH: 5
<212> TYPE: PRT
<213> ORGANISM: Artificial Sequence
<220> FEATURE:
<223> OTHER INFORMATION: FigituVH - CDR1

<400> SEQUENCE: 284

Ser Tyr Ala Met Asn
 1               5

<210> SEQ ID NO 285
<211> LENGTH: 17
<212> TYPE: PRT
<213> ORGANISM: Artificial Sequence
<220> FEATURE:
<223> OTHER INFORMATION: FigituVH - CDR2

<400> SEQUENCE: 285

Ala Ile Ser Gly Ser Gly Gly Thr Thr Phe Tyr Ala Asp Ser Val Lys
 1               5                  10                  15

Gly

<210> SEQ ID NO 286
<211> LENGTH: 16
<212> TYPE: PRT
<213> ORGANISM: Artificial Sequence
<220> FEATURE:
<223> OTHER INFORMATION: FigituVH - CDR3

<400> SEQUENCE: 286

Asp Leu Gly Trp Ser Asp Ser Tyr Tyr Tyr Tyr Gly Met Asp Val
 1               5                  10                  15

<210> SEQ ID NO 287
<211> LENGTH: 239
<212> TYPE: PRT
<213> ORGANISM: Artificial Sequence
<220> FEATURE:
<223> OTHER INFORMATION: Short Chain 1 (PatritumabVH -CH1)

<400> SEQUENCE: 287

Met Glu Phe Gly Leu Ser Trp Leu Phe Leu Val Ala Ile Leu Lys Gly
 1               5                  10                  15

Val Gln Cys Gln Val Gln Leu Gln Gln Trp Gly Ala Gly Leu Leu Lys
                20                  25                  30

Pro Ser Glu Thr Leu Ser Leu Thr Cys Ala Val Tyr Gly Gly Ser Phe
            35                  40                  45

Ser Gly Tyr Tyr Trp Ser Trp Ile Arg Gln Pro Pro Gly Lys Gly Leu
        50                  55                  60

Glu Trp Ile Gly Glu Ile Asn His Ser Gly Ser Thr Asn Tyr Asn Pro
 65                  70                  75                  80
```

```
Ser Leu Lys Ser Arg Val Thr Ile Ser Val Glu Thr Ser Lys Asn Gln
             85                  90                  95

Phe Ser Leu Lys Leu Ser Ser Val Thr Ala Ala Asp Thr Ala Val Tyr
            100                 105                 110

Tyr Cys Ala Arg Asp Lys Trp Thr Trp Tyr Phe Asp Leu Trp Gly Arg
            115                 120                 125

Gly Thr Leu Val Thr Val Ser Ser Ala Ser Thr Lys Gly Pro Ser Val
            130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
            165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
            210                 215                 220

Pro Ser Asn Thr Lys Val Asp Lys Lys Val Glu Pro Lys Ser Cys
225                 230                 235

<210> SEQ ID NO 288
<211> LENGTH: 117
<212> TYPE: PRT
<213> ORGANISM: Artificial Sequence
<220> FEATURE:
<223> OTHER INFORMATION: PatritumabVH

<400> SEQUENCE: 288

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Glu Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Asp Lys Trp Thr Trp Tyr Phe Asp Leu Trp Gly Arg Gly Thr Leu
            100                 105                 110

Val Thr Val Ser Ser
        115

<210> SEQ ID NO 289
<211> LENGTH: 5
<212> TYPE: PRT
<213> ORGANISM: Artificial Sequence
<220> FEATURE:
<223> OTHER INFORMATION: PatritumabVH - CDR1

<400> SEQUENCE: 289

Gly Tyr Tyr Trp Ser
1               5

<210> SEQ ID NO 290
```

```
<211> LENGTH: 16
<212> TYPE: PRT
<213> ORGANISM: Artificial Sequence
<220> FEATURE:
<223> OTHER INFORMATION: PatritumabVH - CDR2

<400> SEQUENCE: 290

Glu Ile Asn His Ser Gly Ser Thr Asn Tyr Asn Pro Ser Leu Lys Ser
1               5                   10                  15

<210> SEQ ID NO 291
<211> LENGTH: 9
<212> TYPE: PRT
<213> ORGANISM: Artificial Sequence
<220> FEATURE:
<223> OTHER INFORMATION: PatritumabVH - CDR3

<400> SEQUENCE: 291

Asp Lys Trp Thr Trp Tyr Phe Asp Leu
1               5

<210> SEQ ID NO 292
<211> LENGTH: 236
<212> TYPE: PRT
<213> ORGANISM: Artificial Sequence
<220> FEATURE:
<223> OTHER INFORMATION: Short Chain 2 (Figitu VL-hCk)

<400> SEQUENCE: 292

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Phe Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Lys Pro Gly Lys
    50                  55                  60

Ala Pro Lys Arg Leu Ile Tyr Ala Ala Ser Arg Leu His Arg Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

His Asn Ser Tyr Pro Cys Ser Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 293
<211> LENGTH: 107
<212> TYPE: PRT
<213> ORGANISM: Artificial Sequence
<220> FEATURE:
<223> OTHER INFORMATION: Figitu VL

<400> SEQUENCE: 293

```
Asp Ile Gln Met Thr Gln Phe Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu His Arg Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Cys
                85                  90                  95

Ser Phe Gly Gln Gly Thr Lys Leu Glu Ile Lys
            100                 105
```

<210> SEQ ID NO 294
<211> LENGTH: 11
<212> TYPE: PRT
<213> ORGANISM: Artificial Sequence
<220> FEATURE:
<223> OTHER INFORMATION: Figitu VL - CDR1

<400> SEQUENCE: 294

```
Arg Ala Ser Gln Gly Ile Arg Asn Asp Leu Gly
1               5                   10
```

<210> SEQ ID NO 295
<211> LENGTH: 7
<212> TYPE: PRT
<213> ORGANISM: Artificial Sequence
<220> FEATURE:
<223> OTHER INFORMATION: Figitu VL - CDR2

<400> SEQUENCE: 295

```
Ala Ala Ser Arg Leu His Arg
1               5
```

<210> SEQ ID NO 296
<211> LENGTH: 9
<212> TYPE: PRT
<213> ORGANISM: Artificial Sequence
<220> FEATURE:
<223> OTHER INFORMATION: Figitu VL - CDR3

<400> SEQUENCE: 296

```
Leu Gln His Asn Ser Tyr Pro Cys Ser
1               5
```

<210> SEQ ID NO 297
<211> LENGTH: 693
<212> TYPE: PRT
<213> ORGANISM: Artificial Sequence
<220> FEATURE:
<223> OTHER INFORMATION: Long Chain (Demci VL-hCk-Bevci VH-hCg1)

<400> SEQUENCE: 297

```
Met Asp Met Arg Val Pro Ala Gln Leu Leu Gly Leu Leu Leu Trp
1               5                   10                  15

Phe Pro Gly Ser Arg Cys Asp Ile Val Met Thr Gln Ser Pro Asp Ser
            20                  25                  30

Leu Ala Val Ser Leu Gly Glu Arg Ala Thr Ile Ser Cys Arg Ala Ser
            35                  40                  45

Glu Ser Val Asp Asn Tyr Gly Ile Ser Phe Met Lys Trp Phe Gln Gln
    50                  55                  60

Lys Pro Gly Gln Pro Pro Lys Leu Leu Ile Tyr Ala Ala Ser Asn Gln
65                  70                  75                  80

Gly Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
                100                 105                 110

Tyr Cys Gln Gln Ser Lys Glu Val Pro Trp Thr Phe Gly Gly Gly Thr
            115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240

Glu Val Gln Leu Val Glu Ser Gly Gly Gly Leu Val Gln Pro Gly Gly
                245                 250                 255

Ser Leu Arg Leu Ser Cys Ala Ala Ser Gly Tyr Thr Phe Thr Asn Tyr
                260                 265                 270

Gly Met Asn Trp Val Arg Gln Ala Pro Gly Lys Gly Leu Glu Trp Val
            275                 280                 285

Gly Trp Ile Asn Thr Tyr Thr Gly Glu Pro Thr Tyr Ala Ala Asp Phe
            290                 295                 300

Lys Arg Arg Phe Thr Phe Ser Leu Asp Thr Ser Lys Ser Thr Ala Tyr
305                 310                 315                 320

Leu Gln Met Asn Ser Leu Arg Ala Glu Asp Thr Ala Val Tyr Tyr Cys
                325                 330                 335

Ala Lys Tyr Pro His Tyr Tyr Gly Ser Ser His Trp Tyr Phe Asp Val
            340                 345                 350

Trp Gly Gln Gly Thr Leu Val Thr Val Ser Ser Ala Ser Thr Lys Gly
            355                 360                 365

Pro Ser Val Phe Pro Leu Ala Pro Ser Ser Lys Ser Thr Ser Gly Gly
    370                 375                 380

Thr Ala Ala Leu Gly Cys Leu Val Lys Asp Tyr Phe Pro Glu Pro Val
385                 390                 395                 400

Thr Val Ser Trp Asn Ser Gly Ala Leu Thr Ser Gly Val His Thr Phe
                405                 410                 415
```

```
Pro Ala Val Leu Gln Ser Ser Gly Leu Tyr Ser Leu Ser Ser Val Val
            420                 425                 430

Thr Val Pro Ser Ser Ser Leu Gly Thr Gln Thr Tyr Ile Cys Asn Val
            435                 440                 445

Asn His Lys Pro Ser Asn Thr Lys Val Asp Lys Lys Val Glu Pro Lys
        450                 455                 460

Ser Cys Asp Lys Thr His Thr Cys Pro Pro Cys Pro Ala Pro Glu Leu
465                 470                 475                 480

Leu Gly Gly Pro Ser Val Phe Leu Phe Pro Pro Lys Pro Lys Asp Thr
                485                 490                 495

Leu Met Ile Ser Arg Thr Pro Glu Val Thr Cys Val Val Val Asp Val
            500                 505                 510

Ser His Glu Asp Pro Glu Val Lys Phe Asn Trp Tyr Val Asp Gly Val
        515                 520                 525

Glu Val His Asn Ala Lys Thr Lys Pro Arg Glu Glu Gln Tyr Asn Ser
530                 535                 540

Thr Tyr Arg Val Val Ser Val Leu Thr Val Leu His Gln Asp Trp Leu
545                 550                 555                 560

Asn Gly Lys Glu Tyr Lys Cys Lys Val Ser Asn Lys Ala Leu Pro Ala
                565                 570                 575

Pro Ile Glu Lys Thr Ile Ser Lys Ala Lys Gly Gln Pro Arg Glu Pro
            580                 585                 590

Gln Val Tyr Thr Leu Pro Pro Ser Arg Glu Glu Met Thr Lys Asn Gln
        595                 600                 605

Val Ser Leu Thr Cys Leu Val Lys Gly Phe Tyr Pro Ser Asp Ile Ala
610                 615                 620

Val Glu Trp Glu Ser Asn Gly Gln Pro Glu Asn Asn Tyr Lys Thr Thr
625                 630                 635                 640

Pro Pro Val Leu Asp Ser Asp Gly Ser Phe Phe Leu Tyr Ser Lys Leu
                645                 650                 655

Thr Val Asp Lys Ser Arg Trp Gln Gln Gly Asn Val Phe Ser Cys Ser
            660                 665                 670

Val Met His Glu Ala Leu His Asn His Tyr Thr Gln Lys Ser Leu Ser
        675                 680                 685

Leu Ser Pro Gly Lys
        690

<210> SEQ ID NO 298
<211> LENGTH: 111
<212> TYPE: PRT
<213> ORGANISM: Artificial Sequence
<220> FEATURE:
<223> OTHER INFORMATION: Demci VL

<400> SEQUENCE: 298

Asp Ile Val Met Thr Gln Ser Pro Asp Ser Leu Ala Val Ser Leu Gly
1               5                   10                  15

Glu Arg Ala Thr Ile Ser Cys Arg Ala Ser Glu Ser Val Asp Asn Tyr
            20                  25                  30

Gly Ile Ser Phe Met Lys Trp Phe Gln Gln Lys Pro Gly Gln Pro Pro
        35                  40                  45

Lys Leu Leu Ile Tyr Ala Ala Ser Asn Gln Gly Ser Gly Val Pro Asp
    50                  55                  60

Arg Phe Ser Gly Ser Gly Ser Gly Thr Asp Phe Thr Leu Thr Ile Ser
65                  70                  75                  80
```

```
Ser Leu Gln Ala Glu Asp Val Ala Val Tyr Tyr Cys Gln Gln Ser Lys
                85                  90                  95

Glu Val Pro Trp Thr Phe Gly Gly Gly Thr Lys Val Glu Ile Lys
            100                 105                 110

<210> SEQ ID NO 299
<211> LENGTH: 15
<212> TYPE: PRT
<213> ORGANISM: Artificial Sequence
<220> FEATURE:
<223> OTHER INFORMATION: Demci VL - CDR1

<400> SEQUENCE: 299

Arg Ala Ser Glu Ser Val Asp Asn Tyr Gly Ile Ser Phe Met Lys
1               5                   10                  15

<210> SEQ ID NO 300
<211> LENGTH: 7
<212> TYPE: PRT
<213> ORGANISM: Artificial Sequence
<220> FEATURE:
<223> OTHER INFORMATION: Demci VL - CDR2

<400> SEQUENCE: 300

Ala Ala Ser Asn Gln Gly Ser
1               5

<210> SEQ ID NO 301
<211> LENGTH: 9
<212> TYPE: PRT
<213> ORGANISM: Artificial Sequence
<220> FEATURE:
<223> OTHER INFORMATION: Demci VL - CDR3

<400> SEQUENCE: 301

Gln Gln Ser Lys Glu Val Pro Trp Thr
1               5

<210> SEQ ID NO 302
<211> LENGTH: 123
<212> TYPE: PRT
<213> ORGANISM: Artificial Sequence
<220> FEATURE:
<223> OTHER INFORMATION: Bevci VH

<400> SEQUENCE: 302

Glu Val Gln Leu Val Glu Ser Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120
```

-continued

```
<210> SEQ ID NO 303
<211> LENGTH: 5
<212> TYPE: PRT
<213> ORGANISM: Artificial Sequence
<220> FEATURE:
<223> OTHER INFORMATION: Bevci VH - CDR1

<400> SEQUENCE: 303

Asn Tyr Gly Met Asn
1               5

<210> SEQ ID NO 304
<211> LENGTH: 17
<212> TYPE: PRT
<213> ORGANISM: Artificial Sequence
<220> FEATURE:
<223> OTHER INFORMATION: Bevci VH - CDR2

<400> SEQUENCE: 304

Trp Ile Asn Thr Tyr Thr Gly Glu Pro Thr Tyr Ala Ala Asp Phe Lys
1               5                   10                  15

Arg

<210> SEQ ID NO 305
<211> LENGTH: 14
<212> TYPE: PRT
<213> ORGANISM: Artificial Sequence
<220> FEATURE:
<223> OTHER INFORMATION: Bevci VH - CDR3

<400> SEQUENCE: 305

Tyr Pro His Tyr Tyr Gly Ser Ser His Trp Tyr Phe Asp Val
1               5                   10

<210> SEQ ID NO 306
<211> LENGTH: 241
<212> TYPE: PRT
<213> ORGANISM: Artificial Sequence
<220> FEATURE:
<223> OTHER INFORMATION: Short Chain 1  (Demci VH -CH1h)

<400> SEQUENCE: 306

Met Glu Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
                20                  25                  30

Pro Gly Ala Ser Val Lys Ile Ser Cys Lys Ala Ser Gly Tyr Ser Phe
            35                  40                  45

Thr Ala Tyr Tyr Ile His Trp Val Lys Gln Ala Pro Gly Gln Gly Leu
        50                  55                  60

Glu Trp Ile Gly Tyr Ile Ser Ser Tyr Asn Gly Ala Thr Asn Tyr Asn
65                  70                  75                  80

Gln Lys Phe Lys Gly Arg Val Thr Phe Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asp Tyr Asp Tyr Asp Val Gly Met Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
```

```
145                 150                 155                 160
Ala Ala Leu Gly Cys Leu Val Lys Asp Tyr Phe Pro Glu Pro Val Thr
            165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
            195                 200                 205

Val Pro Ser Ser Leu Gly Thr Gln Thr Tyr Ile Cys Asn Val Asn
            210                 215                 220

His Lys Pro Ser Asn Thr Lys Val Asp Lys Lys Val Glu Pro Lys Ser
225                 230                 235                 240

Cys

<210> SEQ ID NO 307
<211> LENGTH: 119
<212> TYPE: PRT
<213> ORGANISM: Artificial Sequence
<220> FEATURE:
<223> OTHER INFORMATION: Demci VH

<400> SEQUENCE: 307

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
            20                  25                  30

Tyr Ile His Trp Val Lys Gln Ala Pro Gly Gln Gly Leu Glu Trp Ile
        35                  40                  45

Gly Tyr Ile Ser Ser Tyr Asn Gly Ala Thr Asn Tyr Asn Gln Lys Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
            100                 105                 110

Thr Leu Val Thr Val Ser Ser
        115

<210> SEQ ID NO 308
<211> LENGTH: 5
<212> TYPE: PRT
<213> ORGANISM: Artificial Sequence
<220> FEATURE:
<223> OTHER INFORMATION: Demci VH - CDR1

<400> SEQUENCE: 308

Ala Tyr Tyr Ile His
1               5

<210> SEQ ID NO 309
<211> LENGTH: 17
<212> TYPE: PRT
<213> ORGANISM: Artificial Sequence
<220> FEATURE:
<223> OTHER INFORMATION: Demci VH - CDR2

<400> SEQUENCE: 309

Tyr Ile Ser Ser Tyr Asn Gly Ala Thr Asn Tyr Asn Gln Lys Phe Lys
1               5                   10                  15
```

Gly

<210> SEQ ID NO 310
<211> LENGTH: 10
<212> TYPE: PRT
<213> ORGANISM: Artificial Sequence
<220> FEATURE:
<223> OTHER INFORMATION: Demci VH - CDR3

<400> SEQUENCE: 310

Asp Tyr Asp Tyr Asp Val Gly Met Asp Tyr
1               5                   10

<210> SEQ ID NO 311
<211> LENGTH: 236
<212> TYPE: PRT
<213> ORGANISM: Artificial Sequence
<220> FEATURE:
<223> OTHER INFORMATION: Short Chain 2 (Bevci VL-hCk)

<400> SEQUENCE: 311

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
                20                  25                  30

Leu Ser Ala Ser Val Gly Asp Arg Val Thr Ile Thr Cys Ser Ala Ser
            35                  40                  45

Gln Asp Ile Ser Asn Tyr Leu Asn Trp Tyr Gln Gln Lys Pro Gly Lys
        50                  55                  60

Ala Pro Lys Val Leu Ile Tyr Phe Thr Ser Ser Leu His Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
                100                 105                 110

Tyr Ser Thr Val Pro Trp Thr Phe Gly Gln Gly Thr Lys Val Glu Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 312
<211> LENGTH: 107
<212> TYPE: PRT
<213> ORGANISM: Artificial Sequence
<220> FEATURE:
<223> OTHER INFORMATION: Bevci VL

<400> SEQUENCE: 312

-continued

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105
```

<210> SEQ ID NO 313
<211> LENGTH: 11
<212> TYPE: PRT
<213> ORGANISM: Artificial Sequence
<220> FEATURE:
<223> OTHER INFORMATION: Bevci VL - CDR1

<400> SEQUENCE: 313

```
Ser Ala Ser Gln Asp Ile Ser Asn Tyr Leu Asn
1               5                   10
```

<210> SEQ ID NO 314
<211> LENGTH: 7
<212> TYPE: PRT
<213> ORGANISM: Artificial Sequence
<220> FEATURE:
<223> OTHER INFORMATION: Bevci VL - CDR2

<400> SEQUENCE: 314

```
Phe Thr Ser Ser Leu His Ser
1               5
```

<210> SEQ ID NO 315
<211> LENGTH: 9
<212> TYPE: PRT
<213> ORGANISM: Artificial Sequence
<220> FEATURE:
<223> OTHER INFORMATION: Bevci VL - CDR3

<400> SEQUENCE: 315

```
Gln Gln Tyr Ser Thr Val Pro Trp Thr
1               5
```

<210> SEQ ID NO 316
<211> LENGTH: 691
<212> TYPE: PRT
<213> ORGANISM: Artificial Sequence
<220> FEATURE:
<223> OTHER INFORMATION: Long Chain (OfatuVL-hCk-CD3mAb VH-hCg1mut)

<400> SEQUENCE: 316

```
Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Ala Thr
            20                  25                  30

Leu Ser Leu Ser Pro Gly Glu Arg Ala Thr Leu Ser Cys Arg Ala Ser
        35                  40                  45
```

```
Gln Ser Val Ser Ser Tyr Leu Ala Trp Tyr Gln Gln Lys Pro Gly Gln
     50                  55                  60

Ala Pro Arg Leu Leu Ile Tyr Asp Ala Ser Asn Arg Ala Thr Gly Ile
 65                  70                  75                  80

Pro Ala Arg Phe Ser Gly Ser Gly Ser Gly Thr Asp Phe Thr Leu Thr
                     85                  90                  95

Ile Ser Ser Leu Glu Pro Glu Asp Phe Ala Val Tyr Tyr Cys Gln Gln
            100                 105                 110

Arg Ser Asn Trp Pro Ile Thr Phe Gly Gln Gly Thr Arg Leu Glu Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys Glu Val Gln Leu
225                 230                 235                 240

Leu Glu Ser Gly Gly Gly Leu Val Gln Pro Gly Gly Ser Leu Lys Leu
                245                 250                 255

Ser Cys Ala Ala Ser Gly Phe Thr Phe Asn Thr Tyr Ala Met Asn Trp
            260                 265                 270

Val Arg Gln Ala Pro Gly Lys Gly Leu Glu Trp Val Ala Arg Ile Arg
            275                 280                 285

Ser Lys Tyr Asn Asn Tyr Ala Thr Tyr Tyr Ala Asp Ser Val Lys Asp
        290                 295                 300

Arg Phe Thr Ile Ser Arg Asp Asp Ser Lys Asn Thr Ala Tyr Leu Gln
305                 310                 315                 320

Met Asn Asn Leu Lys Thr Glu Asp Thr Ala Val Tyr Tyr Cys Val Arg
                325                 330                 335

His Gly Asn Phe Gly Asn Ser Tyr Val Ser Trp Phe Ala Tyr Trp Gly
            340                 345                 350

Gln Gly Thr Leu Val Thr Val Ser Ser Ala Ser Thr Lys Gly Pro Ser
            355                 360                 365

Val Phe Pro Leu Ala Pro Ser Ser Lys Ser Thr Ser Gly Gly Thr Ala
        370                 375                 380

Ala Leu Gly Cys Leu Val Lys Asp Tyr Phe Pro Glu Pro Val Thr Val
385                 390                 395                 400

Ser Trp Asn Ser Gly Ala Leu Thr Ser Gly Val His Thr Phe Pro Ala
                405                 410                 415

Val Leu Gln Ser Ser Gly Leu Tyr Ser Leu Ser Ser Val Val Thr Val
            420                 425                 430

Pro Ser Ser Ser Leu Gly Thr Gln Thr Tyr Ile Cys Asn Val Asn His
            435                 440                 445

Lys Pro Ser Asn Thr Lys Val Asp Lys Val Glu Pro Lys Ser Cys
        450                 455                 460
```

```
Asp Lys Thr His Thr Cys Pro Pro Cys Pro Ala Glu Ala Ala Gly
465                 470                 475                 480

Gly Pro Ser Val Phe Leu Phe Pro Pro Lys Pro Lys Asp Thr Leu Met
                485                 490                 495

Ile Ser Arg Thr Pro Glu Val Thr Cys Val Val Val Asp Val Ser His
            500                 505                 510

Glu Asp Pro Glu Val Lys Phe Asn Trp Tyr Val Asp Gly Val Glu Val
        515                 520                 525

His Asn Ala Lys Thr Lys Pro Arg Glu Glu Gln Tyr Asn Ser Thr Tyr
    530                 535                 540

Arg Val Val Ser Val Leu Thr Val Leu His Gln Asp Trp Leu Asn Gly
545                 550                 555                 560

Lys Glu Tyr Lys Cys Lys Val Ser Asn Lys Ala Leu Pro Ala Pro Ile
                565                 570                 575

Glu Lys Thr Ile Ser Lys Ala Lys Gly Gln Pro Arg Glu Pro Gln Val
            580                 585                 590

Tyr Thr Leu Pro Pro Ser Arg Glu Glu Met Thr Lys Asn Gln Val Ser
        595                 600                 605

Leu Thr Cys Leu Val Lys Gly Phe Tyr Pro Ser Asp Ile Ala Val Glu
    610                 615                 620

Trp Glu Ser Asn Gly Gln Pro Glu Asn Asn Tyr Lys Thr Thr Pro Pro
625                 630                 635                 640

Val Leu Asp Ser Asp Gly Ser Phe Phe Leu Tyr Ser Lys Leu Thr Val
                645                 650                 655

Asp Lys Ser Arg Trp Gln Gln Gly Asn Val Phe Ser Cys Ser Val Met
            660                 665                 670

His Glu Ala Leu His Asn His Tyr Thr Gln Lys Ser Leu Ser Leu Ser
        675                 680                 685

Pro Gly Lys
    690

<210> SEQ ID NO 317
<211> LENGTH: 107
<212> TYPE: PRT
<213> ORGANISM: Artificial Sequence
<220> FEATURE:
<223> OTHER INFORMATION: OfatuVL

<400> SEQUENCE: 317

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 318
<211> LENGTH: 11
```

```
<212> TYPE: PRT
<213> ORGANISM: Artificial Sequence
<220> FEATURE:
<223> OTHER INFORMATION: OfatuVL - CDR1

<400> SEQUENCE: 318

Arg Ala Ser Gln Ser Val Ser Ser Tyr Leu Ala
1               5                   10

<210> SEQ ID NO 319
<211> LENGTH: 7
<212> TYPE: PRT
<213> ORGANISM: Artificial Sequence
<220> FEATURE:
<223> OTHER INFORMATION: OfatuVL CDR2

<400> SEQUENCE: 319

Asp Ala Ser Asn Arg Ala Thr
1               5

<210> SEQ ID NO 320
<211> LENGTH: 9
<212> TYPE: PRT
<213> ORGANISM: Artificial Sequence
<220> FEATURE:
<223> OTHER INFORMATION: OfatuVL - CDR3

<400> SEQUENCE: 320

Gln Gln Arg Ser Asn Trp Pro Ile Thr
1               5

<210> SEQ ID NO 321
<211> LENGTH: 125
<212> TYPE: PRT
<213> ORGANISM: Artificial Sequence
<220> FEATURE:
<223> OTHER INFORMATION: CD3mAb VH

<400> SEQUENCE: 321

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 322
<211> LENGTH: 5
<212> TYPE: PRT
<213> ORGANISM: Artificial Sequence
<220> FEATURE:
<223> OTHER INFORMATION: CD3mAb VH CDR1

<400> SEQUENCE: 322
```

Thr Tyr Ala Met Asn
1               5

<210> SEQ ID NO 323
<211> LENGTH: 19
<212> TYPE: PRT
<213> ORGANISM: Artificial Sequence
<220> FEATURE:
<223> OTHER INFORMATION: CD3mAb VH CDR2

<400> SEQUENCE: 323

Arg Ile Arg Ser Lys Tyr Asn Asn Tyr Ala Thr Tyr Tyr Ala Asp Ser
1               5                   10                  15

Val Lys Asp

<210> SEQ ID NO 324
<211> LENGTH: 14
<212> TYPE: PRT
<213> ORGANISM: Artificial Sequence
<220> FEATURE:
<223> OTHER INFORMATION: CD3mAb VH CDR3

<400> SEQUENCE: 324

His Gly Asn Phe Gly Asn Ser Tyr Val Ser Trp Phe Ala Tyr
1               5                   10

<210> SEQ ID NO 325
<211> LENGTH: 244
<212> TYPE: PRT
<213> ORGANISM: Artificial Sequence
<220> FEATURE:
<223> OTHER INFORMATION: Short Chain 1 (Ofatu VH-CH1)

<400> SEQUENCE: 325

Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Gln
                20                  25                  30

Pro Gly Arg Ser Leu Arg Leu Ser Cys Ala Ala Ser Gly Phe Thr Phe
            35                  40                  45

Asn Asp Tyr Ala Met His Trp Val Arg Gln Ala Pro Gly Lys Gly Leu
        50                  55                  60

Glu Trp Val Ser Thr Ile Ser Trp Asn Ser Gly Ser Ile Gly Tyr Ala
65                  70                  75                  80

Asp Ser Val Lys Gly Arg Phe Thr Ile Ser Arg Asp Asn Ala Lys Lys
                85                  90                  95

Ser Leu Tyr Leu Gln Met Asn Ser Leu Arg Ala Glu Asp Thr Ala Leu
            100                 105                 110

Tyr Tyr Cys Ala Lys Asp Ile Gln Tyr Gly Asn Tyr Tyr Tyr Gly Met
        115                 120                 125

Asp Val Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser

```
                195                 200                 205
Val Val Thr Val Pro Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys

<210> SEQ ID NO 326
<211> LENGTH: 122
<212> TYPE: PRT
<213> ORGANISM: Artificial Sequence
<220> FEATURE:
<223> OTHER INFORMATION: Ofatu VH

<400> SEQUENCE: 326

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
        115                 120

<210> SEQ ID NO 327
<211> LENGTH: 5
<212> TYPE: PRT
<213> ORGANISM: Artificial Sequence
<220> FEATURE:
<223> OTHER INFORMATION: Ofatu VH - CDR1

<400> SEQUENCE: 327

Asp Tyr Ala Met His
1               5

<210> SEQ ID NO 328
<211> LENGTH: 17
<212> TYPE: PRT
<213> ORGANISM: Artificial Sequence
<220> FEATURE:
<223> OTHER INFORMATION: Ofatu VH - CDR2

<400> SEQUENCE: 328

Thr Ile Ser Trp Asn Ser Gly Ser Ile Gly Tyr Ala Asp Ser Val Lys
1               5                   10                  15

Gly

<210> SEQ ID NO 329
<211> LENGTH: 13
<212> TYPE: PRT
<213> ORGANISM: Artificial Sequence
<220> FEATURE:
<223> OTHER INFORMATION: Ofatu VH - CDR3
```

<400> SEQUENCE: 329

Asp Ile Gln Tyr Gly Asn Tyr Tyr Tyr Gly Met Asp Val
1               5                   10

<210> SEQ ID NO 330
<211> LENGTH: 235
<212> TYPE: PRT
<213> ORGANISM: Artificial Sequence
<220> FEATURE:
<223> OTHER INFORMATION: Short Chain 2 (CD3mAb VL-hCL)

<400> SEQUENCE: 330

Met Thr Trp Thr Pro Leu Leu Phe Leu Thr Leu Leu His Cys Thr
1               5                   10                  15

Gly Ser Leu Ser Glu Leu Val Val Thr Gln Glu Pro Ser Leu Thr Val
                20                  25                  30

Ser Pro Gly Gly Thr Val Thr Leu Thr Cys Arg Ser Ser Thr Gly Ala
            35                  40                  45

Val Thr Thr Ser Asn Tyr Ala Asn Trp Val Gln Gln Lys Pro Gly Gln
        50                  55                  60

Ala Pro Arg Gly Leu Ile Gly Gly Thr Asn Lys Arg Ala Pro Gly Thr
65                  70                  75                  80

Pro Ala Arg Phe Ser Gly Ser Leu Leu Gly Gly Lys Ala Ala Leu Thr
                85                  90                  95

Leu Ser Gly Val Gln Pro Glu Asp Glu Ala Glu Tyr Tyr Cys Ala Leu
                100                 105                 110

Trp Tyr Ser Asn Leu Trp Val Phe Gly Gly Gly Thr Lys Leu Thr Val
                115                 120                 125

Leu Gly Gln Pro Lys Ala Ala Pro Ser Val Thr Leu Phe Pro Pro Ser
            130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
                180                 185                 190

Asn Lys Tyr Ala Ala Ser Ser Tyr Leu Ser Leu Thr Pro Glu Gln Trp
            195                 200                 205

Lys Ser His Arg Ser Tyr Ser Cys Gln Val Thr His Glu Gly Ser Thr
        210                 215                 220

Val Glu Lys Thr Val Ala Pro Thr Glu Cys Ser
225                 230                 235

<210> SEQ ID NO 331
<211> LENGTH: 109
<212> TYPE: PRT
<213> ORGANISM: Artificial Sequence
<220> FEATURE:
<223> OTHER INFORMATION: CD3mAb VL

<400> SEQUENCE: 331

Glu Leu Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
            35                  40                  45

```
Leu Ile Gly Gly Thr Asn Lys Arg Ala Pro Gly Thr Pro Ala Arg Phe
            50                  55                  60

Ser Gly Ser Leu Leu Gly Lys Ala Ala Leu Thr Leu Ser Gly Val
 65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
                100                 105
```

<210> SEQ ID NO 332
<211> LENGTH: 14
<212> TYPE: PRT
<213> ORGANISM: Artificial Sequence
<220> FEATURE:
<223> OTHER INFORMATION: CD3mAb VL - CDR1

<400> SEQUENCE: 332

```
Arg Ser Ser Thr Gly Ala Val Thr Thr Ser Asn Tyr Ala Asn
 1               5                  10
```

<210> SEQ ID NO 333
<211> LENGTH: 7
<212> TYPE: PRT
<213> ORGANISM: Artificial Sequence
<220> FEATURE:
<223> OTHER INFORMATION: CD3mAb VL - CDR2

<400> SEQUENCE: 333

```
Gly Thr Asn Lys Arg Ala Pro
 1               5
```

<210> SEQ ID NO 334
<211> LENGTH: 9
<212> TYPE: PRT
<213> ORGANISM: Artificial Sequence
<220> FEATURE:
<223> OTHER INFORMATION: CD3mAb VL - CDR3

<400> SEQUENCE: 334

```
Ala Leu Trp Tyr Ser Asn Leu Trp Val
 1               5
```

<210> SEQ ID NO 335
<211> LENGTH: 691
<212> TYPE: PRT
<213> ORGANISM: Artificial Sequence
<220> FEATURE:
<223> OTHER INFORMATION: Long Chain (patritu VL-hCk-PaniVH-hCg1)

<400> SEQUENCE: 335

```
Met Asp Met Arg Val Pro Ala Gln Leu Leu Gly Leu Leu Leu Leu Trp
 1               5                  10                  15

Phe Pro Gly Ser Arg Cys Asp Ile Glu Met Thr Gln Ser Pro Asp Ser
                20                  25                  30

Leu Ala Val Ser Leu Gly Glu Arg Ala Thr Ile Asn Cys Arg Ser Ser
            35                  40                  45

Gln Ser Val Leu Tyr Ser Ser Asn Arg Asn Tyr Leu Ala Trp Tyr
         50                  55                  60

Gln Gln Asn Pro Gly Gln Pro Pro Lys Leu Leu Ile Tyr Trp Ala Ser
 65                  70                  75                  80

Thr Arg Glu Ser Gly Val Pro Asp Arg Phe Ser Gly Ser Gly Ser Gly
                85                  90                  95
```

-continued

```
Thr Asp Phe Thr Leu Thr Ile Ser Ser Leu Gln Ala Glu Asp Val Ala
            100                 105                 110

Val Tyr Tyr Cys Gln Gln Tyr Ser Thr Pro Arg Thr Phe Gly Gln
        115                 120                 125

Gly Thr Lys Val Glu Ile Lys Arg Thr Val Ala Ala Pro Ser Val Phe
    130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

Leu Ser Lys Ala Asp Tyr Glu Lys His Lys Val Tyr Ala Cys Glu Val
    210                 215                 220

Thr His Gln Gly Leu Ser Ser Pro Val Thr Lys Ser Phe Asn Arg Gly
225                 230                 235                 240

Glu Cys Gln Val Gln Leu Gln Glu Ser Gly Pro Gly Leu Val Lys Pro
                245                 250                 255

Ser Glu Thr Leu Ser Leu Thr Cys Thr Val Ser Gly Gly Ser Val Ser
            260                 265                 270

Ser Gly Asp Tyr Tyr Trp Thr Trp Ile Arg Gln Ser Pro Gly Lys Gly
        275                 280                 285

Leu Glu Trp Ile Gly His Ile Tyr Tyr Ser Gly Asn Thr Asn Tyr Asn
    290                 295                 300

Pro Ser Leu Lys Ser Arg Leu Thr Ile Ser Ile Asp Thr Ser Lys Thr
305                 310                 315                 320

Gln Phe Ser Leu Lys Leu Ser Ser Val Thr Ala Ala Asp Thr Ala Ile
                325                 330                 335

Tyr Tyr Cys Val Arg Asp Arg Val Thr Gly Ala Phe Asp Ile Trp Gly
            340                 345                 350

Gln Gly Thr Met Val Thr Val Ser Ser Ala Ser Thr Lys Gly Pro Ser
        355                 360                 365

Val Phe Pro Leu Ala Pro Ser Ser Lys Ser Thr Ser Gly Gly Thr Ala
    370                 375                 380

Ala Leu Gly Cys Leu Val Lys Asp Tyr Phe Pro Glu Pro Val Thr Val
385                 390                 395                 400

Ser Trp Asn Ser Gly Ala Leu Thr Ser Gly Val His Thr Phe Pro Ala
                405                 410                 415

Val Leu Gln Ser Ser Gly Leu Tyr Ser Leu Ser Ser Val Val Thr Val
            420                 425                 430

Pro Ser Ser Ser Leu Gly Thr Gln Thr Tyr Ile Cys Asn Val Asn His
        435                 440                 445

Lys Pro Ser Asn Thr Lys Val Asp Lys Lys Val Glu Pro Lys Ser Cys
    450                 455                 460

Asp Lys Thr His Thr Cys Pro Pro Cys Pro Ala Pro Glu Leu Leu Gly
465                 470                 475                 480

Gly Pro Ser Val Phe Leu Phe Pro Pro Lys Pro Lys Asp Thr Leu Met
                485                 490                 495

Ile Ser Arg Thr Pro Glu Val Thr Cys Val Val Val Asp Val Ser His
            500                 505                 510
```

Glu Asp Pro Glu Val Lys Phe Asn Trp Tyr Val Asp Gly Val Glu Val
            515                 520                 525

His Asn Ala Lys Thr Lys Pro Arg Glu Glu Gln Tyr Asn Ser Thr Tyr
        530                 535                 540

Arg Val Val Ser Val Leu Thr Val Leu His Gln Asp Trp Leu Asn Gly
545                 550                 555                 560

Lys Glu Tyr Lys Cys Lys Val Ser Asn Lys Ala Leu Pro Ala Pro Ile
                565                 570                 575

Glu Lys Thr Ile Ser Lys Ala Lys Gly Gln Pro Arg Glu Pro Gln Val
            580                 585                 590

Tyr Thr Leu Pro Pro Ser Arg Glu Glu Met Thr Lys Asn Gln Val Ser
        595                 600                 605

Leu Thr Cys Leu Val Lys Gly Phe Tyr Pro Ser Asp Ile Ala Val Glu
    610                 615                 620

Trp Glu Ser Asn Gly Gln Pro Glu Asn Asn Tyr Lys Thr Thr Pro Pro
625                 630                 635                 640

Val Leu Asp Ser Asp Gly Ser Phe Phe Leu Tyr Ser Lys Leu Thr Val
                645                 650                 655

Asp Lys Ser Arg Trp Gln Gln Gly Asn Val Phe Ser Cys Ser Val Met
            660                 665                 670

His Glu Ala Leu His Asn His Tyr Thr Gln Lys Ser Leu Ser Leu Ser
        675                 680                 685

Pro Gly Lys
    690

<210> SEQ ID NO 336
<211> LENGTH: 113
<212> TYPE: PRT
<213> ORGANISM: Artificial Sequence
<220> FEATURE:
<223> OTHER INFORMATION: patritu VL

<400> SEQUENCE: 336

Asp Ile Glu Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Ser Asn Arg Asn Tyr Leu Ala Trp Tyr Gln Gln Asn Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys

<210> SEQ ID NO 337
<211> LENGTH: 17
<212> TYPE: PRT
<213> ORGANISM: Artificial Sequence
<220> FEATURE:
<223> OTHER INFORMATION: patritu VL - CDR1

<400> SEQUENCE: 337

Arg Ser Ser Gln Ser Val Leu Tyr Ser Ser Asn Arg Asn Tyr Leu
1               5                   10                  15

Ala

<210> SEQ ID NO 338
<211> LENGTH: 7
<212> TYPE: PRT
<213> ORGANISM: Artificial Sequence
<220> FEATURE:
<223> OTHER INFORMATION: patritu VL CDR2

<400> SEQUENCE: 338

Trp Ala Ser Thr Arg Glu Ser
1               5

<210> SEQ ID NO 339
<211> LENGTH: 8
<212> TYPE: PRT
<213> ORGANISM: Artificial Sequence
<220> FEATURE:
<223> OTHER INFORMATION: patritu VL - CDR3

<400> SEQUENCE: 339

Gln Tyr Tyr Ser Thr Pro Arg Thr
1               5

<210> SEQ ID NO 340
<211> LENGTH: 119
<212> TYPE: PRT
<213> ORGANISM: Artificial Sequence
<220> FEATURE:
<223> OTHER INFORMATION: PaniVH

<400> SEQUENCE: 340

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser
        115

<210> SEQ ID NO 341
<211> LENGTH: 7
<212> TYPE: PRT
<213> ORGANISM: Artificial Sequence
<220> FEATURE:
<223> OTHER INFORMATION: Pani VH - CDR1

<400> SEQUENCE: 341

Ser Gly Asp Tyr Tyr Trp Thr
1               5

```
<210> SEQ ID NO 342
<211> LENGTH: 16
<212> TYPE: PRT
<213> ORGANISM: Artificial Sequence
<220> FEATURE:
<223> OTHER INFORMATION: Pani VH - CDR2

<400> SEQUENCE: 342

His Ile Tyr Tyr Ser Gly Asn Thr Asn Tyr Asn Pro Ser Leu Lys Ser
1               5                   10                  15

<210> SEQ ID NO 343
<211> LENGTH: 9
<212> TYPE: PRT
<213> ORGANISM: Artificial Sequence
<220> FEATURE:
<223> OTHER INFORMATION: Pani VH - CDR3

<400> SEQUENCE: 343

Asp Arg Val Thr Gly Ala Phe Asp Ile
1               5

<210> SEQ ID NO 344
<211> LENGTH: 239
<212> TYPE: PRT
<213> ORGANISM: Artificial Sequence
<220> FEATURE:
<223> OTHER INFORMATION: Short Chain 1 (Patritumab VH -CH1)

<400> SEQUENCE: 344

Met Glu Phe Gly Leu Ser Trp Leu Phe Leu Val Ala Ile Leu Lys Gly
1               5                   10                  15

Val Gln Cys Gln Val Gln Leu Gln Gln Trp Gly Ala Gly Leu Leu Lys
                20                  25                  30

Pro Ser Glu Thr Leu Ser Leu Thr Cys Ala Val Tyr Gly Gly Ser Phe
            35                  40                  45

Ser Gly Tyr Tyr Trp Ser Trp Ile Arg Gln Pro Pro Gly Lys Gly Leu
        50                  55                  60

Glu Trp Ile Gly Glu Ile Asn His Ser Gly Ser Thr Asn Tyr Asn Pro
65                  70                  75                  80

Ser Leu Lys Ser Arg Val Thr Ile Ser Val Glu Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Lys Trp Thr Trp Tyr Phe Asp Leu Trp Gly Arg
        115                 120                 125

Gly Thr Leu Val Thr Val Ser Ser Ala Ser Thr Lys Gly Pro Ser Val
130                 135                 140

Phe Pro Leu Ala Pro Ser Ser Lys Ser Thr Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys
225                 230                 235
```

<210> SEQ ID NO 345
<211> LENGTH: 117
<212> TYPE: PRT
<213> ORGANISM: Artificial Sequence
<220> FEATURE:
<223> OTHER INFORMATION: Patritumab VH

<400> SEQUENCE: 345

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Glu Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Trp Thr Trp Tyr Phe Asp Leu Trp Gly Arg Gly Thr Leu
            100                 105                 110

Val Thr Val Ser Ser
        115
```

<210> SEQ ID NO 346
<211> LENGTH: 5
<212> TYPE: PRT
<213> ORGANISM: Artificial Sequence
<220> FEATURE:
<223> OTHER INFORMATION: Patritumab VH - CDR1

<400> SEQUENCE: 346

```
Gly Tyr Tyr Trp Ser
1               5
```

<210> SEQ ID NO 347
<211> LENGTH: 16
<212> TYPE: PRT
<213> ORGANISM: Artificial Sequence
<220> FEATURE:
<223> OTHER INFORMATION: Patritumab VH - CDR2

<400> SEQUENCE: 347

```
Glu Ile Asn His Ser Gly Ser Thr Asn Tyr Asn Pro Ser Leu Lys Ser
1               5                   10                  15
```

<210> SEQ ID NO 348
<211> LENGTH: 9
<212> TYPE: PRT
<213> ORGANISM: Artificial Sequence
<220> FEATURE:
<223> OTHER INFORMATION: Patritumab VH - CDR3

<400> SEQUENCE: 348

```
Asp Lys Trp Thr Trp Tyr Phe Asp Leu
1               5
```

<210> SEQ ID NO 349
<211> LENGTH: 237
<212> TYPE: PRT
<213> ORGANISM: Artificial Sequence
<220> FEATURE:
<223> OTHER INFORMATION: Short Chain 2 (Pani VL-hCk)

<400> SEQUENCE: 349

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Gln Ala Ser
        35                  40                  45

Gln Asp Ile Ser Asn Tyr Leu Asn Trp Tyr Gln Gln Lys Pro Gly Lys
    50                  55                  60

Ala Pro Lys Leu Leu Ile Tyr Asp Ala Ser Asn Leu Glu Thr Gly Val
65                  70                  75                  80

Pro Ser Pro Arg Phe Ser Gly Ser Gly Ser Gly Thr Asp Phe Thr Phe
                85                  90                  95

Thr Ile Ser Ser Leu Gln Pro Glu Asp Ile Ala Thr Tyr Phe Cys Gln
            100                 105                 110

His Phe Asp His Leu Pro Leu Ala Phe Gly Gly Gly Thr Lys Val Glu
        115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
210                 215                 220

Ser Ser Pro Val Thr Lys Ser Phe Asn Arg Gly Glu Cys
225                 230                 235

<210> SEQ ID NO 350
<211> LENGTH: 107
<212> TYPE: PRT
<213> ORGANISM: Artificial Sequence
<220> FEATURE:
<223> OTHER INFORMATION: Pani VL

<400> SEQUENCE: 350

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys

<210> SEQ ID NO 351
<211> LENGTH: 11
<212> TYPE: PRT
<213> ORGANISM: Artificial Sequence
<220> FEATURE:
<223> OTHER INFORMATION: Pani VL - CDR1

<400> SEQUENCE: 351

```
Gln Ala Ser Gln Asp Ile Ser Asn Tyr Leu Asn
1               5                   10
```

<210> SEQ ID NO 352
<211> LENGTH: 7
<212> TYPE: PRT
<213> ORGANISM: Artificial Sequence
<220> FEATURE:
<223> OTHER INFORMATION: Pani VL - CDR2

<400> SEQUENCE: 352

```
Asp Ala Ser Asn Leu Glu Thr
1               5
```

<210> SEQ ID NO 353
<211> LENGTH: 9
<212> TYPE: PRT
<213> ORGANISM: Artificial Sequence
<220> FEATURE:
<223> OTHER INFORMATION: Pani VL - CDR3

<400> SEQUENCE: 353

```
Gln His Phe Asp His Leu Pro Leu Ala
1               5
```

<210> SEQ ID NO 354
<211> LENGTH: 683
<212> TYPE: PRT
<213> ORGANISM: Artificial Sequence
<220> FEATURE:
<223> OTHER INFORMATION: Long Chain (Panitu VL-hCk-Patritu-hCg1)

<400> SEQUENCE: 354

```
Met Asp Met Arg Val Pro Ala Gln Leu Leu Gly Leu Leu Leu Trp
1               5                   10                  15

Phe Pro Gly Ser Arg Cys Asp Ile Gln Met Thr Gln Ser Pro Ser
                20                  25                  30

Leu Ser Ala Ser Val Gly Asp Arg Val Thr Ile Thr Cys Gln Ala Ser
            35                  40                  45

Gln Asp Ile Ser Asn Tyr Leu Asn Trp Tyr Gln Gln Lys Pro Gly Lys
    50                  55                  60

Ala Pro Lys Leu Leu Ile Tyr Asp Ala Ser Asn Leu Glu Thr Gly Val
65                  70                  75                  80

Pro Ser Arg Phe Ser Gly Ser Gly Ser Gly Thr Asp Phe Thr Phe Thr
                85                  90                  95

Ile Ser Ser Leu Gln Pro Glu Asp Ile Ala Thr Tyr Phe Cys Gln His
            100                 105                 110

Phe Asp His Leu Pro Leu Ala Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
```

-continued

```
            145                 150                 155                 160
        Phe Tyr Pro Arg Glu Ala Lys Val Gln Trp Lys Val Asp Asn Ala Leu
                        165                 170                 175
        Gln Ser Gly Asn Ser Gln Glu Ser Val Thr Glu Gln Asp Ser Lys Asp
                        180                 185                 190
        Ser Thr Tyr Ser Leu Ser Ser Thr Leu Thr Leu Ser Lys Ala Asp Tyr
                        195                 200                 205
        Glu Lys His Lys Val Tyr Ala Cys Glu Val Thr His Gln Gly Leu Ser
                        210                 215                 220
        Ser Pro Val Thr Lys Ser Phe Asn Arg Gly Glu Cys Gln Val Gln Leu
        225                 230                 235                 240
        Gln Gln Trp Gly Ala Gly Leu Leu Lys Pro Ser Glu Thr Leu Ser Leu
                        245                 250                 255
        Thr Cys Ala Val Tyr Gly Gly Ser Phe Ser Gly Tyr Tyr Trp Ser Trp
                        260                 265                 270
        Ile Arg Gln Pro Pro Gly Lys Gly Leu Glu Trp Ile Gly Glu Ile Asn
                        275                 280                 285
        His Ser Gly Ser Thr Asn Tyr Asn Pro Ser Leu Lys Ser Arg Val Thr
                        290                 295                 300
        Ile Ser Val Glu Thr Ser Lys Asn Gln Phe Ser Leu Lys Leu Ser Ser
        305                 310                 315                 320
        Val Thr Ala Ala Asp Thr Ala Val Tyr Tyr Cys Ala Arg Asp Lys Trp
                        325                 330                 335
        Thr Trp Tyr Phe Asp Leu Trp Gly Arg Gly Thr Leu Val Thr Val Ser
                        340                 345                 350
        Ser Ala Ser Thr Lys Gly Pro Ser Val Phe Pro Leu Ala Pro Ser Ser
                        355                 360                 365
        Lys Ser Thr Ser Gly Gly Thr Ala Ala Leu Gly Cys Leu Val Lys Asp
        370                 375                 380
        Tyr Phe Pro Glu Pro Val Thr Val Ser Trp Asn Ser Gly Ala Leu Thr
        385                 390                 395                 400
        Ser Gly Val His Thr Phe Pro Ala Val Leu Gln Ser Ser Gly Leu Tyr
                        405                 410                 415
        Ser Leu Ser Ser Val Val Thr Val Pro Ser Ser Ser Leu Gly Thr Gln
                        420                 425                 430
        Thr Tyr Ile Cys Asn Val Asn His Lys Pro Ser Asn Thr Lys Val Asp
                        435                 440                 445
        Lys Lys Val Glu Pro Lys Ser Cys Asp Lys Thr His Thr Cys Pro Pro
        450                 455                 460
        Cys Pro Ala Pro Glu Leu Leu Gly Gly Pro Ser Val Phe Leu Phe Pro
        465                 470                 475                 480
        Pro Lys Pro Lys Asp Thr Leu Met Ile Ser Arg Thr Pro Glu Val Thr
                        485                 490                 495
        Cys Val Val Val Asp Val Ser His Glu Asp Pro Glu Val Lys Phe Asn
                        500                 505                 510
        Trp Tyr Val Asp Gly Val Glu Val His Asn Ala Lys Thr Lys Pro Arg
                        515                 520                 525
        Glu Glu Gln Tyr Asn Ser Thr Tyr Arg Val Val Ser Val Leu Thr Val
                        530                 535                 540
        Leu His Gln Asp Trp Leu Asn Gly Lys Glu Tyr Lys Cys Lys Val Ser
        545                 550                 555                 560
        Asn Lys Ala Leu Pro Ala Pro Ile Glu Lys Thr Ile Ser Lys Ala Lys
                        565                 570                 575
```

```
Gly Gln Pro Arg Glu Pro Gln Val Tyr Thr Leu Pro Pro Ser Arg Glu
            580                 585                 590

Glu Met Thr Lys Asn Gln Val Ser Leu Thr Cys Leu Val Lys Gly Phe
            595                 600                 605

Tyr Pro Ser Asp Ile Ala Val Glu Trp Glu Ser Asn Gly Gln Pro Glu
            610                 615                 620

Asn Asn Tyr Lys Thr Thr Pro Pro Val Leu Asp Ser Asp Gly Ser Phe
625                 630                 635                 640

Phe Leu Tyr Ser Lys Leu Thr Val Asp Lys Ser Arg Trp Gln Gln Gly
            645                 650                 655

Asn Val Phe Ser Cys Ser Val Met His Glu Ala Leu His Asn His Tyr
            660                 665                 670

Thr Gln Lys Ser Leu Ser Leu Ser Pro Gly Lys
            675                 680

<210> SEQ ID NO 355
<211> LENGTH: 107
<212> TYPE: PRT
<213> ORGANISM: Artificial Sequence
<220> FEATURE:
<223> OTHER INFORMATION: Panitu VL

<400> SEQUENCE: 355

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105

<210> SEQ ID NO 356
<211> LENGTH: 11
<212> TYPE: PRT
<213> ORGANISM: Artificial Sequence
<220> FEATURE:
<223> OTHER INFORMATION: Panitu VL - CDR1

<400> SEQUENCE: 356

Gln Ala Ser Gln Asp Ile Ser Asn Tyr Leu Asn
1               5                   10

<210> SEQ ID NO 357
<211> LENGTH: 7
<212> TYPE: PRT
<213> ORGANISM: Artificial Sequence
<220> FEATURE:
<223> OTHER INFORMATION: Panitu VL CDR2

<400> SEQUENCE: 357

Asp Ala Ser Asn Leu Glu Thr
1               5
```

```
<210> SEQ ID NO 358
<211> LENGTH: 9
<212> TYPE: PRT
<213> ORGANISM: Artificial Sequence
<220> FEATURE:
<223> OTHER INFORMATION: Panitu VL - CDR3

<400> SEQUENCE: 358

Gln His Phe Asp His Leu Pro Leu Ala
1               5

<210> SEQ ID NO 359
<211> LENGTH: 117
<212> TYPE: PRT
<213> ORGANISM: Artificial Sequence
<220> FEATURE:
<223> OTHER INFORMATION: PatrituVH

<400> SEQUENCE: 359

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Glu Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Trp Thr Trp Tyr Phe Asp Leu Trp Gly Arg Gly Thr Leu
            100                 105                 110

Val Thr Val Ser Ser
        115

<210> SEQ ID NO 360
<211> LENGTH: 5
<212> TYPE: PRT
<213> ORGANISM: Artificial Sequence
<220> FEATURE:
<223> OTHER INFORMATION: Patritu VH - CDR1

<400> SEQUENCE: 360

Gly Tyr Tyr Trp Ser
1               5

<210> SEQ ID NO 361
<211> LENGTH: 16
<212> TYPE: PRT
<213> ORGANISM: Artificial Sequence
<220> FEATURE:
<223> OTHER INFORMATION: Patritu VH - CDR2

<400> SEQUENCE: 361

Glu Ile Asn His Ser Gly Ser Thr Asn Tyr Asn Pro Ser Leu Lys Ser
1               5                   10                  15

<210> SEQ ID NO 362
<211> LENGTH: 9
<212> TYPE: PRT
<213> ORGANISM: Artificial Sequence
<220> FEATURE:
```

<223> OTHER INFORMATION: Patritu VH - CDR3

<400> SEQUENCE: 362

Asp Lys Trp Thr Trp Tyr Phe Asp Leu
1               5

<210> SEQ ID NO 363
<211> LENGTH: 241
<212> TYPE: PRT
<213> ORGANISM: Artificial Sequence
<220> FEATURE:
<223> OTHER INFORMATION: Short Chain 1 (Panitu VH -CH1)

<400> SEQUENCE: 363

Met Glu Phe Gly Leu Ser Trp Leu Phe Leu Val Ala Ile Leu Lys Gly
1               5                   10                  15

Val Gln Cys Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Val
        35                  40                  45

Ser Ser Gly Asp Tyr Tyr Trp Thr Trp Ile Arg Gln Ser Pro Gly Lys
    50                  55                  60

Gly Leu Glu Trp Ile Gly His Ile Tyr Tyr Ser Gly Asn Thr Asn Tyr
65                  70                  75                  80

Asn Pro Ser Leu Lys Ser Arg Leu Thr Ile Ser Ile Asp Thr Ser Lys
                85                  90                  95

Thr Gln Phe Ser Leu Lys Leu Ser Ser Val Thr Ala Ala Asp Thr Ala
            100                 105                 110

Ile Tyr Tyr Cys Val Arg Asp Arg Val Thr Gly Ala Phe Asp Ile Trp
        115                 120                 125

Gly Gln Gly Thr Met Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys

<210> SEQ ID NO 364
<211> LENGTH: 119
<212> TYPE: PRT
<213> ORGANISM: Artificial Sequence
<220> FEATURE:
<223> OTHER INFORMATION: Panitu VH

<400> SEQUENCE: 364

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

```
Asp Tyr Tyr Trp Thr Trp Ile Arg Gln Ser Pro Gly Lys Gly Leu Glu
            35                  40                  45

Trp Ile Gly His Ile Tyr Tyr Ser Gly Asn Thr Asn Tyr Asn Pro Ser
 50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser
        115

<210> SEQ ID NO 365
<211> LENGTH: 5
<212> TYPE: PRT
<213> ORGANISM: Artificial Sequence
<220> FEATURE:
<223> OTHER INFORMATION: Panitu VH - CDR1

<400> SEQUENCE: 365

Asp Tyr Tyr Trp Thr
1               5

<210> SEQ ID NO 366
<211> LENGTH: 16
<212> TYPE: PRT
<213> ORGANISM: Artificial Sequence
<220> FEATURE:
<223> OTHER INFORMATION: Panitu VH - CDR2

<400> SEQUENCE: 366

His Ile Tyr Tyr Ser Gly Asn Thr Asn Tyr Asn Pro Ser Leu Lys Ser
1               5                   10                  15

<210> SEQ ID NO 367
<211> LENGTH: 9
<212> TYPE: PRT
<213> ORGANISM: Artificial Sequence
<220> FEATURE:
<223> OTHER INFORMATION: Panitu VH - CDR3

<400> SEQUENCE: 367

Asp Arg Val Thr Gly Ala Phe Asp Ile
1               5

<210> SEQ ID NO 368
<211> LENGTH: 242
<212> TYPE: PRT
<213> ORGANISM: Artificial Sequence
<220> FEATURE:
<223> OTHER INFORMATION: Short Chain 2 (Patritu VL-hCk)

<400> SEQUENCE: 368

Met Asp Met Arg Val Pro Ala Gln Leu Leu Gly Leu Leu Leu Leu Trp
1               5                   10                  15

Phe Pro Gly Ser Arg Cys Asp Ile Glu Met Thr Gln Ser Pro Asp Ser
            20                  25                  30

Leu Ala Val Ser Leu Gly Glu Arg Ala Thr Ile Asn Cys Arg Ser Ser
        35                  40                  45

Gln Ser Val Leu Tyr Ser Ser Ser Asn Arg Asn Tyr Leu Ala Trp Tyr
    50                  55                  60
```

Gln Gln Asn Pro Gly Gln Pro Pro Lys Leu Leu Ile Tyr Trp Ala Ser
65                  70                  75                  80

Thr Arg Glu Ser Gly Val Pro Asp Arg Phe Ser Gly Ser Gly Ser Gly
            85                  90                  95

Thr Asp Phe Thr Leu Thr Ile Ser Ser Leu Gln Ala Glu Asp Val Ala
            100                 105                 110

Val Tyr Tyr Cys Gln Gln Tyr Tyr Ser Thr Pro Arg Thr Phe Gly Gln
        115                 120                 125

Gly Thr Lys Val Glu Ile Lys Arg Thr Val Ala Ala Pro Ser Val Phe
    130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

Leu Ser Lys Ala Asp Tyr Glu Lys His Lys Val Tyr Ala Cys Glu Val
    210                 215                 220

Thr His Gln Gly Leu Ser Ser Pro Val Thr Lys Ser Phe Asn Arg Gly
225                 230                 235                 240

Glu Cys

<210> SEQ ID NO 369
<211> LENGTH: 113
<212> TYPE: PRT
<213> ORGANISM: Artificial Sequence
<220> FEATURE:
<223> OTHER INFORMATION: Patritu VL

<400> SEQUENCE: 369

Asp Ile Glu Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Ser Asn Arg Asn Tyr Leu Ala Trp Tyr Gln Gln Asn Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys

<210> SEQ ID NO 370
<211> LENGTH: 17
<212> TYPE: PRT
<213> ORGANISM: Artificial Sequence
<220> FEATURE:
<223> OTHER INFORMATION: Patritu VL - CDR1

<400> SEQUENCE: 370

```
Arg Ser Ser Gln Ser Val Leu Tyr Ser Ser Asn Arg Asn Tyr Leu
1               5                   10                  15

Ala

<210> SEQ ID NO 371
<211> LENGTH: 7
<212> TYPE: PRT
<213> ORGANISM: Artificial Sequence
<220> FEATURE:
<223> OTHER INFORMATION: Patritu  VL - CDR2

<400> SEQUENCE: 371

Trp Ala Ser Thr Arg Glu Ser
1               5

<210> SEQ ID NO 372
<211> LENGTH: 9
<212> TYPE: PRT
<213> ORGANISM: Artificial Sequence
<220> FEATURE:
<223> OTHER INFORMATION: Patritu  VL - CDR3

<400> SEQUENCE: 372

Gln Gln Tyr Tyr Ser Thr Pro Arg Thr
1               5

<210> SEQ ID NO 373
<211> LENGTH: 678
<212> TYPE: PRT
<213> ORGANISM: Artificial Sequence
<220> FEATURE:
<223> OTHER INFORMATION: Long Chain (1B12 VL-hCk-Nivolu VH-hCg1Mut)

<400> SEQUENCE: 373

Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Ala Thr
            20                  25                  30

Leu Ser Leu Ser Pro Gly Glu Arg Ala Thr Leu Ser Cys Arg Ala Ser
        35                  40                  45

Gln Ser Val Ser Ser Tyr Leu Ala Trp Tyr Gln Gln Lys Pro Gly Gln
    50                  55                  60

Ala Pro Arg Leu Leu Ile Tyr Asp Ala Ser Asn Arg Ala Thr Gly Ile
65                  70                  75                  80

Pro Ala Arg Phe Ser Gly Ser Gly Ser Gly Thr Asp Phe Thr Leu Thr
                85                  90                  95

Ile Ser Ser Leu Glu Pro Glu Asp Phe Ala Val Tyr Tyr Cys Gln Gln
            100                 105                 110

Arg Ser Asn Trp Pro Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205
```

-continued

```
Lys His Lys Val Tyr Ala Cys Glu Val Thr His Gln Gly Leu Ser Ser
    210                 215                 220
Pro Val Thr Lys Ser Phe Asn Arg Gly Glu Cys Gln Val Gln Leu Val
225                 230                 235                 240
Glu Ser Gly Gly Gly Val Val Gln Pro Gly Arg Ser Leu Arg Leu Asp
                245                 250                 255
Cys Lys Ala Ser Gly Ile Thr Phe Ser Asn Ser Gly Met His Trp Val
            260                 265                 270
Arg Gln Ala Pro Gly Lys Gly Leu Glu Trp Val Ala Val Ile Trp Tyr
        275                 280                 285
Asp Gly Ser Lys Arg Tyr Tyr Ala Asp Ser Val Lys Gly Arg Phe Thr
    290                 295                 300
Ile Ser Arg Asp Asn Ser Lys Asn Thr Leu Phe Leu Gln Met Asn Ser
305                 310                 315                 320
Leu Arg Ala Glu Asp Thr Ala Val Tyr Tyr Cys Ala Thr Asn Asp Asp
                325                 330                 335
Tyr Trp Gly Gln Gly Thr Leu Val Thr Val Ser Ser Ala Ser Thr Lys
            340                 345                 350
Gly Pro Ser Val Phe Pro Leu Ala Pro Ser Ser Lys Ser Thr Ser Gly
        355                 360                 365
Gly Thr Ala Ala Leu Gly Cys Leu Val Lys Asp Tyr Phe Pro Glu Pro
    370                 375                 380
Val Thr Val Ser Trp Asn Ser Gly Ala Leu Thr Ser Gly Val His Thr
385                 390                 395                 400
Phe Pro Ala Val Leu Gln Ser Ser Gly Leu Tyr Ser Leu Ser Ser Val
                405                 410                 415
Val Thr Val Pro Ser Ser Ser Leu Gly Thr Gln Thr Tyr Ile Cys Asn
            420                 425                 430
Val Asn His Lys Pro Ser Asn Thr Lys Val Asp Lys Lys Val Glu Pro
        435                 440                 445
Lys Ser Cys Asp Lys Thr His Thr Cys Pro Pro Cys Pro Ala Pro Glu
    450                 455                 460
Leu Leu Gly Gly Pro Ser Val Phe Leu Phe Pro Pro Lys Pro Lys Asp
465                 470                 475                 480
Thr Leu Met Ile Ser Arg Thr Pro Glu Val Thr Cys Val Val Val Asp
                485                 490                 495
Val Ser His Glu Asp Pro Glu Val Lys Phe Asn Trp Tyr Val Asp Gly
            500                 505                 510
Val Glu Val His Asn Ala Lys Thr Lys Pro Arg Glu Glu Gln Tyr Asn
        515                 520                 525
Ser Thr Tyr Arg Val Val Ser Val Leu Thr Val Leu His Gln Asp Trp
    530                 535                 540
Leu Asn Gly Lys Glu Tyr Lys Cys Lys Val Ser Asn Lys Ala Leu Pro
545                 550                 555                 560
Ala Pro Ile Glu Lys Thr Ile Ser Lys Ala Lys Gly Gln Pro Arg Glu
                565                 570                 575
Pro Gln Val Tyr Thr Leu Pro Pro Ser Arg Glu Glu Met Thr Lys Asn
            580                 585                 590
Gln Val Ser Leu Thr Cys Leu Val Lys Gly Phe Tyr Pro Ser Asp Ile
        595                 600                 605
Ala Val Glu Trp Glu Ser Asn Gly Gln Pro Glu Asn Asn Tyr Lys Thr
    610                 615                 620
```

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
            645                 650                 655

Ser Val Met His Glu Ala Leu His Asn His Tyr Thr Gln Lys Ser Leu
        660                 665                 670

Ser Leu Ser Pro Gly Lys
        675

<210> SEQ ID NO 374
<211> LENGTH: 106
<212> TYPE: PRT
<213> ORGANISM: Artificial Sequence
<220> FEATURE:
<223> OTHER INFORMATION: I1B12 VL

<400> SEQUENCE: 374

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 375
<211> LENGTH: 11
<212> TYPE: PRT
<213> ORGANISM: Artificial Sequence
<220> FEATURE:
<223> OTHER INFORMATION: 1B12 VL - CDR1

<400> SEQUENCE: 375

Arg Ala Ser Gln Ser Val Ser Ser Tyr Leu Ala
1               5                   10

<210> SEQ ID NO 376
<211> LENGTH: 7
<212> TYPE: PRT
<213> ORGANISM: Artificial Sequence
<220> FEATURE:
<223> OTHER INFORMATION: 1B12 VL - CDR2

<400> SEQUENCE: 376

Asp Ala Ser Asn Arg Ala Thr
1               5

<210> SEQ ID NO 377
<211> LENGTH: 8
<212> TYPE: PRT
<213> ORGANISM: Artificial Sequence
<220> FEATURE:
<223> OTHER INFORMATION: 1B12 VL - CDR3

<400> SEQUENCE: 377

Gln Gln Arg Ser Asn Trp Pro Thr
1               5

<210> SEQ ID NO 378
<211> LENGTH: 113
<212> TYPE: PRT
<213> ORGANISM: Artificial Sequence
<220> FEATURE:
<223> OTHER INFORMATION: NivoluVH

<400> SEQUENCE: 378

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 379
<211> LENGTH: 5
<212> TYPE: PRT
<213> ORGANISM: Artificial Sequence
<220> FEATURE:
<223> OTHER INFORMATION: NivoluVH - CDR1

<400> SEQUENCE: 379

Asn Ser Gly Met His
1               5

<210> SEQ ID NO 380
<211> LENGTH: 17
<212> TYPE: PRT
<213> ORGANISM: Artificial Sequence
<220> FEATURE:
<223> OTHER INFORMATION: NivoluVH - CDR2

<400> SEQUENCE: 380

Val Ile Trp Tyr Asp Gly Ser Lys Arg Tyr Tyr Ala Asp Ser Val Lys
1               5                   10                  15

Gly

<210> SEQ ID NO 381
<211> LENGTH: 4
<212> TYPE: PRT
<213> ORGANISM: Artificial Sequence
<220> FEATURE:
<223> OTHER INFORMATION: NivoluVH - CDR3

<400> SEQUENCE: 381

Asn Asp Asp Tyr
1

<210> SEQ ID NO 382

```
<211> LENGTH: 245
<212> TYPE: PRT
<213> ORGANISM: Artificial Sequence
<220> FEATURE:
<223> OTHER INFORMATION: Short Chain 1 (1B12 VH-CH1)

<400> SEQUENCE: 382

Met Glu Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ser Ser Val Lys Val Ser Cys Lys Thr Ser Gly Asp Thr Phe
        35                  40                  45

Ser Ser Tyr Ala Ile Ser Trp Val Arg Gln Ala Pro Gly Gln Gly Leu
    50                  55                  60

Glu Trp Met Gly Gly Ile Ile Pro Ile Phe Gly Arg Ala His Tyr Ala
65                  70                  75                  80

Gln Lys Phe Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Phe Cys Ala Arg Lys Phe His Phe Val Ser Gly Ser Pro Phe Gly
        115                 120                 125

Met Asp Val Trp Gly Gln Gly Thr Thr Val Thr Val Ser Ser Ala Ser
130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys
                245

<210> SEQ ID NO 383
<211> LENGTH: 123
<212> TYPE: PRT
<213> ORGANISM: Artificial Sequence
<220> FEATURE:
<223> OTHER INFORMATION: 1B12 VH

<400> SEQUENCE: 383

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Arg Ala His Tyr Ala Gln Lys Phe
    50                  55                  60

Gln Gly Arg Val Thr Ile Thr Ala Asp Glu Ser Thr Ser Thr Ala Tyr
```

```
                65                  70                  75                  80
Met Glu Leu Ser Ser Leu Arg Ser Glu Asp Thr Ala Val Tyr Phe Cys
                        85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120

<210> SEQ ID NO 384
<211> LENGTH: 5
<212> TYPE: PRT
<213> ORGANISM: Artificial Sequence
<220> FEATURE:
<223> OTHER INFORMATION: 1B12 VH - CDR1

<400> SEQUENCE: 384

Ser Tyr Ala Ile Ser
1               5

<210> SEQ ID NO 385
<211> LENGTH: 17
<212> TYPE: PRT
<213> ORGANISM: Artificial Sequence
<220> FEATURE:
<223> OTHER INFORMATION: 1B12 VH - CDR2

<400> SEQUENCE: 385

Gly Ile Ile Pro Ile Phe Gly Arg Ala His Tyr Ala Gln Lys Phe Gln
1               5                   10                  15

Gly

<210> SEQ ID NO 386
<211> LENGTH: 14
<212> TYPE: PRT
<213> ORGANISM: Artificial Sequence
<220> FEATURE:
<223> OTHER INFORMATION: 1B12 VH - CDR3

<400> SEQUENCE: 386

Lys Phe His Phe Val Ser Gly Ser Pro Phe Gly Met Asp Val
1               5                   10

<210> SEQ ID NO 387
<211> LENGTH: 236
<212> TYPE: PRT
<213> ORGANISM: Artificial Sequence
<220> FEATURE:
<223> OTHER INFORMATION: Short Chain 2 (Nivolu VL-hCK)

<400> SEQUENCE: 387

Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Ala Thr
            20                  25                  30

Leu Ser Leu Ser Pro Gly Glu Arg Ala Thr Leu Ser Cys Arg Ala Ser
        35                  40                  45

Gln Ser Val Ser Ser Tyr Leu Ala Trp Tyr Gln Gln Lys Pro Gly Gln
    50                  55                  60

Ala Pro Arg Leu Leu Ile Tyr Asp Ala Ser Asn Arg Ala Thr Gly Ile
65                  70                  75                  80

Pro Ala Arg Phe Ser Gly Ser Gly Ser Gly Thr Asp Phe Thr Leu Thr
                85                  90                  95
```

```
Ile Ser Ser Leu Glu Pro Glu Asp Phe Ala Val Tyr Tyr Cys Gln Gln
            100                 105                 110

Ser Ser Asn Trp Pro Arg Thr Phe Gly Gln Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 388
<211> LENGTH: 107
<212> TYPE: PRT
<213> ORGANISM: Artificial Sequence
<220> FEATURE:
<223> OTHER INFORMATION: Nivolu VL

<400> SEQUENCE: 388

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 389
<211> LENGTH: 11
<212> TYPE: PRT
<213> ORGANISM: Artificial Sequence
<220> FEATURE:
<223> OTHER INFORMATION: Nivolu VL - CDR1

<400> SEQUENCE: 389

Arg Ala Ser Gln Ser Val Ser Ser Tyr Leu Ala
1               5                   10

<210> SEQ ID NO 390
<211> LENGTH: 7
<212> TYPE: PRT
<213> ORGANISM: Artificial Sequence
<220> FEATURE:
<223> OTHER INFORMATION: Nivolu VL - CDR2
```

```
<400> SEQUENCE: 390

Asp Ala Ser Asn Arg Ala Thr
1               5

<210> SEQ ID NO 391
<211> LENGTH: 9
<212> TYPE: PRT
<213> ORGANISM: Artificial Sequence
<220> FEATURE:
<223> OTHER INFORMATION: Nivolu VL - CDR3

<400> SEQUENCE: 391

Gln Gln Ser Ser Asn Trp Pro Arg Thr
1               5

<210> SEQ ID NO 392
<211> LENGTH: 682
<212> TYPE: PRT
<213> ORGANISM: Artificial Sequence
<220> FEATURE:
<223> OTHER INFORMATION: Long Chain (Ofatu VL-hCk-Epratu VH-hCg1)

<400> SEQUENCE: 392

Met Asp Met Arg Val Pro Ala Gln Leu Leu Gly Leu Leu Leu Leu Trp
1               5                  10                  15

Phe Pro Gly Ser Arg Cys Glu Ile Val Leu Thr Gln Ser Pro Ala Thr
            20                  25                  30

Leu Ser Leu Ser Pro Gly Glu Arg Ala Thr Leu Ser Cys Arg Ala Ser
        35                  40                  45

Gln Ser Val Ser Ser Tyr Leu Ala Trp Tyr Gln Gln Lys Pro Gly Gln
    50                  55                  60

Ala Pro Arg Leu Leu Ile Tyr Asp Ala Ser Asn Arg Ala Thr Gly Ile
65                  70                  75                  80

Pro Ala Arg Phe Ser Gly Ser Gly Ser Gly Thr Asp Phe Thr Leu Thr
                85                  90                  95

Ile Ser Ser Leu Glu Pro Glu Asp Phe Ala Val Tyr Tyr Cys Gln Gln
            100                 105                 110

Arg Ser Asn Trp Pro Ile Thr Phe Gly Gln Gly Thr Arg Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Gln Val Gln Leu
225                 230                 235                 240

Val Gln Ser Gly Ala Glu Val Lys Lys Pro Gly Ser Ser Val Lys Val
                245                 250                 255

Ser Cys Lys Ala Ser Gly Tyr Thr Phe Thr Ser Tyr Trp Leu His Trp
            260                 265                 270
```

```
Val Arg Gln Ala Pro Gly Gln Gly Leu Glu Trp Ile Gly Tyr Ile Asn
            275                 280                 285

Pro Arg Asn Asp Tyr Thr Glu Tyr Asn Gln Asn Phe Lys Asp Lys Ala
        290                 295                 300

Thr Ile Thr Ala Asp Glu Ser Thr Asn Thr Ala Tyr Met Glu Leu Ser
305                 310                 315                 320

Ser Leu Arg Ser Glu Asp Thr Ala Phe Tyr Phe Cys Ala Arg Arg Asp
                325                 330                 335

Ile Thr Thr Phe Tyr Trp Gly Gln Gly Thr Thr Val Thr Val Ser Ser
            340                 345                 350

Ala Ser Thr Lys Gly Pro Ser Val Phe Pro Leu Ala Pro Ser Ser Lys
            355                 360                 365

Ser Thr Ser Gly Gly Thr Ala Ala Leu Gly Cys Leu Val Lys Asp Tyr
        370                 375                 380

Phe Pro Glu Pro Val Thr Val Ser Trp Asn Ser Gly Ala Leu Thr Ser
385                 390                 395                 400

Gly Val His Thr Phe Pro Ala Val Leu Gln Ser Ser Gly Leu Tyr Ser
                405                 410                 415

Leu Ser Ser Val Val Thr Val Pro Ser Ser Ser Leu Gly Thr Gln Thr
            420                 425                 430

Tyr Ile Cys Asn Val Asn His Lys Pro Ser Asn Thr Lys Val Asp Lys
            435                 440                 445

Lys Val Glu Pro Lys Ser Cys Asp Lys Thr His Thr Cys Pro Pro Cys
        450                 455                 460

Pro Ala Pro Glu Leu Leu Gly Gly Pro Ser Val Phe Leu Phe Pro Pro
465                 470                 475                 480

Lys Pro Lys Asp Thr Leu Met Ile Ser Arg Thr Pro Glu Val Thr Cys
                485                 490                 495

Val Val Val Asp Val Ser His Glu Asp Pro Glu Val Lys Phe Asn Trp
            500                 505                 510

Tyr Val Asp Gly Val Glu Val His Asn Ala Lys Thr Lys Pro Arg Glu
            515                 520                 525

Glu Gln Tyr Asn Ser Thr Tyr Arg Val Val Ser Val Leu Thr Val Leu
        530                 535                 540

His Gln Asp Trp Leu Asn Gly Lys Glu Tyr Lys Cys Lys Val Ser Asn
545                 550                 555                 560

Lys Ala Leu Pro Ala Pro Ile Glu Lys Thr Ile Ser Lys Ala Lys Gly
                565                 570                 575

Gln Pro Arg Glu Pro Gln Val Tyr Thr Leu Pro Pro Ser Arg Glu Glu
            580                 585                 590

Met Thr Lys Asn Gln Val Ser Leu Thr Cys Leu Val Lys Gly Phe Tyr
            595                 600                 605

Pro Ser Asp Ile Ala Val Glu Trp Glu Ser Asn Gly Gln Pro Glu Asn
        610                 615                 620

Asn Tyr Lys Thr Thr Pro Pro Val Leu Asp Ser Asp Gly Ser Phe Phe
625                 630                 635                 640

Leu Tyr Ser Lys Leu Thr Val Asp Lys Ser Arg Trp Gln Gln Gly Asn
                645                 650                 655

Val Phe Ser Cys Ser Val Met His Glu Ala Leu His Asn His Tyr Thr
            660                 665                 670

Gln Lys Ser Leu Ser Leu Ser Pro Gly Lys
            675                 680
```

<210> SEQ ID NO 393
<211> LENGTH: 107
<212> TYPE: PRT
<213> ORGANISM: Artificial Sequence
<220> FEATURE:
<223> OTHER INFORMATION: OfatuVL

<400> SEQUENCE: 393

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 394
<211> LENGTH: 11
<212> TYPE: PRT
<213> ORGANISM: Artificial Sequence
<220> FEATURE:
<223> OTHER INFORMATION: Ofatu VL - CDR1

<400> SEQUENCE: 394

Arg Ala Ser Gln Ser Val Ser Ser Tyr Leu Ala
1               5                   10

<210> SEQ ID NO 395
<211> LENGTH: 7
<212> TYPE: PRT
<213> ORGANISM: Artificial Sequence
<220> FEATURE:
<223> OTHER INFORMATION: Ofatu VL - CDR2

<400> SEQUENCE: 395

Asp Ala Ser Asn Arg Ala Thr
1               5

<210> SEQ ID NO 396
<211> LENGTH: 9
<212> TYPE: PRT
<213> ORGANISM: Artificial Sequence
<220> FEATURE:
<223> OTHER INFORMATION: Ofatu VL - CDR3

<400> SEQUENCE: 396

Gln Gln Arg Ser Asn Trp Pro Ile Thr
1               5

<210> SEQ ID NO 397
<211> LENGTH: 116
<212> TYPE: PRT
<213> ORGANISM: Artificial Sequence
<220> FEATURE:
<223> OTHER INFORMATION: Epratu VH

<400> SEQUENCE: 397

```
Gln Val Gln Leu Val Gln Ser Gly Ala Glu Val Lys Pro Gly Ser
1               5                   10                  15

Ser Val Lys Val Ser Cys Lys Ala Ser Gly Tyr Thr Phe Thr Ser Tyr
            20                  25                  30

Trp Leu His Trp Val Arg Gln Ala Pro Gly Gln Gly Leu Glu Trp Ile
        35                  40                  45

Gly Tyr Ile Asn Pro Arg Asn Asp Tyr Thr Glu Tyr Asn Gln Asn Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Arg Asp Ile Thr Thr Phe Tyr Trp Gly Gln Gly Thr Thr Val
            100                 105                 110

Thr Val Ser Ser
        115

<210> SEQ ID NO 398
<211> LENGTH: 5
<212> TYPE: PRT
<213> ORGANISM: Artificial Sequence
<220> FEATURE:
<223> OTHER INFORMATION: Epratu VH - CDR1

<400> SEQUENCE: 398

Ser Tyr Trp Leu His
1               5

<210> SEQ ID NO 399
<211> LENGTH: 17
<212> TYPE: PRT
<213> ORGANISM: Artificial Sequence
<220> FEATURE:
<223> OTHER INFORMATION: Epratu VH - CDR2

<400> SEQUENCE: 399

Tyr Ile Asn Pro Arg Asn Asp Tyr Thr Glu Tyr Asn Gln Asn Phe Lys
1               5                   10                  15

Asp

<210> SEQ ID NO 400
<211> LENGTH: 7
<212> TYPE: PRT
<213> ORGANISM: Artificial Sequence
<220> FEATURE:
<223> OTHER INFORMATION: Epratu VH - CDR3

<400> SEQUENCE: 400

Arg Asp Ile Thr Thr Phe Tyr
1               5

<210> SEQ ID NO 401
<211> LENGTH: 244
<212> TYPE: PRT
<213> ORGANISM: Artificial Sequence
<220> FEATURE:
<223> OTHER INFORMATION: Short Chain 1 (Ofatu VH-CH1)

<400> SEQUENCE: 401

Met Glu Phe Gly Leu Ser Trp Leu Phe Leu Val Ala Ile Leu Lys Gly
1               5                   10                  15
```

Val Gln Cys Glu Val Gln Leu Val Glu Ser Gly Gly Gly Leu Val Gln
             20                  25                  30

Pro Gly Arg Ser Leu Arg Leu Ser Cys Ala Ala Ser Gly Phe Thr Phe
         35                  40                  45

Asn Asp Tyr Ala Met His Trp Val Arg Gln Ala Pro Gly Lys Gly Leu
     50                  55                  60

Glu Trp Val Ser Thr Ile Ser Trp Asn Ser Gly Ser Ile Gly Tyr Ala
65                  70                  75                  80

Asp Ser Val Lys Gly Arg Phe Thr Ile Ser Arg Asp Asn Ala Lys Lys
                 85                  90                  95

Ser Leu Tyr Leu Gln Met Asn Ser Leu Arg Ala Glu Asp Thr Ala Leu
            100                 105                 110

Tyr Tyr Cys Ala Lys Asp Ile Gln Tyr Gly Asn Tyr Tyr Gly Met
        115                 120                 125

Asp Val Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys

<210> SEQ ID NO 402
<211> LENGTH: 122
<212> TYPE: PRT
<213> ORGANISM: Artificial Sequence
<220> FEATURE:
<223> OTHER INFORMATION: Ofatu VH

<400> SEQUENCE: 402

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Gly Met Asp Val Trp
            100                 105                 110

Gly Gln Gly Thr Thr Val Thr Val Ser Ser
        115                 120

-continued

```
<210> SEQ ID NO 403
<211> LENGTH: 5
<212> TYPE: PRT
<213> ORGANISM: Artificial Sequence
<220> FEATURE:
<223> OTHER INFORMATION: Ofatu VH - CDR1

<400> SEQUENCE: 403

Asp Tyr Ala Met His
1               5

<210> SEQ ID NO 404
<211> LENGTH: 17
<212> TYPE: PRT
<213> ORGANISM: Artificial Sequence
<220> FEATURE:
<223> OTHER INFORMATION: Ofatu VH - CDR2

<400> SEQUENCE: 404

Thr Ile Ser Trp Asn Ser Gly Ser Ile Gly Tyr Ala Asp Ser Val Lys
1               5                   10                  15

Gly

<210> SEQ ID NO 405
<211> LENGTH: 13
<212> TYPE: PRT
<213> ORGANISM: Artificial Sequence
<220> FEATURE:
<223> OTHER INFORMATION: Ofatu VH - CDR3

<400> SEQUENCE: 405

Asp Ile Gln Tyr Gly Asn Tyr Tyr Tyr Gly Met Asp Val
1               5                   10

<210> SEQ ID NO 406
<211> LENGTH: 241
<212> TYPE: PRT
<213> ORGANISM: Artificial Sequence
<220> FEATURE:
<223> OTHER INFORMATION: Short Chain 2 (Epratu VL-hCk)

<400> SEQUENCE: 406

Met Asp Met Arg Val Pro Ala Gln Leu Leu Gly Leu Leu Leu Leu Trp
1               5                   10                  15

Phe Pro Gly Ser Arg Cys Asp Ile Gln Leu Thr Gln Ser Pro Ser Ser
            20                  25                  30

Leu Ser Ala Ser Val Gly Asp Arg Val Thr Met Ser Cys Lys Ser Ser
        35                  40                  45

Gln Ser Val Leu Tyr Ser Ala Asn His Lys Asn Tyr Leu Ala Trp Tyr
    50                  55                  60

Gln Gln Lys Pro Gly Lys Ala Pro Lys Leu Leu Ile Tyr Trp Ala Ser
65                  70                  75                  80

Thr Arg Glu Ser Gly Val Pro Ser Arg Phe Ser Gly Ser Gly Ser Gly
                85                  90                  95

Thr Asp Phe Thr Phe Thr Ile Ser Ser Leu Gln Pro Glu Asp Ile Ala
            100                 105                 110

Thr Tyr Tyr Cys His Gln Tyr Leu Ser Ser Trp Thr Phe Gly Gly Gly
        115                 120                 125

Thr Lys Leu Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160
```

```
Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 407
<211> LENGTH: 112
<212> TYPE: PRT
<213> ORGANISM: Artificial Sequence
<220> FEATURE:
<223> OTHER INFORMATION: Epratu VL

<400> SEQUENCE: 407

Asp Ile Gln Leu Thr Gln Ser Pro Ser Ser Leu Ser Ala Ser Val Gly
1               5                   10                  15

Asp Arg Val Thr Met Ser Cys Lys Ser Ser Gln Ser Val Leu Tyr Ser
            20                  25                  30

Ala Asn His Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys His Gln
                85                  90                  95

Tyr Leu Ser Ser Trp Thr Phe Gly Gly Gly Thr Lys Leu Glu Ile Lys
            100                 105                 110

<210> SEQ ID NO 408
<211> LENGTH: 17
<212> TYPE: PRT
<213> ORGANISM: Artificial Sequence
<220> FEATURE:
<223> OTHER INFORMATION: Epratu VL - CDR1

<400> SEQUENCE: 408

Lys Ser Ser Gln Ser Val Leu Tyr Ser Ala Asn His Lys Asn Tyr Leu
1               5                   10                  15

Ala

<210> SEQ ID NO 409
<211> LENGTH: 7
<212> TYPE: PRT
<213> ORGANISM: Artificial Sequence
<220> FEATURE:
<223> OTHER INFORMATION: Epratu VL - CDR2

<400> SEQUENCE: 409

Trp Ala Ser Thr Arg Glu Ser
1               5

<210> SEQ ID NO 410
```

```
<211> LENGTH: 8
<212> TYPE: PRT
<213> ORGANISM: Artificial Sequence
<220> FEATURE:
<223> OTHER INFORMATION: Epratu VL - CDR3

<400> SEQUENCE: 410

His Gln Tyr Leu Ser Ser Trp Thr
1               5

<210> SEQ ID NO 411
<211> LENGTH: 685
<212> TYPE: PRT
<213> ORGANISM: Artificial Sequence
<220> FEATURE:
<223> OTHER INFORMATION: Long Chain (patritu VL-hCk-Nivolu VH-hCg1mut)

<400> SEQUENCE: 411

Met Asp Met Arg Val Pro Ala Gln Leu Leu Gly Leu Leu Leu Leu Trp
1               5                   10                  15

Phe Pro Gly Ser Arg Cys Asp Ile Glu Met Thr Gln Ser Pro Asp Ser
            20                  25                  30

Leu Ala Val Ser Leu Gly Glu Arg Ala Thr Ile Asn Cys Arg Ser Ser
        35                  40                  45

Gln Ser Val Leu Tyr Ser Ser Asn Arg Asn Tyr Leu Ala Trp Tyr
    50                  55                  60

Gln Gln Asn Pro Gly Gln Pro Pro Lys Leu Leu Ile Tyr Trp Ala Ser
65                  70                  75                  80

Thr Arg Glu Ser Gly Val Pro Asp Arg Phe Ser Gly Ser Gly Ser Gly
                85                  90                  95

Thr Asp Phe Thr Leu Thr Ile Ser Ser Leu Gln Ala Glu Asp Val Ala
            100                 105                 110

Val Tyr Tyr Cys Gln Gln Tyr Tyr Ser Thr Pro Arg Thr Phe Gly Gln
        115                 120                 125

Gly Thr Lys Val Glu Ile Lys Arg Thr Val Ala Ala Pro Ser Val Phe
    130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

Leu Ser Lys Ala Asp Tyr Glu Lys His Lys Val Tyr Ala Cys Glu Val
    210                 215                 220

Thr His Gln Gly Leu Ser Ser Pro Val Thr Lys Ser Phe Asn Arg Gly
225                 230                 235                 240

Glu Cys Gln Val Gln Leu Val Glu Ser Gly Gly Gly Val Val Gln Pro
                245                 250                 255

Gly Arg Ser Leu Arg Leu Asp Cys Lys Ala Ser Gly Ile Thr Phe Ser
            260                 265                 270

Asn Ser Gly Met His Trp Val Arg Gln Ala Pro Gly Lys Gly Leu Glu
        275                 280                 285

Trp Val Ala Val Ile Trp Tyr Asp Gly Ser Lys Arg Tyr Tyr Ala Asp
    290                 295                 300

Ser Val Lys Gly Arg Phe Thr Ile Ser Arg Asp Asn Ser Lys Asn Thr
```

```
                305                 310                 315                 320
Leu Phe Leu Gln Met Asn Ser Leu Arg Ala Glu Asp Thr Ala Val Tyr
                    325                 330                 335

Tyr Cys Ala Thr Asn Asp Asp Tyr Trp Gly Gln Gly Thr Leu Val Thr
                340                 345                 350

Val Ser Ser Ala Ser Thr Lys Gly Pro Ser Val Phe Pro Leu Ala Pro
            355                 360                 365

Ser Ser Lys Ser Thr Ser Gly Gly Thr Ala Ala Leu Gly Cys Leu Val
370                 375                 380

Lys Asp Tyr Phe Pro Glu Pro Val Thr Val Ser Trp Asn Ser Gly Ala
385                 390                 395                 400

Leu Thr Ser Gly Val His Thr Phe Pro Ala Val Leu Gln Ser Ser Gly
                    405                 410                 415

Leu Tyr Ser Leu Ser Ser Val Val Thr Val Pro Ser Ser Ser Leu Gly
                420                 425                 430

Thr Gln Thr Tyr Ile Cys Asn Val Asn His Lys Pro Ser Asn Thr Lys
            435                 440                 445

Val Asp Lys Lys Val Glu Pro Lys Ser Cys Asp Lys Thr His Thr Cys
450                 455                 460

Pro Pro Cys Pro Ala Pro Glu Leu Leu Gly Gly Pro Ser Val Phe Leu
465                 470                 475                 480

Phe Pro Pro Lys Pro Lys Asp Thr Leu Met Ile Ser Arg Thr Pro Glu
                    485                 490                 495

Val Thr Cys Val Val Val Asp Val Ser His Glu Asp Pro Glu Val Lys
                500                 505                 510

Phe Asn Trp Tyr Val Asp Gly Val Glu Val His Asn Ala Lys Thr Lys
            515                 520                 525

Pro Arg Glu Glu Gln Tyr Asn Ser Thr Tyr Arg Val Val Ser Val Leu
            530                 535                 540

Thr Val Leu His Gln Asp Trp Leu Asn Gly Lys Glu Tyr Lys Cys Lys
545                 550                 555                 560

Val Ser Asn Lys Ala Leu Pro Ala Pro Ile Glu Lys Thr Ile Ser Lys
                    565                 570                 575

Ala Lys Gly Gln Pro Arg Glu Pro Gln Val Tyr Thr Leu Pro Pro Ser
                580                 585                 590

Arg Glu Glu Met Thr Lys Asn Gln Val Ser Leu Thr Cys Leu Val Lys
            595                 600                 605

Gly Phe Tyr Pro Ser Asp Ile Ala Val Glu Trp Glu Ser Asn Gly Gln
610                 615                 620

Pro Glu Asn Asn Tyr Lys Thr Thr Pro Pro Val Leu Asp Ser Asp Gly
625                 630                 635                 640

Ser Phe Phe Leu Tyr Ser Lys Leu Thr Val Asp Lys Ser Arg Trp Gln
                    645                 650                 655

Gln Gly Asn Val Phe Ser Cys Ser Val Met His Glu Ala Leu His Asn
                660                 665                 670

His Tyr Thr Gln Lys Ser Leu Ser Leu Ser Pro Gly Lys
            675                 680                 685

<210> SEQ ID NO 412
<211> LENGTH: 113
<212> TYPE: PRT
<213> ORGANISM: Artificial Sequence
<220> FEATURE:
<223> OTHER INFORMATION: patrituVL
```

-continued

<400> SEQUENCE: 412

Asp Ile Glu Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Ser Asn Arg Asn Tyr Leu Ala Trp Tyr Gln Gln Asn Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
                100                 105                 110

Lys

<210> SEQ ID NO 413
<211> LENGTH: 17
<212> TYPE: PRT
<213> ORGANISM: Artificial Sequence
<220> FEATURE:
<223> OTHER INFORMATION: patritu VL - CDR1

<400> SEQUENCE: 413

Arg Ser Ser Gln Ser Val Leu Tyr Ser Ser Asn Arg Asn Tyr Leu
1               5                   10                  15

Ala

<210> SEQ ID NO 414
<211> LENGTH: 7
<212> TYPE: PRT
<213> ORGANISM: Artificial Sequence
<220> FEATURE:
<223> OTHER INFORMATION: patritu VL - CDR2

<400> SEQUENCE: 414

Trp Ala Ser Thr Arg Glu Ser
1               5

<210> SEQ ID NO 415
<211> LENGTH: 9
<212> TYPE: PRT
<213> ORGANISM: Artificial Sequence
<220> FEATURE:
<223> OTHER INFORMATION: patritu VL - CDR3

<400> SEQUENCE: 415

Gln Gln Tyr Tyr Ser Thr Pro Arg Thr
1               5

<210> SEQ ID NO 416
<211> LENGTH: 113
<212> TYPE: PRT
<213> ORGANISM: Artificial Sequence
<220> FEATURE:
<223> OTHER INFORMATION: Nivolu VH

<400> SEQUENCE: 416

Gln Val Gln Leu Val Glu Ser Gly Gly Gly Val Val Gln Pro Gly Arg
1               5                   10                  15

-continued

```
Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 417
<211> LENGTH: 5
<212> TYPE: PRT
<213> ORGANISM: Artificial Sequence
<220> FEATURE:
<223> OTHER INFORMATION: Nivolu VH - CDR1

<400> SEQUENCE: 417

Asn Ser Gly Met His
1               5

<210> SEQ ID NO 418
<211> LENGTH: 17
<212> TYPE: PRT
<213> ORGANISM: Artificial Sequence
<220> FEATURE:
<223> OTHER INFORMATION: Nivolu VH - CDR2

<400> SEQUENCE: 418

Val Ile Trp Tyr Asp Gly Ser Lys Arg Tyr Tyr Ala Asp Ser Val Lys
1               5                   10                  15

Gly

<210> SEQ ID NO 419
<211> LENGTH: 4
<212> TYPE: PRT
<213> ORGANISM: Artificial Sequence
<220> FEATURE:
<223> OTHER INFORMATION: Nivolu VH - CDR3

<400> SEQUENCE: 419

Asn Asp Asp Tyr
1

<210> SEQ ID NO 420
<211> LENGTH: 239
<212> TYPE: PRT
<213> ORGANISM: Artificial Sequence
<220> FEATURE:
<223> OTHER INFORMATION: Short Chain 1 (Patritumab -CH1)

<400> SEQUENCE: 420

Met Glu Phe Gly Leu Ser Trp Leu Phe Leu Val Ala Ile Leu Lys Gly
1               5                   10                  15

Val Gln Cys Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45
```

-continued

Ser Gly Tyr Tyr Trp Ser Trp Ile Arg Gln Pro Gly Lys Gly Leu
        50                  55                  60

Glu Trp Ile Gly Glu Ile Asn His Ser Gly Ser Thr Asn Tyr Asn Pro
65                  70                  75                  80

Ser Leu Lys Ser Arg Val Thr Ile Ser Val Glu Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Lys Trp Thr Trp Tyr Phe Asp Leu Trp Gly Arg
            115                 120                 125

Gly Thr Leu Val Thr Val Ser Ser Ala Ser Thr Lys Gly Pro Ser Val
        130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys
225                 230                 235

<210> SEQ ID NO 421
<211> LENGTH: 117
<212> TYPE: PRT
<213> ORGANISM: Artificial Sequence
<220> FEATURE:
<223> OTHER INFORMATION: Patritumab VH

<400> SEQUENCE: 421

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
50                  55                  60

Ser Arg Val Thr Ile Ser Val Glu Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Trp Thr Trp Tyr Phe Asp Leu Trp Gly Arg Gly Thr Leu
            100                 105                 110

Val Thr Val Ser Ser
        115

<210> SEQ ID NO 422
<211> LENGTH: 5
<212> TYPE: PRT
<213> ORGANISM: Artificial Sequence
<220> FEATURE:
<223> OTHER INFORMATION: Patritumab VH - CDR1

```
<400> SEQUENCE: 422

Gly Tyr Tyr Trp Ser
1               5

<210> SEQ ID NO 423
<211> LENGTH: 16
<212> TYPE: PRT
<213> ORGANISM: Artificial Sequence
<220> FEATURE:
<223> OTHER INFORMATION: Patritumab VH - CDR2

<400> SEQUENCE: 423

Glu Ile Asn His Ser Gly Ser Thr Asn Tyr Asn Pro Ser Leu Lys Ser
1               5                   10                  15

<210> SEQ ID NO 424
<211> LENGTH: 9
<212> TYPE: PRT
<213> ORGANISM: Artificial Sequence
<220> FEATURE:
<223> OTHER INFORMATION: Patritumab VH - CDR3

<400> SEQUENCE: 424

Asp Lys Trp Thr Trp Tyr Phe Asp Leu
1               5

<210> SEQ ID NO 425
<211> LENGTH: 236
<212> TYPE: PRT
<213> ORGANISM: Artificial Sequence
<220> FEATURE:
<223> OTHER INFORMATION: Short Chain 2 (NivoVL-hCK)

<400> SEQUENCE: 425

Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Ala Thr
            20                  25                  30

Leu Ser Leu Ser Pro Gly Glu Arg Ala Thr Leu Ser Cys Arg Ala Ser
        35                  40                  45

Gln Ser Val Ser Ser Tyr Leu Ala Trp Tyr Gln Gln Lys Pro Gly Gln
    50                  55                  60

Ala Pro Arg Leu Leu Ile Tyr Asp Ala Ser Asn Arg Ala Thr Gly Ile
65                  70                  75                  80

Pro Ala Arg Phe Ser Gly Ser Gly Ser Gly Thr Asp Phe Thr Leu Thr
                85                  90                  95

Ile Ser Ser Leu Glu Pro Glu Asp Phe Ala Val Tyr Tyr Cys Gln Gln
            100                 105                 110

Ser Ser Asn Trp Pro Arg Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205
```

-continued

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 426
<211> LENGTH: 107
<212> TYPE: PRT
<213> ORGANISM: Artificial Sequence
<220> FEATURE:
<223> OTHER INFORMATION: Nivo VL

<400> SEQUENCE: 426

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 427
<211> LENGTH: 11
<212> TYPE: PRT
<213> ORGANISM: Artificial Sequence
<220> FEATURE:
<223> OTHER INFORMATION: Nivo VL - CDR1

<400> SEQUENCE: 427

Arg Ala Ser Gln Ser Val Ser Ser Tyr Leu Ala
1               5                   10

<210> SEQ ID NO 428
<211> LENGTH: 7
<212> TYPE: PRT
<213> ORGANISM: Artificial Sequence
<220> FEATURE:
<223> OTHER INFORMATION: Nivo VL - CDR2

<400> SEQUENCE: 428

Asp Ala Ser Asn Arg Ala Thr
1               5

<210> SEQ ID NO 429
<211> LENGTH: 9
<212> TYPE: PRT
<213> ORGANISM: Artificial Sequence
<220> FEATURE:
<223> OTHER INFORMATION: Nivo VL - CDR3

<400> SEQUENCE: 429

Gln Gln Ser Ser Asn Trp Pro Arg Thr
1               5

<210> SEQ ID NO 430

<211> LENGTH: 689
<212> TYPE: PRT
<213> ORGANISM: Artificial Sequence
<220> FEATURE:
<223> OTHER INFORMATION: Long Chain (h1332 VL-hCk-1B12 VH-hCg1)

<400> SEQUENCE: 430

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Asn Thr Trp Leu Ala Trp Tyr Gln Gln Lys Pro Gly Lys
    50                  55                  60

Ala Pro Lys Leu Leu Ile Tyr Ala Ala Ser Ser Leu Lys Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ala Asn Ser Phe Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Gln Val Gln Leu
225                 230                 235                 240

Val Gln Ser Gly Ala Glu Val Lys Lys Pro Gly Ser Ser Val Lys Val
                245                 250                 255

Ser Cys Lys Thr Ser Gly Asp Thr Phe Ser Ser Tyr Ala Ile Ser Trp
            260                 265                 270

Val Arg Gln Ala Pro Gly Gln Gly Leu Glu Trp Met Gly Gly Ile Ile
        275                 280                 285

Pro Ile Phe Gly Arg Ala His Tyr Ala Gln Lys Phe Gln Gly Arg Val
    290                 295                 300

Thr Ile Thr Ala Asp Glu Ser Thr Ser Thr Ala Tyr Met Glu Leu Ser
305                 310                 315                 320

Ser Leu Arg Ser Glu Asp Thr Ala Val Tyr Phe Cys Ala Arg Lys Phe
                325                 330                 335

His Phe Val Ser Gly Ser Pro Phe Gly Met Asp Val Trp Gly Gln Gly
            340                 345                 350

Thr Thr Val Thr Val Ser Ser Ala Ser Thr Lys Gly Pro Ser Val Phe
        355                 360                 365

Pro Leu Ala Pro Ser Ser Lys Ser Thr Ser Gly Gly Thr Ala Ala Leu
    370                 375                 380

Gly Cys Leu Val Lys Asp Tyr Phe Pro Glu Pro Val Thr Val Ser Trp
385                 390                 395                 400

Asn Ser Gly Ala Leu Thr Ser Gly Val His Thr Phe Pro Ala Val Leu
            405                 410                 415

Gln Ser Ser Gly Leu Tyr Ser Leu Ser Ser Val Val Thr Val Pro Ser
        420                 425                 430

Ser Ser Leu Gly Thr Gln Thr Tyr Ile Cys Asn Val Asn His Lys Pro
    435                 440                 445

Ser Asn Thr Lys Val Asp Lys Lys Val Glu Pro Lys Ser Cys Asp Lys
450                 455                 460

Thr His Thr Cys Pro Pro Cys Pro Ala Pro Glu Leu Leu Gly Gly Pro
465                 470                 475                 480

Ser Val Phe Leu Phe Pro Pro Lys Pro Lys Asp Thr Leu Met Ile Ser
            485                 490                 495

Arg Thr Pro Glu Val Thr Cys Val Val Val Asp Val Ser His Glu Asp
        500                 505                 510

Pro Glu Val Lys Phe Asn Trp Tyr Val Asp Gly Val Glu Val His Asn
    515                 520                 525

Ala Lys Thr Lys Pro Arg Glu Glu Gln Tyr Asn Ser Thr Tyr Arg Val
530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Pro Ala Pro Ile Glu Lys
            565                 570                 575

Thr Ile Ser Lys Ala Lys Gly Gln Pro Arg Glu Pro Gln Val Tyr Thr
        580                 585                 590

Leu Pro Pro Ser Arg Glu Glu Met Thr Lys Asn Gln Val Ser Leu Thr
    595                 600                 605

Cys Leu Val Lys Gly Phe Tyr Pro Ser Asp Ile Ala Val Glu Trp Glu
610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
            645                 650                 655

Ser Arg Trp Gln Gln Gly Asn Val Phe Ser Cys Ser Val Met His Glu
        660                 665                 670

Ala Leu His Asn His Tyr Thr Gln Lys Ser Leu Ser Leu Ser Pro Gly
    675                 680                 685

Lys

<210> SEQ ID NO 431
<211> LENGTH: 107
<212> TYPE: PRT
<213> ORGANISM: Artificial Sequence
<220> FEATURE:
<223> OTHER INFORMATION: h1332 VL

<400> SEQUENCE: 431

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Thr Trp
            20                  25                  30

Leu Ala Trp Tyr Gln Gln Lys Pro Gly Lys Ala Pro Lys Leu Leu Ile
        35                  40                  45

```
Tyr Ala Ala Ser Ser Leu Lys Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Leu
                 85                  90                  95

Thr Phe Gly Gly Gly Thr Lys Val Glu Ile Lys
            100                 105
```

<210> SEQ ID NO 432
<211> LENGTH: 11
<212> TYPE: PRT
<213> ORGANISM: Artificial Sequence
<220> FEATURE:
<223> OTHER INFORMATION: h1332 VL - CDR1

<400> SEQUENCE: 432

```
Arg Ala Ser Gln Gly Ile Asn Thr Trp Leu Ala
 1               5                  10
```

<210> SEQ ID NO 433
<211> LENGTH: 7
<212> TYPE: PRT
<213> ORGANISM: Artificial Sequence
<220> FEATURE:
<223> OTHER INFORMATION: h1332 VL - CDR2

<400> SEQUENCE: 433

```
Ala Ala Ser Ser Leu Lys Ser
 1               5
```

<210> SEQ ID NO 434
<211> LENGTH: 9
<212> TYPE: PRT
<213> ORGANISM: Artificial Sequence
<220> FEATURE:
<223> OTHER INFORMATION: h1332 VL - CDR3

<400> SEQUENCE: 434

```
Gln Gln Ala Asn Ser Phe Pro Leu Thr
 1               5
```

<210> SEQ ID NO 435
<211> LENGTH: 123
<212> TYPE: PRT
<213> ORGANISM: Artificial Sequence
<220> FEATURE:
<223> OTHER INFORMATION: 1B12 VH

<400> SEQUENCE: 435

```
Gln Val Gln Leu Val Gln Ser Gly Ala Glu Val Lys Lys Pro Gly Ser
 1               5                  10                  15

Ser Val Lys Val Ser Cys Lys Thr Ser Gly Asp Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Arg Ala His Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Phe Cys
                 85                  90                  95
```

```
Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120
```

<210> SEQ ID NO 436
<211> LENGTH: 5
<212> TYPE: PRT
<213> ORGANISM: Artificial Sequence
<220> FEATURE:
<223> OTHER INFORMATION: 1B12 VH - CDR1

<400> SEQUENCE: 436

```
Ser Tyr Ala Ile Ser
1               5
```

<210> SEQ ID NO 437
<211> LENGTH: 11
<212> TYPE: PRT
<213> ORGANISM: Artificial Sequence
<220> FEATURE:
<223> OTHER INFORMATION: 1B12 VH - CDR2

<400> SEQUENCE: 437

```
Gly Ile Ile Pro Ile Phe Gly Arg Ala His Tyr
1               5                   10
```

<210> SEQ ID NO 438
<211> LENGTH: 14
<212> TYPE: PRT
<213> ORGANISM: Artificial Sequence
<220> FEATURE:
<223> OTHER INFORMATION: 1B12 VH - CDR3

<400> SEQUENCE: 438

```
Lys Phe His Phe Val Ser Gly Ser Pro Phe Gly Met Asp Val
1               5                   10
```

<210> SEQ ID NO 439
<211> LENGTH: 239
<212> TYPE: PRT
<213> ORGANISM: Artificial Sequence
<220> FEATURE:
<223> OTHER INFORMATION: Short Chain 1 (h1332 VH-CH1)

<400> SEQUENCE: 439

```
Met Glu Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Phe Ser Trp Val Arg Gln Ala Pro Gly Gln Gly Leu
    50                  55                  60

Glu Trp Met Gly Trp Ile Ser Ala Ser Asn Gly Asn Thr Tyr Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Val Tyr Ala Asp Tyr Ala Asp Tyr Trp Gly Gln
        115                 120                 125
```

Gly Thr Leu Val Thr Val Ser Ser Ala Ser Thr Lys Gly Pro Ser Val
        130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
        210                 215                 220

Pro Ser Asn Thr Lys Val Asp Lys Lys Val Glu Pro Lys Ser Cys
225                 230                 235

<210> SEQ ID NO 440
<211> LENGTH: 117
<212> TYPE: PRT
<213> ORGANISM: Artificial Sequence
<220> FEATURE:
<223> OTHER INFORMATION: h1332 VH

<400> SEQUENCE: 440

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Phe Ser Trp Val Arg Gln Ala Pro Gly Gln Gly Leu Glu Trp Met
        35                  40                  45

Gly Trp Ile Ser Ala Ser Asn Gly Asn Thr Tyr Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Tyr Ala Asp Tyr Ala Asp Tyr Trp Gly Gln Gly Thr Leu
            100                 105                 110

Val Thr Val Ser Ser
        115

<210> SEQ ID NO 441
<211> LENGTH: 5
<212> TYPE: PRT
<213> ORGANISM: Artificial Sequence
<220> FEATURE:
<223> OTHER INFORMATION: h1332 VH - CDR1

<400> SEQUENCE: 441

Ser Tyr Gly Phe Ser
1               5

<210> SEQ ID NO 442
<211> LENGTH: 17
<212> TYPE: PRT
<213> ORGANISM: Artificial Sequence
<220> FEATURE:
<223> OTHER INFORMATION: h1332 VH - CDR2

<400> SEQUENCE: 442

Trp Ile Ser Ala Ser Asn Gly Asn Thr Tyr Tyr Ala Gln Lys Leu Gln

Gly

<210> SEQ ID NO 443
<211> LENGTH: 8
<212> TYPE: PRT
<213> ORGANISM: Artificial Sequence
<220> FEATURE:
<223> OTHER INFORMATION: h1332 VH - CDR3

<400> SEQUENCE: 443

Val Tyr Ala Asp Tyr Ala Asp Tyr
1               5

<210> SEQ ID NO 444
<211> LENGTH: 235
<212> TYPE: PRT
<213> ORGANISM: Artificial Sequence
<220> FEATURE:
<223> OTHER INFORMATION: Short Chain 2 (1B12 VL-hCK)

<400> SEQUENCE: 444

Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Ala Thr
                20                  25                  30

Leu Ser Leu Ser Pro Gly Glu Arg Ala Thr Leu Ser Cys Arg Ala Ser
            35                  40                  45

Gln Ser Val Ser Ser Tyr Leu Ala Trp Tyr Gln Gln Lys Pro Gly Gln
        50                  55                  60

Ala Pro Arg Leu Leu Ile Tyr Asp Ala Ser Asn Arg Ala Thr Gly Ile
65                  70                  75                  80

Pro Ala Arg Phe Ser Gly Ser Gly Ser Gly Thr Asp Phe Thr Leu Thr
                85                  90                  95

Ile Ser Ser Leu Glu Pro Glu Asp Phe Ala Val Tyr Tyr Cys Gln Gln
            100                 105                 110

Arg Ser Asn Trp Pro Thr Phe Gly Gln Gly Thr Lys Val Glu Ile Lys
        115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 445
<211> LENGTH: 106
<212> TYPE: PRT
<213> ORGANISM: Artificial Sequence
<220> FEATURE:
<223> OTHER INFORMATION: 1B12 VL

<400> SEQUENCE: 445

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 446
<211> LENGTH: 11
<212> TYPE: PRT
<213> ORGANISM: Artificial Sequence
<220> FEATURE:
<223> OTHER INFORMATION: 1B12 VL - CDR1

<400> SEQUENCE: 446

Arg Ala Ser Gln Ser Val Ser Ser Tyr Leu Ala
1               5                   10

<210> SEQ ID NO 447
<211> LENGTH: 7
<212> TYPE: PRT
<213> ORGANISM: Artificial Sequence
<220> FEATURE:
<223> OTHER INFORMATION: 1B12 VL - CDR2

<400> SEQUENCE: 447

Asp Ala Ser Asn Arg Ala Thr
1               5

<210> SEQ ID NO 448
<211> LENGTH: 8
<212> TYPE: PRT
<213> ORGANISM: Artificial Sequence
<220> FEATURE:
<223> OTHER INFORMATION: 1B12 VL - CDR3

<400> SEQUENCE: 448

Gln Gln Arg Ser Asn Trp Pro Thr
1               5

<210> SEQ ID NO 449
<211> LENGTH: 681
<212> TYPE: PRT
<213> ORGANISM: Artificial Sequence
<220> FEATURE:
<223> OTHER INFORMATION: Long Chain (6A5 VL-hCk-Nivolu VH-hCg1mut)

<400> SEQUENCE: 449

Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Gly Thr
            20                  25                  30

```
Leu Ser Leu Ser Pro Gly Glu Arg Ala Thr Leu Ser Cys Arg Ala Ser
         35                  40                  45

Gln Ser Val Ser Ser Thr Tyr Leu Ala Trp Tyr Gln Gln Lys Pro Gly
 50                  55                  60

Gln Ala Pro Arg Leu Leu Ile Tyr Gly Ala Ser Ser Arg Ala Thr Gly
 65                  70                  75                  80

Ile Pro Asp Arg Phe Ser Gly Ser Gly Ser Gly Thr Asp Phe Thr Leu
                 85                  90                  95

Thr Ile Ser Arg Leu Glu Pro Glu Asp Phe Ala Val Tyr Tyr Cys Gln
                100                 105                 110

Gln Tyr Gly Ser Ser Pro Pro Ile Thr Phe Gly Gln Gly Thr Arg Leu
            115                 120                 125

Glu Ile Lys Arg Thr Val Ala Ala Pro Ser Val Phe Ile Phe Pro Pro
        130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys Gln Val
225                 230                 235                 240

Gln Leu Val Glu Ser Gly Gly Val Val Gln Pro Gly Arg Ser Leu
            245                 250                 255

Arg Leu Asp Cys Lys Ala Ser Gly Ile Thr Phe Ser Asn Ser Gly Met
            260                 265                 270

His Trp Val Arg Gln Ala Pro Gly Lys Gly Leu Glu Trp Val Ala Val
        275                 280                 285

Ile Trp Tyr Asp Gly Ser Lys Arg Tyr Tyr Ala Asp Ser Val Lys Gly
        290                 295                 300

Arg Phe Thr Ile Ser Arg Asp Asn Ser Lys Asn Thr Leu Phe Leu Gln
305                 310                 315                 320

Met Asn Ser Leu Arg Ala Glu Asp Thr Ala Val Tyr Tyr Cys Ala Thr
                325                 330                 335

Asn Asp Asp Tyr Trp Gly Gln Gly Thr Leu Val Thr Val Ser Ser Ala
            340                 345                 350

Ser Thr Lys Gly Pro Ser Val Phe Pro Leu Ala Pro Ser Ser Lys Ser
        355                 360                 365

Thr Ser Gly Gly Thr Ala Ala Leu Gly Cys Leu Val Lys Asp Tyr Phe
    370                 375                 380

Pro Glu Pro Val Thr Val Ser Trp Asn Ser Gly Ala Leu Thr Ser Gly
385                 390                 395                 400

Val His Thr Phe Pro Ala Val Leu Gln Ser Ser Gly Leu Tyr Ser Leu
                405                 410                 415

Ser Ser Val Val Thr Val Pro Ser Ser Ser Leu Gly Thr Gln Thr Tyr
            420                 425                 430

Ile Cys Asn Val Asn His Lys Pro Ser Asn Thr Lys Val Asp Lys Lys
        435                 440                 445

Val Glu Pro Lys Ser Cys Asp Lys Thr His Thr Cys Pro Pro Cys Pro
```

```
                450                 455                 460
Ala Pro Glu Ala Ala Gly Gly Pro Ser Val Phe Leu Phe Pro Pro Lys
465                 470                 475                 480

Pro Lys Asp Thr Leu Met Ile Ser Arg Thr Pro Glu Val Thr Cys Val
                485                 490                 495

Val Val Asp Val Ser His Glu Asp Pro Glu Val Lys Phe Asn Trp Tyr
                500                 505                 510

Val Asp Gly Val Glu Val His Asn Ala Lys Thr Lys Pro Arg Glu Glu
                515                 520                 525

Gln Tyr Asn Ser Thr Tyr Arg Val Val Ser Val Leu Thr Val Leu His
                530                 535                 540

Gln Asp Trp Leu Asn Gly Lys Glu Tyr Lys Cys Lys Val Ser Asn Lys
545                 550                 555                 560

Ala Leu Pro Ala Pro Ile Glu Lys Thr Ile Ser Lys Ala Lys Gly Gln
                565                 570                 575

Pro Arg Glu Pro Gln Val Tyr Thr Leu Pro Pro Ser Arg Glu Glu Met
                580                 585                 590

Thr Lys Asn Gln Val Ser Leu Thr Cys Leu Val Lys Gly Phe Tyr Pro
                595                 600                 605

Ser Asp Ile Ala Val Glu Trp Glu Ser Asn Gly Gln Pro Glu Asn Asn
                610                 615                 620

Tyr Lys Thr Thr Pro Pro Val Leu Asp Ser Asp Gly Ser Phe Phe Leu
625                 630                 635                 640

Tyr Ser Lys Leu Thr Val Asp Lys Ser Arg Trp Gln Gln Gly Asn Val
                645                 650                 655

Phe Ser Cys Ser Val Met His Glu Ala Leu His Asn His Tyr Thr Gln
                660                 665                 670

Lys Ser Leu Ser Leu Ser Pro Gly Lys
                675                 680

<210> SEQ ID NO 450
<211> LENGTH: 109
<212> TYPE: PRT
<213> ORGANISM: Artificial Sequence
<220> FEATURE:
<223> OTHER INFORMATION: 6A5 VL

<400> SEQUENCE: 450

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Ile Thr Phe Gly Gln Gly Thr Arg Leu Glu Ile Lys
                100                 105

<210> SEQ ID NO 451
<211> LENGTH: 12
<212> TYPE: PRT
```

<213> ORGANISM: Artificial Sequence
<220> FEATURE:
<223> OTHER INFORMATION: 6A5 VL - CDR1

<400> SEQUENCE: 451

Arg Ala Ser Gln Ser Val Ser Ser Thr Tyr Leu Ala
1               5                   10

<210> SEQ ID NO 452
<211> LENGTH: 7
<212> TYPE: PRT
<213> ORGANISM: Artificial Sequence
<220> FEATURE:
<223> OTHER INFORMATION: 6A5 VL - CDR2

<400> SEQUENCE: 452

Gly Ala Ser Ser Arg Ala Thr
1               5

<210> SEQ ID NO 453
<211> LENGTH: 10
<212> TYPE: PRT
<213> ORGANISM: Artificial Sequence
<220> FEATURE:
<223> OTHER INFORMATION: 6A5 VL - CDR3

<400> SEQUENCE: 453

Gln Gln Tyr Gly Ser Ser Pro Pro Ile Thr
1               5                   10

<210> SEQ ID NO 454
<211> LENGTH: 113
<212> TYPE: PRT
<213> ORGANISM: Artificial Sequence
<220> FEATURE:
<223> OTHER INFORMATION: Nivolu VH

<400> SEQUENCE: 454

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 455
<211> LENGTH: 5
<212> TYPE: PRT
<213> ORGANISM: Artificial Sequence
<220> FEATURE:
<223> OTHER INFORMATION: Nivolu  VH - CDR1

<400> SEQUENCE: 455

Asn Ser Gly Met His

<210> SEQ ID NO 456
<211> LENGTH: 17
<212> TYPE: PRT
<213> ORGANISM: Artificial Sequence
<220> FEATURE:
<223> OTHER INFORMATION: Nivolu VH - CDR2

<400> SEQUENCE: 456

Val Ile Trp Tyr Asp Gly Ser Lys Arg Tyr Tyr Ala Asp Ser Val Lys
1               5                   10                  15
Gly

<210> SEQ ID NO 457
<211> LENGTH: 4
<212> TYPE: PRT
<213> ORGANISM: Artificial Sequence
<220> FEATURE:
<223> OTHER INFORMATION: Nivolu VH - CDR3

<400> SEQUENCE: 457

Asn Asp Asp Tyr
1

<210> SEQ ID NO 458
<211> LENGTH: 250
<212> TYPE: PRT
<213> ORGANISM: Artificial Sequence
<220> FEATURE:
<223> OTHER INFORMATION: Short Chain 1 (6A5 VH-CH1)

<400> SEQUENCE: 458

Met Glu Phe Gly Leu Ser Trp Leu Phe Leu Val Ala Ile Leu Lys Gly
1               5                   10                  15

Val Gln Cys Gln Ile Thr Leu Lys Glu Ser Gly Pro Thr Leu Val Lys
                20                  25                  30

Pro Thr Gln Thr Leu Thr Leu Thr Cys Thr Phe Ser Gly Phe Ser Leu
            35                  40                  45

Ser Thr Ser Gly Val Gly Val Gly Trp Ile Arg Gln Pro Pro Gly Lys
        50                  55                  60

Ala Leu Glu Trp Leu Ala Leu Ile Tyr Trp Asp Asp Lys Arg Tyr
65                  70                  75                  80

Ser Pro Ser Leu Lys Ser Arg Leu Thr Ile Thr Lys Asp Thr Ser Lys
                85                  90                  95

Asn Gln Val Val Leu Thr Met Ala Asn Met Asp Pro Val Asp Thr Ala
                100                 105                 110

Thr Tyr Tyr Cys Ala His Ile Arg Ile Thr Glu Val Arg Gly Val Ile
            115                 120                 125

Ile Ser Tyr Tyr Gly Met Asp Val Trp Gly Gln Gly Thr Thr Val Thr
        130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
                180                 185                 190

Leu Thr Ser Gly Val His Thr Phe Pro Ala Val Leu Gln Ser Ser Gly
            195                 200                 205

```
Leu Tyr Ser Leu Ser Ser Val Val Thr Val Pro Ser Ser Leu Gly
        210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser Cys
                245                 250

<210> SEQ ID NO 459
<211> LENGTH: 128
<212> TYPE: PRT
<213> ORGANISM: Artificial Sequence
<220> FEATURE:
<223> OTHER INFORMATION: 6A5 VH

<400> SEQUENCE: 459

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Val Gly Val Gly Trp Ile Arg Gln Pro Pro Gly Lys Ala Leu Glu
            35                  40                  45

Trp Leu Ala Leu Ile Tyr Trp Asp Asp Asp Lys Arg Tyr Ser Pro Ser
50                  55                  60

Leu Lys Ser Arg Leu Thr Ile Thr Lys Asp Thr Ser Lys Asn Gln Val
65                  70                  75                  80

Val Leu Thr Met Ala Asn Met Asp Pro Val Asp Thr Ala Thr Tyr Tyr
                85                  90                  95

Cys Ala His Ile Arg Ile Thr Glu Val Arg Gly Val Ile Ile Ser Tyr
            100                 105                 110

Tyr Gly Met Asp Val Trp Gly Gln Gly Thr Thr Val Thr Val Ser Ser
        115                 120                 125

<210> SEQ ID NO 460
<211> LENGTH: 7
<212> TYPE: PRT
<213> ORGANISM: Artificial Sequence
<220> FEATURE:
<223> OTHER INFORMATION: 6A5 VH - CDR1

<400> SEQUENCE: 460

Thr Ser Gly Val Gly Val Gly
1               5

<210> SEQ ID NO 461
<211> LENGTH: 16
<212> TYPE: PRT
<213> ORGANISM: Artificial Sequence
<220> FEATURE:
<223> OTHER INFORMATION: 6A5 VH - CDR2

<400> SEQUENCE: 461

Leu Ile Tyr Trp Asp Asp Asp Lys Arg Tyr Ser Pro Ser Leu Lys Ser
1               5                   10                  15

<210> SEQ ID NO 462
<211> LENGTH: 18
<212> TYPE: PRT
<213> ORGANISM: Artificial Sequence
<220> FEATURE:
<223> OTHER INFORMATION: 6A5 VH - CDR3

<400> SEQUENCE: 462
```

Ile Arg Ile Thr Glu Val Arg Gly Val Ile Ile Ser Tyr Tyr Gly Met
1               5                   10                  15

Asp Val

<210> SEQ ID NO 463
<211> LENGTH: 236
<212> TYPE: PRT
<213> ORGANISM: Artificial Sequence
<220> FEATURE:
<223> OTHER INFORMATION: Short Chain 2 (Nivolu VL-hCK)

<400> SEQUENCE: 463

Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Ala Thr
                20                  25                  30

Leu Ser Leu Ser Pro Gly Glu Arg Ala Thr Leu Ser Cys Arg Ala Ser
            35                  40                  45

Gln Ser Val Ser Ser Tyr Leu Ala Trp Tyr Gln Gln Lys Pro Gly Gln
    50                  55                  60

Ala Pro Arg Leu Leu Ile Tyr Asp Ala Ser Asn Arg Ala Thr Gly Ile
65                  70                  75                  80

Pro Ala Arg Phe Ser Gly Ser Gly Ser Gly Thr Asp Phe Thr Leu Thr
                85                  90                  95

Ile Ser Ser Leu Glu Pro Glu Asp Phe Ala Val Tyr Tyr Cys Gln Gln
            100                 105                 110

Ser Ser Asn Trp Pro Arg Thr Phe Gly Gln Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 464
<211> LENGTH: 107
<212> TYPE: PRT
<213> ORGANISM: Artificial Sequence
<220> FEATURE:
<223> OTHER INFORMATION: Nivolu VL

<400> SEQUENCE: 464

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

```
Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys
            100                 105
```

<210> SEQ ID NO 465
<211> LENGTH: 11
<212> TYPE: PRT
<213> ORGANISM: Artificial Sequence
<220> FEATURE:
<223> OTHER INFORMATION: Nivolu VL - CDR1

<400> SEQUENCE: 465

```
Arg Ala Ser Gln Ser Val Ser Ser Tyr Leu Ala
 1               5                  10
```

<210> SEQ ID NO 466
<211> LENGTH: 7
<212> TYPE: PRT
<213> ORGANISM: Artificial Sequence
<220> FEATURE:
<223> OTHER INFORMATION: Nivolu VL - CDR2

<400> SEQUENCE: 466

```
Asp Ala Ser Asn Arg Ala Thr
 1               5
```

<210> SEQ ID NO 467
<211> LENGTH: 9
<212> TYPE: PRT
<213> ORGANISM: Artificial Sequence
<220> FEATURE:
<223> OTHER INFORMATION: Nivolu VL - CDR3

<400> SEQUENCE: 467

```
Gln Gln Ser Ser Asn Trp Pro Arg Thr
 1               5
```

<210> SEQ ID NO 468
<211> LENGTH: 694
<212> TYPE: PRT
<213> ORGANISM: Artificial Sequence
<220> FEATURE:
<223> OTHER INFORMATION: Long Chain (Nivolu VL-hCk-6A5 VH-hCg1mut)

<400> SEQUENCE: 468

```
Met Asp Met Arg Val Pro Ala Gln Leu Leu Gly Leu Leu Leu Leu Trp
 1               5                  10                  15

Phe Pro Gly Ser Arg Cys Glu Ile Val Leu Thr Gln Ser Pro Ala Thr
                20                  25                  30

Leu Ser Leu Ser Pro Gly Glu Arg Ala Thr Leu Ser Cys Arg Ala Ser
            35                  40                  45

Gln Ser Val Ser Ser Tyr Leu Ala Trp Tyr Gln Gln Lys Pro Gly Gln
     50                  55                  60

Ala Pro Arg Leu Leu Ile Tyr Asp Ala Ser Asn Arg Ala Thr Gly Ile
 65                  70                  75                  80

Pro Ala Arg Phe Ser Gly Ser Gly Ser Gly Thr Asp Phe Thr Leu Thr
                 85                  90                  95
```

-continued

```
Ile Ser Ser Leu Glu Pro Glu Asp Phe Ala Val Tyr Tyr Cys Gln Gln
            100                 105                 110

Ser Ser Asn Trp Pro Arg Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Gln Ile Thr Leu
225                 230                 235                 240

Lys Glu Ser Gly Pro Thr Leu Val Lys Pro Thr Gln Thr Leu Thr Leu
                245                 250                 255

Thr Cys Thr Phe Ser Gly Phe Ser Leu Ser Thr Ser Gly Val Gly Val
            260                 265                 270

Gly Trp Ile Arg Gln Pro Pro Gly Lys Ala Leu Glu Trp Leu Ala Leu
        275                 280                 285

Ile Tyr Trp Asp Asp Asp Lys Arg Tyr Ser Pro Ser Leu Lys Ser Arg
    290                 295                 300

Leu Thr Ile Thr Lys Asp Thr Ser Lys Asn Gln Val Val Leu Thr Met
305                 310                 315                 320

Ala Asn Met Asp Pro Val Asp Thr Ala Thr Tyr Tyr Cys Ala His Ile
                325                 330                 335

Arg Ile Thr Glu Val Arg Gly Val Ile Ile Ser Tyr Tyr Gly Met Asp
            340                 345                 350

Val Trp Gly Gln Gly Thr Thr Val Thr Val Ser Ser Ala Ser Thr Lys
        355                 360                 365

Gly Pro Ser Val Phe Pro Leu Ala Pro Ser Ser Lys Ser Thr Ser Gly
    370                 375                 380

Gly Thr Ala Ala Leu Gly Cys Leu Val Lys Asp Tyr Phe Pro Glu Pro
385                 390                 395                 400

Val Thr Val Ser Trp Asn Ser Gly Ala Leu Thr Ser Gly Val His Thr
                405                 410                 415

Phe Pro Ala Val Leu Gln Ser Ser Gly Leu Tyr Ser Leu Ser Ser Val
            420                 425                 430

Val Thr Val Pro Ser Ser Ser Leu Gly Thr Gln Thr Tyr Ile Cys Asn
        435                 440                 445

Val Asn His Lys Pro Ser Asn Thr Lys Val Asp Lys Lys Val Glu Pro
    450                 455                 460

Lys Ser Cys Asp Lys Thr His Thr Cys Pro Pro Cys Pro Ala Pro Glu
465                 470                 475                 480

Ala Ala Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
            500                 505                 510

Val Ser His Glu Asp Pro Glu Val Lys Phe Asn Trp Tyr Val Asp Gly
```

```
                515                 520                 525
Val Glu Val His Asn Ala Lys Thr Lys Pro Arg Glu Glu Gln Tyr Asn
530                 535                 540

Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Pro
                565                 570                 575

Ala Pro Ile Glu Lys Thr Ile Ser Lys Ala Lys Gly Gln Pro Arg Glu
            580                 585                 590

Pro Gln Val Tyr Thr Leu Pro Pro Ser Arg Glu Glu Met Thr Lys Asn
        595                 600                 605

Gln Val Ser Leu Thr Cys Leu Val Lys Gly Phe Tyr Pro Ser Asp Ile
    610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
                645                 650                 655

Leu Thr Val Asp Lys Ser Arg Trp Gln Gln Gly Asn Val Phe Ser Cys
            660                 665                 670

Ser Val Met His Glu Ala Leu His Asn His Tyr Thr Gln Lys Ser Leu
        675                 680                 685

Ser Leu Ser Pro Gly Lys
    690

<210> SEQ ID NO 469
<211> LENGTH: 107
<212> TYPE: PRT
<213> ORGANISM: Artificial Sequence
<220> FEATURE:
<223> OTHER INFORMATION: Nivolu VL

<400> SEQUENCE: 469

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 470
<211> LENGTH: 11
<212> TYPE: PRT
<213> ORGANISM: Artificial Sequence
<220> FEATURE:
<223> OTHER INFORMATION: Nivolu VL - CDR1

<400> SEQUENCE: 470

Arg Ala Ser Gln Ser Val Ser Ser Tyr Leu Ala
1               5                   10
```

<210> SEQ ID NO 471
<211> LENGTH: 7
<212> TYPE: PRT
<213> ORGANISM: Artificial Sequence
<220> FEATURE:
<223> OTHER INFORMATION: Nivolu VL - CDR2

<400> SEQUENCE: 471

Asp Ala Ser Asn Arg Ala Thr
1               5

<210> SEQ ID NO 472
<211> LENGTH: 9
<212> TYPE: PRT
<213> ORGANISM: Artificial Sequence
<220> FEATURE:
<223> OTHER INFORMATION: Nivolu VL - CDR3

<400> SEQUENCE: 472

Gln Gln Ser Ser Asn Trp Pro Arg Thr
1               5

<210> SEQ ID NO 473
<211> LENGTH: 128
<212> TYPE: PRT
<213> ORGANISM: Artificial Sequence
<220> FEATURE:
<223> OTHER INFORMATION: 6A5 VH

<400> SEQUENCE: 473

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Ala Asn Met Asp Pro Val Asp Thr Ala Thr Tyr Tyr
                85                  90                  95

Cys Ala His Ile Arg Ile Thr Glu Val Arg Gly Val Ile Ile Ser Tyr
            100                 105                 110

Tyr Gly Met Asp Val Trp Gly Gln Gly Thr Thr Val Thr Val Ser Ser
        115                 120                 125

<210> SEQ ID NO 474
<211> LENGTH: 7
<212> TYPE: PRT
<213> ORGANISM: Artificial Sequence
<220> FEATURE:
<223> OTHER INFORMATION: 6A5 VH - CDR1

<400> SEQUENCE: 474

Thr Ser Gly Val Gly Val Gly
1               5

<210> SEQ ID NO 475
<211> LENGTH: 16
<212> TYPE: PRT
<213> ORGANISM: Artificial Sequence
<220> FEATURE:

<223> OTHER INFORMATION: 6A5 VH - CDR2

<400> SEQUENCE: 475

Leu Ile Tyr Trp Asp Asp Lys Arg Tyr Ser Pro Ser Leu Lys Ser
1               5                   10                  15

<210> SEQ ID NO 476
<211> LENGTH: 18
<212> TYPE: PRT
<213> ORGANISM: Artificial Sequence
<220> FEATURE:
<223> OTHER INFORMATION: 6A5 VH - CDR3

<400> SEQUENCE: 476

Ile Arg Ile Thr Glu Val Arg Gly Val Ile Ile Ser Tyr Tyr Gly Met
1               5                   10                  15

Asp Val

<210> SEQ ID NO 477
<211> LENGTH: 235
<212> TYPE: PRT
<213> ORGANISM: Artificial Sequence
<220> FEATURE:
<223> OTHER INFORMATION: Short Chain 1 (Nivolu VH-CH1)

<400> SEQUENCE: 477

Met Glu Phe Gly Leu Ser Trp Leu Phe Leu Val Ala Ile Leu Lys Gly
1               5                   10                  15

Val Gln Cys Gln Val Gln Leu Val Glu Ser Gly Gly Gly Val Val Gln
                20                  25                  30

Pro Gly Arg Ser Leu Arg Leu Asp Cys Lys Ala Ser Gly Ile Thr Phe
            35                  40                  45

Ser Asn Ser Gly Met His Trp Val Arg Gln Ala Pro Gly Lys Gly Leu
        50                  55                  60

Glu Trp Val Ala Val Ile Trp Tyr Asp Gly Ser Lys Arg Tyr Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Arg Ala Glu Asp Thr Ala Val
            100                 105                 110

Tyr Tyr Cys Ala Thr Asn Asp Asp Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
210                 215                 220

Lys Val Asp Lys Lys Val Glu Pro Lys Ser Cys
225                 230                 235

<210> SEQ ID NO 478

```
<211> LENGTH: 113
<212> TYPE: PRT
<213> ORGANISM: Artificial Sequence
<220> FEATURE:
<223> OTHER INFORMATION: Nivolu VH

<400> SEQUENCE: 478

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
                35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 479
<211> LENGTH: 5
<212> TYPE: PRT
<213> ORGANISM: Artificial Sequence
<220> FEATURE:
<223> OTHER INFORMATION: Nivolu VH - CDR1

<400> SEQUENCE: 479

Asn Ser Gly Met His
1               5

<210> SEQ ID NO 480
<211> LENGTH: 17
<212> TYPE: PRT
<213> ORGANISM: Artificial Sequence
<220> FEATURE:
<223> OTHER INFORMATION: Nivolu VH - CDR2

<400> SEQUENCE: 480

Val Ile Trp Tyr Asp Gly Ser Lys Arg Tyr Tyr Ala Asp Ser Val Lys
1               5                   10                  15

Gly

<210> SEQ ID NO 481
<211> LENGTH: 4
<212> TYPE: PRT
<213> ORGANISM: Artificial Sequence
<220> FEATURE:
<223> OTHER INFORMATION: Nivolu VH - CDR3

<400> SEQUENCE: 481

Asn Asp Asp Tyr
1

<210> SEQ ID NO 482
<211> LENGTH: 238
<212> TYPE: PRT
<213> ORGANISM: Artificial Sequence
<220> FEATURE:
<223> OTHER INFORMATION: Short Chain 2 (6A5 VL-hCK)
```

<400> SEQUENCE: 482

Met Asp Met Arg Val Pro Ala Gln Leu Leu Gly Leu Leu Leu Leu Trp
1               5                   10                  15

Phe Pro Gly Ser Arg Cys Glu Ile Val Leu Thr Gln Ser Pro Gly Thr
            20                  25                  30

Leu Ser Leu Ser Pro Gly Glu Arg Ala Thr Leu Ser Cys Arg Ala Ser
        35                  40                  45

Gln Ser Val Ser Ser Thr Tyr Leu Ala Trp Tyr Gln Gln Lys Pro Gly
    50                  55                  60

Gln Ala Pro Arg Leu Leu Ile Tyr Gly Ala Ser Ser Arg Ala Thr Gly
65                  70                  75                  80

Ile Pro Asp Arg Phe Ser Gly Ser Gly Ser Gly Thr Asp Phe Thr Leu
                85                  90                  95

Thr Ile Ser Arg Leu Glu Pro Glu Asp Phe Ala Val Tyr Tyr Cys Gln
            100                 105                 110

Gln Tyr Gly Ser Ser Pro Pro Ile Thr Phe Gly Gln Gly Thr Arg Leu
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 483
<211> LENGTH: 109
<212> TYPE: PRT
<213> ORGANISM: Artificial Sequence
<220> FEATURE:
<223> OTHER INFORMATION: 6A5 VL

<400> SEQUENCE: 483

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Ile Thr Phe Gly Gln Gly Thr Arg Leu Glu Ile Lys
            100                 105

<210> SEQ ID NO 484
<211> LENGTH: 12
<212> TYPE: PRT
<213> ORGANISM: Artificial Sequence
<220> FEATURE:
<223> OTHER INFORMATION: 6A5 VL - CDR1

<400> SEQUENCE: 484

Arg Ala Ser Gln Ser Val Ser Ser Thr Tyr Leu Ala
1               5                   10

<210> SEQ ID NO 485
<211> LENGTH: 7
<212> TYPE: PRT
<213> ORGANISM: Artificial Sequence
<220> FEATURE:
<223> OTHER INFORMATION: 6A5 VL - CDR2

<400> SEQUENCE: 485

Gly Ala Ser Ser Arg Ala Thr
1               5

<210> SEQ ID NO 486
<211> LENGTH: 10
<212> TYPE: PRT
<213> ORGANISM: Artificial Sequence
<220> FEATURE:
<223> OTHER INFORMATION: 6A5 VL - CDR3

<400> SEQUENCE: 486

Gln Gln Tyr Gly Ser Ser Pro Pro Ile Thr
1               5                   10

<210> SEQ ID NO 487
<211> LENGTH: 22
<212> TYPE: PRT
<213> ORGANISM: Artificial Sequence
<220> FEATURE:
<223> OTHER INFORMATION: leader sequence

<400> SEQUENCE: 487

Met Asp Met Arg Val Pro Ala Gln Leu Leu Gly Leu Leu Leu Leu Trp
1               5                   10                  15

Phe Pro Gly Ser Arg Cys
                20

<210> SEQ ID NO 488
<211> LENGTH: 19
<212> TYPE: PRT
<213> ORGANISM: Artificial Sequence
<220> FEATURE:
<223> OTHER INFORMATION: leader sequence

<400> SEQUENCE: 488

Met Glu Phe Gly Leu Ser Trp Leu Phe Leu Val Ala Ile Leu Lys Gly
1               5                   10                  15

Val Gln Cys

<210> SEQ ID NO 489
<211> LENGTH: 4
<212> TYPE: PRT
<213> ORGANISM: Artificial Sequence
<220> FEATURE:
<223> OTHER INFORMATION: linker sequence

<400> SEQUENCE: 489

Gly Gly Gly Ser
1

<210> SEQ ID NO 490
<211> LENGTH: 4
<212> TYPE: PRT
<213> ORGANISM: Artificial Sequence
<220> FEATURE:
<223> OTHER INFORMATION: Linker sequence

<400> SEQUENCE: 490

Ser Gly Gly Gly
1

<210> SEQ ID NO 491
<211> LENGTH: 5
<212> TYPE: PRT
<213> ORGANISM: Artificial Sequence
<220> FEATURE:
<223> OTHER INFORMATION: Linker sequence

<400> SEQUENCE: 491

Gly Gly Gly Gly Ser
1               5

<210> SEQ ID NO 492
<211> LENGTH: 7
<212> TYPE: PRT
<213> ORGANISM: Artificial Sequence
<220> FEATURE:
<223> OTHER INFORMATION: Linker sequence

<400> SEQUENCE: 492

Gly Gly Gly Gly Ser Gly Ser
1               5

<210> SEQ ID NO 493
<211> LENGTH: 8
<212> TYPE: PRT
<213> ORGANISM: Artificial Sequence
<220> FEATURE:
<223> OTHER INFORMATION: Linker sequence

<400> SEQUENCE: 493

Gly Gly Gly Gly Ser Gly Gly Ser
1               5

<210> SEQ ID NO 494
<211> LENGTH: 10
<212> TYPE: PRT
<213> ORGANISM: Artificial Sequence
<220> FEATURE:
<223> OTHER INFORMATION: Linker sequence

<400> SEQUENCE: 494

Gly Gly Gly Gly Ser Gly Gly Gly Gly Ser
1               5                   10

<210> SEQ ID NO 495
<211> LENGTH: 15
<212> TYPE: PRT
<213> ORGANISM: Artificial Sequence
<220> FEATURE:
<223> OTHER INFORMATION: Linker sequence

<400> SEQUENCE: 495

```
Gly Gly Gly Gly Ser Gly Gly Gly Ser Gly Gly Gly Ser
1               5                   10                  15
```

<210> SEQ ID NO 496
<211> LENGTH: 16
<212> TYPE: PRT
<213> ORGANISM: Artificial Sequence
<220> FEATURE:
<223> OTHER INFORMATION: Linker sequence

<400> SEQUENCE: 496

```
Ala Lys Thr Thr Pro Lys Leu Glu Glu Gly Glu Phe Ser Glu Ala Arg
1               5                   10                  15
```

<210> SEQ ID NO 497
<211> LENGTH: 17
<212> TYPE: PRT
<213> ORGANISM: Artificial Sequence
<220> FEATURE:
<223> OTHER INFORMATION: Linker sequence

<400> SEQUENCE: 497

```
Ala Lys Thr Thr Pro Lys Leu Glu Glu Gly Glu Phe Ser Glu Ala Arg
1               5                   10                  15

Val
```

<210> SEQ ID NO 498
<211> LENGTH: 9
<212> TYPE: PRT
<213> ORGANISM: Artificial Sequence
<220> FEATURE:
<223> OTHER INFORMATION: Linker sequence

<400> SEQUENCE: 498

```
Ala Lys Thr Thr Pro Lys Leu Gly Gly
1               5
```

<210> SEQ ID NO 499
<211> LENGTH: 10
<212> TYPE: PRT
<213> ORGANISM: Artificial Sequence
<220> FEATURE:
<223> OTHER INFORMATION: Linker sequence

<400> SEQUENCE: 499

```
Ser Ala Lys Thr Thr Pro Lys Leu Gly Gly
1               5                   10
```

<210> SEQ ID NO 500
<211> LENGTH: 6
<212> TYPE: PRT
<213> ORGANISM: Artificial Sequence
<220> FEATURE:
<223> OTHER INFORMATION: Linker sequence

<400> SEQUENCE: 500

```
Ser Ala Lys Thr Thr Pro
1               5
```

<210> SEQ ID NO 501
<211> LENGTH: 6
<212> TYPE: PRT
<213> ORGANISM: Artificial Sequence
<220> FEATURE:
<223> OTHER INFORMATION: Linker sequence

<400> SEQUENCE: 501

Arg Ala Asp Ala Ala Pro
1               5

<210> SEQ ID NO 502
<211> LENGTH: 9
<212> TYPE: PRT
<213> ORGANISM: Artificial Sequence
<220> FEATURE:
<223> OTHER INFORMATION: Linker sequence

<400> SEQUENCE: 502

Arg Ala Asp Ala Ala Pro Thr Val Ser
1               5

<210> SEQ ID NO 503
<211> LENGTH: 12
<212> TYPE: PRT
<213> ORGANISM: Artificial Sequence
<220> FEATURE:
<223> OTHER INFORMATION: Linker sequence

<400> SEQUENCE: 503

Arg Ala Asp Ala Ala Ala Ala Gly Gly Pro Gly Ser
1               5                   10

<210> SEQ ID NO 504
<211> LENGTH: 27
<212> TYPE: PRT
<213> ORGANISM: Artificial Sequence
<220> FEATURE:
<223> OTHER INFORMATION: Linker sequence

<400> SEQUENCE: 504

Arg Ala Asp Ala Ala Ala Ala Gly Gly Gly Gly Ser Gly Gly Gly Gly
1               5                   10                  15

Ser Gly Gly Gly Gly Ser Gly Gly Gly Gly Ser
            20                  25

<210> SEQ ID NO 505
<211> LENGTH: 18
<212> TYPE: PRT
<213> ORGANISM: Artificial Sequence
<220> FEATURE:
<223> OTHER INFORMATION: Linker sequence

<400> SEQUENCE: 505

Ser Ala Lys Thr Thr Pro Lys Leu Glu Glu Gly Glu Phe Ser Glu Ala
1               5                   10                  15

Arg Val

<210> SEQ ID NO 506
<211> LENGTH: 5
<212> TYPE: PRT
<213> ORGANISM: Artificial Sequence
<220> FEATURE:
<223> OTHER INFORMATION: Linker sequence

<400> SEQUENCE: 506

Ala Asp Ala Ala Pro
1               5

<210> SEQ ID NO 507
<211> LENGTH: 12
<212> TYPE: PRT
<213> ORGANISM: Artificial Sequence

```
<220> FEATURE:
<223> OTHER INFORMATION: Linker sequence

<400> SEQUENCE: 507

Ala Asp Ala Ala Pro Thr Val Ser Ile Phe Pro Pro
1               5                   10

<210> SEQ ID NO 508
<211> LENGTH: 5
<212> TYPE: PRT
<213> ORGANISM: Artificial Sequence
<220> FEATURE:
<223> OTHER INFORMATION: Linker sequence

<400> SEQUENCE: 508

Thr Val Ala Ala Pro
1               5

<210> SEQ ID NO 509
<211> LENGTH: 12
<212> TYPE: PRT
<213> ORGANISM: Artificial Sequence
<220> FEATURE:
<223> OTHER INFORMATION: Linker sequence

<400> SEQUENCE: 509

Thr Val Ala Ala Pro Ser Val Phe Ile Phe Pro Pro
1               5                   10

<210> SEQ ID NO 510
<211> LENGTH: 6
<212> TYPE: PRT
<213> ORGANISM: Artificial Sequence
<220> FEATURE:
<223> OTHER INFORMATION: Linker sequence

<400> SEQUENCE: 510

Gln Pro Lys Ala Ala Pro
1               5

<210> SEQ ID NO 511
<211> LENGTH: 13
<212> TYPE: PRT
<213> ORGANISM: Artificial Sequence
<220> FEATURE:
<223> OTHER INFORMATION: Linker sequence

<400> SEQUENCE: 511

Gln Pro Lys Ala Ala Pro Ser Val Thr Leu Phe Pro Pro
1               5                   10

<210> SEQ ID NO 512
<211> LENGTH: 6
<212> TYPE: PRT
<213> ORGANISM: Artificial Sequence
<220> FEATURE:
<223> OTHER INFORMATION: Linker sequence

<400> SEQUENCE: 512

Ala Lys Thr Thr Pro Pro
1               5

<210> SEQ ID NO 513
<211> LENGTH: 13
<212> TYPE: PRT
<213> ORGANISM: Artificial Sequence
<220> FEATURE:
```

<223> OTHER INFORMATION: Linker sequence

<400> SEQUENCE: 513

Ala Lys Thr Thr Pro Pro Ser Val Thr Pro Leu Ala Pro
1               5                   10

<210> SEQ ID NO 514
<211> LENGTH: 13
<212> TYPE: PRT
<213> ORGANISM: Artificial Sequence
<220> FEATURE:
<223> OTHER INFORMATION: Linker sequence

<400> SEQUENCE: 514

Ala Lys Thr Thr Ala Pro Ser Val Tyr Pro Leu Ala Pro
1               5                   10

<210> SEQ ID NO 515
<211> LENGTH: 6
<212> TYPE: PRT
<213> ORGANISM: Artificial Sequence
<220> FEATURE:
<223> OTHER INFORMATION: Linker sequence

<400> SEQUENCE: 515

Ala Ser Thr Lys Gly Pro
1               5

<210> SEQ ID NO 516
<211> LENGTH: 13
<212> TYPE: PRT
<213> ORGANISM: Artificial Sequence
<220> FEATURE:
<223> OTHER INFORMATION: Linker sequence

<400> SEQUENCE: 516

Ala Ser Thr Lys Gly Pro Ser Val Phe Pro Leu Ala Pro
1               5                   10

<210> SEQ ID NO 517
<211> LENGTH: 15
<212> TYPE: PRT
<213> ORGANISM: Artificial Sequence
<220> FEATURE:
<223> OTHER INFORMATION: Linker sequence

<400> SEQUENCE: 517

Gly Glu Asn Lys Val Glu Tyr Ala Pro Ala Leu Met Ala Leu Ser
1               5                   10                  15

<210> SEQ ID NO 518
<211> LENGTH: 15
<212> TYPE: PRT
<213> ORGANISM: Artificial Sequence
<220> FEATURE:
<223> OTHER INFORMATION: Linker sequence

<400> SEQUENCE: 518

Gly Pro Ala Lys Glu Leu Thr Pro Leu Lys Glu Ala Lys Val Ser
1               5                   10                  15

```
<210> SEQ ID NO 519
<211> LENGTH: 15
<212> TYPE: PRT
<213> ORGANISM: Artificial Sequence
<220> FEATURE:
<223> OTHER INFORMATION: Linker sequence

<400> SEQUENCE: 519

Gly His Glu Ala Ala Ala Val Met Gln Val Gln Tyr Pro Ala Ser
1               5                   10                  15
```